US012666865B2

(12) United States Patent
Cho et al.

(10) Patent No.: US 12,666,865 B2
(45) Date of Patent: Jun. 23, 2026

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Sang-Hee Cho, Gyeonggi-do (KR); Young-Jae Kim, Gyeonggi-do (KR); HaeYeon Kim, Gyeonggi-do (KR); Young-Jun Cho, Gyeonggi-do (KR); Kyung-Hoon Choi, Gyeonggi-do (KR); So-Young Jung, Gyeonggi-do (KR); Su-Hyun Lee, Gyeonggi-do (KR); Mi-Ja Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 980 days.

(21) Appl. No.: 17/890,926

(22) Filed: Aug. 18, 2022

(65) Prior Publication Data

US 2023/0139032 A1 May 4, 2023

(30) Foreign Application Priority Data

Aug. 27, 2021 (KR) ........................ 10-2021-0113823
Jan. 5, 2022 (KR) ........................ 10-2022-0001374
Jun. 24, 2022 (KR) ........................ 10-2022-0077232

(51) Int. Cl.
*H10K 85/60* (2023.01)
*C07D 209/56* (2006.01)
(Continued)

(52) U.S. Cl.
CPC ......... *H10K 85/636* (2023.02); *C07D 209/56* (2013.01); *C07D 263/52* (2013.01); *C07D 307/91* (2013.01); *C07D 405/10* (2013.01); *C07D 413/12* (2013.01); *C07D 413/14* (2013.01); *C07D 487/16* (2013.01); *C09K 11/06* (2013.01); *H10K 85/615* (2023.02); *H10K 85/633* (2023.02); *H10K 85/654* (2023.02); *H10K 85/6572* (2023.02); *H10K 85/6574* (2023.02); *C09K 2211/1018* (2013.01); *H10K 50/11* (2023.02); *H10K 85/622* (2023.02);
(Continued)

(58) Field of Classification Search
CPC ............. H10K 2101/90; H10K 85/633; H10K 85/636; H10K 85/6572; C07D 487/04; C07D 251/24
See application file for complete search history.

(56) References Cited

U.S. PATENT DOCUMENTS 9,705,099 B2 7/2017 Adamovich et al.
2011/0037381 A1 2/2011 Rostovtsev et al.
(Continued)

FOREIGN PATENT DOCUMENTS

WO WO-2020045976 A1 * 3/2020 ............ H10K 50/11
WO 2020153733 A1 7/2020

*Primary Examiner* — Vu A Nguyen
(74) *Attorney, Agent, or Firm* — G. Creston Campbell

(57) ABSTRACT

The present disclosure relates to three different types of host materials, and an organic electroluminescent device comprising the same, and it is possible to provide an organic electroluminescent device having higher luminous efficiency and/or improved lifetime properties compared to a conventional organic electroluminescent device.

11 Claims, 3 Drawing Sheets

(51) Int. Cl.

| | |
|---|---|
| ***C07D 263/52*** | (2006.01) |
| ***C07D 307/91*** | (2006.01) |
| ***C07D 405/10*** | (2006.01) |
| ***C07D 413/12*** | (2006.01) |
| ***C07D 413/14*** | (2006.01) |
| ***C07D 487/16*** | (2006.01) |
| ***C09K 11/06*** | (2006.01) |
| ***H10K 50/11*** | (2023.01) |
| ***H10K 101/00*** | (2023.01) |
| ***H10K 101/10*** | (2023.01) |
| ***H10K 101/30*** | (2023.01) |

(52) U.S. Cl.
CPC ....... *H10K 85/657* (2023.02); *H10K 85/6576* (2023.02); *H10K 2101/10* (2023.02); *H10K 2101/30* (2023.02); *H10K 2101/90* (2023.02)

(56) References Cited

U.S. PATENT DOCUMENTS

| | | | | |
|---|---|---|---|---|
| 2014/0299865 | A1* | 10/2014 | Nishimura | H10K 85/626<br>252/500 |
| 2020/0028089 | A1 | 1/2020 | Cho et al. | |
| 2021/0135142 | A1* | 5/2021 | Li | H10K 85/658 |
| 2021/0265569 | A1 | 8/2021 | Kim et al. | |

* cited by examiner

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

In 1987, Tang et al. of Eastman Kodak first developed a small molecule green organic electroluminescent device (OLED) of TPD/Alq3 bilayer consisting of a light-emitting layer and a charge transport layer. Since then, the research on an OLED has been rapidly carried out, and it has been commercialized. At present, phosphorescent materials, which provide excellent luminous efficiency in realizing panels, are mainly used in OLEDs. In many applications such as TVs and lightings, the lifetime of OLEDs is insufficient and higher efficiency of OLEDs is still required. Typically, the higher the luminance of an OLED, the shorter the lifetime that the OLED has. Thus, an OLED which has high luminous efficiency and/or long lifetime is required for long time uses and high resolution of displays.

In order to enhance luminous efficiency, driving voltage and/or lifetime, various materials or concepts for an organic layer of an OLED have been proposed. However, they were not satisfactory in practical use.

U.S. Pat. No. 9,705,099 discloses an OLED using a carbazolyl-containing compound as three types of host materials. However, the aforementioned reference does not specifically disclose the specific combination of host materials claimed in the present disclosure. In addition, there is still a need to develop host materials for improving OLED performance.

DISCLOSURE OF INVENTION

Technical Problem

The objective of the present disclosure is firstly, to provide a plurality of host materials capable of producing an organic electroluminescent device having low driving voltage, high luminous efficiency, and/or long lifetime properties, and secondly, to provide an organic electroluminescent device comprising the host materials.

The objective of the present disclosure is to provide an organic electroluminescent device having low driving voltage, high luminous efficiency and/or improved lifetime properties while improving the charge balance in a light-emitting layer by facilitating control of the energy level and mobility of a phosphorescent host material, by comprising at least three different types of host materials including a specific combination of compounds.

Solution to Problem

As a result of intensive studies to solve the technical problems, the present inventors have found that the above objective can be achieved by a plurality of host materials comprising a first host material, a second host material, and a third host material, wherein each of the first host material, the second host material and the third host material does not comprise a carbazole or fused carbazole structure, and the first host material, the second host material and the third host material are different from each other.

In addition, the present inventors have discovered that when the combination of a compound represented by formula 1 of the present disclosure, a compound represented by any one of formulas 2 to 4 of the present disclosure, and a third compound different from the compounds and represented by any one of formulas of 1 to 4 of the present disclosure is used in a light-emitting layer, hole and electronic properties are better balanced by appropriate HOMO (highest occupied molecular orbital) and LUMO (lowest unoccupied molecular orbital) energy levels, thereby providing an OLED having lower driving voltage, higher luminous efficiency and/or longer lifetime properties compared to a conventional OLED.

Advantageous Effects of Invention

An organic electroluminescent device having lower driving voltage, higher luminous efficiency, and/or improved lifespan properties compared to a conventional organic electroluminescent device is provided by comprising three different types of host materials according to the present disclosure, and it is possible to produce a display system or lighting system using the same.

MODE FOR THE INVENTION

Figure 1:
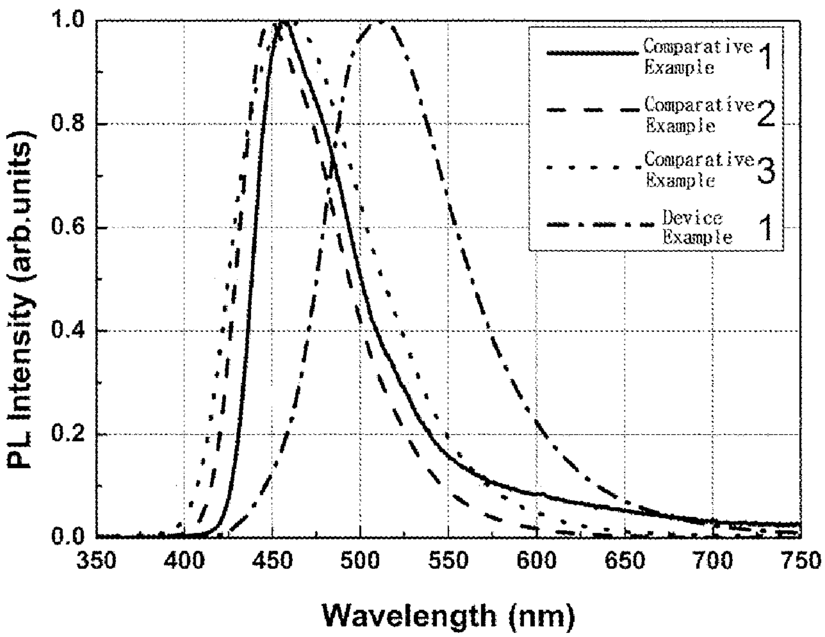
FIG. 1 illustrates a graph showing the PL (photoluminescence) results of thin film of an organic electroluminescent material according to an embodiment of the present disclosure.

Hereinafter, the present disclosure will be described in detail. However, the following description is intended to explain the present disclosure and is not meant in any way to restrict the scope of the present disclosure.

The term "an organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term "a plurality of organic electroluminescent materials" in the present disclosure means organic electroluminescent materials comprising a combination of at least three types of compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, the plurality of host materials is a combination of at least three types of materials, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. These at least three types of compounds may be included in the same layer or different layers through common methods used in the art. For example, the at least three materials may be mixture-evaporated or co-evaporated, or may be individually evaporated.

All three types of host materials used herein may be a material having strong hole transport properties or a material having strong electron transport properties. It is preferable to use a material having strong hole transport properties for the first host material, a material having strong electron transport properties for the second host material, and a material having both strong hole transport property and strong electron transport property or only one of the two properties for the third host material.

Herein, the term "fused carbazole structure" refers to a structure in which one or more rings are fused to a carbazole structure, but the structure including a ring formed by fusion to both the two benzene rings and the nitrogen-containing 5-membered ring of carbazole is excluded.

Herein, "substituted" in the expression "substituted or unsubstituted" means that a hydrogen atom in a certain functional group is replaced with another atom or another functional group, i.e., a substituent, and also includes that the hydrogen atom is replaced with a group formed by a linkage of two or more substituents of the above substituents. For example, the "group formed by a linkage of two or more substituents" may be pyridine-triazine. That is, pyridine-triazine may be interpreted as a heteroaryl substituent, or as substituents in which two heteroaryl substituents are linked. Herein, the substituent(s) of the substituted alkyl, the substituted cycloalkyl, the substituted heterocycloalkyl, the substituted fused ring group of a aliphatic ring(s) and a aromatic ring(s), the substituted aryl, the substituted arylene, the substituted heteroaryl, the substituted heteroarylene, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-alkenylamino, the substituted alkylalkenylamino, the substituted mono- or di-arylamino, the substituted alkylarylamino, the substituted mono- or di-heteroarylamino, the substituted alkylheteroarylamino, the substituted alkenylarylamino, the substituted alkenylheteroarylamino, and the substituted arylheteroarylamino, each independently, are at least one selected from the group consisting of deuterium; a halogen; a cyano; a carboxyl; a nitro; a hydroxyl; a phosphine oxide; a (C1-C30)alkyl; a halo(C1-C30)alkyl; a (C2-C30)alkenyl unsubstituted or substituted with a (C6-C30)aryl(s); a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30)alkyl(s) and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring group of a (C3-C30) aliphatic ring(s) and a (C6-C30) aromatic ring(s); an amino; a mono- or di-(C1-C30)alkylamino; a mono- or di-(C2-C30)alkenylamino; a mono- or di-(C6-C30)arylamino unsubstituted or substituted with a (C1-C30)alkyl(s); a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituent(s), each independently, are at least one selected from the group consisting of deuterium; a halogen; a cyano; a (C1-C20)alkyl; a (C6-C25)aryl unsubstituted or substituted with a (C1-C20)alkyl(s); a (5- to 25-membered)heteroaryl unsubstituted or substituted with a (C6-C25)aryl(s); and a tri(C6-C25)arylsilyl. According to another embodiment of the present disclosure, the substituent(s), each independently, are at least one selected from the group consisting of deuterium; a halogen; a cyano; a (C1-C10)alkyl; a (C6-C18)aryl unsubstituted or substituted with a (C1-C10)alkyl(s); an unsubstituted (5- to 20-membered)heteroaryl; and a tri(C6-C18)arylsilyl. For example, the substituent(s), each independently, may be one selected from the group consisting of deuterium, a halogen, a cyano, a methyl, a tert-butyl, a phenyl, a naphthyl, a biphenyl, a phenanthrenyl, a dimethylfluorenyl, a pyridyl, a dibenzofuranyl, a dibenzothiophenyl, a benzonaphthofuranyl, a benzonaphthothiophenyl, and a triphenylsilyl, or a combination thereof.

Herein, a ring formed by a linkage of adjacent substituents means that at least two adjacent substituents are linked to or fused with each other to form a substituted or unsubstituted, mono- or polycyclic, (3- to 30-membered) alicyclic or aromatic ring, or the combination thereof. Preferably, the ring may be a substituted or unsubstituted, mono- or polycyclic, (3- to 26-membered) alicyclic or aromatic ring, or the combination thereof. More preferably, the ring may be a mono- or polycyclic, (5- to 25-membered) aromatic ring unsubstituted or substituted with at least one of (C1-C6) alkyl(s), a (C6-C18)aryl(s), and a (3- to 20-membered) heteroaryl(s). In addition, the formed ring may contain at least one heteroatom selected from the group consisting of B, N, O, S, Si, and P, preferably at least one heteroatom selected from the group consisting of N, O, and S. For example, the ring may be a benzene ring unsubstituted or substituted with a phenyl(s), a benzonaphthofuran ring, an acenaphthylene ring, a dihydrodimethylanthracene ring, a cyclopentane ring, an indene ring, an indane ring, a fluorene ring, a phenanthrene ring, an indole ring, a benzofuran ring, a xanthene ring, etc., and the ring may also form a spiro ring.

In the present disclosure, heteroaryl, heteroarylene, and heterocycloalkyl may, each independently, contain at least one heteroatom selected from the group consisting of B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30) alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered) heteroarylamino, and a substituted or unsubstituted (C6-C30)aryl(3- to 30-membered)heteroarylamino.

For example, when using a host having a lower HOMO energy level than a conventional hole type host among the compounds having the core of formula 1, even if there is an advantage in efficiency increase, excess carriers in one direction will occur, which may have an effect such as exciton quenching, resulting in problems of reduced efficiency and lifetime. The present inventors have found that the combination of a hole-type host capable of forming an appropriate HOMO energy level in the core of formula 1 and materials of formulas 2 to 4 having fast electron transport properties results in the hole and electron properties being more balanced by appropriate HOMO and LUMO energy levels, which can provide an OLED having higher luminous efficiency and/or longer lifetime properties compared to a conventional OLED.

To be specific, the present disclosure provides at least three different types of host materials comprising a first host material comprising a compound represented by the following formula 1; a second host material comprising a compound represented by any one of the following formulas 2 to 4; and a third host material belonging to the first or second host material group while having a structure different from those of the first and second host materials.

$$T\text{-}L_1\text{-}Ar_1 \quad (1)$$

In formula 1,

T represents any one selected from the group consisting of the following formulas 1-1 to 1-5:

(1-1)

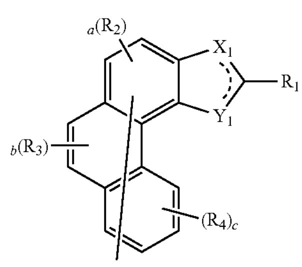

(1-2)

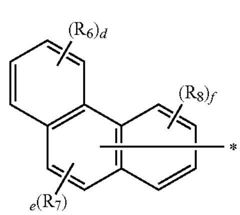

-continued (1-3)

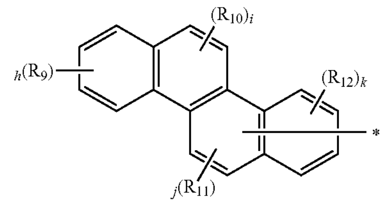

(1-4)

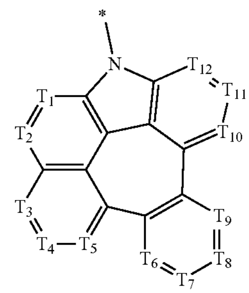

(1-5)

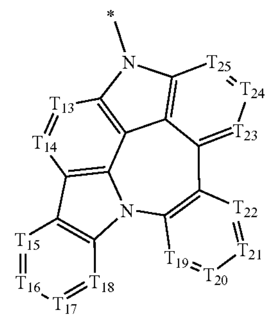

wherein, $X_1$ and $Y_1$, each independently, represent —N═, —$NR_5$—, —O—, or —S—, with the proviso that any one of $X_1$ and $Y_1$ represents —N═, and the other of $X_1$ and $Y_1$ represents —$NR_5$—, —O—, or —S—;

$R_1$ represents a substituted or unsubstituted (C6-C30)aryl, or a substituted or unsubstituted (3- to 30-membered) heteroaryl;

$R_2$ to $R_5$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C6-C30) aryl(3- to 30-membered)heteroarylamino, or a substituted or unsubstituted (C1-C30)alkyl(C6-C30) arylamino; or may be linked to an adjacent substituent(s) to form a ring(s);

$T_1$ to $T_{25}$, each independently, represent N or $CV_1$;

$V_1$, each independently, represents hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted (C1-C30) alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, or a substituted or unsubstituted (C6-C30)aryl(3- to 30-membered)heteroarylamino; or may be linked to an adjacent substituent(s) to form a ring(s);

a and b, each independently, represent 1 or 2; c represents an integer of 1 to 4; where if each of a to c is an integer of 2 or more, each of $R_2$ to each of $R_4$ may be the same or different;

$R_6$ to $R_{12}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

d, f, h, and k, each independently, represent an integer of 1 to 4; e, i, and j, each independently, represent an integer of 1 or 2; where if each of d to f and h to k is an integer of 2 or more, each of $R_6$ to each of $R_{11}$ may be the same or different;

$Ar_1$ represents a substituted or unsubstituted (C6-C30) aryl, a substituted or unsubstituted (3- to 30-membered) heteroaryl, or

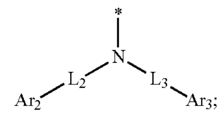

$Ar_2$ and $Ar_3$, each independently, represent a substituted or unsubstituted (C6-C30)aryl, a substituted or unsubstituted (3- to 30-membered)heteroaryl, or a substituted or unsubstituted (C3-C30)cycloalkyl; and $L_1$ to $L_3$, each independently, represent a single bond, a substituted or unsubstituted (C6-C30)arylene, or a substituted or unsubstituted (3- to 30-membered)heteroarylene.

According to one embodiment of the present disclosure, in formula 1, $X_1$ and $Y_1$, each independently, represent —N=, —O—, or —S—, with the proviso that any one of $X_1$ and $Y_1$ represents —N=, the other of $X_1$ and $Y_1$ represents —O— or —S—.

According to one embodiment of the present disclosure, $R_1$ represents a substituted or unsubstituted (C6-C25)aryl, or a substituted or unsubstituted (5- to 25-membered)heteroaryl. According to another embodiment of the present disclosure, $R_1$ represents an unsubstituted (C6-C18)aryl, or an unsubstituted (5- to 20-membered)heteroaryl. For example, $R_1$ may be a phenyl, a biphenyl, a quinolyl, an isoquinolyl, etc.

According to one embodiment of the present disclosure, $R_2$ to $R_5$, each independently, represent hydrogen.

According to one embodiment of the present disclosure, $R_6$ to $R_{12}$, each independently, represent hydrogen, deuterium, a substituted or unsubstituted (C6-C25)aryl, a substituted or unsubstituted (5- to 25-membered)heteroaryl, or a substituted or unsubstituted mono- or di-(C6-C25)arylamino. According to another embodiment of the present disclosure, $R_6$ to $R_{12}$, each independently, represent hydrogen, deuterium, a (C6-C28)aryl unsubstituted or substituted with a (C6-C18)aryl(s), an unsubstituted (5- to 20-membered)heteroaryl, or an unsubstituted di(C6-C18)arylamino. For example, $R_6$ to $R_{12}$, each independently, may be hydrogen, deuterium, a phenyl, a naphthyl, a phenylnaphthyl, a naphthylphenyl, a phenanthrenyl, a terphenyl, a triphenylenyl, a pyridyl, a quinolyl, a dibenzofuranyl, a dibenzothiophenyl, a diphenylamino, etc.

According to one embodiment of the present disclosure, $T_1$ to $T_{25}$, each independently, represent $CV_1$.

According to one embodiment of the present disclosure, $V_1$, each independently, represents hydrogen, a substituted or unsubstituted (C6-C25)aryl, or a substituted or unsubstituted (5- to 20-membered)heteroaryl; or adjacent $V_1$'s may be linked to each other to form a substituted or unsubstituted, mono- or polycyclic, (3- to 30-membered) alicyclic or aromatic ring, or the combination thereof. According to another embodiment of the present disclosure, $V_1$, each independently, represents hydrogen, an unsubstituted (C6-C18)aryl, or an unsubstituted (5- to 20-membered)heteroaryl; or adjacent $V_1$'s may be linked to each other to form an unsubstituted (3- to 10-membered) aromatic ring. For example, $V_1$, each independently, represents hydrogen or phenyl; or adjacent $V_1$'s may be linked to each other to form an unsubstituted benzene ring.

According to one embodiment of the present disclosure, $Ar_1$ represents a substituted or unsubstituted (C6-C30)aryl, a substituted or unsubstituted (5- to 20-membered) heteroaryl, or

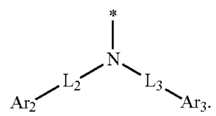

According to another embodiment of the present disclosure, $Ar_1$ represents a (C6-C30)aryl unsubstituted or substituted with at least one of a (C1-C10)alkyl(s) and a (C6-C18)aryl (s); an unsubstituted (5- to 20-membered)heteroaryl; or

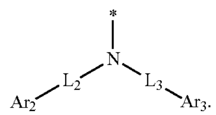

For example, $Ar_1$ may be a phenyl, a naphthyl, a biphenyl, a phenanthrenyl, a triphenylenyl, a fluoranthenyl, a terphenyl, a dimethylfluorenyl, a diphenylfluorenyl, a dimethylbenzofluorenyl, a diphenylbenzofluorenyl, a spirobifluorenyl, a spiro[cyclopentane-fluoren]yl, a spiro[dihydroindene-fluoren]yl, a spiro[fluorene-benzofluoren]yl, a dibenzofuranyl, a dibenzothiophenyl, a benzonaphthofuranyl, a benzonaphthothiophenyl, etc.

According to one embodiment of the present disclosure, $Ar_2$ and $Ar_3$, each independently, represent a substituted or unsubstituted (C6-C25)aryl, or a substituted or unsubstituted (5- to 25-membered)heteroaryl. According to another embodiment of the present disclosure, $Ar_2$ and $Ar_3$, each independently, represent a (C6-C25)aryl unsubstituted or substituted with at least one of deuterium, a (C1-C10)alkyl (s), a (5- to 20-membered)heteroaryl(s), and a tri(C6-C18) arylsilyl(s); or a (5- to 20-membered)heteroaryl unsubstituted or substituted with a (C6-C18)aryl(s). For example, $Ar_2$ and $Ar_3$, each independently, may be a phenyl unsubstituted or substituted with a tert-butyl(s), a pyridyl(s) or a triphenylsilyl(s); a naphthyl; a naphthylphenyl; a phenylnaphthyl; a biphenyl unsubstituted or substituted with deuterium or a tert-butyl(s); a phenanthrenyl; a terphenyl; a dimethylfluorenyl unsubstituted or substituted with a phenyl(s); a diphenylfluorenyl; a spirobifluorenyl; a pyridyl unsubstituted or substituted with a phenyl(s); a benzofuranyl substituted with a phenyl(s); a dibenzofuranyl unsubstituted or substituted with a phenyl(s); a dibenzothiophenyl unsubstituted or substituted with a phenyl(s); a benzonaphthofuranyl; a benzonaphthothiophenyl, etc.

According to one embodiment of the present disclosure, $L_1$ to $L_3$, each independently, represent a single bond, a substituted or unsubstituted (C6-C25)arylene, or a substituted or unsubstituted (5- to 25-membered)heteroarylene. According to another embodiment of the present disclosure, $L_1$ to $L_3$, each independently, represent a single bond, a (C6-C18)arylene unsubstituted or substituted with a (C6-C18)aryl(s), or an unsubstituted (5- to 20-membered)heteroarylene. For example, $L_1$ may be a single bond, a phenylene unsubstituted or substituted with a phenyl(s); a naphthylene; a biphenylene; a pyridylene, etc., and $L_2$ and $L_3$, each independently, may be a single bond, a phenylene, a naphthylene, a dibenzofluorenylene, etc.

According to one embodiment of the present disclosure, the formula 1 may be represented by any one of the following formulas 1-11 to 1-16:

(1-11)

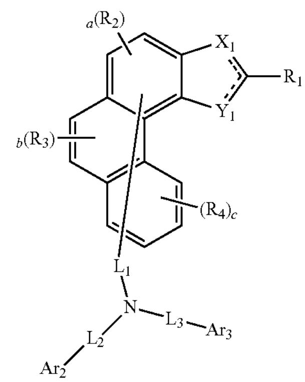

(1-12)

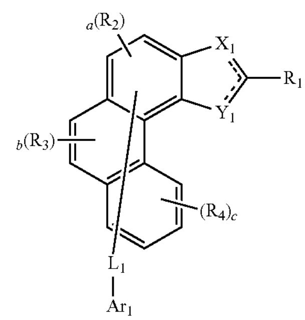

(1-13)

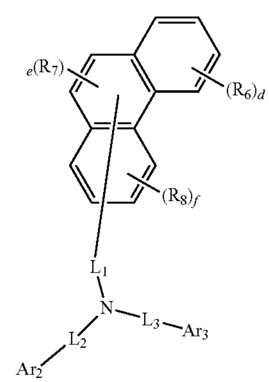

(1-14)

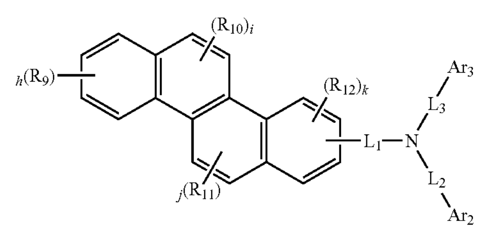

-continued (1-15)

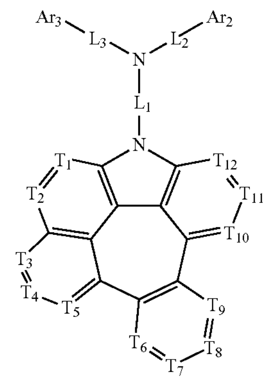

(1-16)

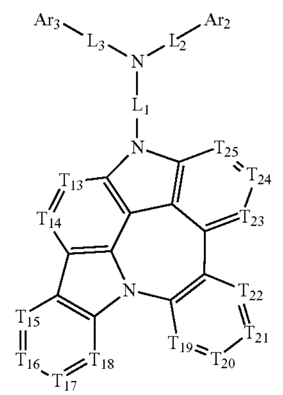

in formulas 1-11 to 1-16, $Ar_1$ represents a substituted or unsubstituted (C6-C30) aryl, or a substituted or unsubstituted (3- to 30-membered)heteroaryl; and $X_1$, $Y_1$, $R_1$ to $R_4$, $R_6$ to $R_{12}$, $T_1$ to $T_{25}$, $L_1$ to $L_3$, $Ar_2$, $Ar_3$, a to f, and h to k are as defined in formula 1.

(2)

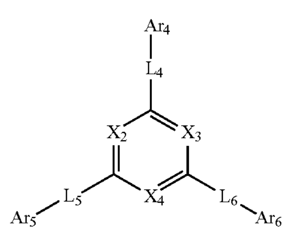

(3)

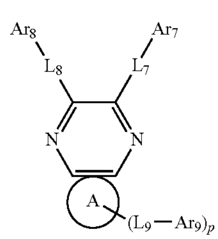

-continued (4)

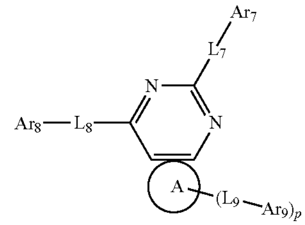

In formulas 2 to 4, $X_2$ to $X_4$, each independently, represent $CR_{13}$ or N, with the proviso that at least one of $X_2$ to $X_4$ represents N;

$R_{13}$, each independently, represents hydrogen, deuterium, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30) aryl, or a substituted or unsubstituted (3- to 30-membered)heteroaryl; or may be linked to an adjacent substituent(s) to form a ring(s);

ring A represents a benzene ring or a naphthalene ring;

$L_4$ to $L_9$, each independently, represent a single bond, a substituted or unsubstituted (C6-C30)arylene, or a substituted or unsubstituted (3- to 30-membered)heteroarylene;

$Ar_4$ to $Ar_9$, each independently, represent a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri(C6-C30)arylsilyl; or may be linked to an adjacent substituent(s) to form a ring(s); and p represents an integer of 0 to 6; where if p is an integer of 2 or more, each of $L_9$ and each of $Ar_9$ may be the same or different.

According to one embodiment of the present disclosure, any one of $X_2$ to $X_4$ may be N; any two of $X_2$ to $X_4$ may be N; or all of $X_2$ to $X_4$ may be N.

According to one embodiment of the present disclosure, $R_{13}$, each independently, represents hydrogen or deuterium; or may be linked to an adjacent substituent(s) to form a ring(s). According to another embodiment of the present disclosure, $R_{13}$, each independently, represents hydrogen or deuterium; or may be linked to an adjacent substituent(s) to form an unsubstituted (6- to 17-membered) ring(s). For example, $R_{13}$, each independently, may be hydrogen or deuterium; or may be linked to an adjacent substituent(s) to form a benzene ring, a benzonaphthofuran ring, an acenaphthylene ring, or a dihydrodimethylanthracene ring.

According to one embodiment of the present disclosure, $L_4$ to $L_9$, each independently, represent a single bond, a substituted or unsubstituted (C6-C25)arylene, or a substituted or unsubstituted (5- to 25-membered)heteroarylene. According to another embodiment of the present disclosure, $L_4$ to $L_9$, each independently, represent a single bond, a (C6-C28)arylene unsubstituted or substituted with a (C6-C18)aryl(s), or an unsubstituted (5- to 20-membered)heteroarylene. For example, $L_4$ to $L_9$, each independently, may be a single bond, a phenylene unsubstituted or substituted with a phenyl(s), a naphthylene, a biphenylene, a phenylene-naphthylene, a naphthylene-phenylene, a phenanthrenylene, a pyridylene, a dibenzofuranylene, a naphthooxazolylene, a benzonaphthothiophenylene, etc., which may be further substituted with deuterium.

According to one embodiment of the present disclosure, $Ar_4$ to $Ar_9$, each independently, represent a substituted or unsubstituted (C1-C20)alkyl, a substituted or unsubstituted (C3-C25)cycloalkyl, a substituted or unsubstituted (C6-C30)aryl, a substituted or unsubstituted (5- to 25-membered) heteroaryl, a substituted or unsubstituted tri(C6-C25)arylsilyl, or a substituted or unsubstituted tri(C1-C20)alkylsilyl; or may be linked to an adjacent substituent(s) to form a ring(s). According to another embodiment of the present disclosure, $Ar_4$ to $Ar_9$, each independently, represent an unsubstituted (C1-C10)alkyl; an unsubstituted (C3-C18)cycloalkyl; a (C6-C30)aryl unsubstituted or substituted with at least one of deuterium, a halogen(s), a cyano(s), and a (5- to 25-membered)heteroaryl(s); a (5- to 25-membered)heteroaryl unsubstituted or substituted with deuterium, a (C6-C18)aryl(s), or a (5- to 25-membered)heteroaryl(s); an unsubstituted tri(C6-C18)arylsilyl; or an unsubstituted tri (C1-C10)alkylsilyl; or may be linked to an adjacent substituent(s) to form an unsubstituted (6- to 17-membered) ring(s). For example, $Ar_4$ to $Ar_9$, each independently, may be a tert-butyl; a cyclohexyl; a phenyl unsubstituted or substituted with a fluoro(s) or a cyano(s); a naphthyl unsubstituted or substituted with a dibenzofuranyl(s) or a benzonaphthofuranyl(s); a naphthylphenyl; a phenylnaphthyl; a biphenyl; a phenanthrenyl; a dihydrophenanthrenyl substituted with a methyl(s); an anthracenyl; a terphenyl; a triphenylenyl; a dimethylfluorenyl; a phenylfluorenyl; a diphenylfluorenyl unsubstituted or substituted with a phenyl(s); a dimethylbenzofluorenyl; a diphenylbenzofluorenyl; a spirobifluorenyl; a spiro[benzofluoren-fluoren]yl; a terphenyl; a chrysenyl unsubstituted or substituted with a phenyl(s); a (C22) aryl; a carbazolyl unsubstituted or substituted with a phenyl(s); a benzothiophenyl; a dibenzofuranyl unsubstituted or substituted with a phenyl(s) or a biphenyl(s); a dibenzothiophenyl; a substituted or unsubstituted benzonaphthothiophenyl; a substituted or unsubstituted benzonaphthofuranyl; a benzophenanthrofuranyl; a naphthooxazolyl substituted with a phenyl(s); a phenanthrooxazolyl substituted with a phenyl(s); a phenoxazinyl; a triphenylsilyl; or a trimethylsilyl; or may be linked to an adjacent substituent(s) to form a benzene ring, a benzonaphthofuran ring, an acenaphthylene ring, or a dihydrodimethylanthracene ring, which may be further substituted with deuterium. The substituent(s) of the substituted benzonaphthothiophenyl and the substituted benzonaphthofuranyl, each independently, may be at least one selected from the group consisting of deuterium, a phenyl, a naphthyl, a biphenyl, a dimethylfluorenyl, a dibenzofuranyl, a dibenzothiophenyl, and a phenanthrenyl.

According to one embodiment of the present disclosure, p represents an integer of 0 to 4. According to another embodiment of the present disclosure, p may be 0 or 1.

According to one embodiment of the present disclosure, at least one of $Ar_4$ to $Ar_9$ is selected from the group consisting of the following formulas a-1 to a-7:

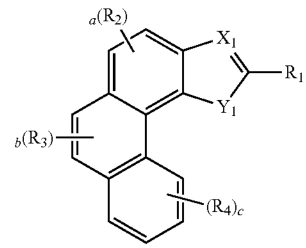

(a-1)

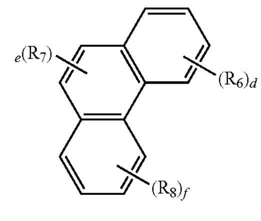

(a-2)

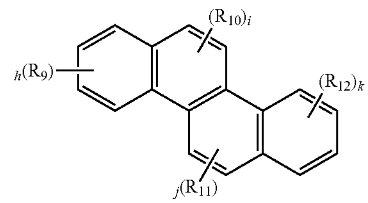

(a-3)

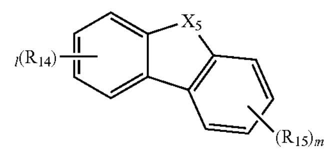

(a-4)

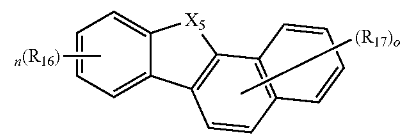

(a-5)

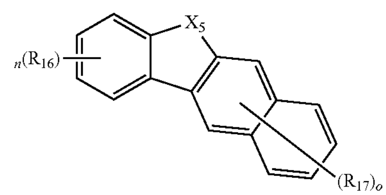

(a-6)

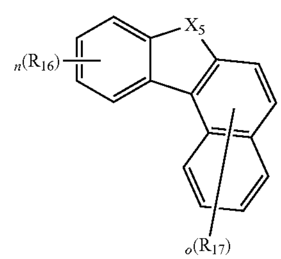

(a-7)

in formulas a-1 to a-7, $X_5$, each independently, represents O, S, or $CR_{18}R_{19}$;

$R_{18}$ and $R_{19}$, each independently, represent a substituted or unsubstituted (C1-C30)alkyl, a substituted or unsubstituted (C3-C30)cycloalkyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl; or $R_{18}$ and $R_{19}$ may be linked to each other to form a spiro ring;

$R_{14}$ and $R_{15}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

l to n, each independently, represent an integer of 1 to 4; o represents an integer of 1 to 6; where if each of l to o is an integer of 2 or more, each of $R_{14}$ to each of $R_{17}$ may be the same or different;

$R_6$ to $R_8$, $R_{16}$, and $R_{17}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi (C6-C30)arylsilyl, a substituted or unsubstituted tri (C6-C30)arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30) arylamino, a substituted or unsubstituted (C1-C30) alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to an adjacent substituent(s) to form a ring(s); and $X_1$, $Y_1$, $R_1$ to $R_4$, $R_9$ to $R_{12}$, a to f, and h to k are as defined in formula 2.

According to one embodiment of the present disclosure, $R_{18}$ and $R_{19}$, each independently, represent a substituted or unsubstituted (C1-C20)alkyl, a substituted or unsubstituted (C6-C25)aryl, or a substituted or unsubstituted (3- to 30-membered)heteroaryl; or $R_{18}$ and $R_{19}$ may be linked to each other to form a spiro ring. According to another embodiment of the present disclosure, $R_{18}$ and $R_{19}$, each independently, represent an unsubstituted (C1-C10)alkyl, or an unsubstituted (C6-C18)aryl; or $R_{18}$ and $R_{19}$ may be linked to each other to form a spiro ring. For example, $R_{18}$ and $R_{19}$, each independently, may be a methyl or a phenyl; or $R_{18}$ and $R_{19}$ may be linked to each other to form a spiro fluorene ring.

According to one embodiment of the present disclosure, $R_{14}$ and $R_{15}$, each independently, represent hydrogen, deuterium, a substituted or unsubstituted (C6-C25)aryl, or a substituted or unsubstituted (5- to 25-membered)heteroaryl. According to another embodiment of the present disclosure, $R_{14}$ and $R_{15}$, each independently, represent hydrogen, deuterium, a (C6-C18)aryl unsubstituted or substituted with a (C1-C10)alkyl(s), or an unsubstituted (5- to 20-membered) heteroaryl. For example, $R_{14}$ and $R_{15}$, each independently, represent hydrogen, deuterium, a phenyl, a naphthyl, a biphenyl, a phenanthrenyl, a dimethylfluorenyl, a dibenzofuranyl, a dibenzothiophenyl, etc.

According to one embodiment of the present disclosure, $R_{16}$ and $R_{17}$, each independently, represent hydrogen, deuterium, a substituted or unsubstituted (C6-C25)aryl, or a substituted or unsubstituted (5- to 25-membered)heteroaryl; or may be linked to an adjacent substituent(s) to form a ring(s). According to another embodiment of the present disclosure, $R_{16}$ and $R_{17}$, each independently, represent hydrogen, deuterium, a (C6-C18)aryl unsubstituted or substituted with a (C1-C10)alkyl(s), or an unsubstituted (5- to 20-membered)heteroaryl; or may be linked to an adjacent substituent(s) to form a ring(s). For example, $R_{16}$ and $R_{17}$, each independently, may be hydrogen, deuterium, a phenyl, a naphthyl, a biphenyl, a phenanthrenyl, a dimethylfluorenyl, a dibenzofuranyl, a dibenzothiophenyl, etc.; or may be linked to an adjacent substituent to form a benzene ring.

According to one embodiment of the present disclosure, $R_6$ to $R_8$, each independently, represent hydrogen or a substituted or unsubstituted (C6-C25)aryl; or may be linked to an adjacent substituent(s) to form a ring(s). According to another embodiment of the present disclosure, $R_6$ to $R_8$, each independently, represent hydrogen or an unsubstituted (C6-C18)aryl; or may be linked to an adjacent substituent(s) to form a substituted or unsubstituted (C6-C18) aromatic ring (s). For example, $R_6$ to $R_8$, each independently, may be hydrogen or a phenyl; or may be linked to an adjacent substituent to form a benzene ring unsubstituted or substituted with a phenyl(s).

The compound represented by formula 1 may be at least one selected from the group consisting of the following compounds, but is not limited thereto.

H1-1

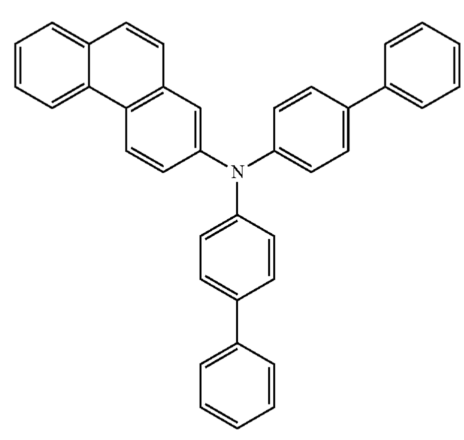

-continued
H1-2
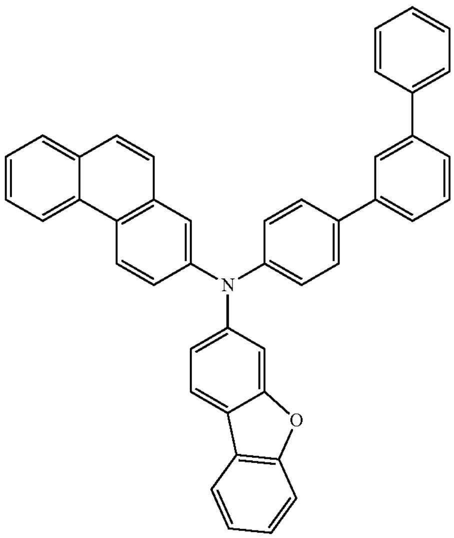
H1-3
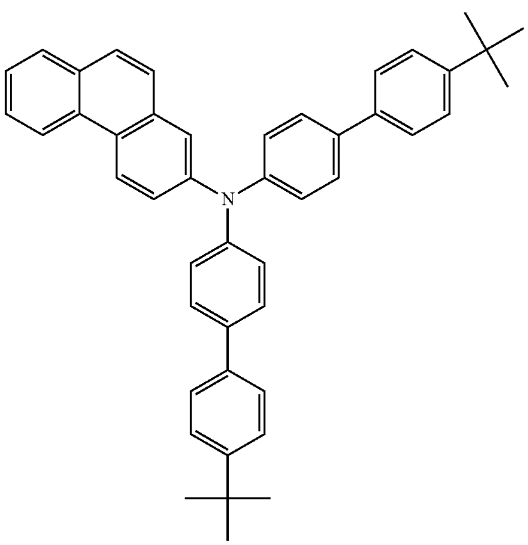
H1-4
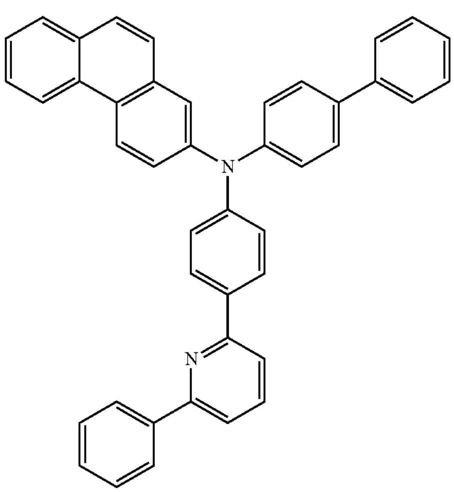
-continued
H1-5
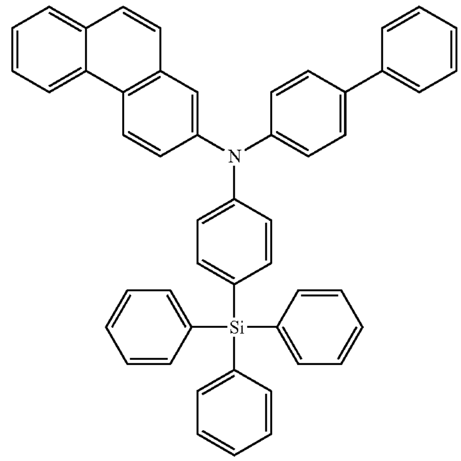
H1-6
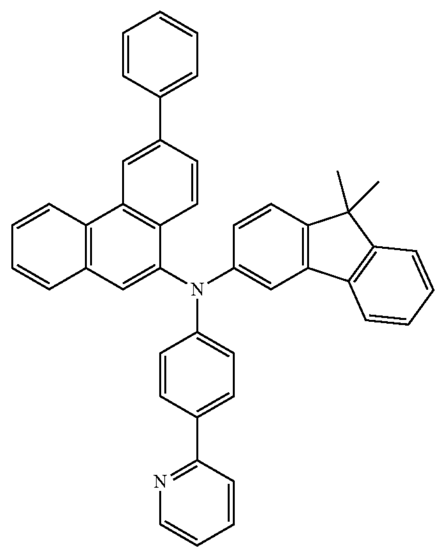
H1-7
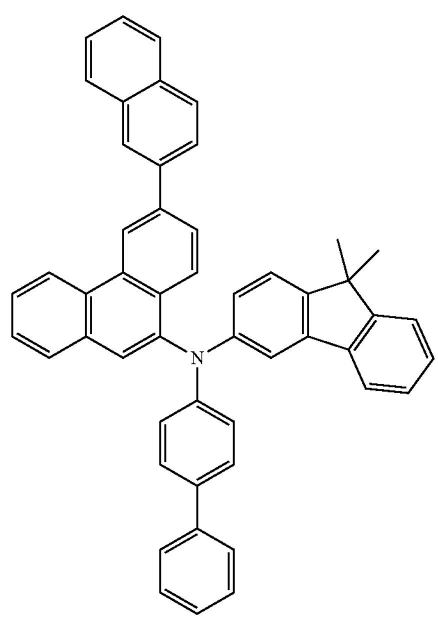

-continued
H1-8
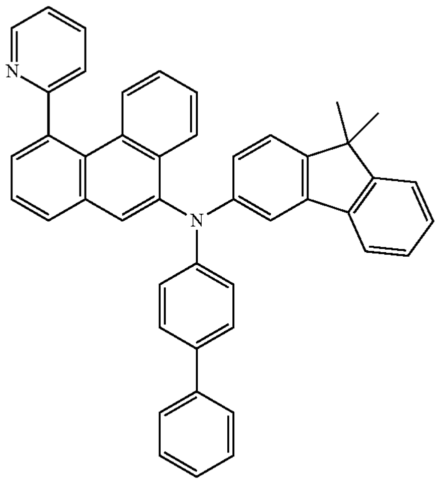
H1-9
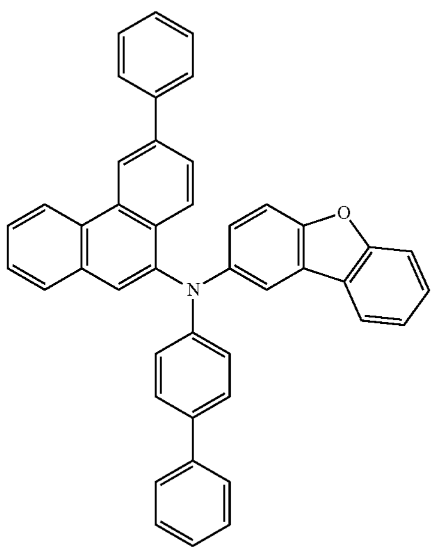
H1-10
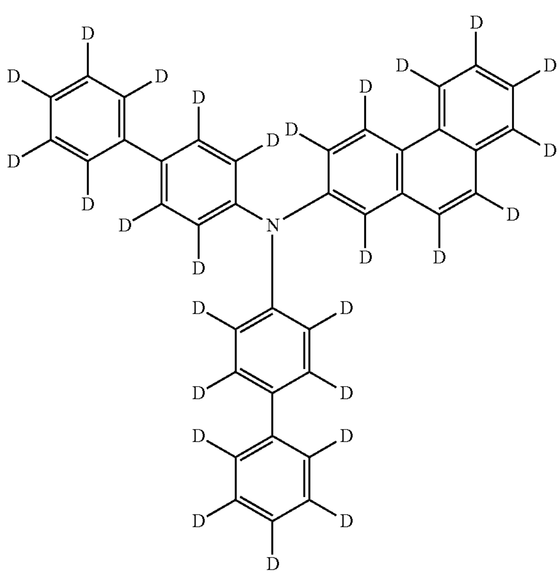
-continued
H1-11
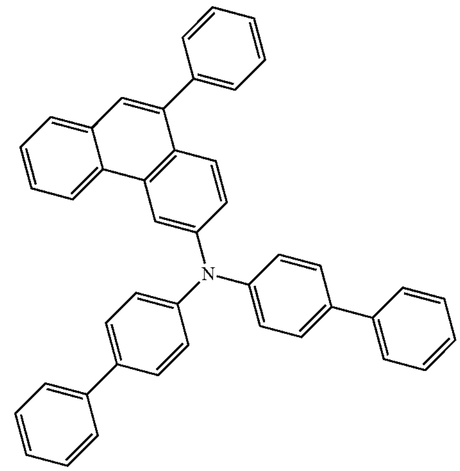
H1-12
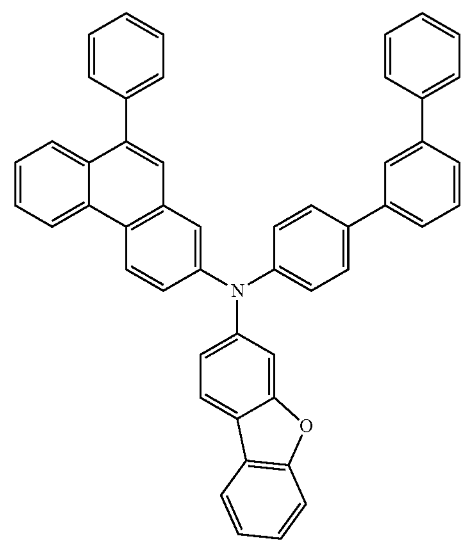
H1-13
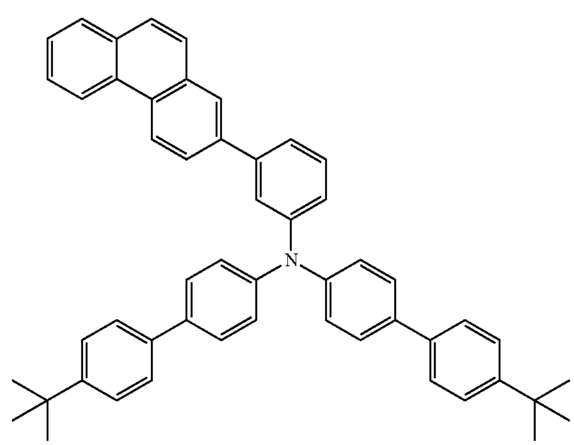

H1-14
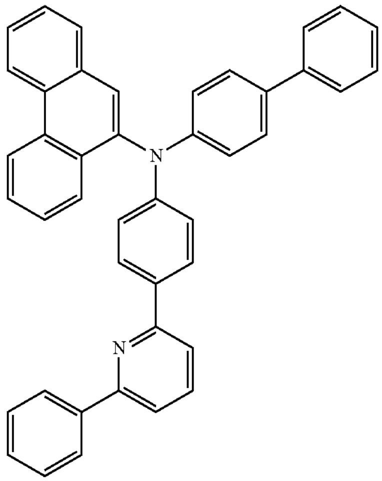
H1-15
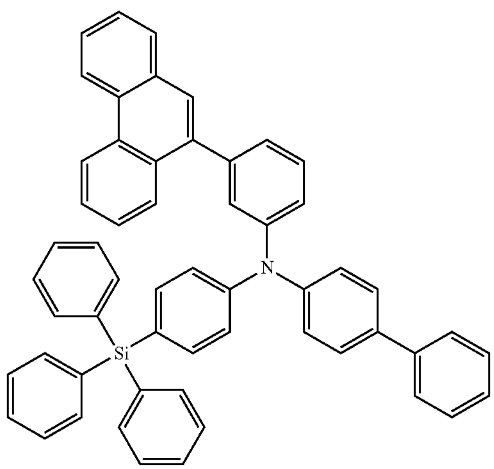
H1-16
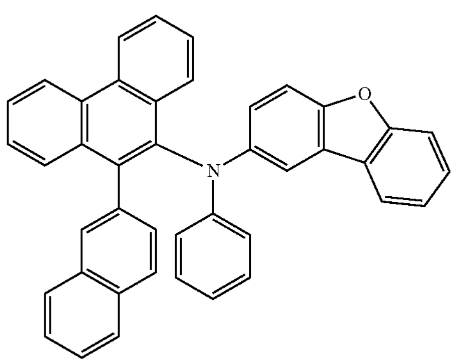
H1-17
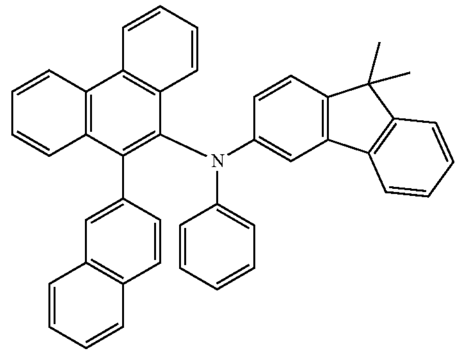
H1-18
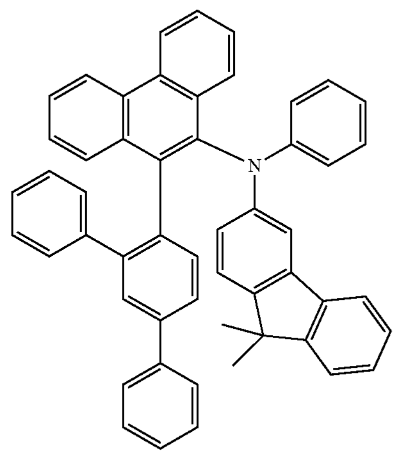
H1-19
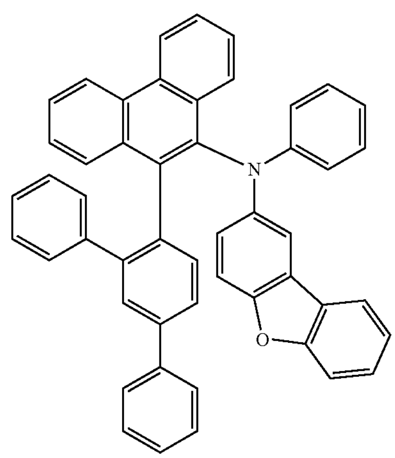

-continued
H1-20
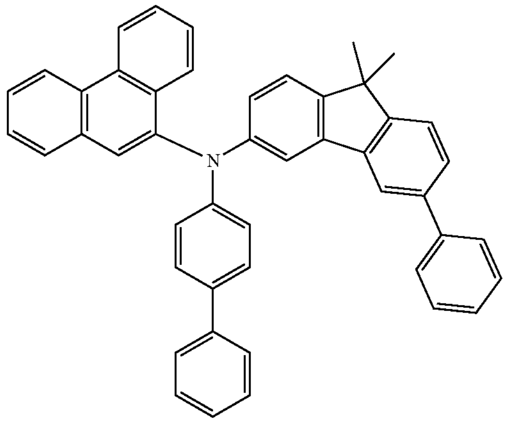
H1-21
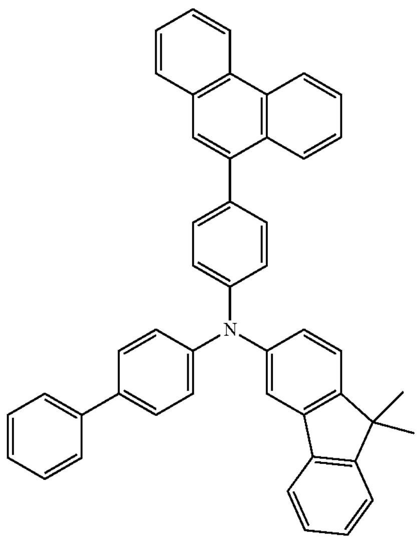
H1-22
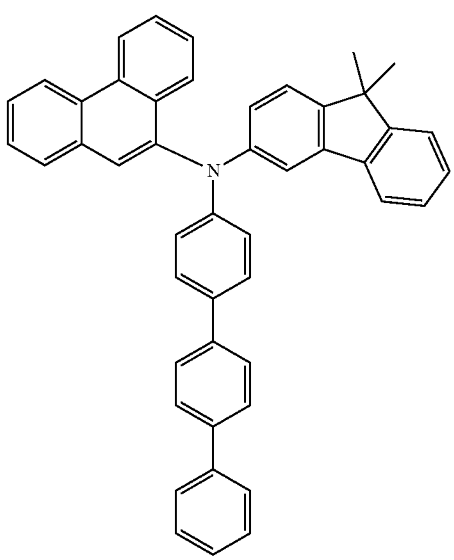
-continued
H1-23
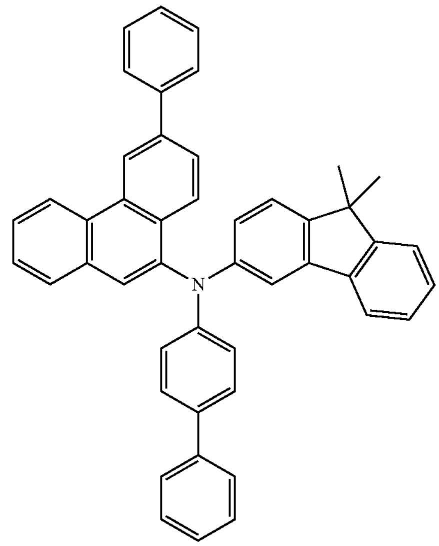
H1-24
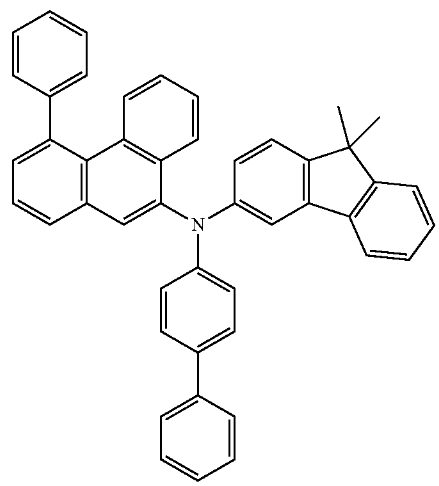
H1-25
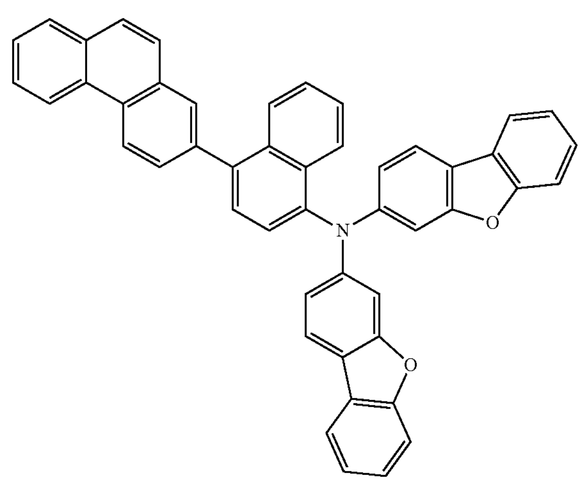

H1-26
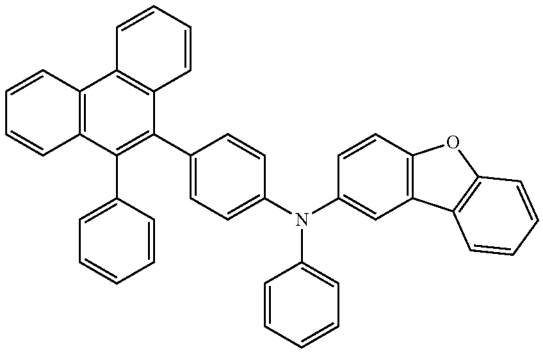
H1-27
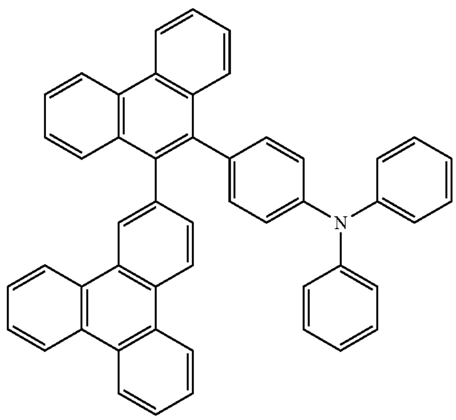
H1-28
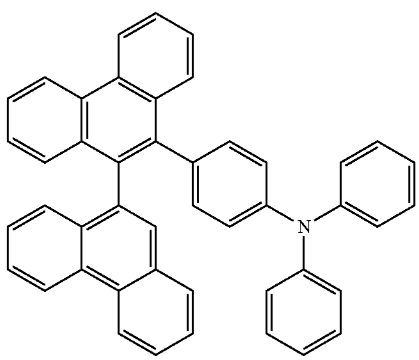
H1-29
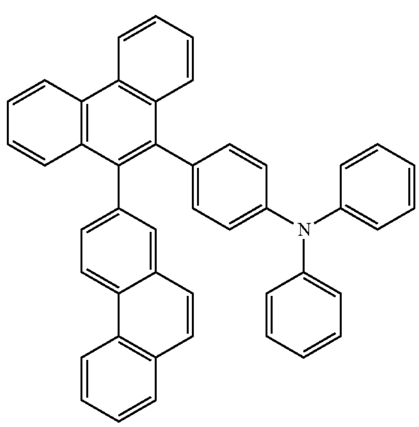
H1-30
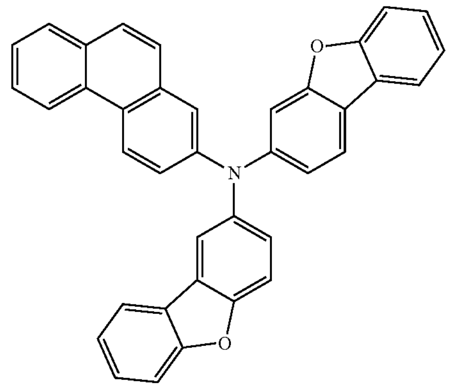
H1-31
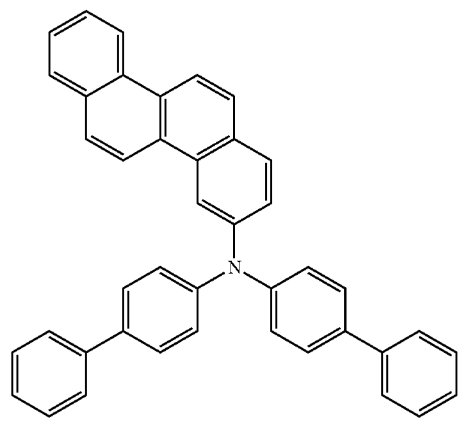
H1-32
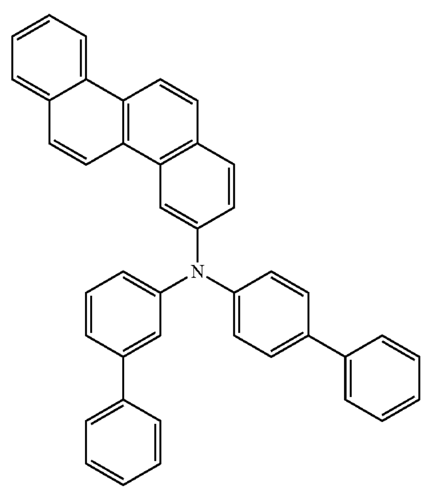

-continued
H1-33
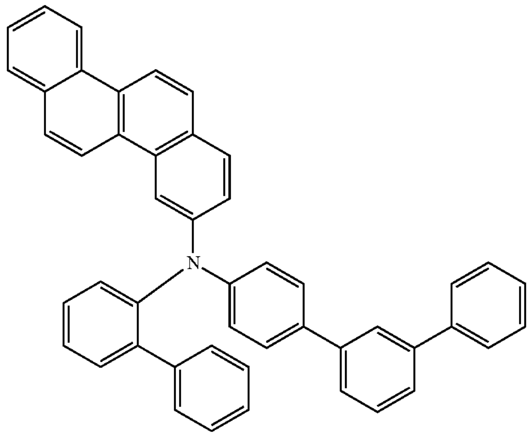
H1-34
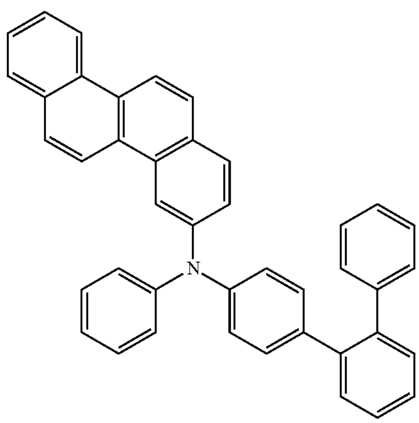
H1-35
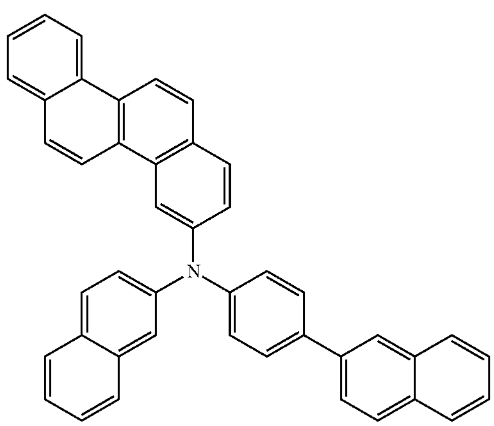
-continued
H1-36
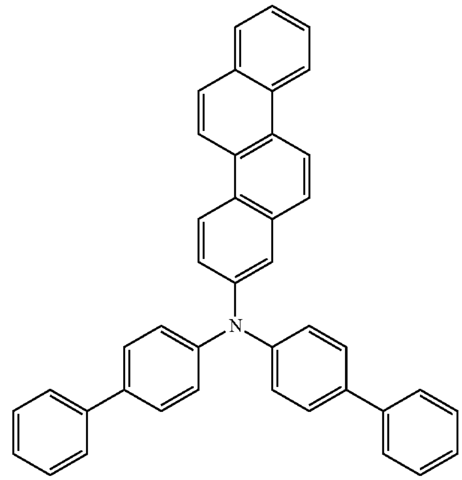
H1-37
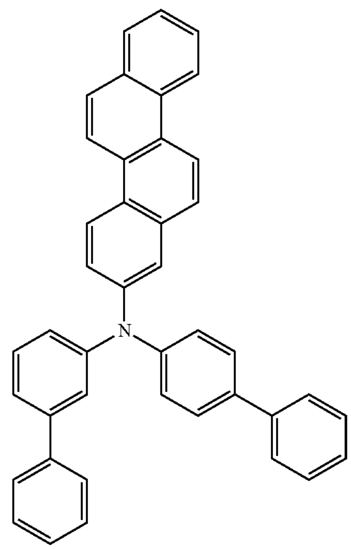
H1-38
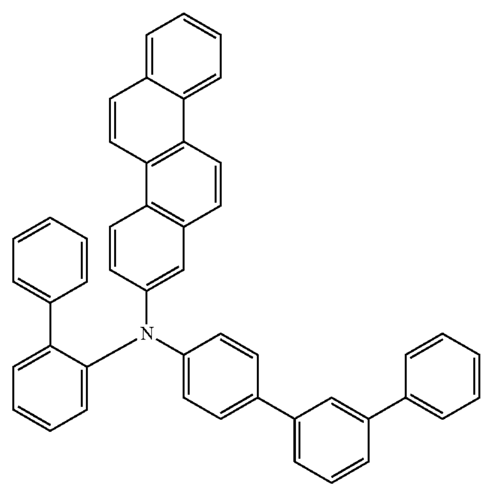

-continued
H1-39
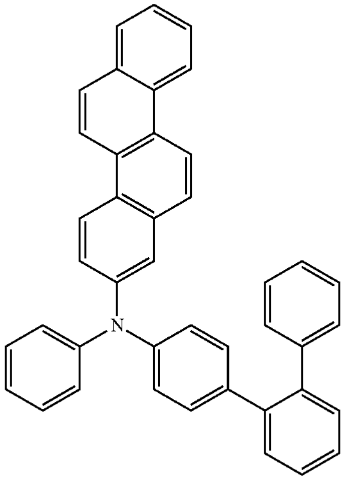
H1-40
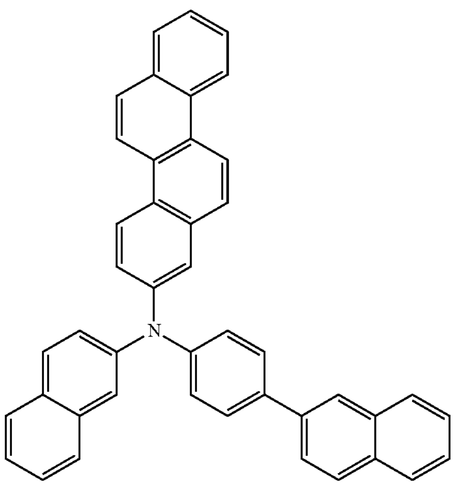
H1-41
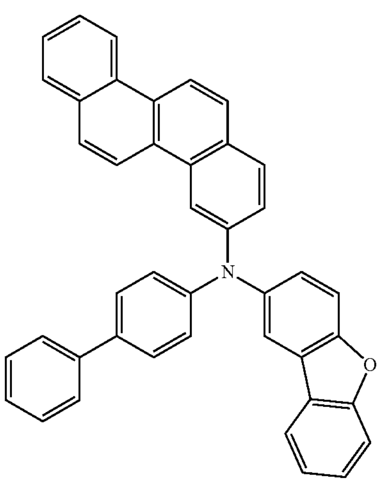
-continued
H1-42
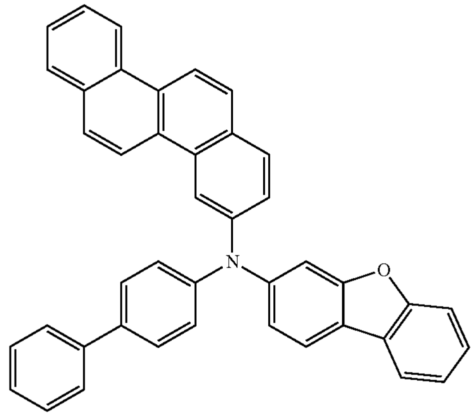
H1-43
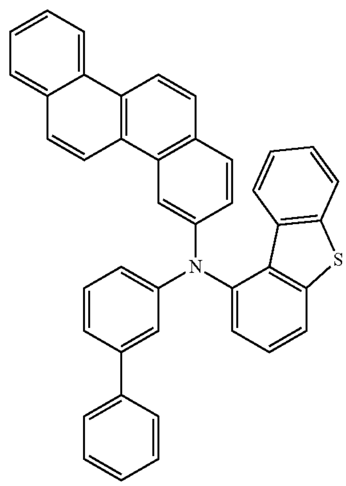
H1-44
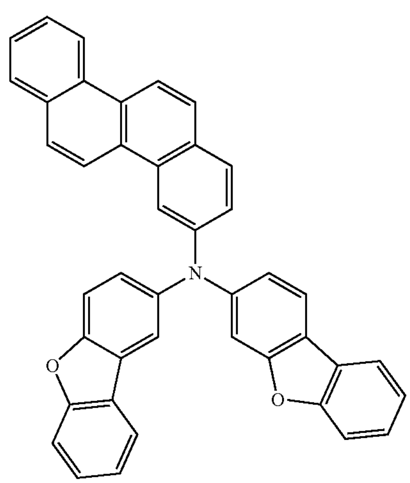

-continued
H1-45
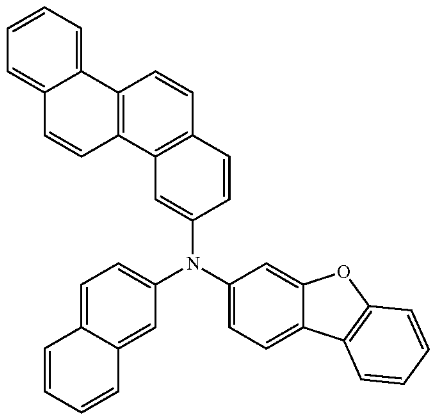
H1-46
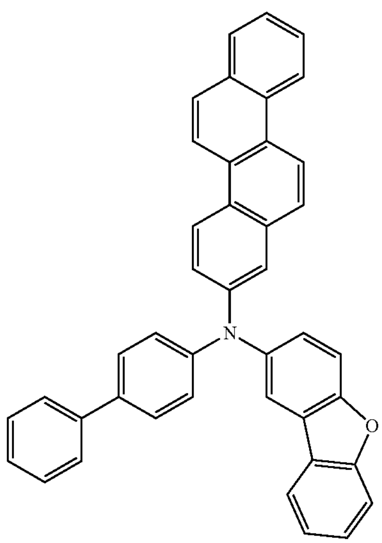
H1-47
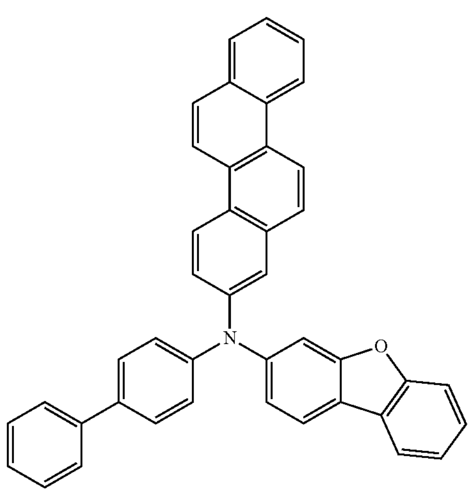
-continued
H1-48
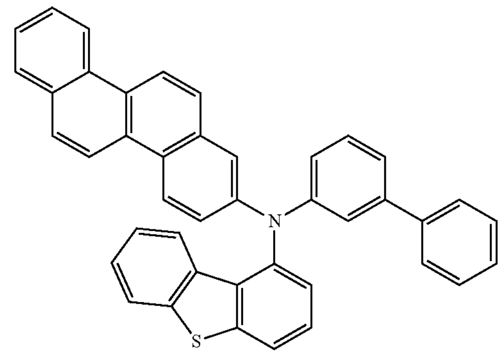
H1-49
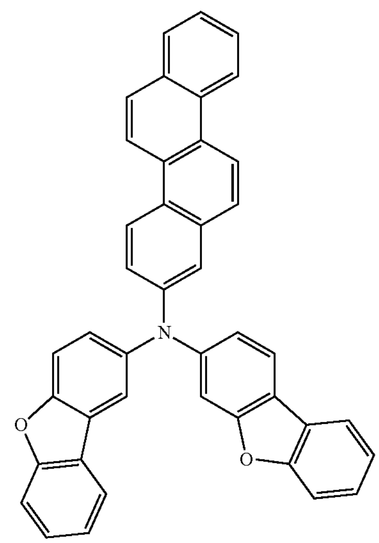
H1-50
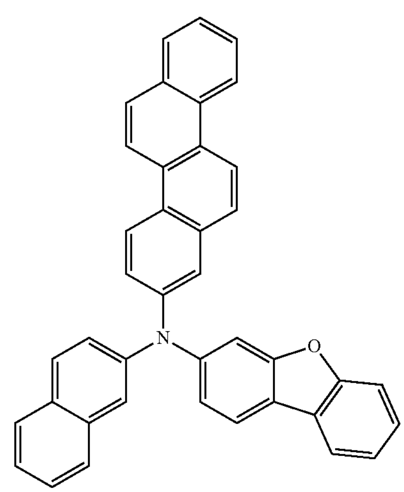

-continued
H1-51
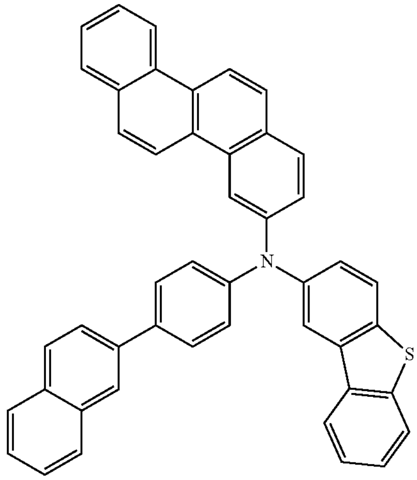
H1-52
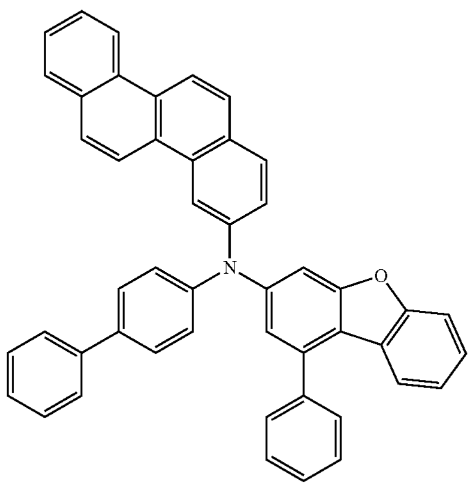
H1-53
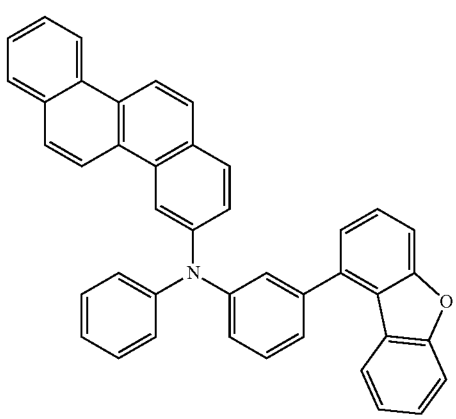
-continued
H1-54
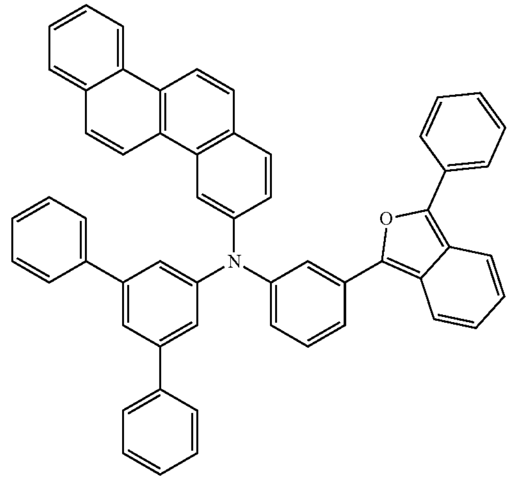
H1-55
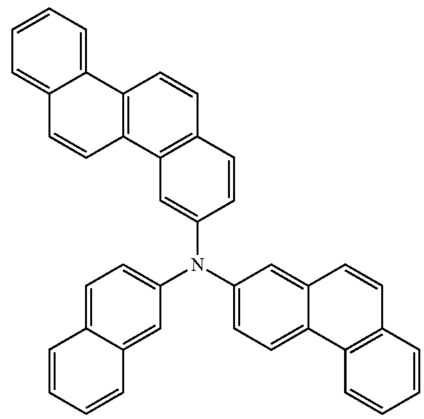
H1-56
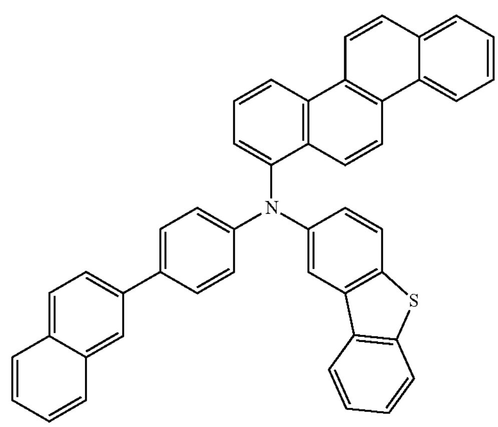

-continued
H1-57
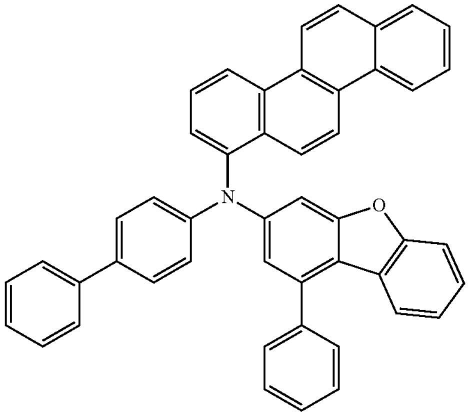
H1-58
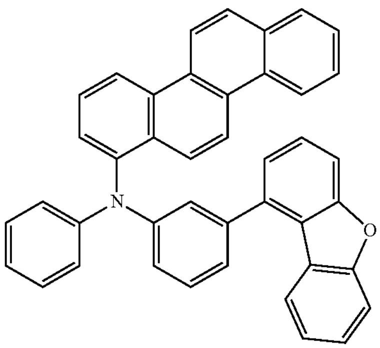
H1-59
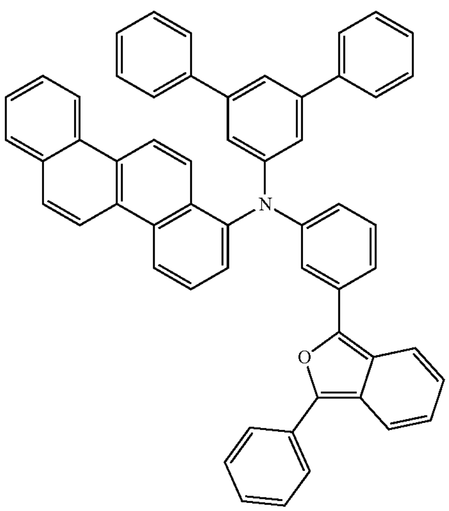
H1-60
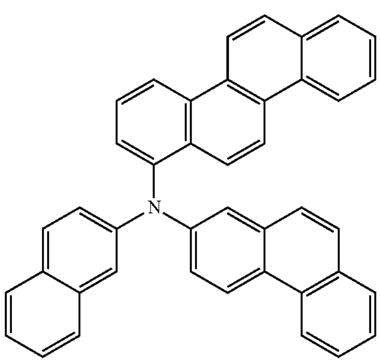
-continued
H1-61
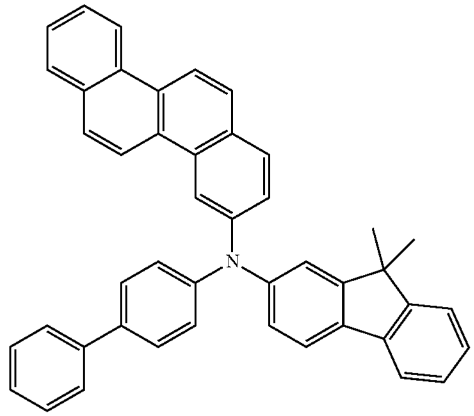
H1-62
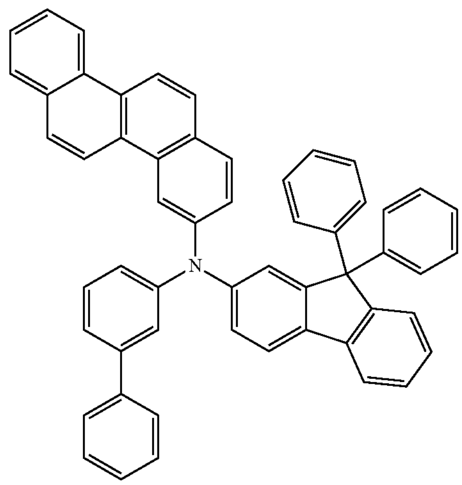
H1-63
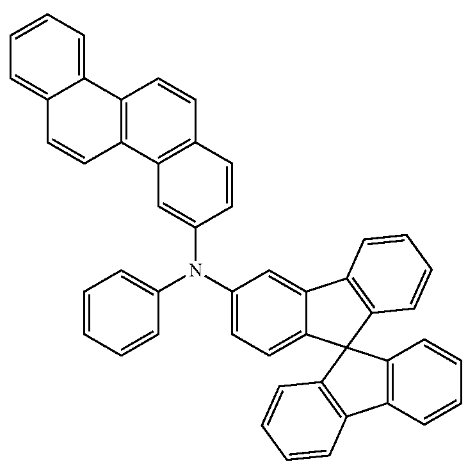

-continued
H1-64
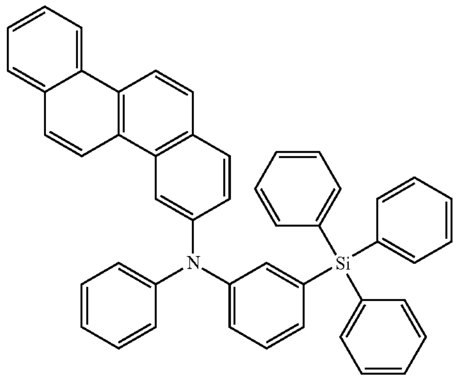
H1-65
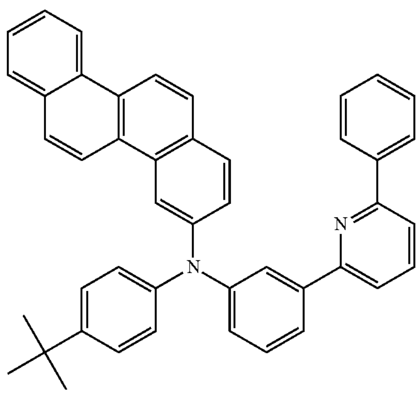
H1-66
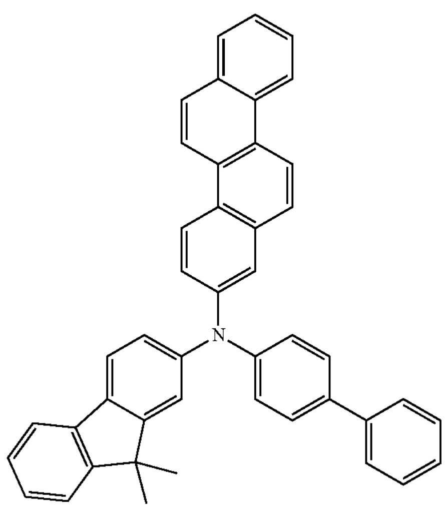
-continued
H1-67
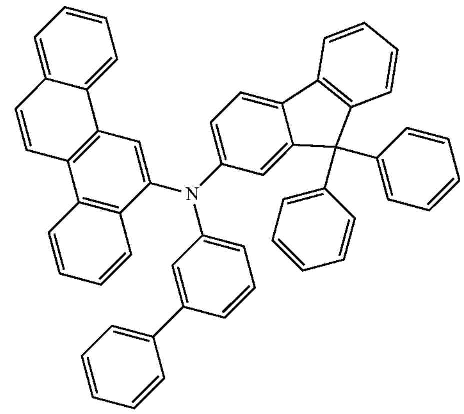
H1-68
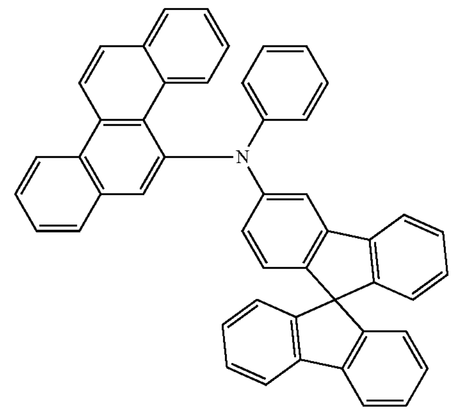
H1-69
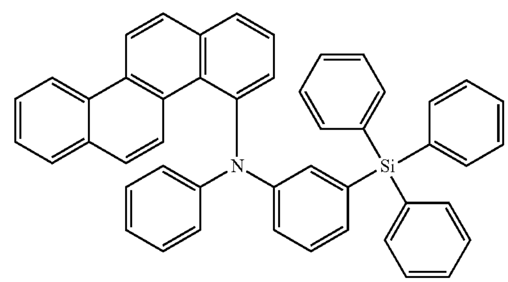
H1-70
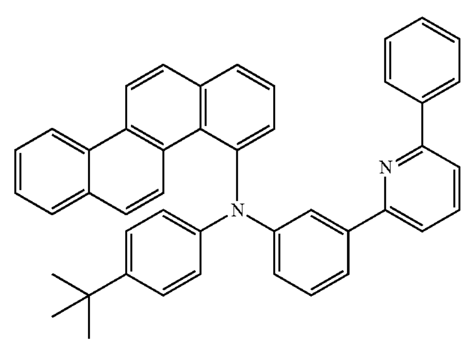

-continued
H1-71
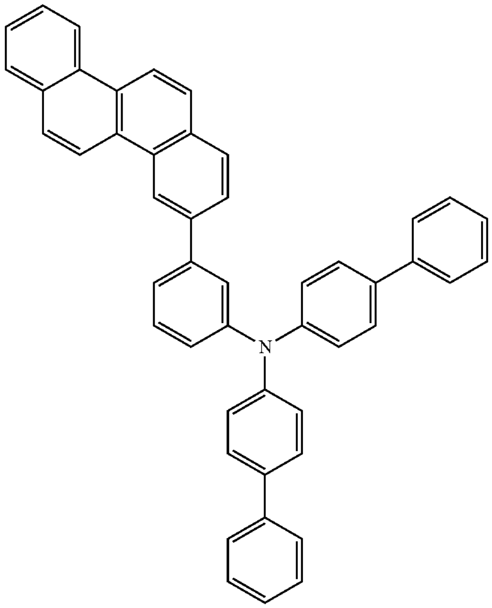
H1-72
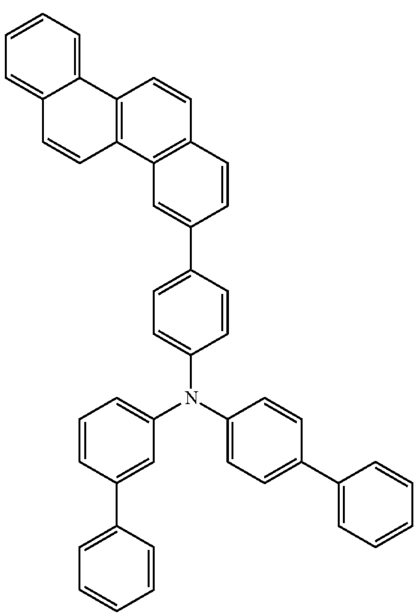
-continued
H1-73
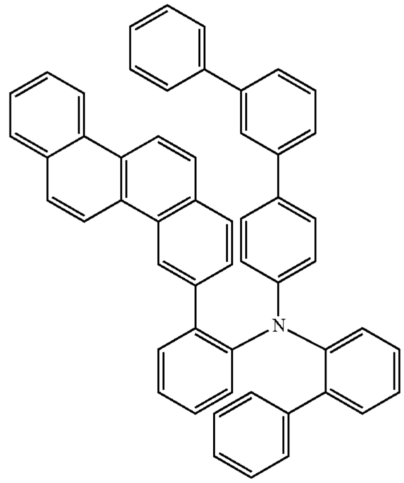
H1-74
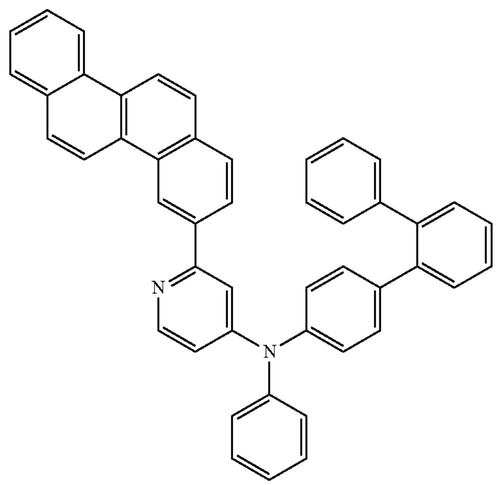
H1-75
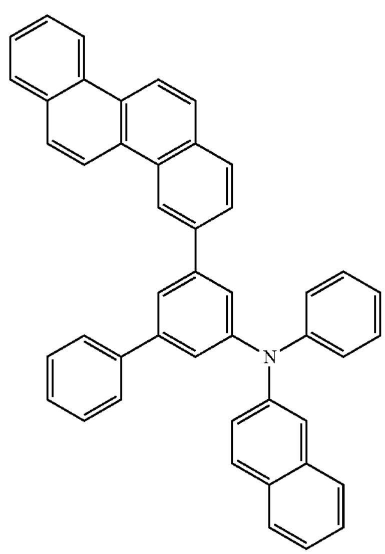

-continued
H1-76
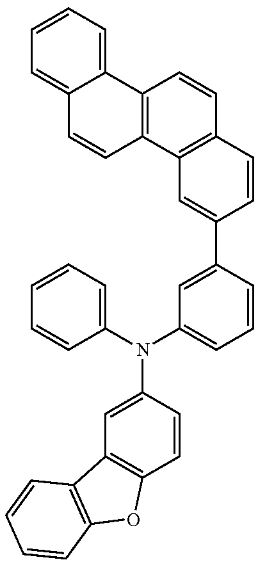
H1-77
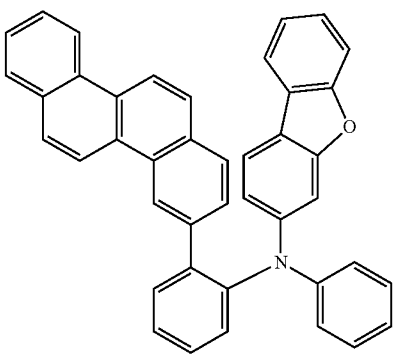
H1-78
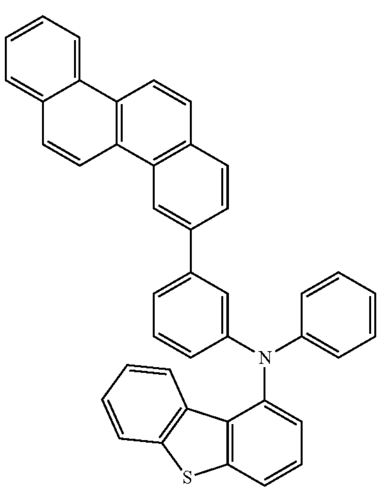
-continued
H1-79
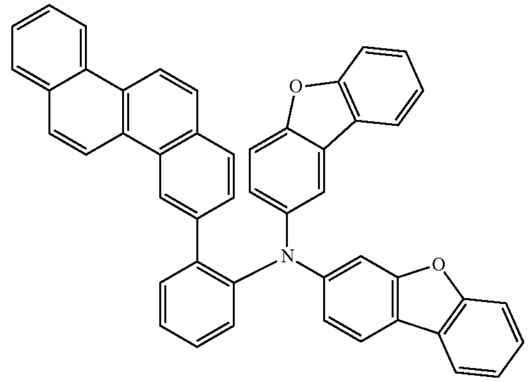
H1-80
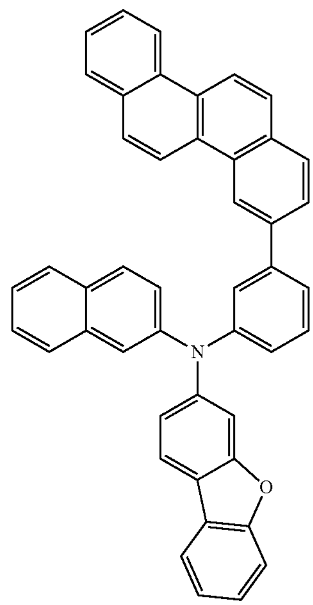
H1-81
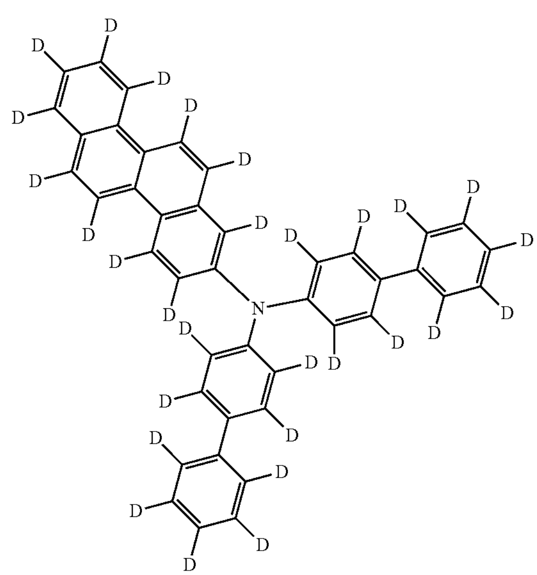

-continued
H1-82
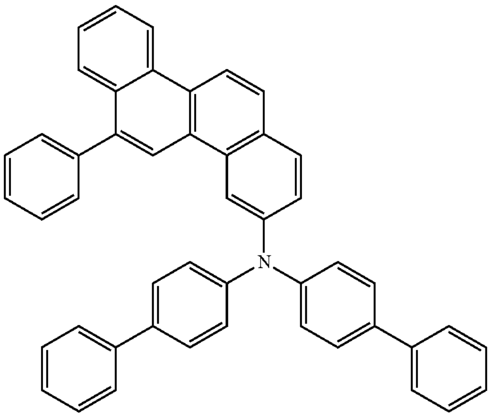
H1-83
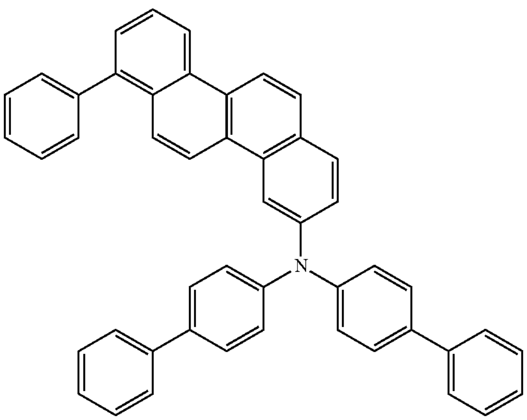
H1-84
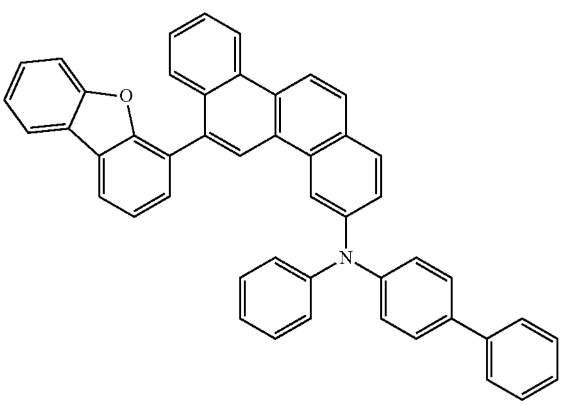
H1-85
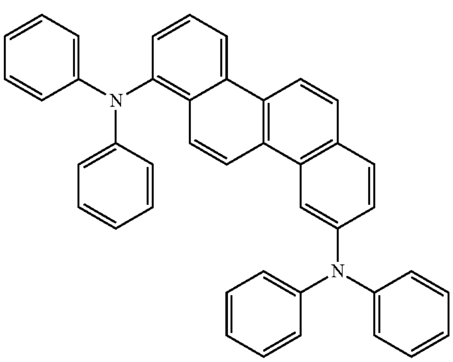
-continued
H1-86
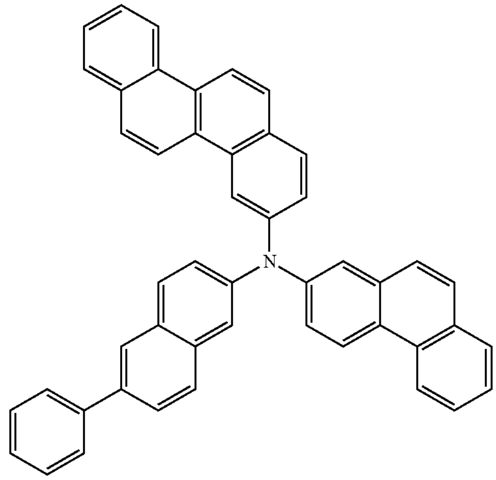
H1-87
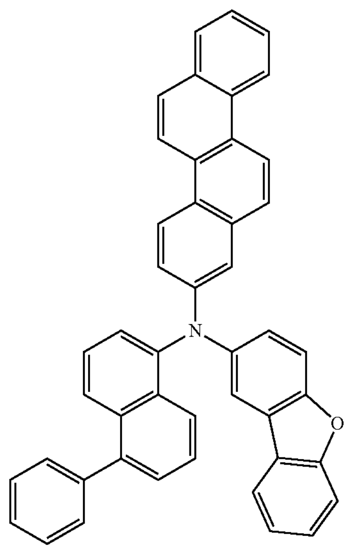
H1-88
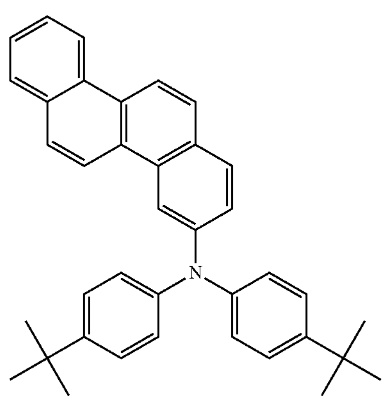

-continued
H1-89
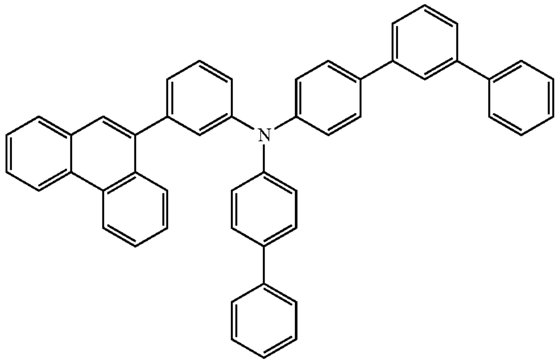
H1-90
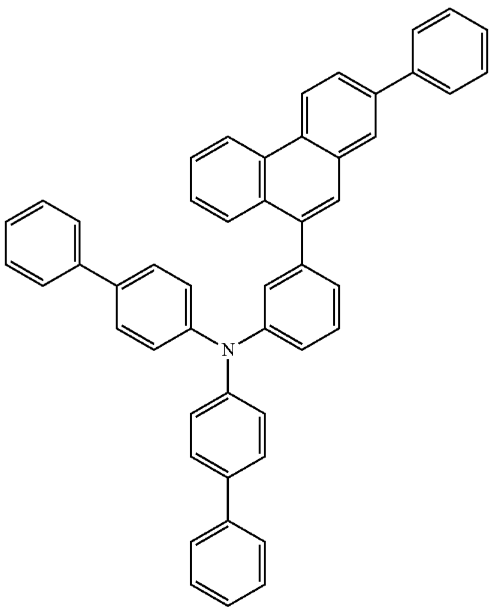
H1-91
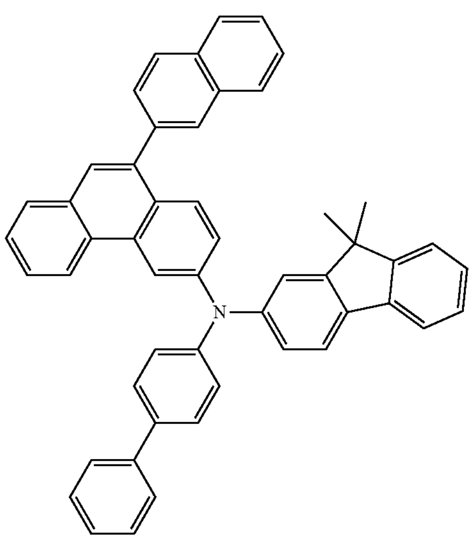
-continued
H1-92
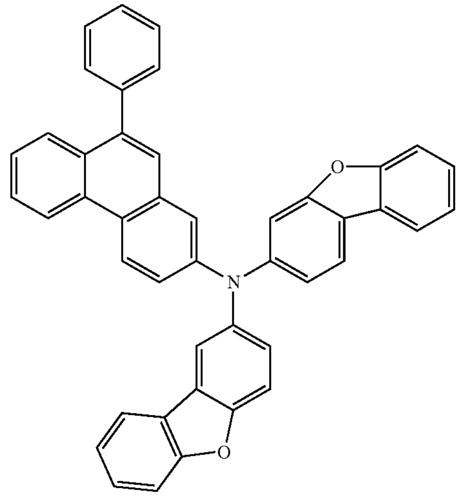
H1-93
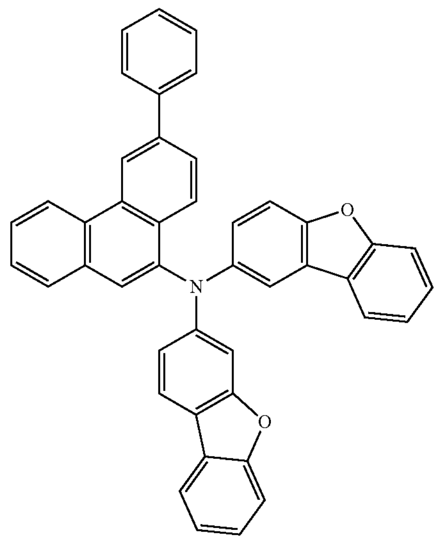
H1-94
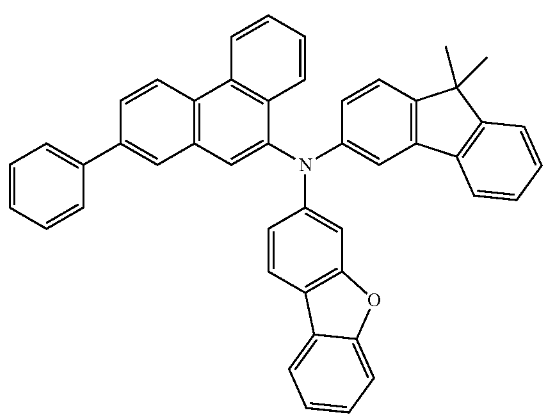

-continued
H1-95
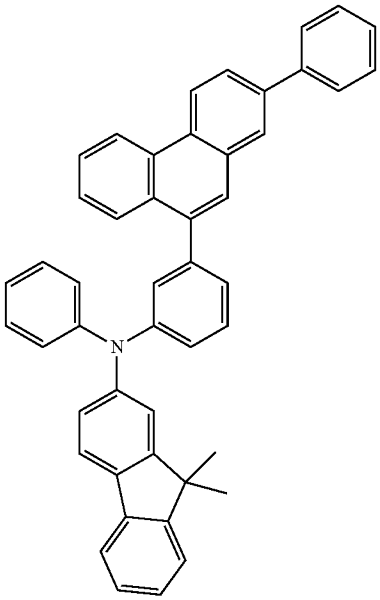
H1-96
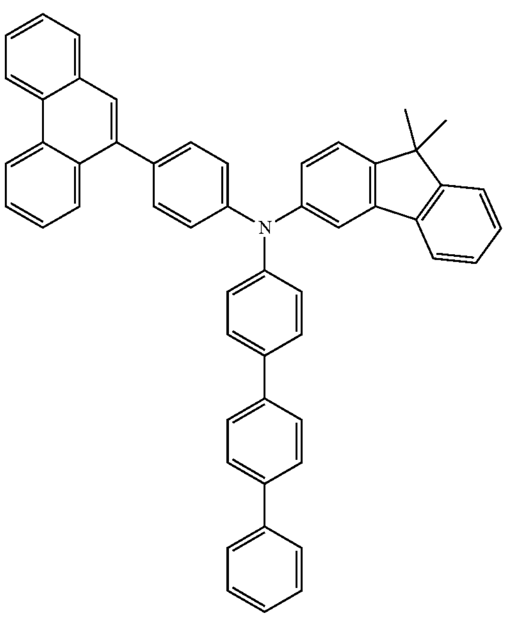
-continued
H1-97
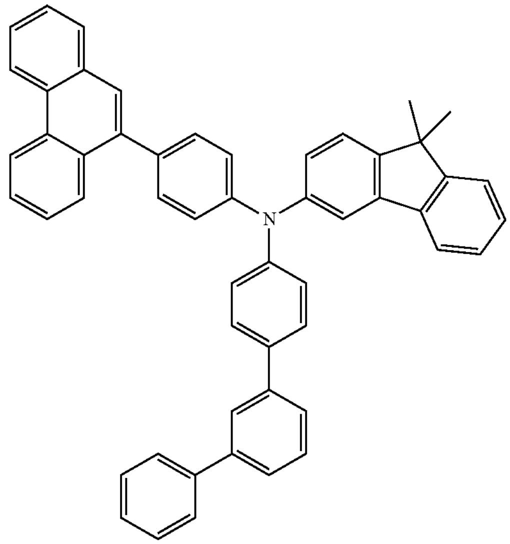
H1-98
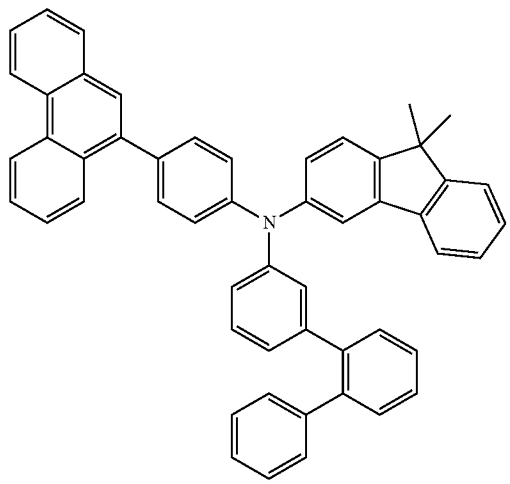
H1-99
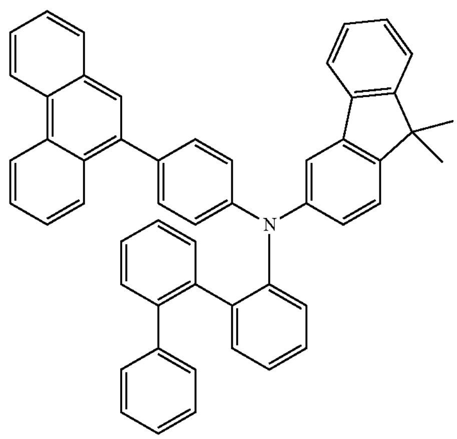

-continued
H1-100
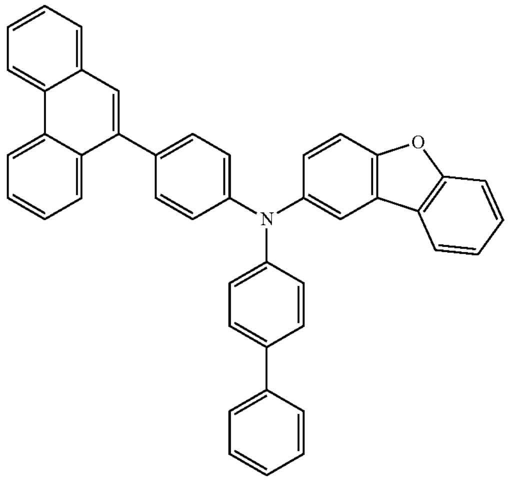
H1-101
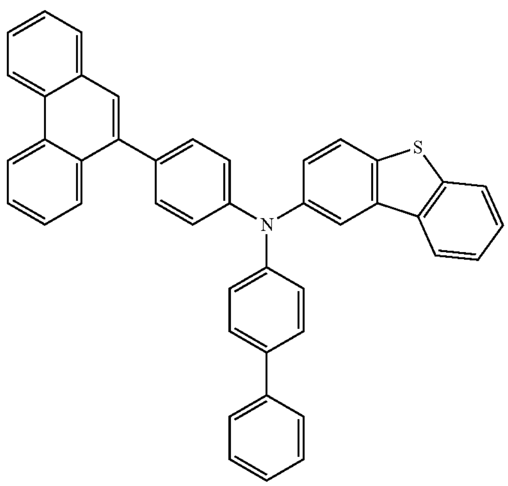
H1-102
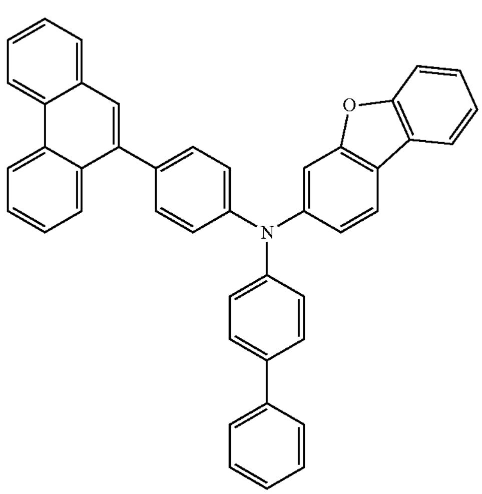
-continued
H1-103
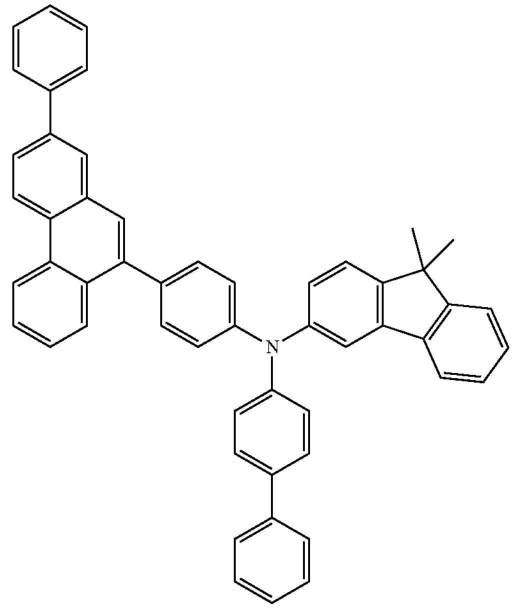
H1-104
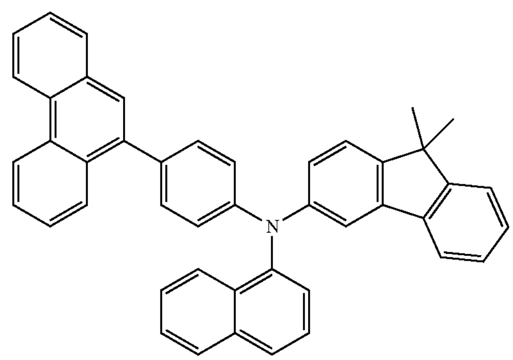
H1-105
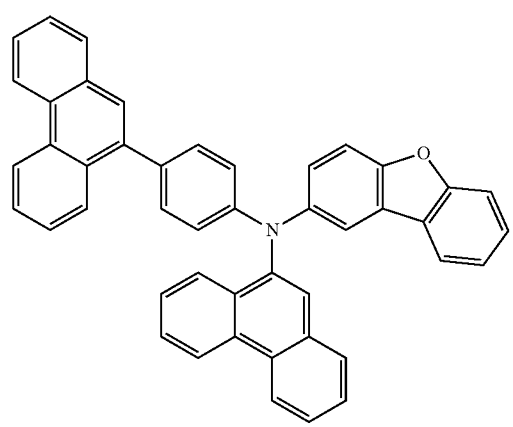

-continued
H1-106
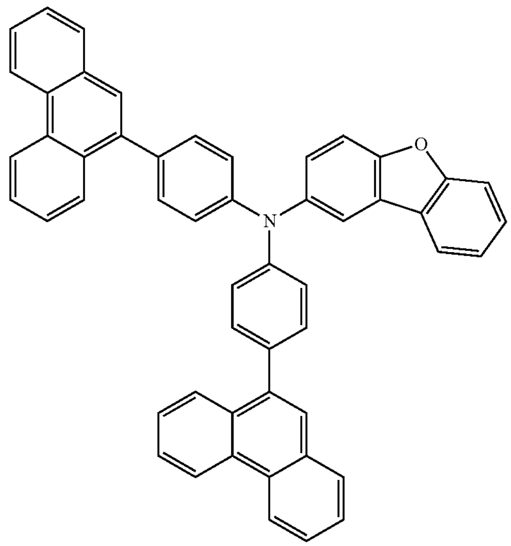
H1-107
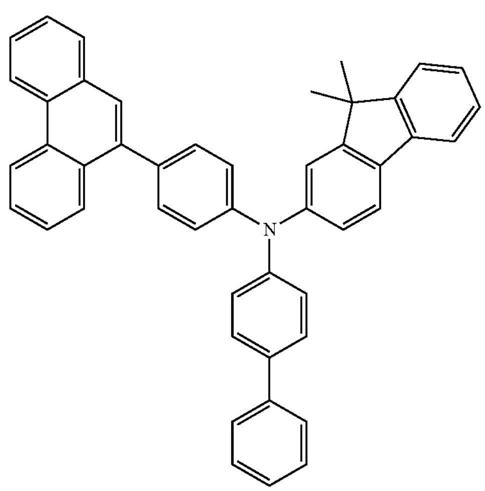
-continued
H1-108
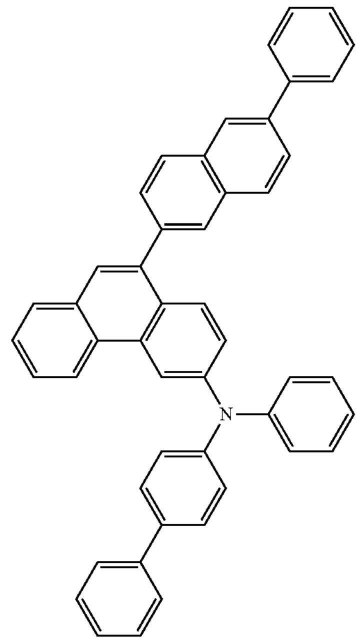
H1-109
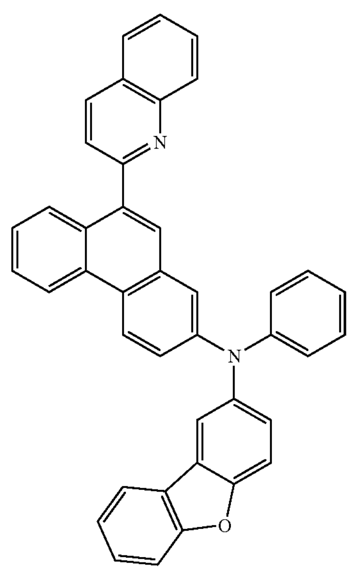

-continued
H1-110
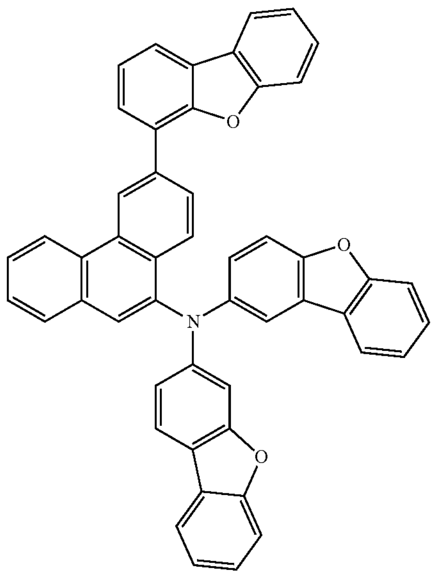
H1-111
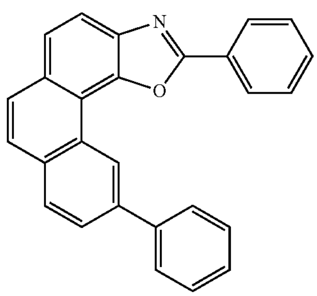
H1-112
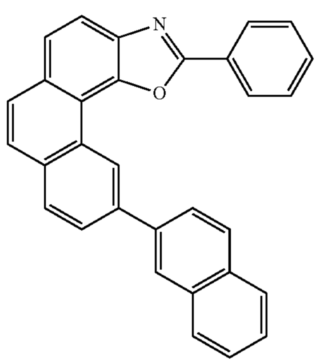
H1-113
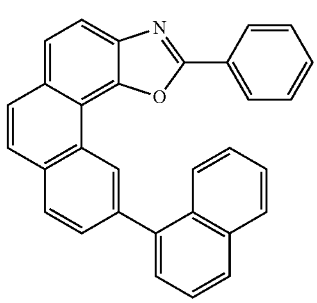
-continued
H1-114
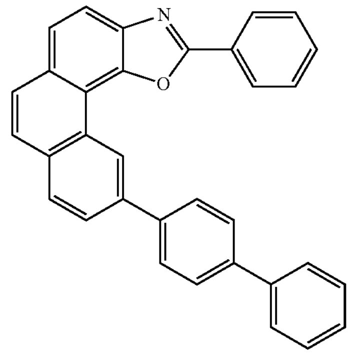
H1-115
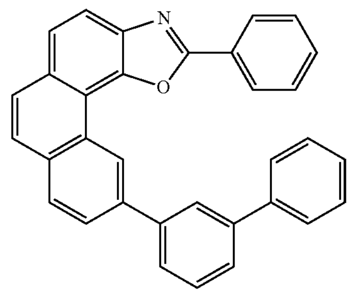
H1-116
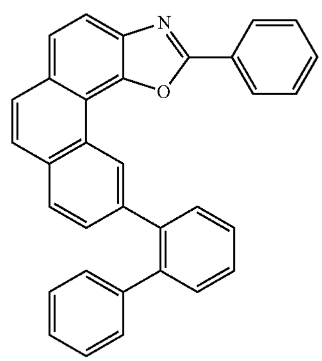
H1-117
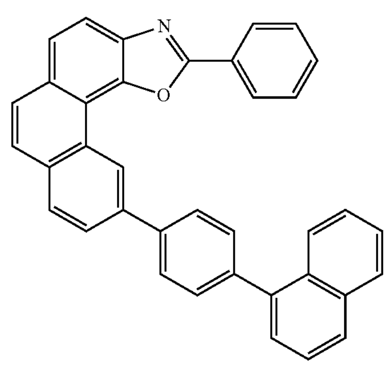

-continued
H1-118
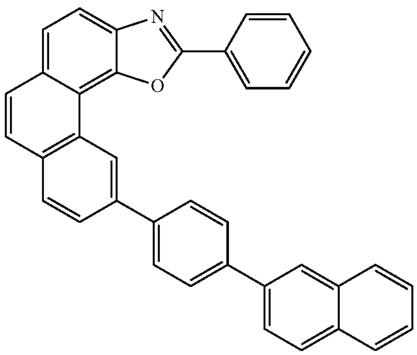
H1-119
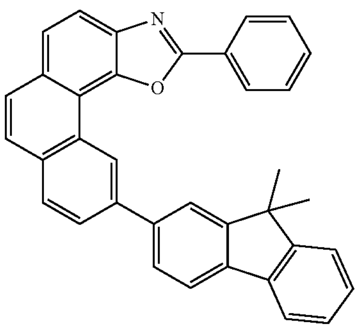
H1-120
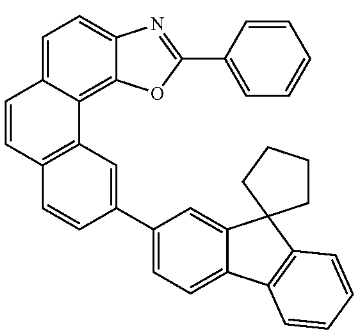
H1-121
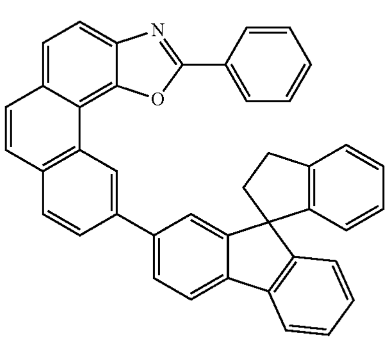
-continued
H1-122
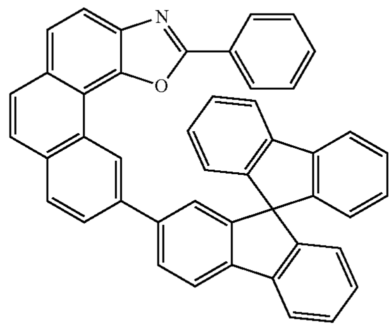
H1-123
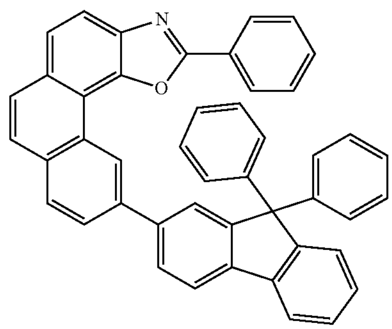
H1-124
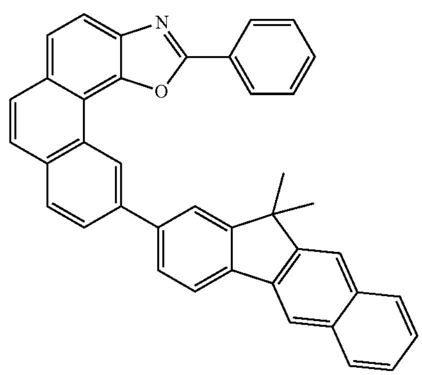
H1-125
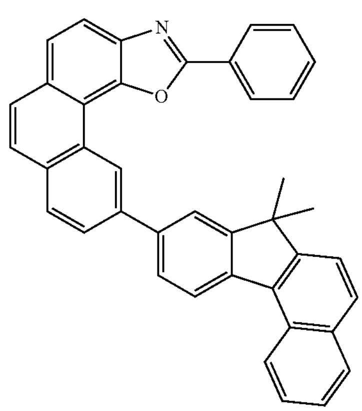

-continued
H1-126
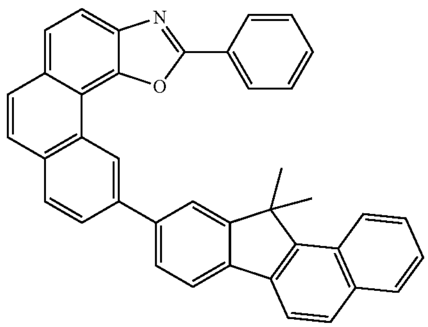
H1-127
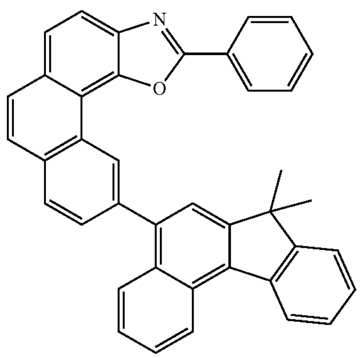
H1-128
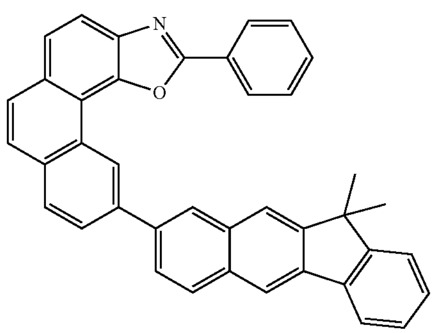
H1-129
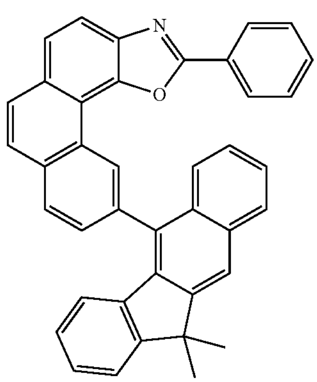
-continued
H1-130
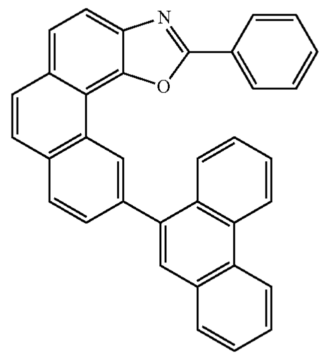
H1-131
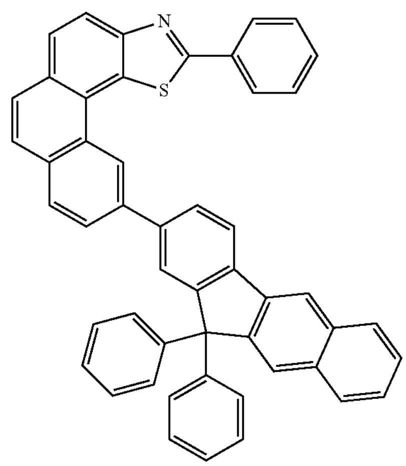
H1-132
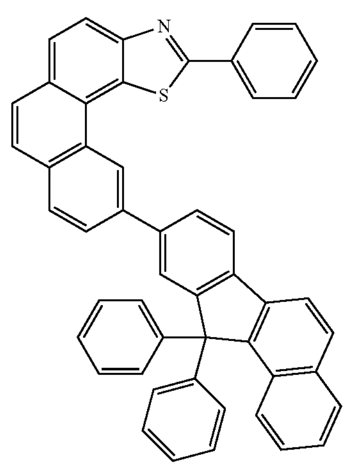

H1-133
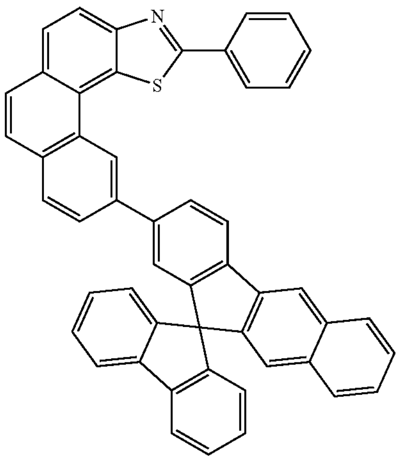
H1-134
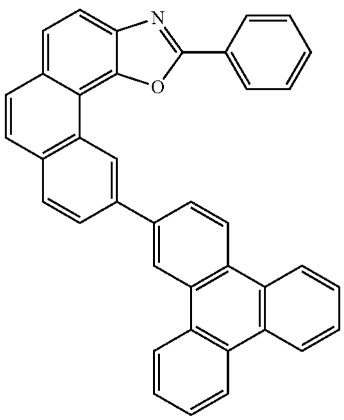
H1-135
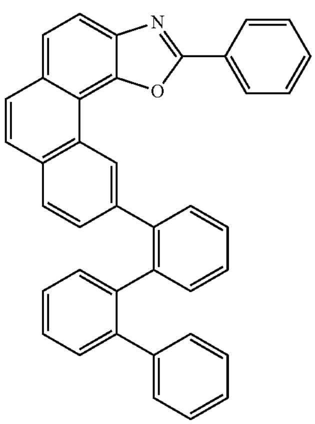
H1-136
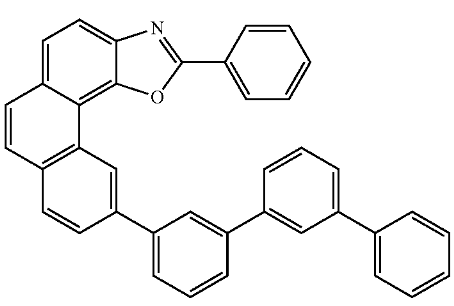
H1-137
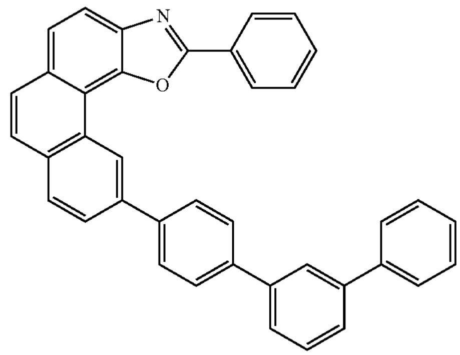
H1-138
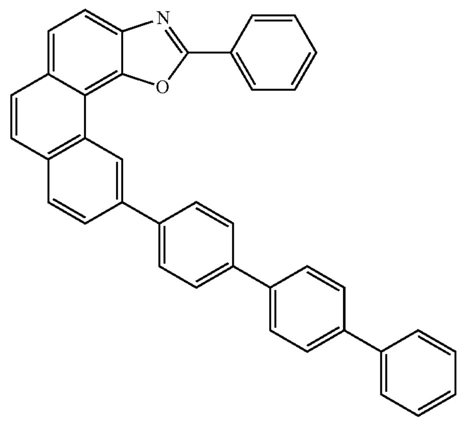
H1-139
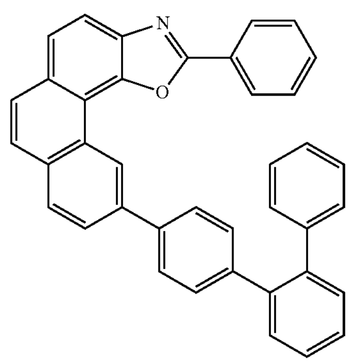
H1-140
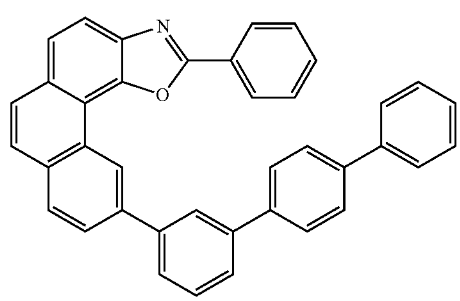

-continued
H1-141
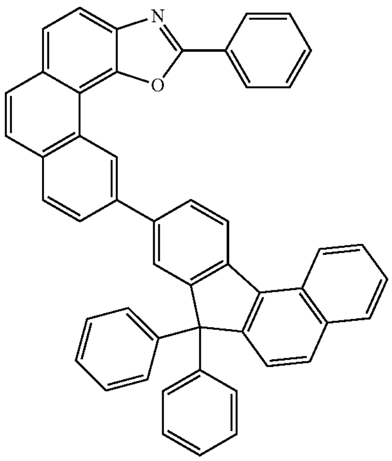
H1-142
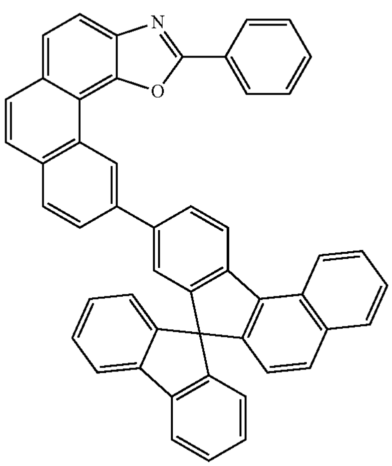
H1-143
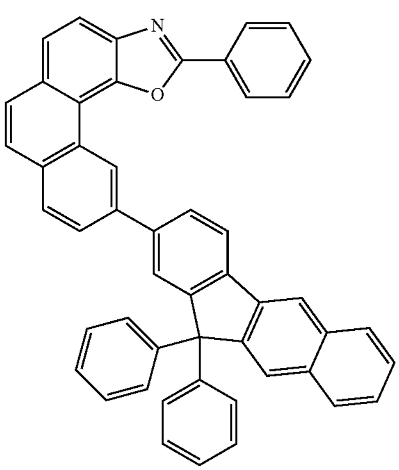
-continued
H1-144
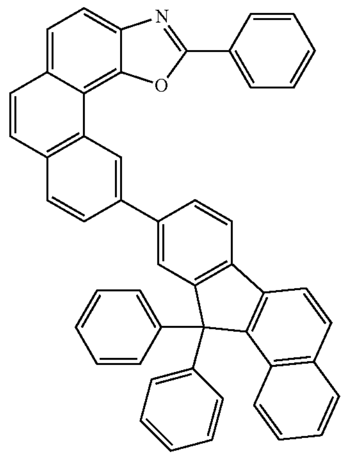
H1-145
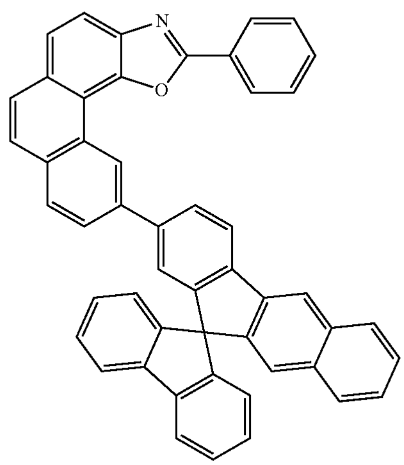
H1-146
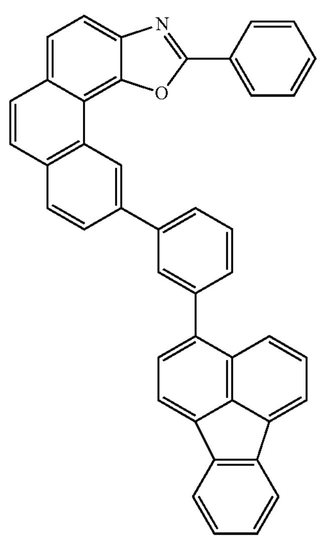

-continued
H1-147
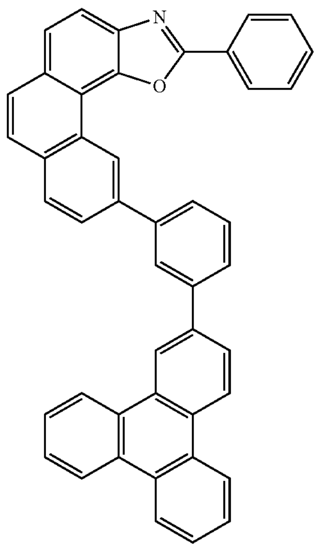
H1-148
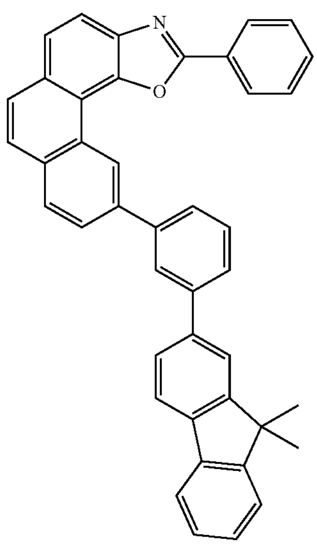
H1-149
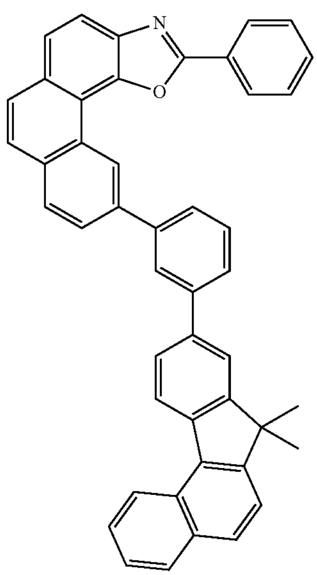
-continued
H1-150
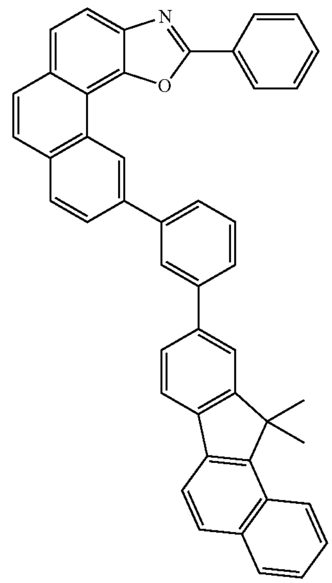
H1-151
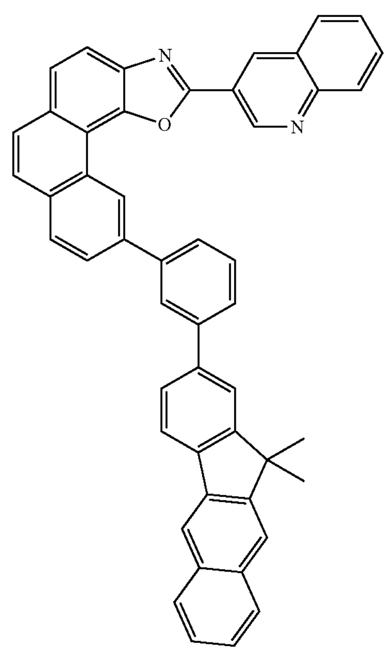

H1-152
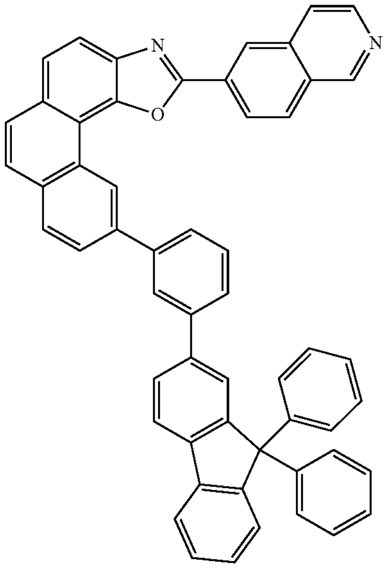
H1-153
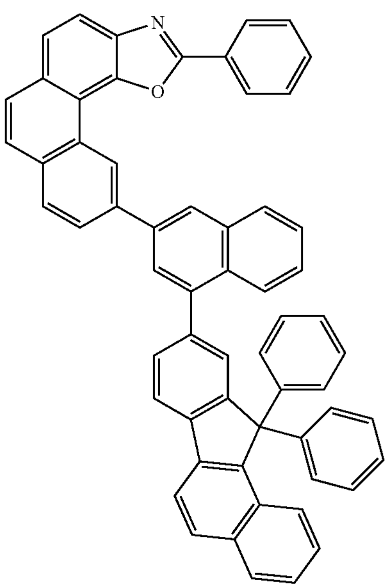
H1-154
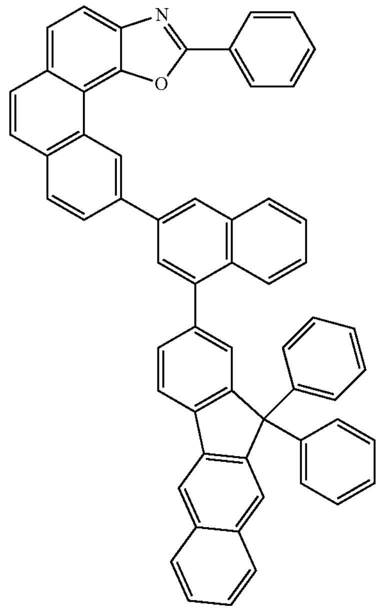
H1-155
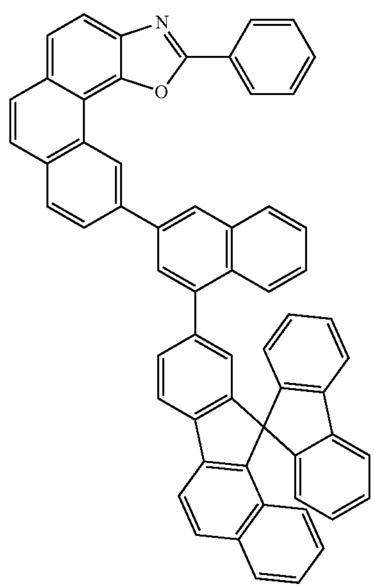

H1-156
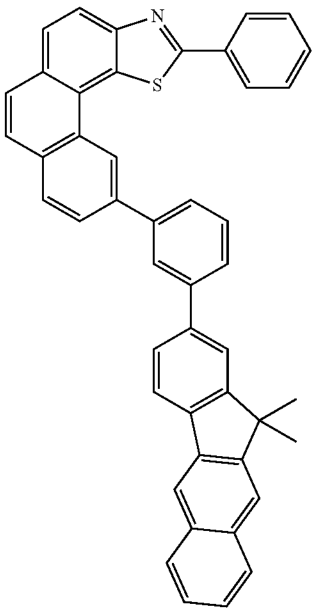
H1-157
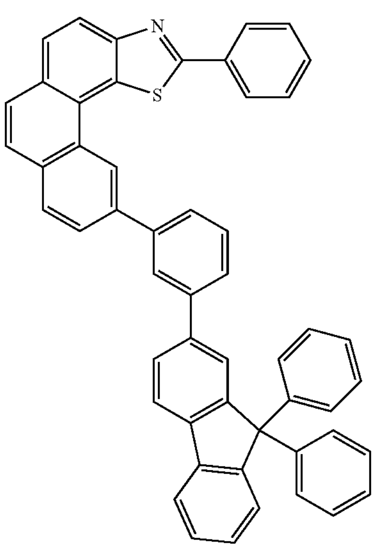
H1-158
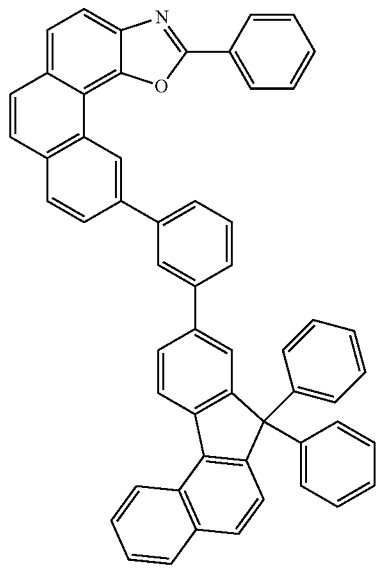
H1-159
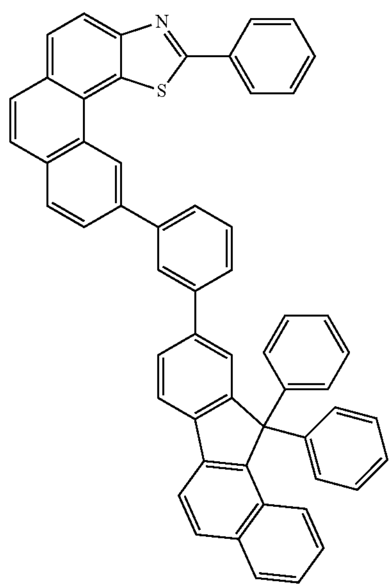
H1-160
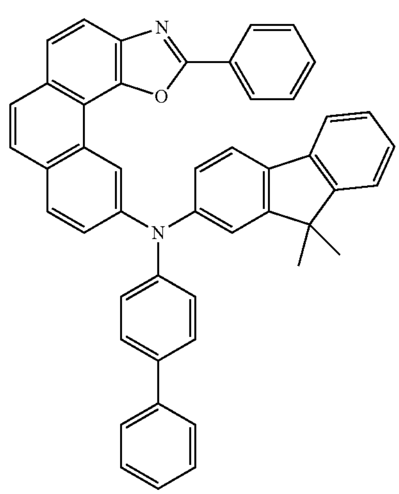

-continued
H1-161
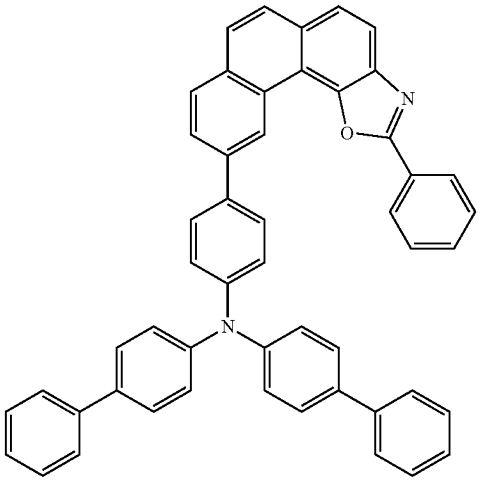
H1-162
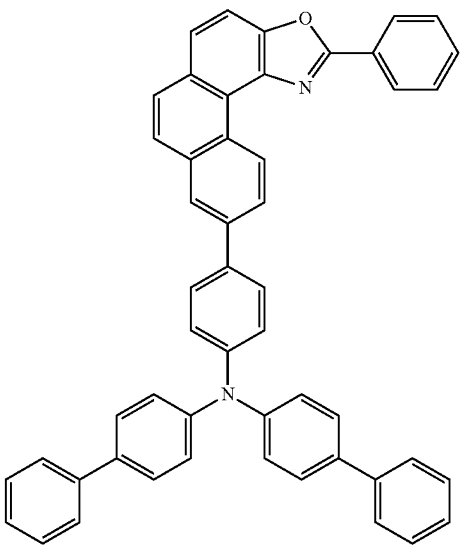
H1-163
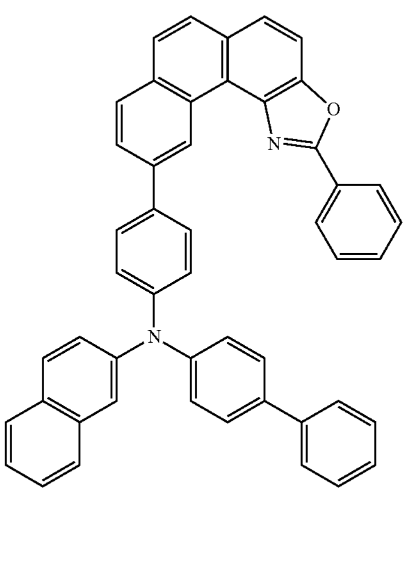
-continued
H1-164
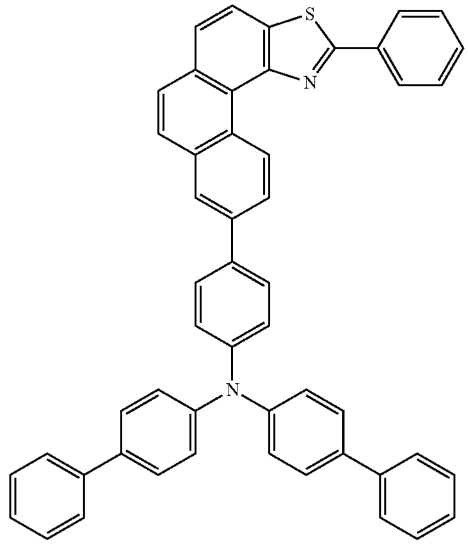
H1-165
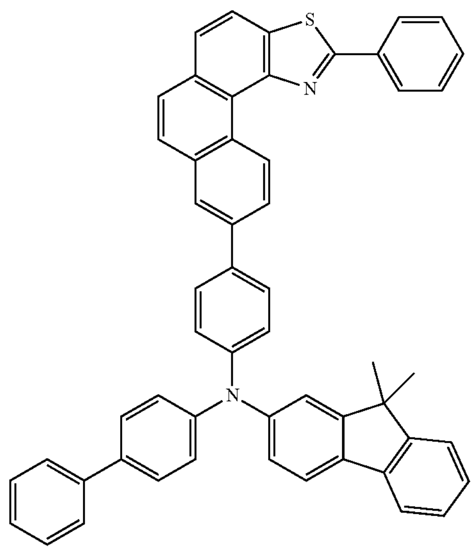
H1-166
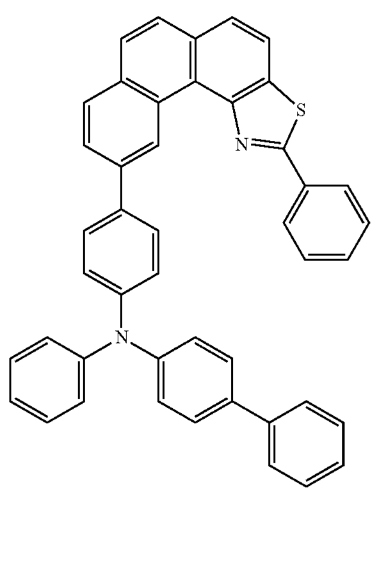

-continued
H1-167
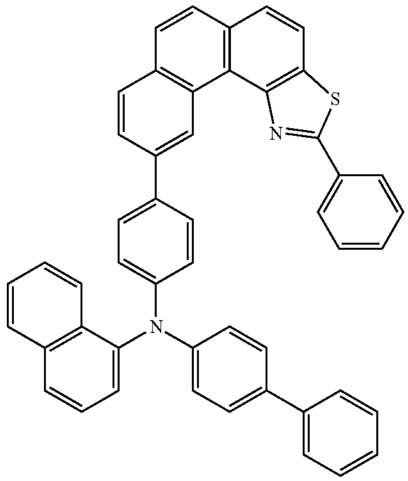
H1-168
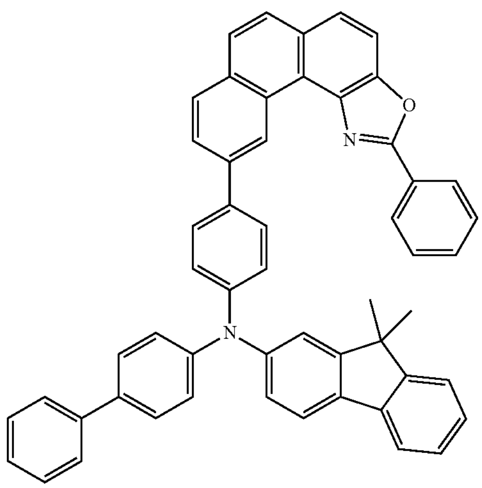
H1-169
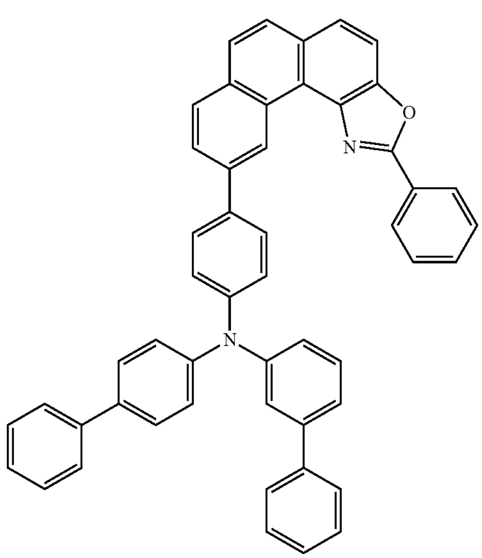
-continued
H1-170
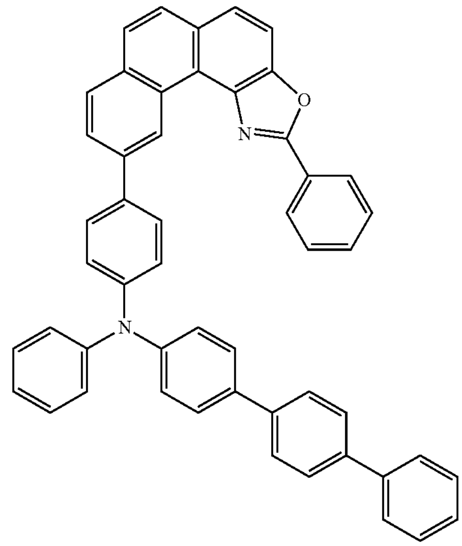
H1-171
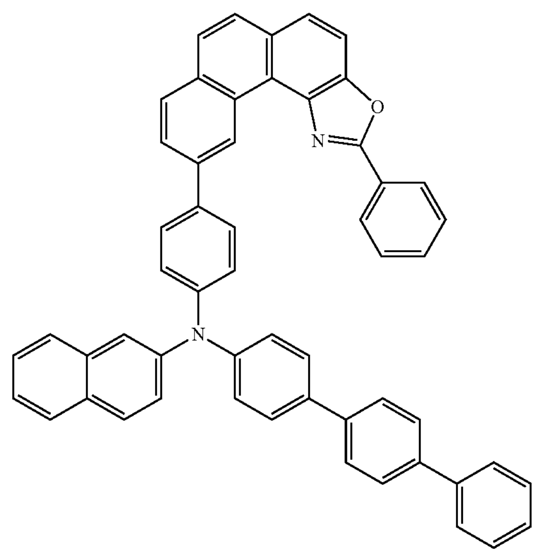
H1-172
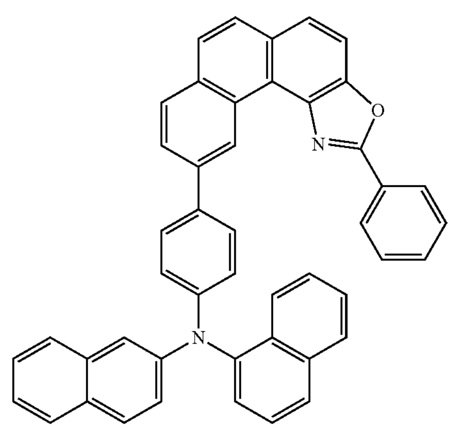

-continued
H1-173
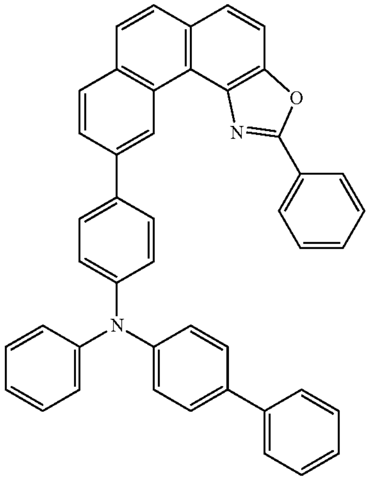
H1-174
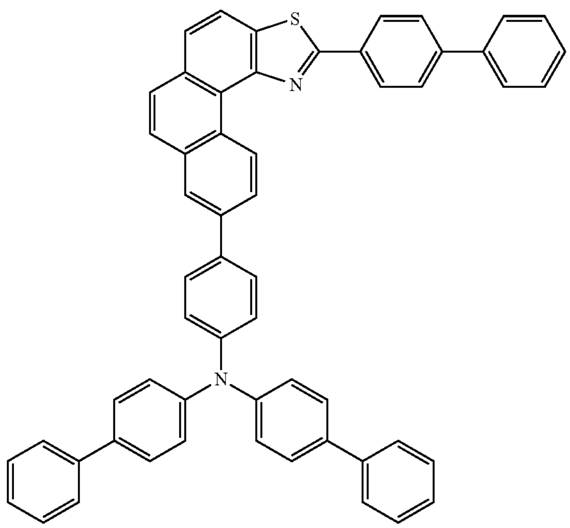
H1-175
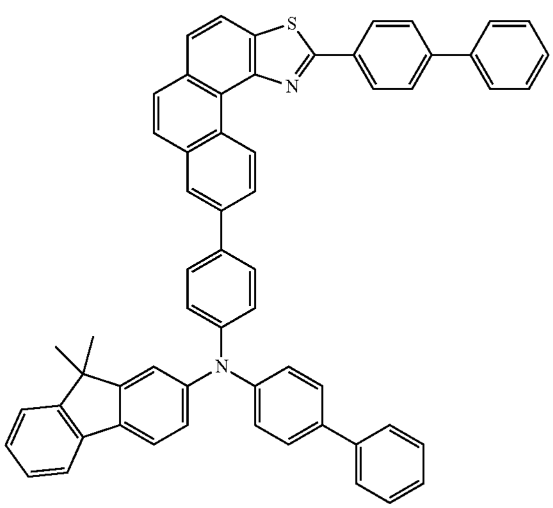
-continued
H1-176
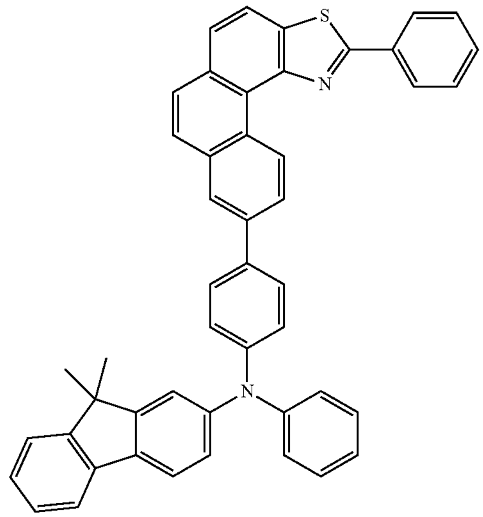
H1-177
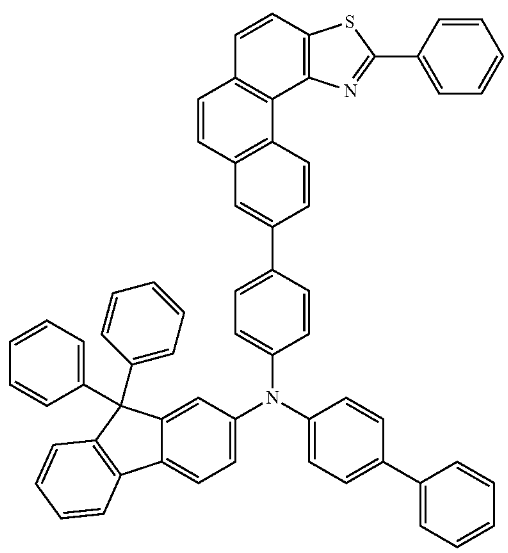
H1-178
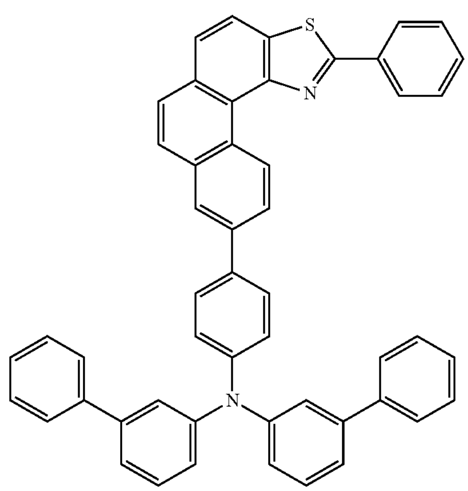

-continued
H1-179
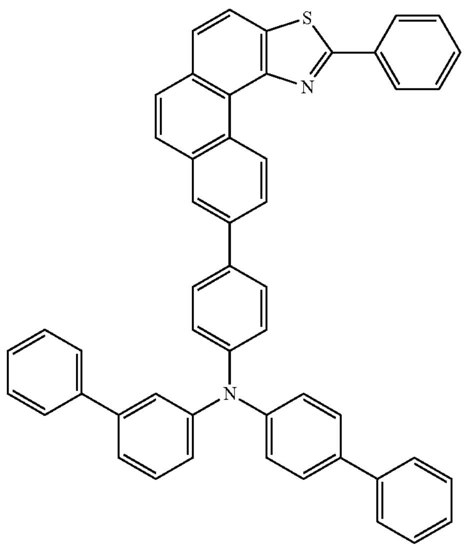
H1-180
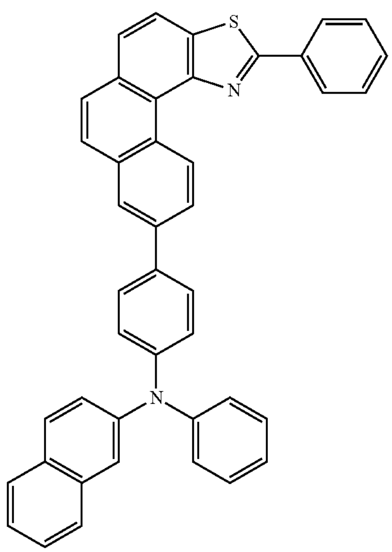
H1-181
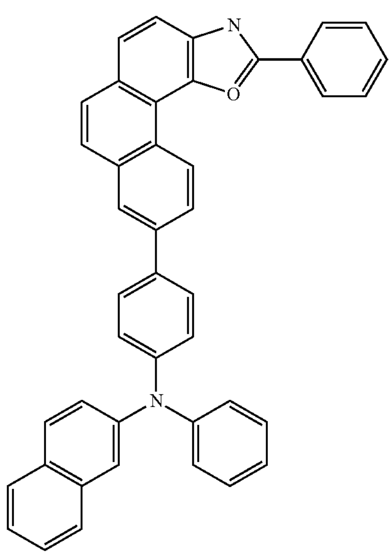
-continued
H1-182
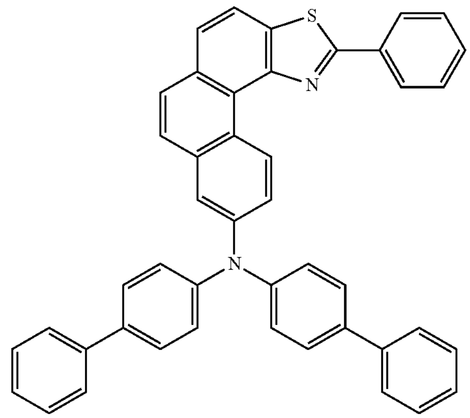
H1-183
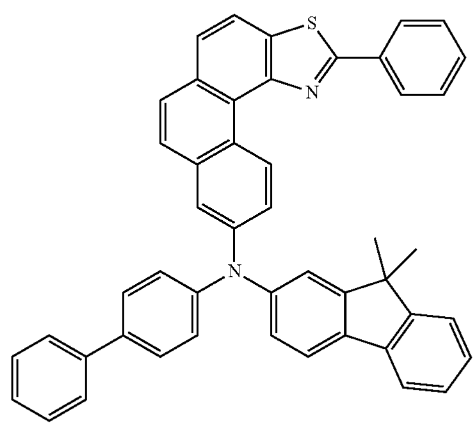
H1-184
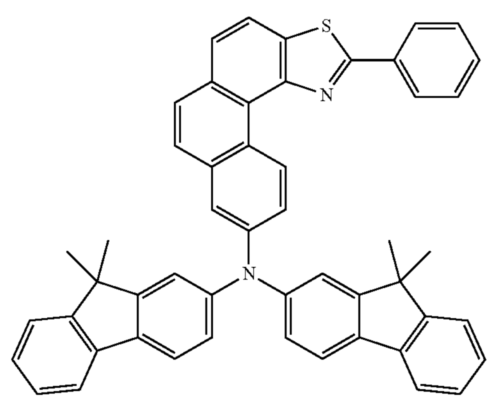

-continued
H1-185
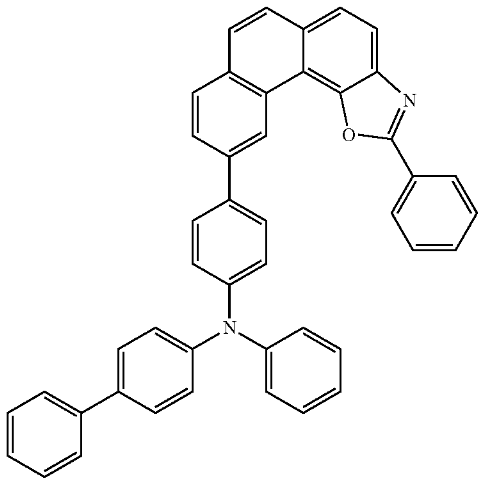
H1-186
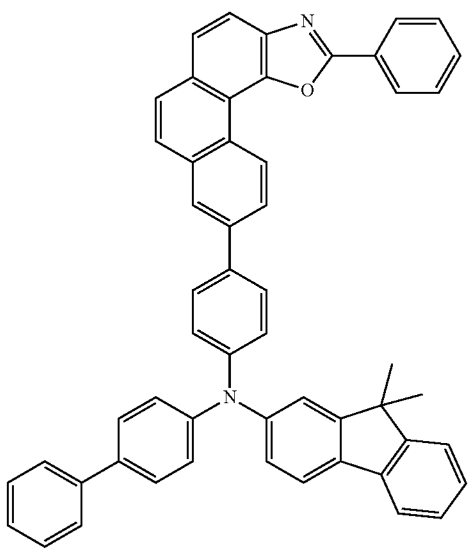
H1-187
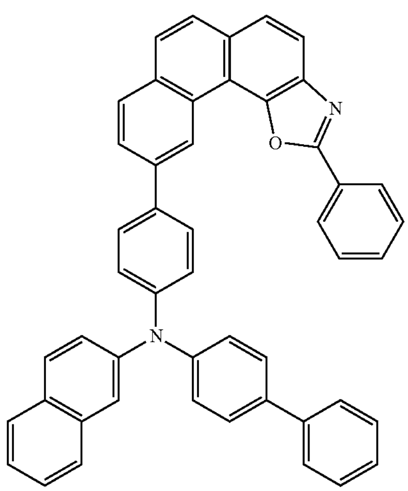
-continued
H1-188
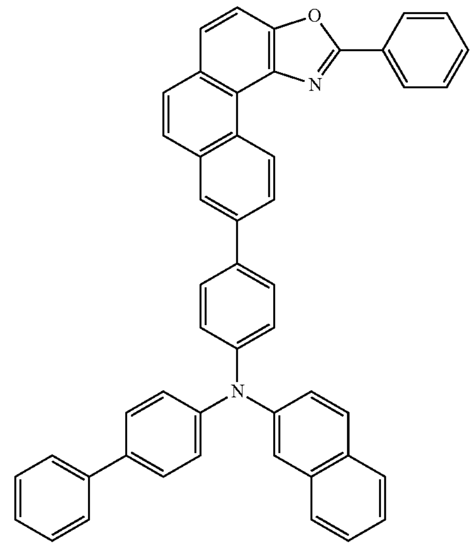
H1-189
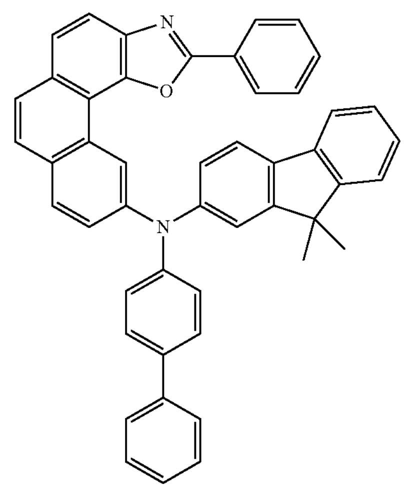
H1-190
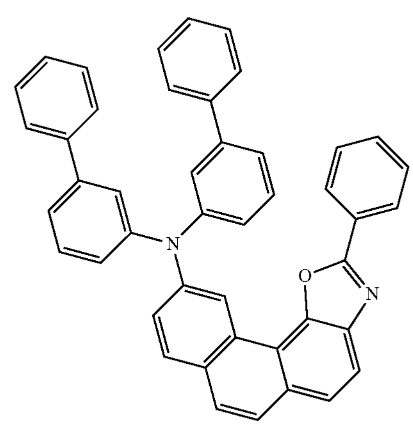

-continued
H1-191
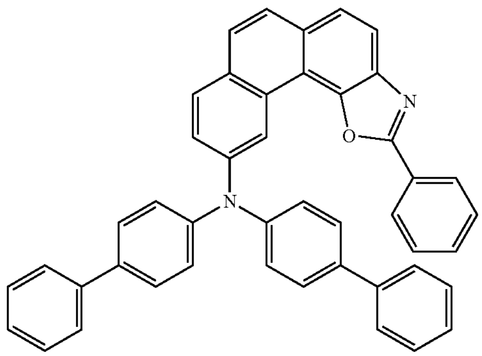
H1-192
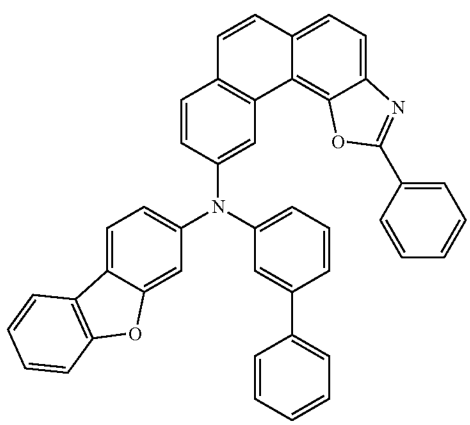
H1-193
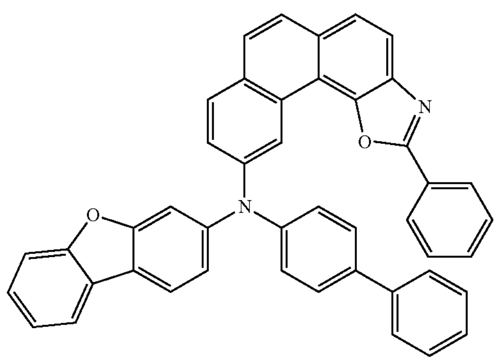
H1-194
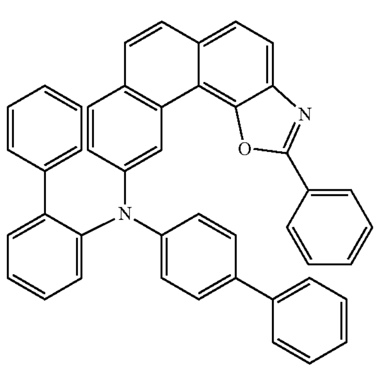
-continued
H1-195
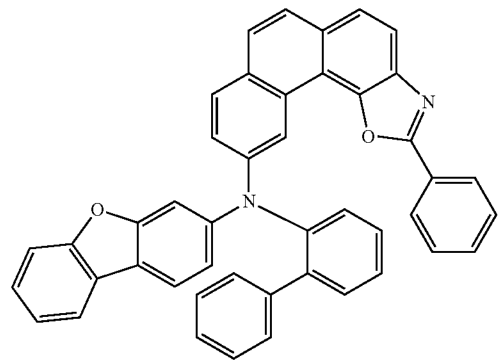
H1-196
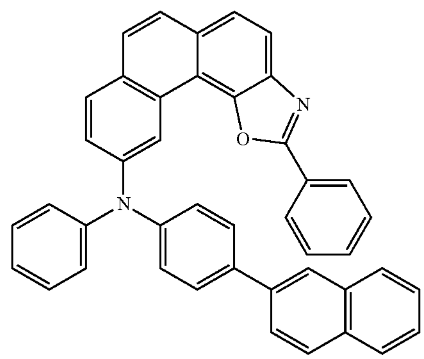
H1-197
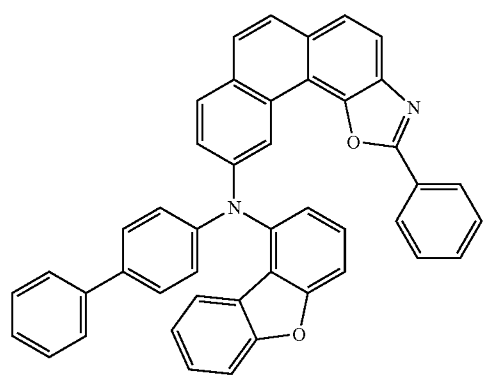
H1-198
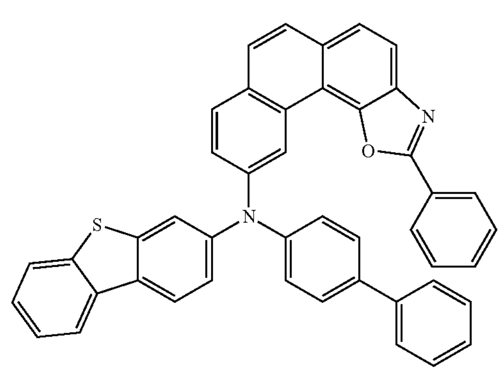

-continued
H1-199
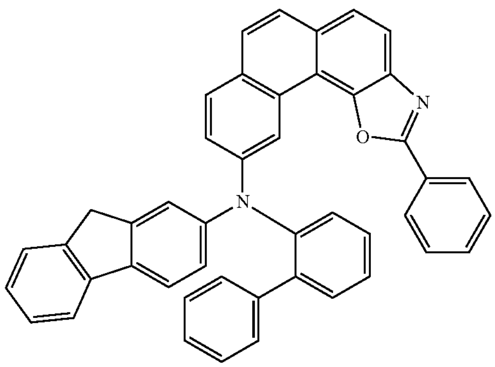
H1-200
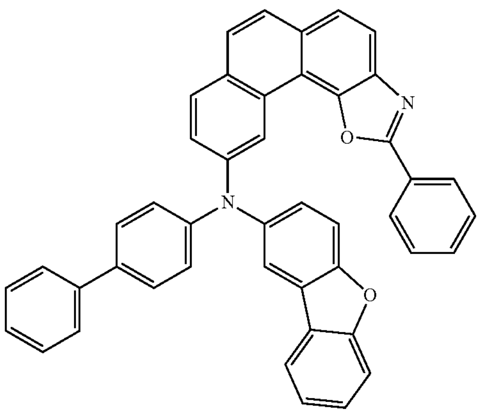
H1-201
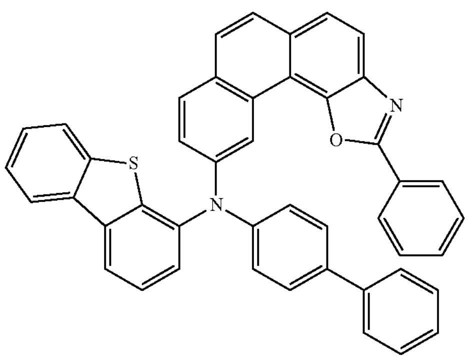
H1-202
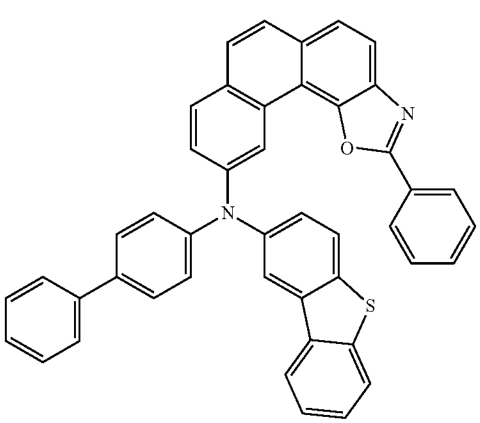
-continued
H1-203
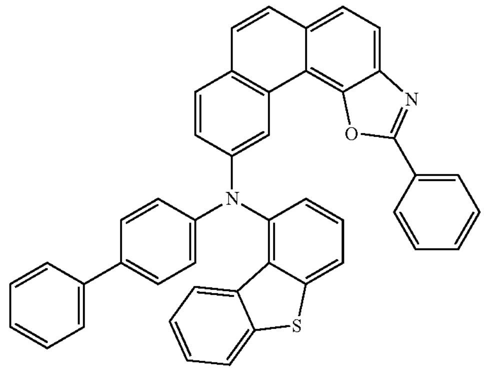
H1-204
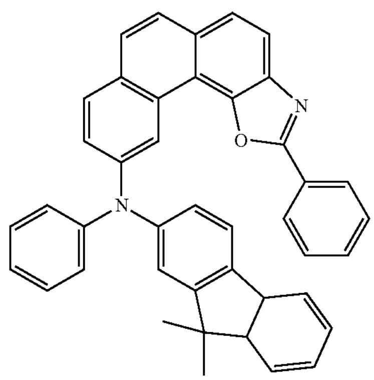
H1-205
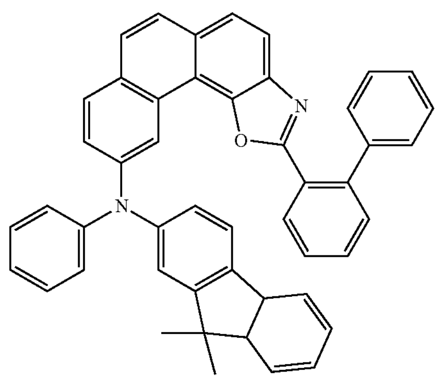
H1-206
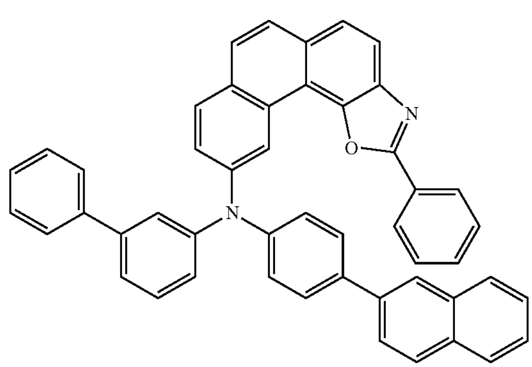

-continued
H1-207
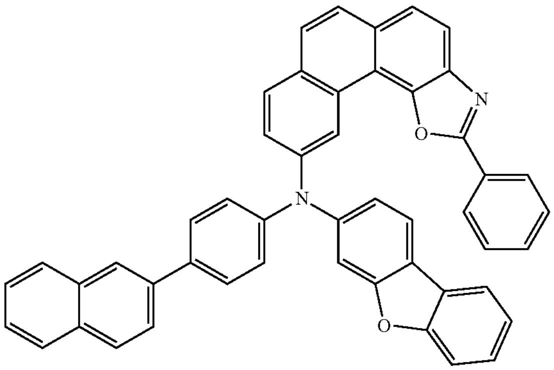
H1-208
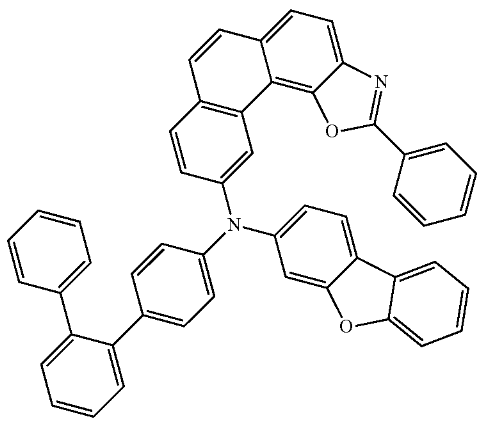
H1-209
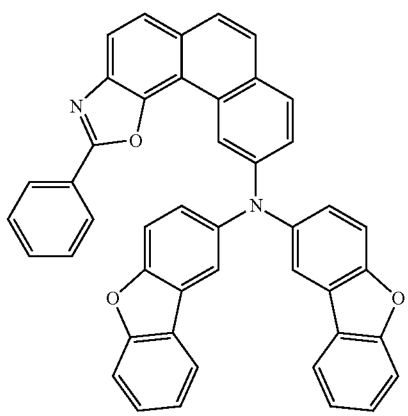
H1-210
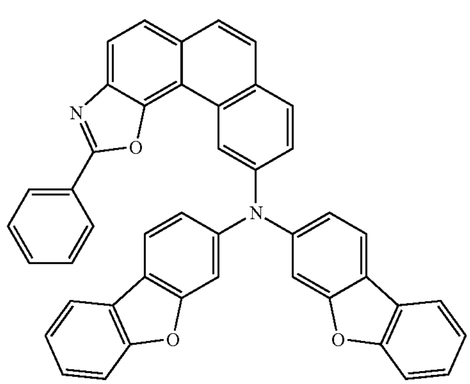
-continued
H1-211
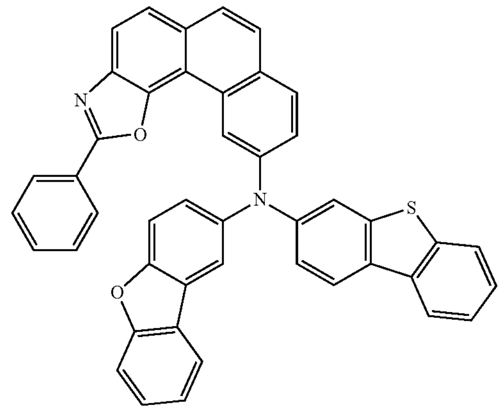
H1-212
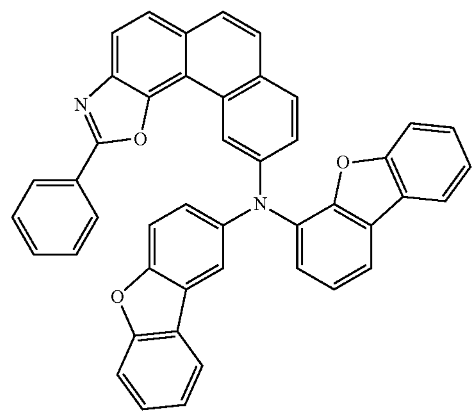
H1-213
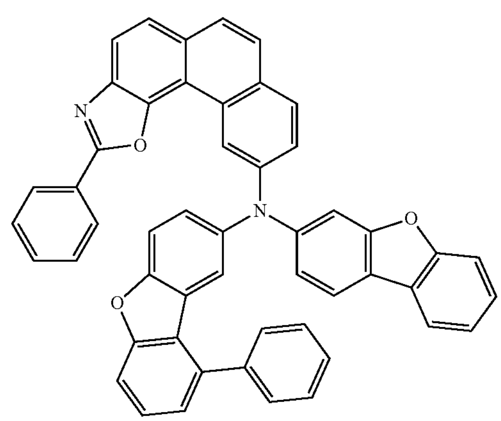

-continued
H1-214
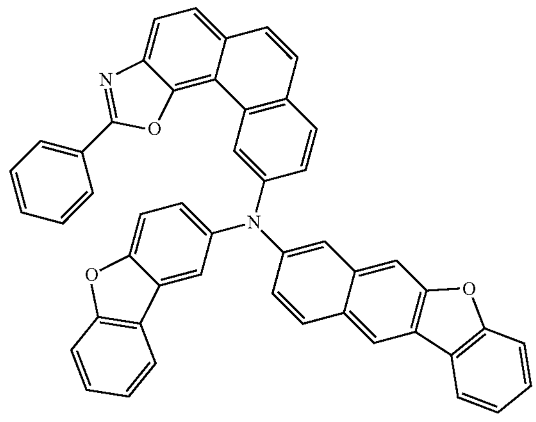
H1-215
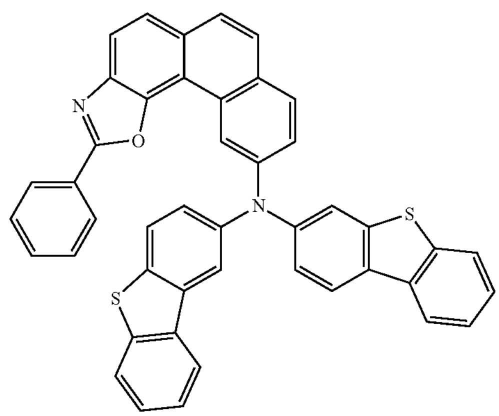
H1-216
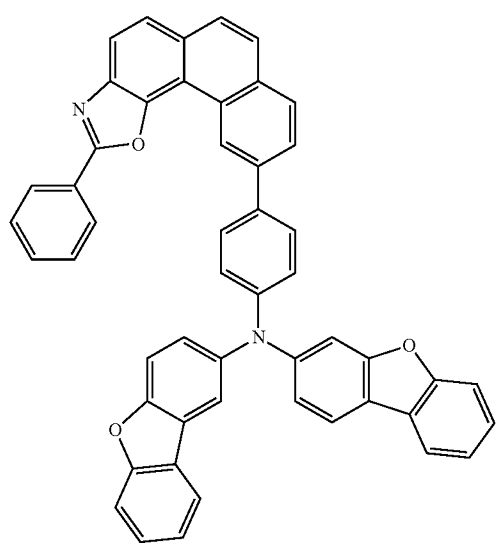
-continued
H1-217
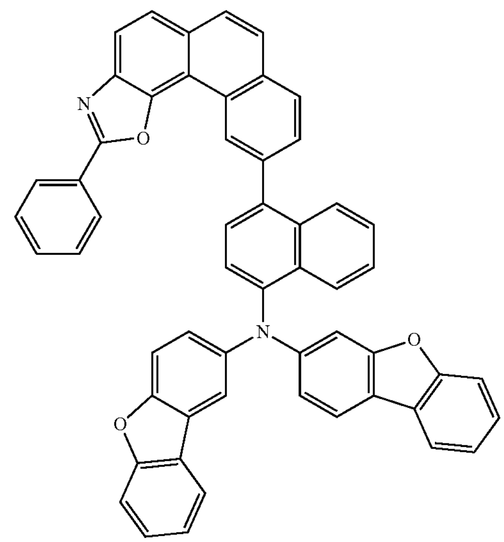
H1-218
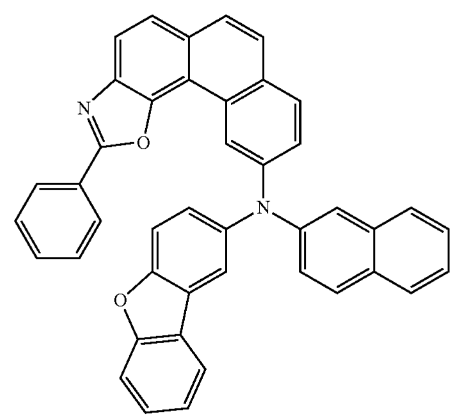
H1-219
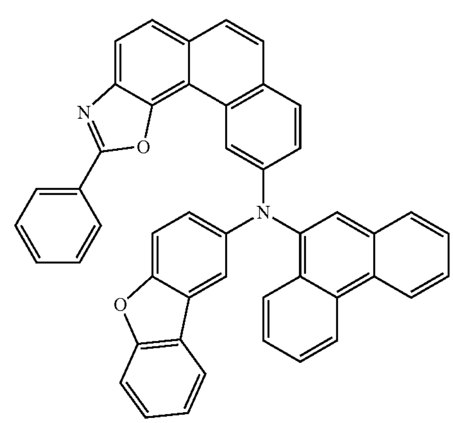

H1-220
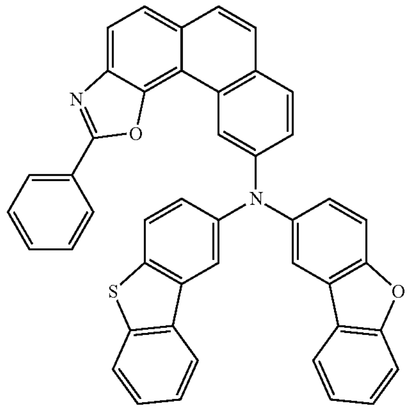
H1-221
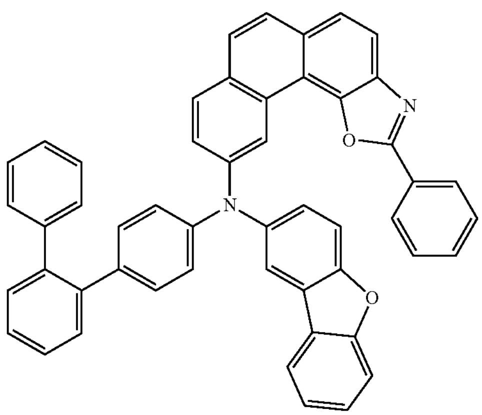
H1-222
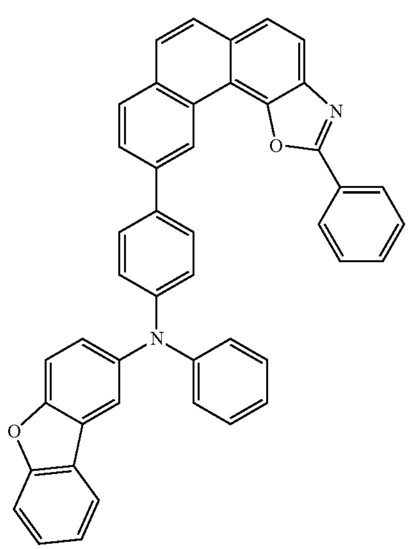
H1-223
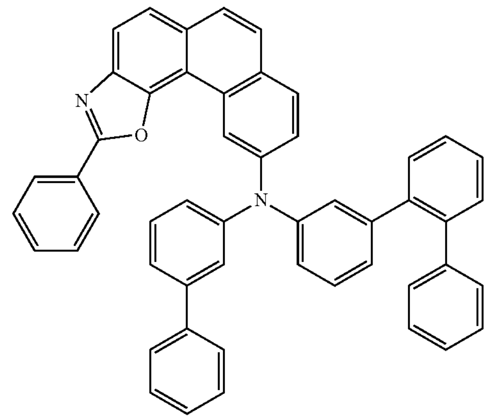
H1-224
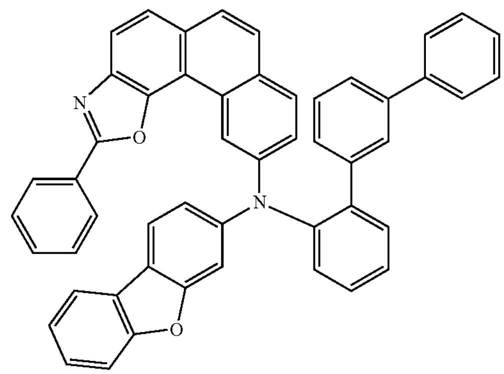
H1-225
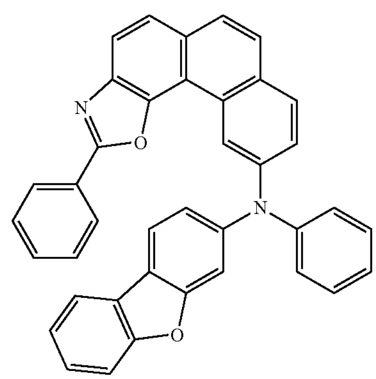
H1-226
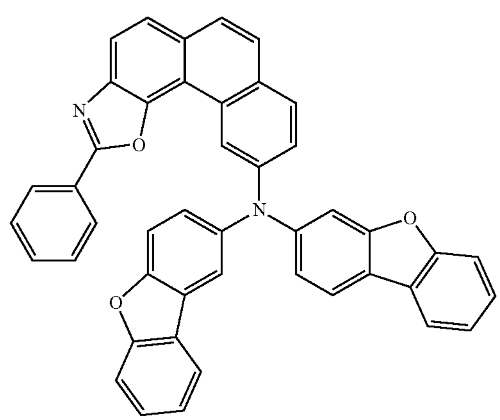

-continued
H1-227
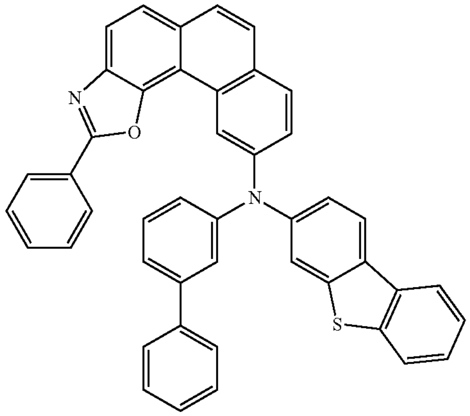
H1-228
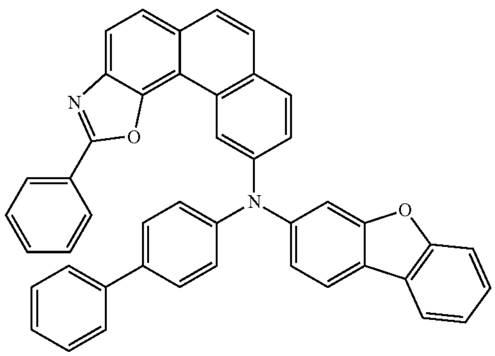
H1-229
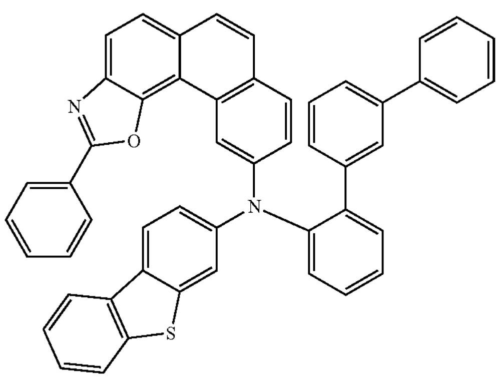
H1-230
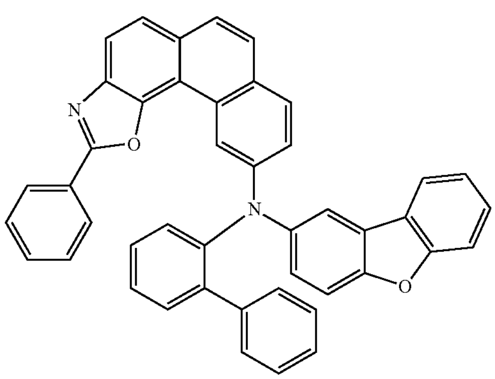
-continued
H1-231
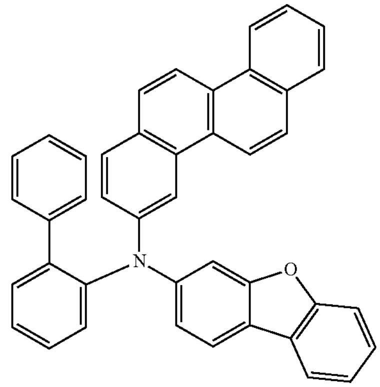
H1-232
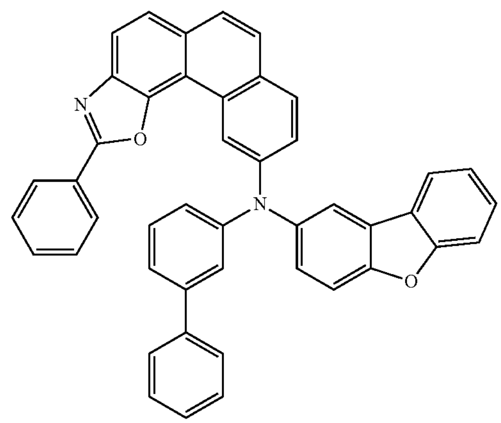
H1-233
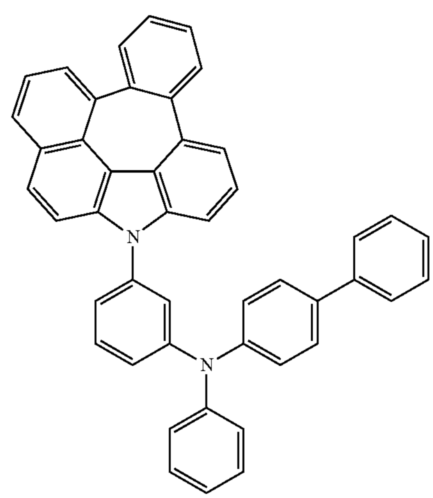

-continued
H1-234
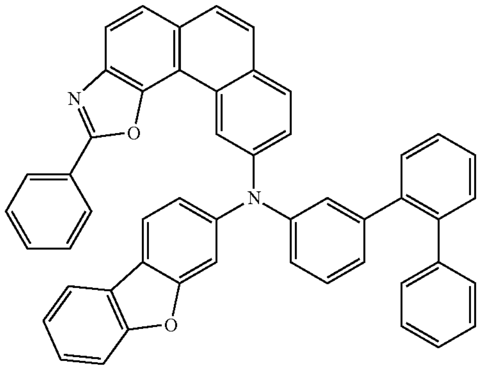
H1-235
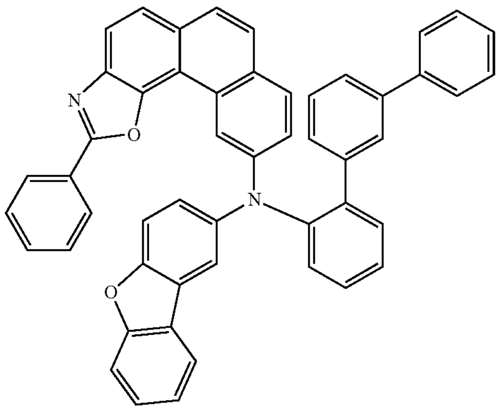
H1-236
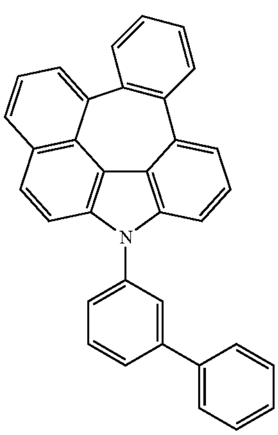
-continued
H1-237
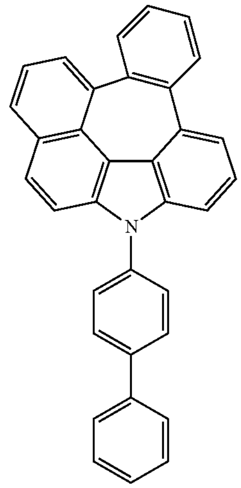
H1-238
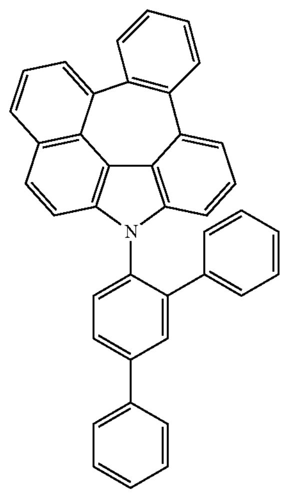
H1-239
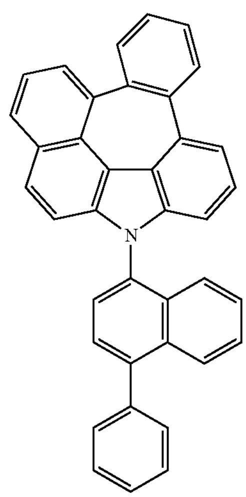

-continued
H1-240
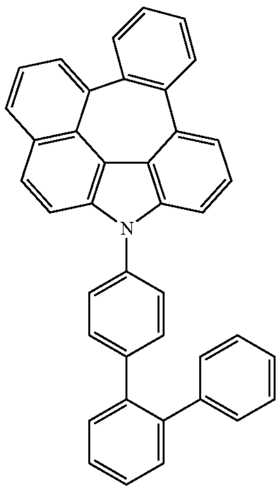
H1-241
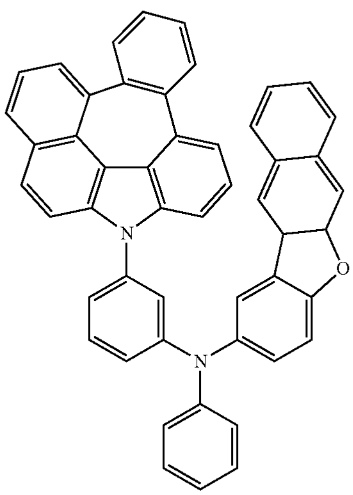
H1-242
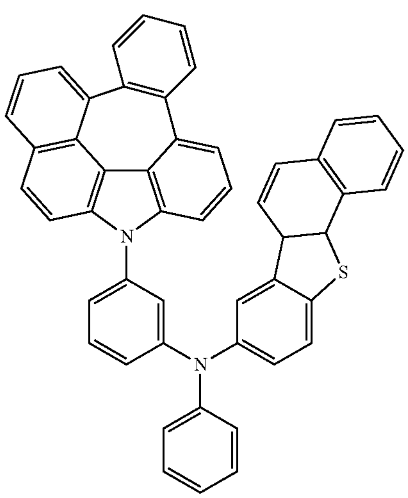
-continued
H1-243
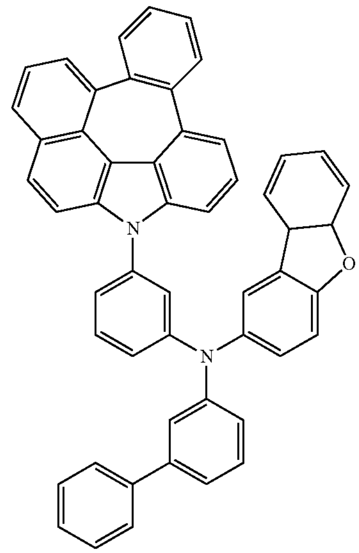
H1-244
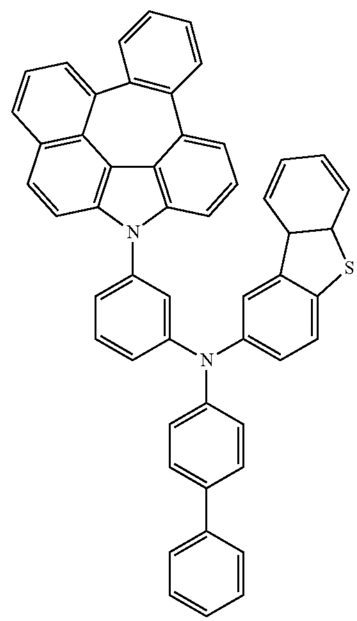
H1-245
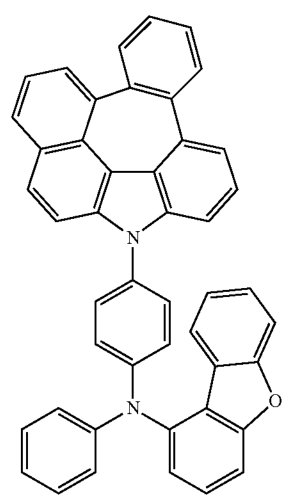

-continued
H1-246
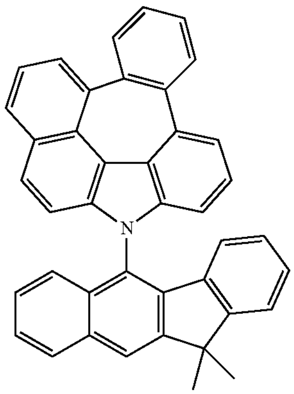
H1-247
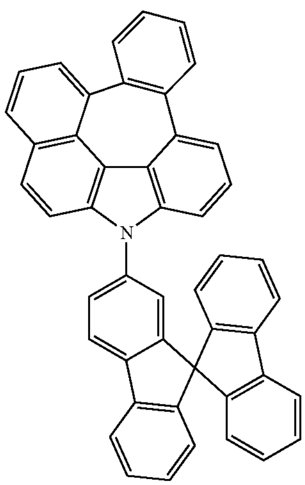
H1-248
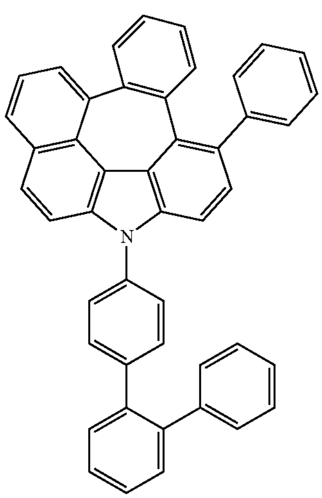
-continued
H1-249
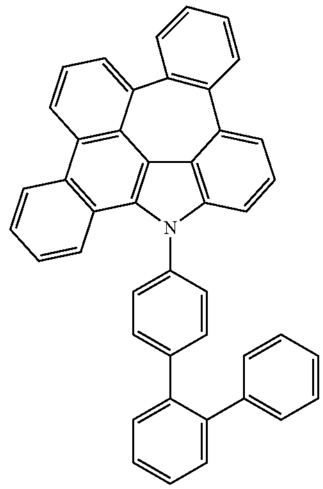
H1-250
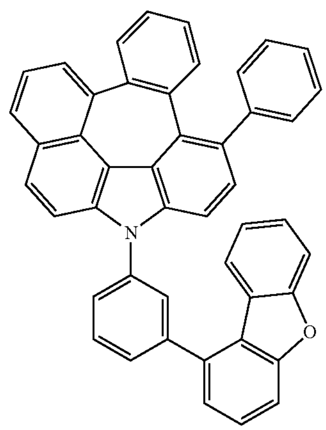
H1-251
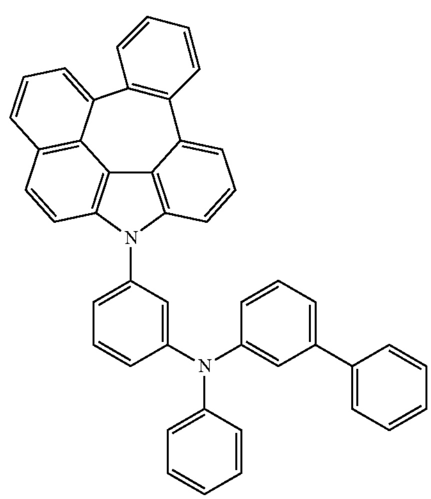

-continued
H1-252
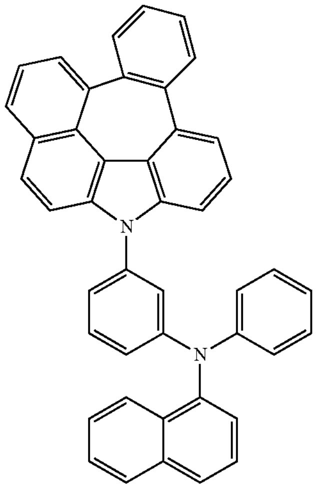
H1-253
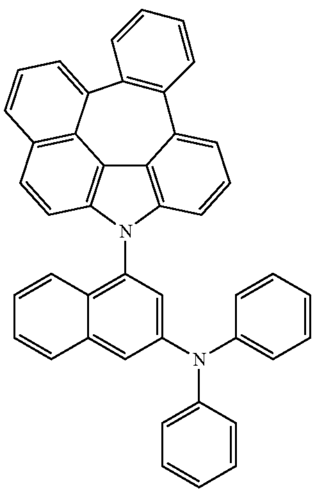
H1-254
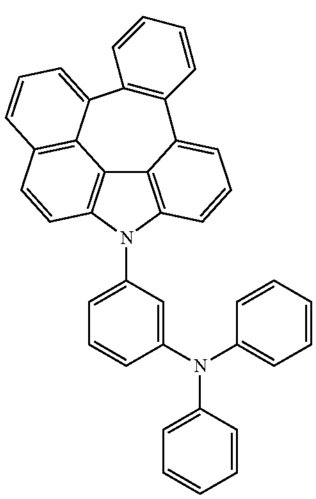
-continued
H1-255
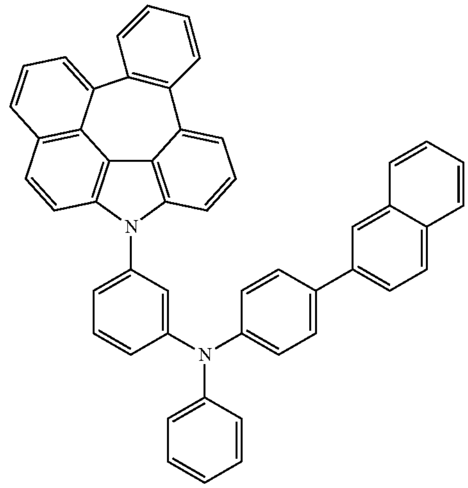
H1-256
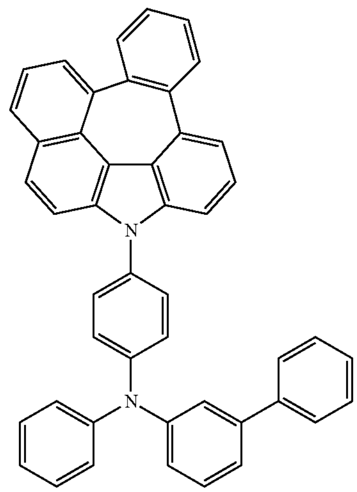
H1-257
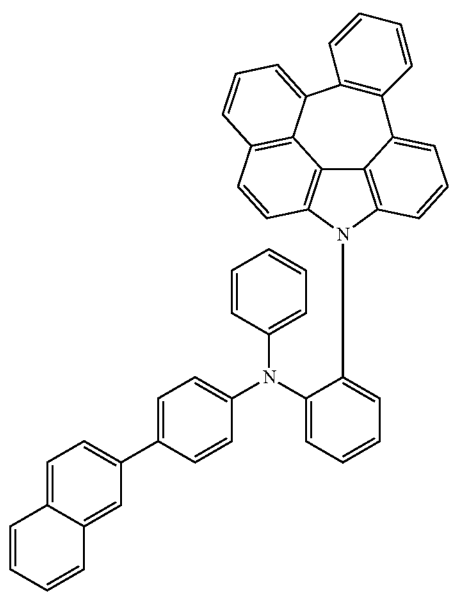

-continued
H1-258
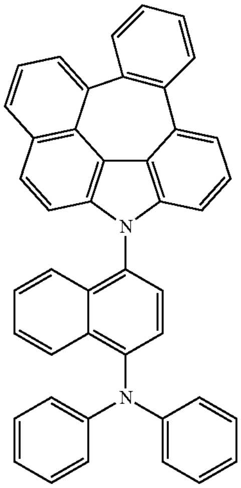
H1-259
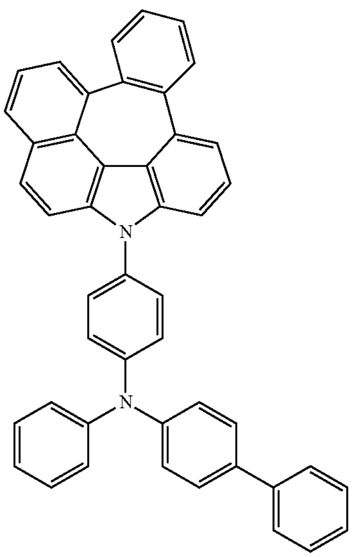
H1-260
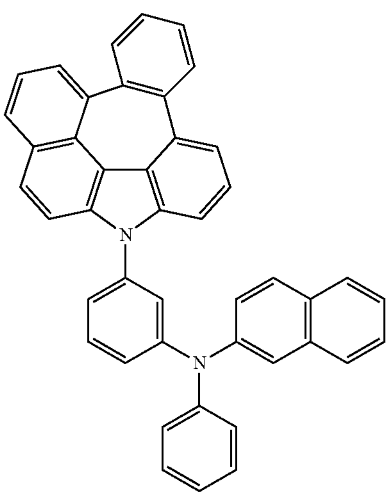
-continued
H1-261
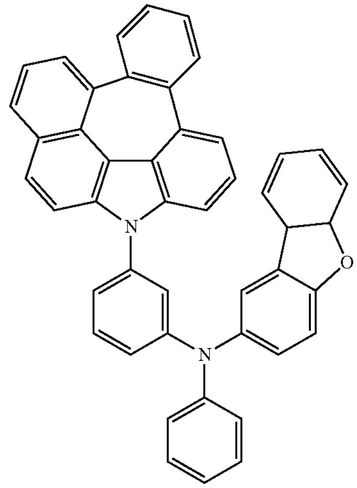
H1-262
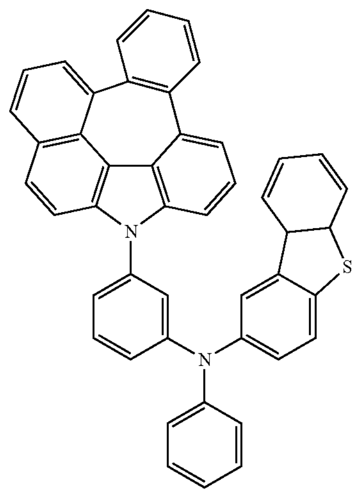
H1-263
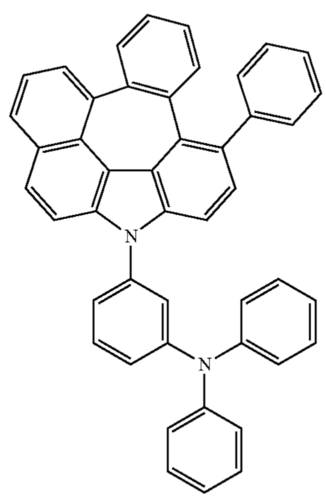

-continued
H1-264
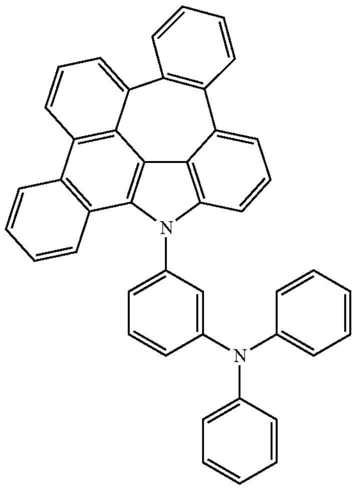
H1-265
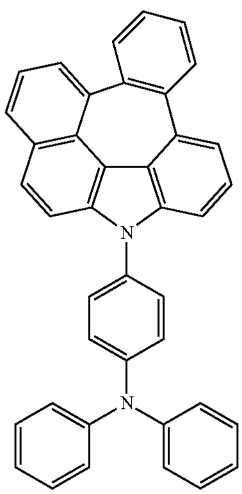
H1-266
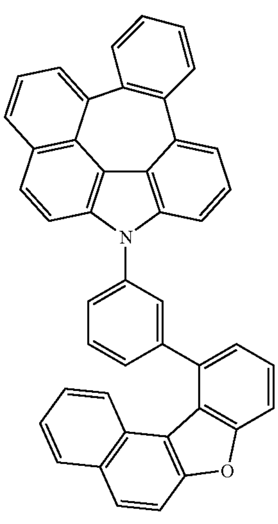
-continued
H1-267
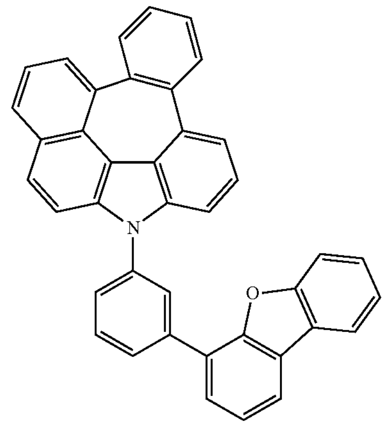
H1-268
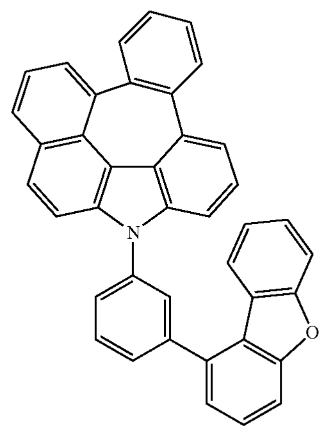
H1-269
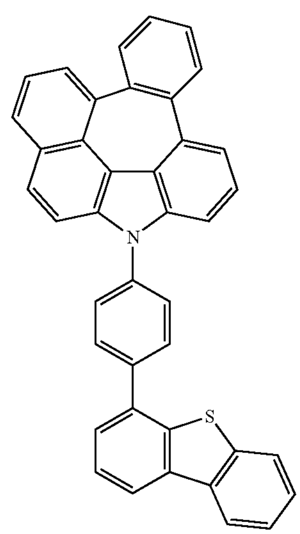

-continued
H1-270
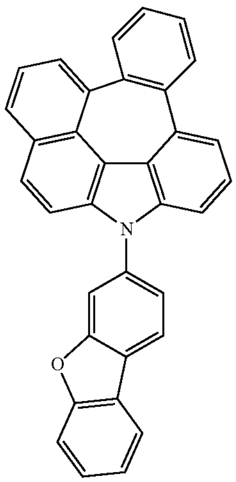
H1-271
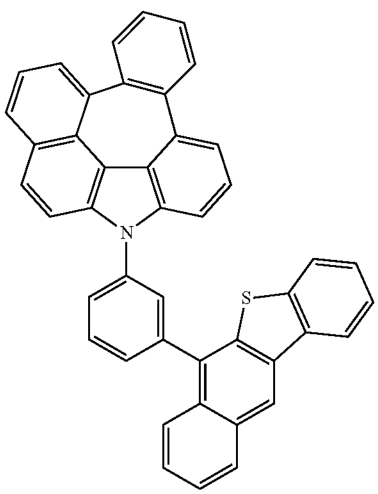
H1-272
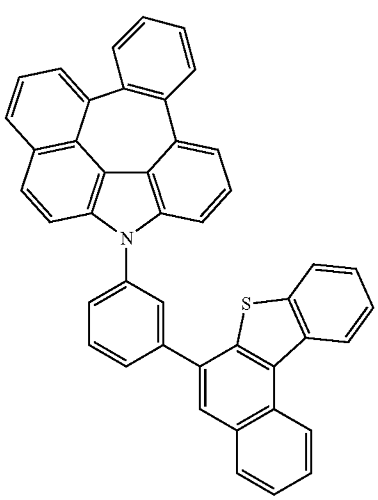
-continued
H1-273
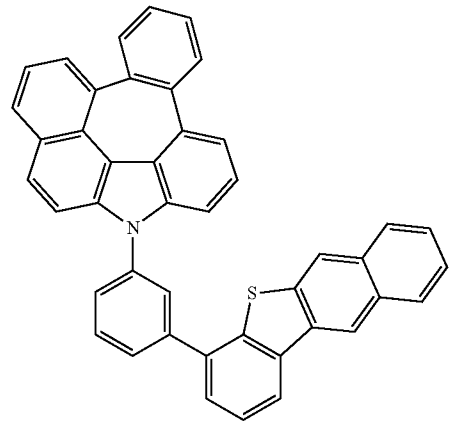
H1-274
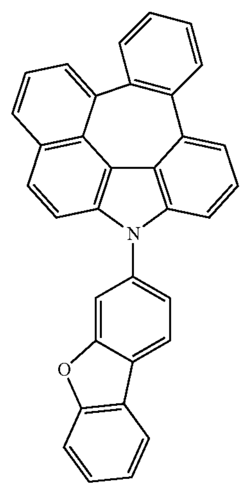
H1-275
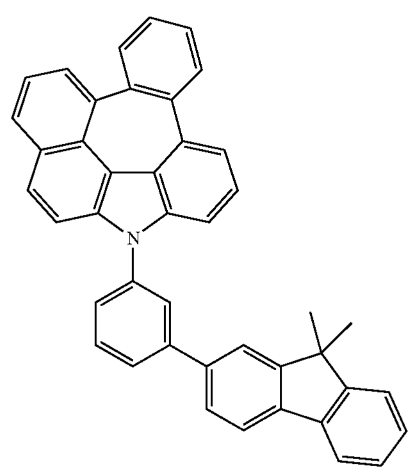

-continued
H1-276
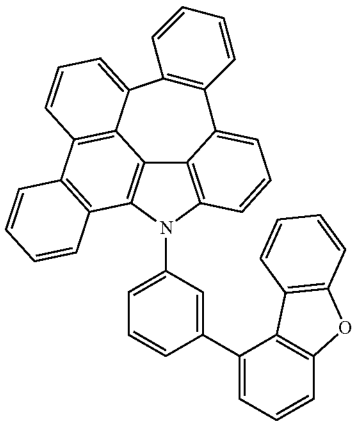
H1-277
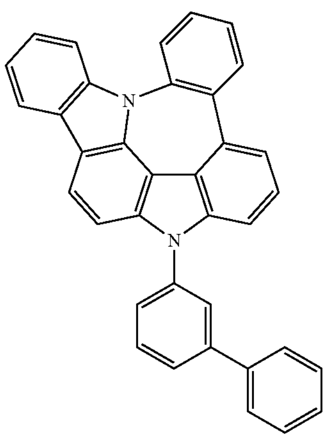
H1-278
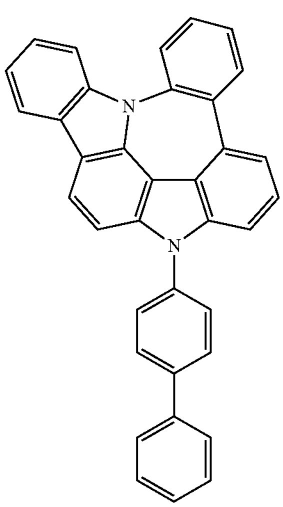
-continued
H1-279
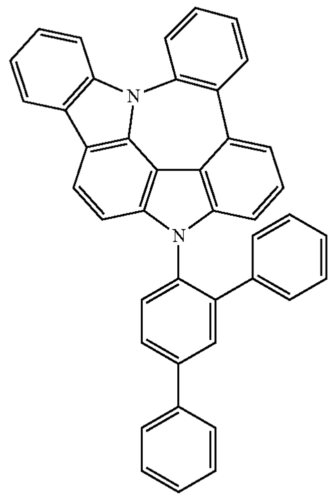
H1-280
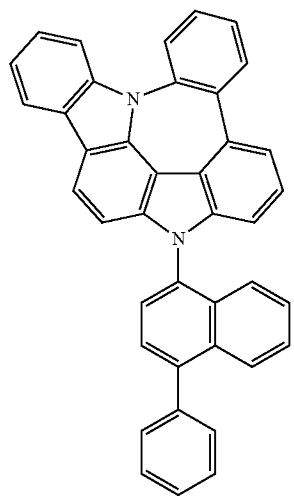
H1-281
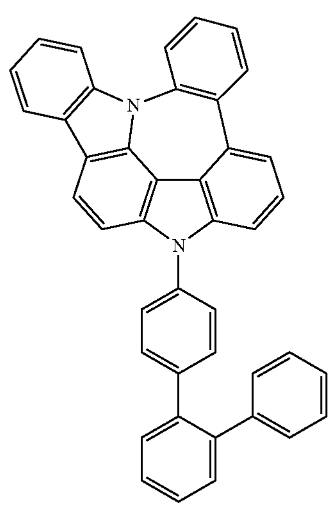

-continued
H1-282
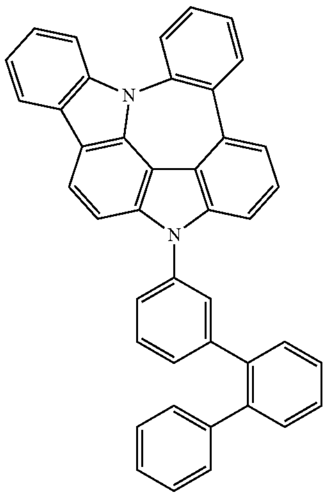
H1-283
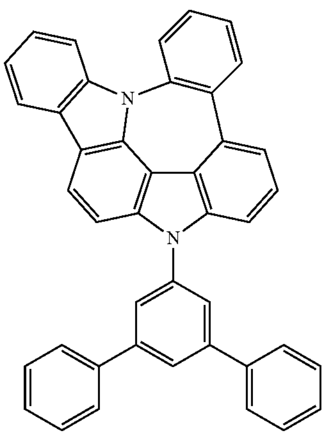
H1-284
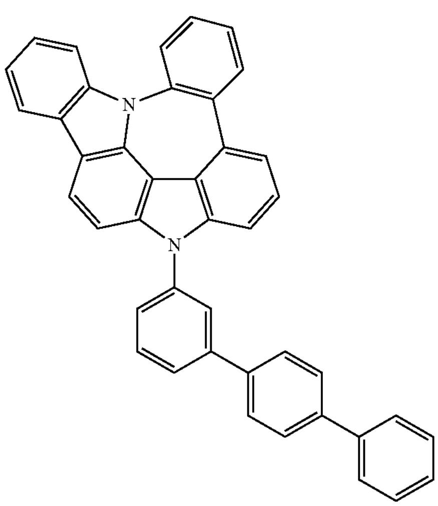
-continued
H1-285
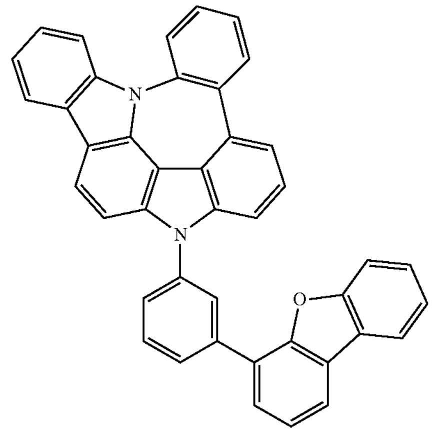
H1-286
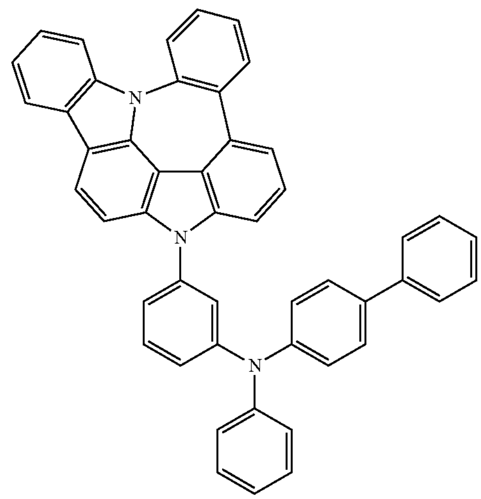
H1-287
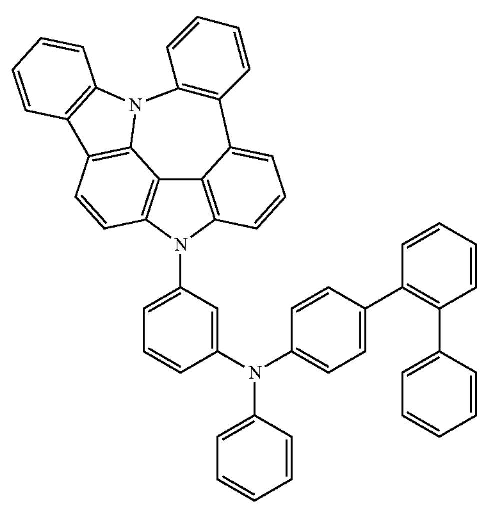

-continued
H1-288
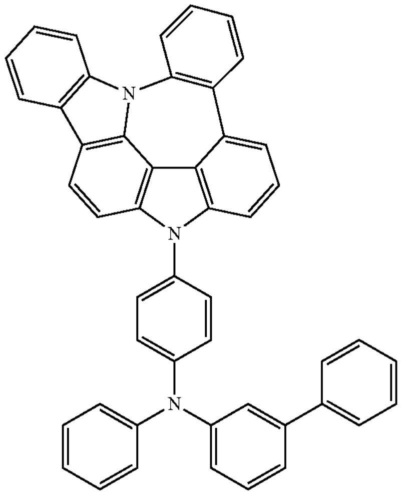
H1-289
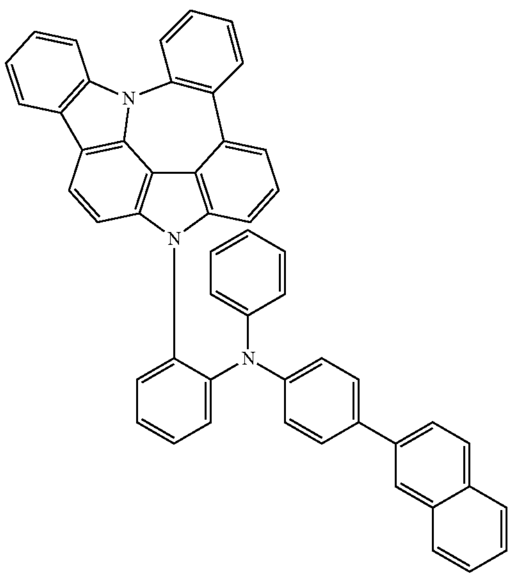
H1-290
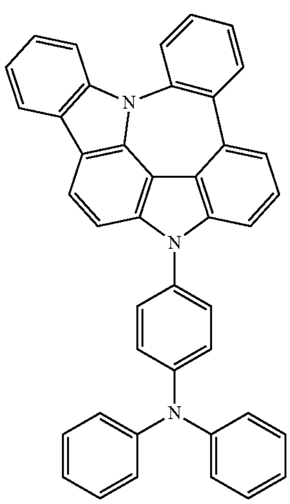
H1-291
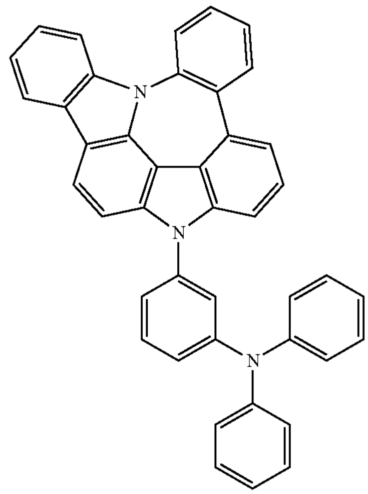
H1-292
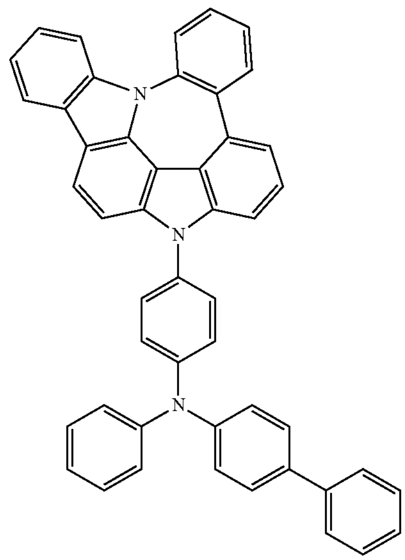
H1-293
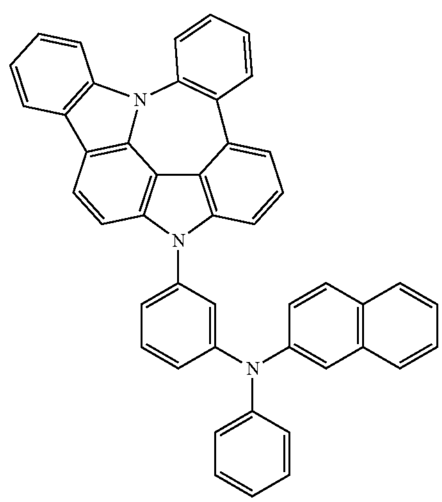

-continued
H1-294
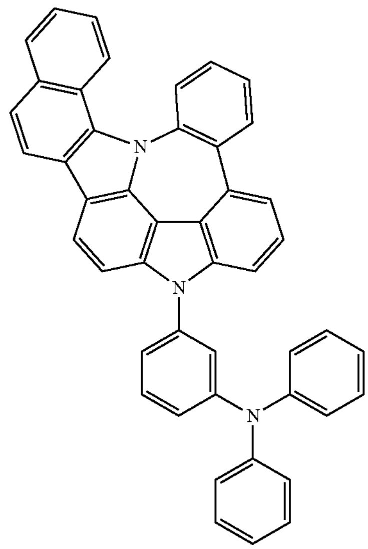
H1-295
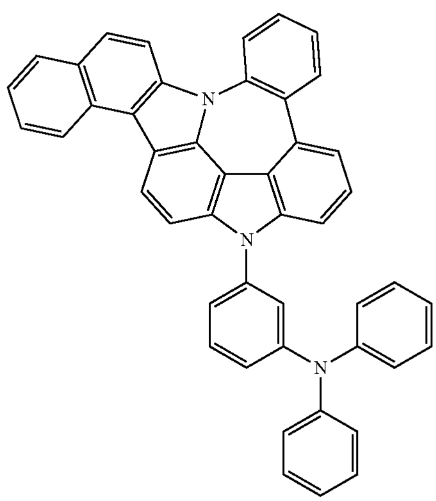
H1-296
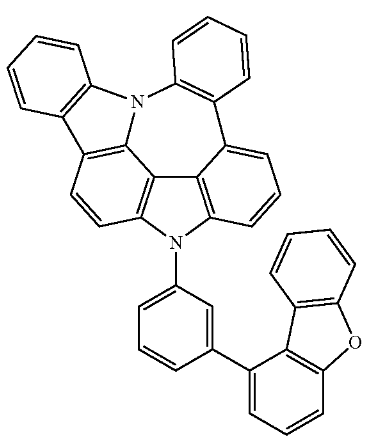
-continued
H1-297
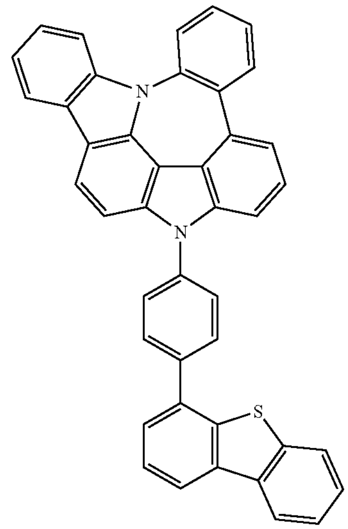
H1-298
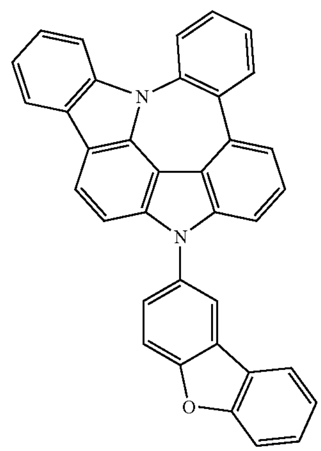
H1-299
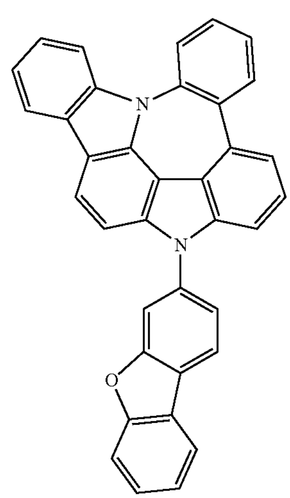

-continued
H1-300
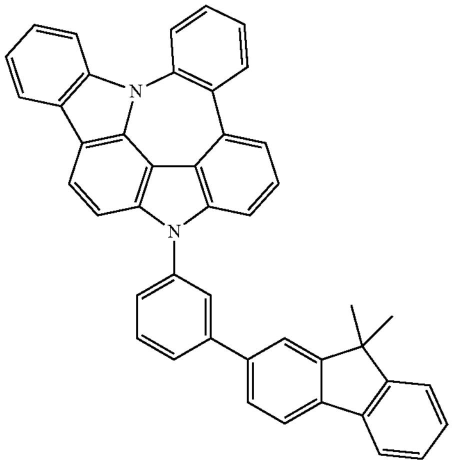
H1-301
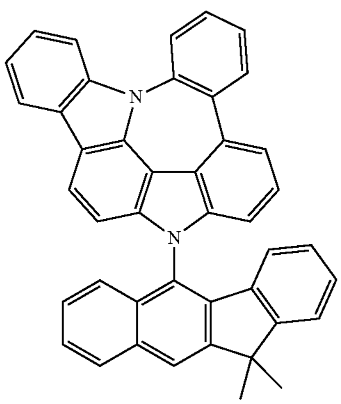
H1-302
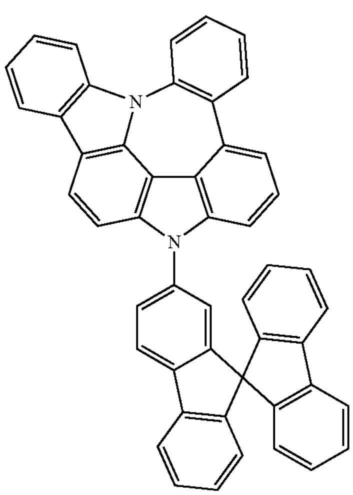
-continued
H1-303
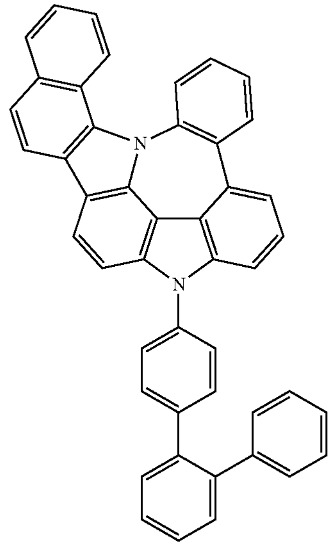
H1-304
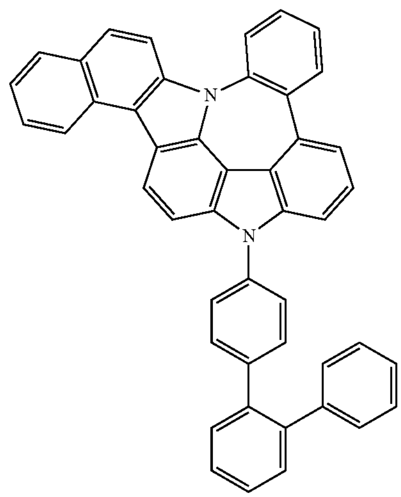
H1-305
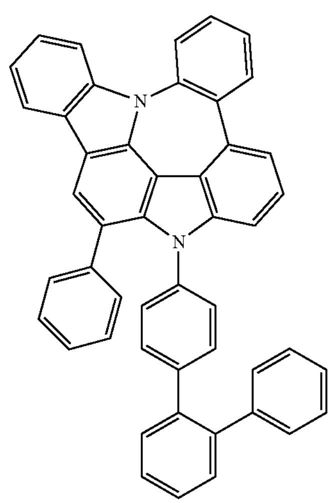

-continued
H1-306
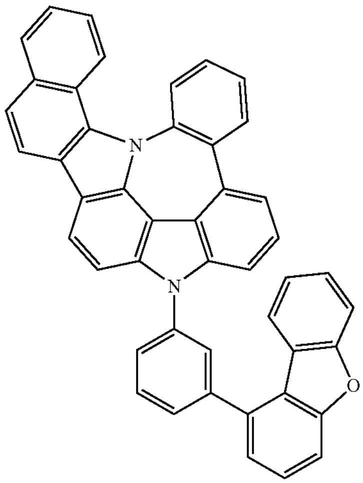
H1-307
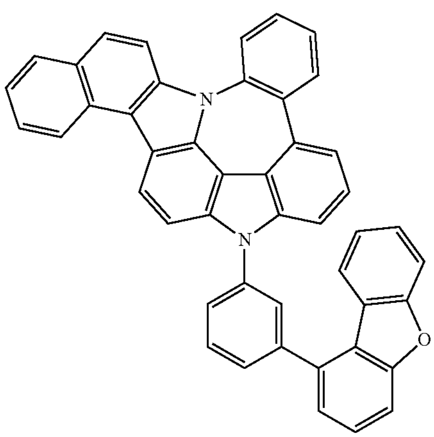
H1-308
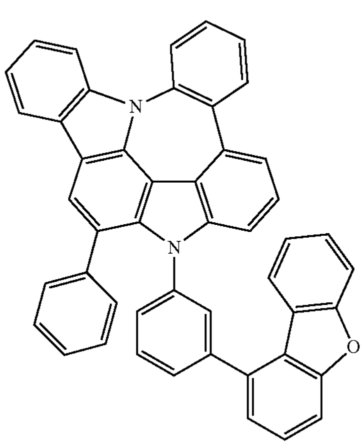
-continued
H1-309
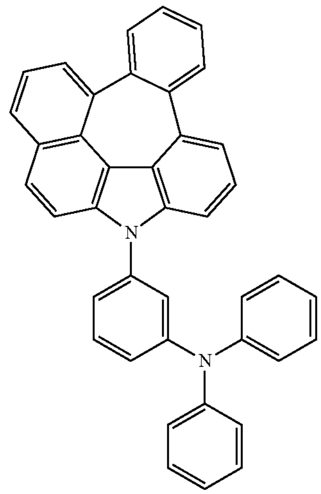
H1-310
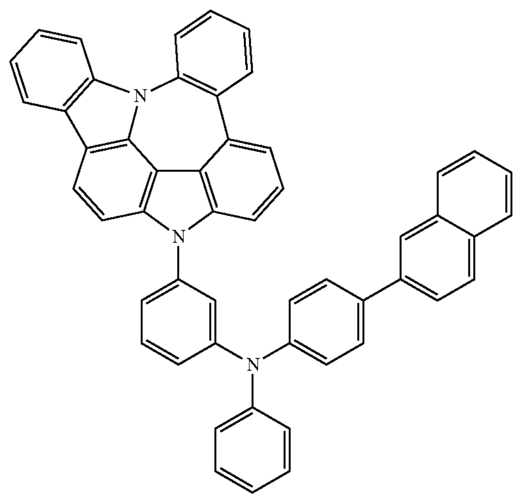
The compound represented by any one of formulas 2 to 4 may be at least one selected from the group consisting of the following compounds, but is not limited thereto.
H2-1
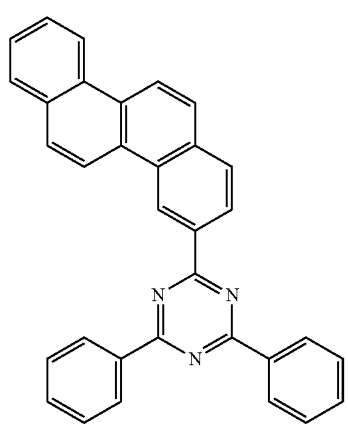

-continued
H2-2
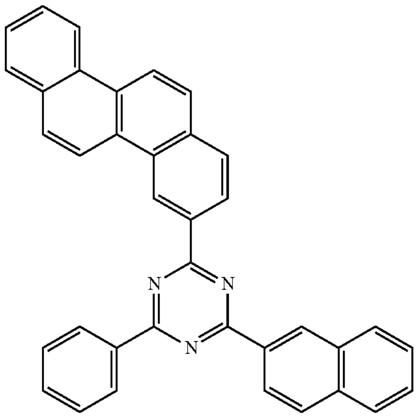
H2-3
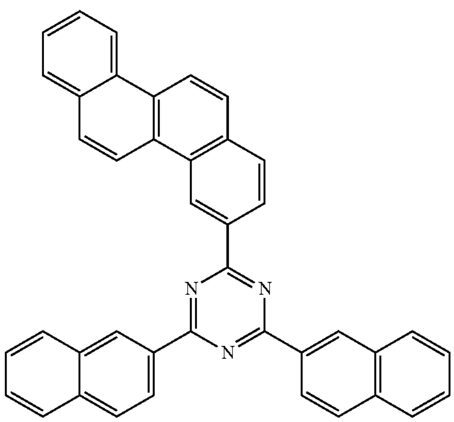
H2-4
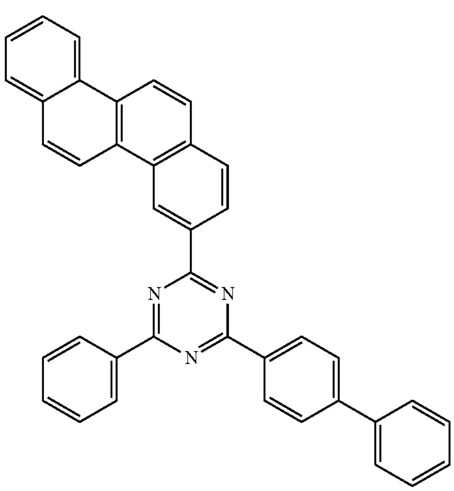
-continued
H2-5
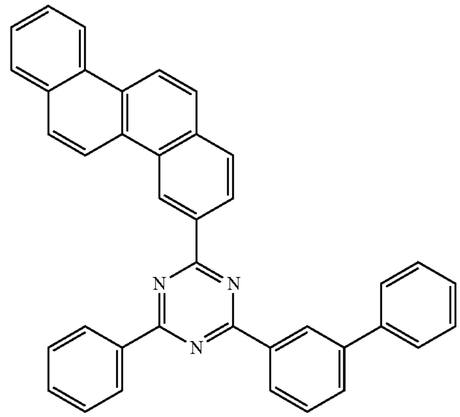
H2-6
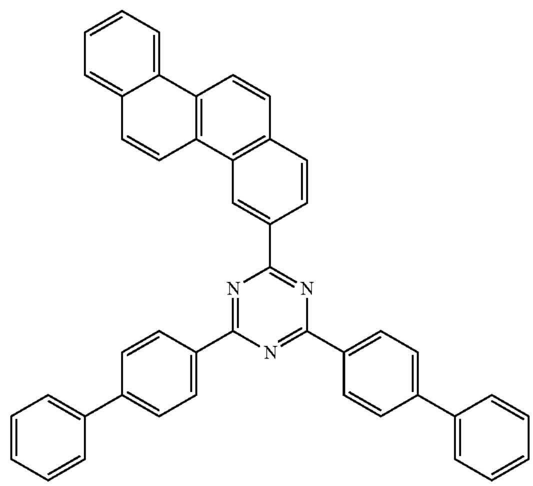
H2-7
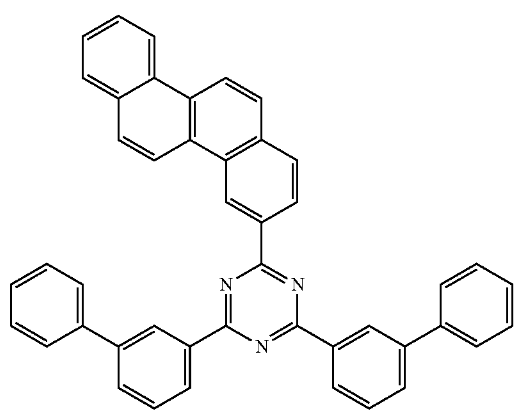

-continued
H2-8
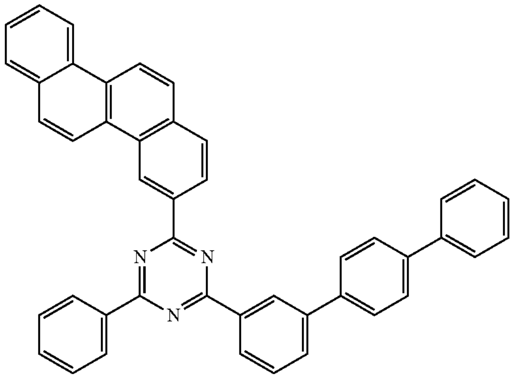
H2-9
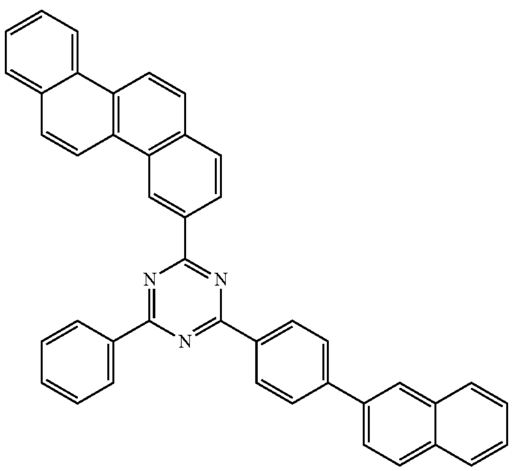
H2-10
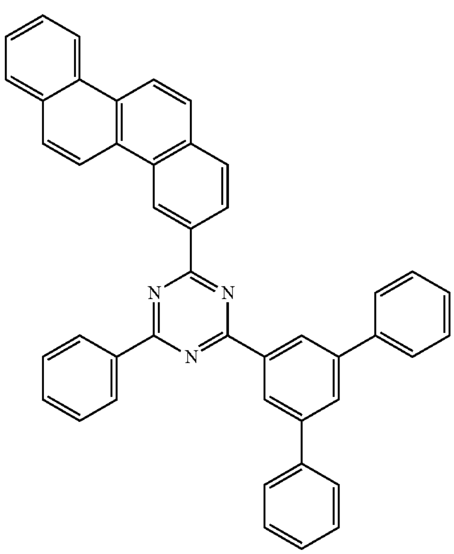
-continued
H2-11
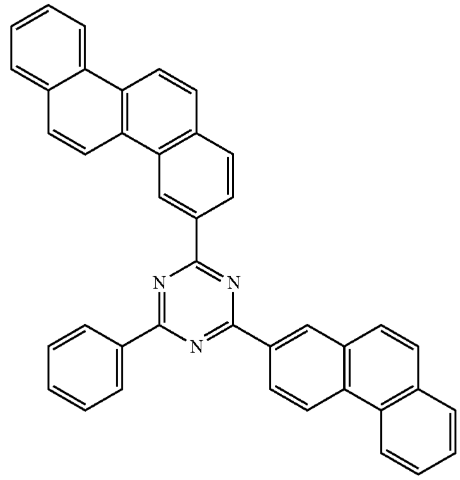
H2-12
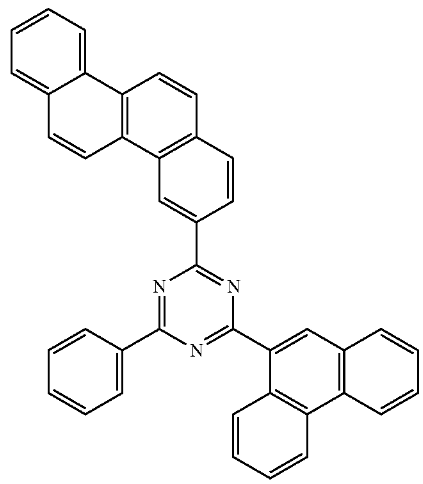
H2-13
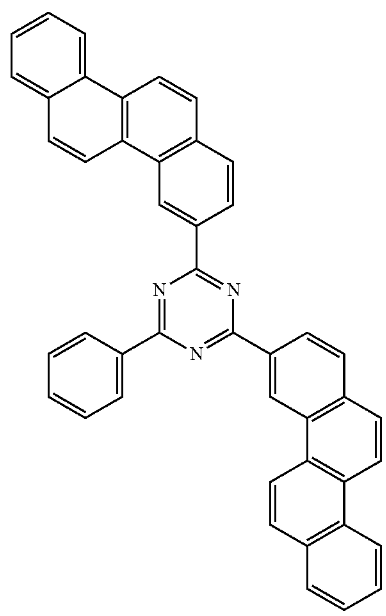

-continued
H2-14
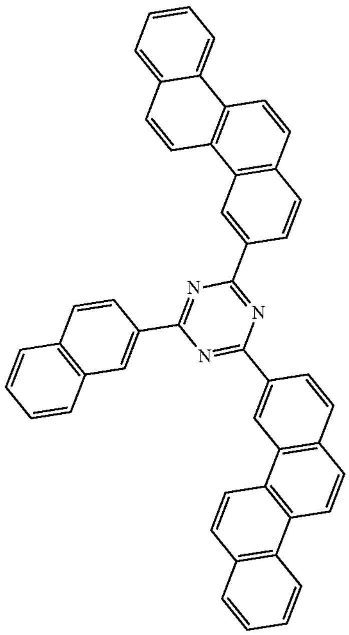
H2-15
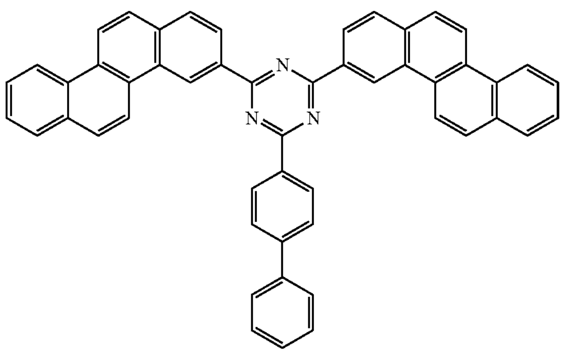
H2-16
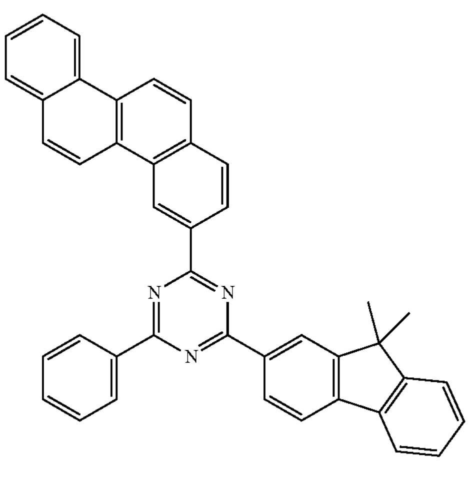
-continued
H2-17
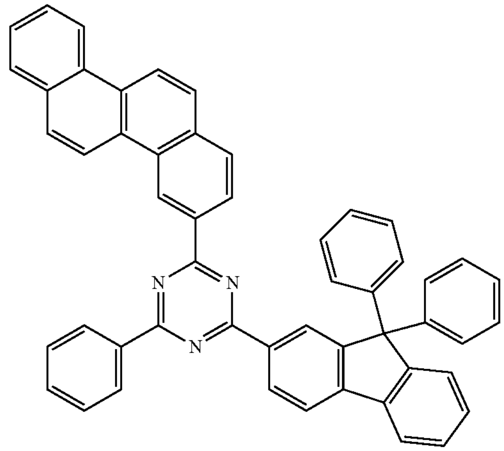
H2-18
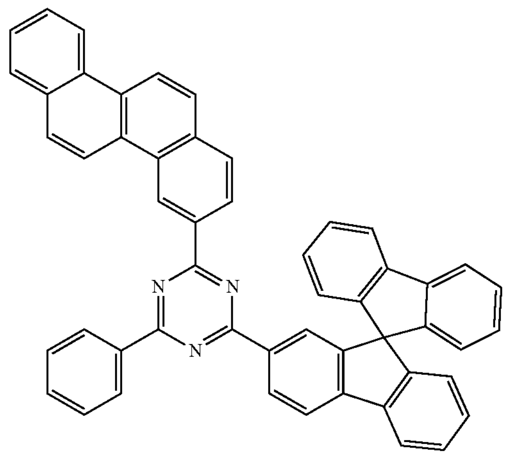
H2-19
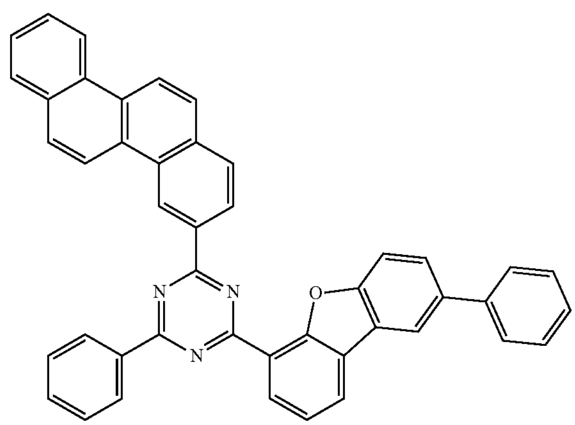

-continued
H2-20
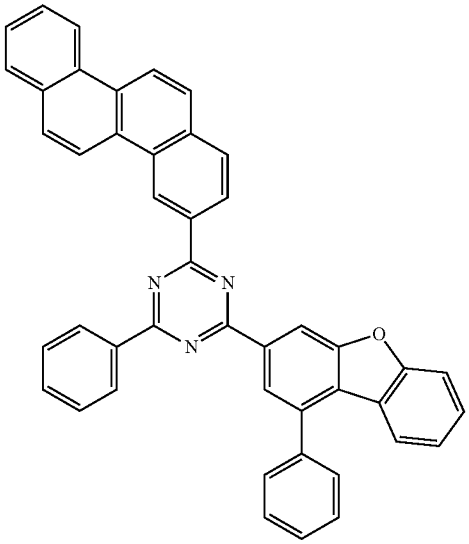
H2-21
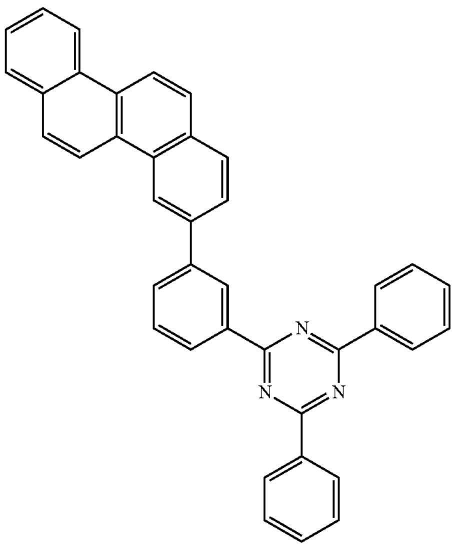
H2-22
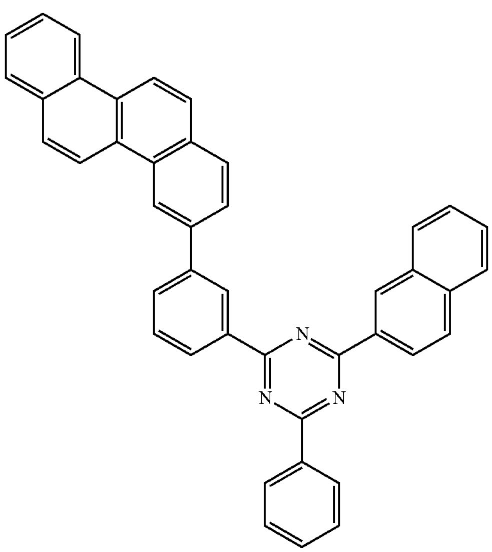
-continued
H2-23
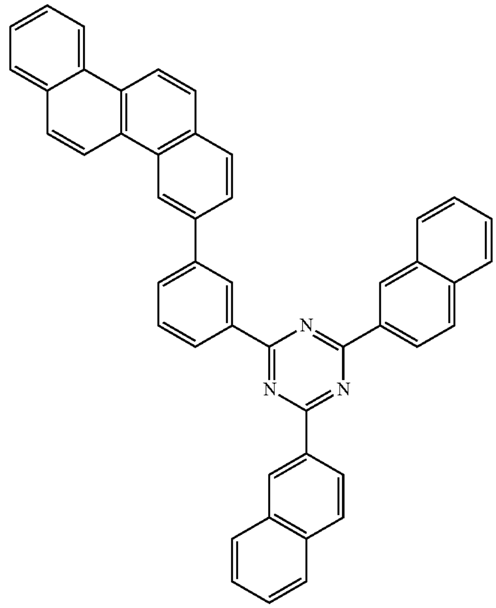
H2-24
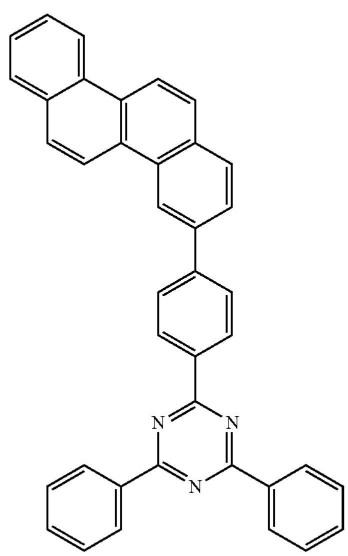

-continued
H2-25
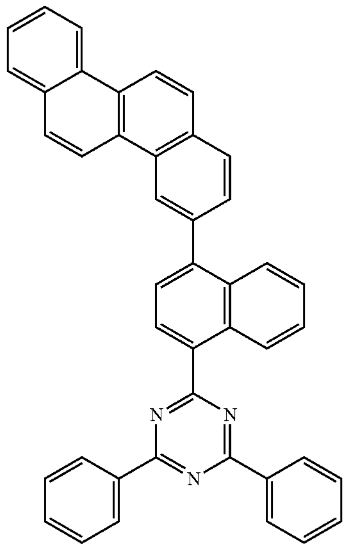
H2-26
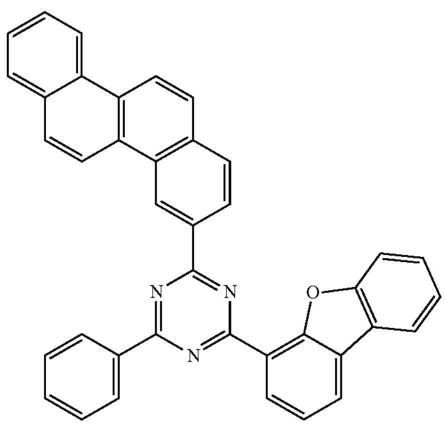
H2-27
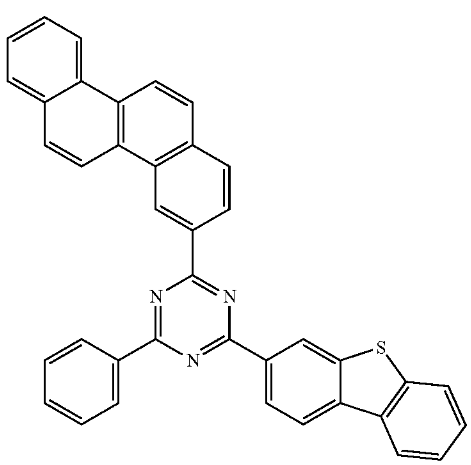
-continued
H2-28
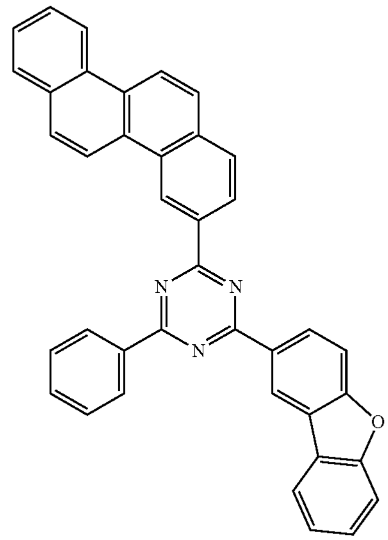
H2-29
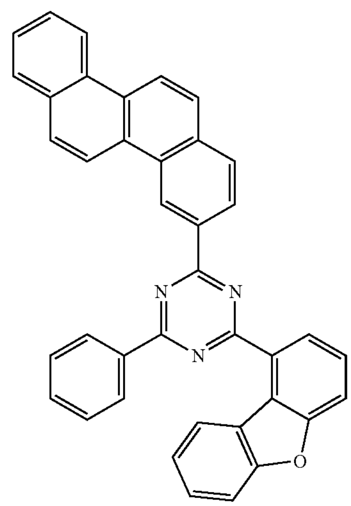
H2-30
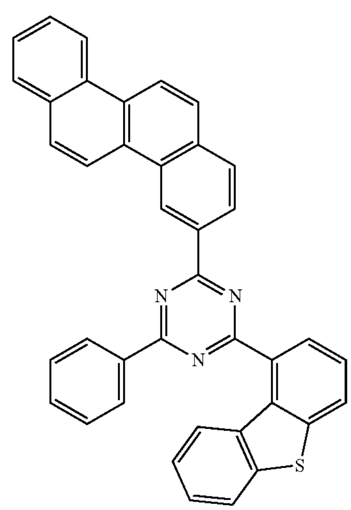

-continued
H2-31
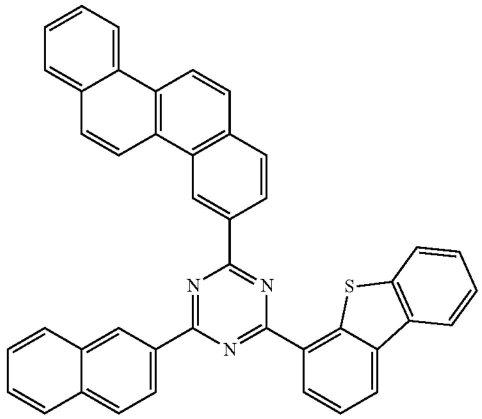
H2-32
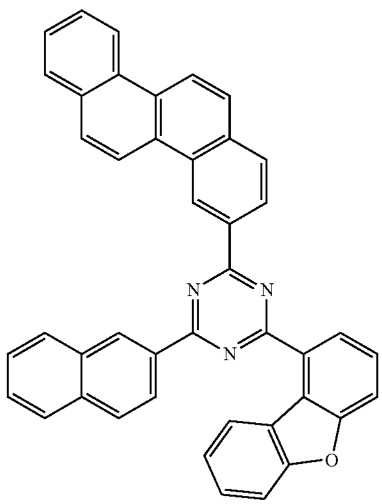
H2-33
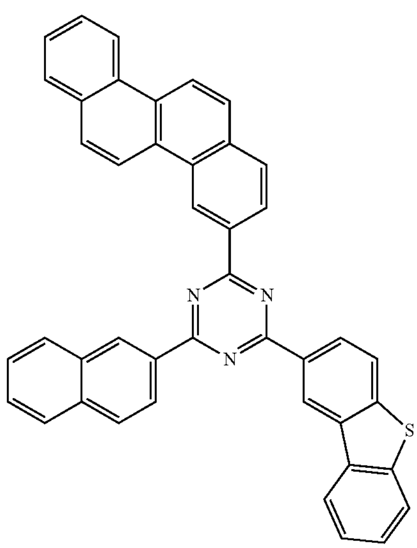
-continued
H2-34
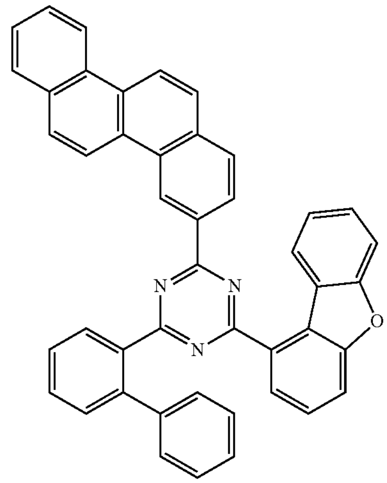
H2-35
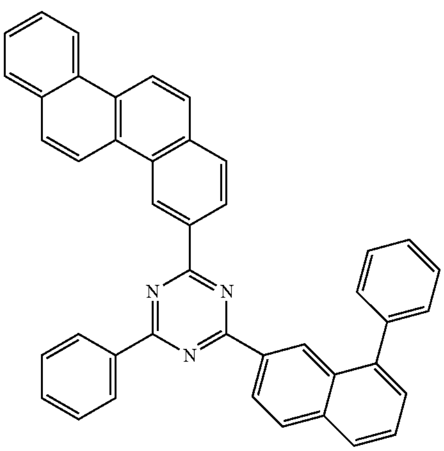
H2-36
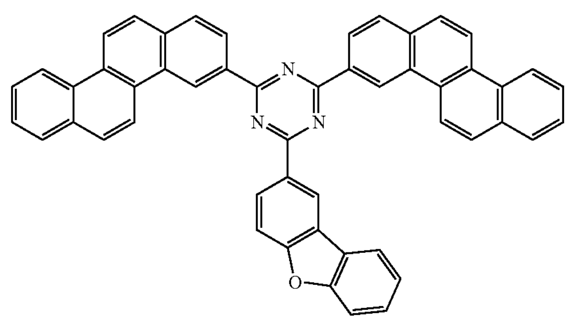

-continued
H2-37
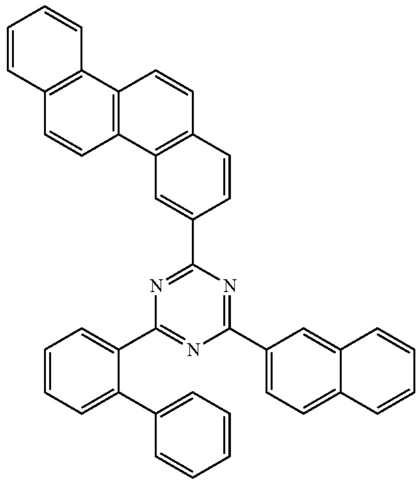
H2-38
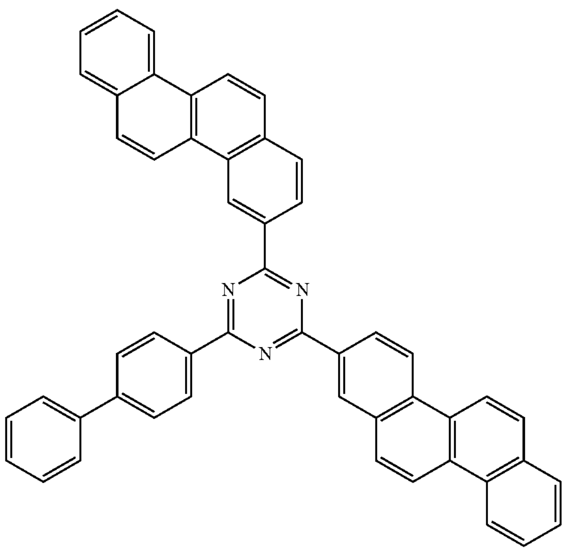
H2-39
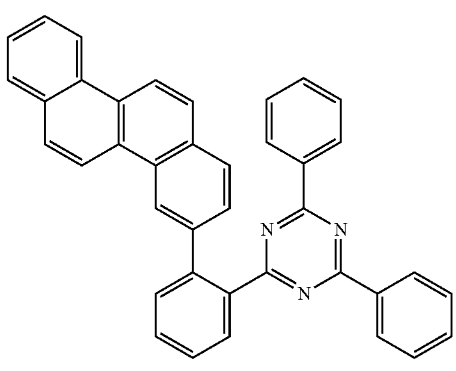
-continued
H2-40
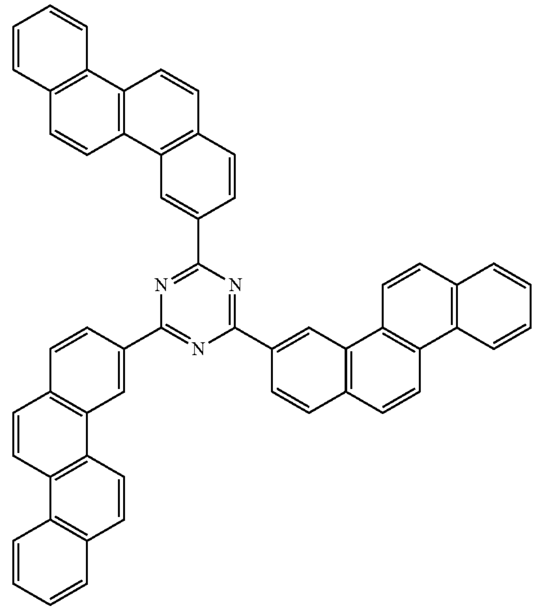
H2-41
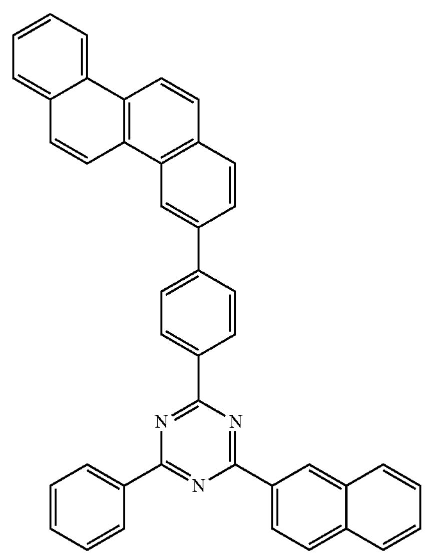

-continued
H2-42
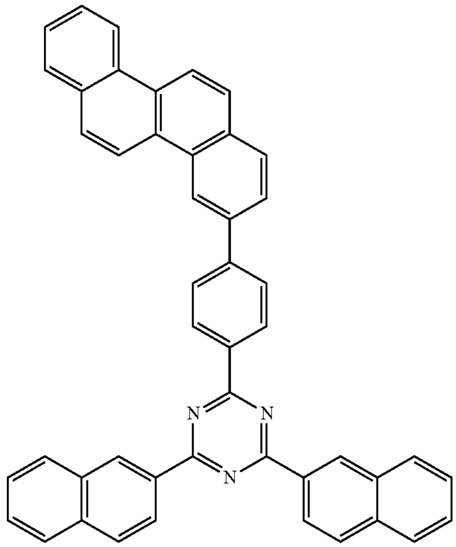
H2-43
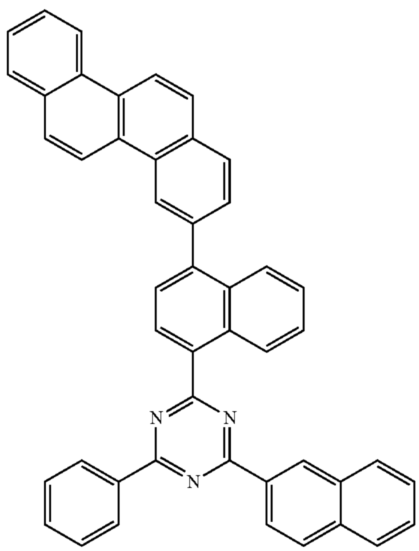
H2-44
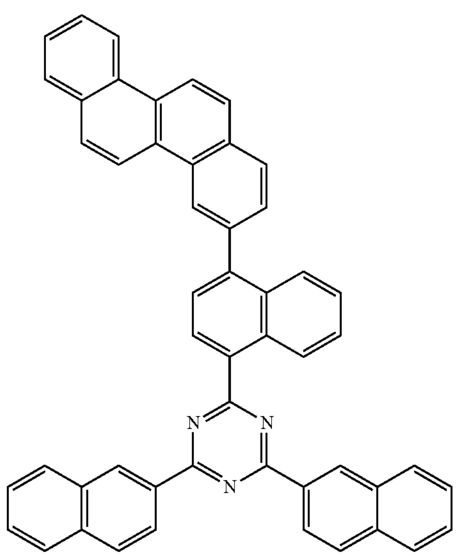
-continued
H2-45
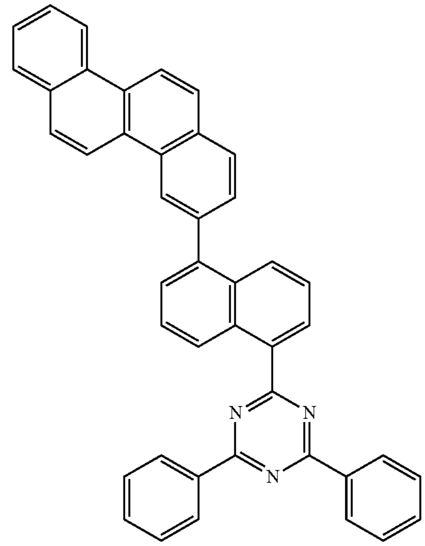
H2-46
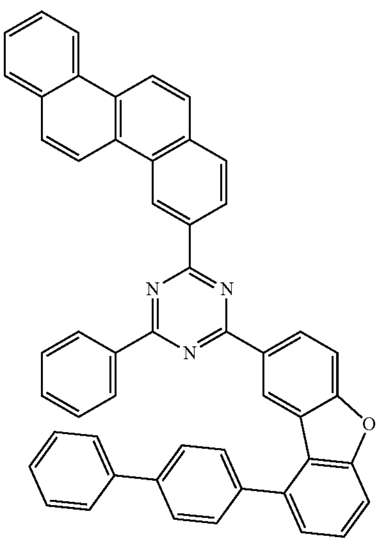
H2-47
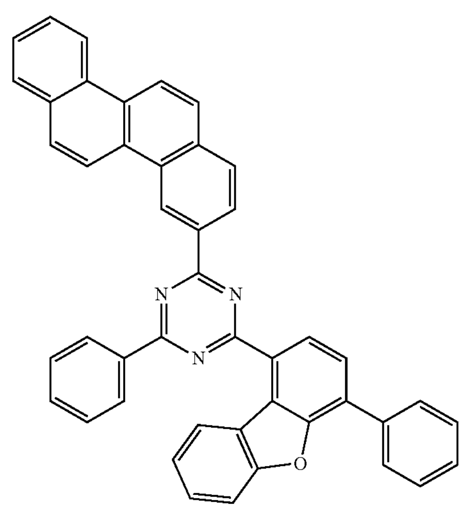

-continued
H2-48
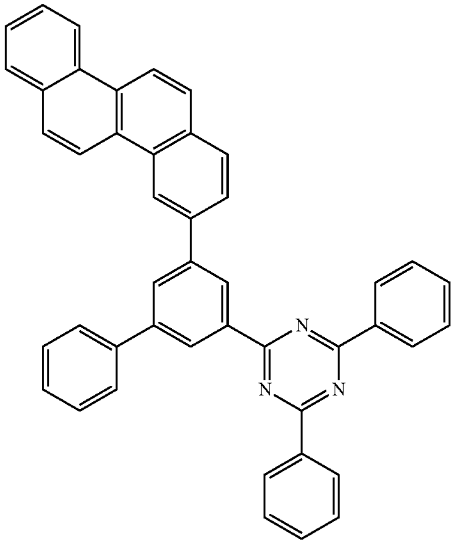
H2-49
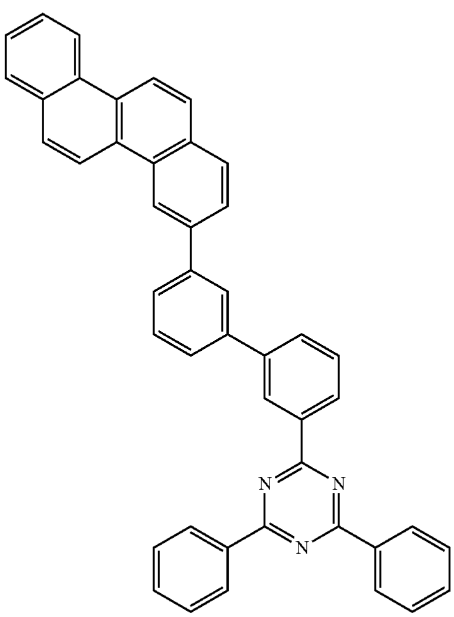
-continued
H2-50
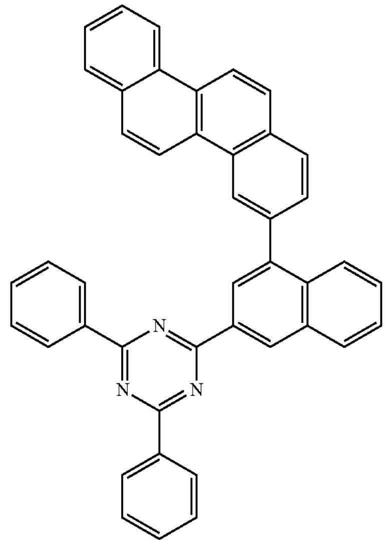
H2-51
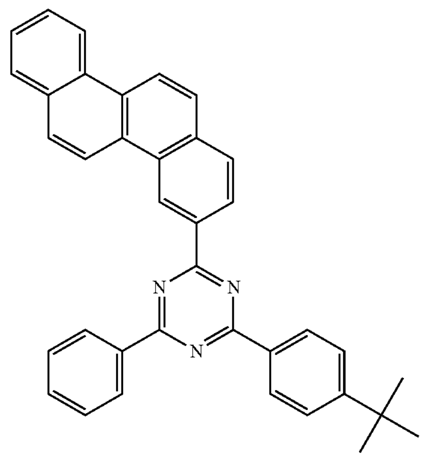
H2-52
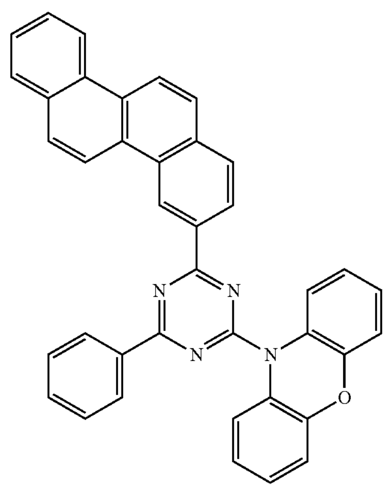

-continued
H2-53
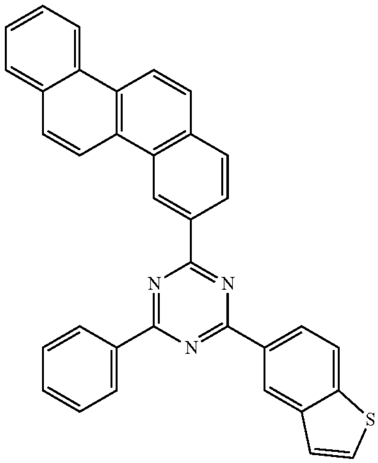
H2-54
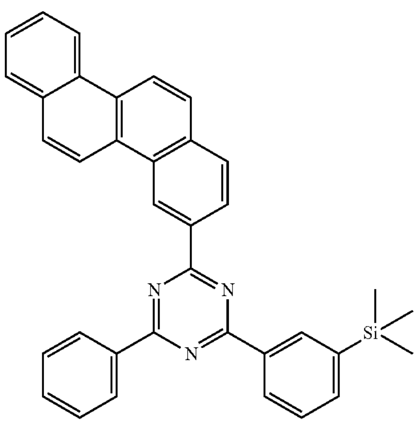
H2-55
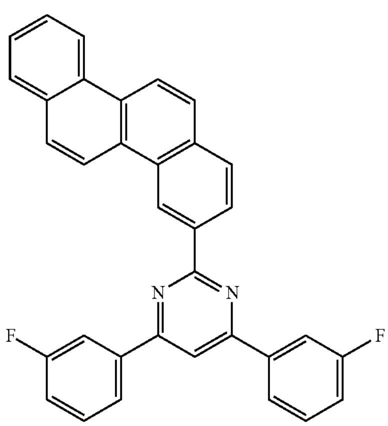
-continued
H2-56
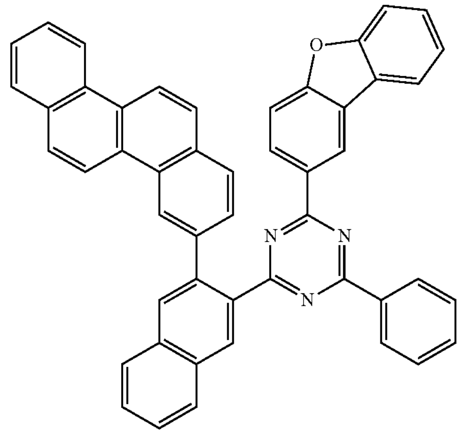
H2-57
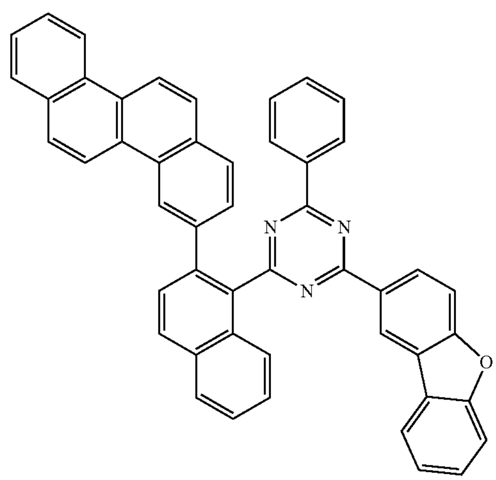
H2-58
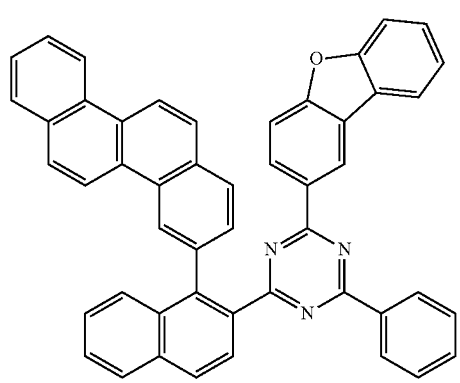

H2-59
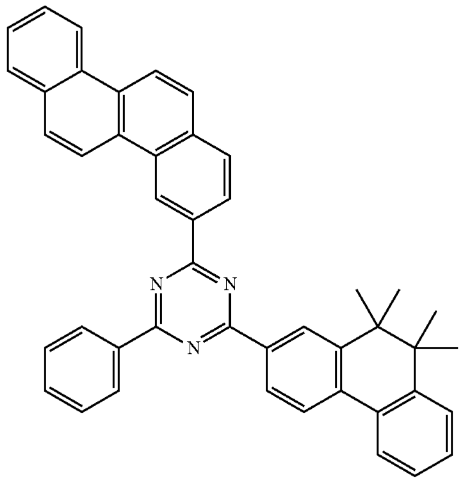
H2-60
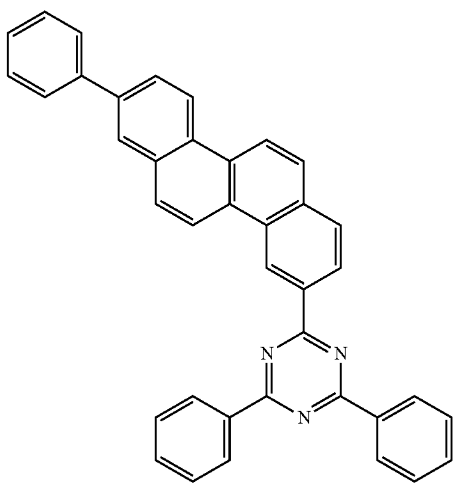
H2-61
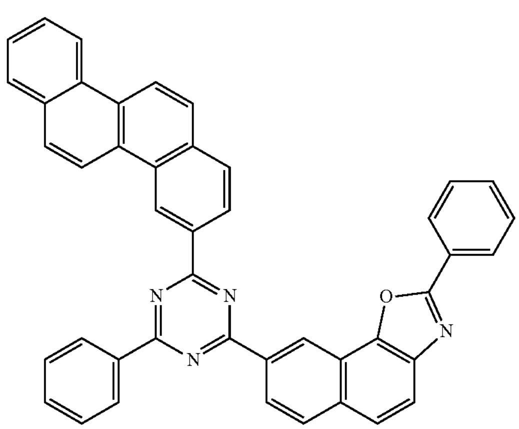
H2-62
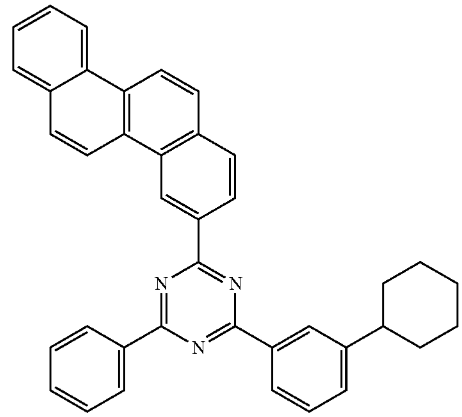
H2-63
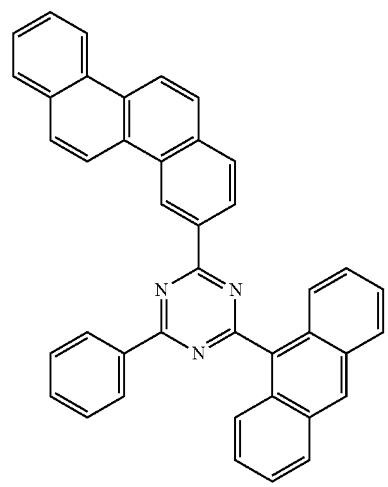
H2-64
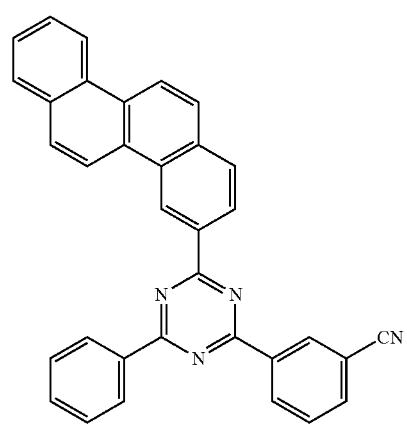

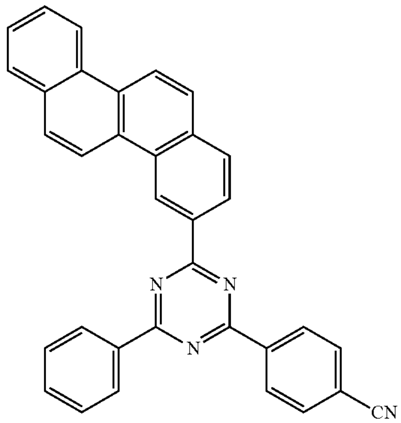
H2-65
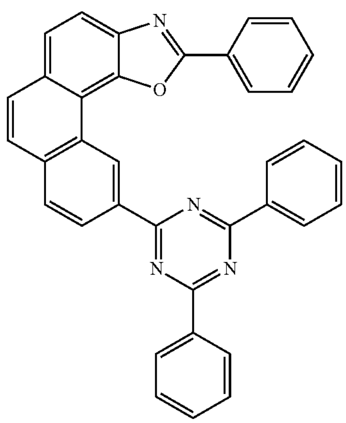
H2-66
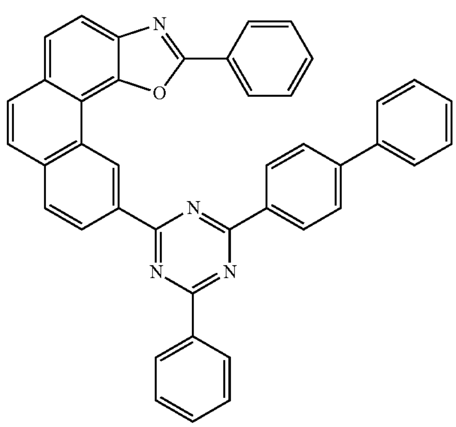
H2-67
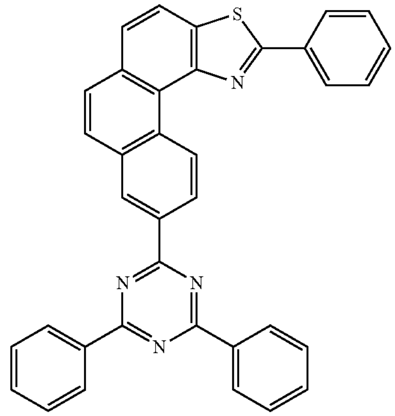
H2-68
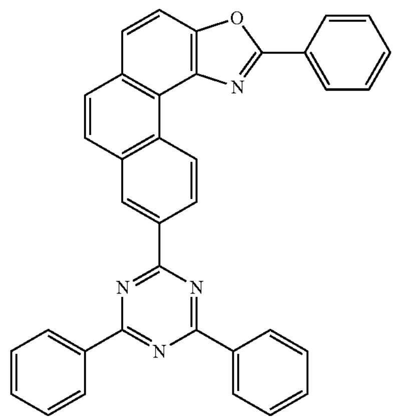
H2-69
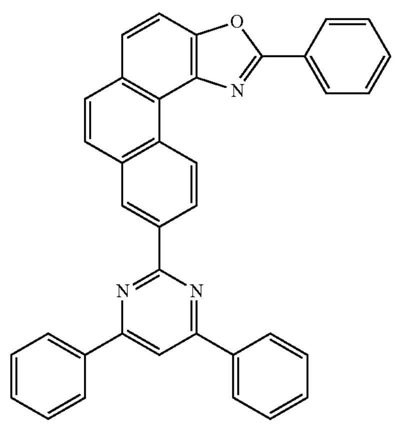
H2-70
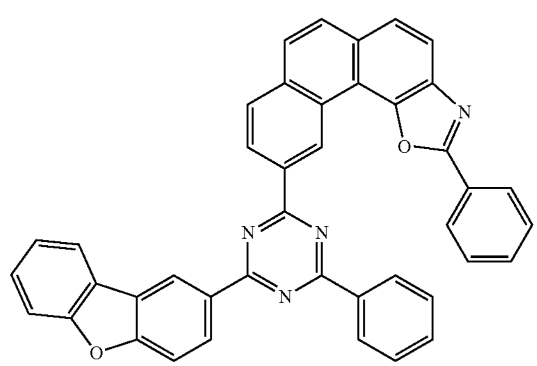
H2-71

-continued
H2-72
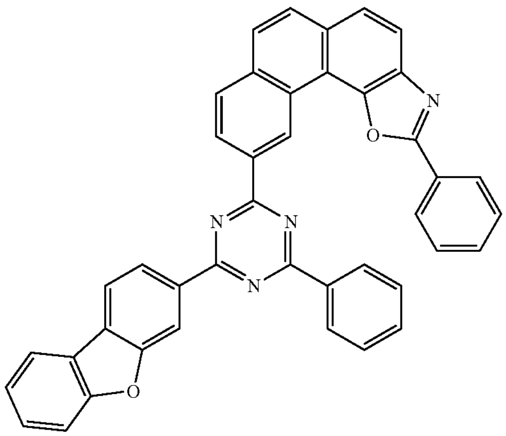
H2-73
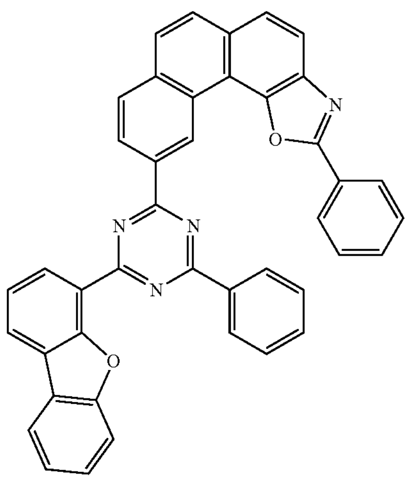
H2-74
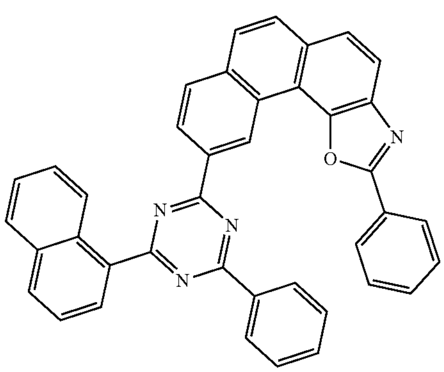
-continued
H2-75
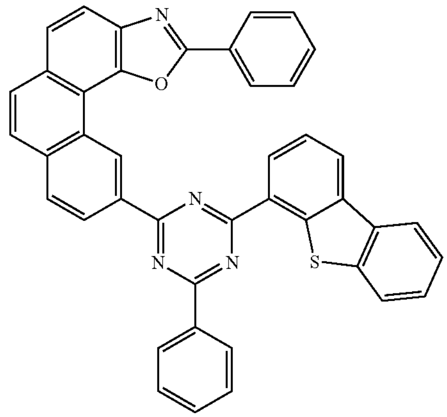
H2-76
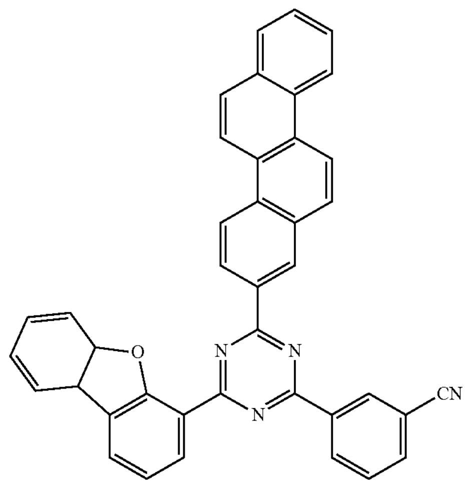
H2-77
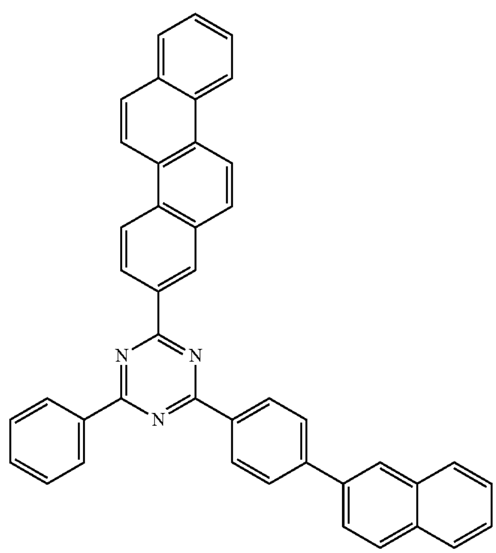

-continued
H2-78
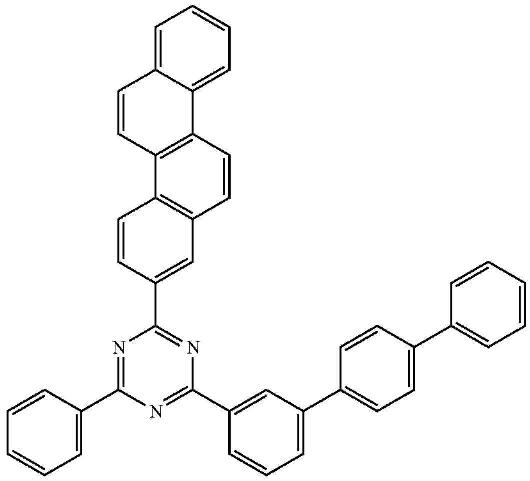
H2-79
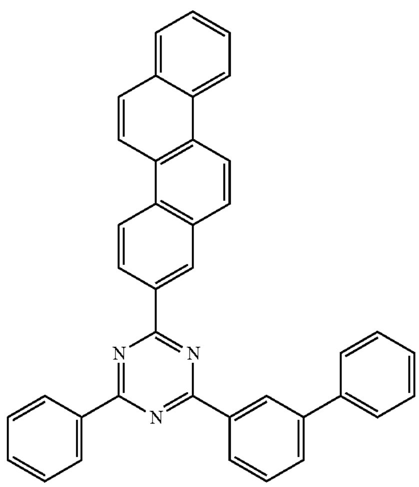
H2-80
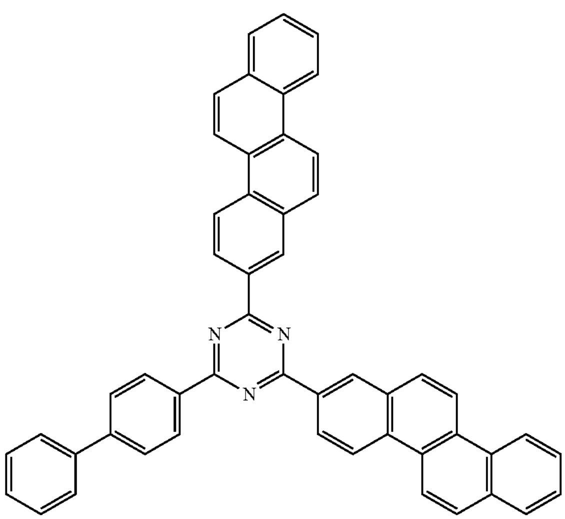
-continued
H2-81
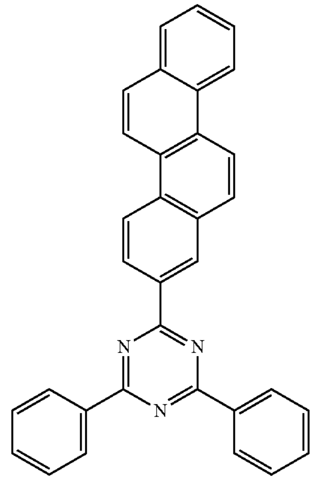
H2-82
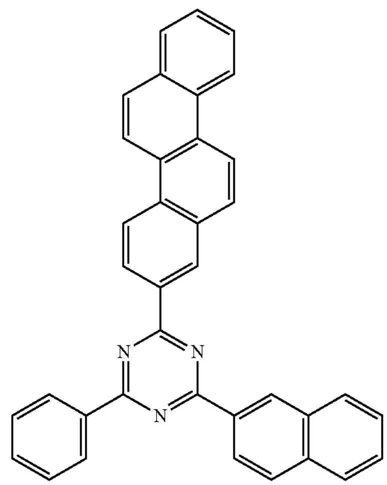
H2-83
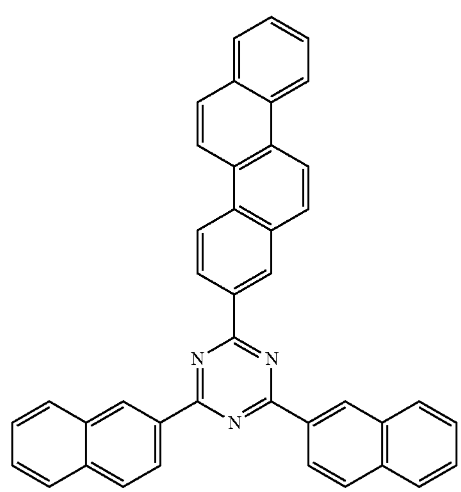

-continued
H2-84
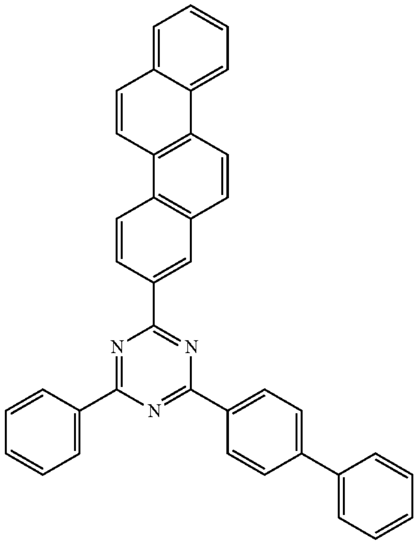
H2-85
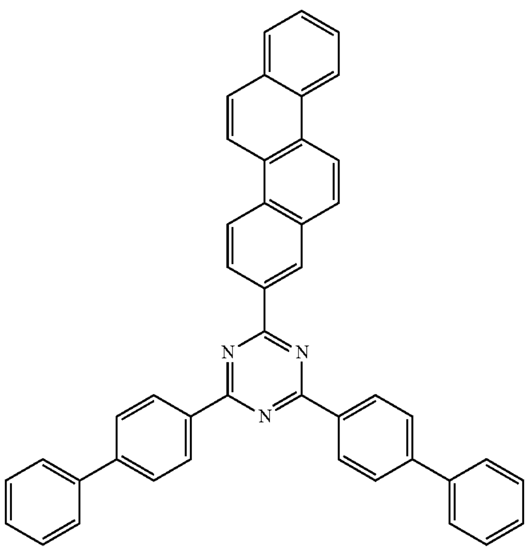
H2-86
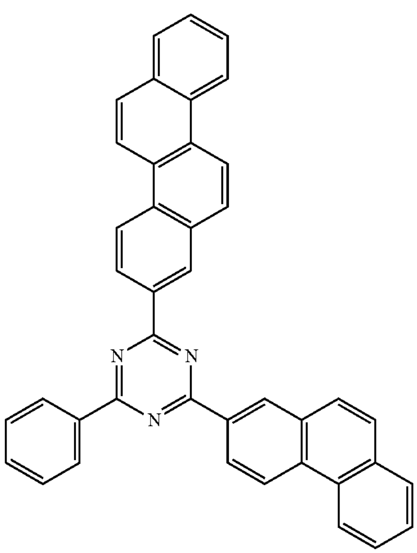
-continued
H2-87
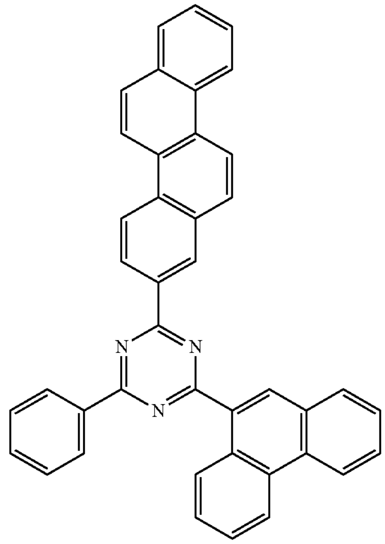
H2-88
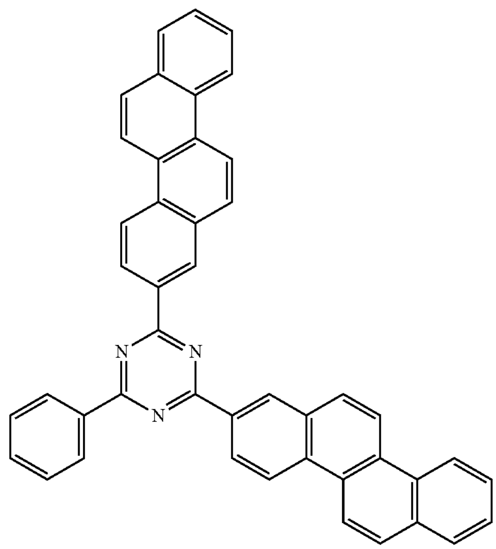
H2-89
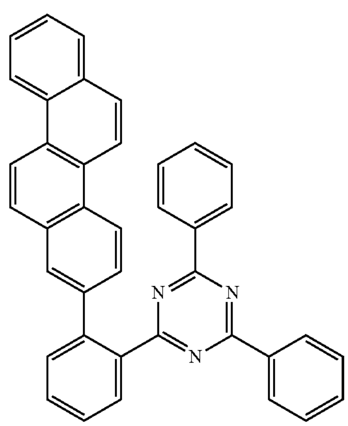

-continued
H2-90
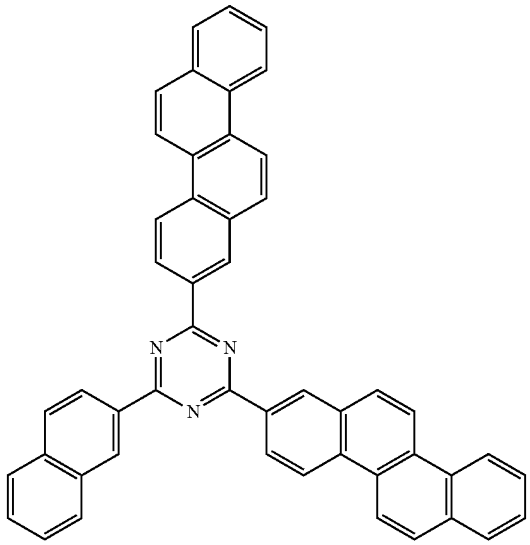
H2-91
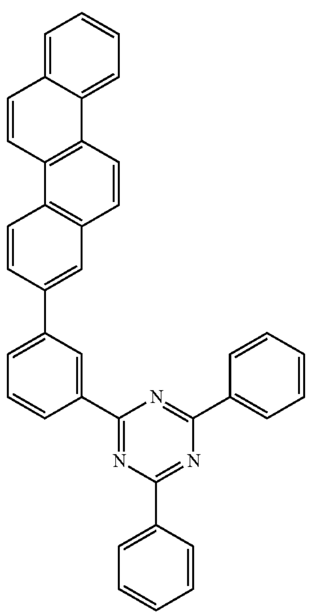
-continued
H2-92
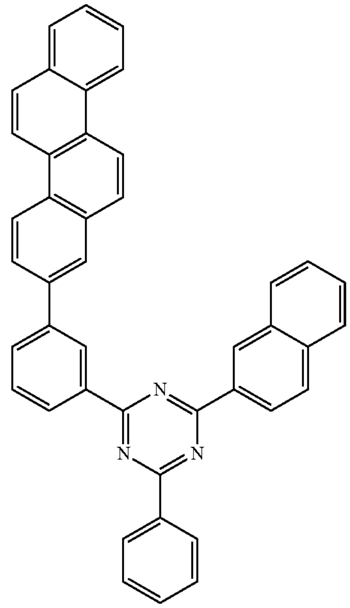
H2-93
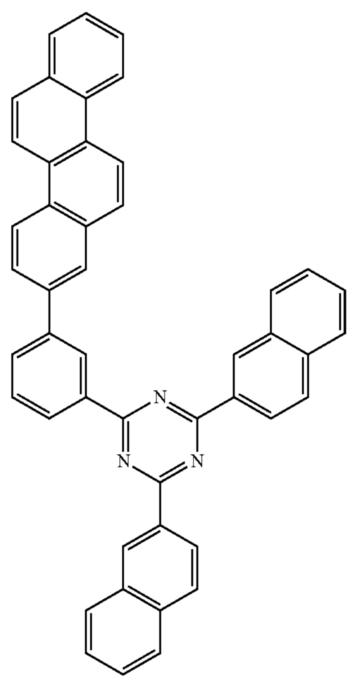

-continued
H2-94
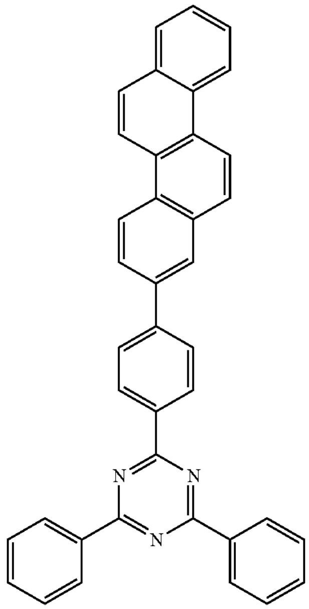
H2-95
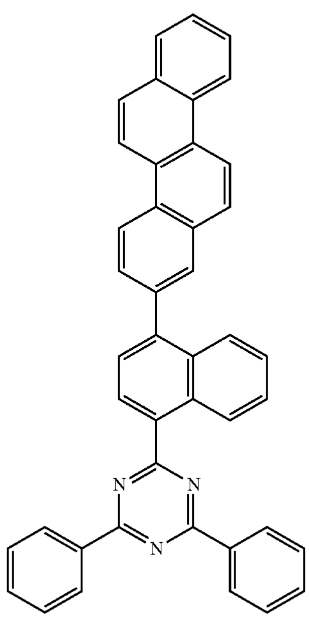
-continued
H2-96
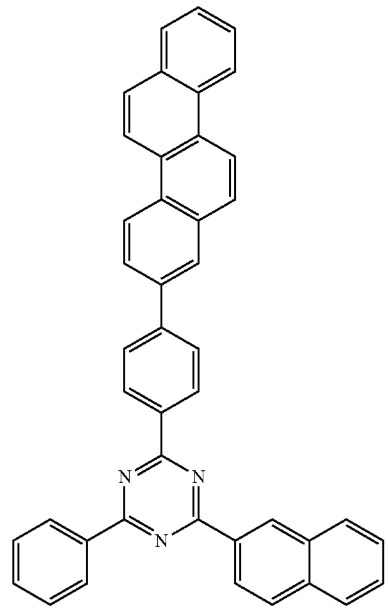
H2-97
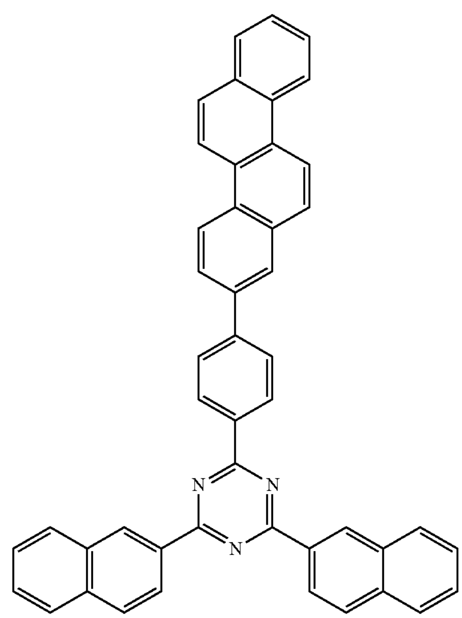

-continued
H2-98
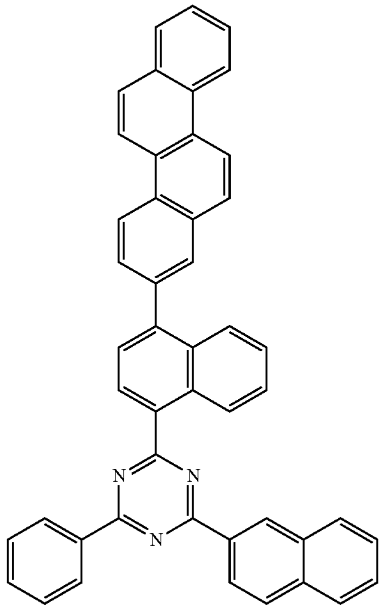
H2-99
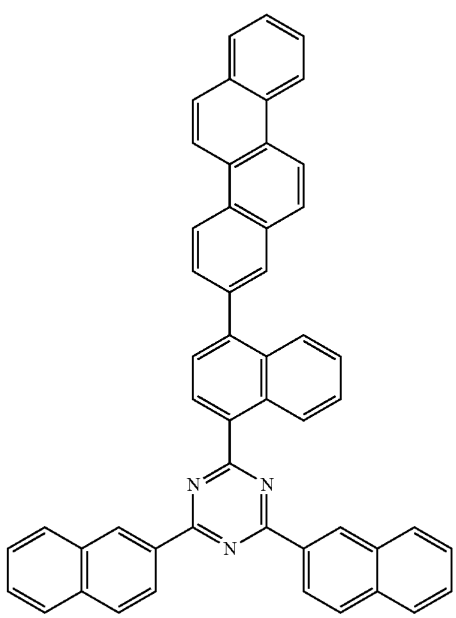
-continued
H2-100
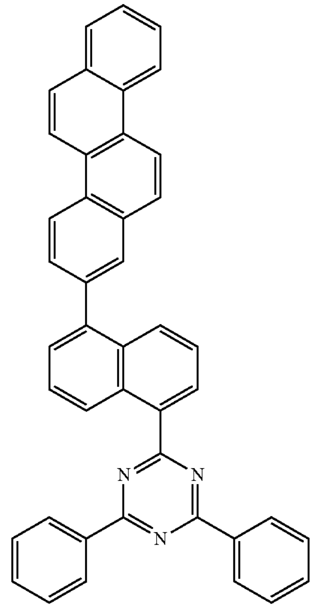
H2-101
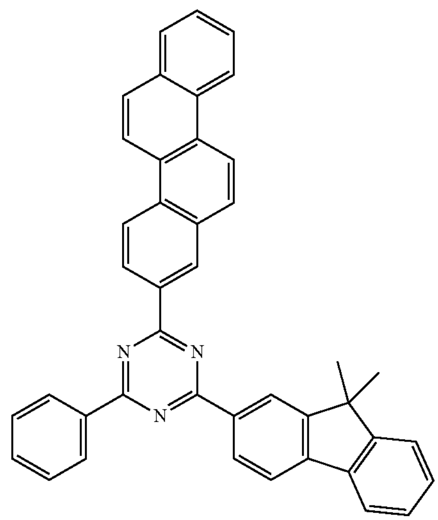
H2-102
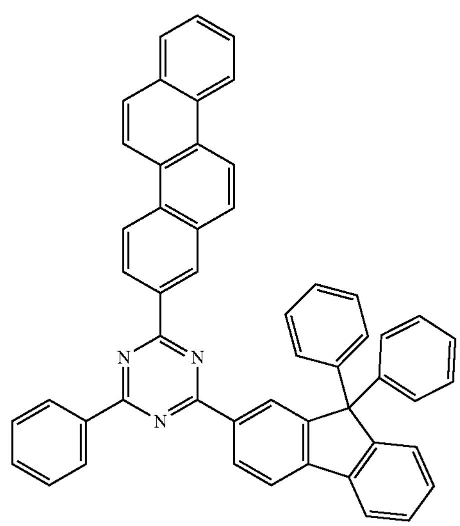

-continued
H2-103
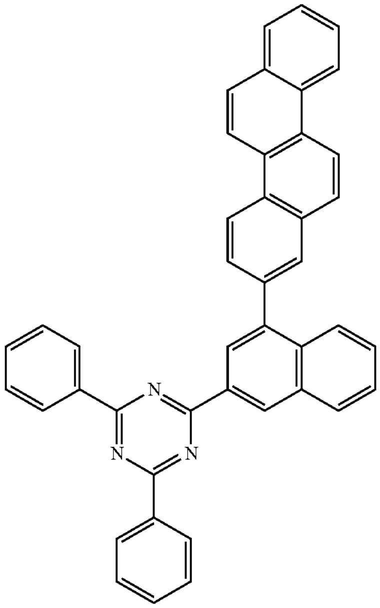
H2-104
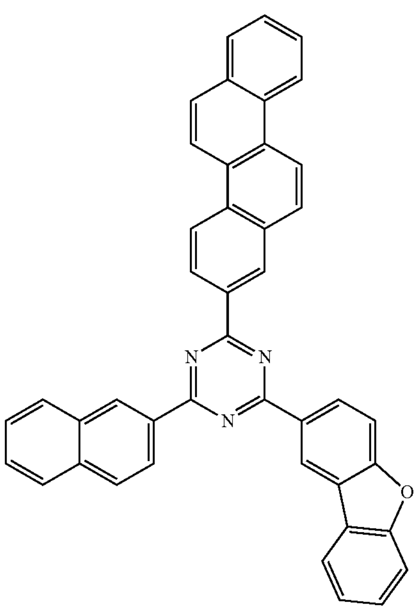
-continued
H2-105
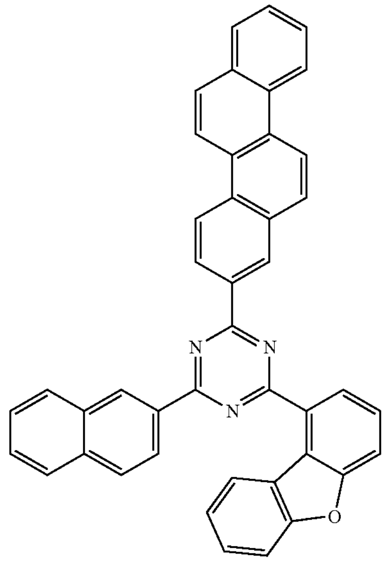
H2-106
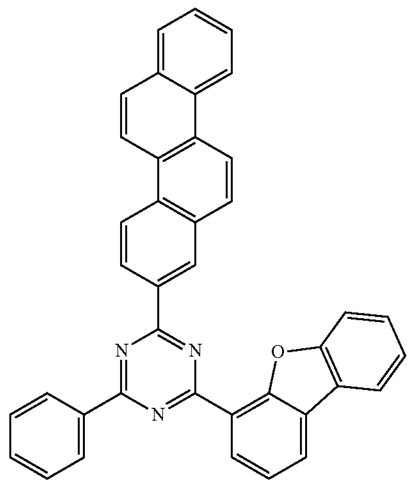
H2-107
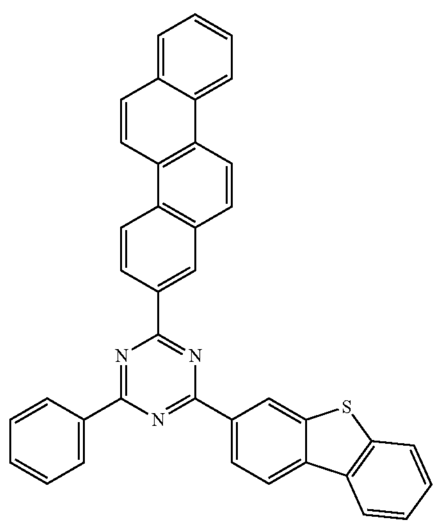

-continued
H2-108
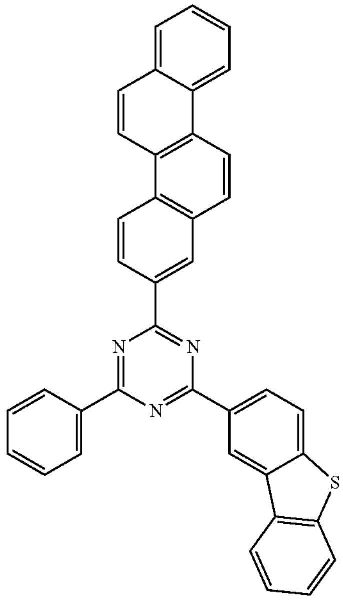
H2-109
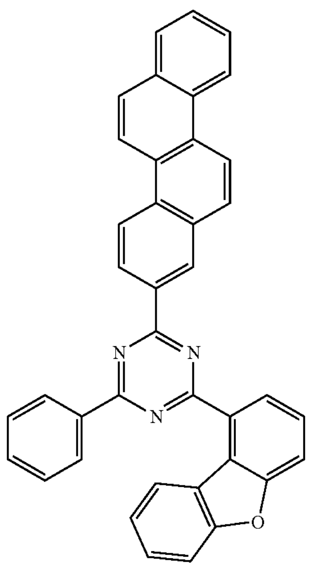
H2-110
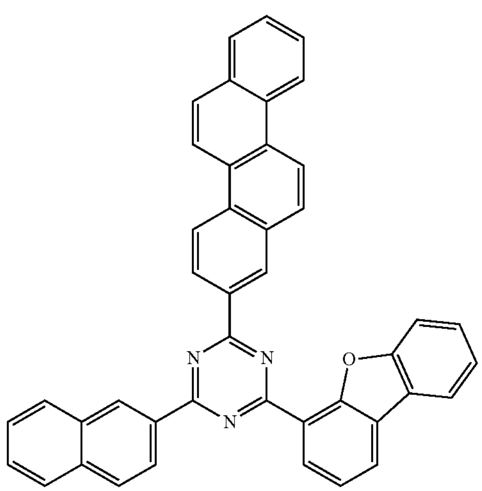
-continued
H2-111
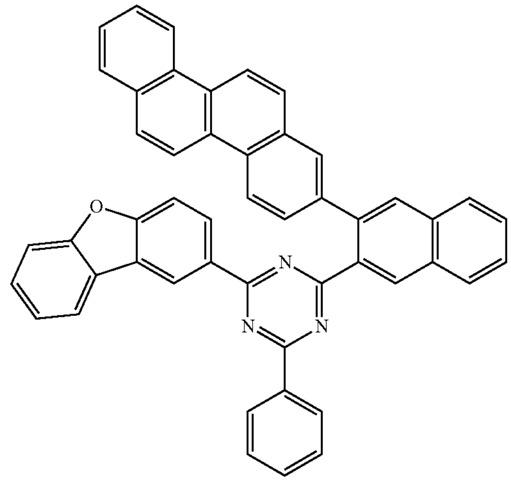
H2-112
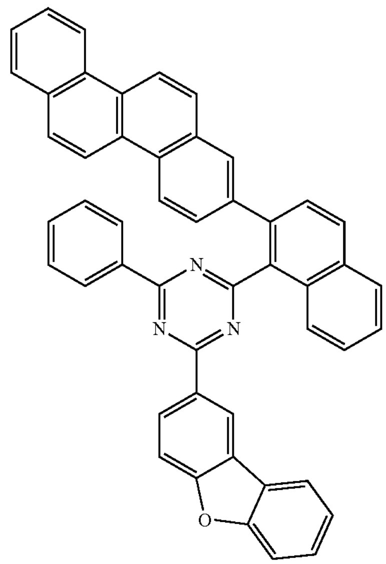
H2-113
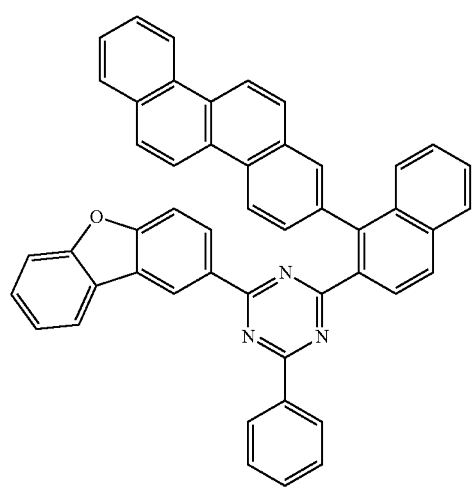

-continued
H2-114
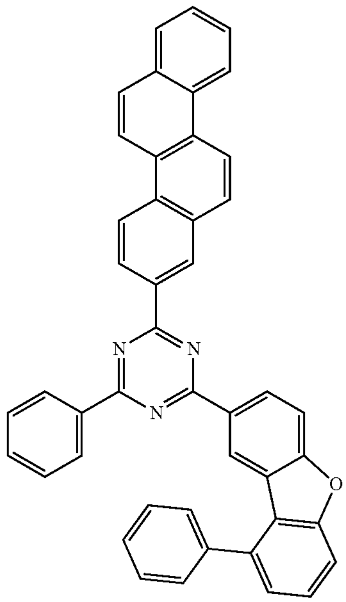
H2-115
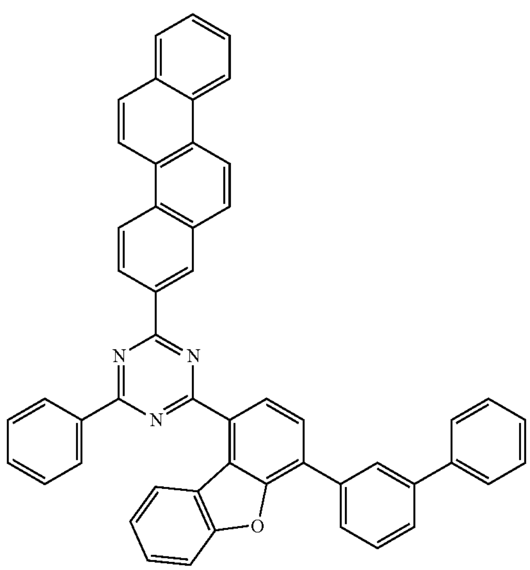
-continued
H2-116
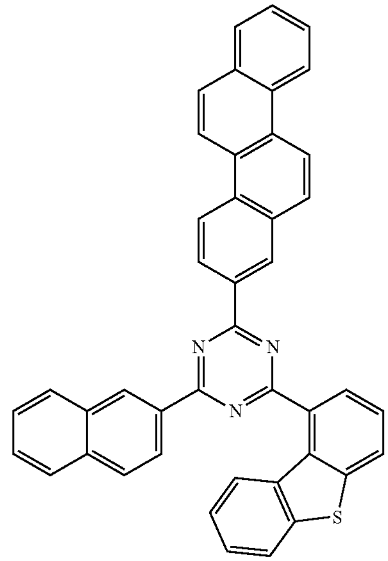
H2-117
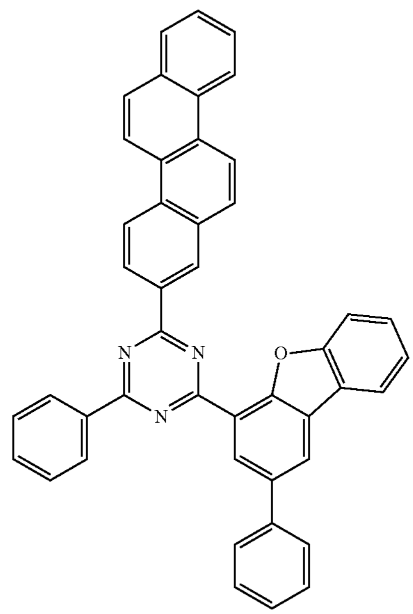
H2-118
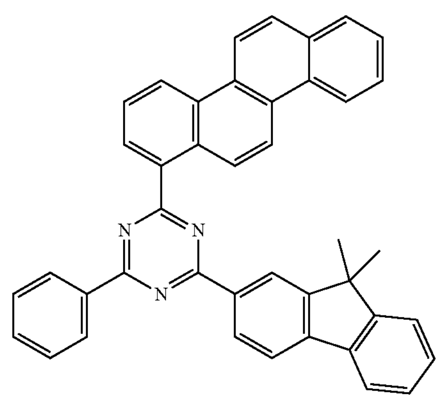

-continued
H2-119
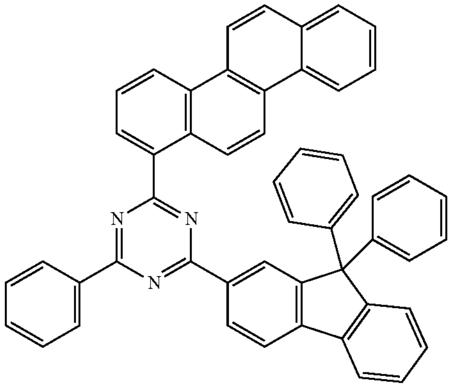
H2-120
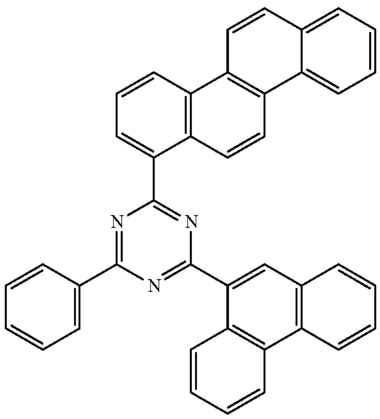
H2-121
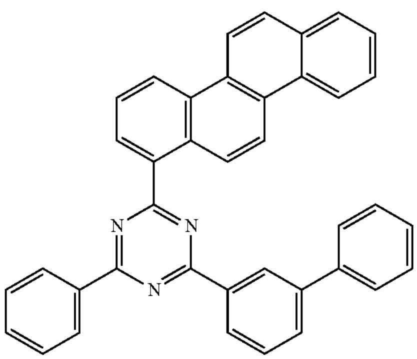
H2-122
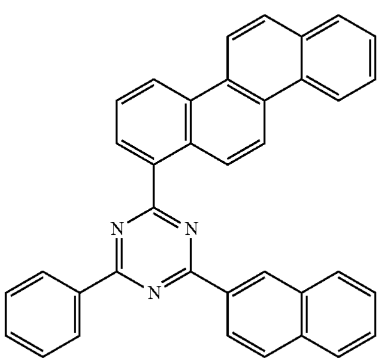
-continued
H2-123
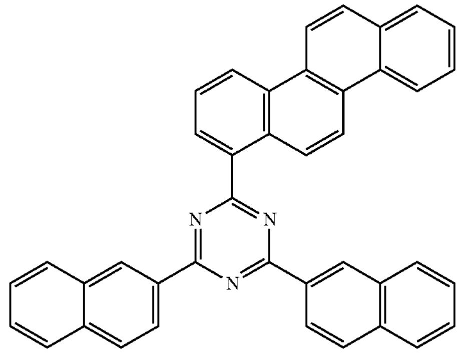
H2-124
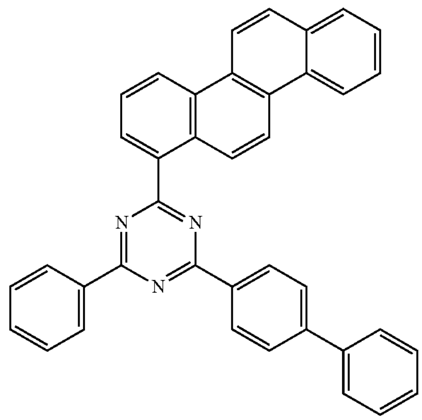
H2-125
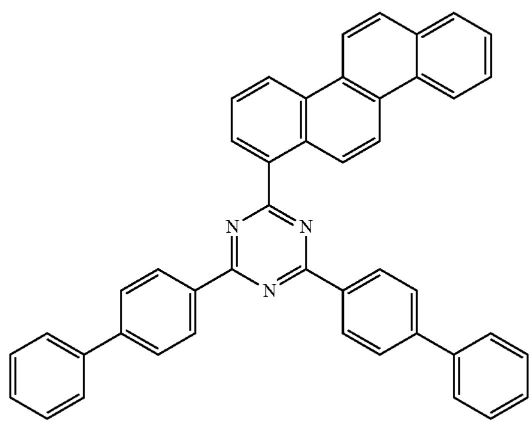
H2-126
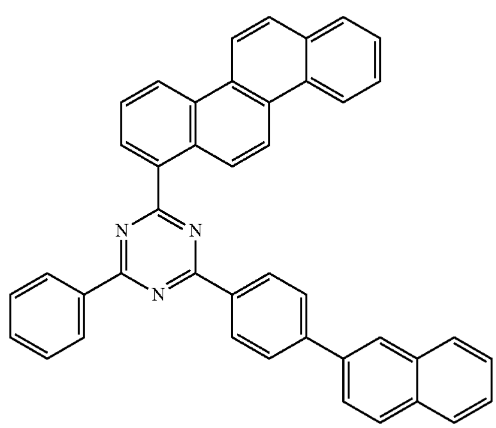

-continued
H2-127
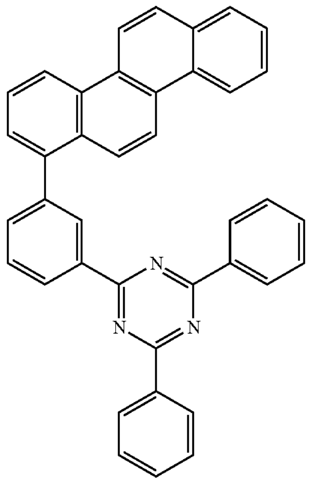
H2-128
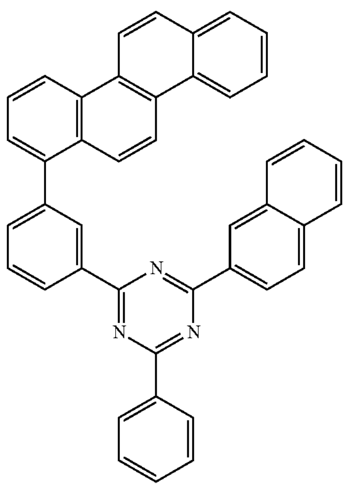
H2-129
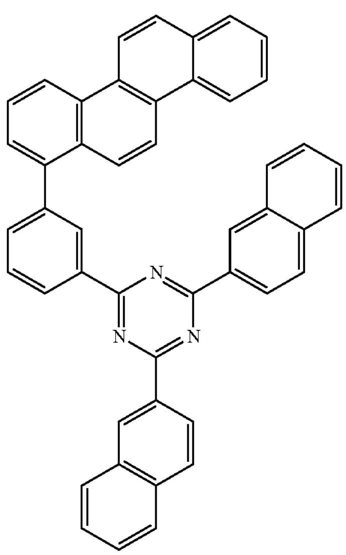
-continued
H2-130
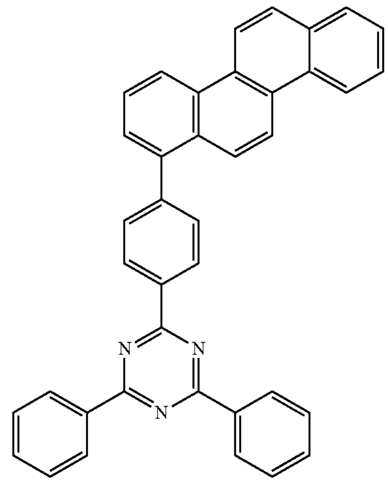
H2-131
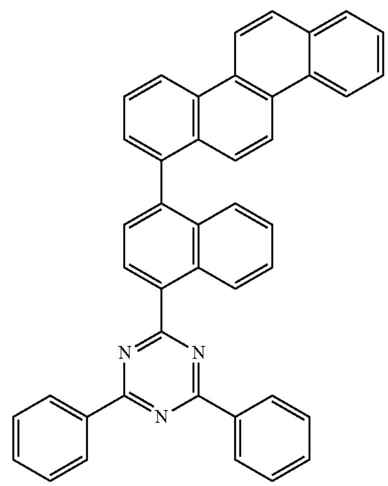
H2-132
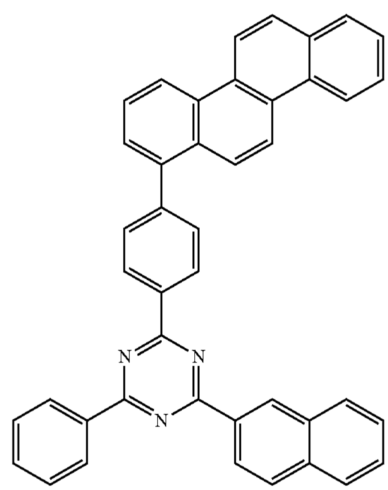

-continued
H2-133
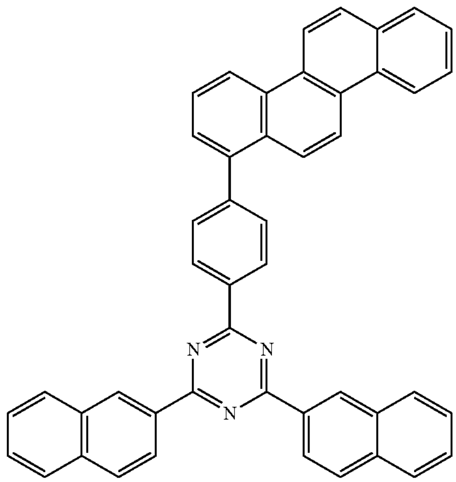
H2-134
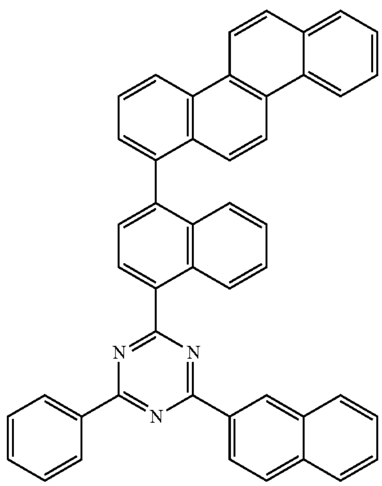
H2-135
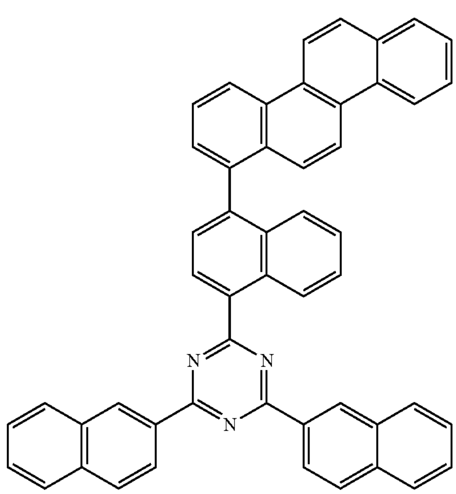
-continued
H2-136
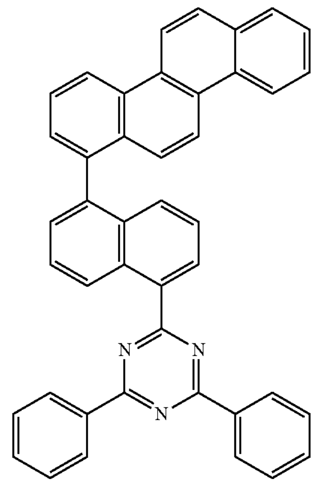
H2-137
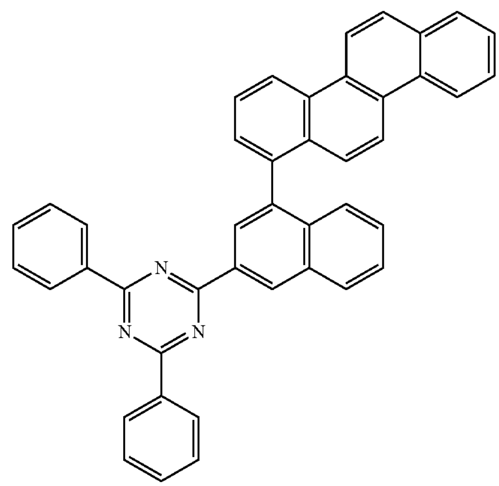
H2-138
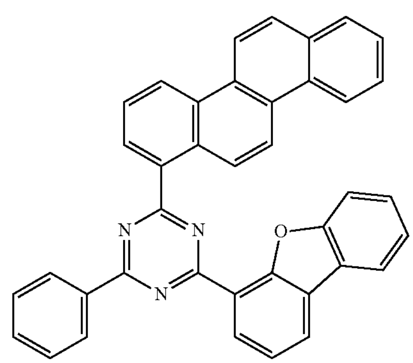

-continued
H2-139
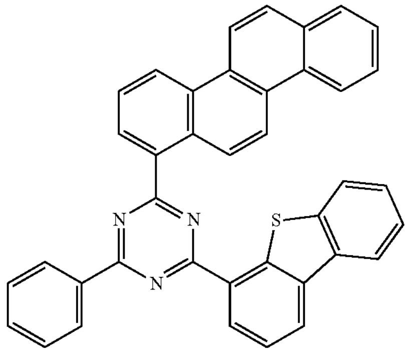
H2-140
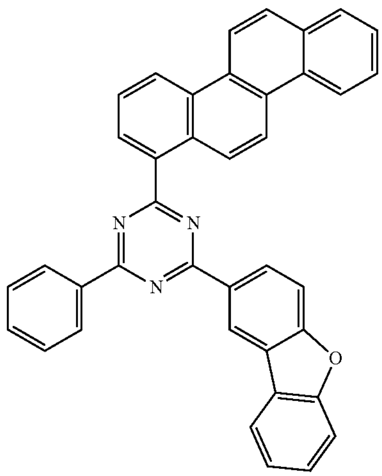
H2-141
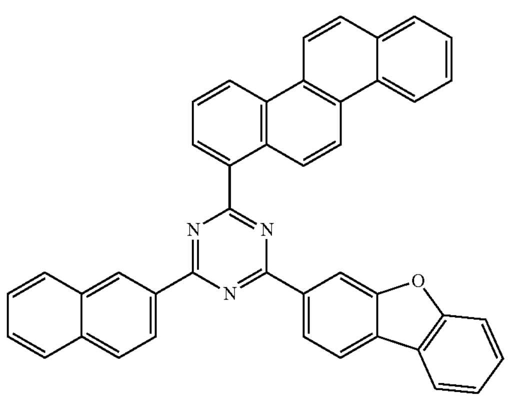
-continued
H2-142
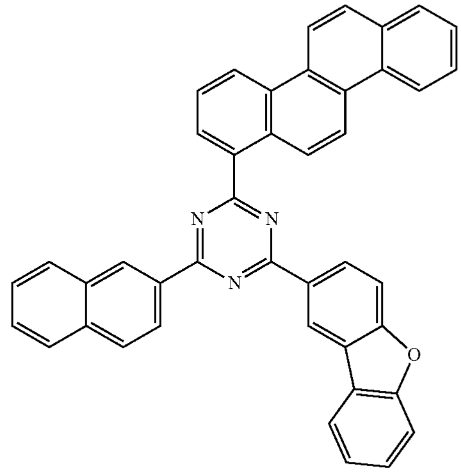
H2-143
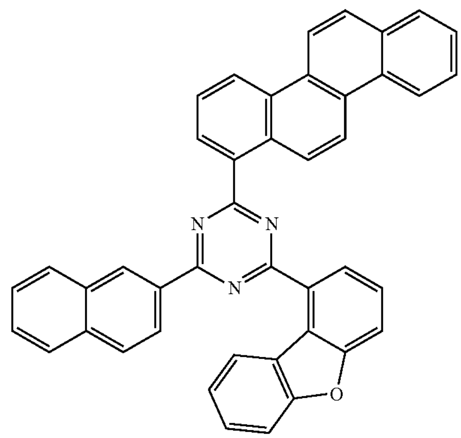
H2-144
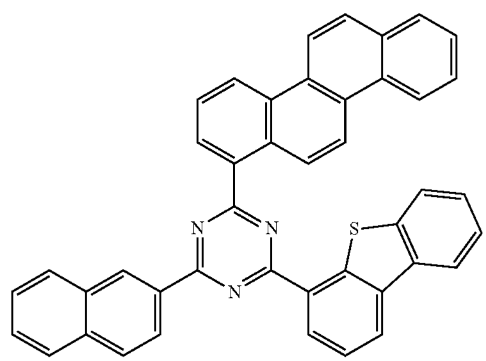

-continued
H2-145
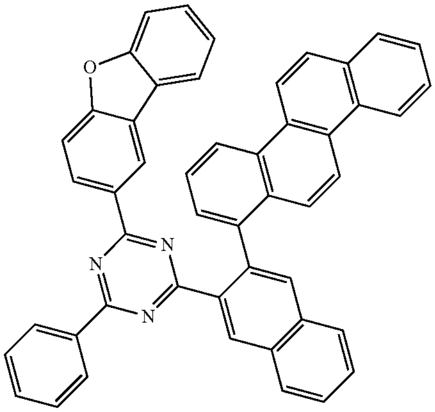
H2-146
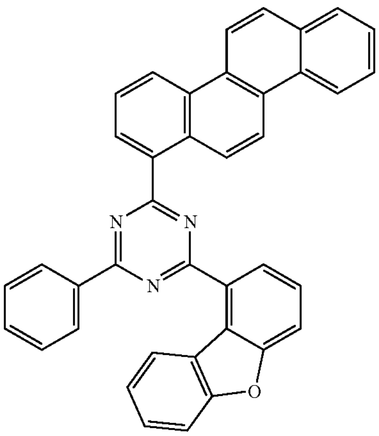
H2-147
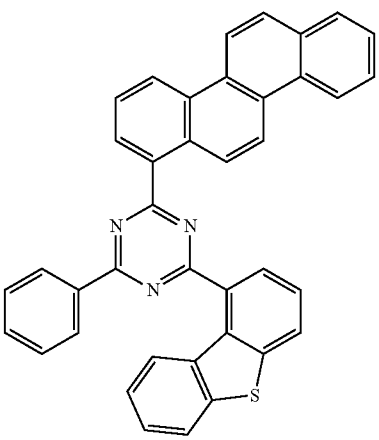
H2-148
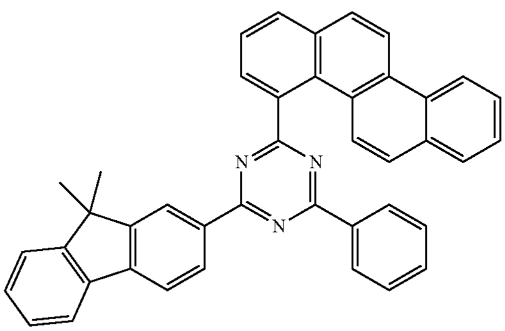
-continued
H2-149
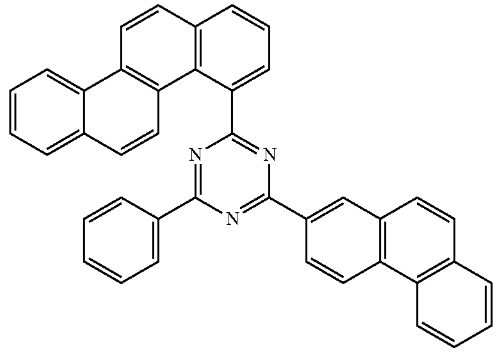
H2-150
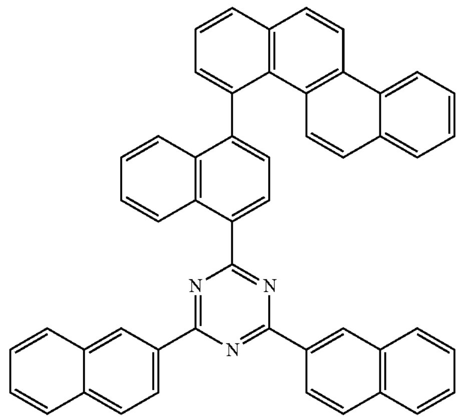
H2-151
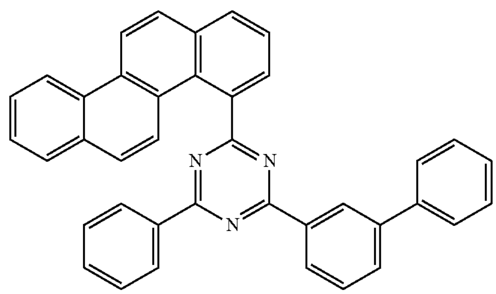
H2-152
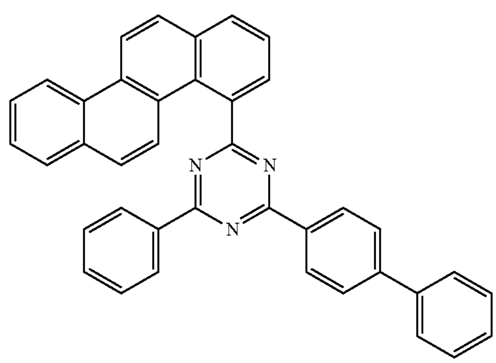

-continued
H2-153
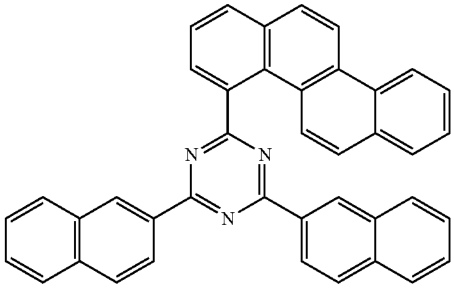
H2-154
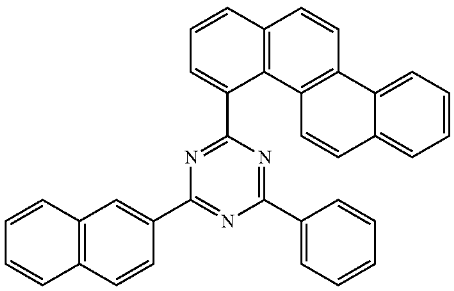
H2-155
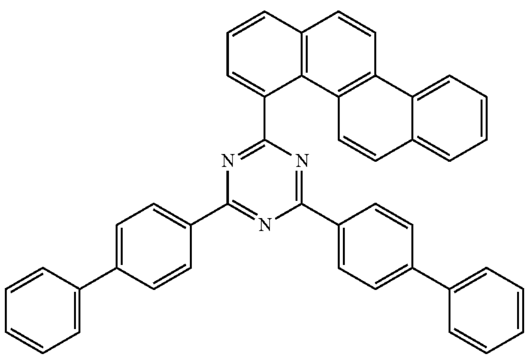
H2-156
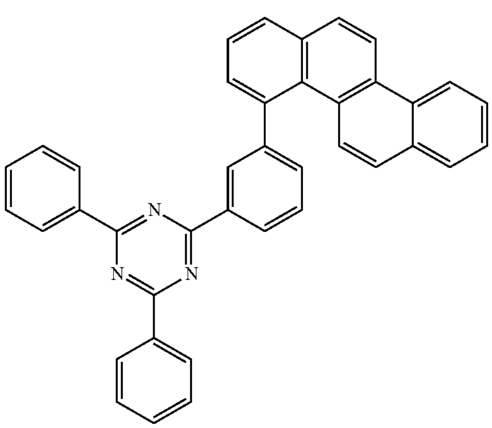
-continued
H2-157
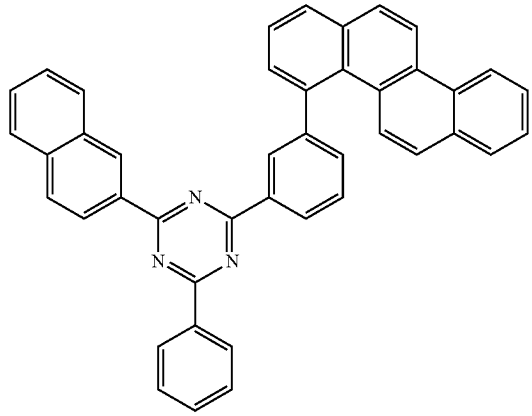
H2-158
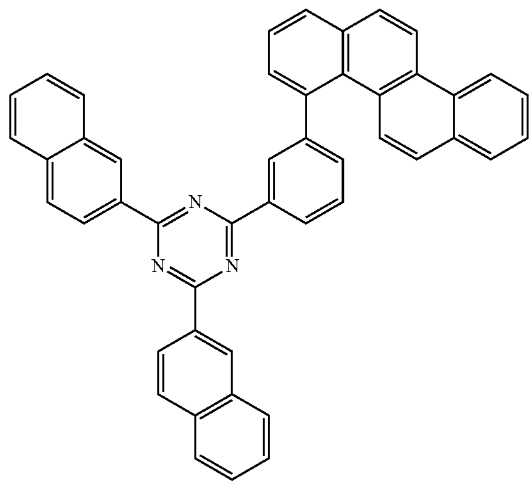
H2-159
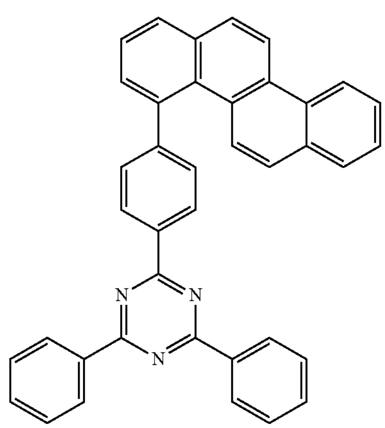

-continued
H2-160
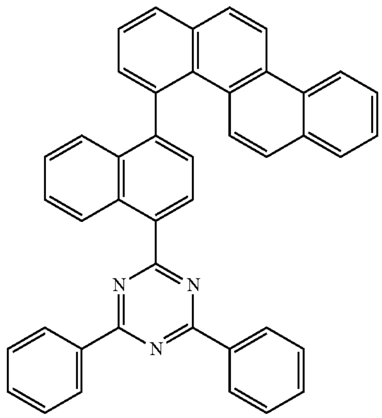
H2-161
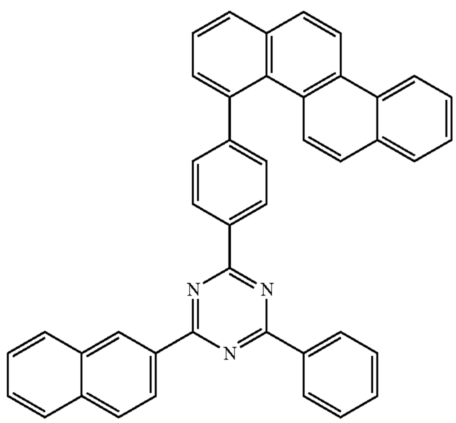
H2-162
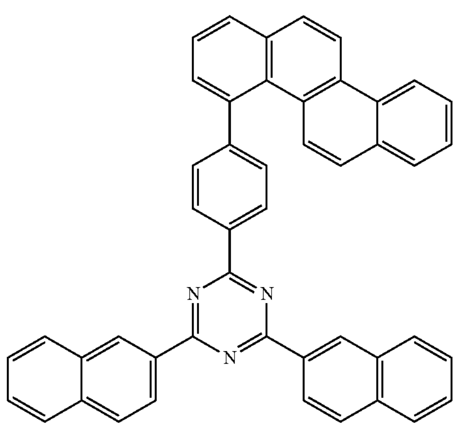
-continued
H2-163
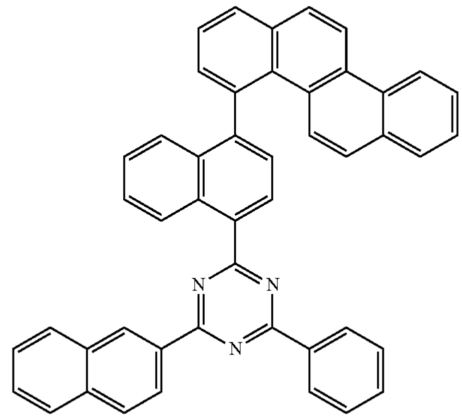
H2-164
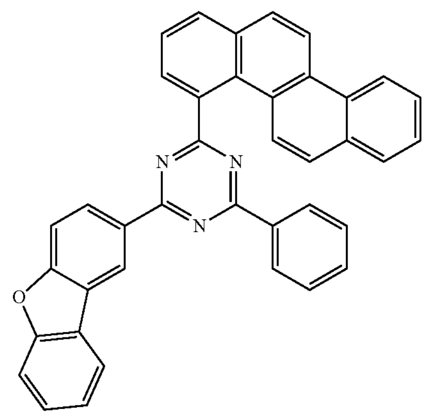
H2-165
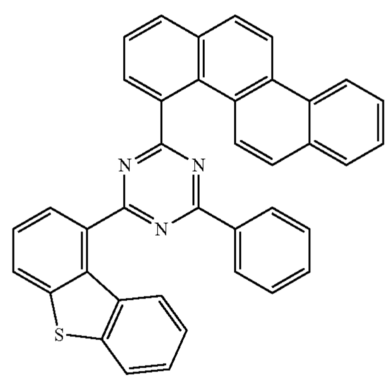
H2-166
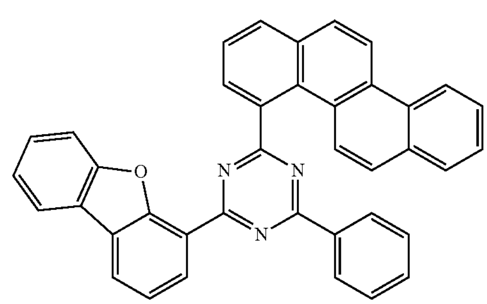

-continued
H2-167
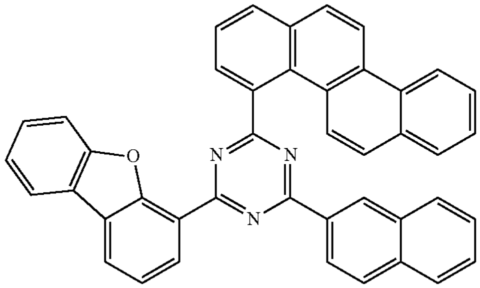
H2-168
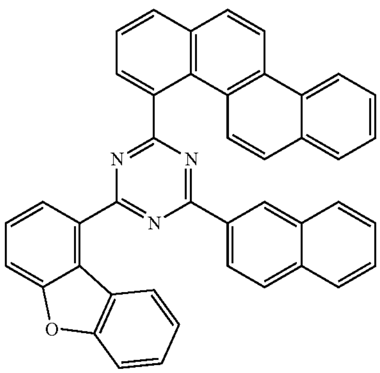
H2-169
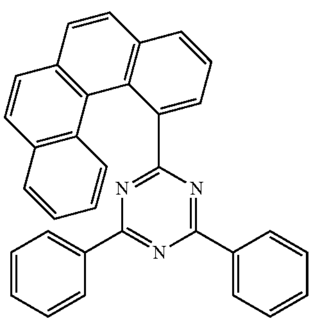
H2-170
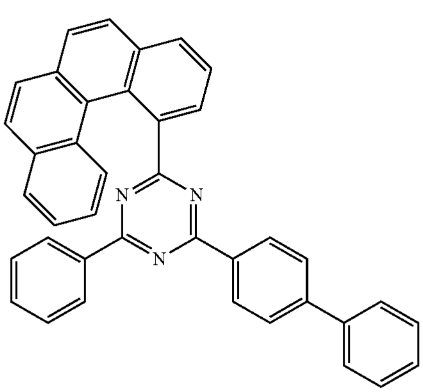
-continued
H2-171
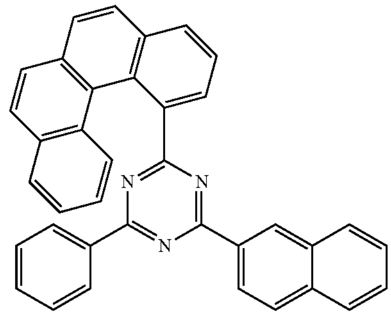
H2-172
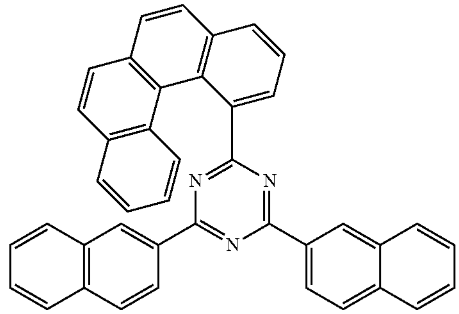
H2-173
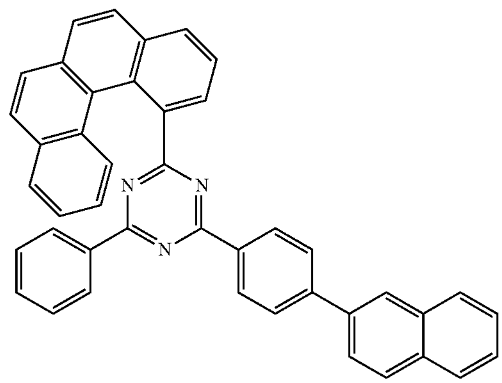
H2-174
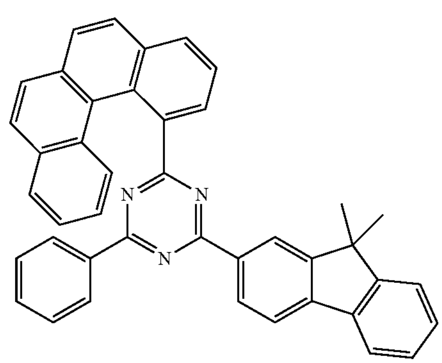

-continued
H2-175
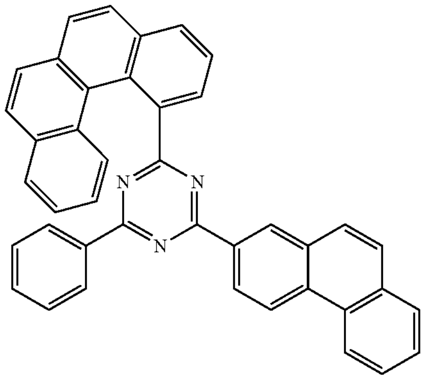
H2-176
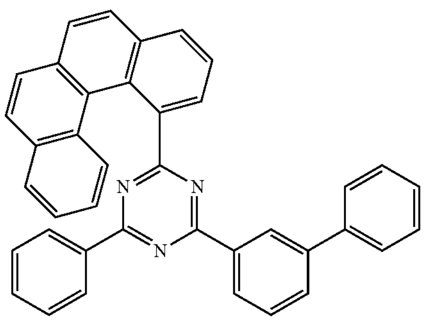
H2-177
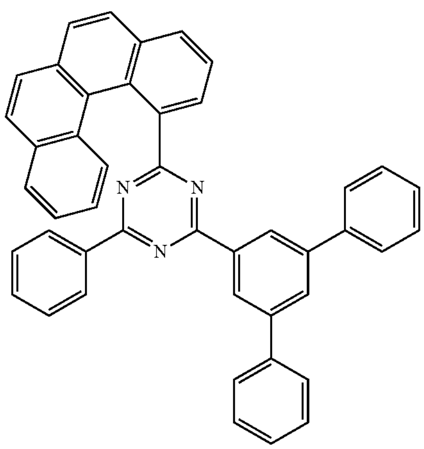
H2-178
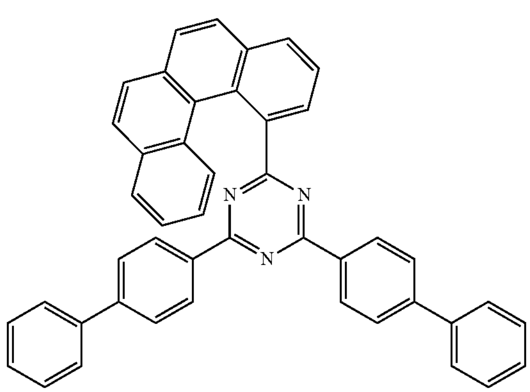
-continued
H2-179
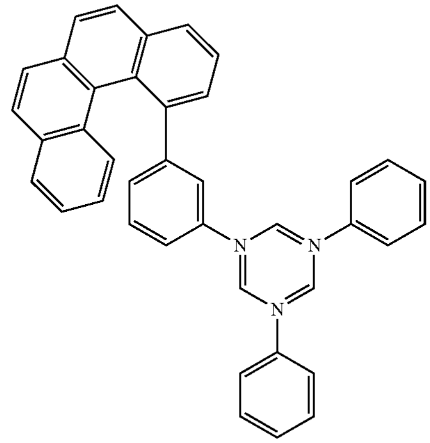
H2-180
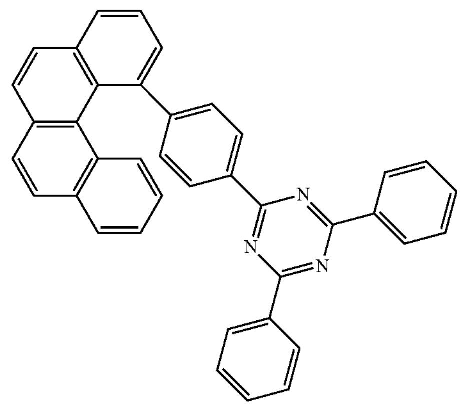
H2-181
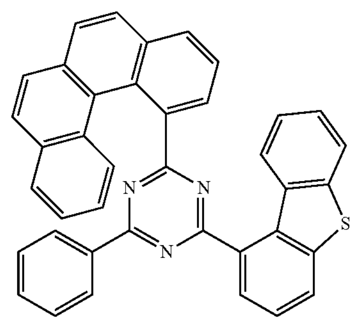
H2-182
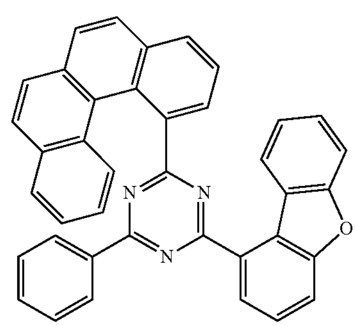

-continued
H2-183
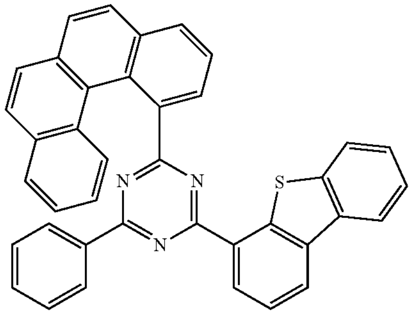
H2-184
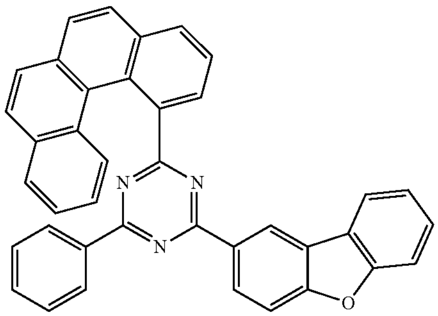
H2-185
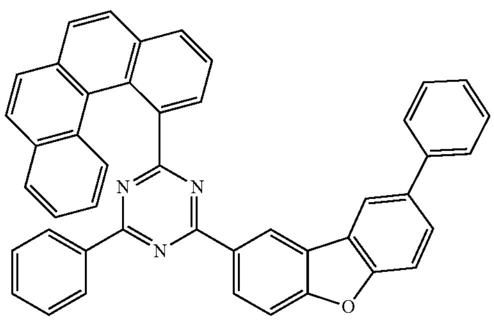
H2-186
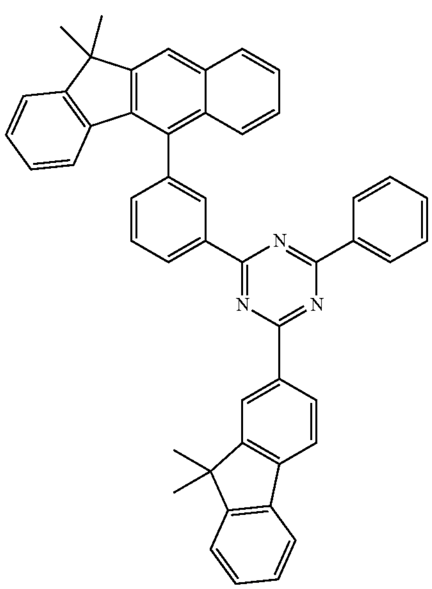
-continued
H2-187
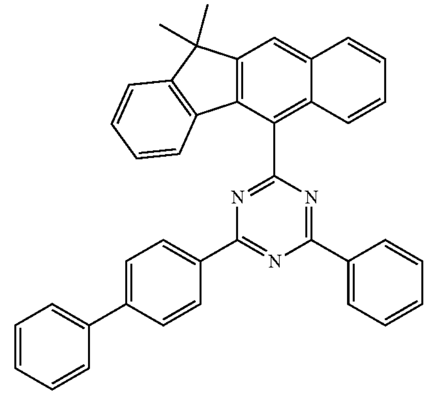
H2-188
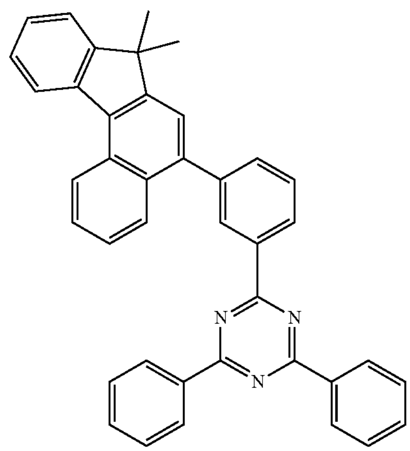
H2-189
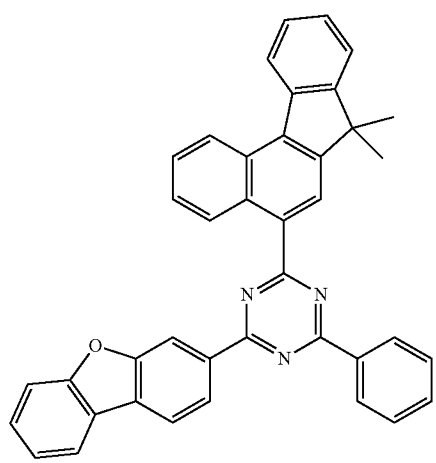

-continued
H2-190
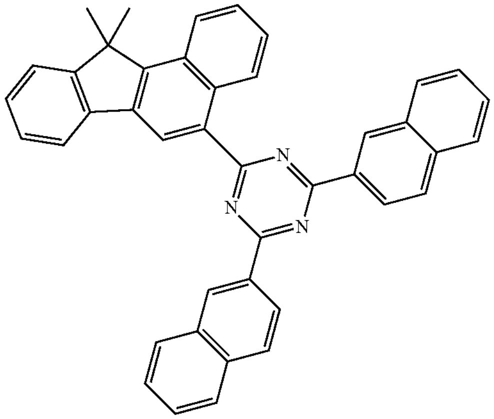
H2-191
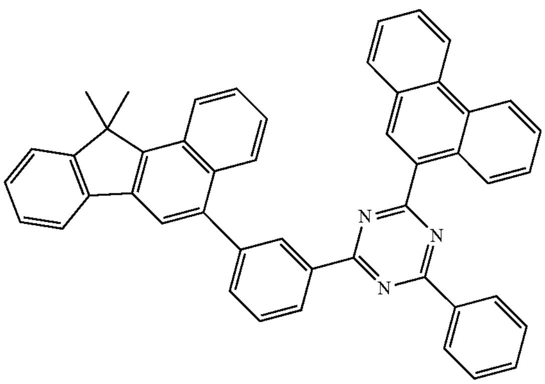
H2-192
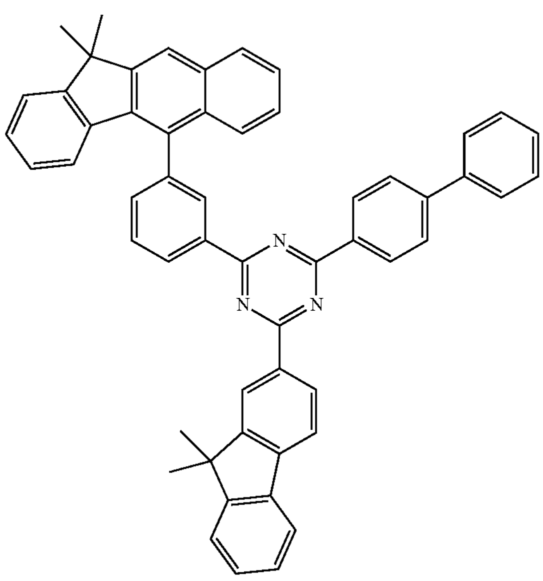
-continued
H2-193
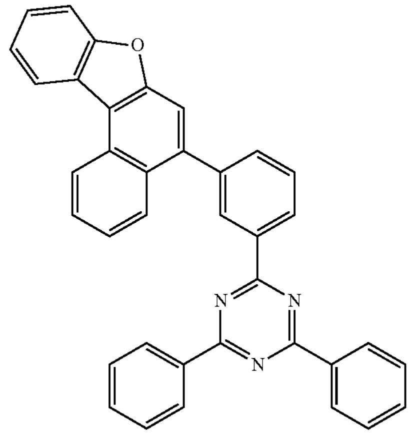
H2-194
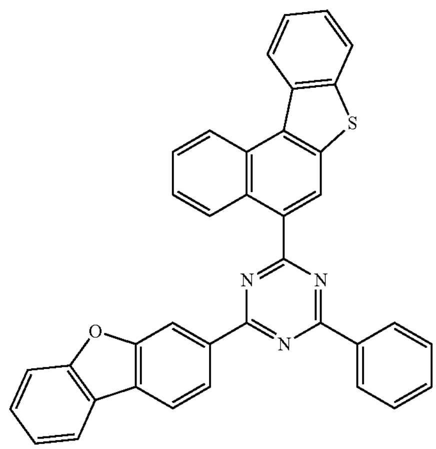
H2-195
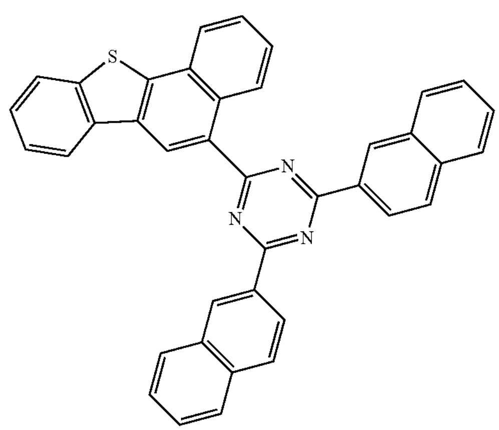

-continued
H2-196
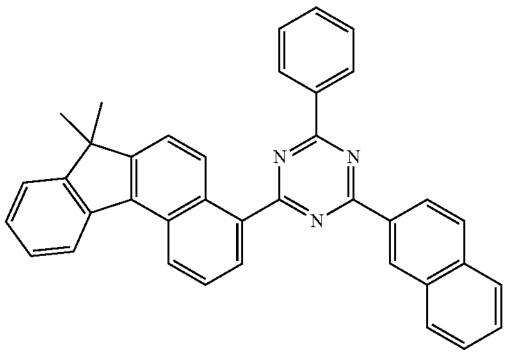
H2-197
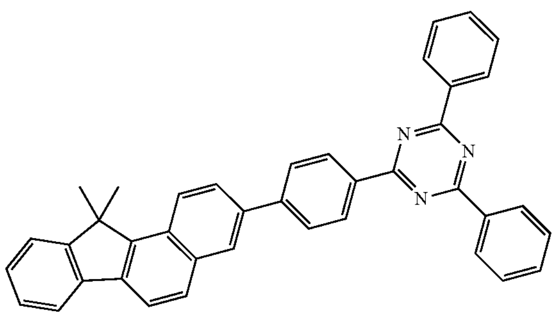
H2-198
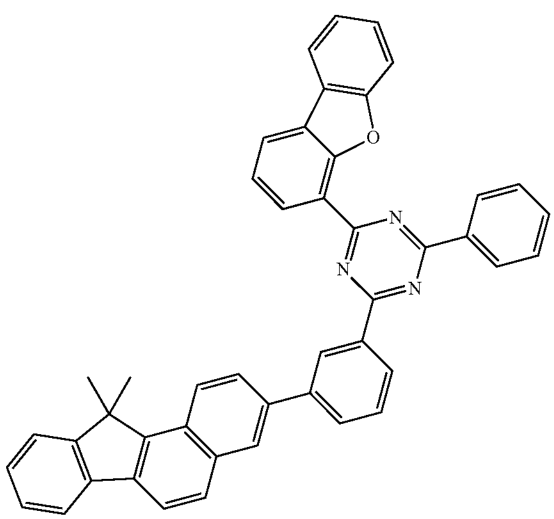
-continued
H2-199
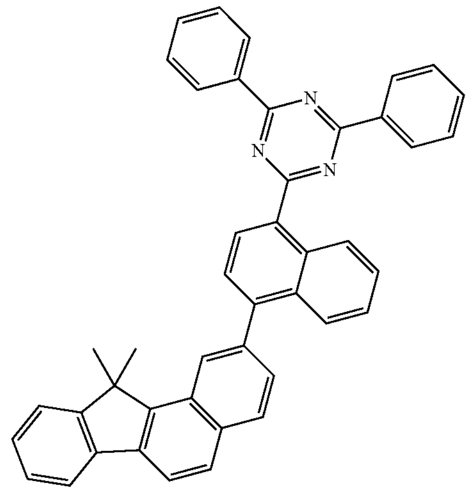
H2-200
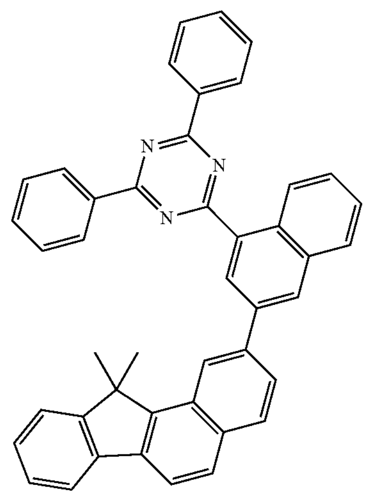
H2-201
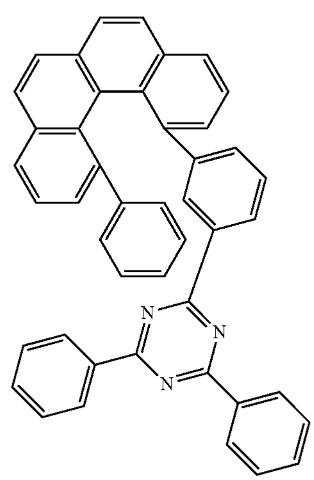

-continued
H2-202
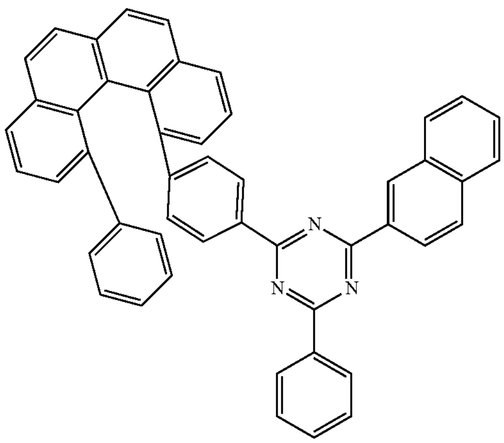
H2-203
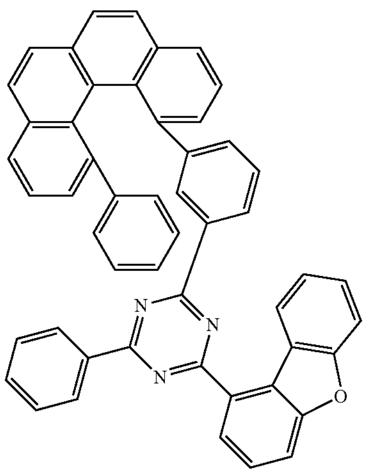
H2-204
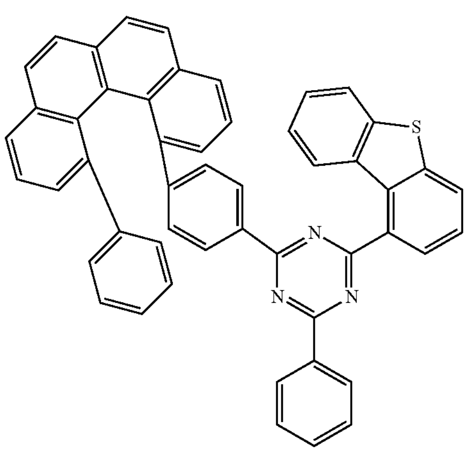
-continued
H2-205
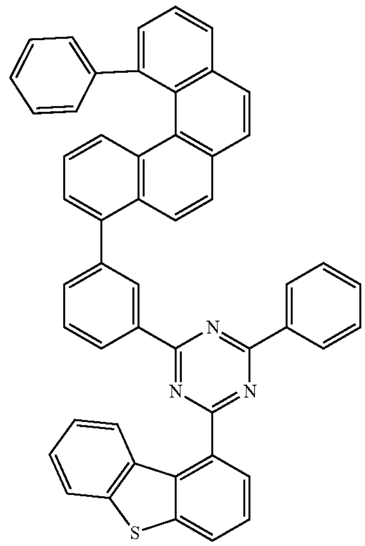
H2-206
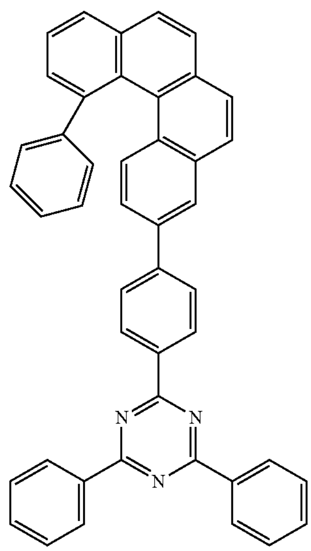
H2-207
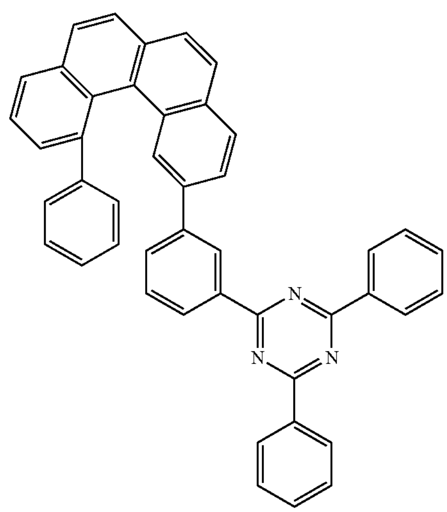

-continued
H2-208
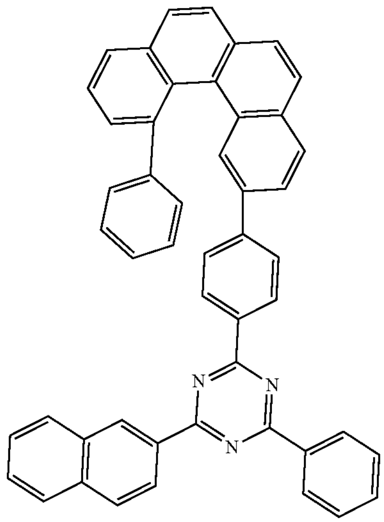
H2-209
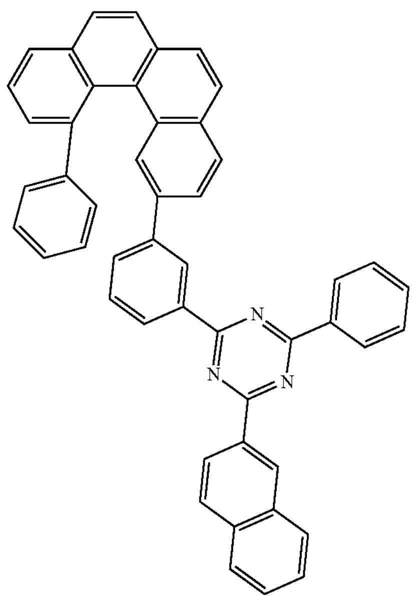
H2-210
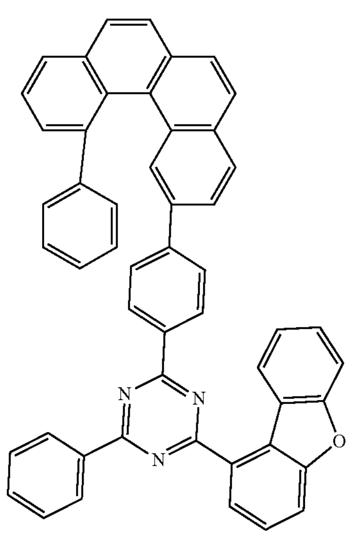
-continued
H2-211
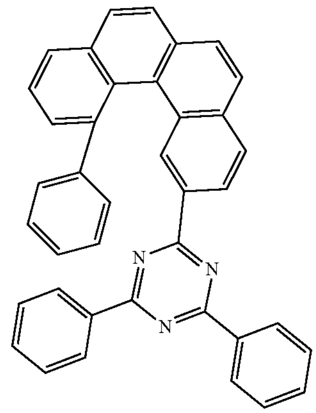
H2-212
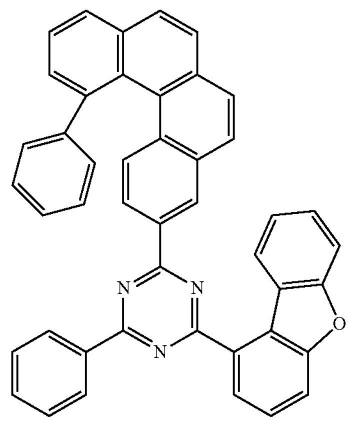
H2-213
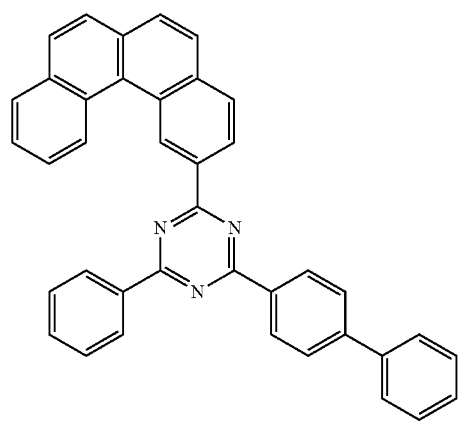
H2-214
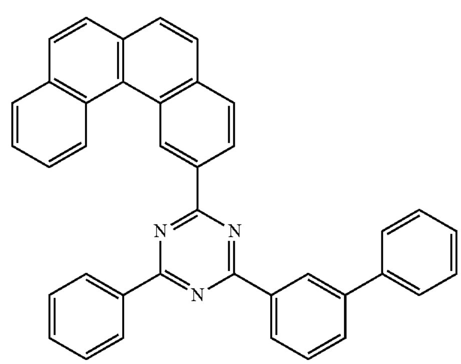

-continued
H2-215
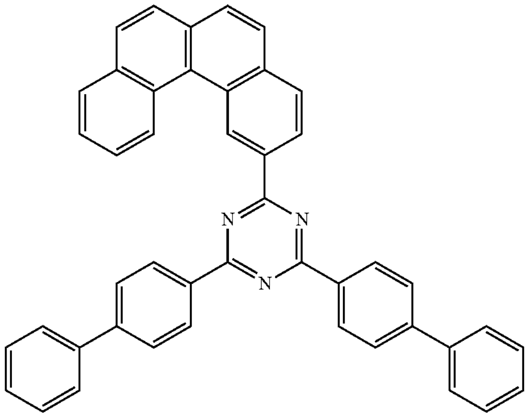
H2-216
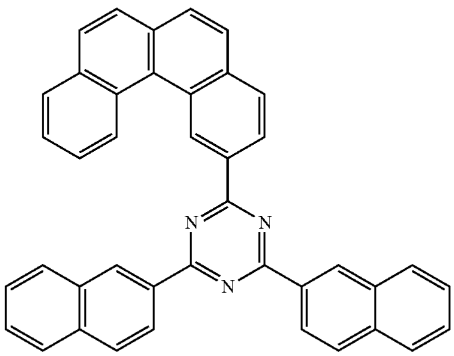
H2-217
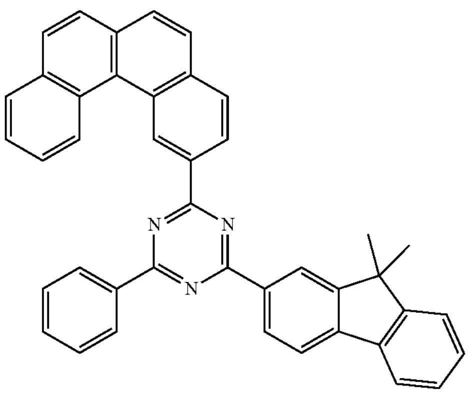
H2-218
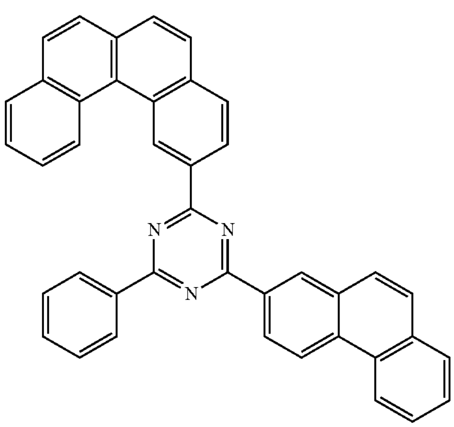
-continued
H2-219
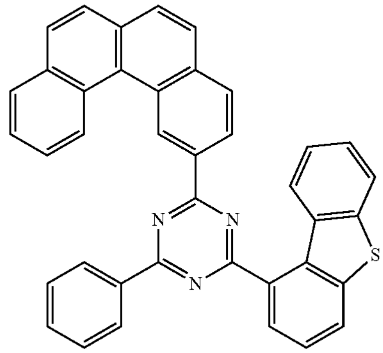
H2-220
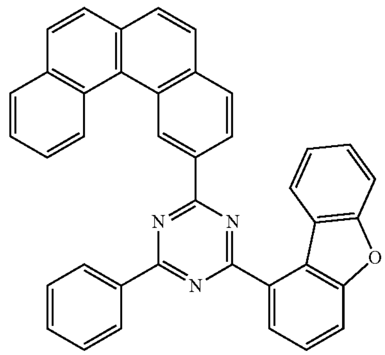
H2-221
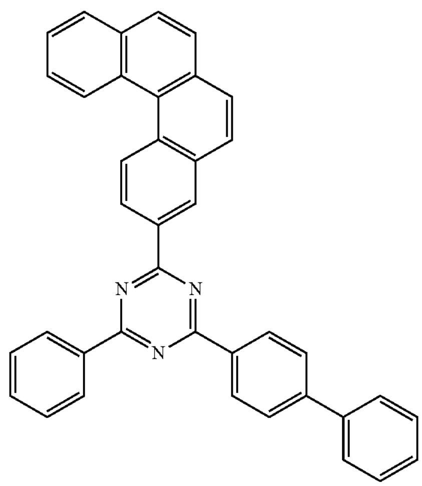
H2-222
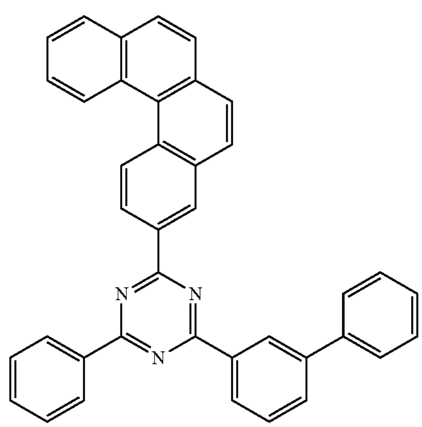

-continued
H2-223
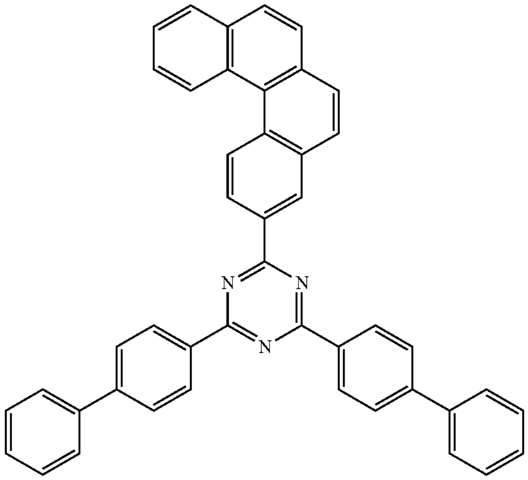
H2-224
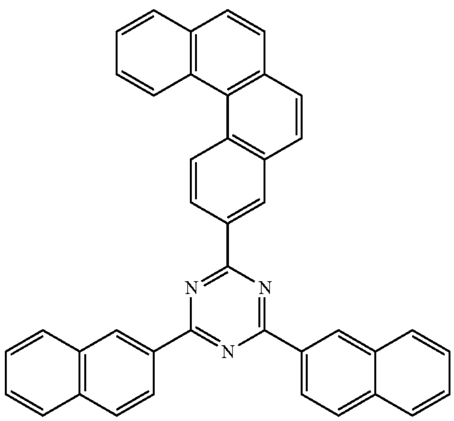
H2-225
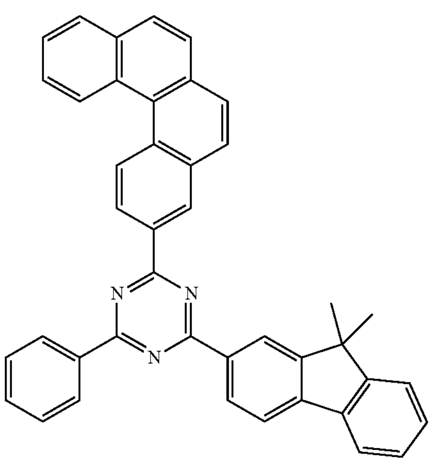
-continued
H2-226
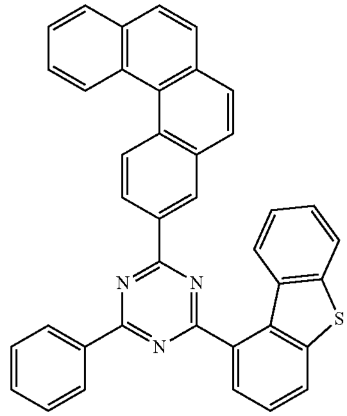
H2-227
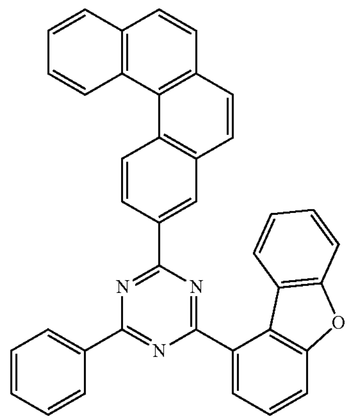
H2-228
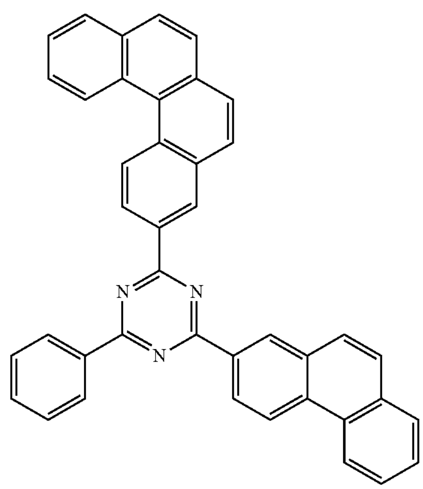

-continued
H2-229
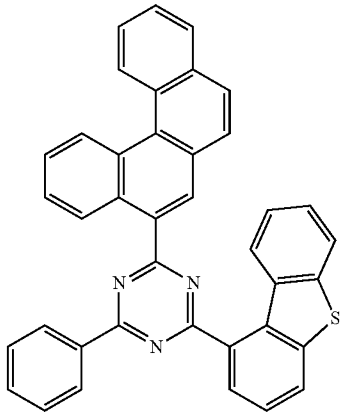
H2-230
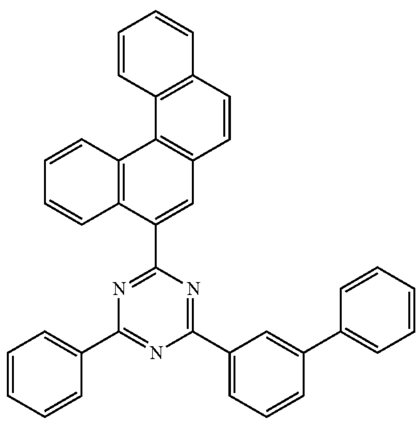
H2-231
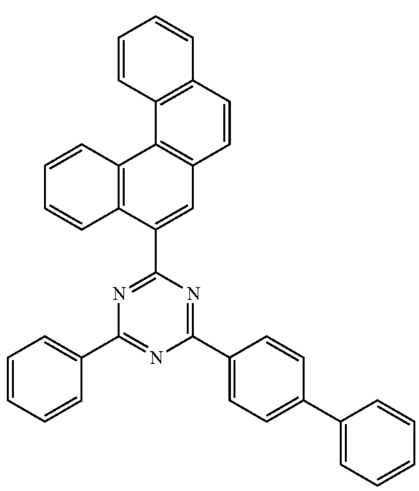
-continued
H2-232
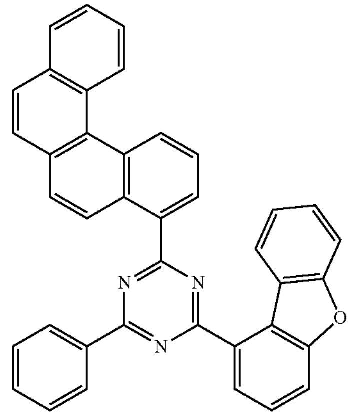
H2-233
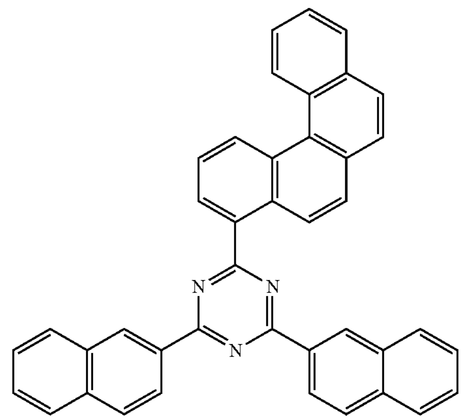
H2-234
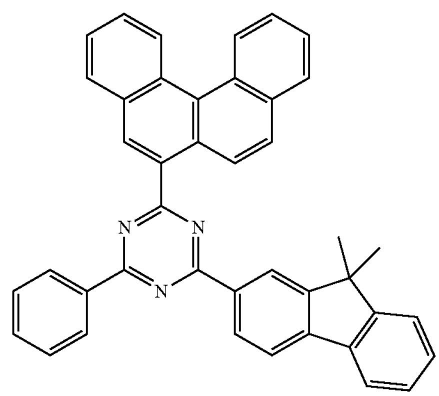
H2-235
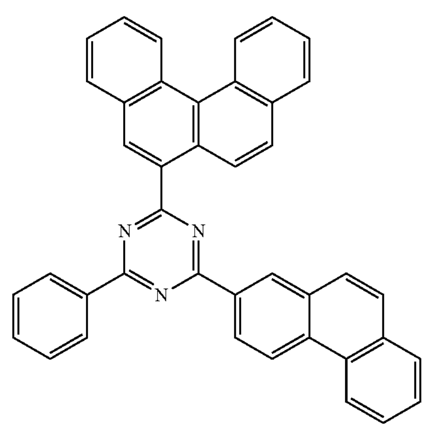

-continued
H2-236
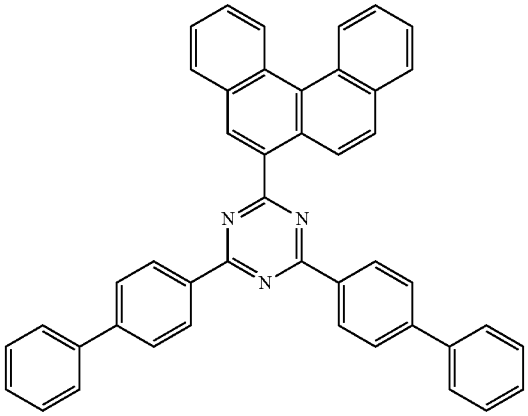
H2-237
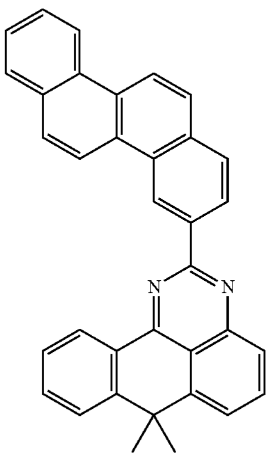
H2-238
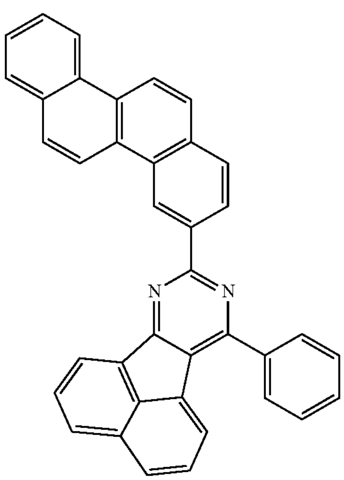
-continued
H2-239
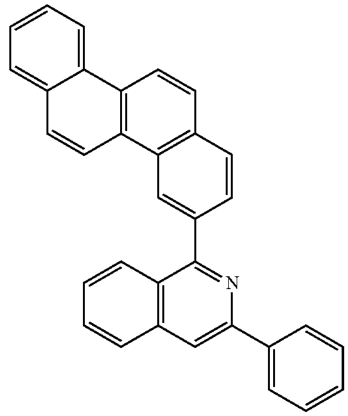
H2-240
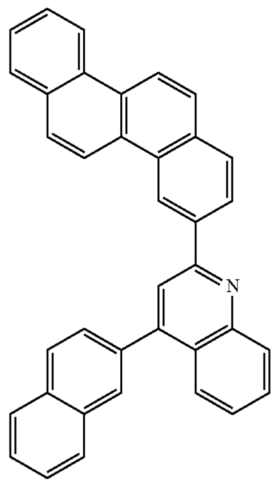
H2-241
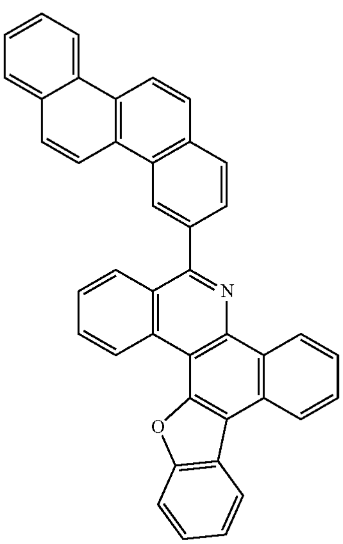

-continued
H2-242
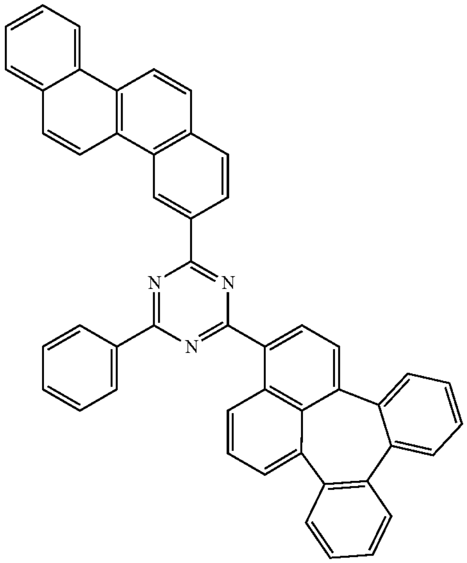
H2-243
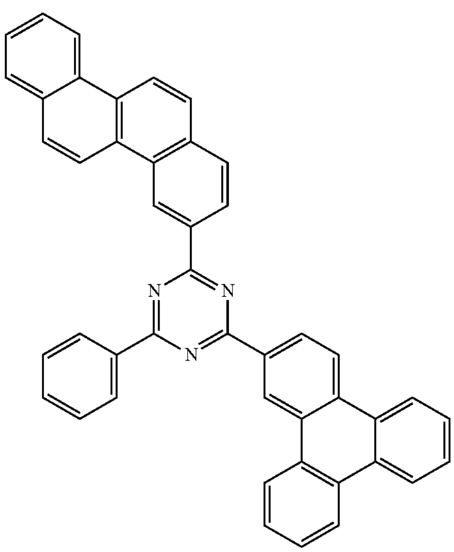
-continued
H2-244
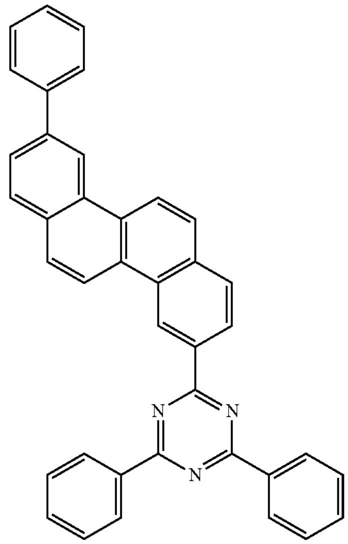
H2-245
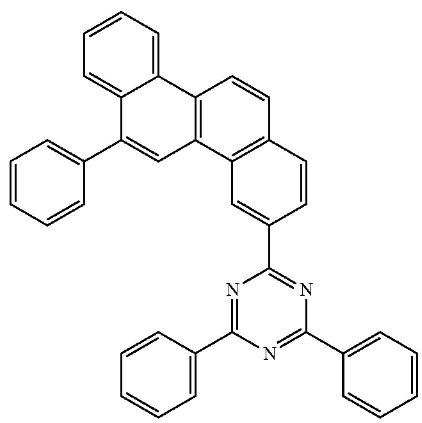
H2-246
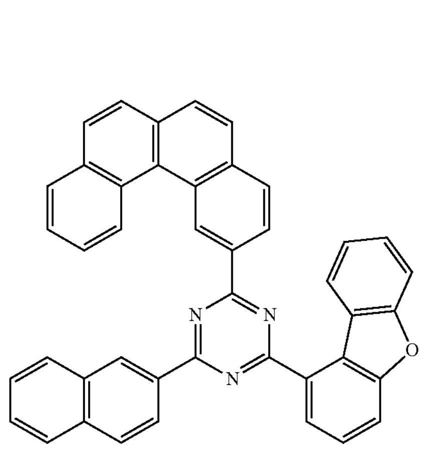

-continued
H2-247
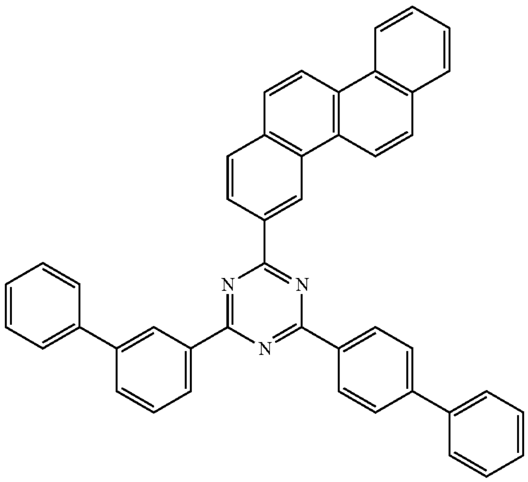
H2-248
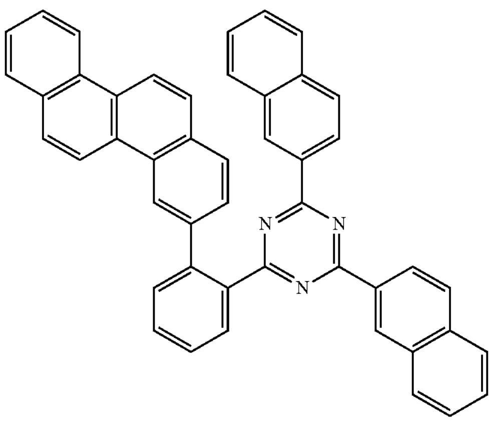
H2-249
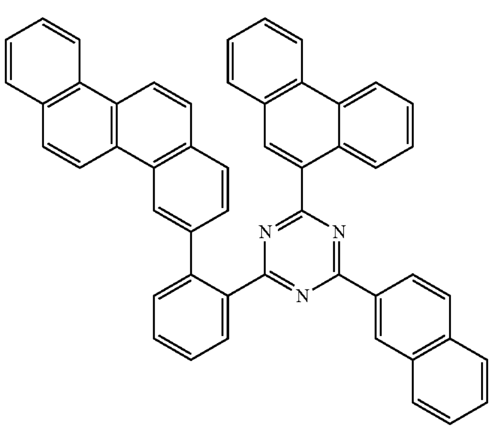
-continued
H2-250
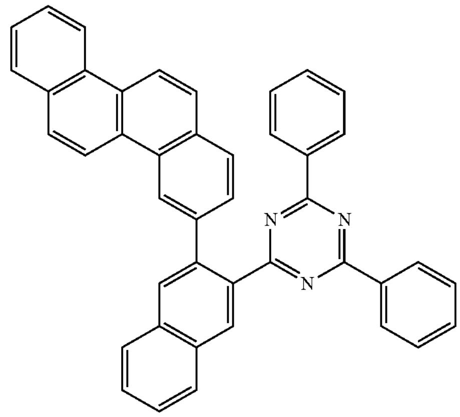
H2-251
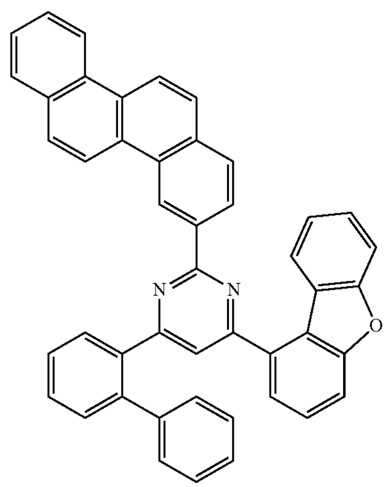
H2-252
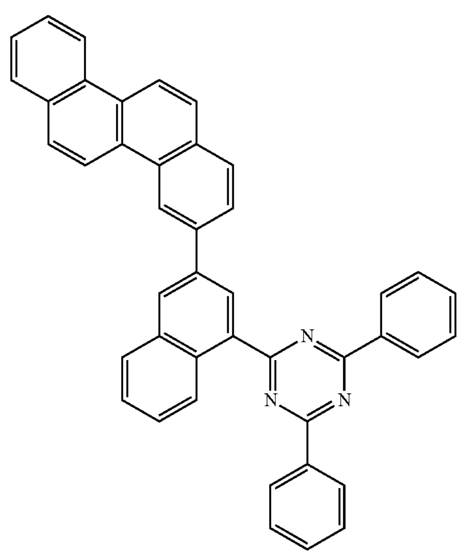

-continued
H2-253
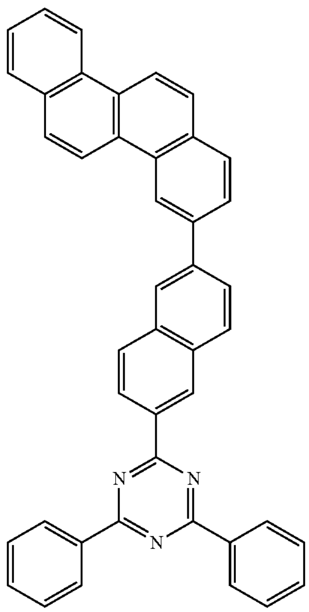
H2-254
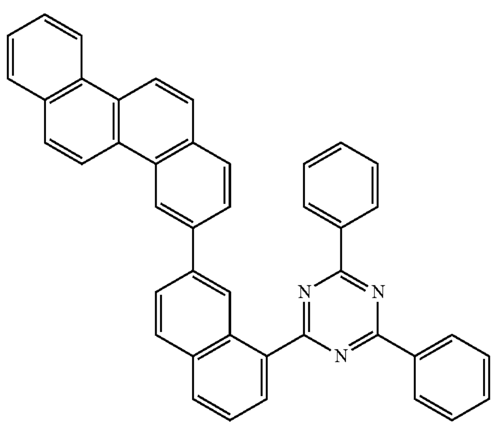
H2-255
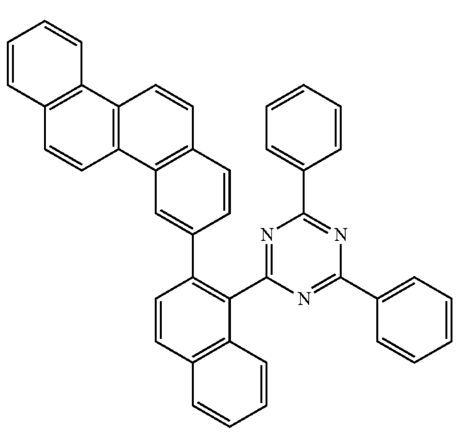
-continued
H2-256
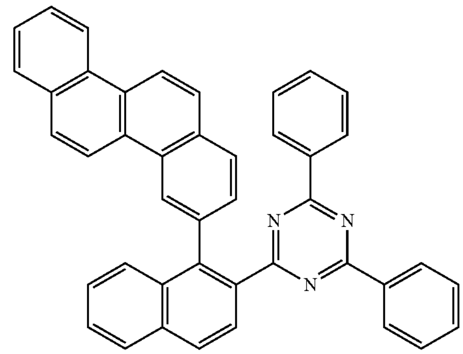
H2-257
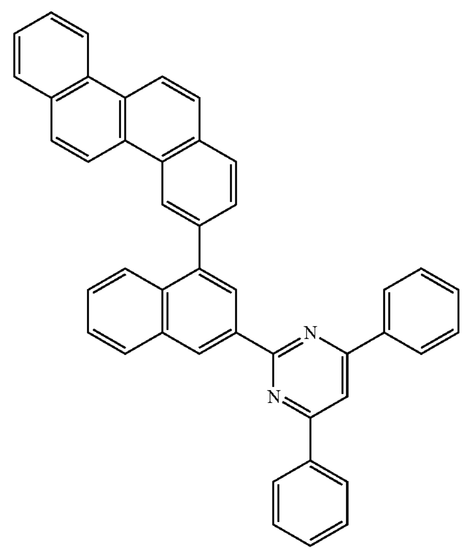
H2-258
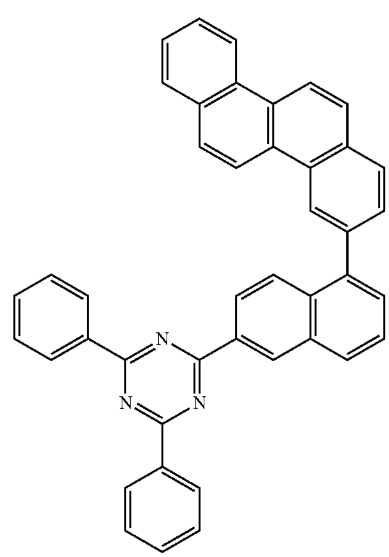

-continued
H2-259
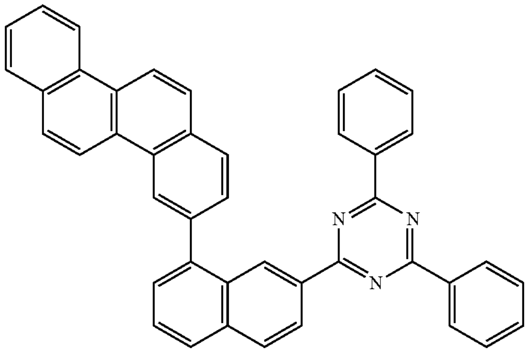
H2-260
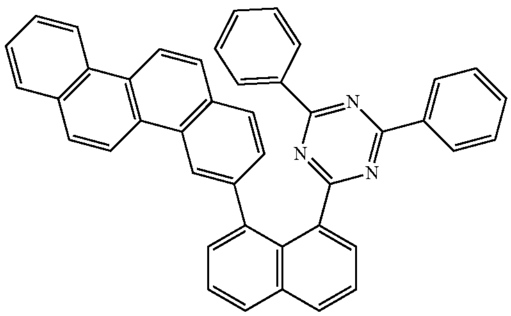
H2-261
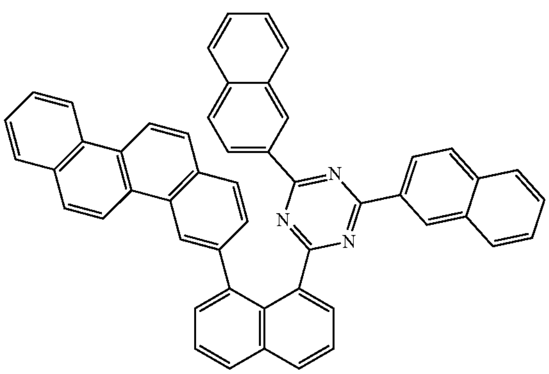
H2-262
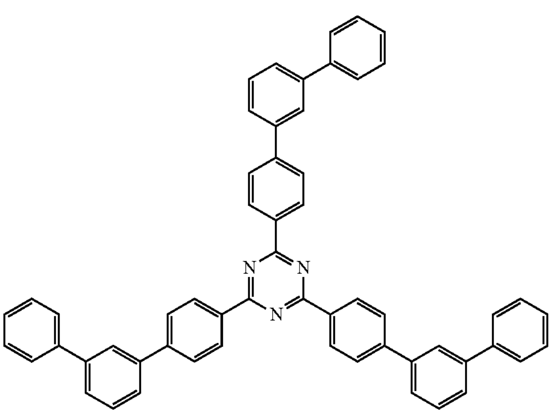
-continued
H2-263
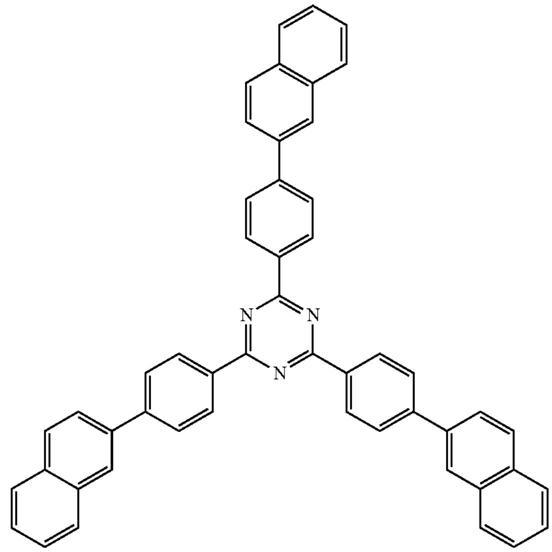
H2-264
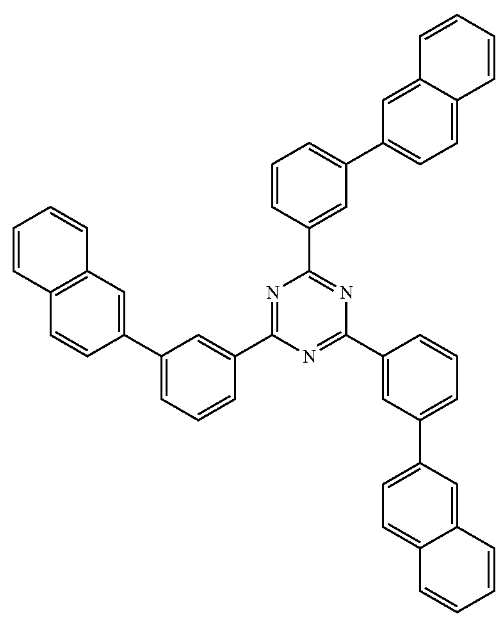

-continued
H2-265
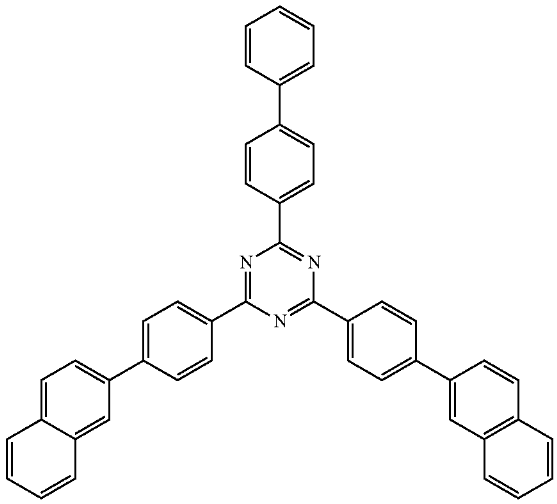
H2-266
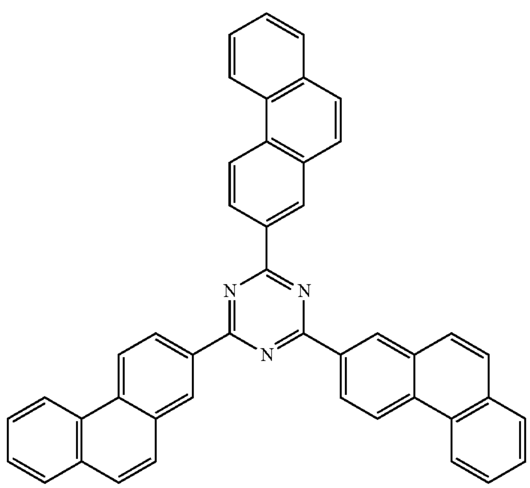
H2-267
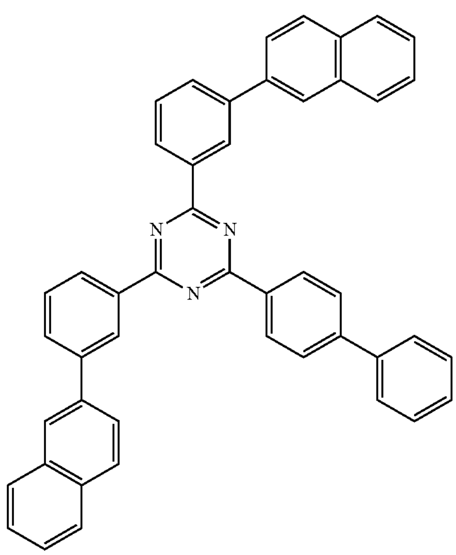
-continued
H2-268
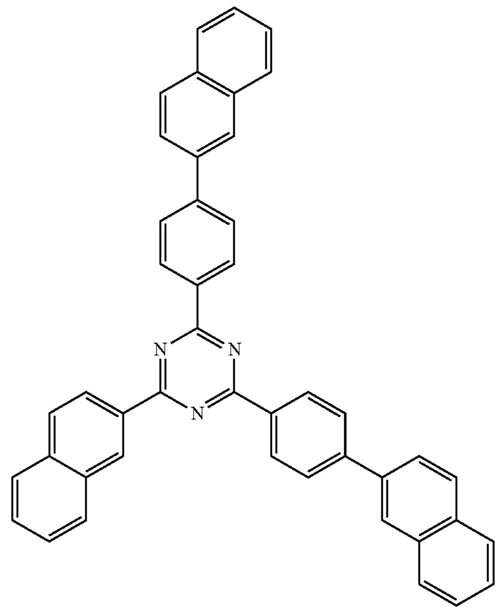
H2-269
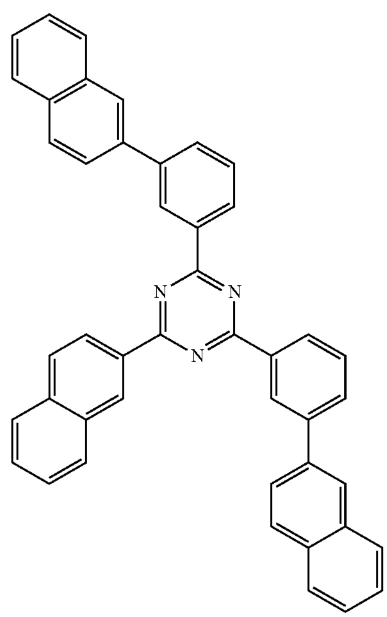

-continued
H2-270
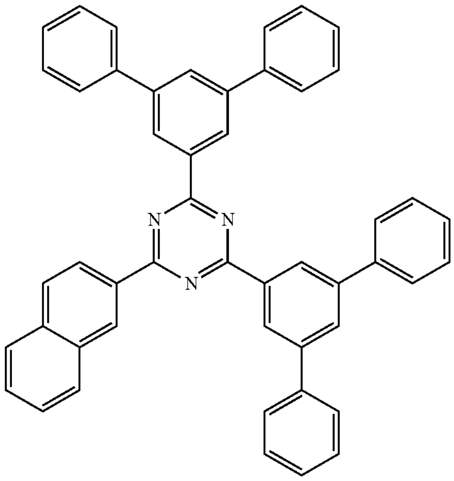
H2-271
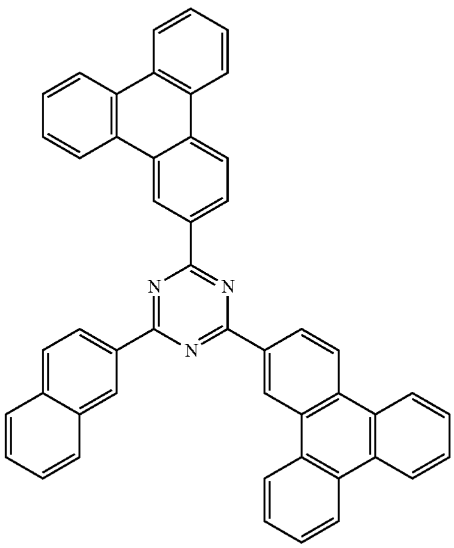
H2-272
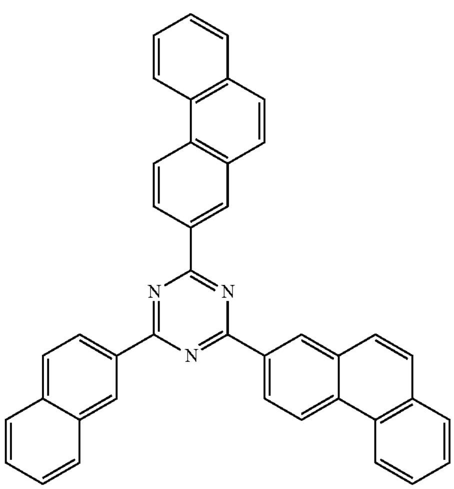
-continued
H2-273
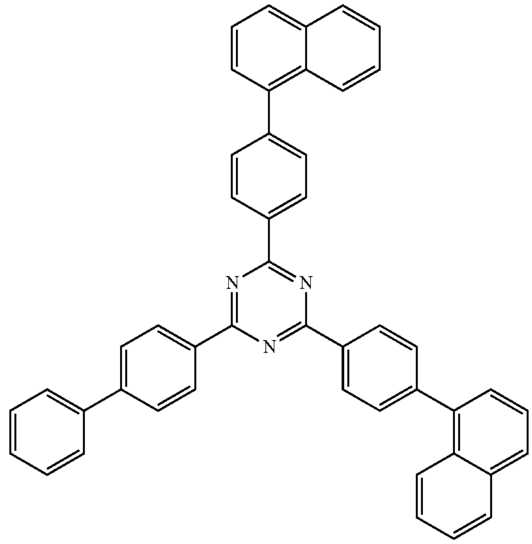
H2-274
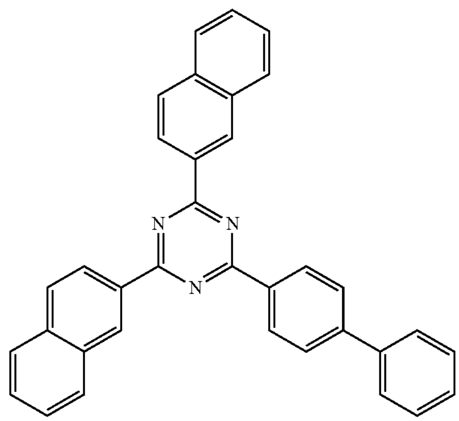
H2-275
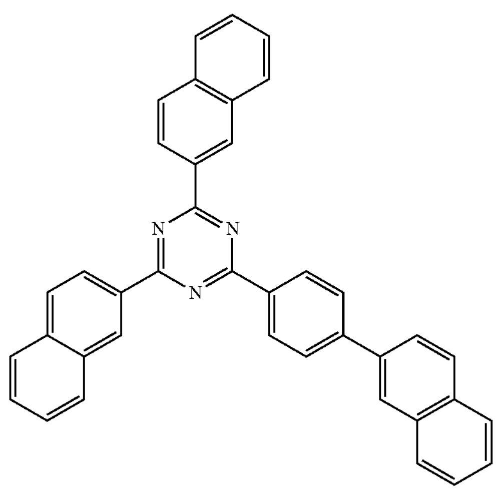

-continued
H2-276
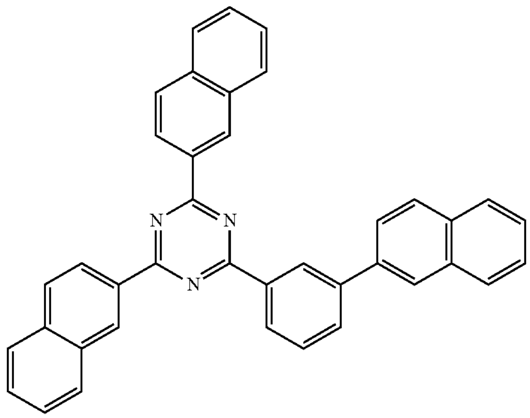
H2-277
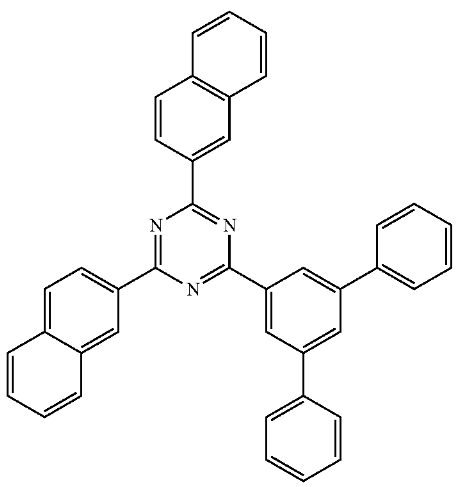
H2-278
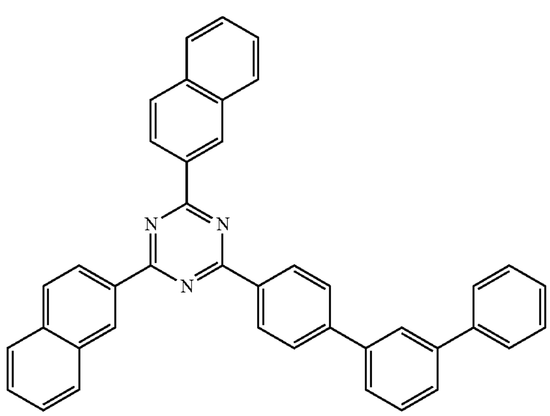
-continued
H2-279
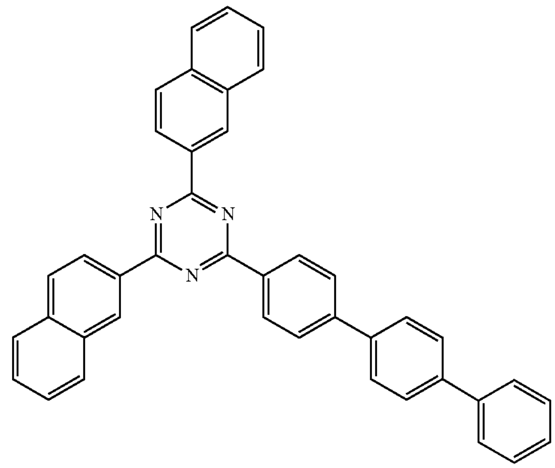
H2-280
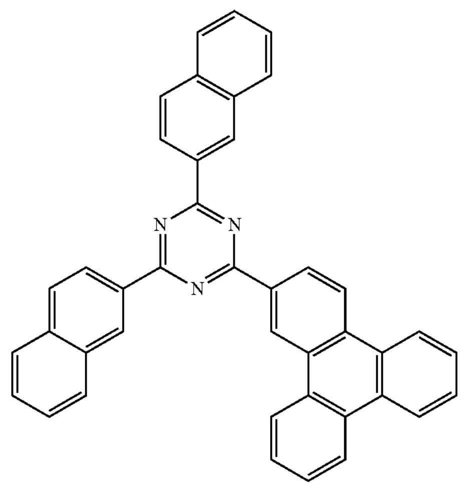
H2-281
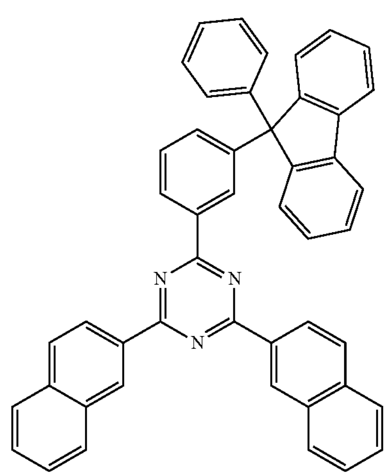

-continued
H2-282
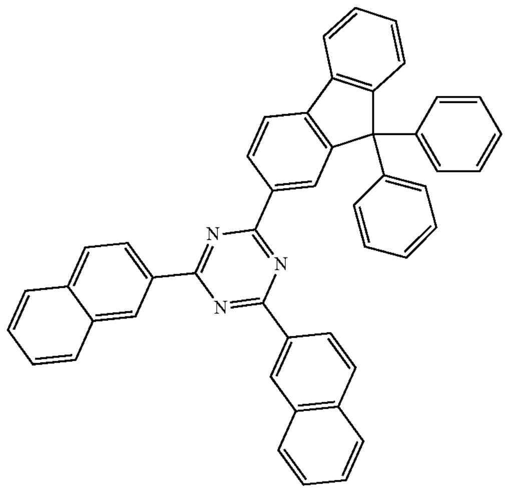
H2-283
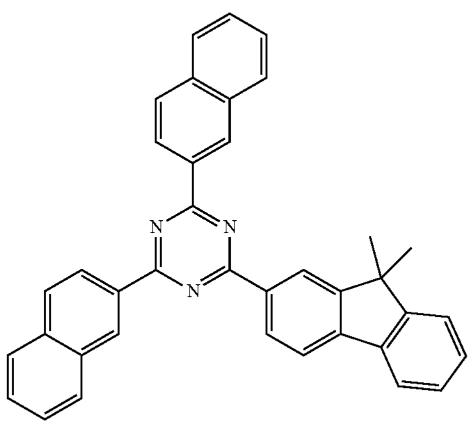
H2-284
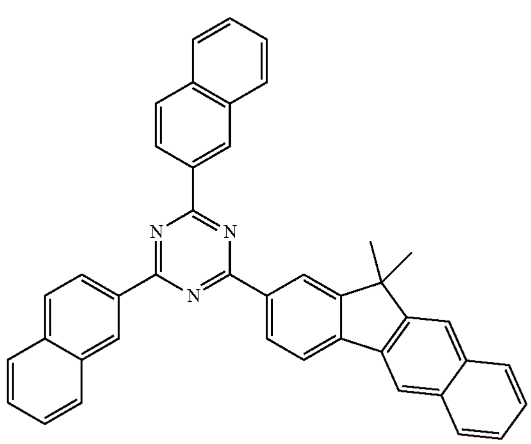
-continued
H2-285
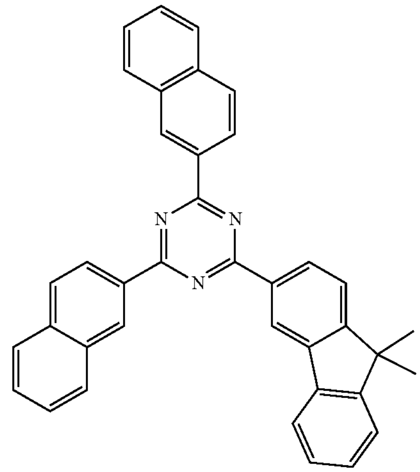
H2-286
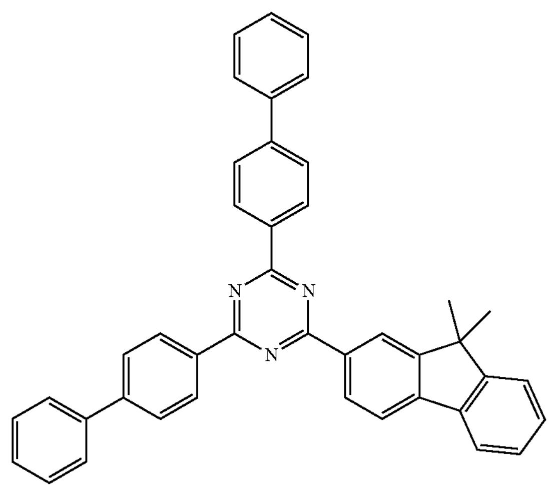
H2-287
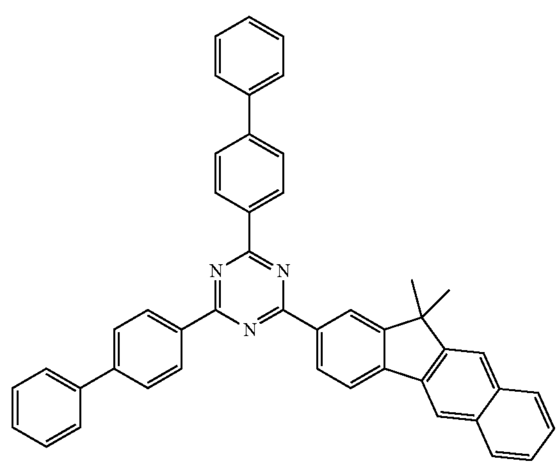

-continued
H2-288
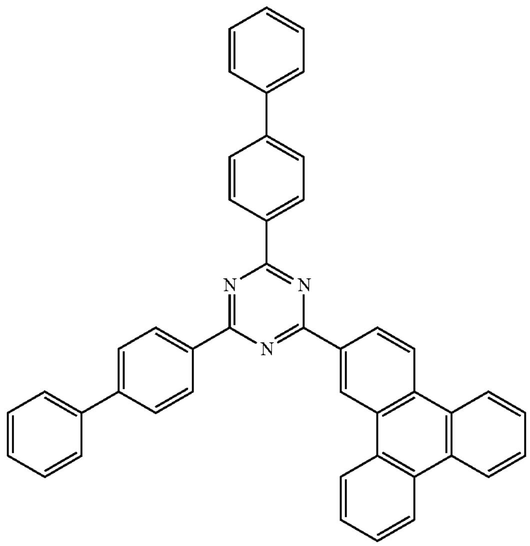
H2-289
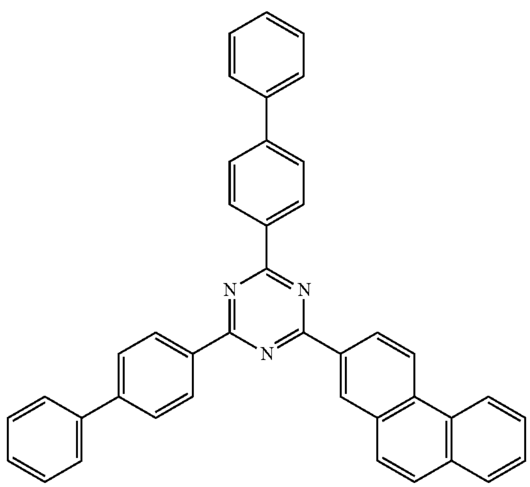
H2-290
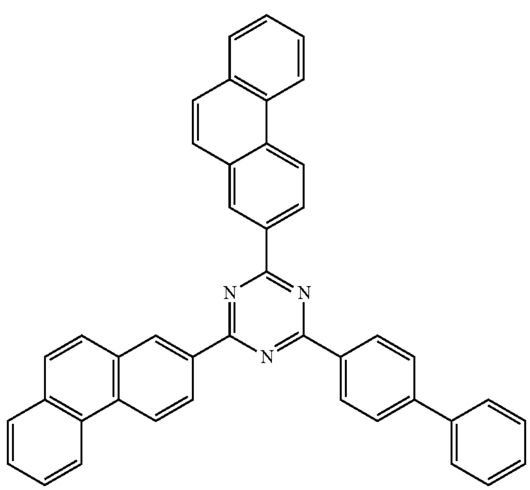
-continued
H2-291
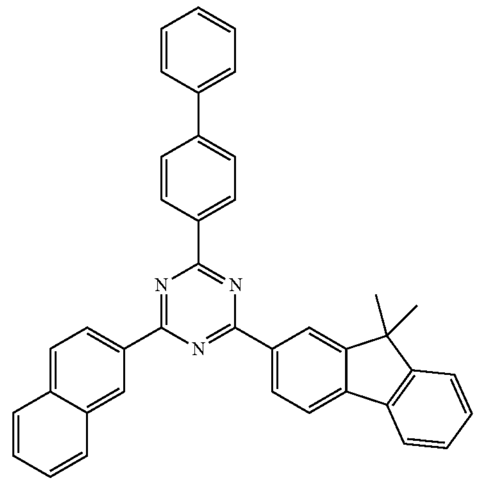
H2-292
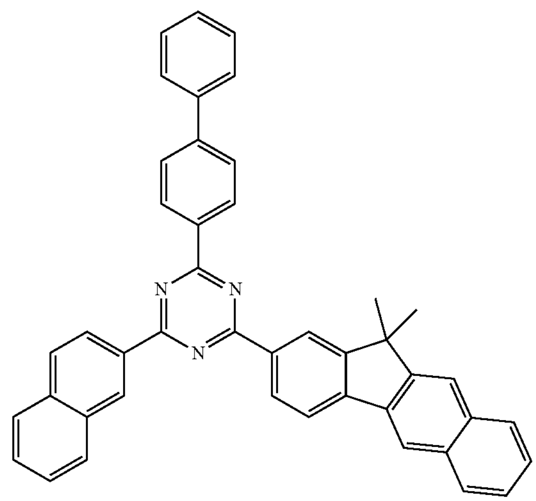
H2-293
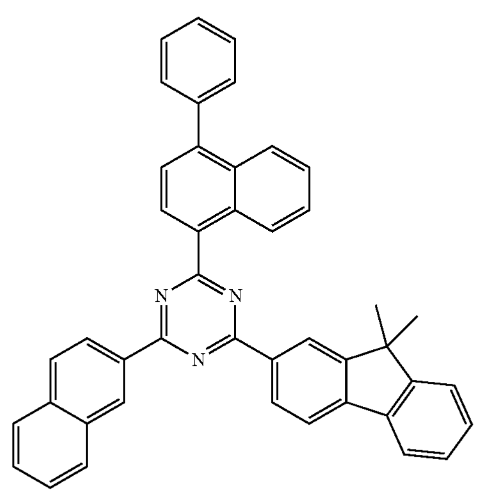

H2-294
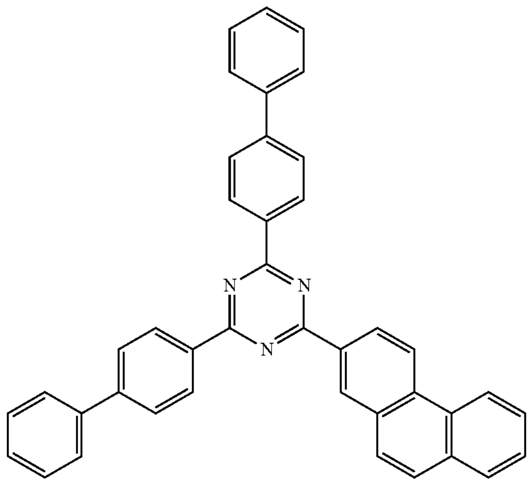
H2-295
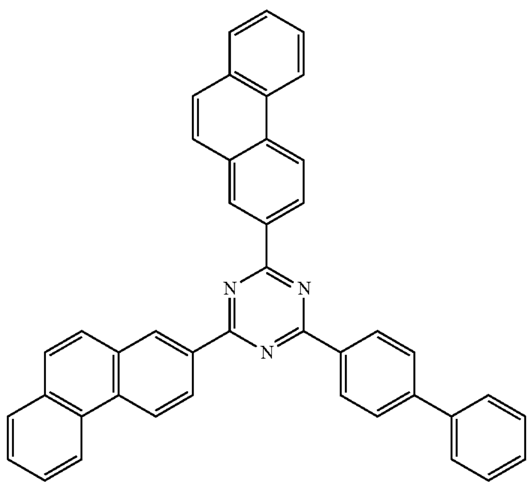
H2-296
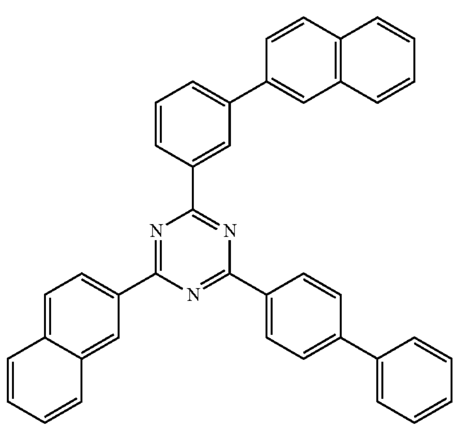
H2-297
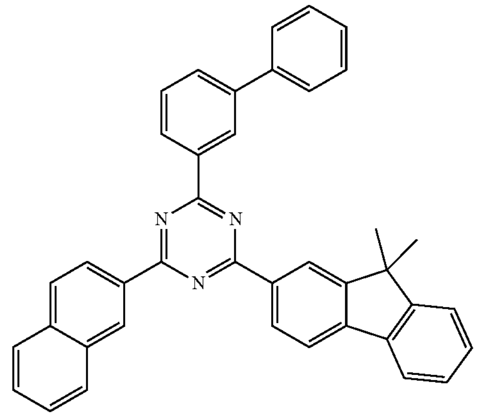
H2-298
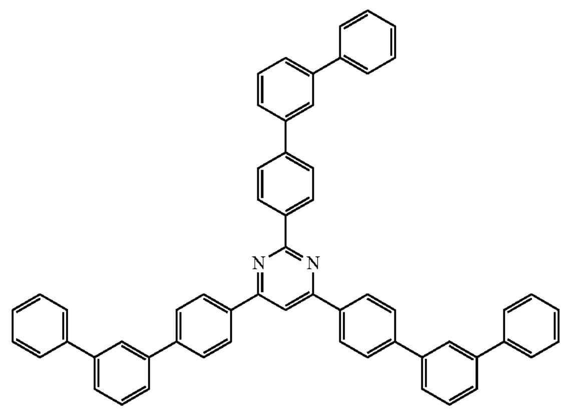
H2-299
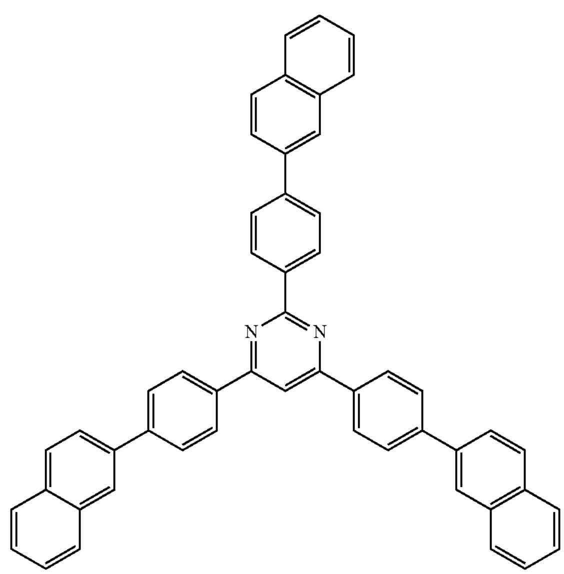

-continued
H2-300
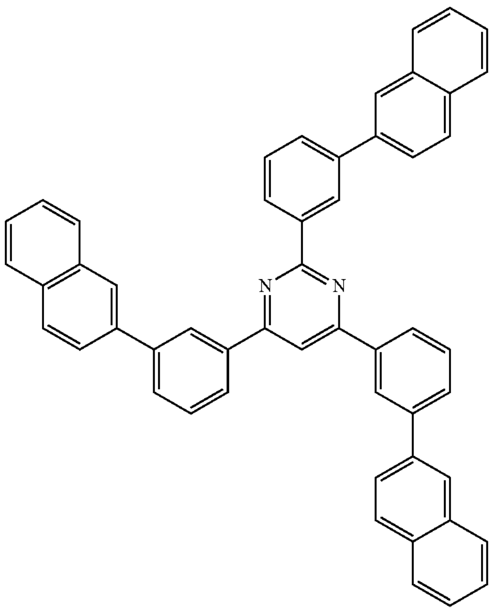
H2-301
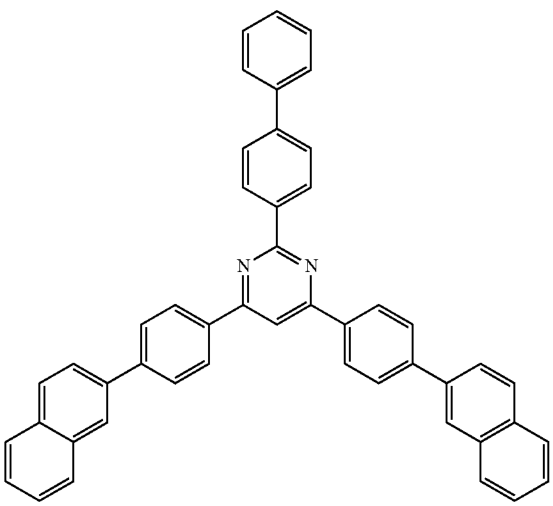
H2-302
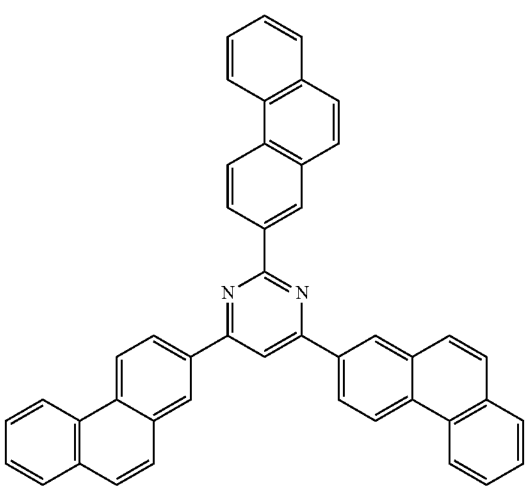
-continued
H2-303
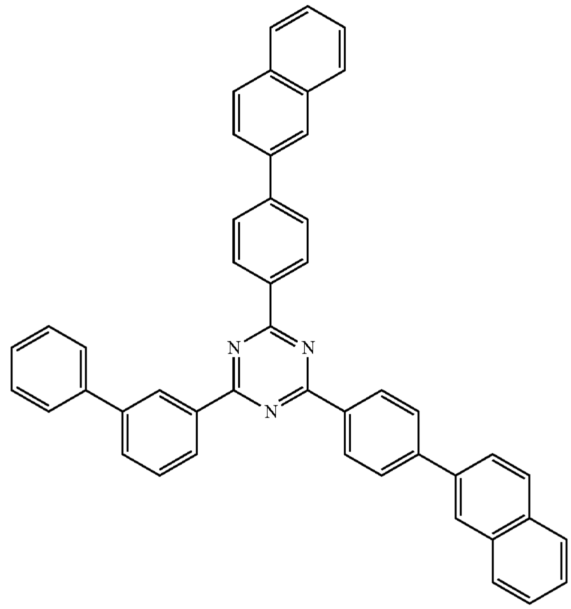
H2-304
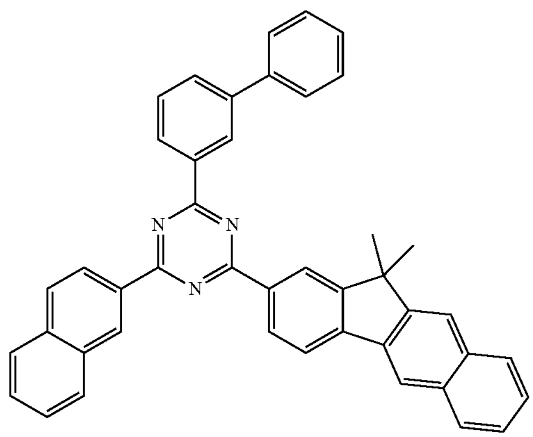
H2-305
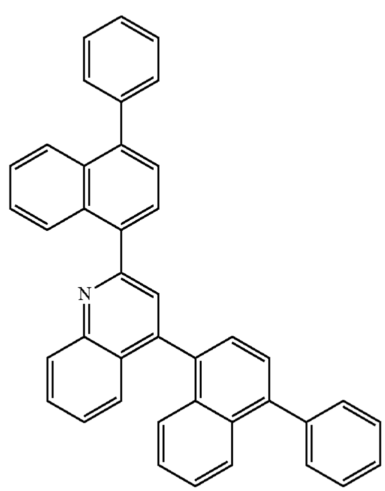

-continued
H2-306
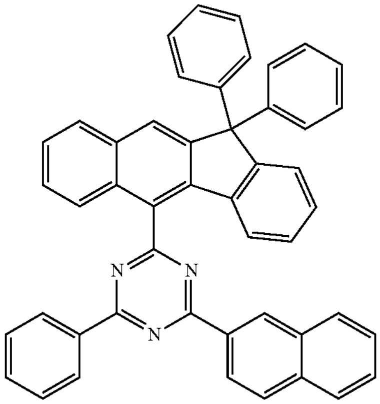
H2-307
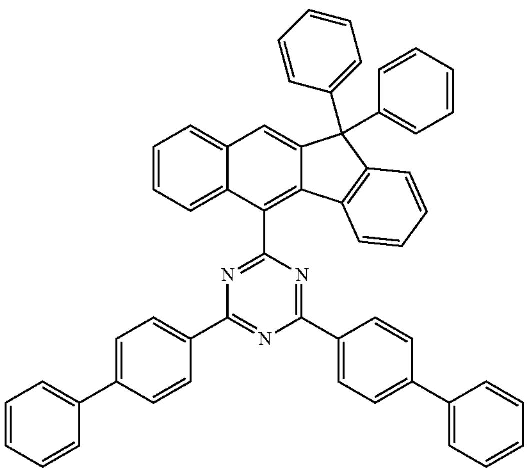
H2-308
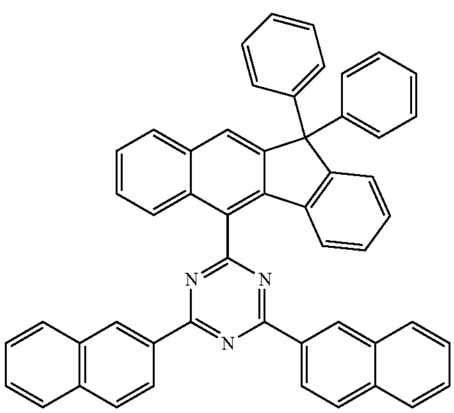
H2-309
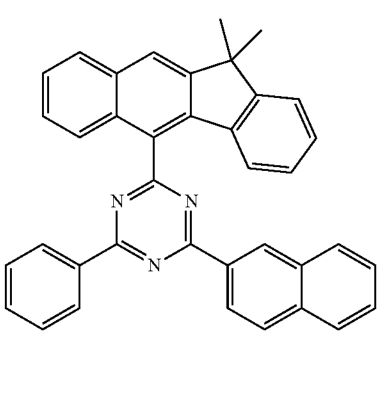
-continued
H2-10
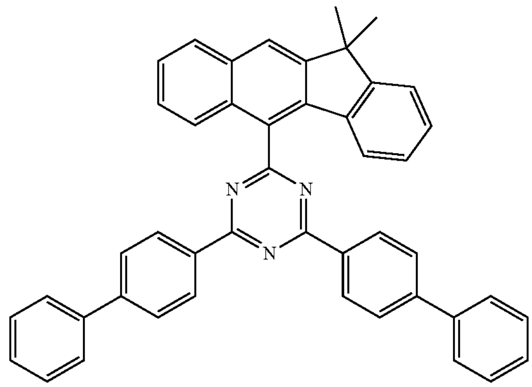
H2-311
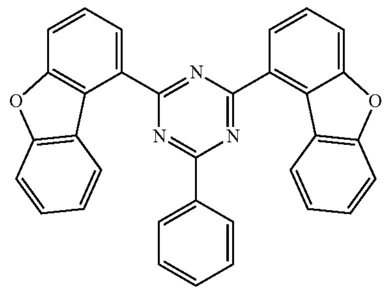
H2-312
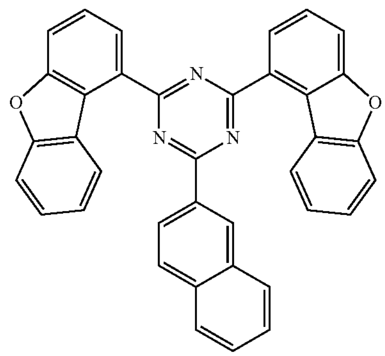
H2-313
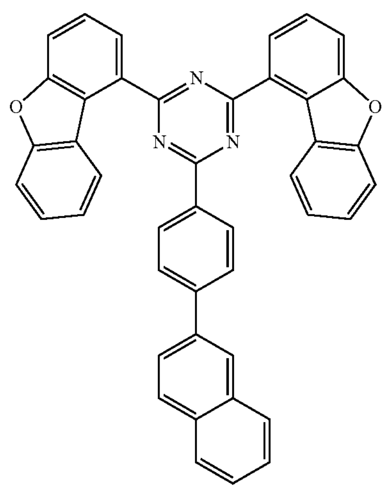

-continued
H2-314
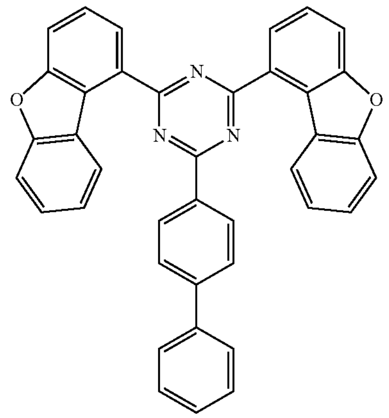
H2-315
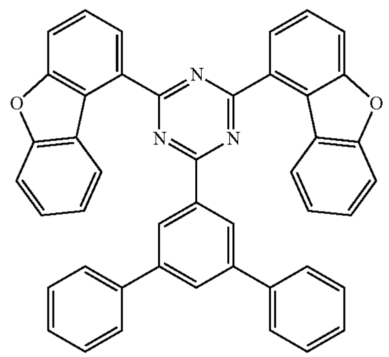
H2-316
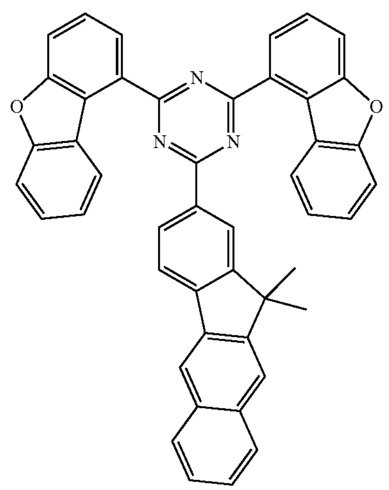
H2-317
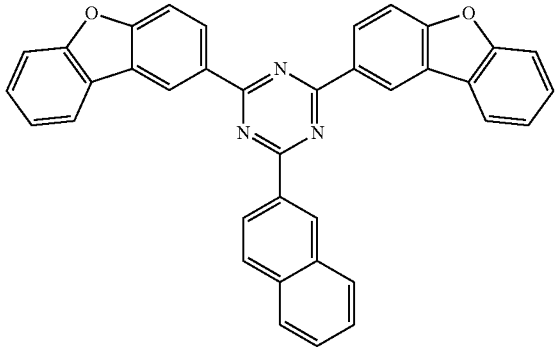
-continued
H2-318
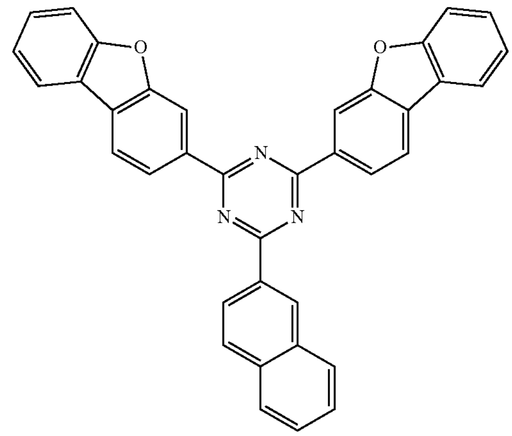
H2-319
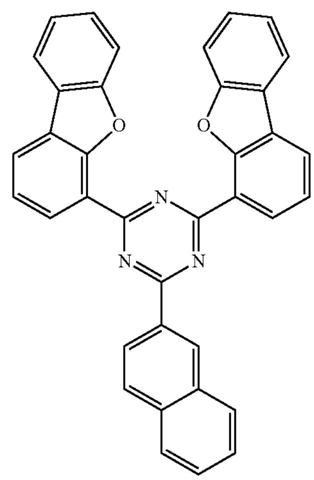
H2-320
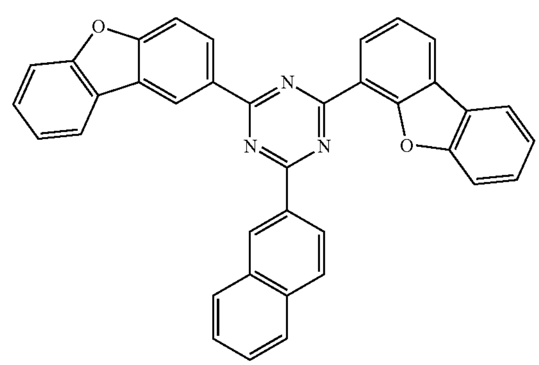

-continued
H2-321
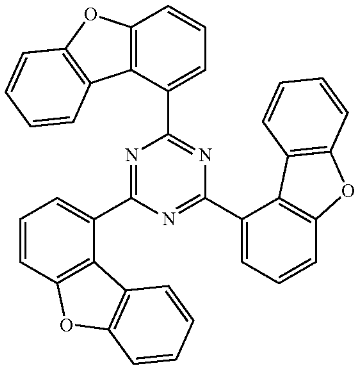
H2-322
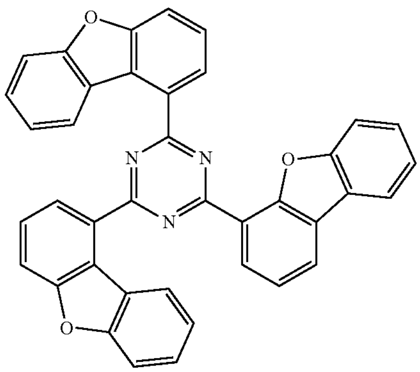
H2-323
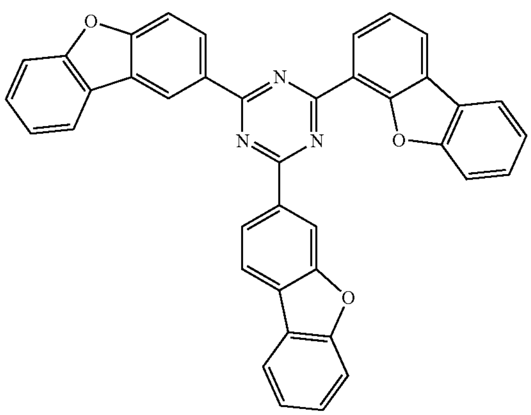
H2-324
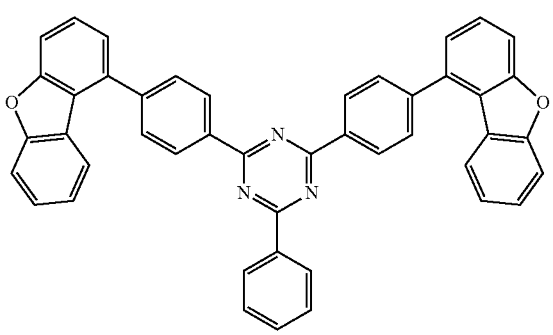
-continued
H2-325
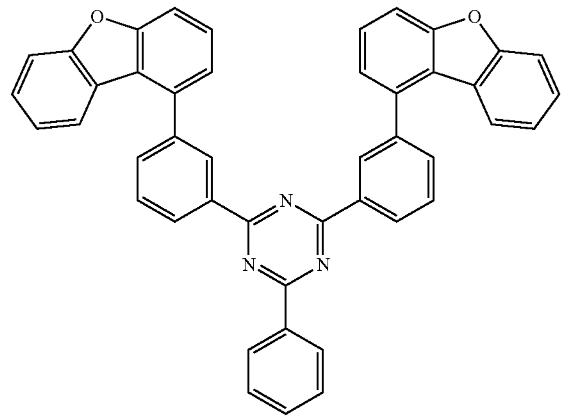
H2-326
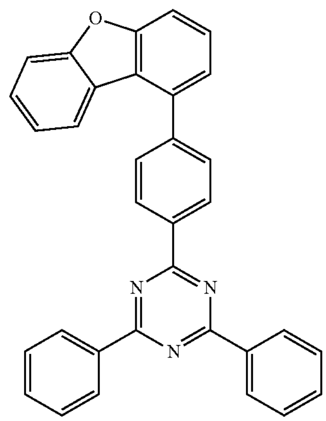
H2-327
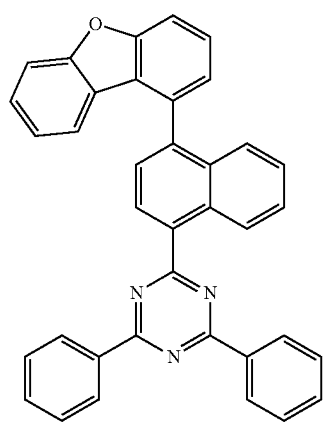

-continued
H2-328
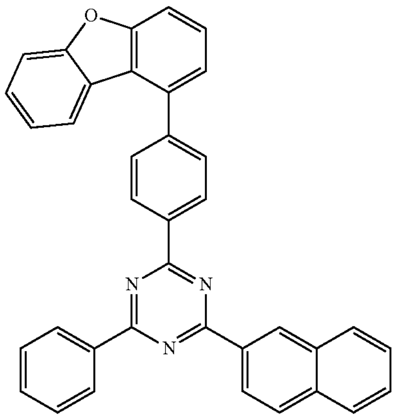
H2-329
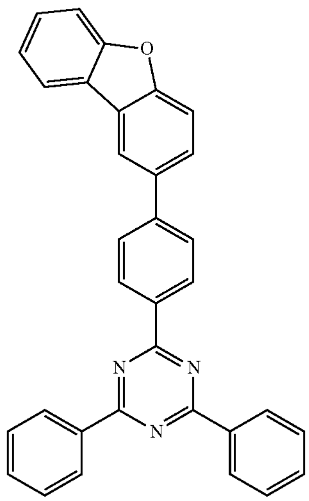
H2-330
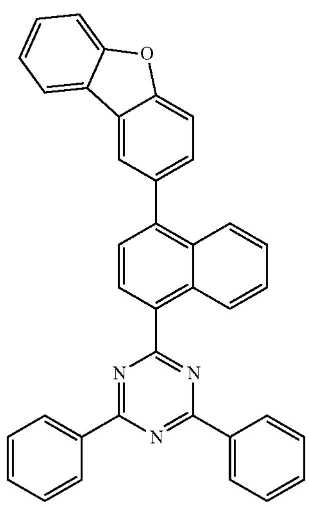
-continued
H2-331
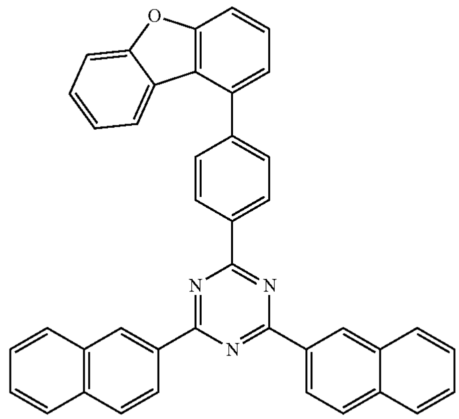
H2-332
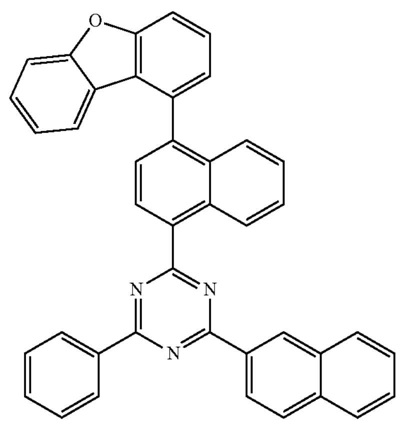
H2-333
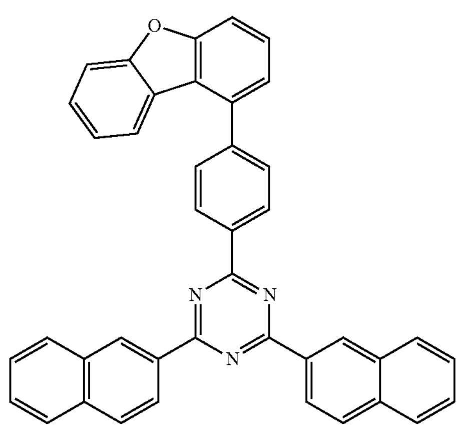

-continued
H2-334
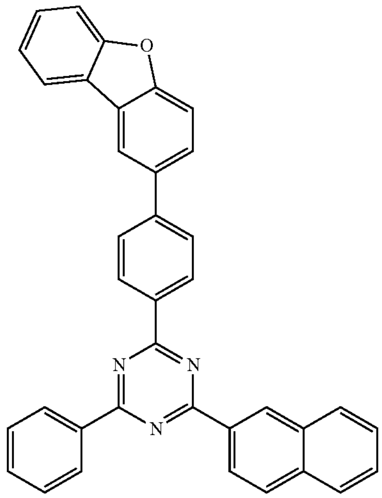
H2-335
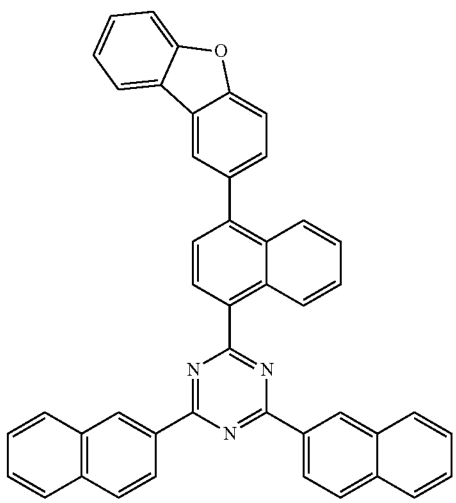
H2-336
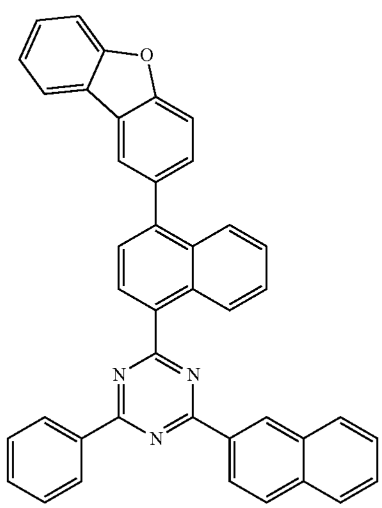
-continued
H2-337
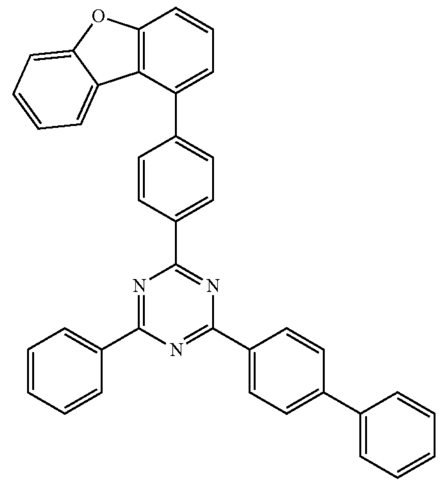
H2-338
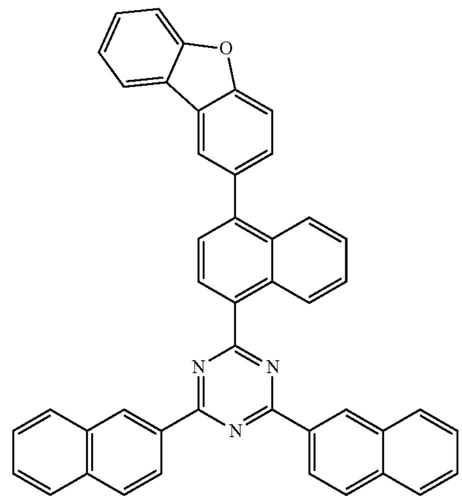
H2-339
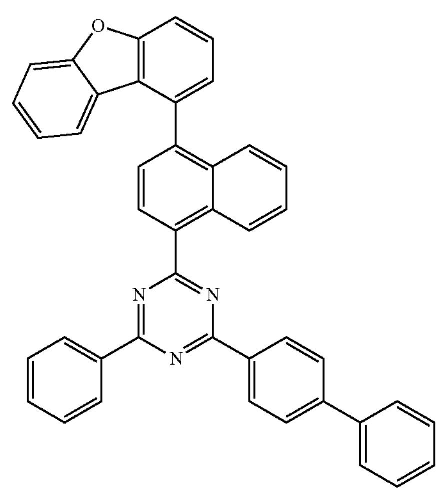

228
-continued
H2-340
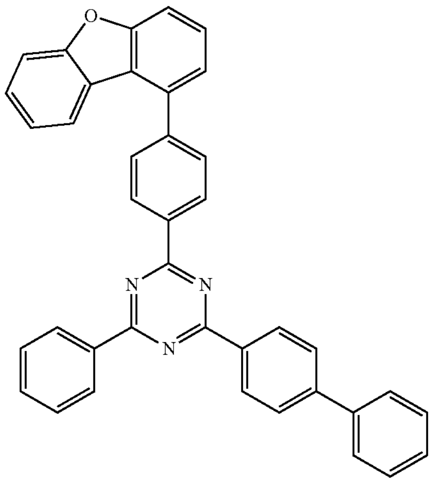
H2-341
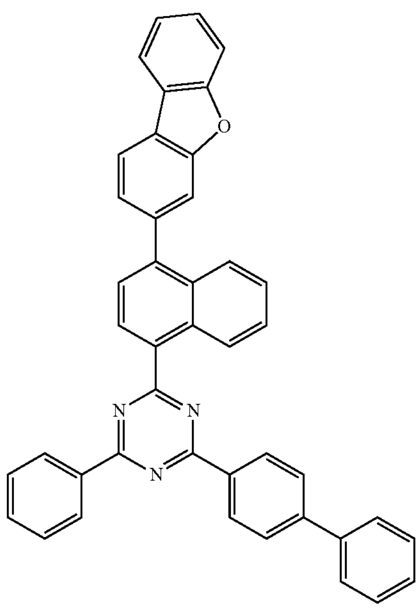
H2-342
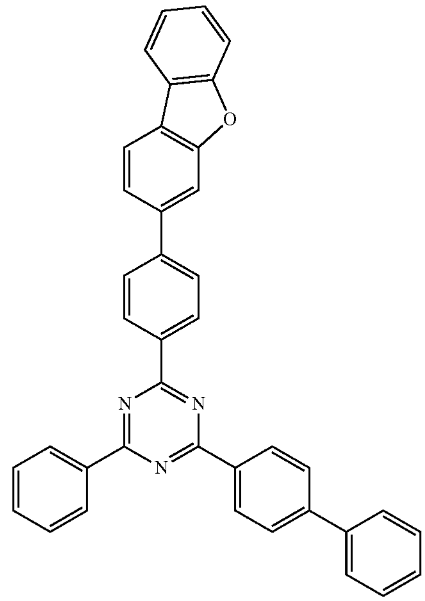
H2-343
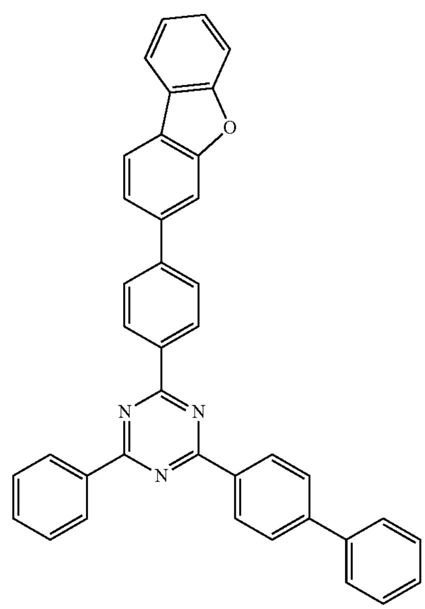

-continued
H2-344
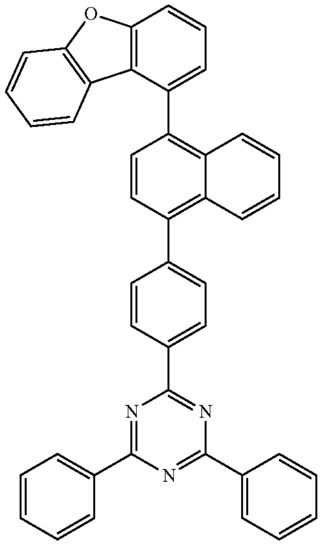
H2-345
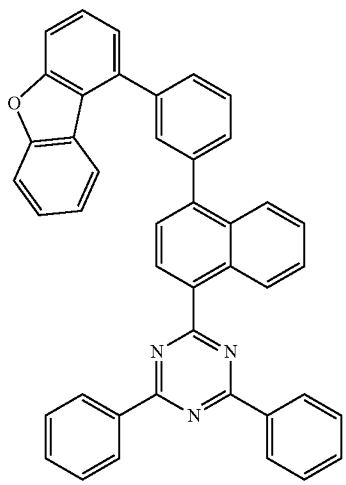
H2-346
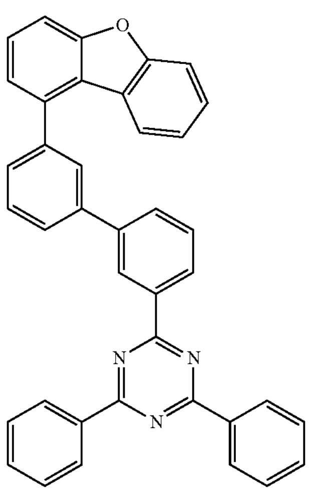
-continued
H2-347
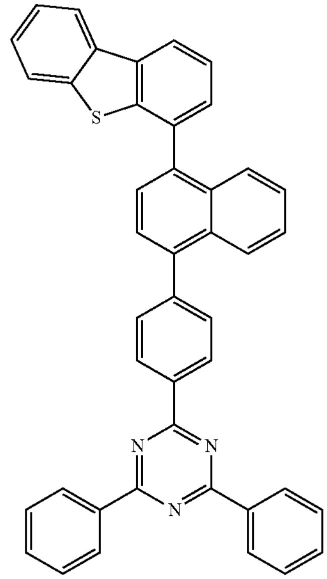
H2-348
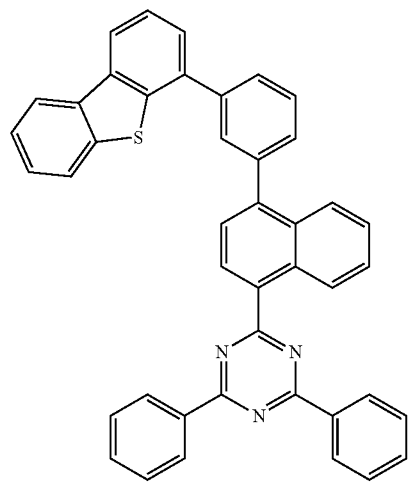
H2-349
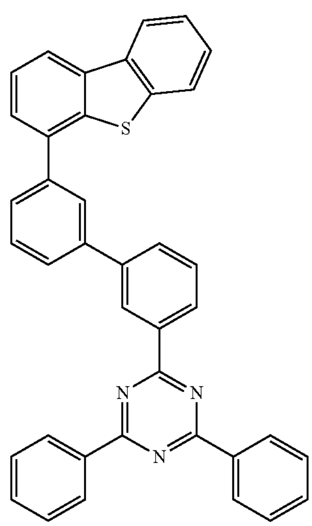

-continued
H2-350
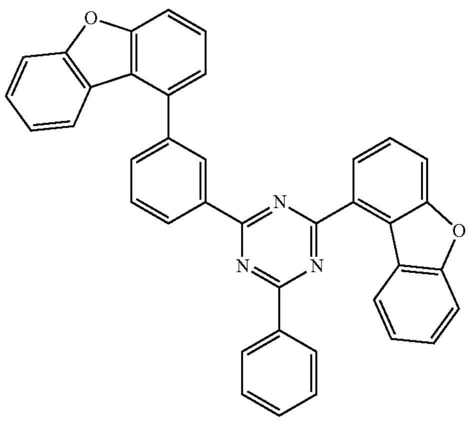
H2-351
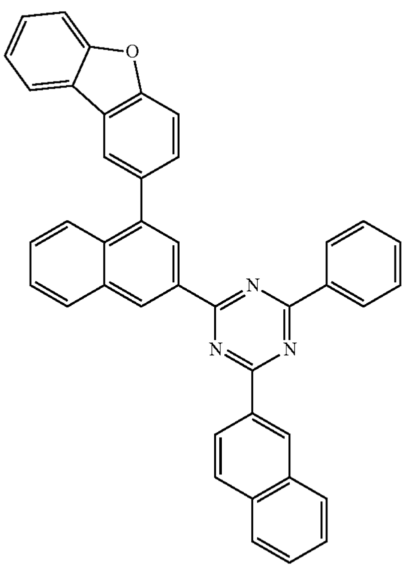
H2-352
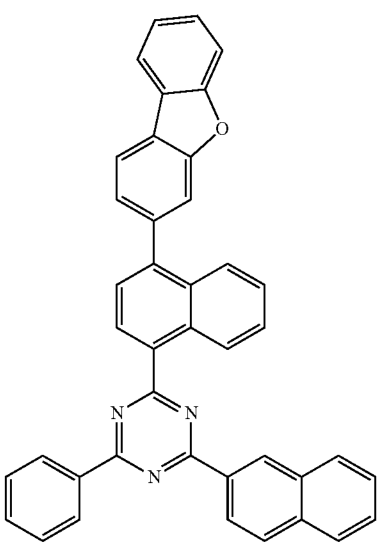
-continued
H2-353
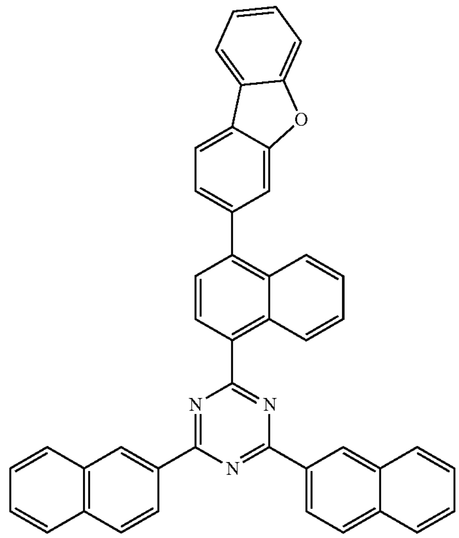
H2-354
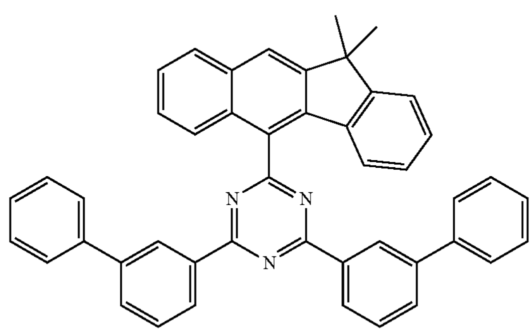
H2-355
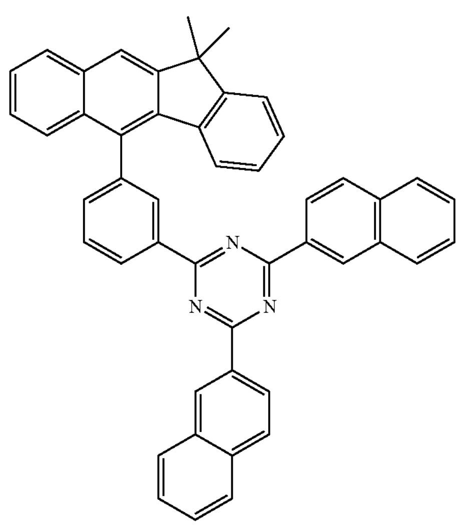

-continued
H2-356
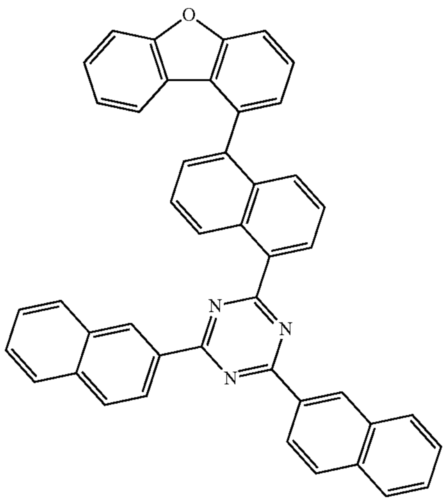
H-357
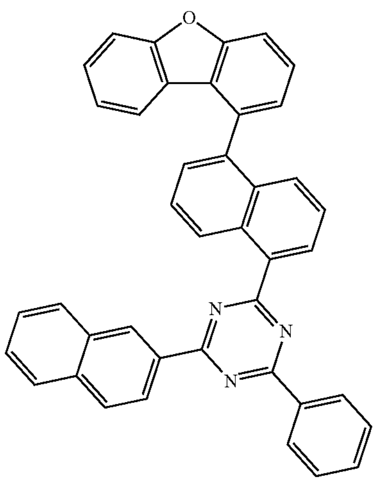
H2-358
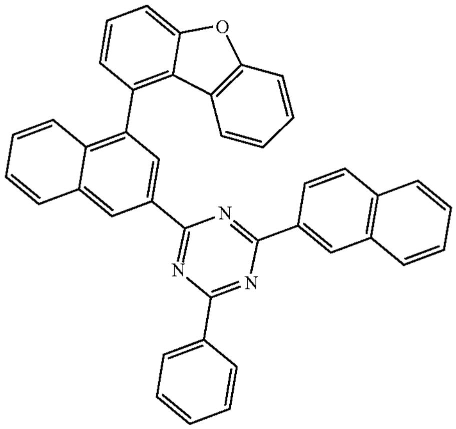
-continued
H2-359
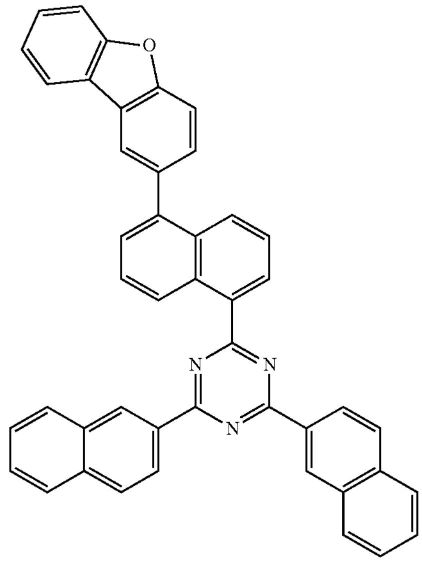
H2-360
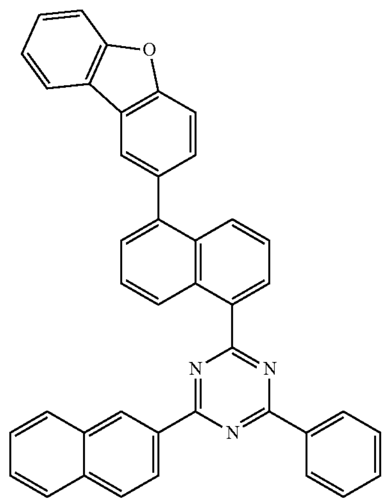
H2-361
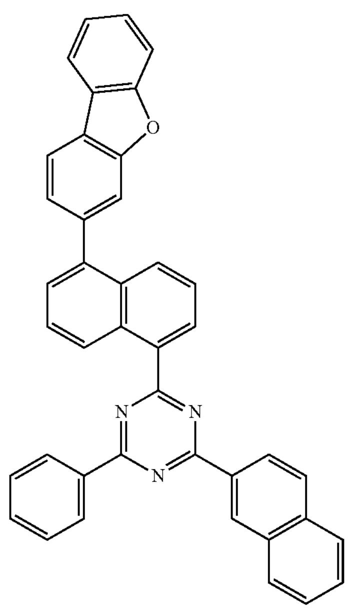

-continued
H2-363
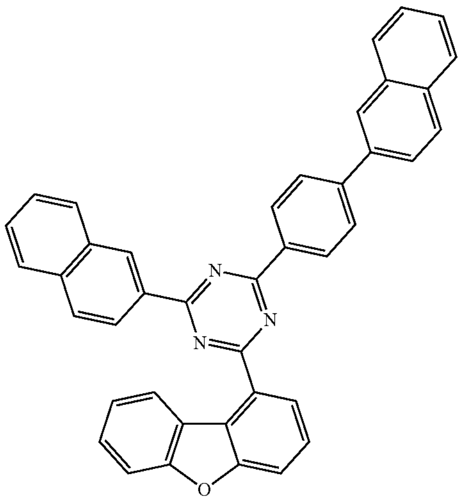
H2-363
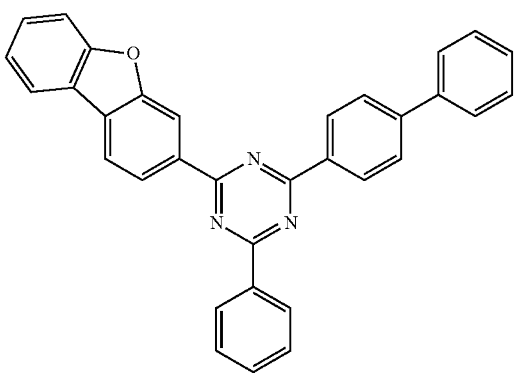
H2-364
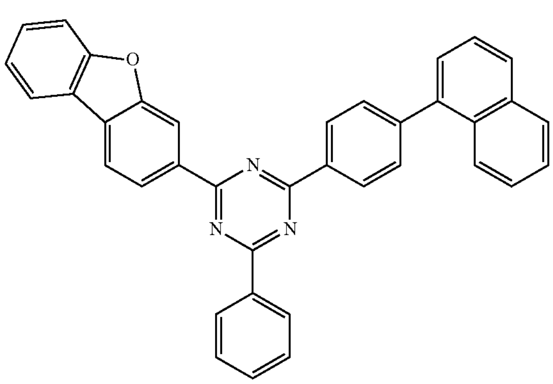
-continued
H2-365
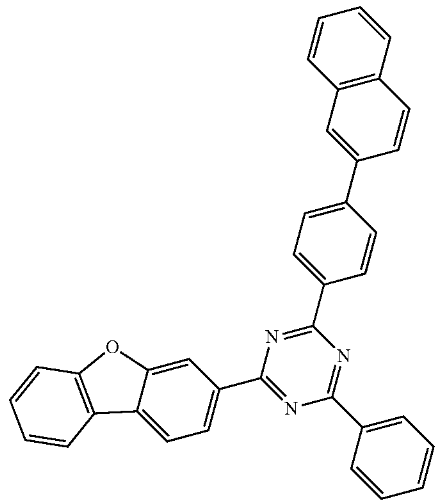
H2-366
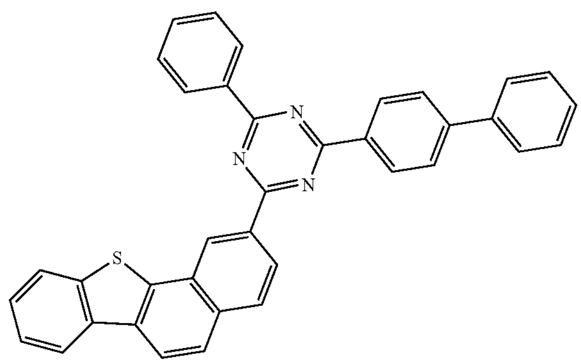
H2-367
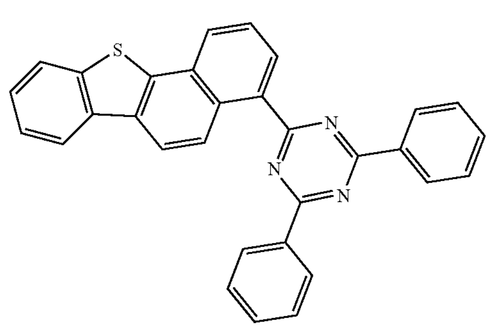

-continued
H2-368
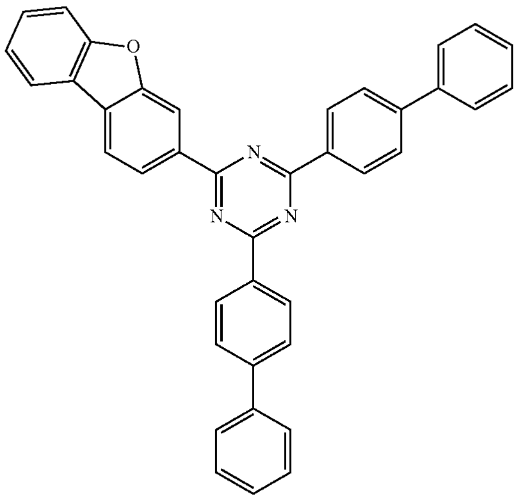
H2-369
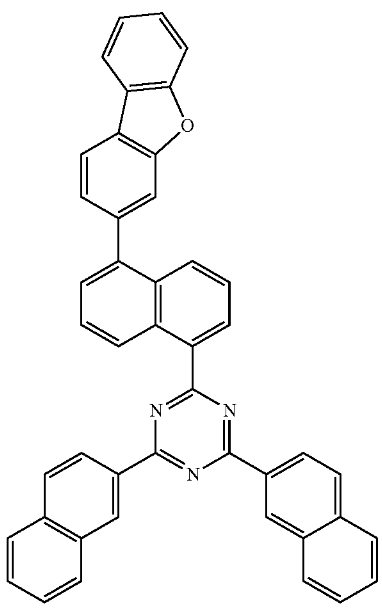
H2-370
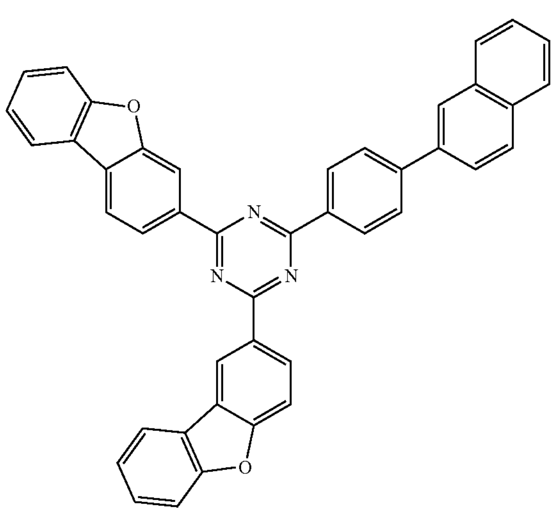
-continued
H2-371
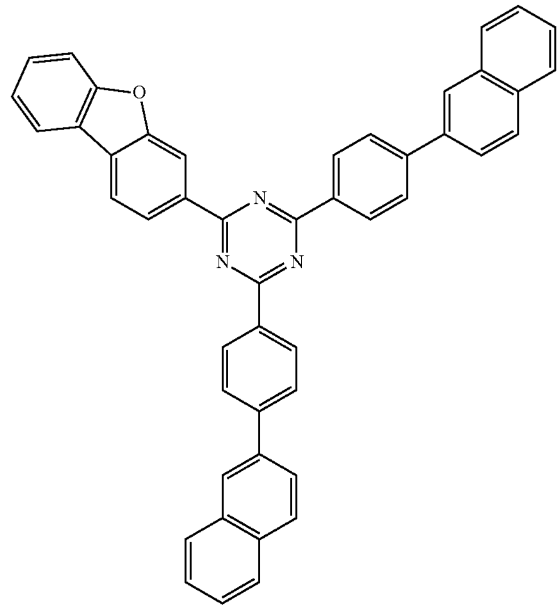
H2-372
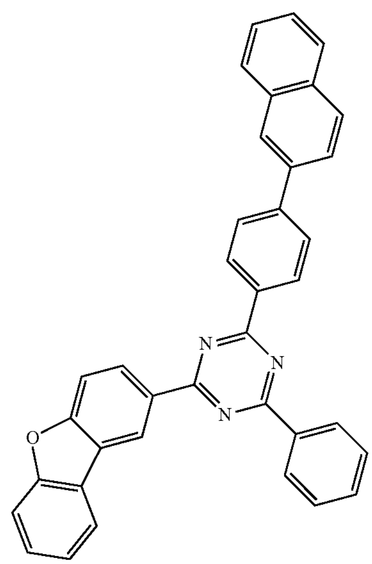
H2-373
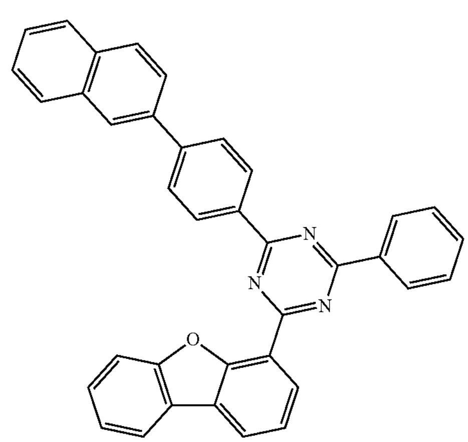

-continued
H2-374
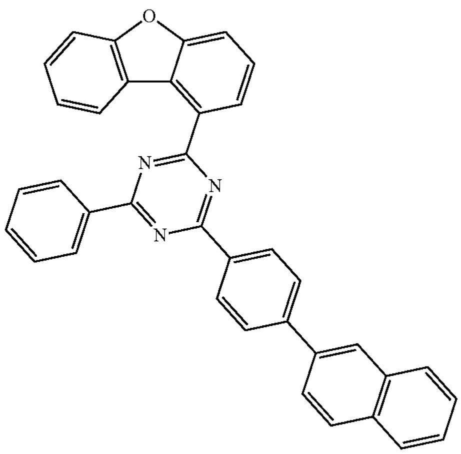
H2-375
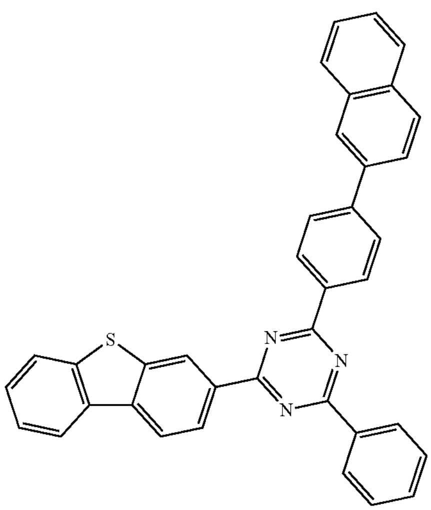
H2-376
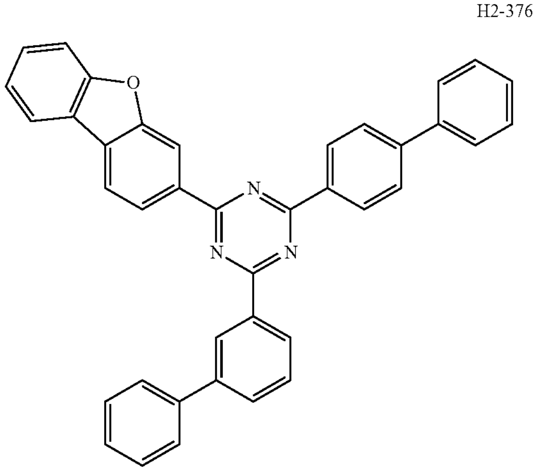
-continued
H2-377
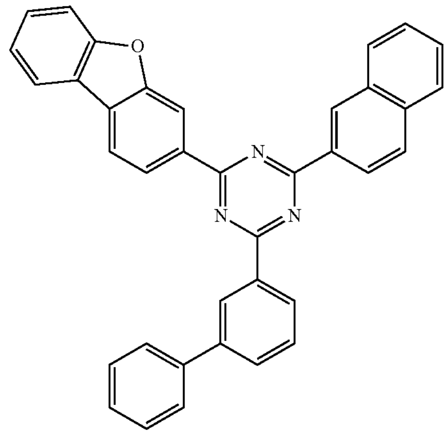
H2-378
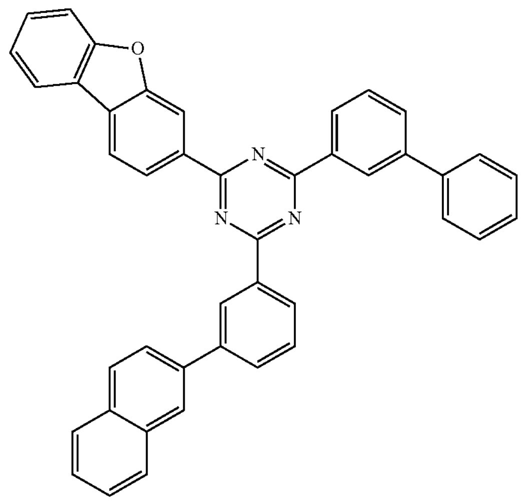
H2-379
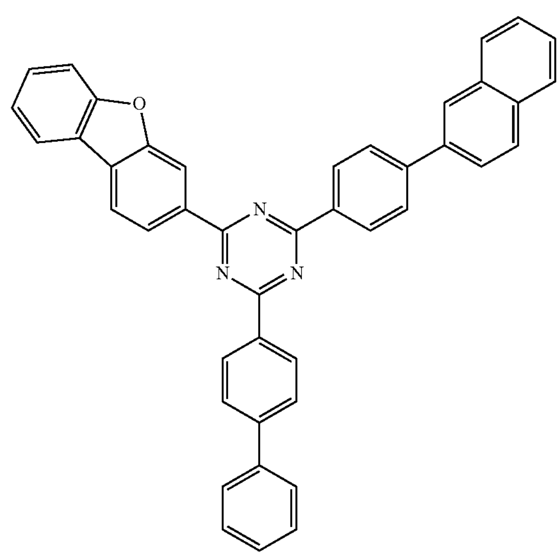

H2-380
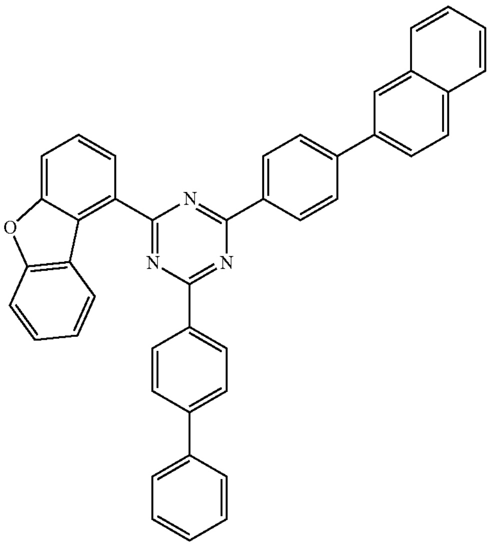
H2-381
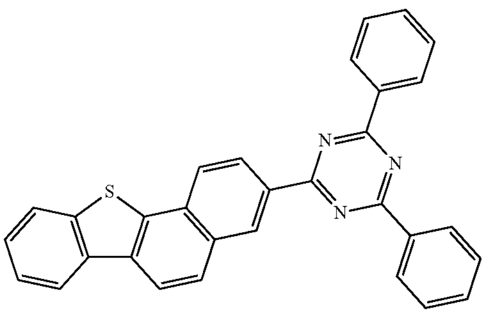
H2-382
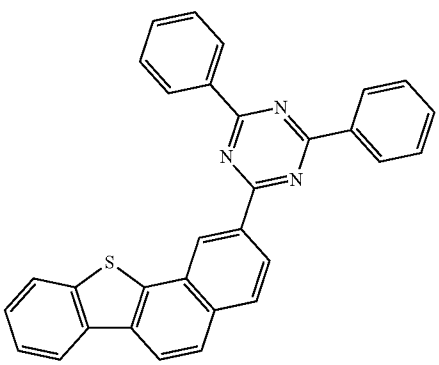
H2-383
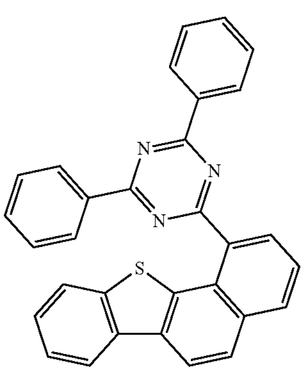
H2-384
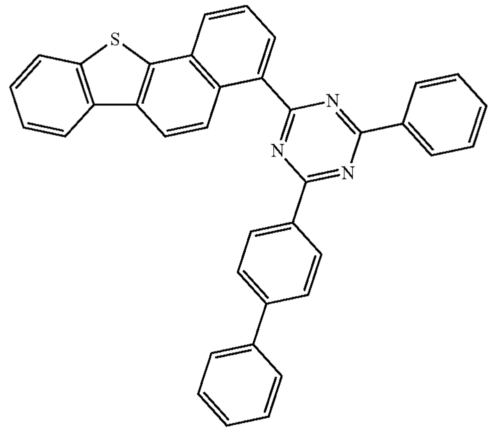
H2-385
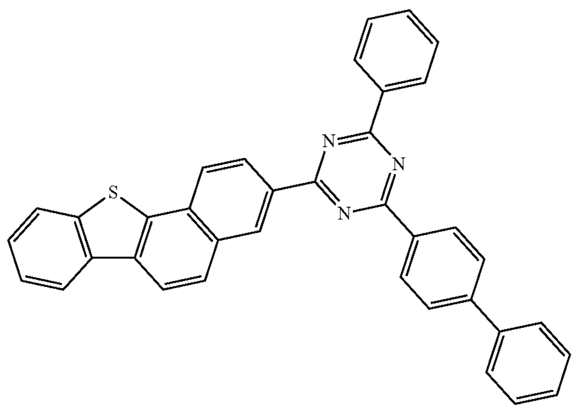
H2-386
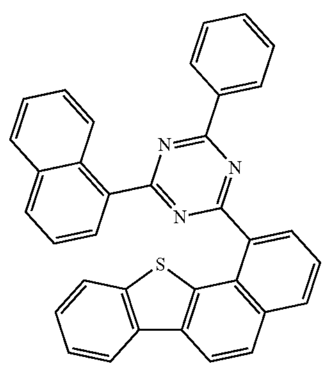
H2-387
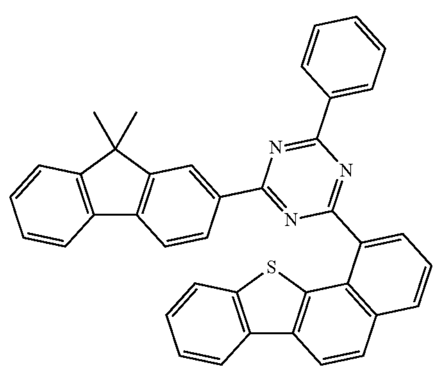

-continued
H2-388
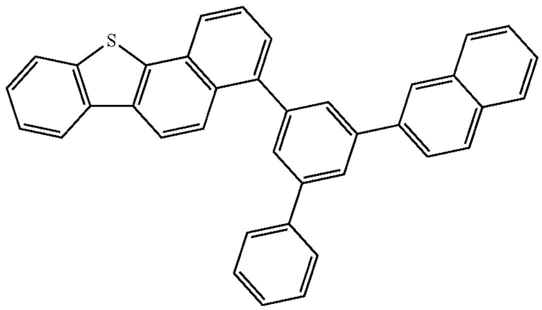
H2-389
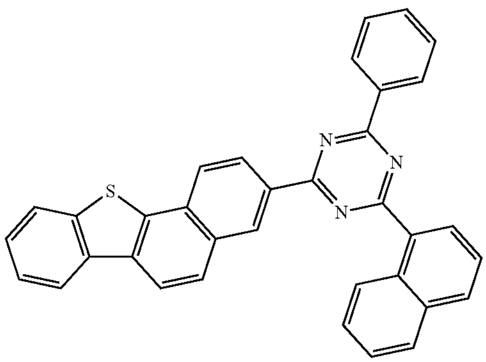
H2-390
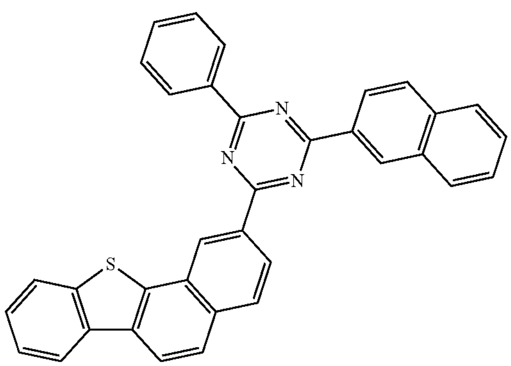
H2-391
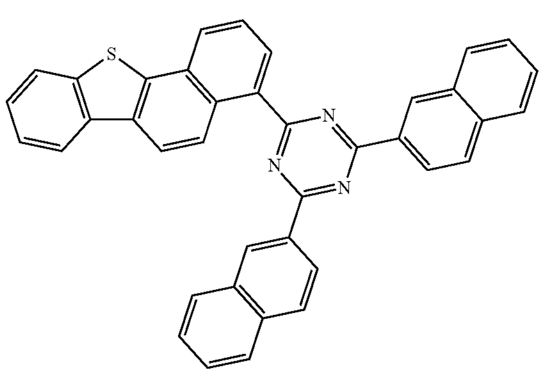
-continued
H2-392
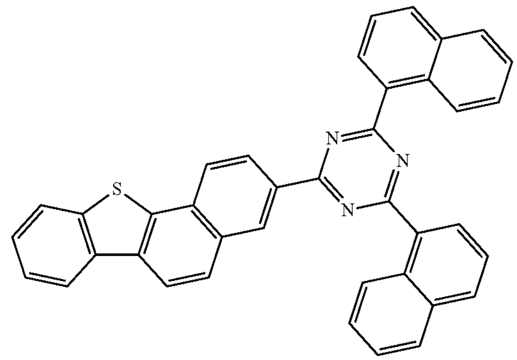
H2-393
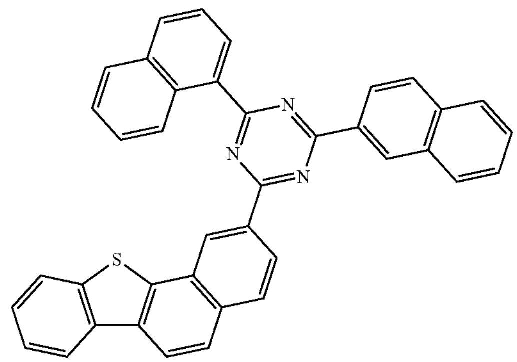
H2-394
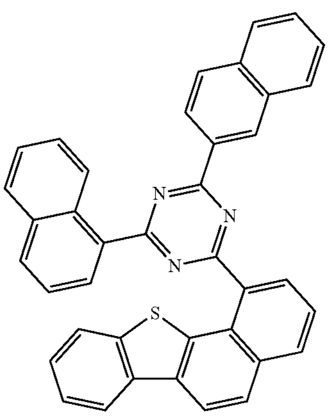
H2-395
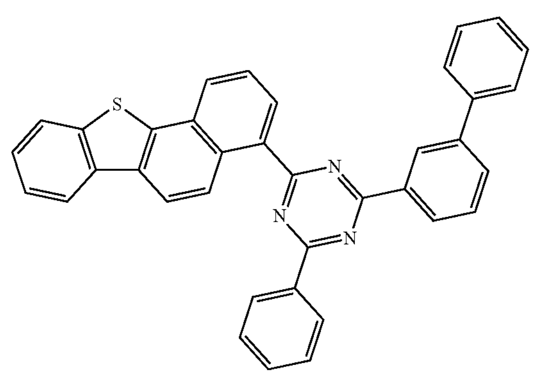

-continued
H2-396
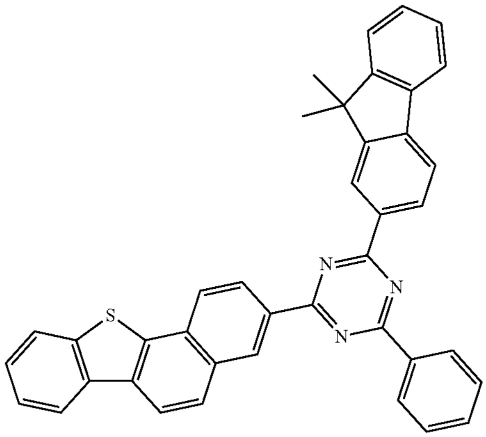
H2-397
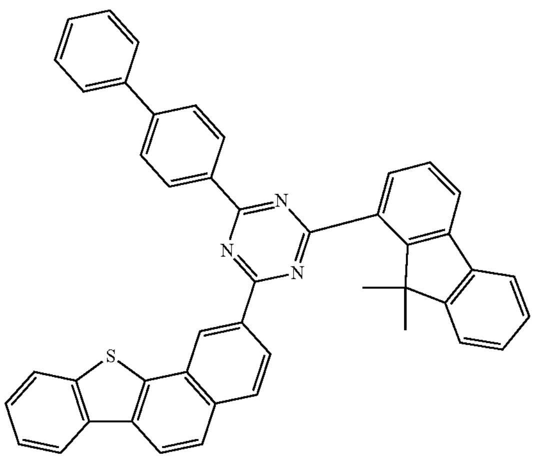
H2-398
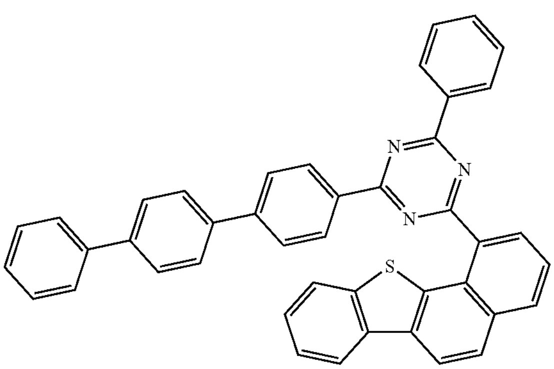
-continued
H2-399
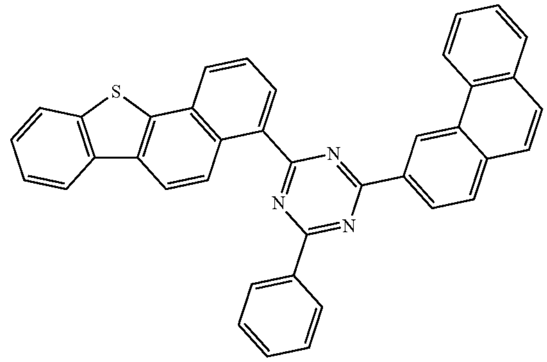
H2-400
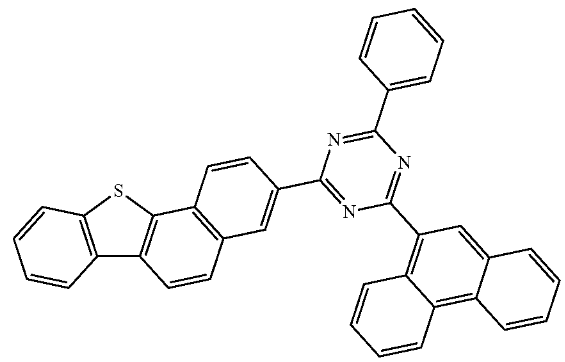
H2-401
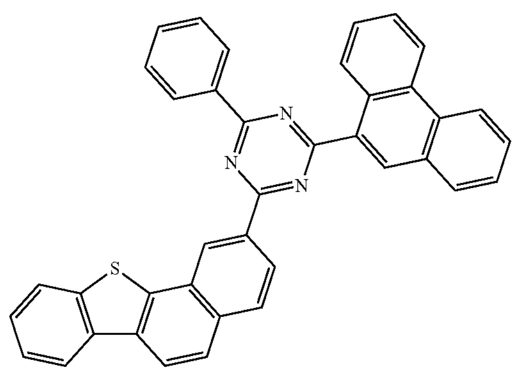
H2-402
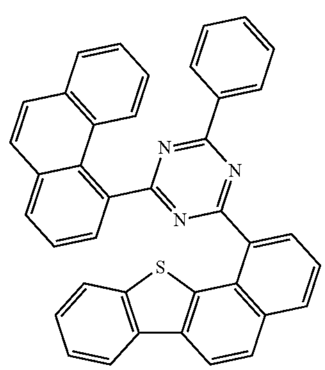

-continued
H2-403
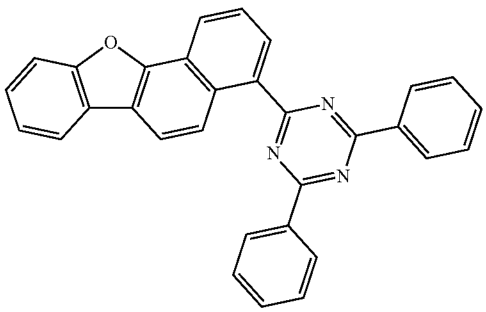
H2-404
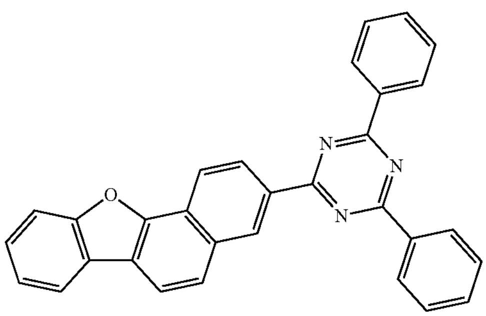
H2-405
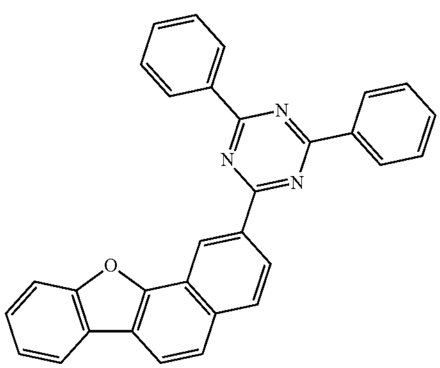
H2-406
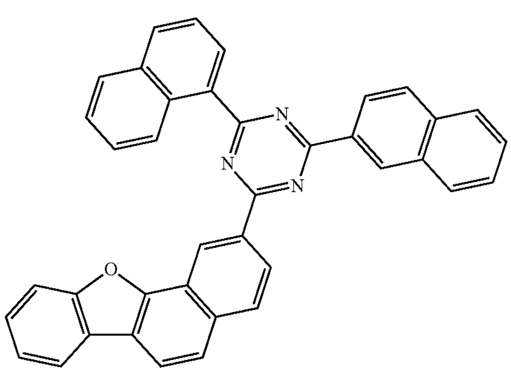
-continued
H2-407
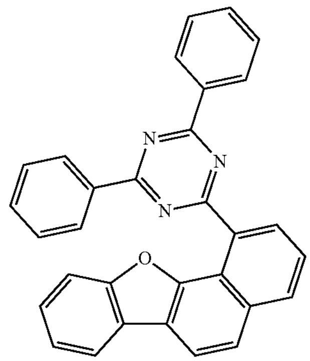
H2-408
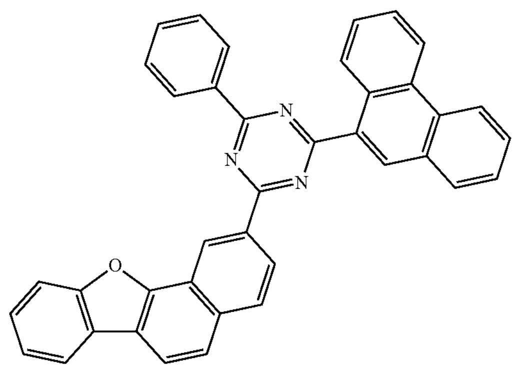
H2-409
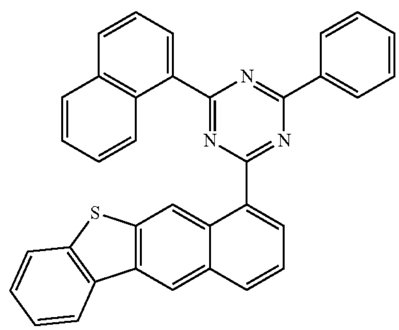
H2-410
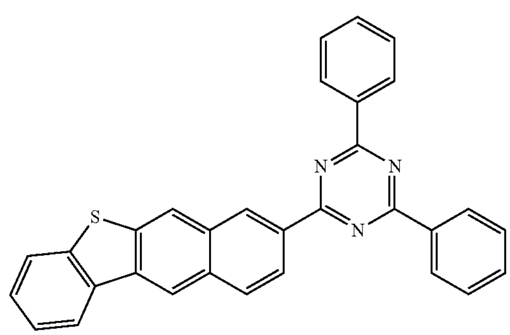

-continued
H2-411
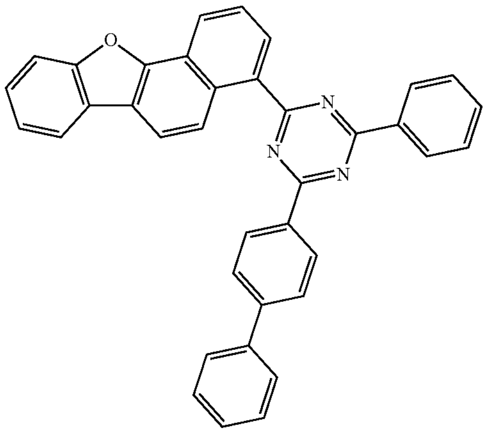
H2-412
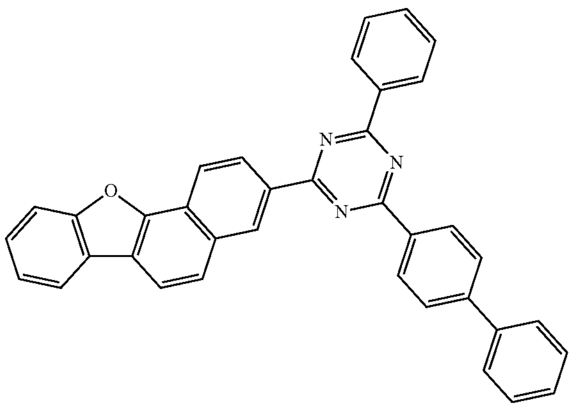
H2-413
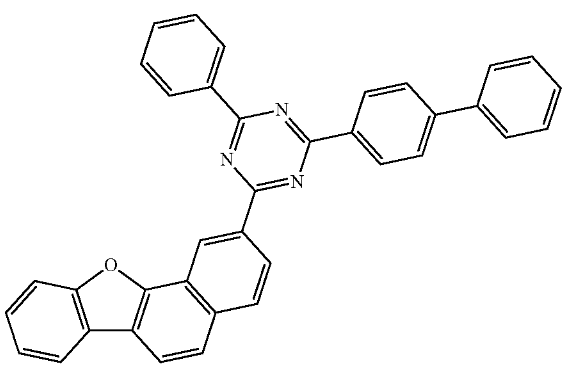
H2-414
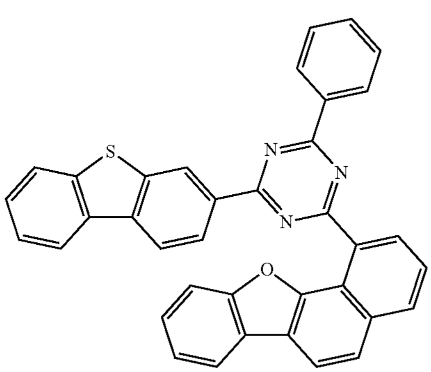
-continued
H2-415
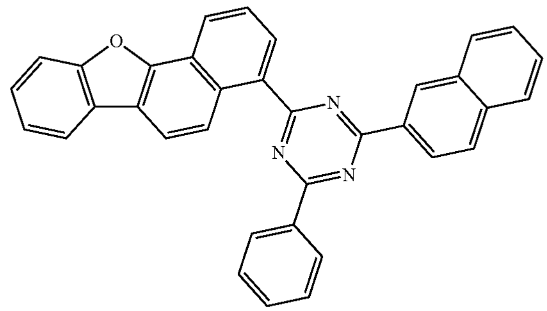
H2-416
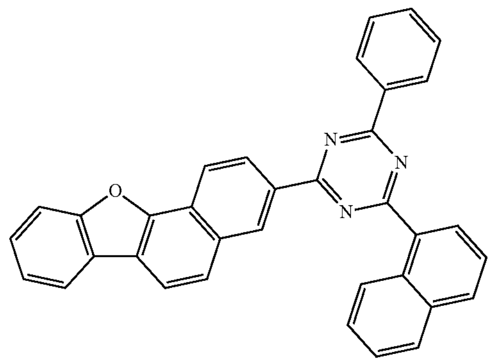
H2-417
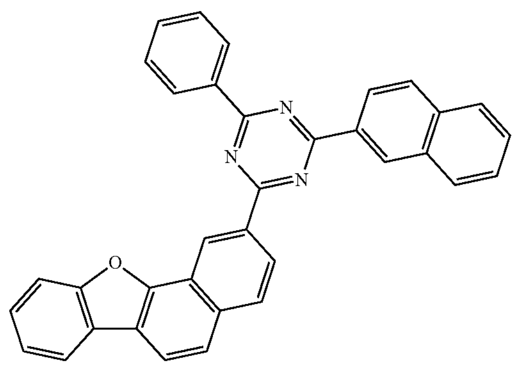
H2-418
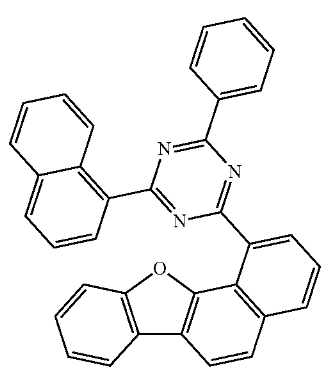

-continued
H2-419
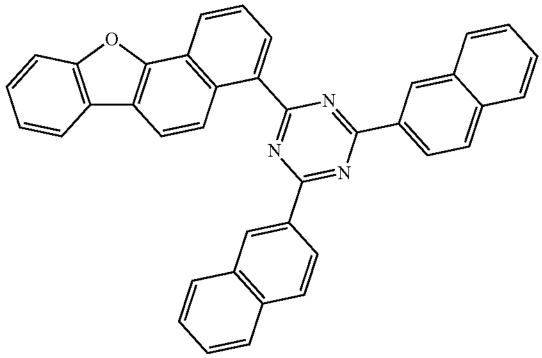
H2-420
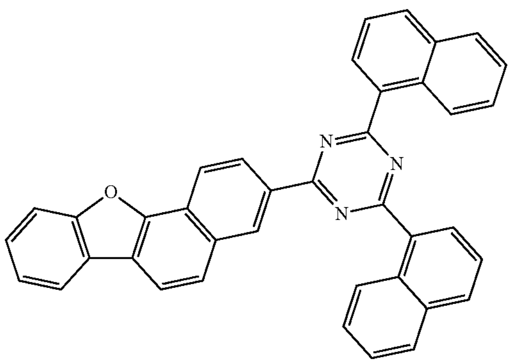
H2-421
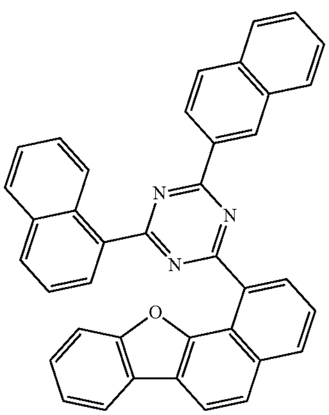
H2-422
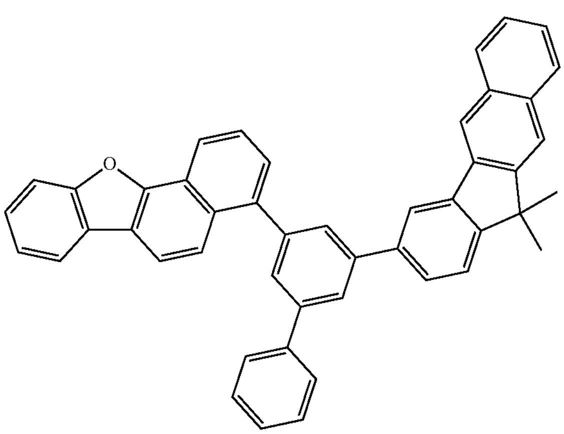
-continued
H2-423
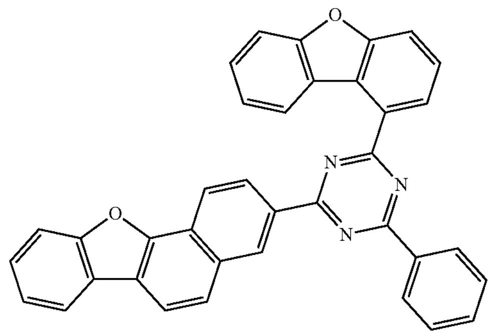
H2-424
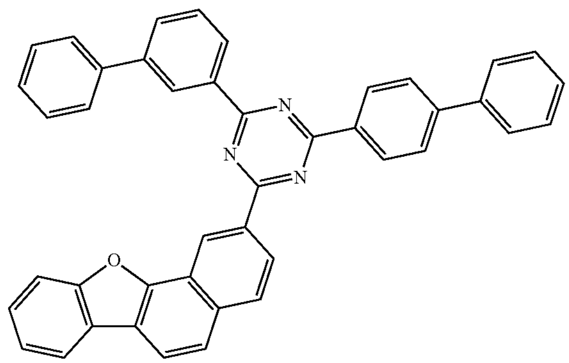
H2-425
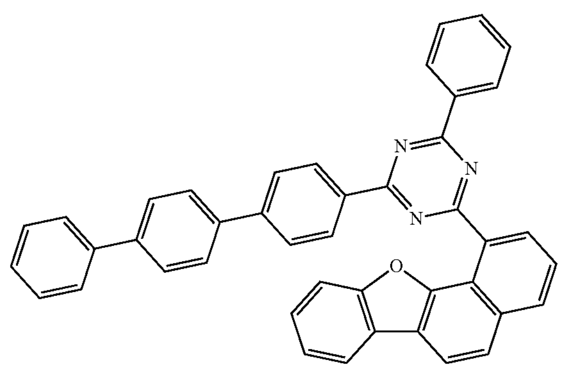
H2-426
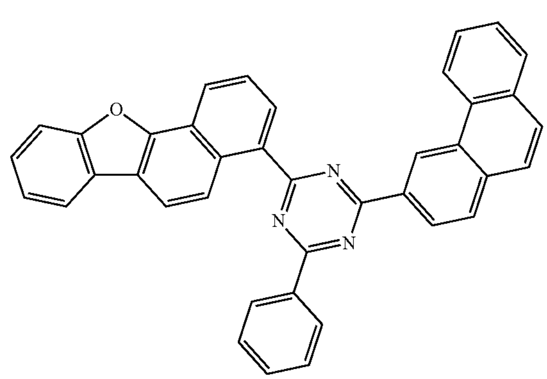

-continued
H2-427
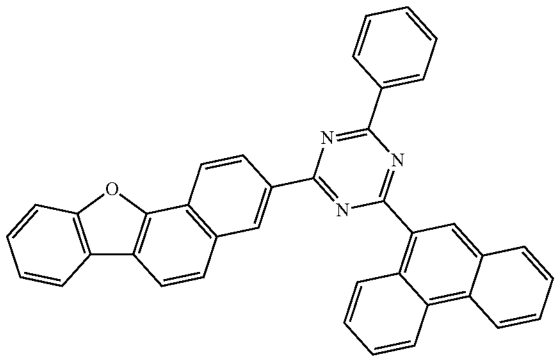
H2-428
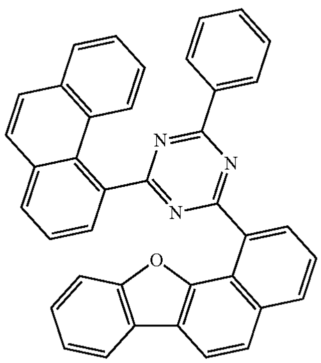
H2-429
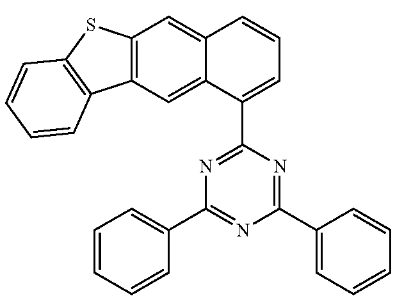
H2-430
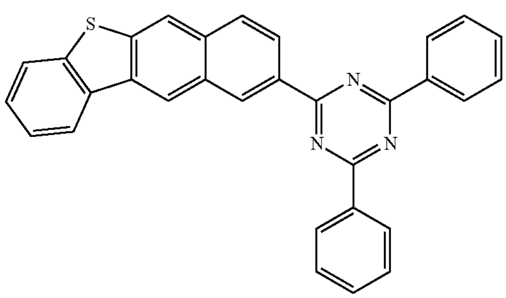
-continued
H2-431
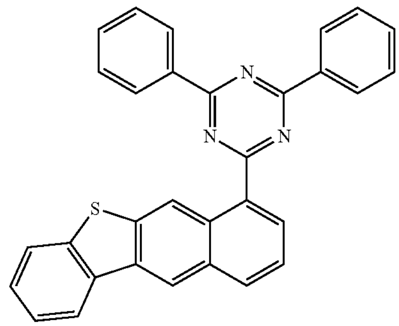
H2-432
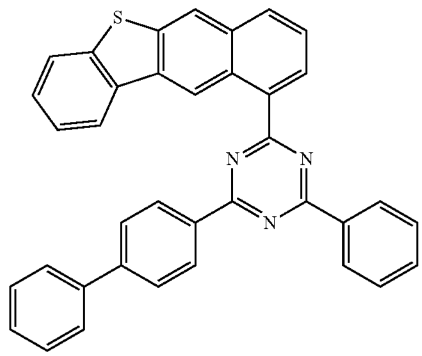
H2433
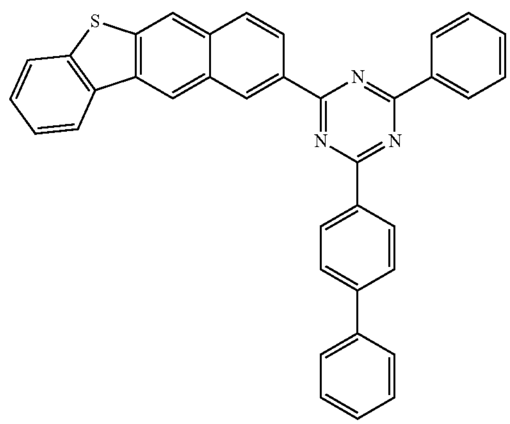
H2-434
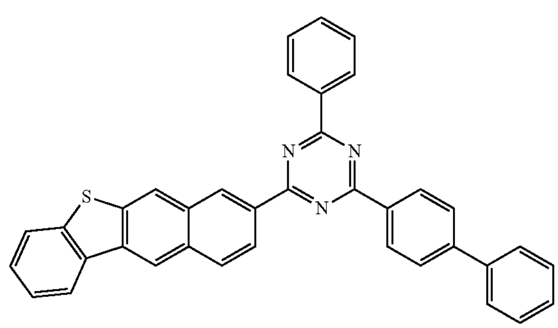

-continued
H2-435
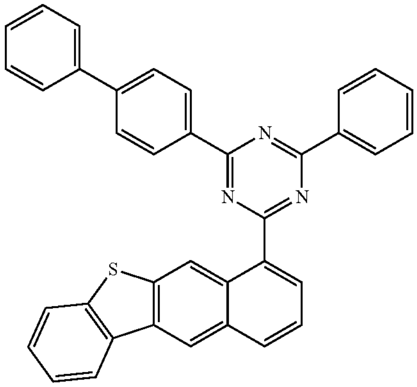
H2-436
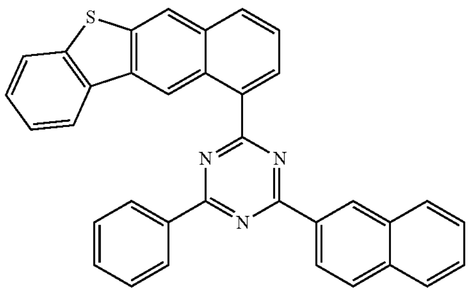
H2-437
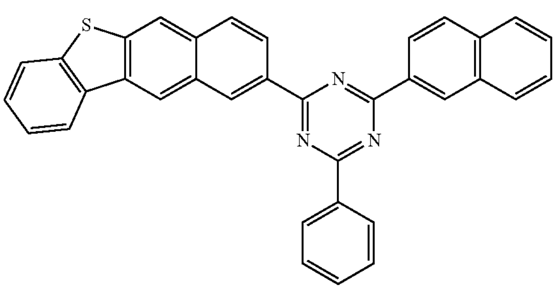
H2-438
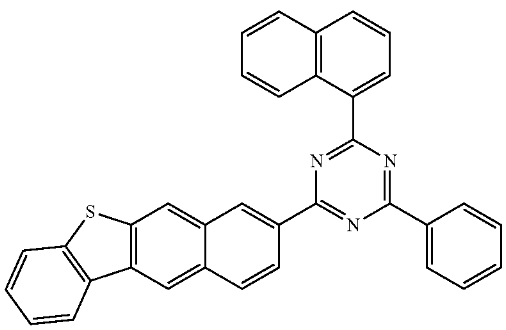
-continued
H2-439
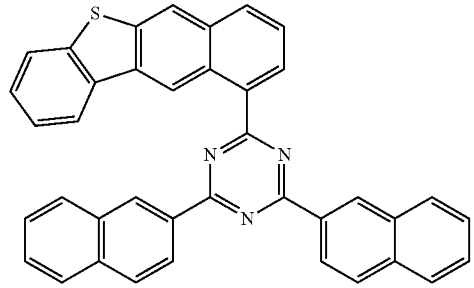
H2-440
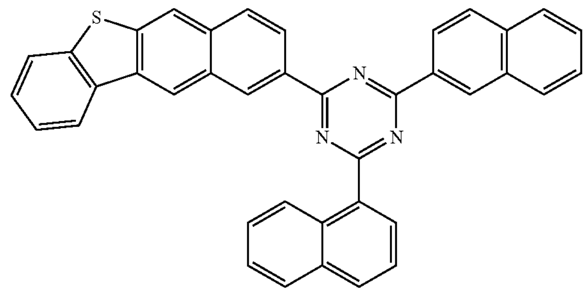
H2-441
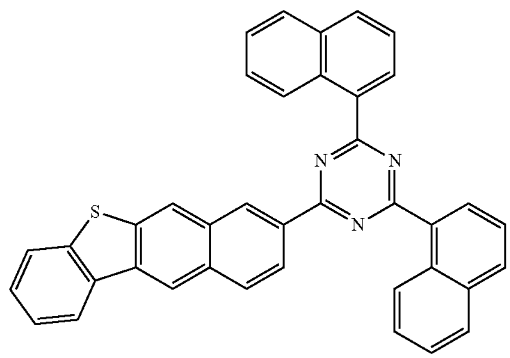
H2-442
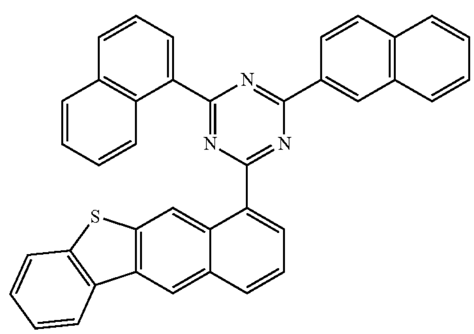

-continued
H2-443
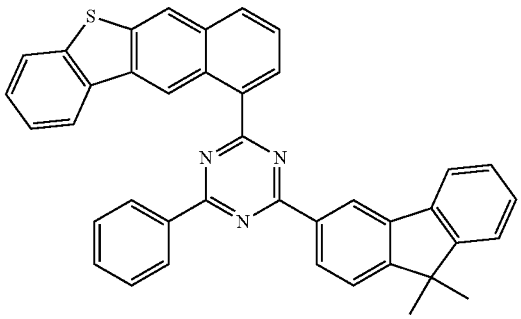
H2-444
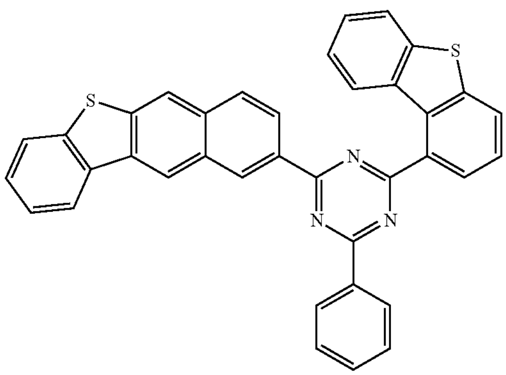
H2-445
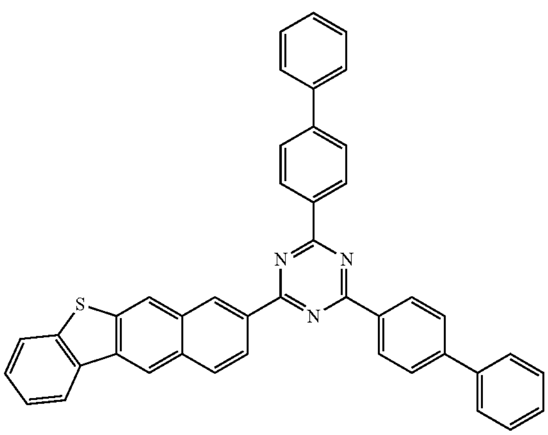
H2-446
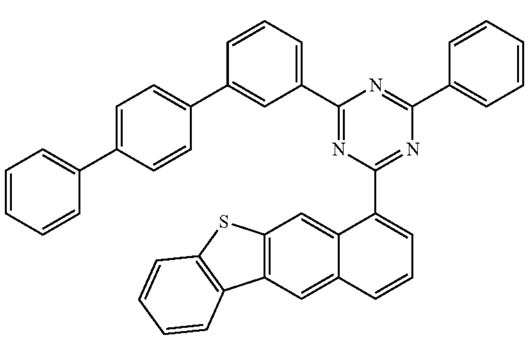
-continued
H2-447
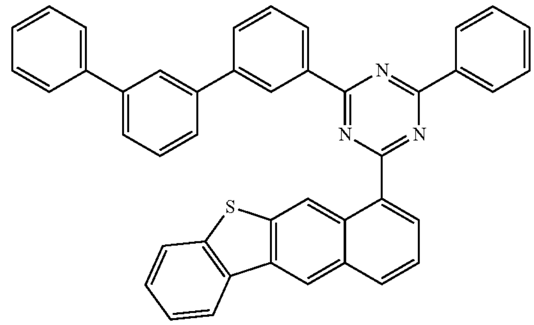
H2-448
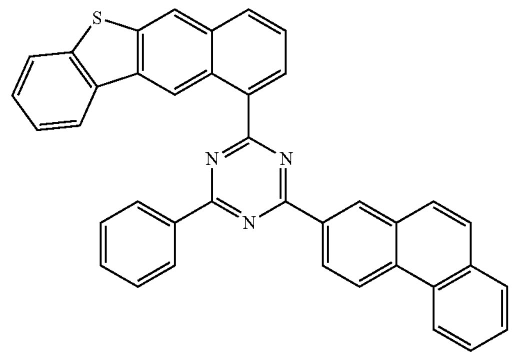
H2-449
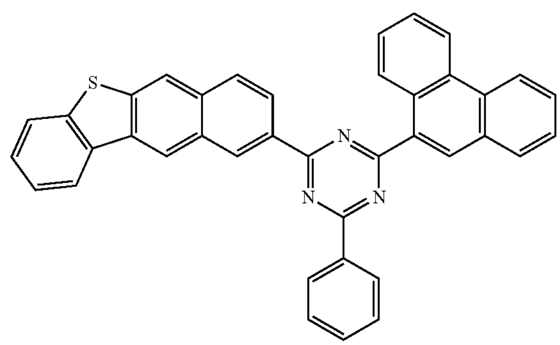
H2-450
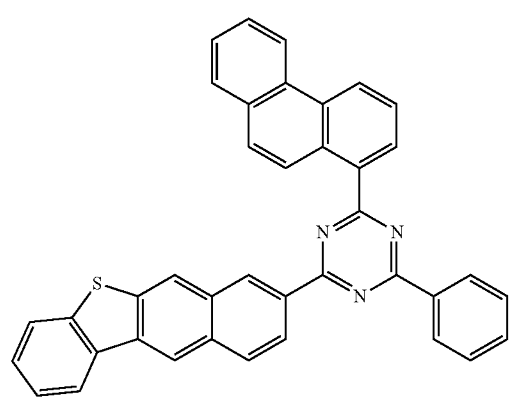

-continued
H2-451
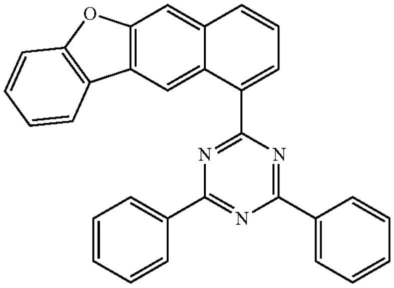
H2-452
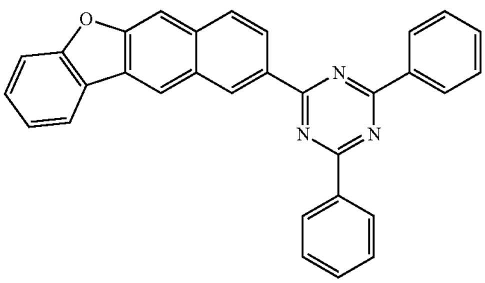
H2-453
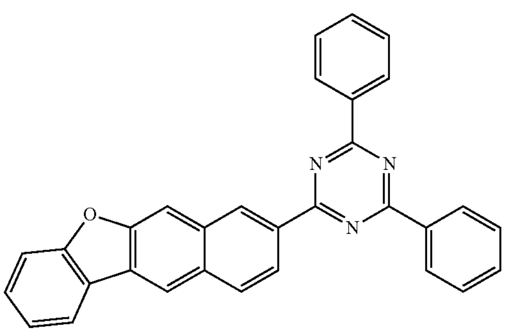
H2-454
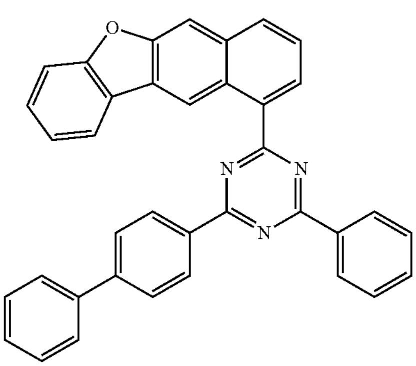
-continued
H2-455
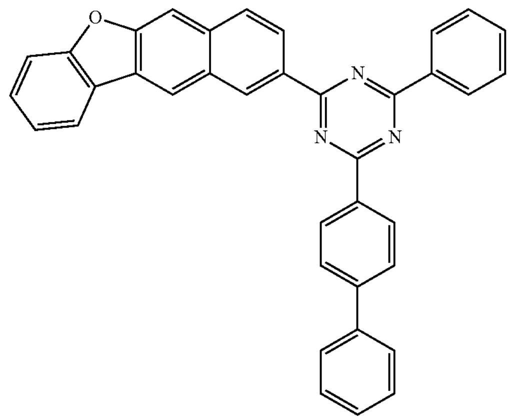
H2-456
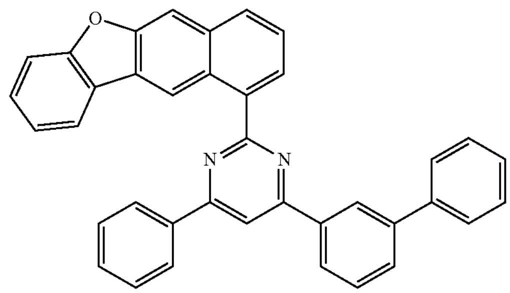
H2-457
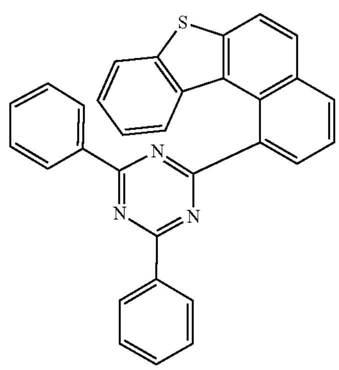
H2-458
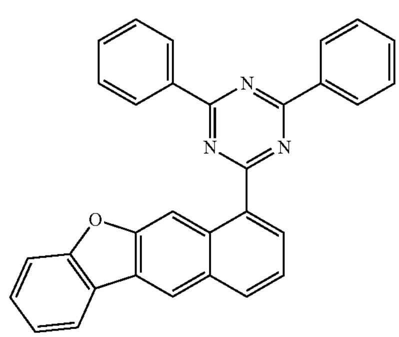

-continued
H2-459
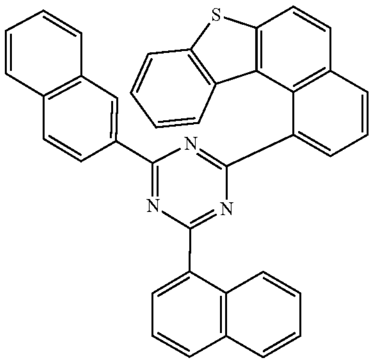
H2-460
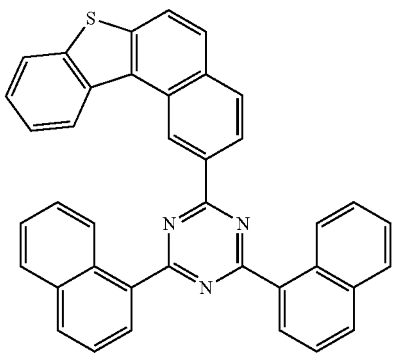
H2-461
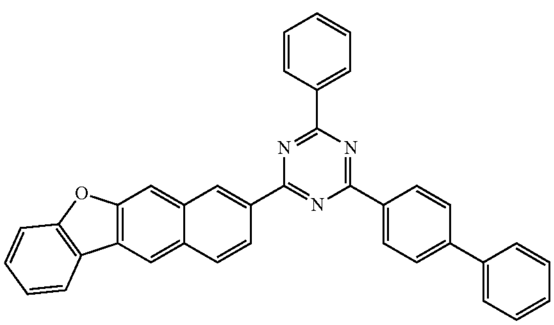
H2-462
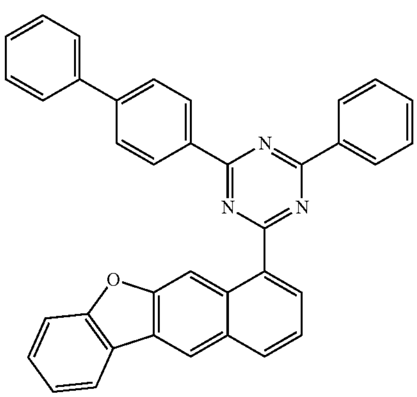
-continued
H2-463
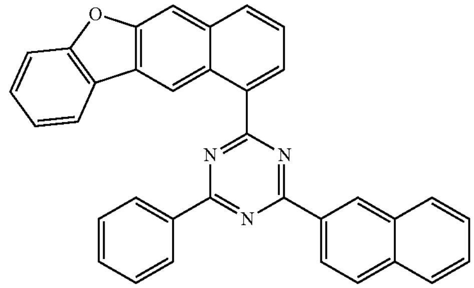
H2-464
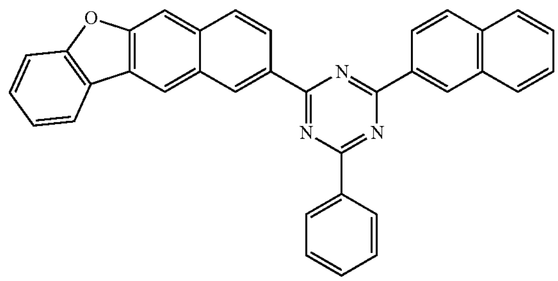
H2-465
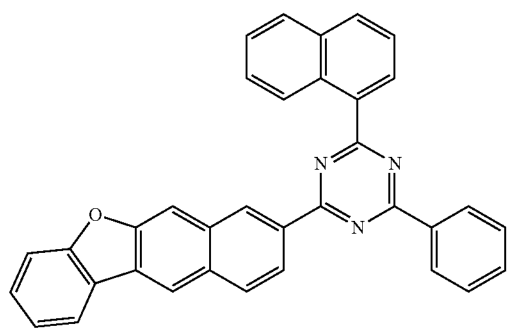
H2-466
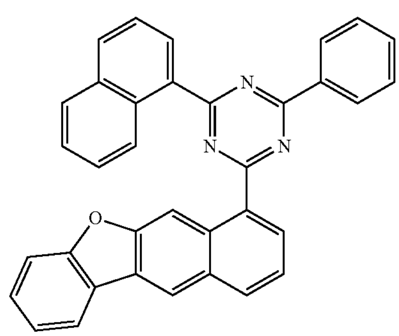
H2-467
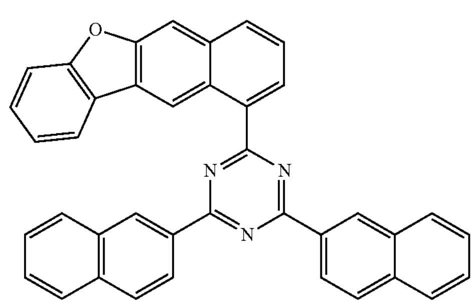

-continued
H2-468
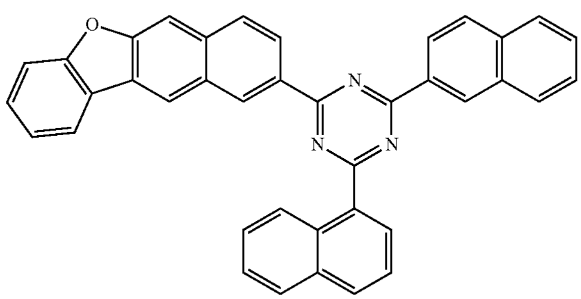
H2-469
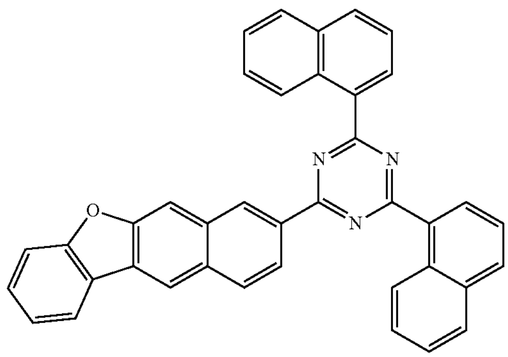
H2-470
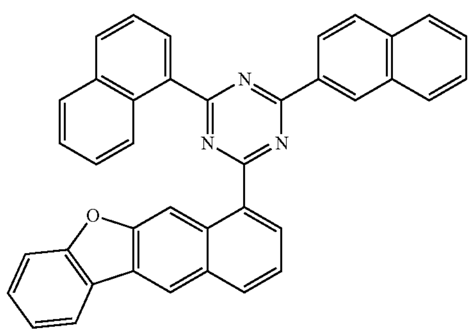
H2-471
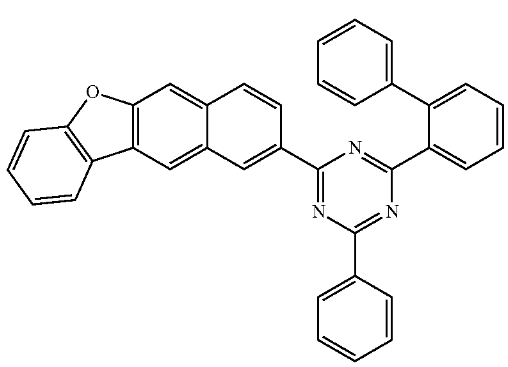
-continued
H2-472
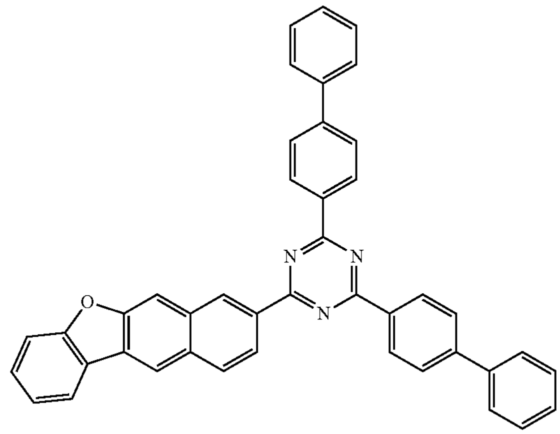
H2-473
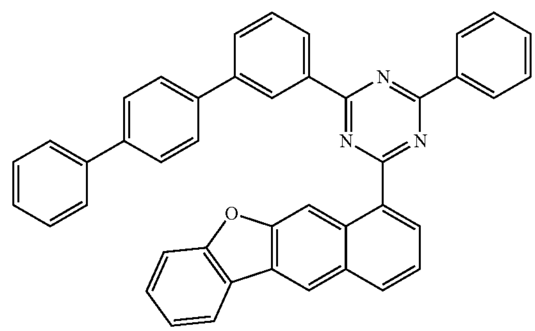
H2-474
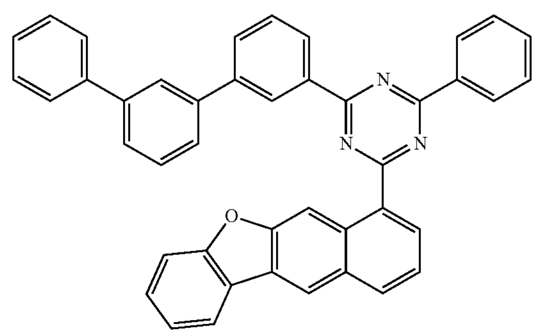
H2-475
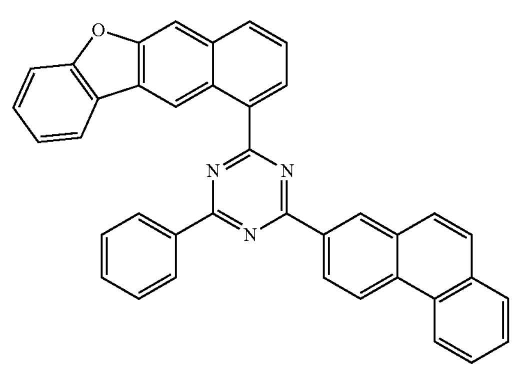

-continued
H2-476
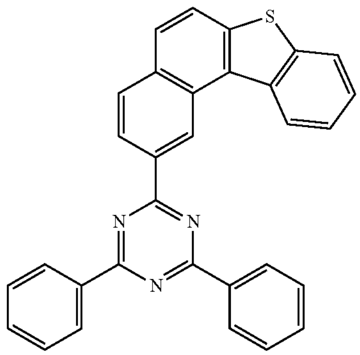
H2-477
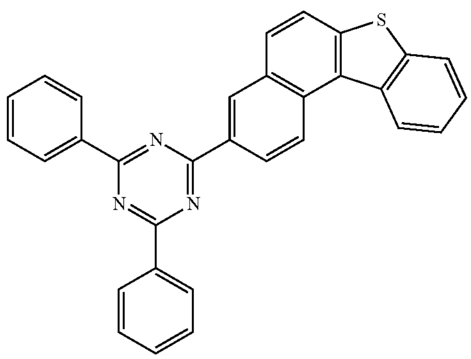
H2-478
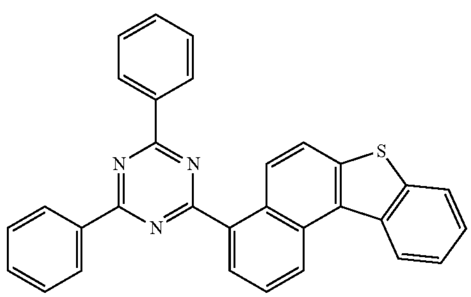
H2-479
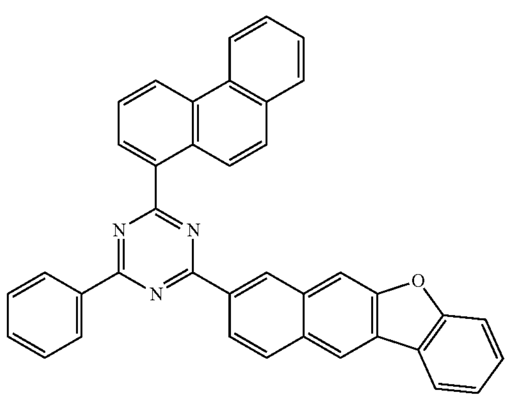
-continued
H2-480
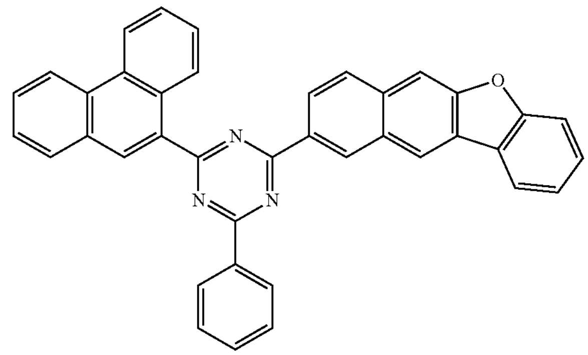
H2-481
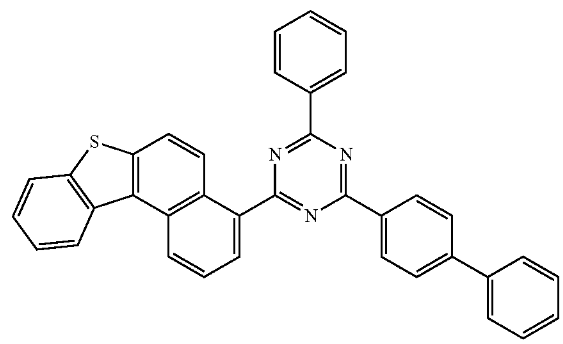
H2-482
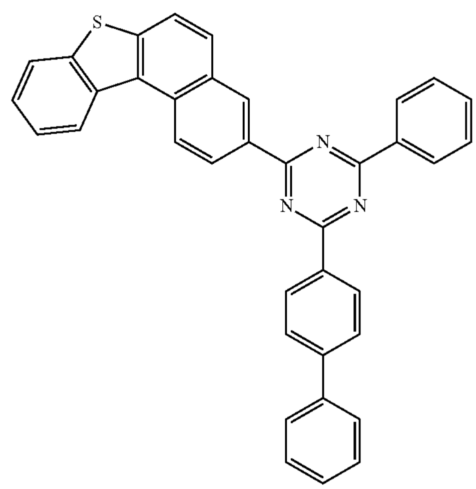
H2-483
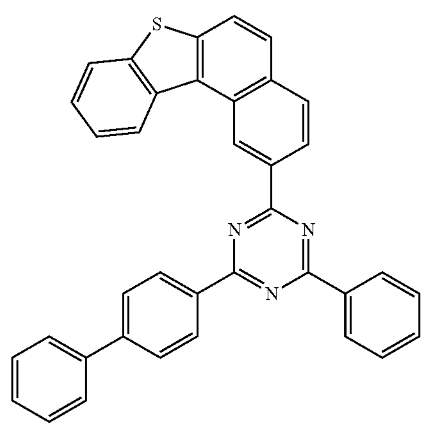

-continued
H2-484
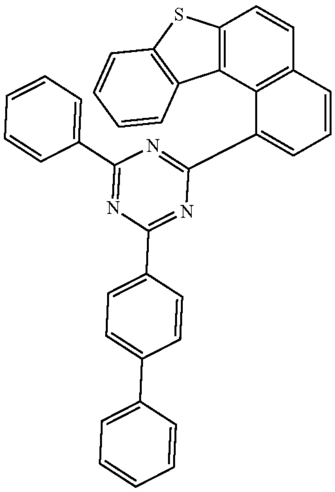
H2-485
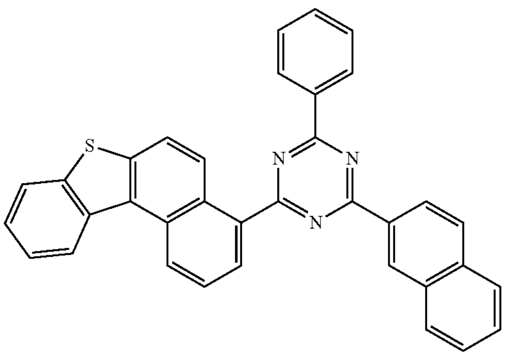
H2-486
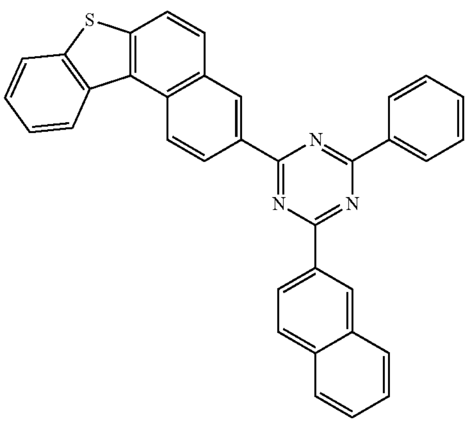
H2-487
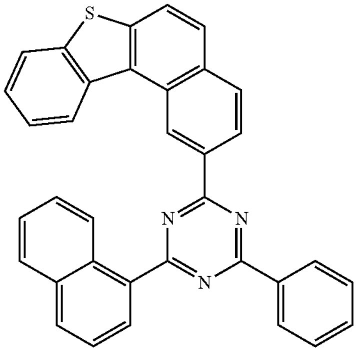
-continued
H2-488
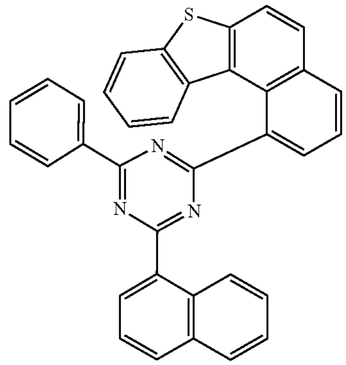
H2-489
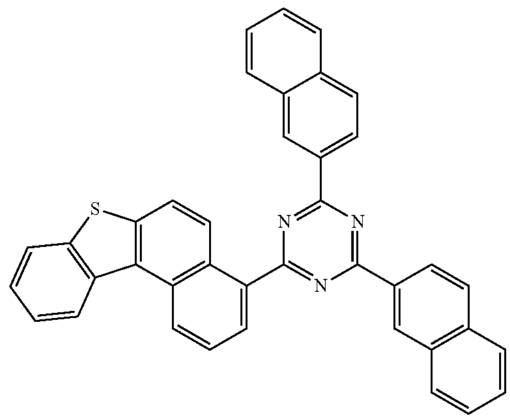
H2-490
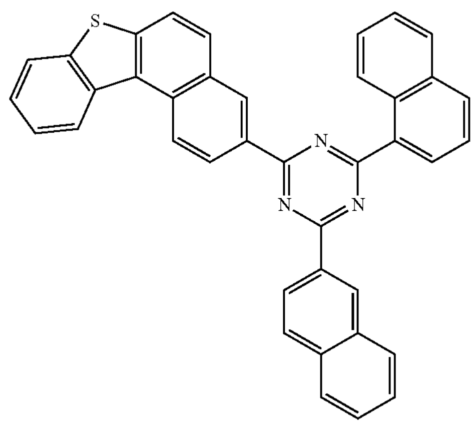
H2-491
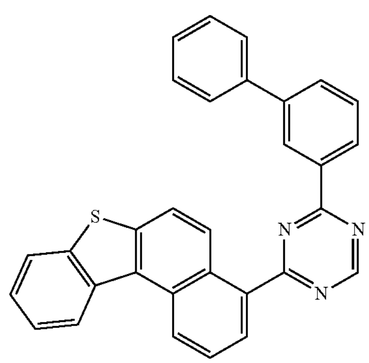

-continued
H2-494
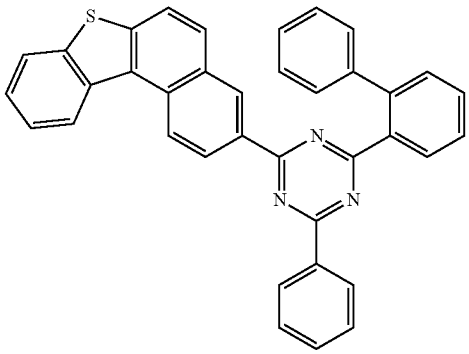
H2-493
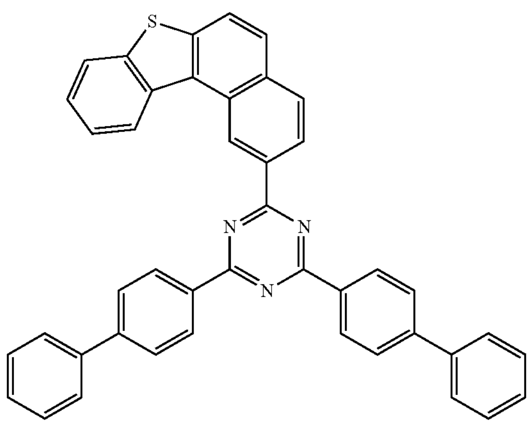
H2-494
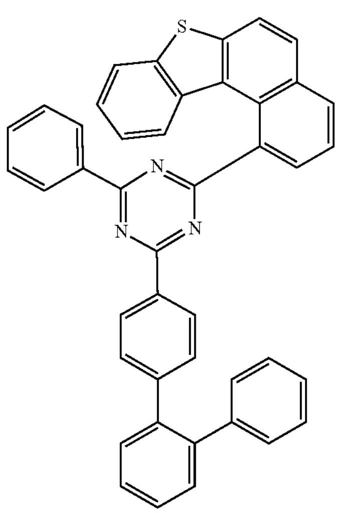
-continued
H2-495
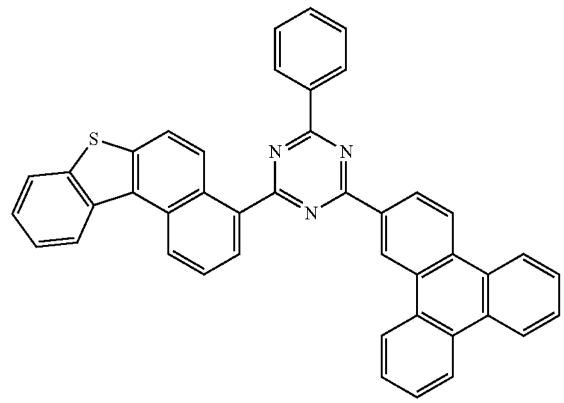
H2-496
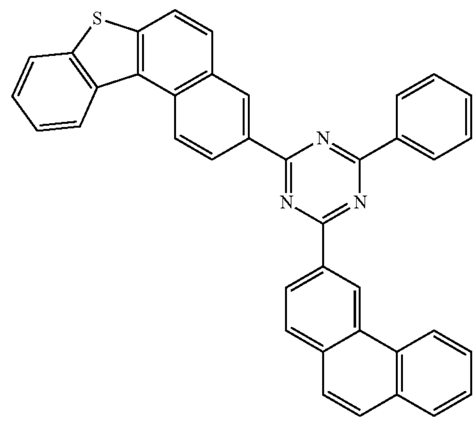
H2-497
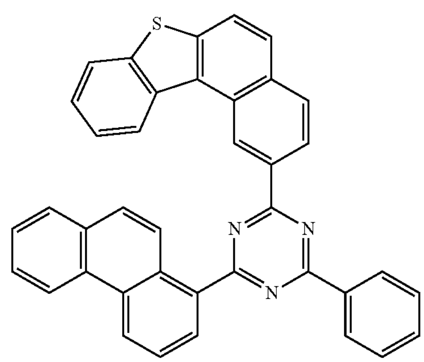
H2-498
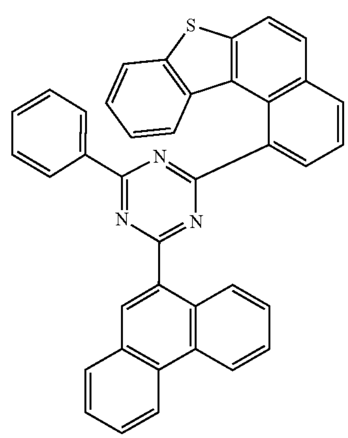

-continued
H2-499
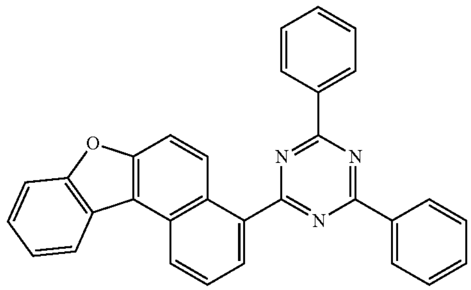
H2-500
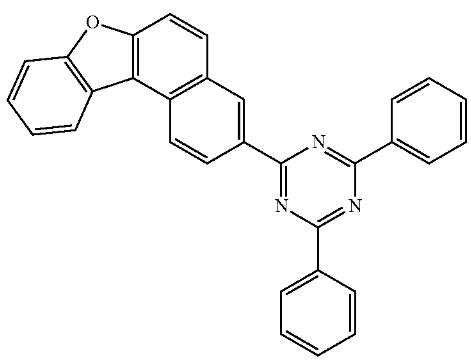
H2-501
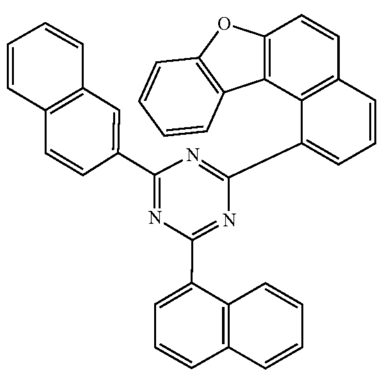
H2-502
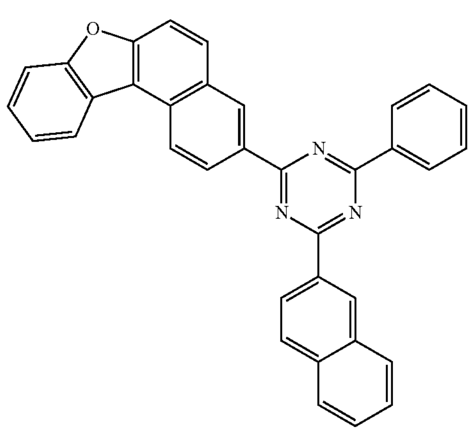
-continued
H2-503
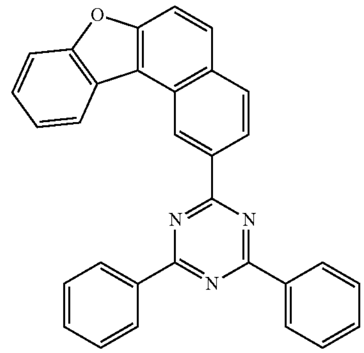
H2-504
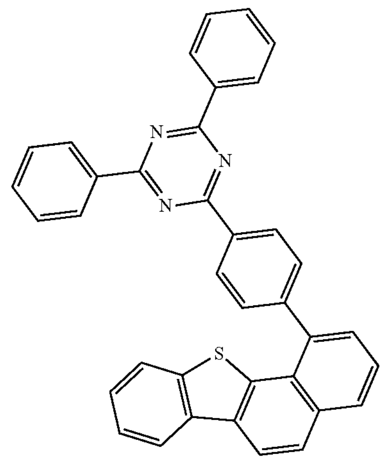
H2-505
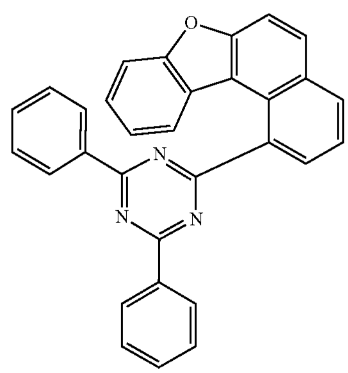
H2-506
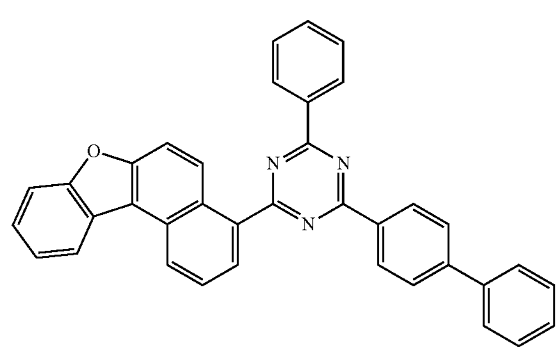

-continued
H2-507
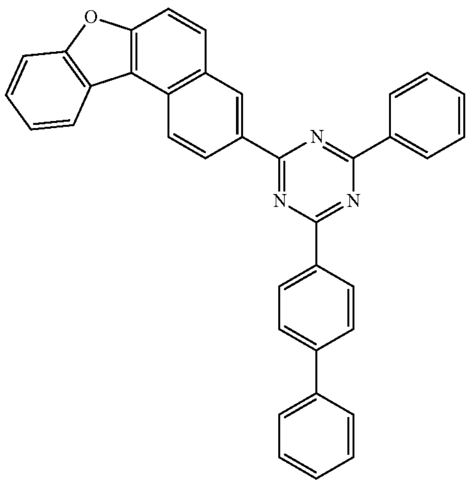
H2-508
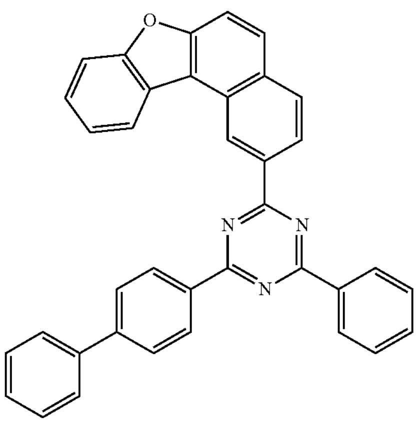
H2-509
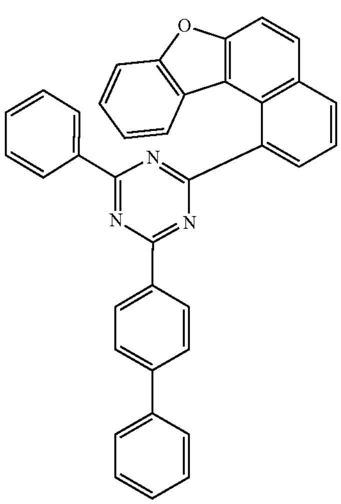
-continued
H2-510
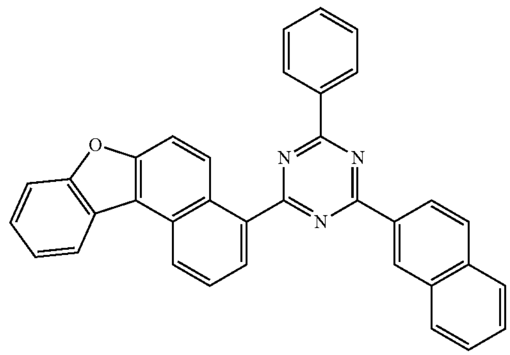
H2-511
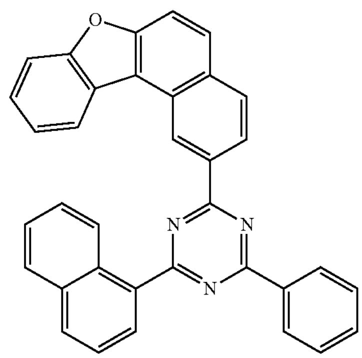
H2-512
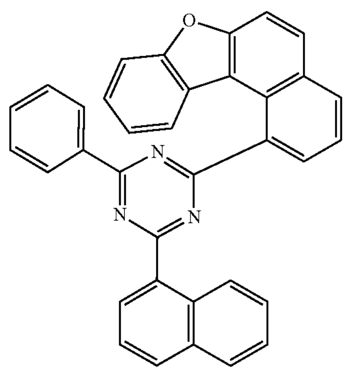
H2-513
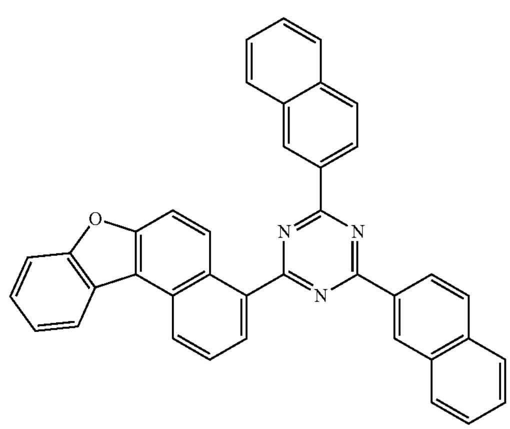

-continued
H2-514
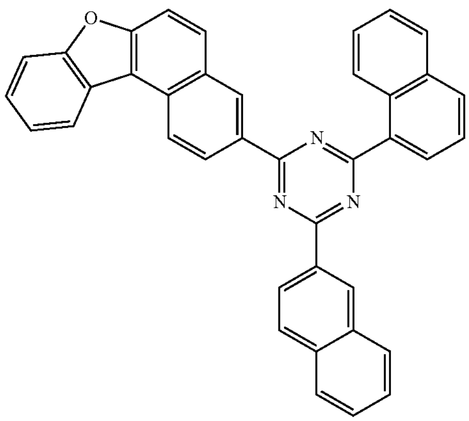
H2-515
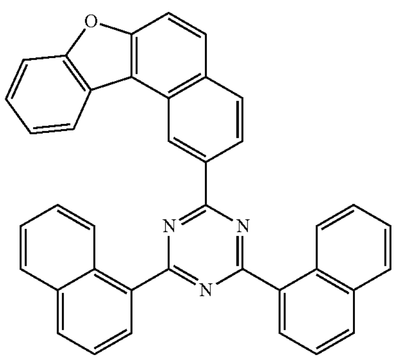
H2-516
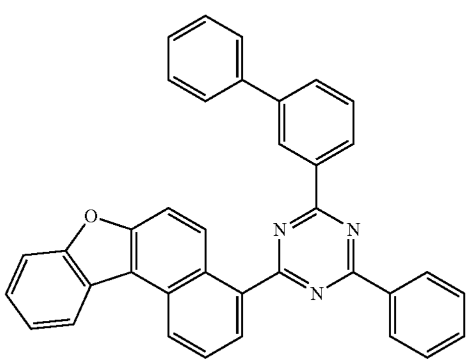
H2-517
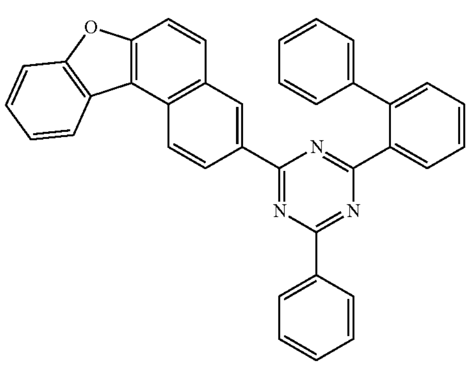
-continued
H2-518
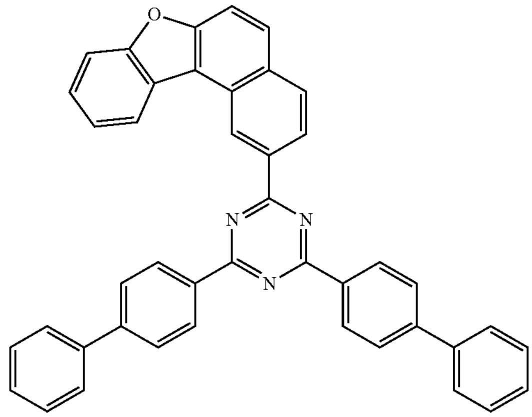
H2-519
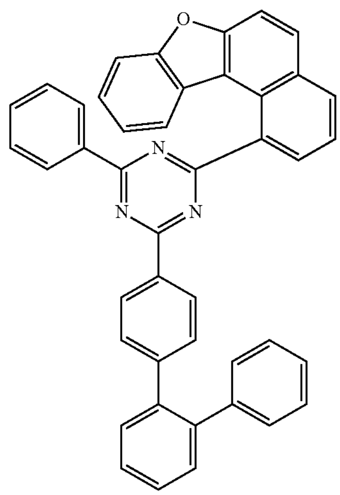
H2-520
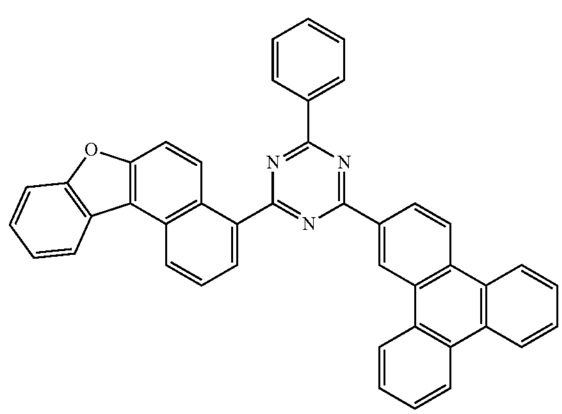

-continued
H2-521
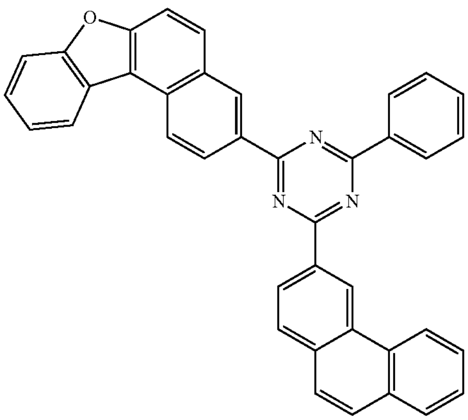
H2-522
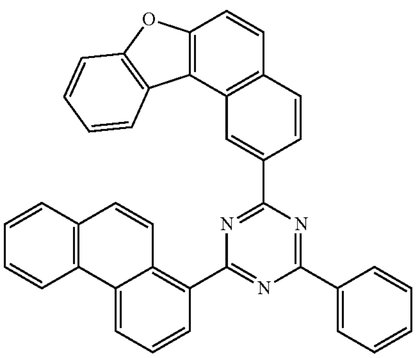
H2-523
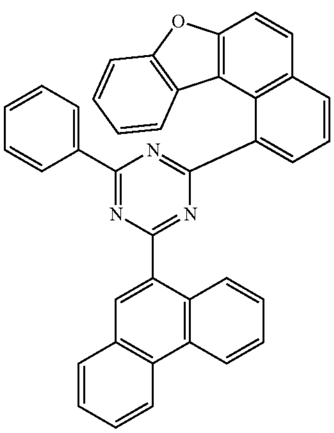
H2-524
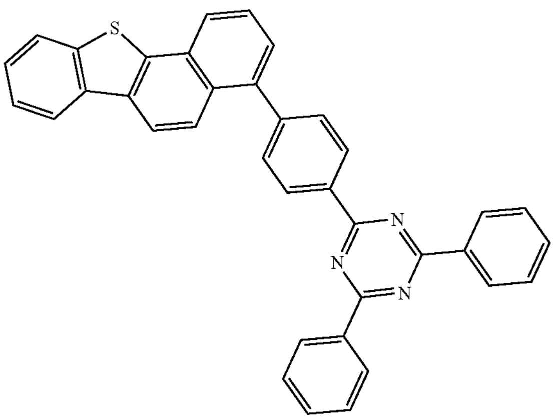
-continued
H2-525
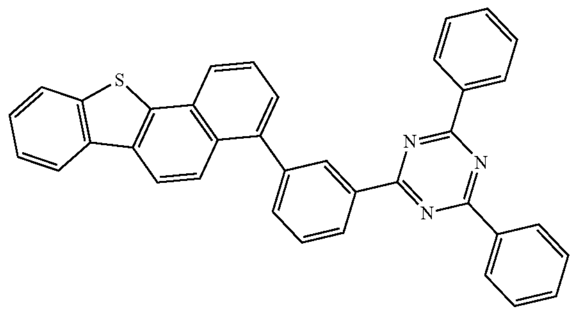
H2-526
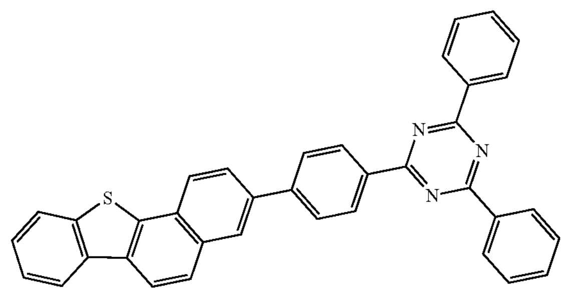
H2-527
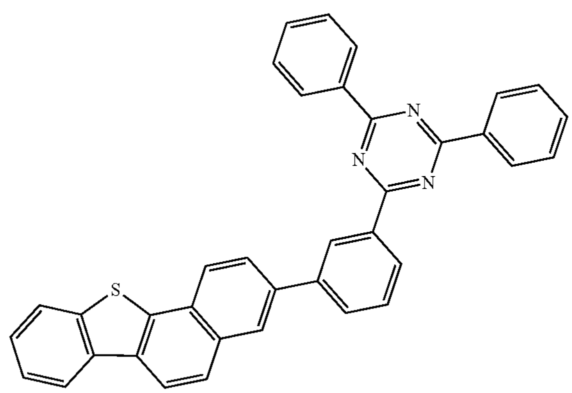
H2-528
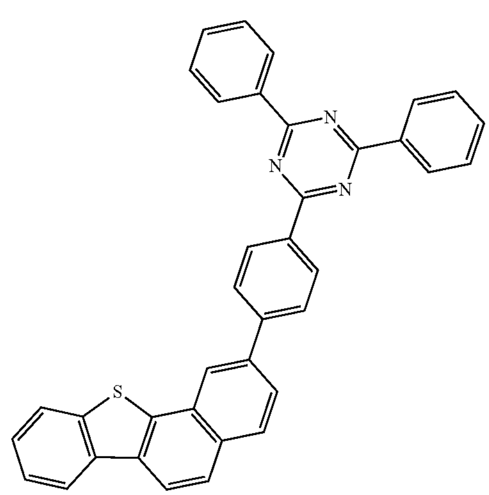

-continued
H2-529
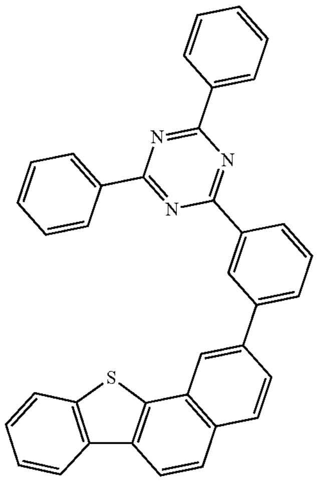
H2-530
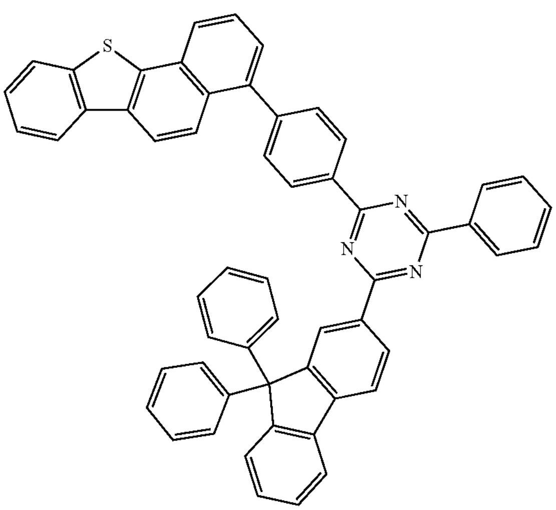
H2-531
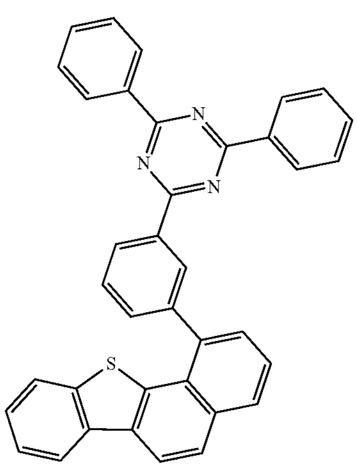
-continued
H2-532
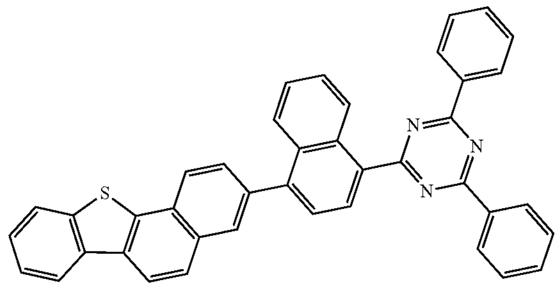
H2-533
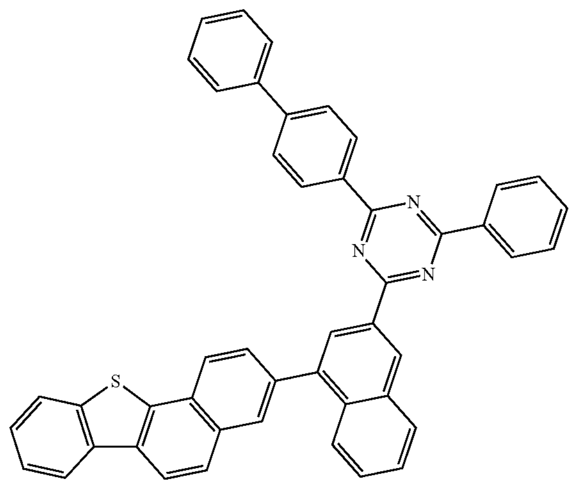
H2-534
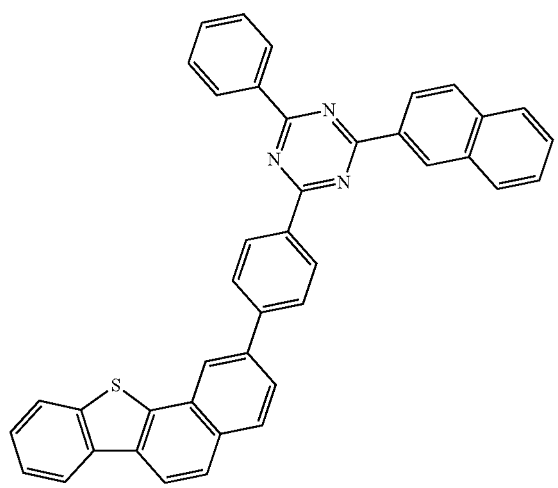

H2-535
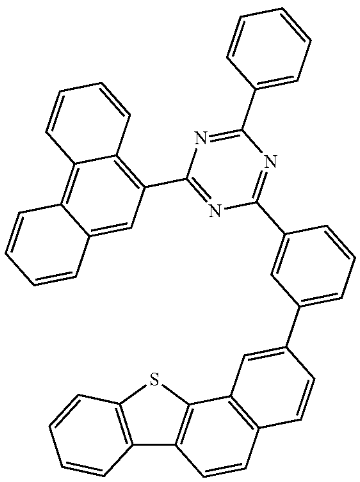
H2-536
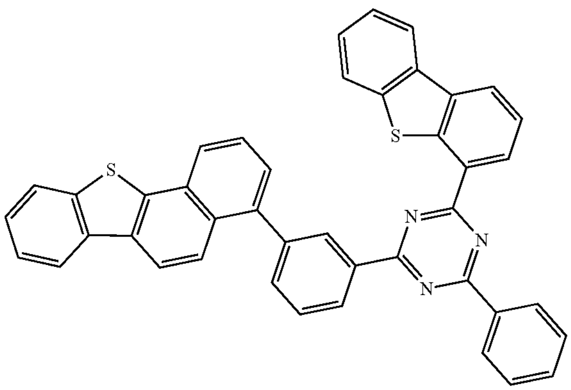
H2-537
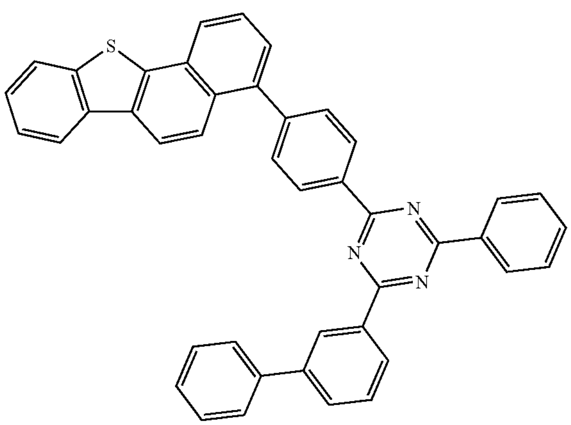
H2-538
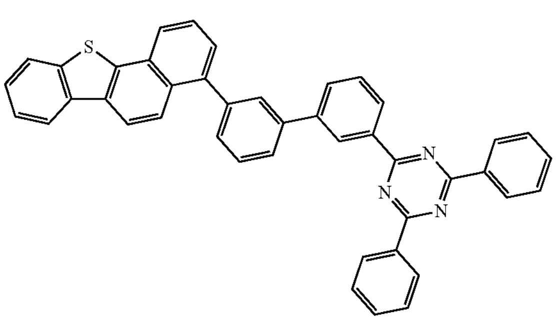
H2-539
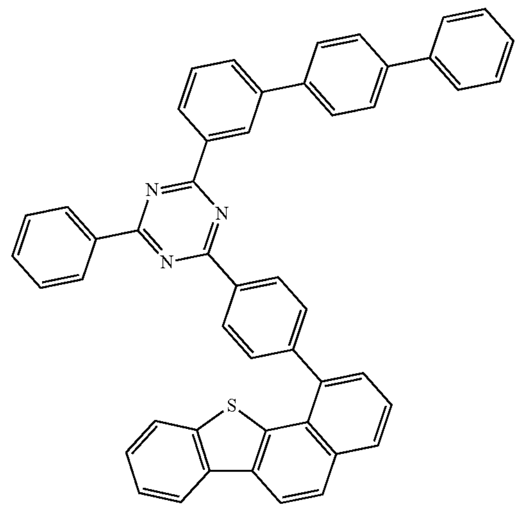
H2-540
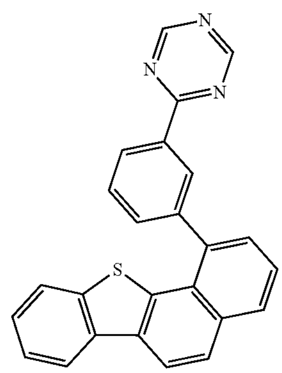
H2-541
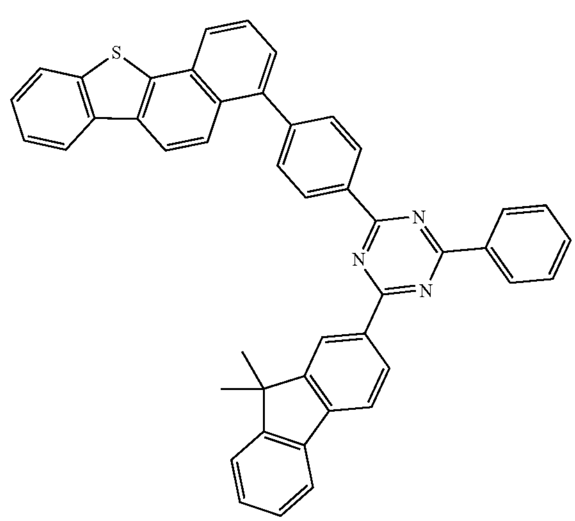

-continued
H2-542
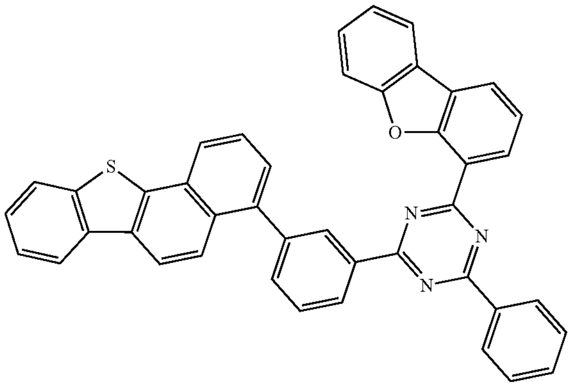
H2-543
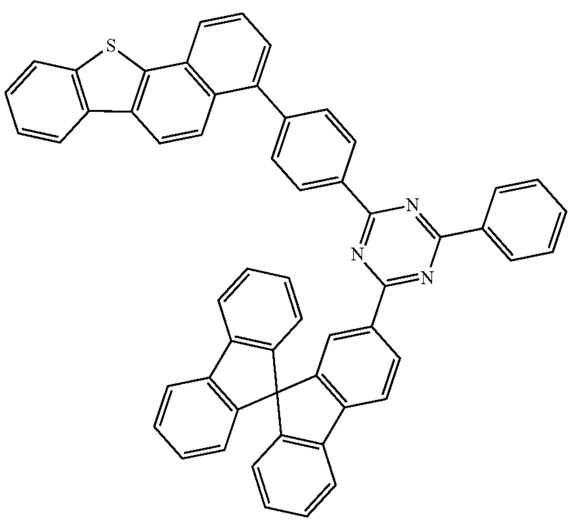
H2-544
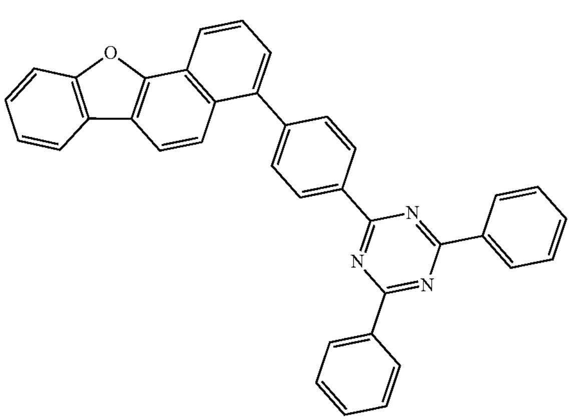
-continued
H2-545
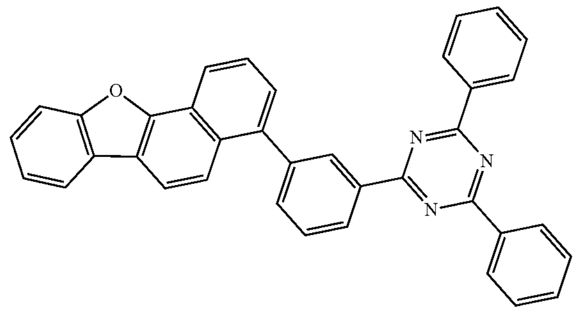
H2-546
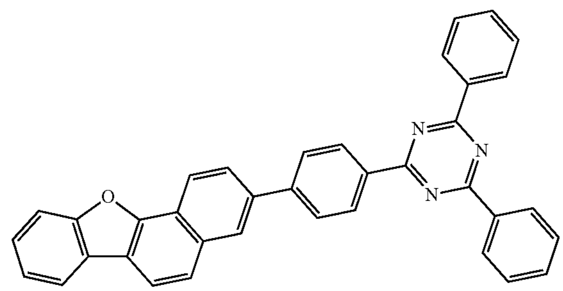
H2-547
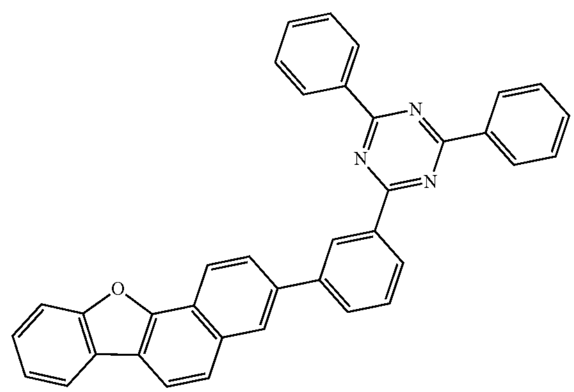
H2-548
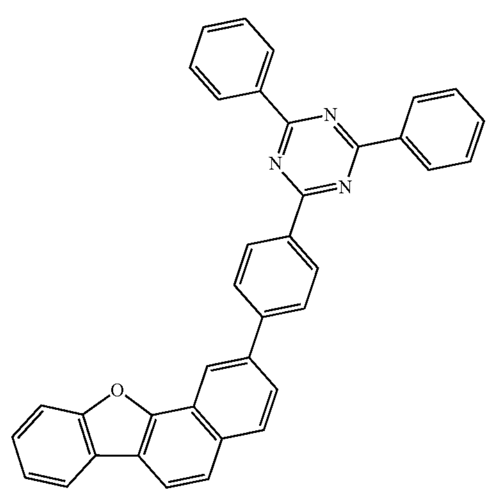

H2-549
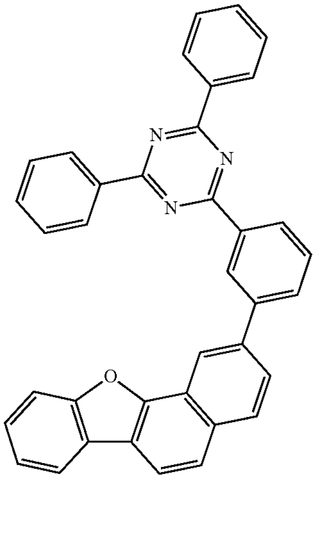
H2-550
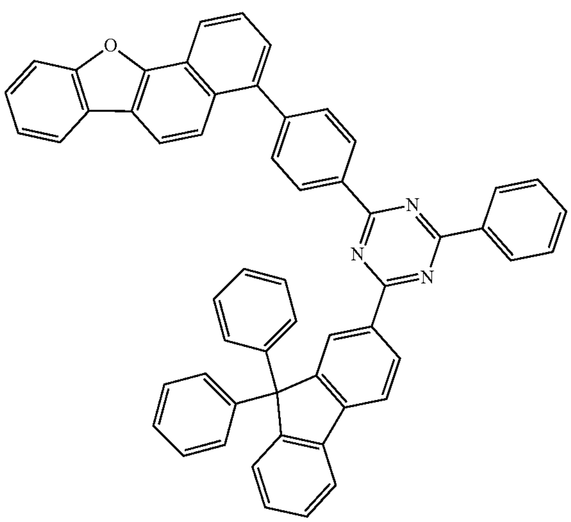
H2-551
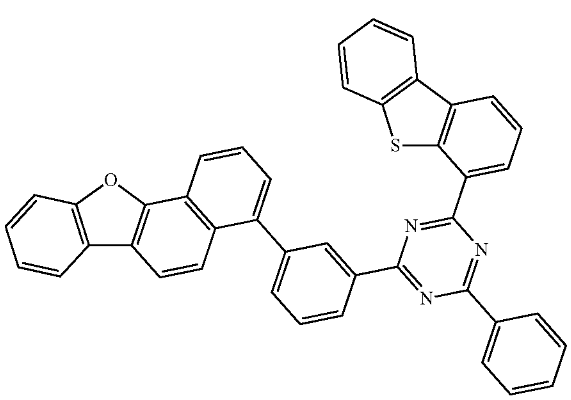
H2-552
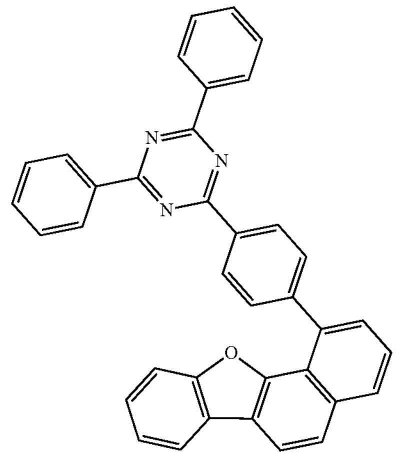
H2-553
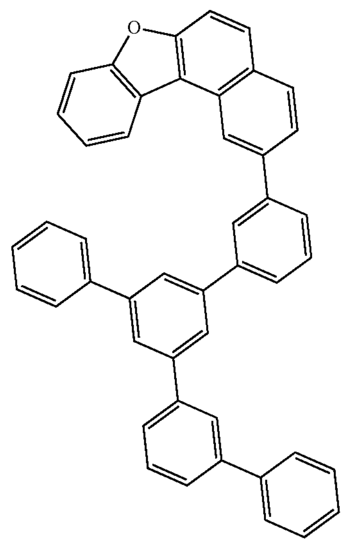
H2-554
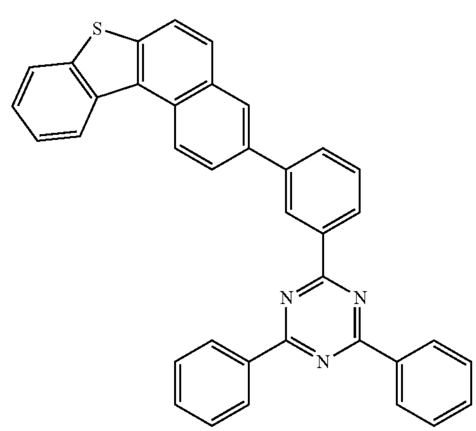

-continued
H2-555
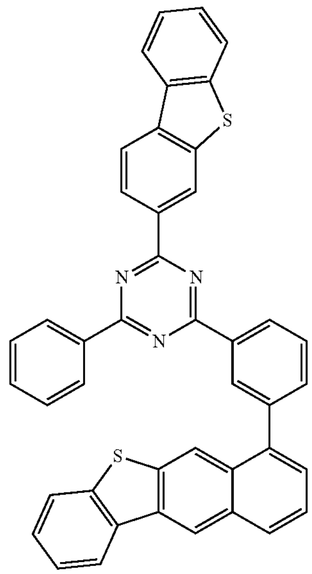
H2-556
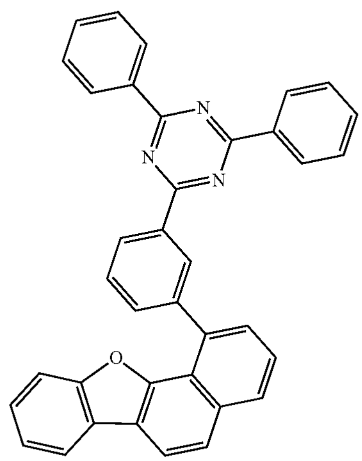
H2-557
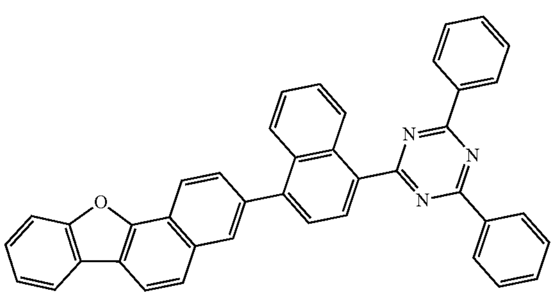
-continued
H2-558
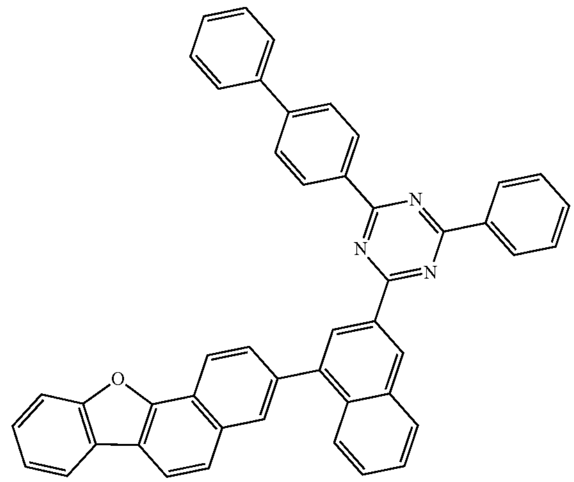
H2-559
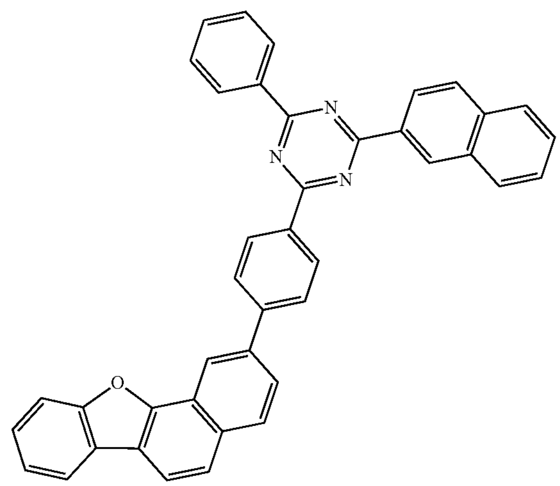
H2-560
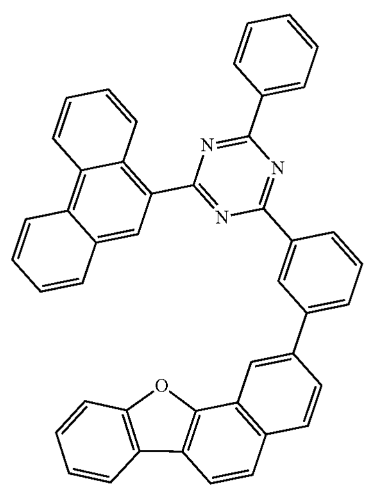

-continued
H2-561
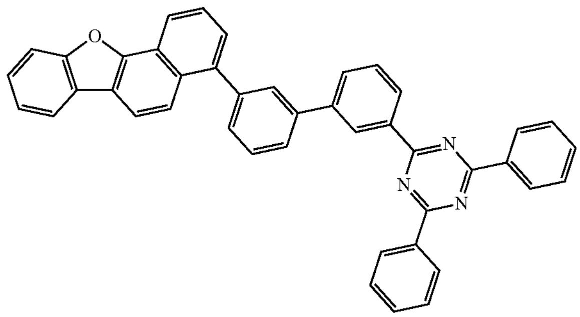
H2-562
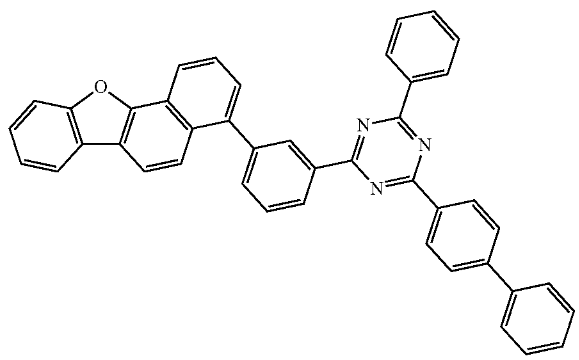
H2-563
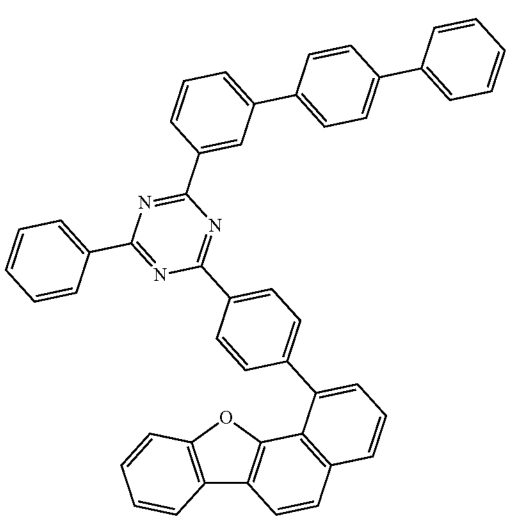
H2-564
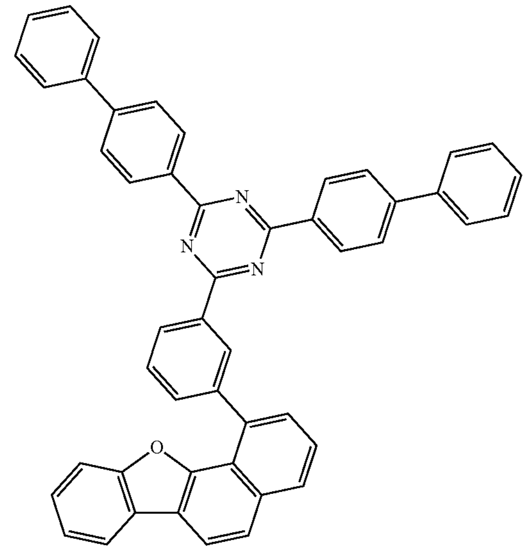
H2-565
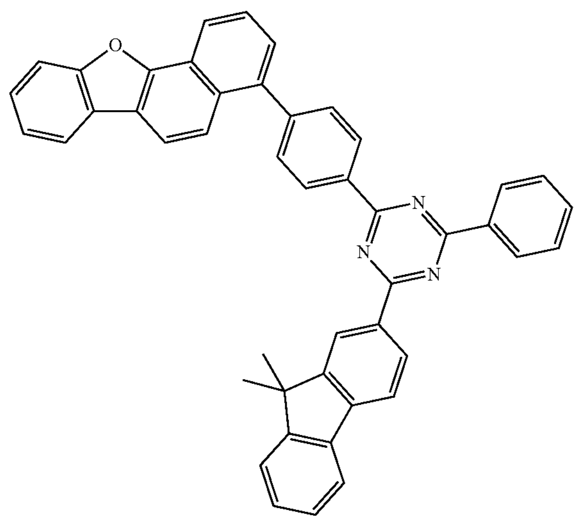
H2-566
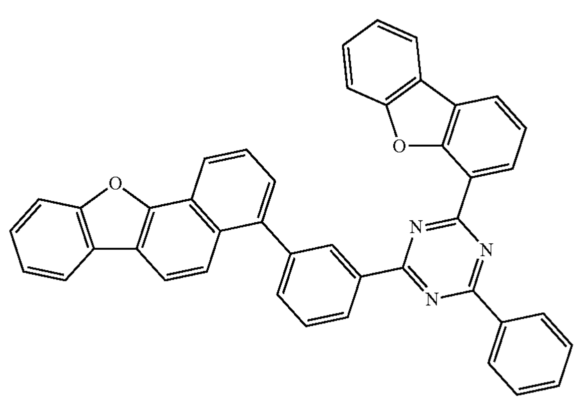

-continued
H2-567
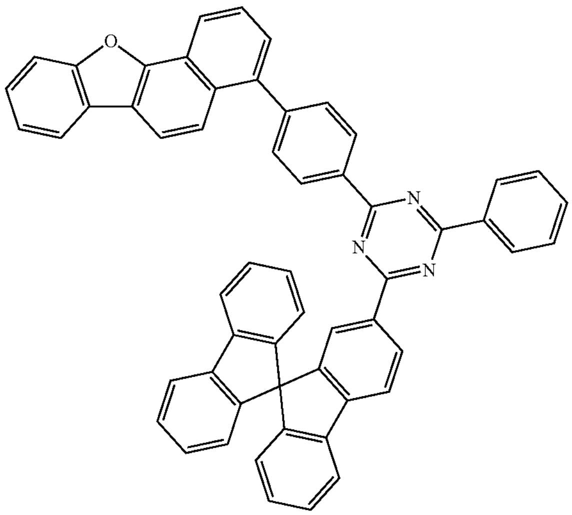
H2-568
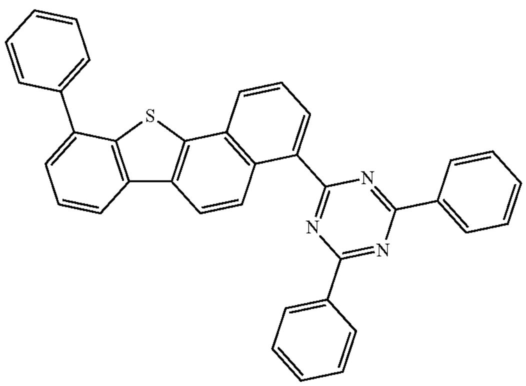
H2-569
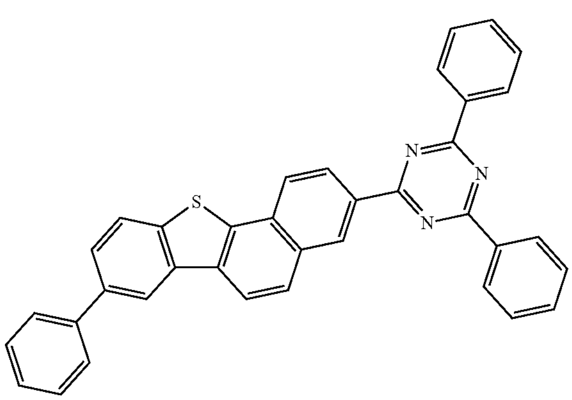
-continued
H2-570
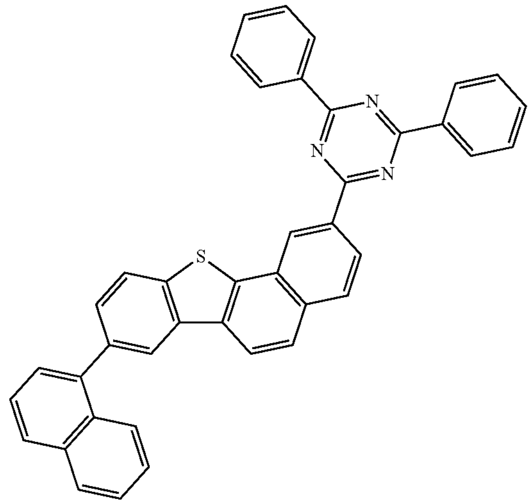
H2-571
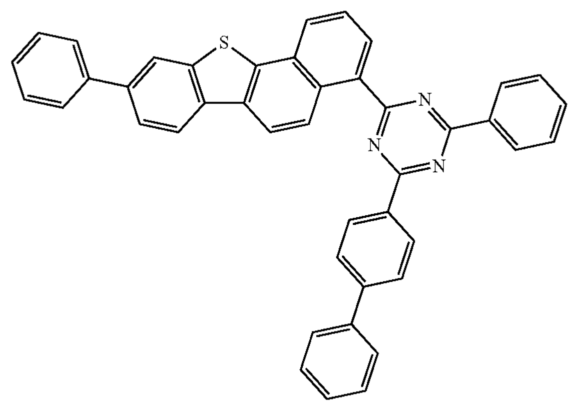
H2-572
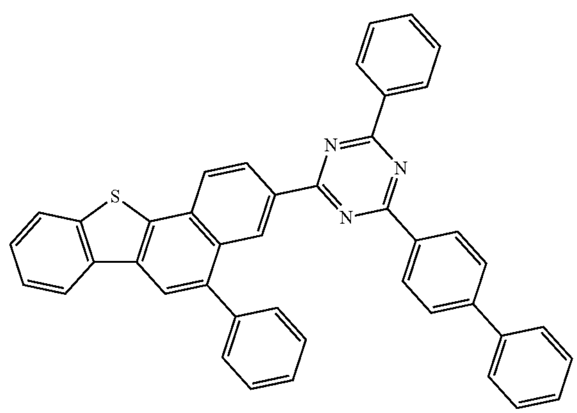

-continued
H2-573
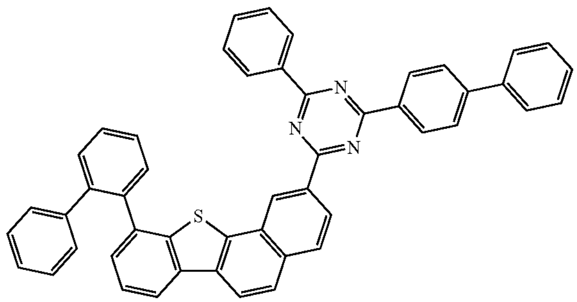
H2-574
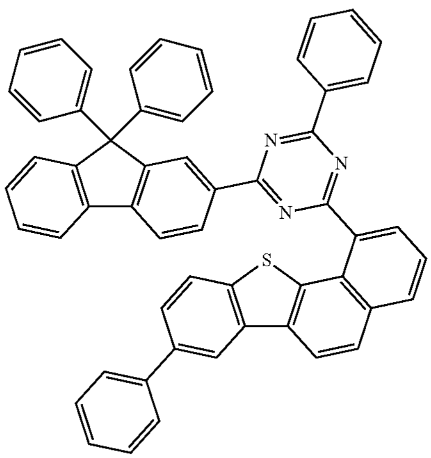
H2-575
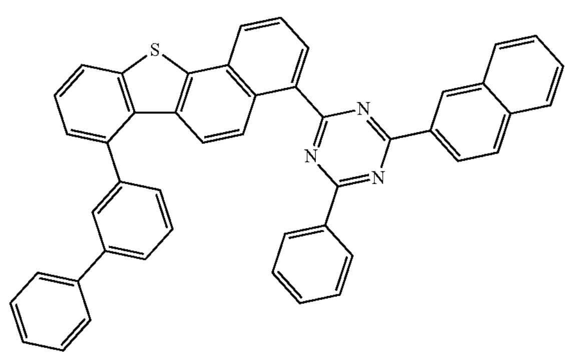
H2-576
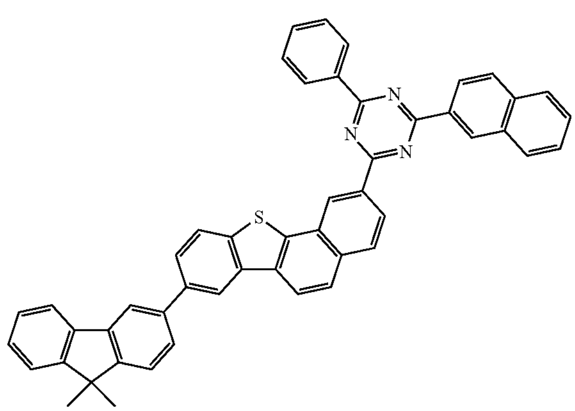
-continued
H2-577
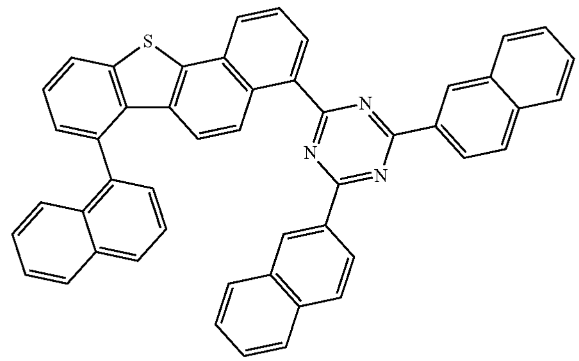
H2-578
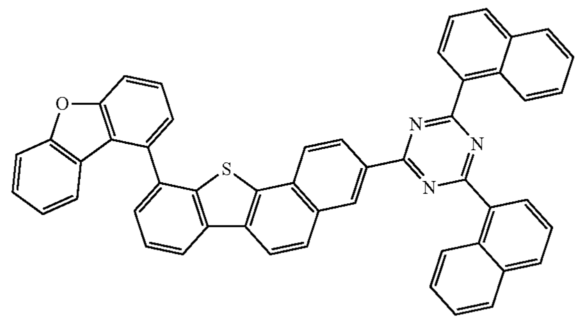
H2-579
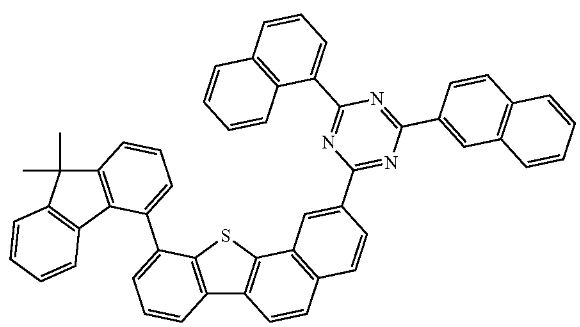
H2-580
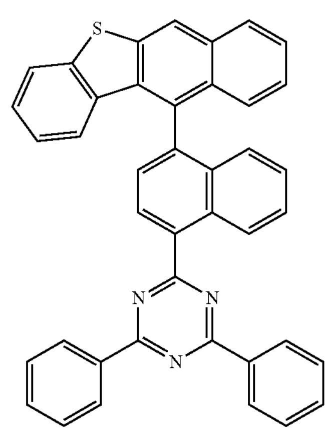

-continued
H2-581
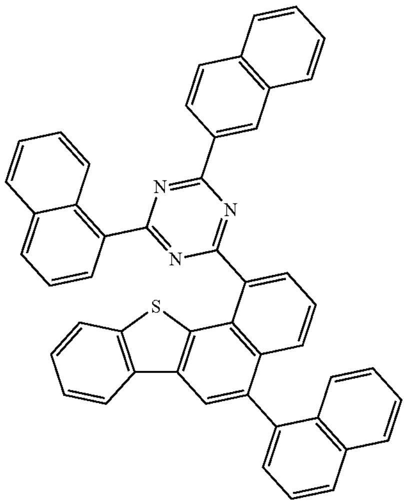
H2-582
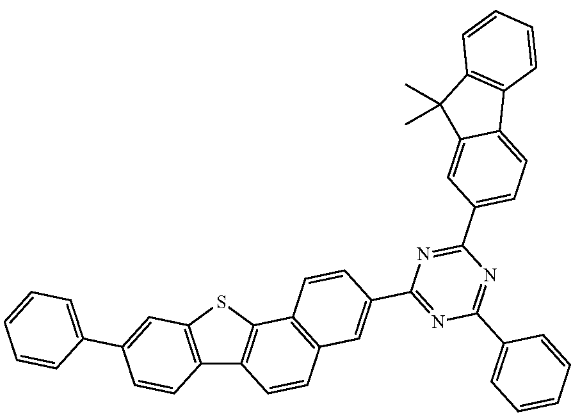
H2-583
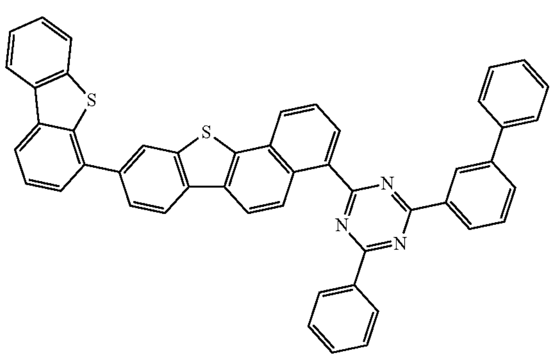
-continued
H2-584
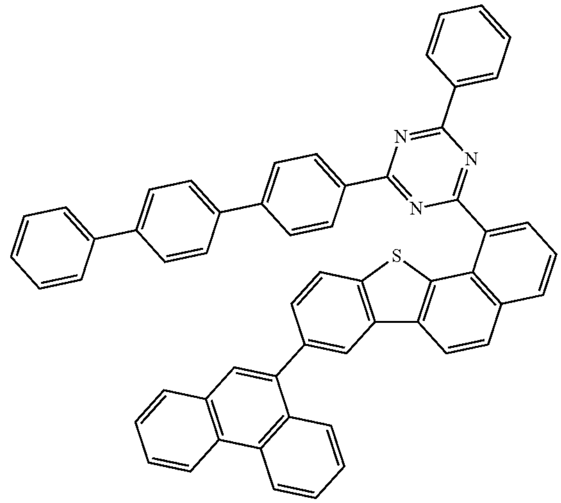
H2-585
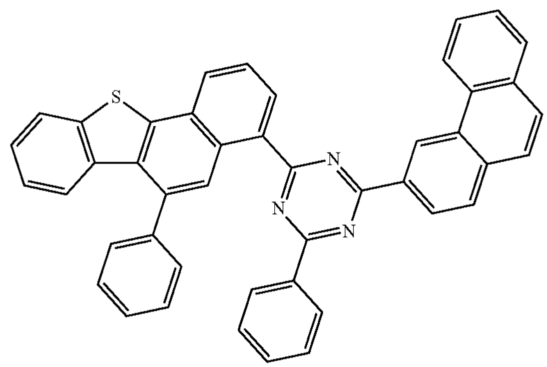
H2-586
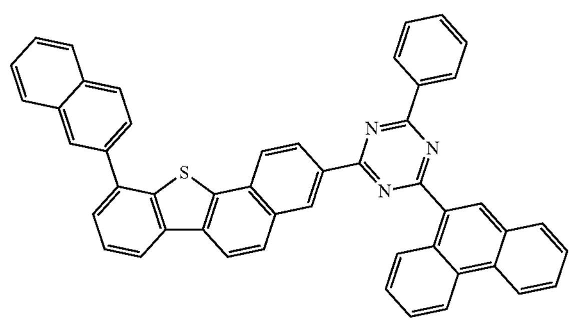
H2-587
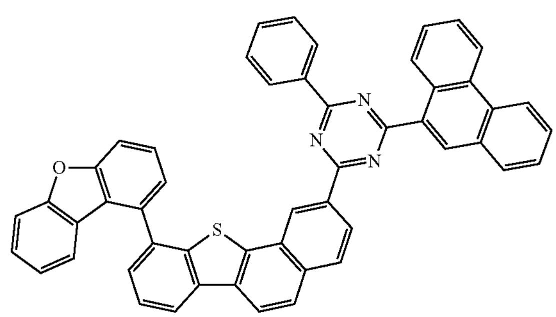

-continued
H2-588
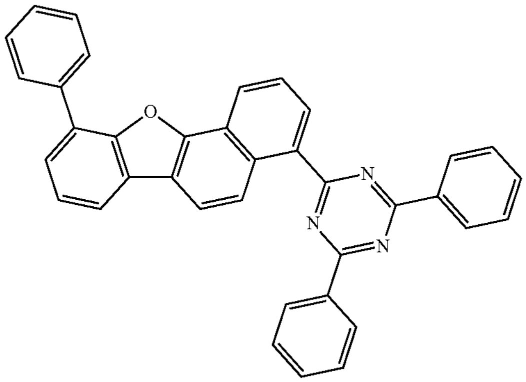
H2-589
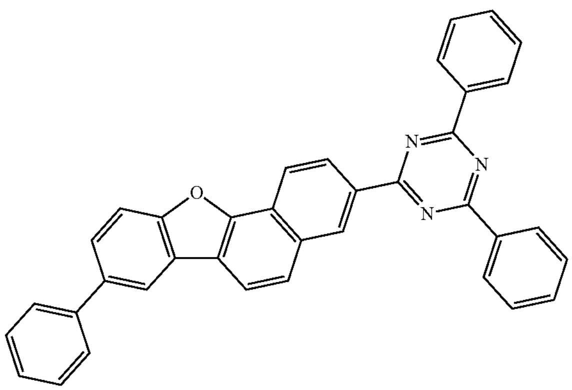
H2-590
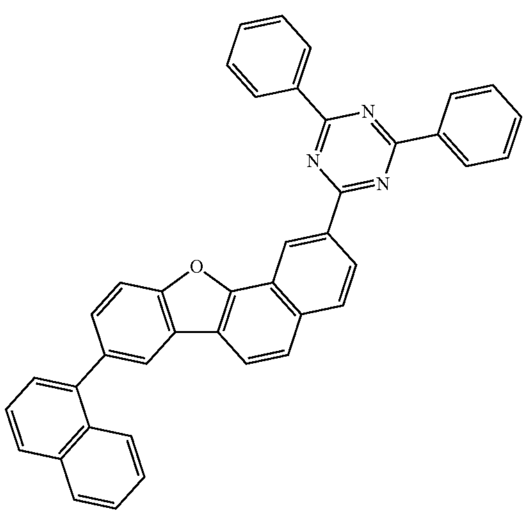
-continued
H2-591
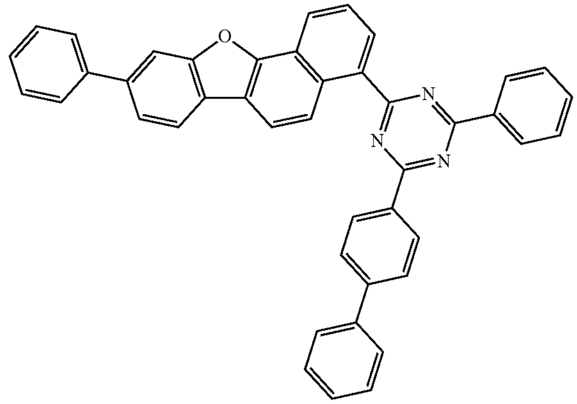
H2-592
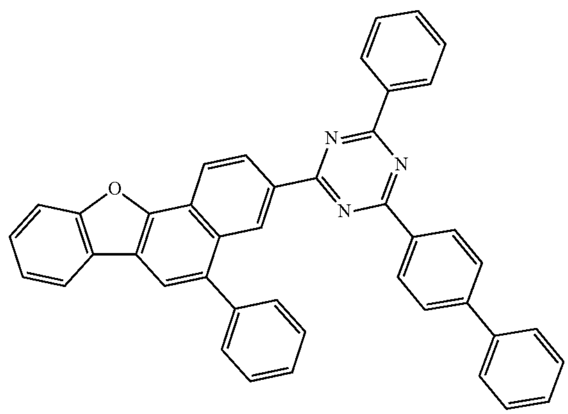
H2-593
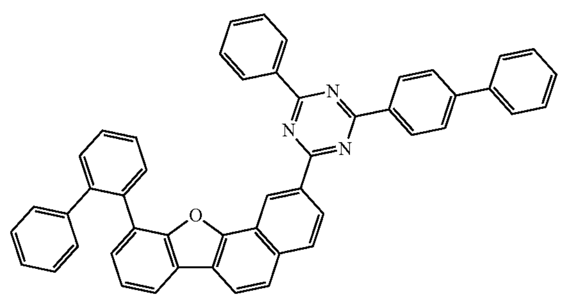
H2-594
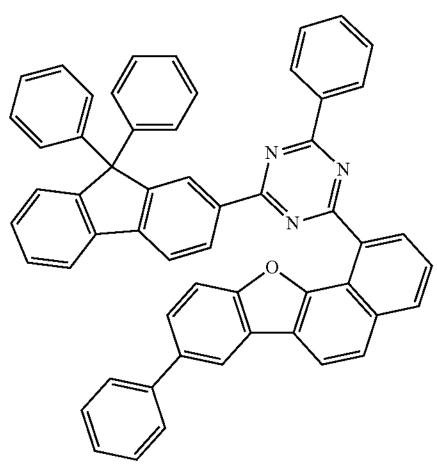

-continued
H2-595
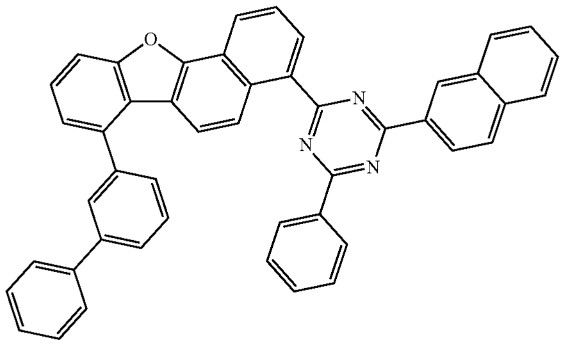
H2-596
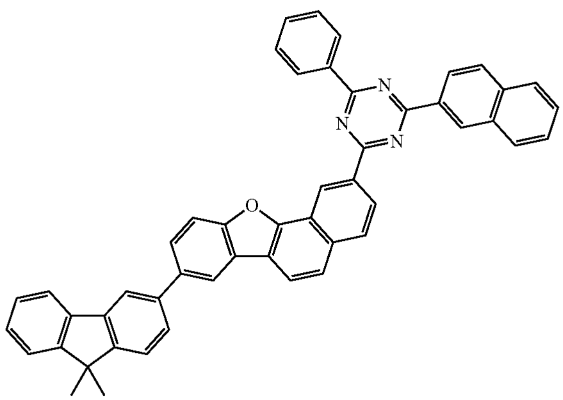
H2-597
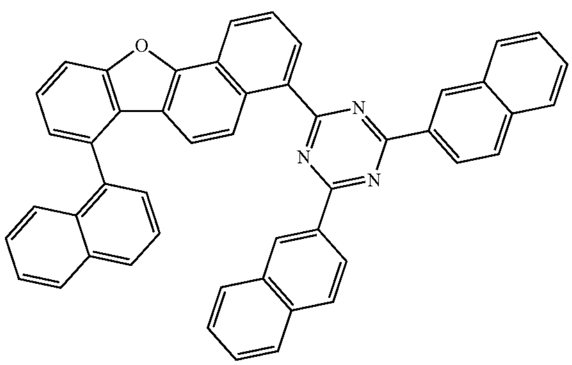
H2-598
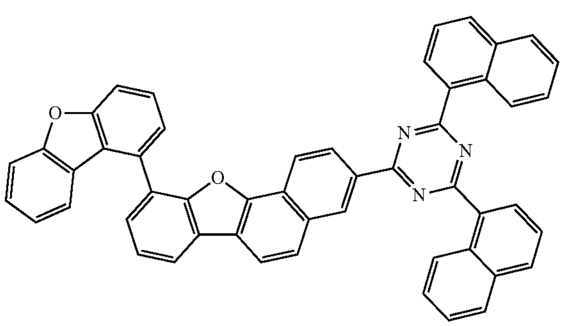
-continued
H2-599
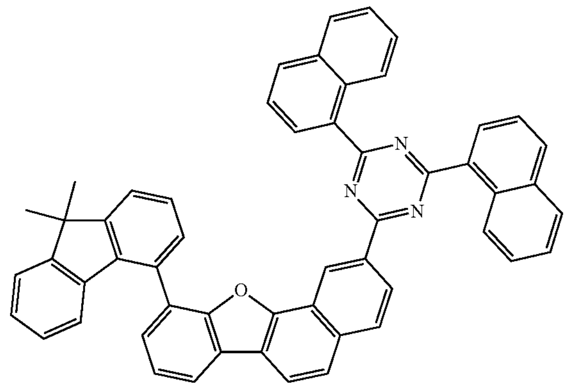
H2-600
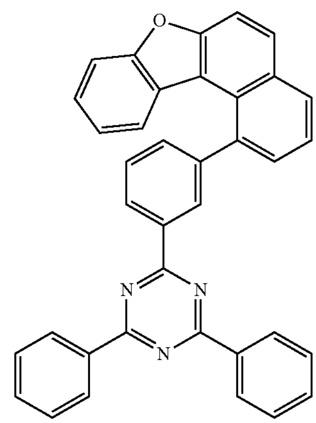
H2-601
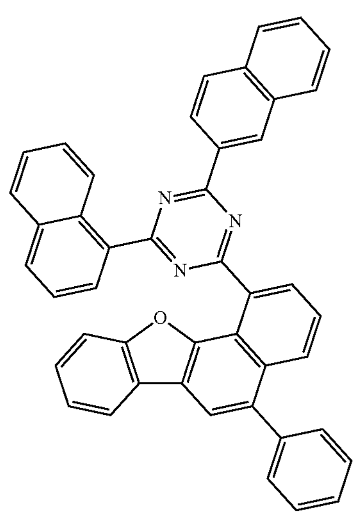

-continued
H2-602
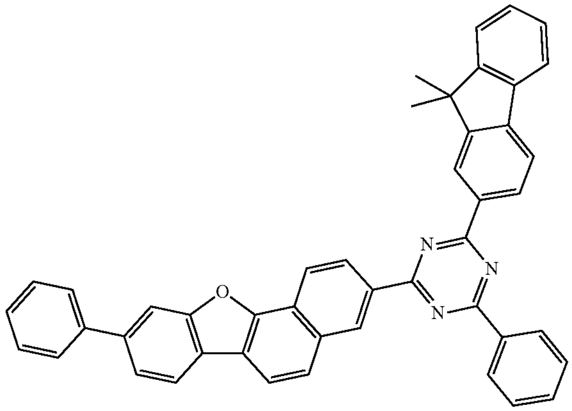
H2-603
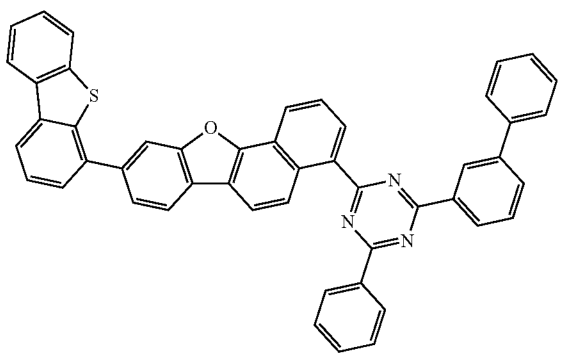
H2-604
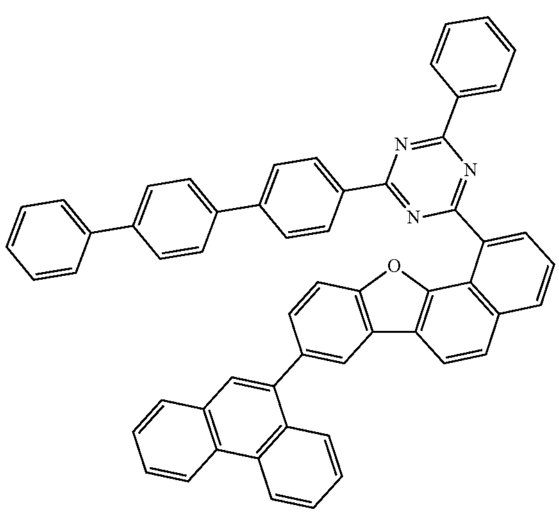
-continued
H2-605
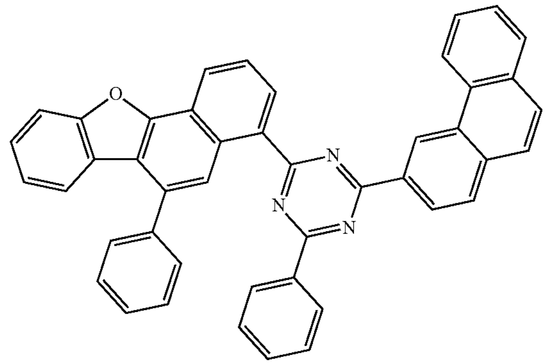
H2-606
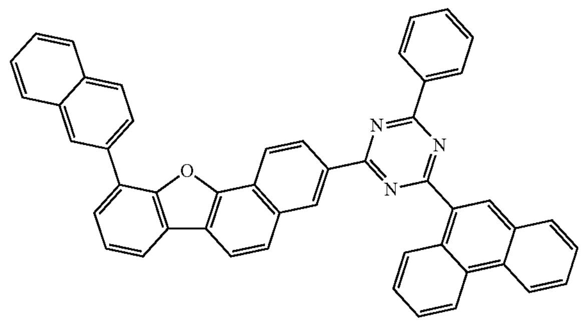
H2-607
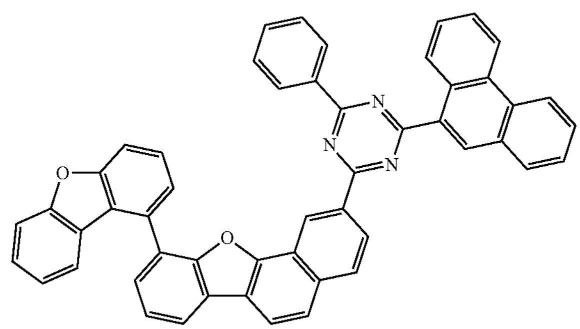
H2-608
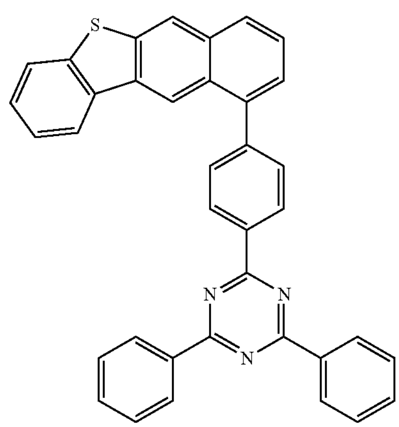

-continued
H2-609
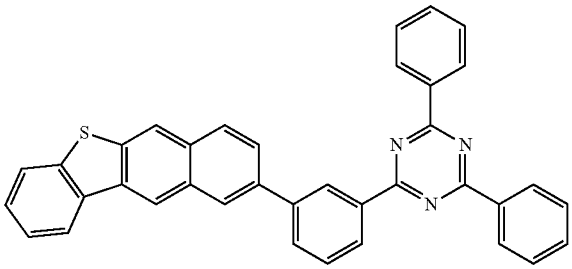
H2-610
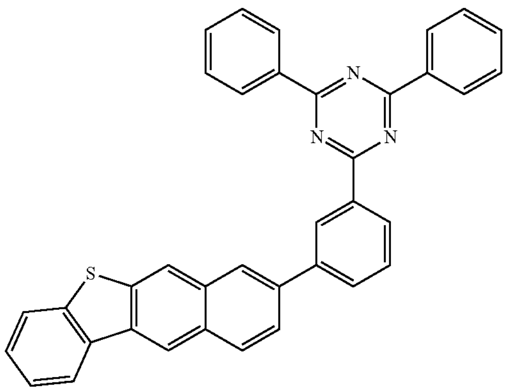
H2-611
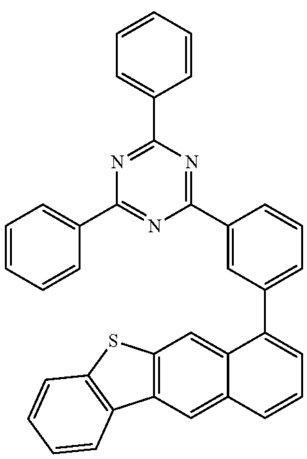
H2-612
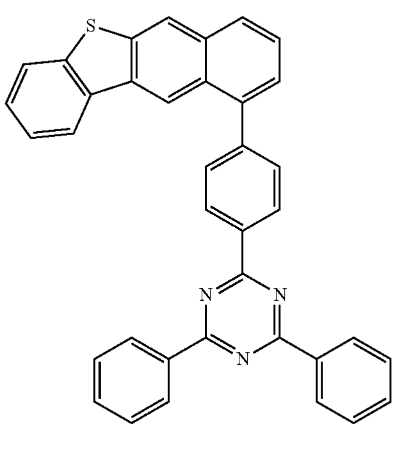
-continued
H2-613
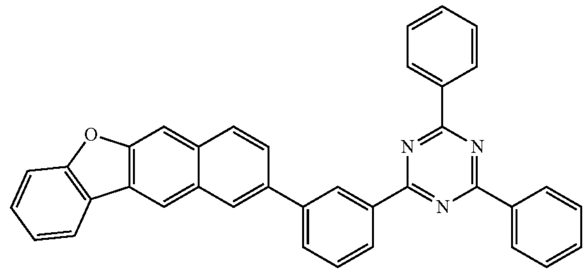
H2-614
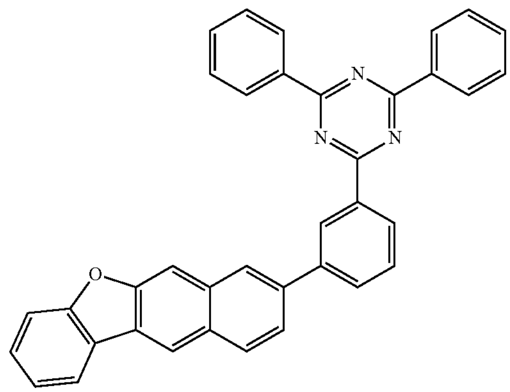
H2-615
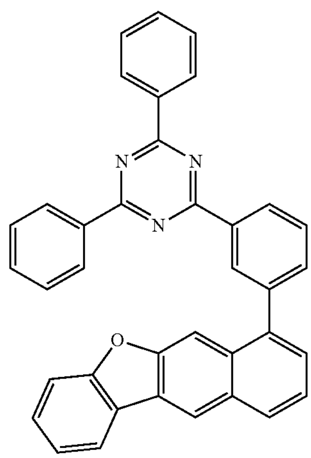
H2-616
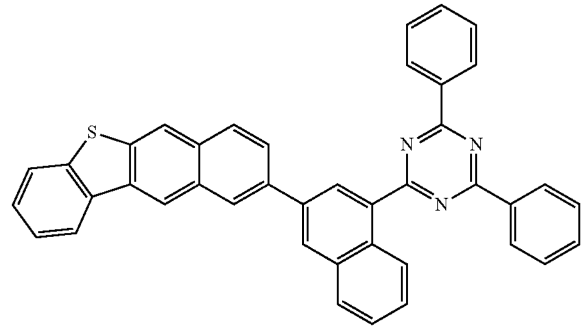

-continued
H2-617
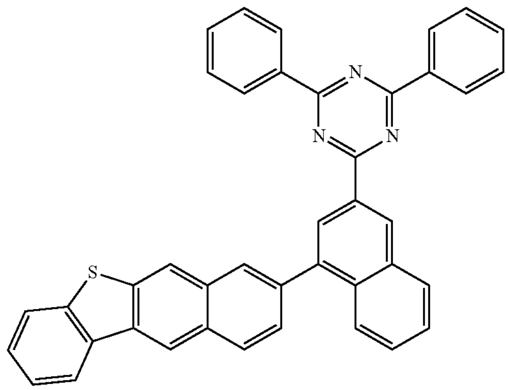
H2-618
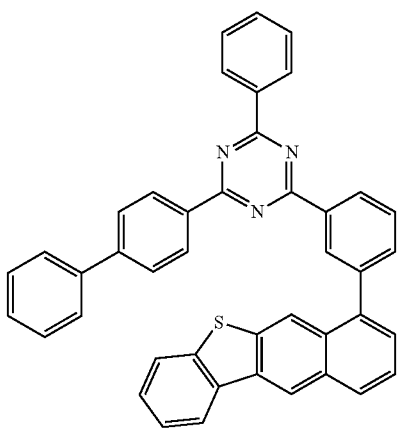
H2-619
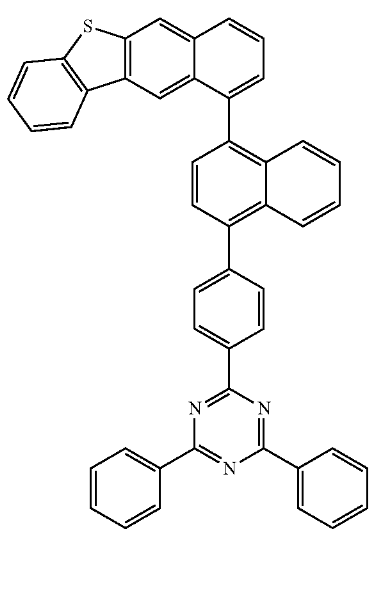
-continued
H2-620
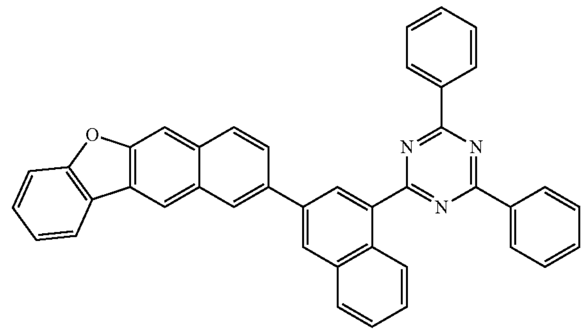
H2-621
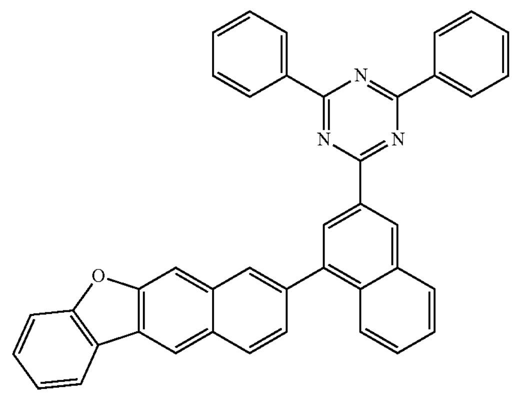
H2-622
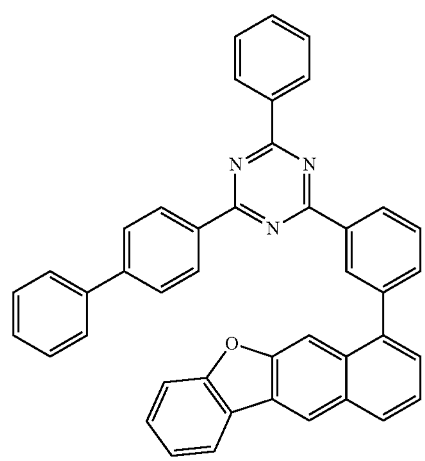

-continued
H2-623
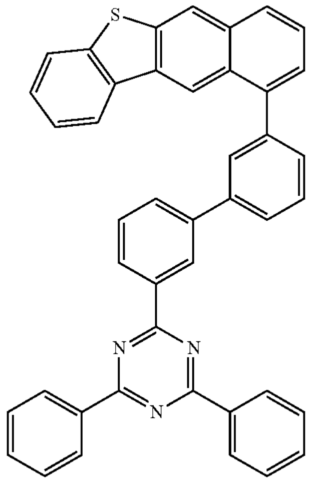
H2-624
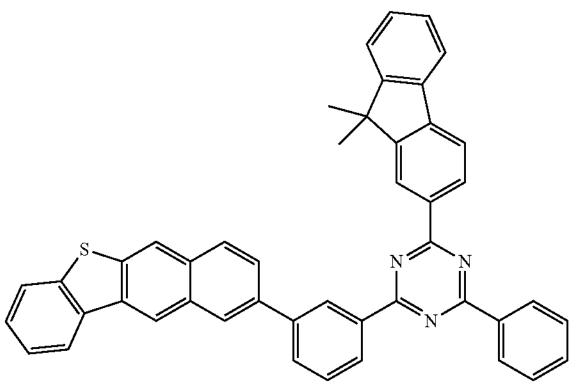
H2-846
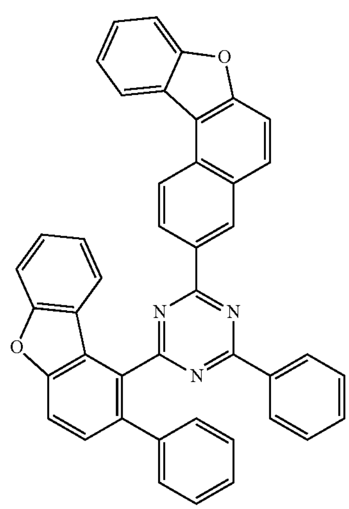
-continued
H2-847
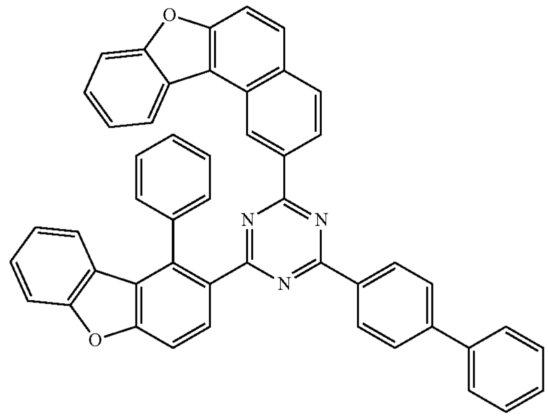
H2-848
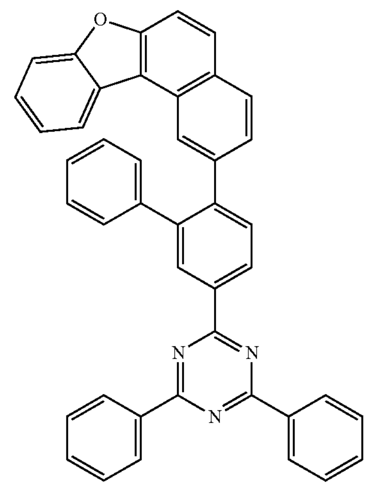
H2-849
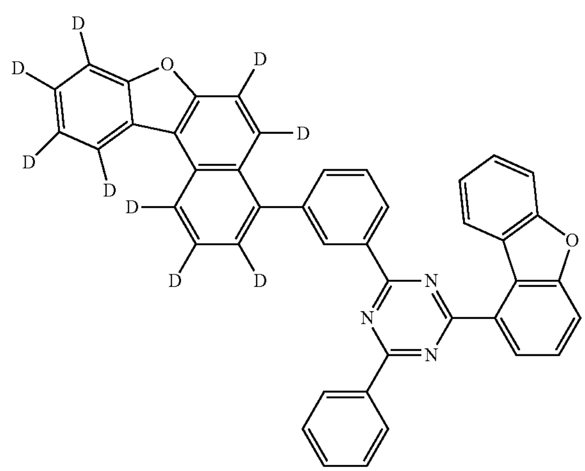

-continued
H2-850
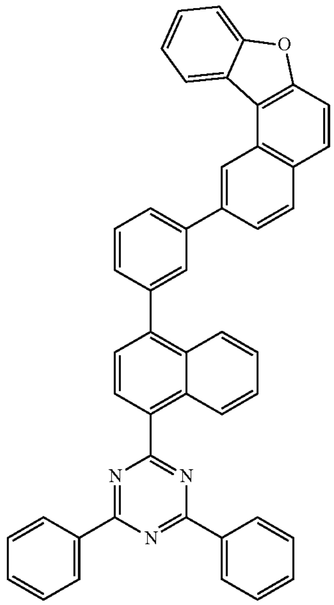
H2-851
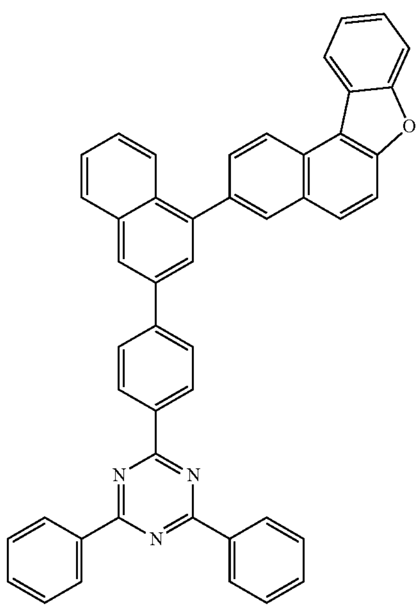
-continued
H2-852
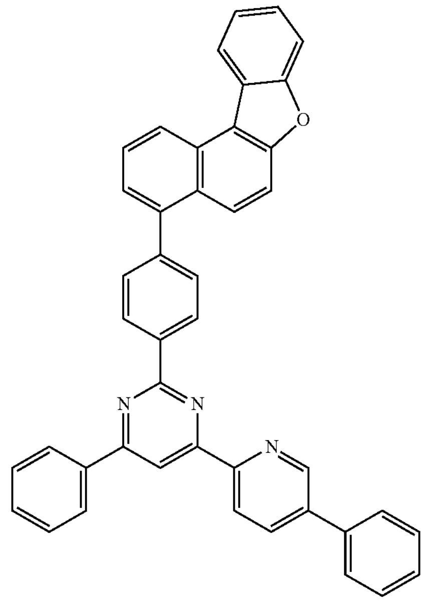
H2-853
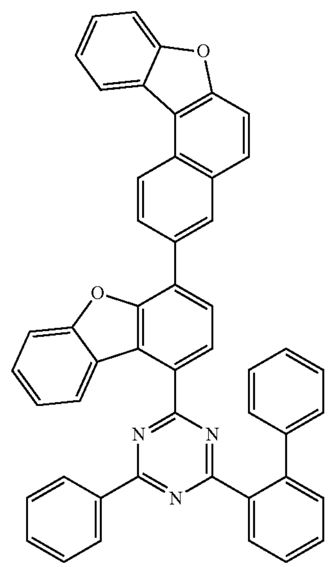
H2-854
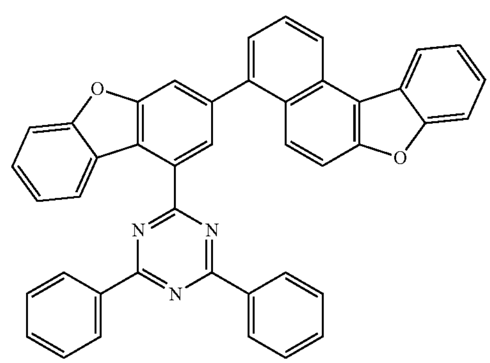

-continued
H2-855
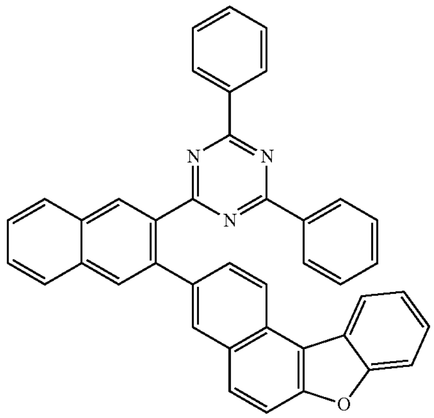
H2-856
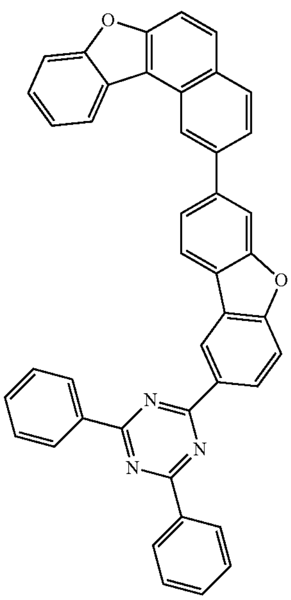
H2-857
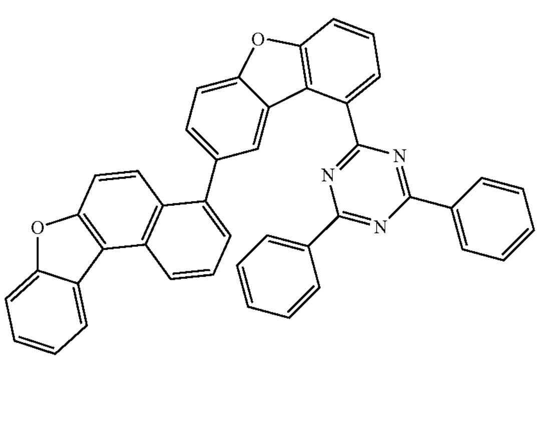
-continued
H2-858
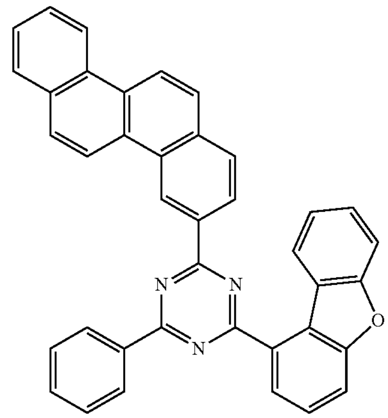
H2-859
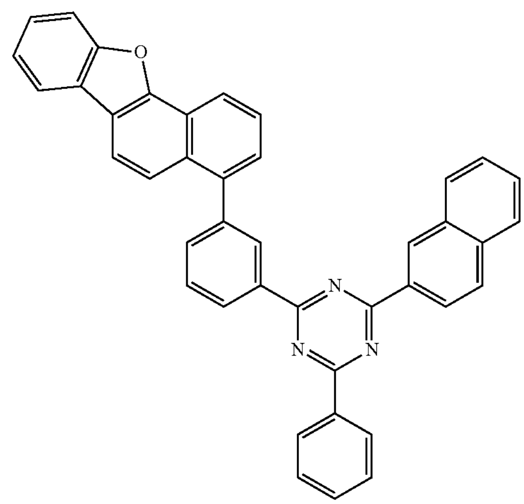
H2-860
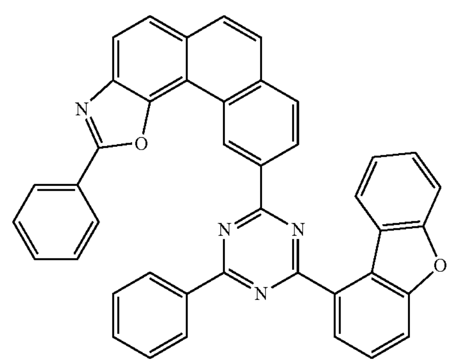

-continued

H2-861

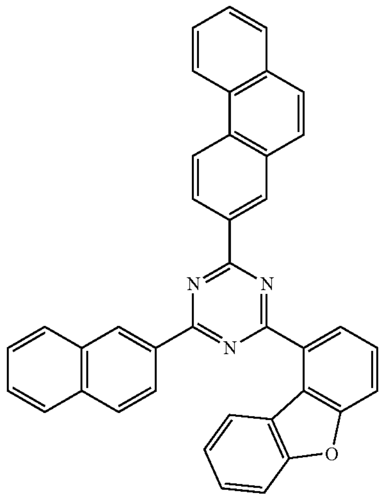

H2-862

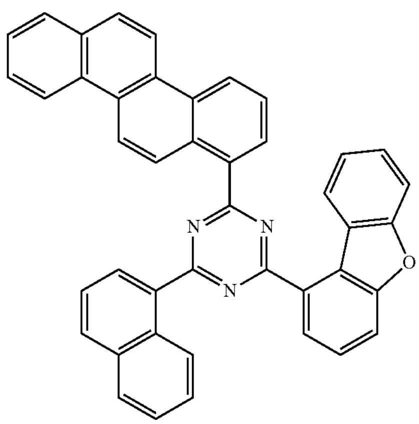

H2-863

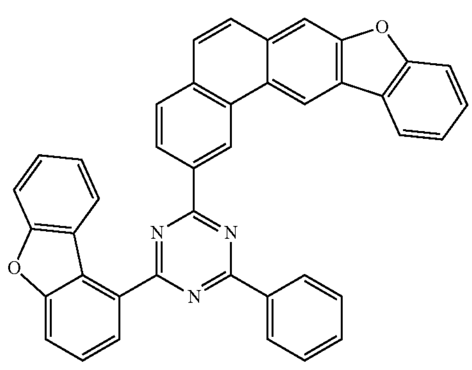

-continued

H2-864

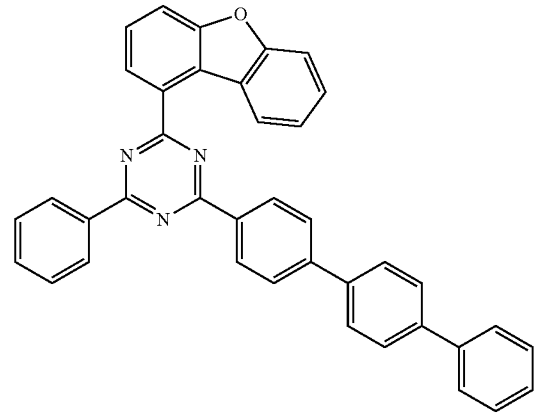

The combination of at least one of compounds H1-1 to H1-320 and at least one of compounds H2-1 to H2-864 may be used in an organic electroluminescent device. For example, the combination of any one of compounds H1-1 to H1-320, any one of compounds H2-1 to H2-864, and any one of compounds H1-1 to H1-320 and compounds H2-1 to H2-864 may be used in an organic electroluminescent device as the three types of host materials.

The compounds represented by formulas 1 to 4 according to the present disclosure may be produced by synthetic methods known to one skilled in the art. For example, the compounds represented by formulas 1 to 4 of the present disclosure may be produced by referring to Korean Patent Application Laid-Open Nos. 2020-0007644 (published on Jan. 22, 2020). 2018-0099487 (published on Sep. 5, 2018), 2020-0092879 (published on Aug. 4, 2020). 2020-0011884 (published on Feb. 4, 2020), and 2018-0099510 (published on Sep. 5, 2018), Korean Patent Publication No. 1545774 (published on Aug. 19, 2015), etc., and the compound represented by formula 2 of the present disclosure may be produced by referring to the following reaction schemes 1 and 2, but is not limited thereto.

[Reaction Scheme 1]
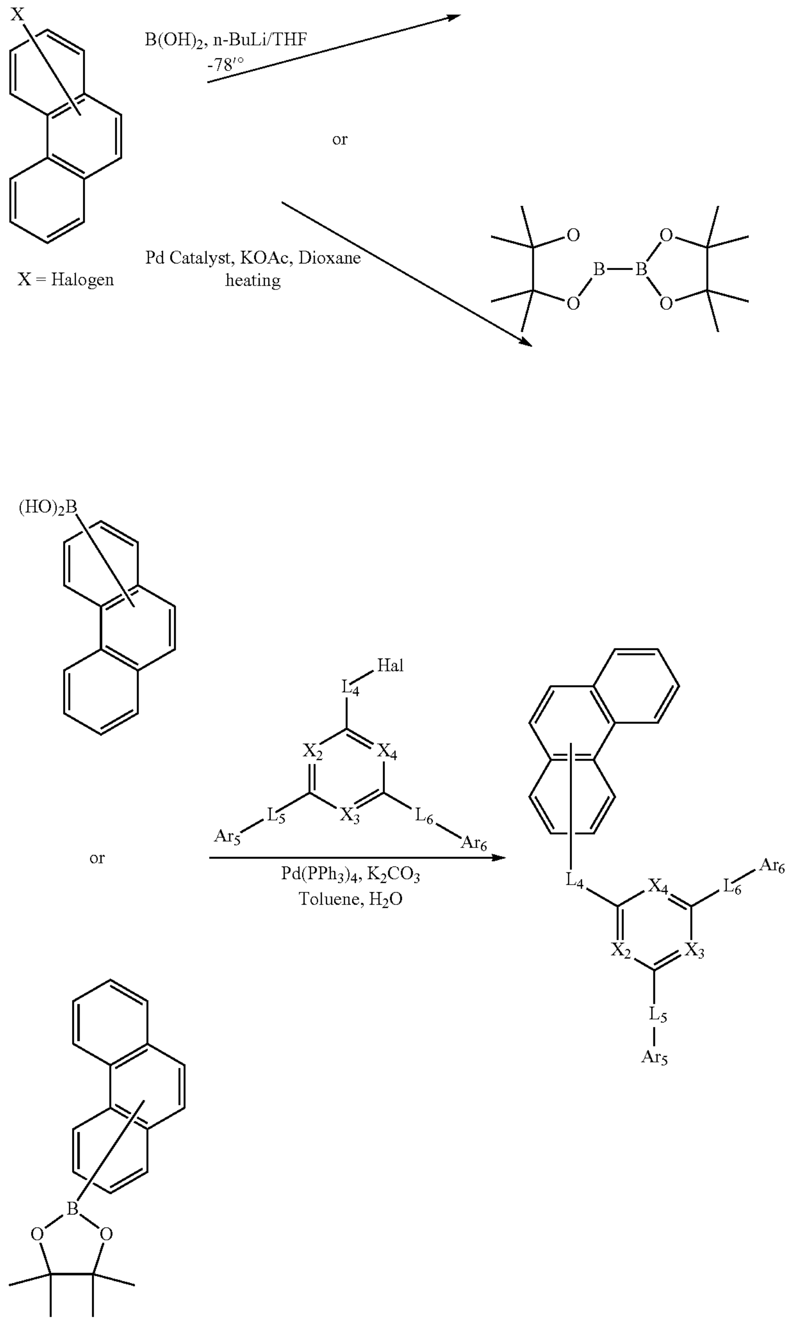
[Reaction Scheme 2]
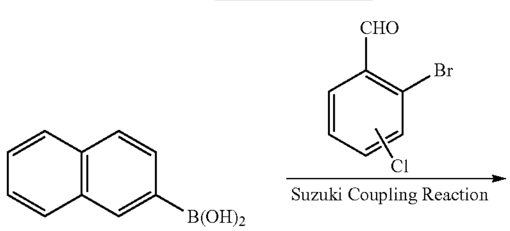
-continued
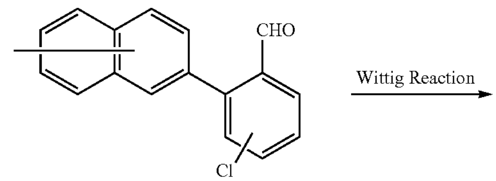

-continued

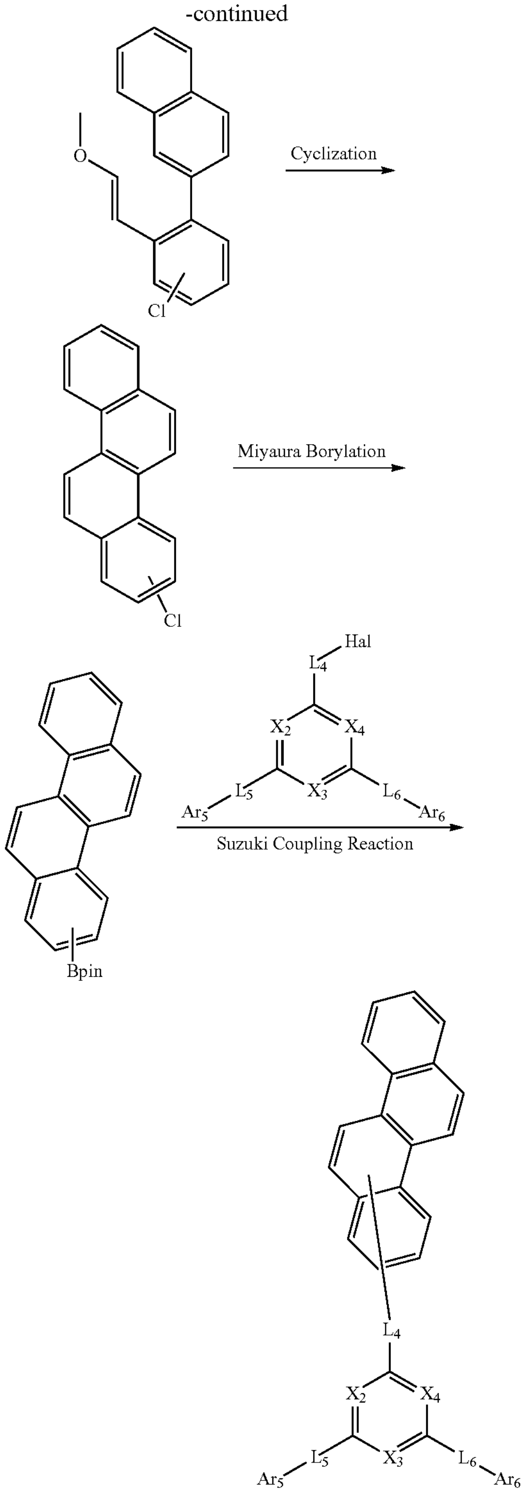

In reaction schemes 1 and 2, Hal represents a halogen, and $X_2$ to $X_4$, $L_4$ to $L_6$, $Ar_5$, and $Ar_6$ are as defined in formula 2.

Although illustrative synthesis examples of the compound represented by formula 2 of the present disclosure are described above, one skilled in the art will be able to readily understand that all of them are based on a Buchwald-Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents, which are defined in formula 2 but are not specified in the specific synthesis examples, are bonded.

An organic electroluminescent device according to the present disclosure has a first electrode, a second electrode, and at least one organic layer between the first electrode and the second electrode.

One of the first and second electrodes may be an anode, and the other may be a cathode. The organic layer comprises a light-emitting layer and may further comprise at least one layer selected from the group consisting of a hole injection layer, a hole transport layer, a hole auxiliary layer, a light-emitting auxiliary layer, an electron transport layer, an electron buffer layer, an electron injection layer, an inter-layer, a hole blocking layer, and an electron blocking layer. Herein, the second electrode may be a transflective electrode or a reflective electrode, and may be a top emission type, a bottom emission type, or a both-sides emission type, depending on the material. In addition, the hole injection layer may be further doped with a p-dopant(s), and the electron injection layer may be further doped with an n-dopant(s).

An organic electroluminescent device according to the present disclosure comprises an anode, a cathode, and at least one organic layer between the anode and the cathode. The organic layer may comprise at least three types of the organic electroluminescent materials comprising the compound represented by formula 1 as the first organic electroluminescent material, the compound represented by any one of formulas 2 to 4 as the second organic electroluminescent material, and the compound represented by any one of formulas 1 to 4 as the third organic electroluminescent material. According to one embodiment, the organic electroluminescent device according to the present disclosure comprises an anode, a cathode, and at least one light-emitting layer between the anode and the cathode, wherein the light-emitting layer may comprise the compound represented by formula 1 and the compound represented by formula 2.

The light-emitting layer comprises a host and a dopant, and the host comprises a plurality of host materials. The compound represented by formula 1 may be comprised as the first host compound of the plurality of host materials. The compound represented by formula 2 may be comprised as the second host compound of the plurality of host materials. The compound represented by formula 1 or 2 while being different from the first and second host compounds may be comprised as the third host compound of the plurality of host materials. Herein, the first host material of the plurality of host materials of the present disclosure may be from about 5 wt % to about 90 wt %, preferably from about 10 wt % to about 90 wt %, more preferably from about 10 wt % to about 80 wt %, even more preferably from about 15 wt % to about 70 wt %, even more preferably from about 30 wt % to about 70 wt %, even more preferably from about 20 wt % to about 60 wt %, even more preferably from about 30 wt % to about 60 wt %. The second host material of the plurality of host materials of the present disclosure may be from about 5 wt % to about 90 wt %, preferably from about 10 wt % to about 90 wt %, more preferably from about 10 wt % to about 80 wt %, even more preferably from about 15 wt % to about 70 wt %, even more preferably from about 30 wt % to about 70 wt %, even more preferably from about 20 wt % to about 60 wt %, even more preferably from about 30 wt % to about 60 wt %. The third host material of the plurality of host materials of the present disclosure may be about 5 wt % to about 90 wt %, preferably about 10 wt % to about 90 wt %, more preferably about 10 wt % to about 80 wt %, even more preferably from about 15 wt % to about 70 wt %, even more preferably from about 30 wt % to about 70 wt %, even more preferably from about 20 wt % to about 60 wt %, even more preferably from about 30 wt % to about 60 wt %. For example, the plurality of host materials may comprise about 5 wt % to about 70 wt % of the first host material, about 5 wt % to about 70 wt % of the second host material, and about 10 wt % to about 90 wt % of the third host material.

According to one embodiment, any two of the first, second and third host materials of the present disclosure may have a difference in deposition temperature of about 0° C. to about 20° C. at $10^{-3}$ torr or less.

According to one embodiment, the maximum emission wavelength of the plurality of host materials of the present disclosure may be shifted by about 20 nm or more from the maximum emission wavelength of each of the first, second and third host materials.

In the present disclosure, the light-emitting layer is a layer from which light is emitted, and may be a single layer or a multi-layer of which two or more layers are stacked. All of the first, second and third host materials may be included in one layer; any two of the first, second and third host materials may be included in one layer; or the first, second and third host materials may be included in respective different light-emitting layers. According to one embodiment of the present disclosure, the doping concentration of the dopant compound with respect to the host compound(s) in the light-emitting layer may be less than about 20 wt %.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. According to one embodiment of the present disclosure, the organic electroluminescent device of the present disclosure may further comprise an amine-based compound besides the plurality of host materials of the present disclosure as at least one of a hole injection material, a hole transport material, a hole auxiliary material, a light-emitting material, a light-emitting auxiliary material, and an electron blocking material. Further, according to one embodiment of the present disclosure, the organic electroluminescent device of the present disclosure may further comprise an azine-based compound besides the plurality of host materials of the present disclosure as at least one of an electron transport material, an electron injection material, an electron buffer material, and a hole blocking material.

The dopant comprised in the organic electroluminescent device of the present disclosure may be at least one phosphorescent or fluorescent dopant, and preferably a phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise a compound represented by the following formula 101, but is not limited thereto.

(101)

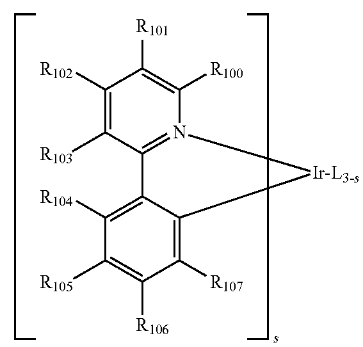

In formula 101, L is selected from the group consisting of the following structures 1 to 3:

[Structure 1]

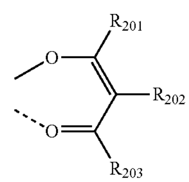

[Structure 2]

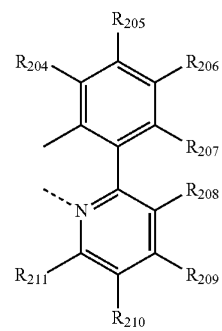

[Structure 3]

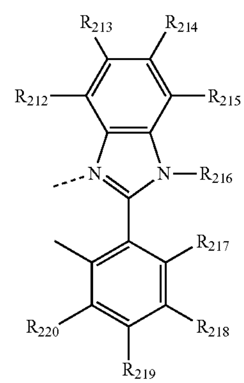

$R_{100}$ to $R_{103}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline ring, together with pyridine:

$R_{104}$ to $R_{107}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a substituted or unsubstituted ring(s), e.g., a substituted or unsubstituted, naphthalene, fluorene, dibenzothiophene, dibenzofuran, indenopyridine, benzofuropyridine or benzothienopyridine ring, together with benzene;

$R_{201}$ to $R_{220}$, each independently, represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or may be linked to an adjacent substituent to form a ring(s); and s represents an integer of 1 to 3.

The specific examples of the dopant compound are as follows, but are not limited thereto.

D-1

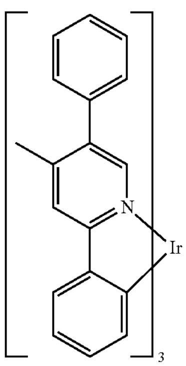

D-2

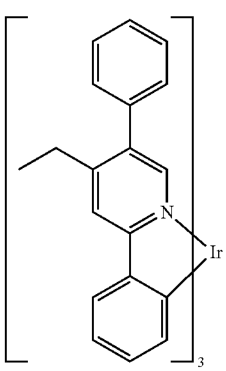

-continued

D-3

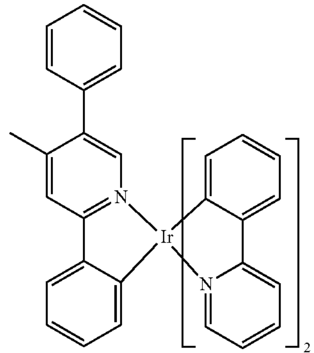

D-4

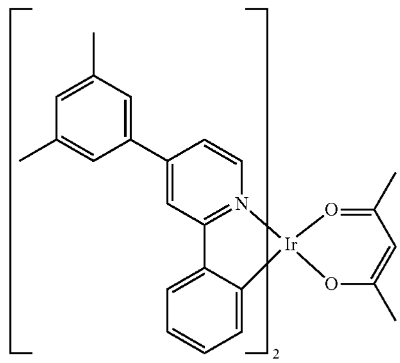

D-5

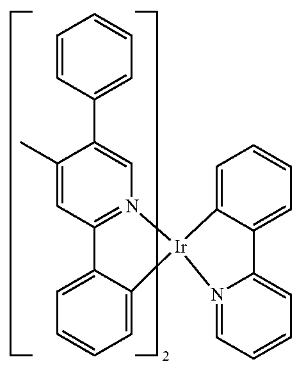

D-6

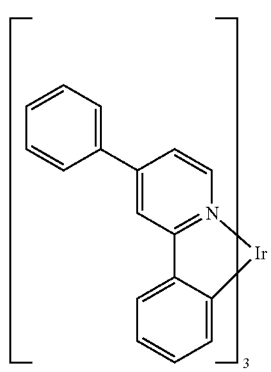

-continued
D-7
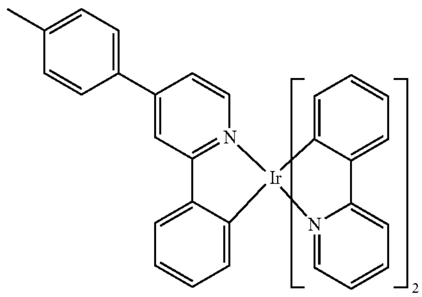
D-8
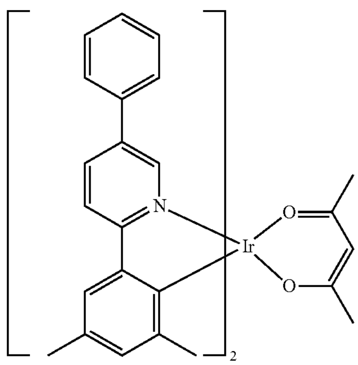
D-9
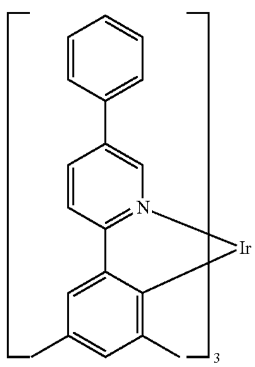
D-10
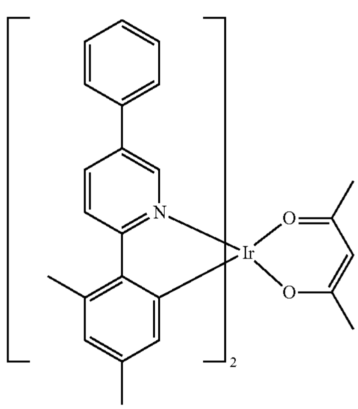
-continued
D-11
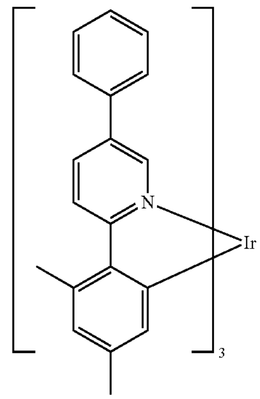
D-12
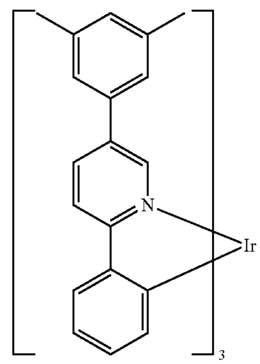
D-13
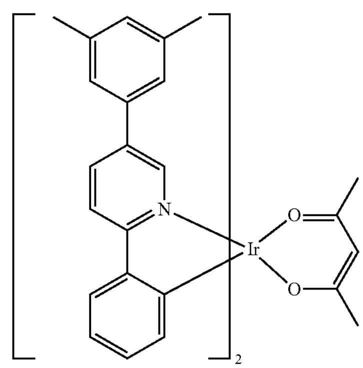
D-14
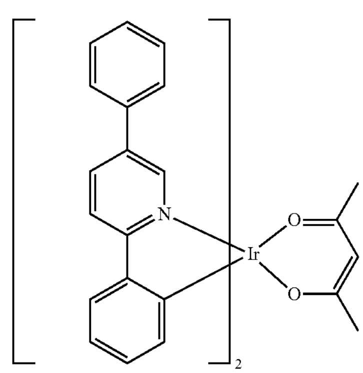

-continued
D-15
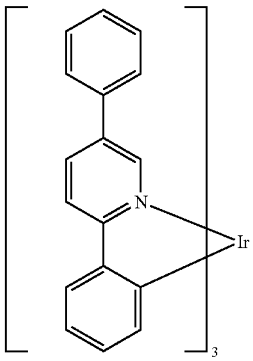
D-16
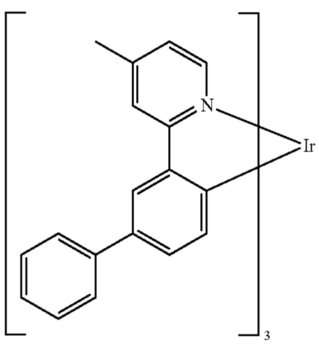
D-17
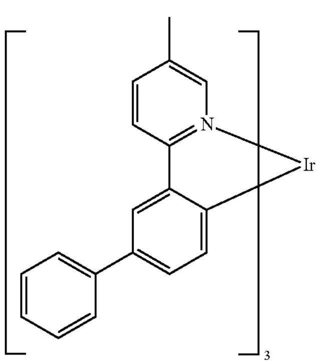
D-18
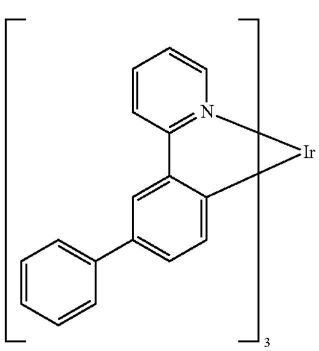
-continued
D-19
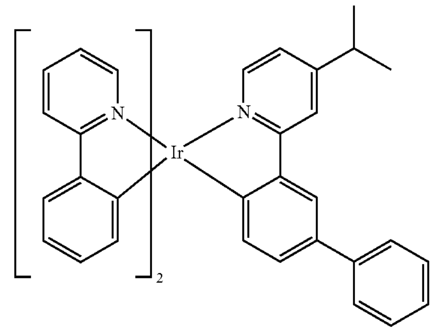
D-20
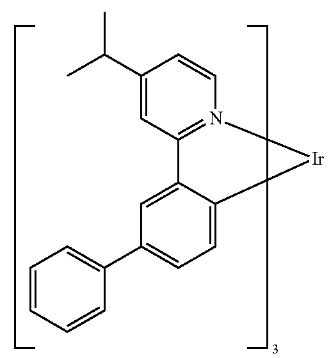
D-21
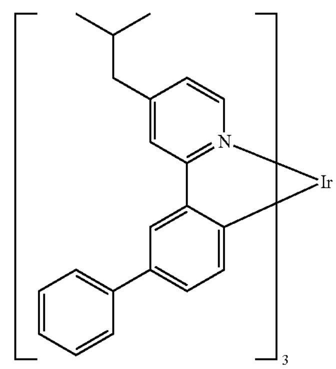
D-22
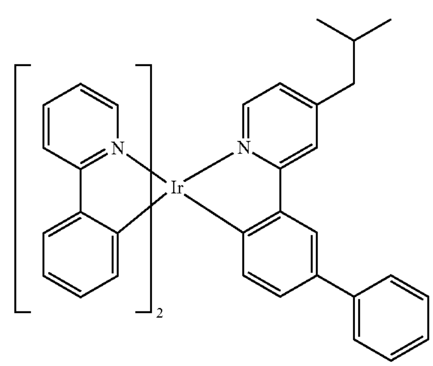

-continued
D-23
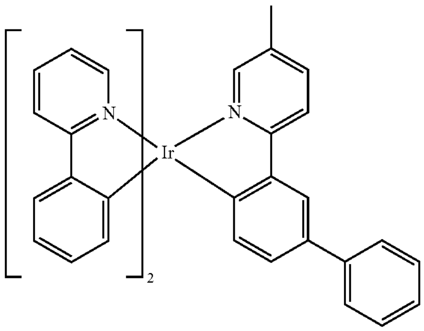
D-24
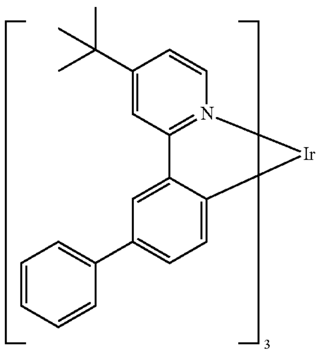
D-25
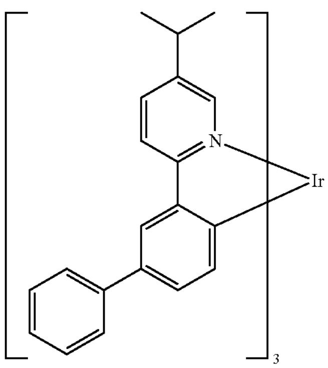
D-26
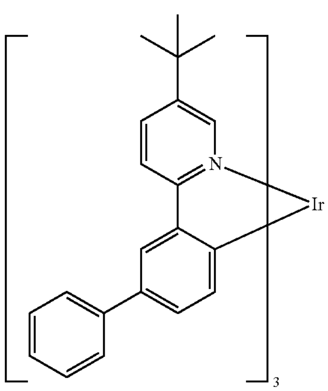
-continued
D-27
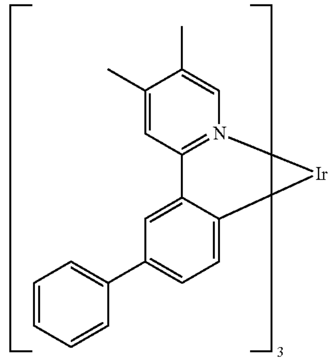
D-28
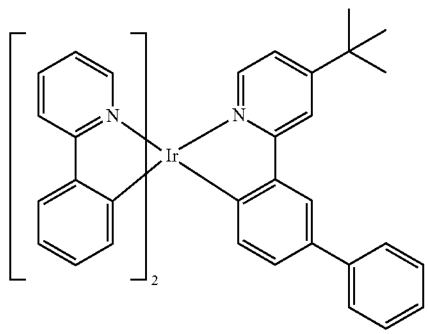
D-29
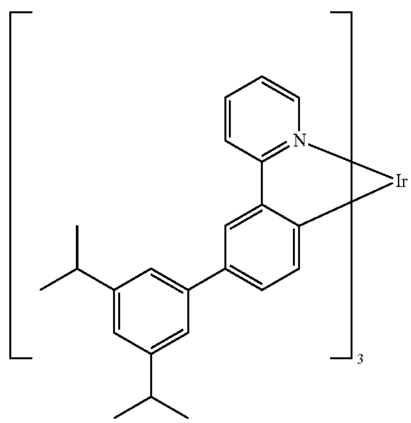
D-30
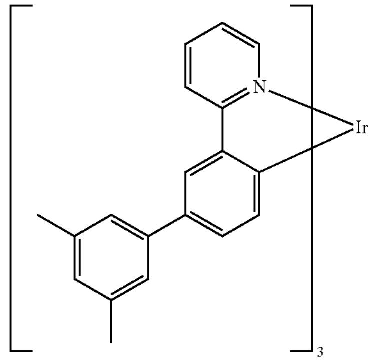

D-31
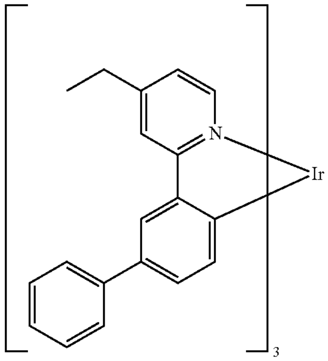
D-32
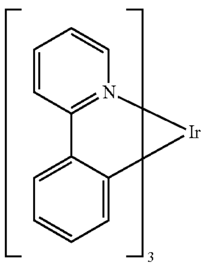
D-33
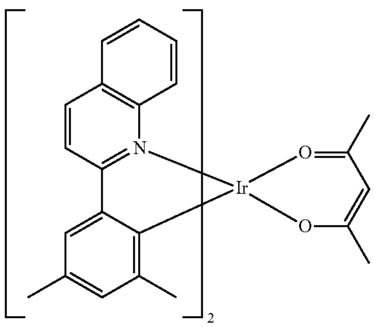
D-34
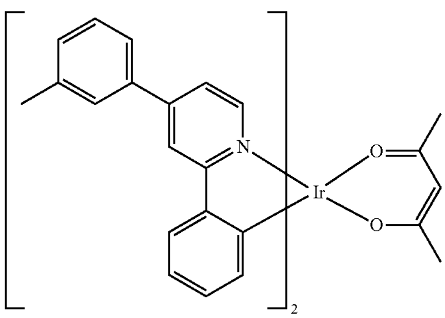
D-35
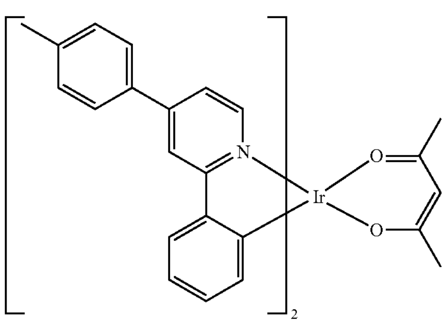
D-36
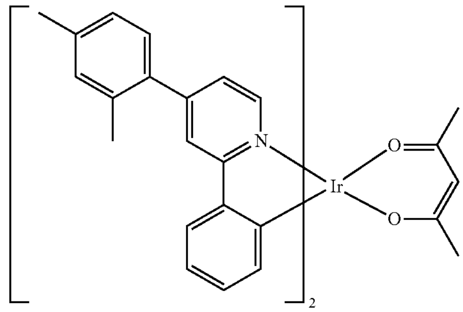
D-37
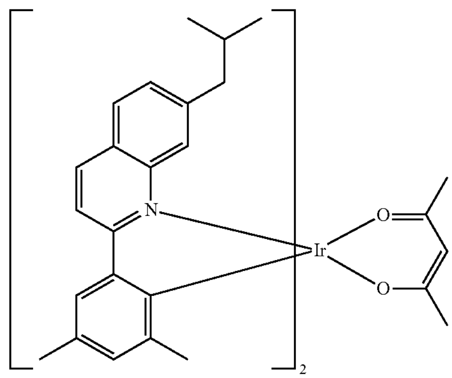
D-38
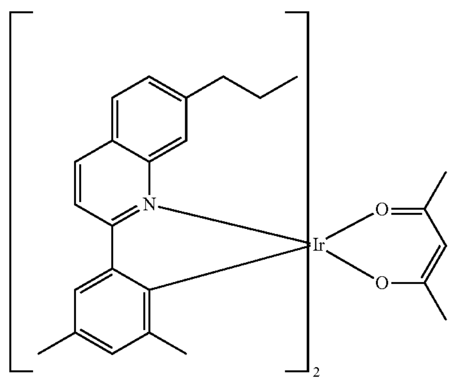
D-39
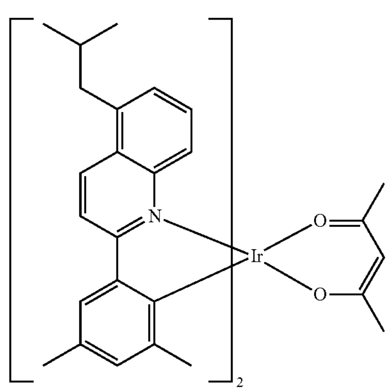

-continued
D-40
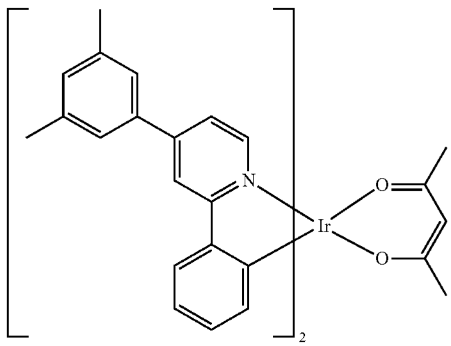
D-41
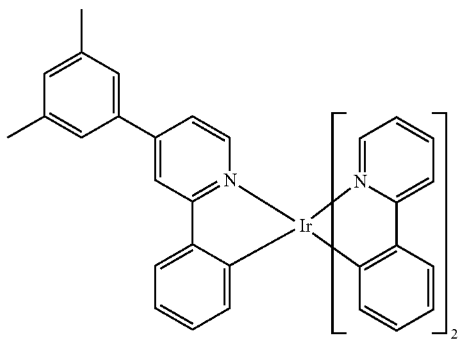
D-42
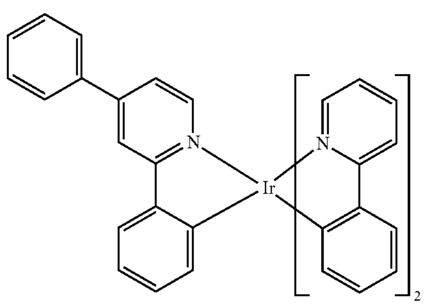
D-43
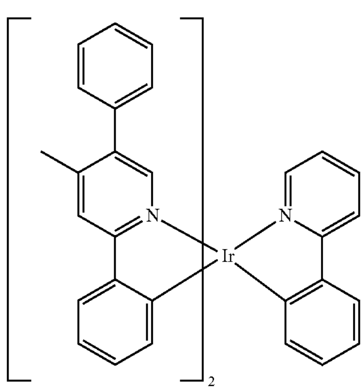
-continued
D-44
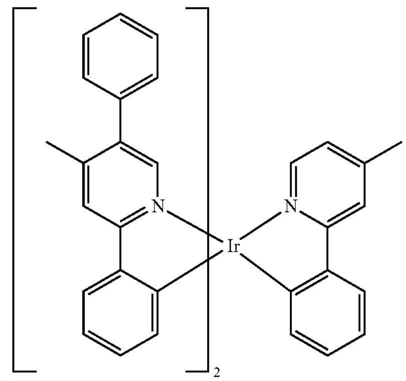
D-45
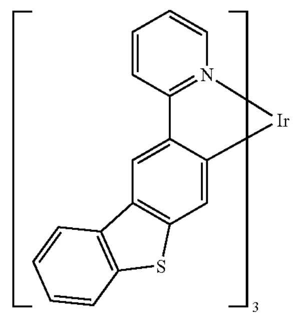
D-46
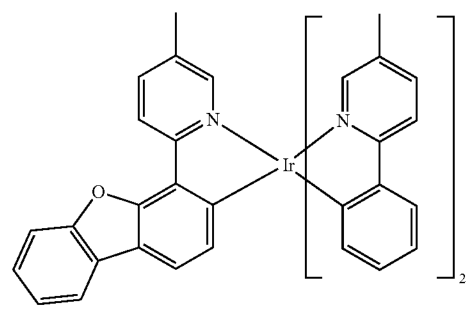
D-47
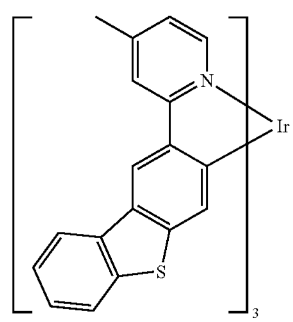
D-48
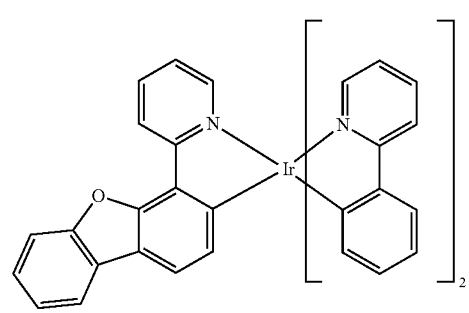

D-49
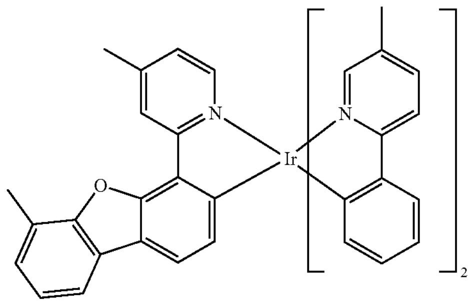
D-50
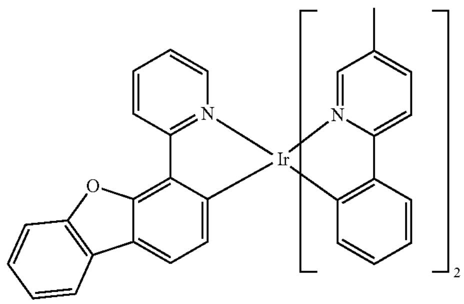
D-51
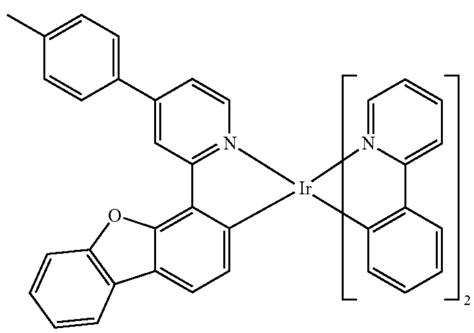
D-52
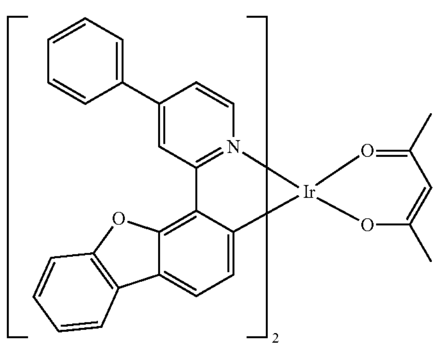
D-53
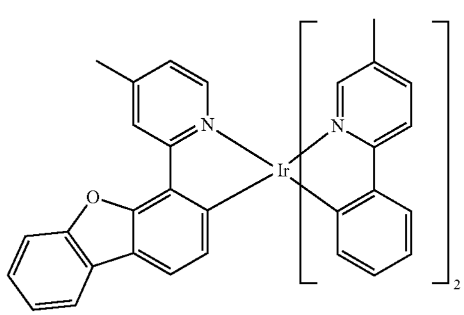
D-54
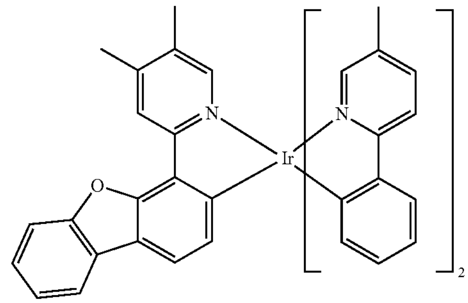
D-55
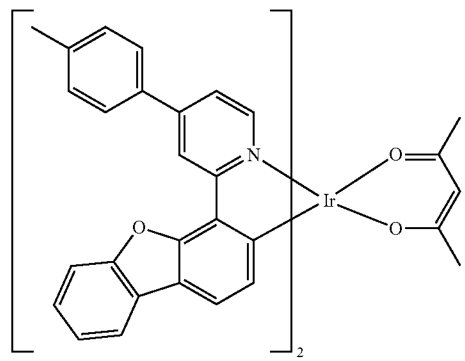
D-56
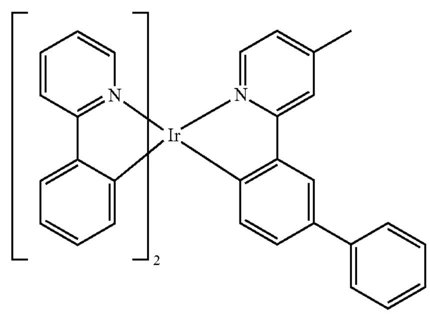
D-57
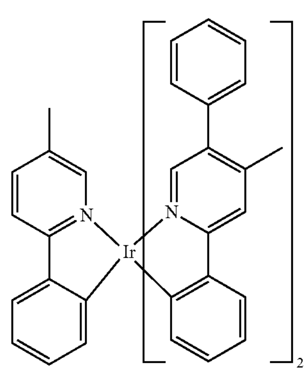

D-58
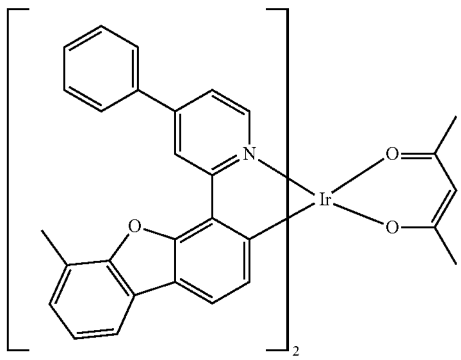
D-59
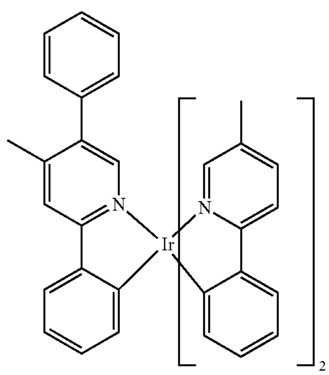
D-60
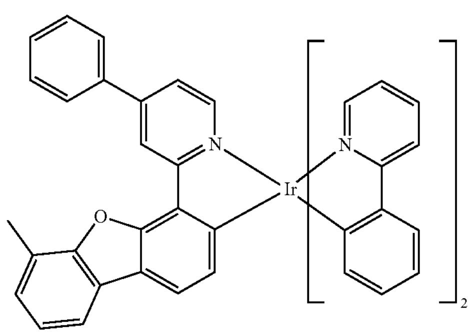
D-61
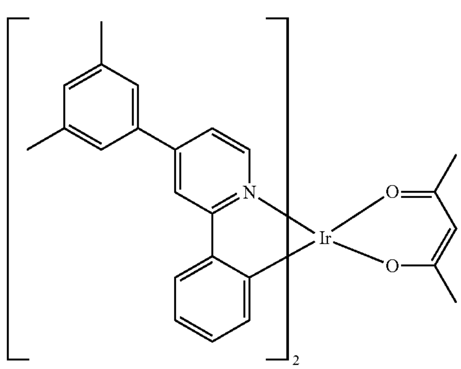
D-62
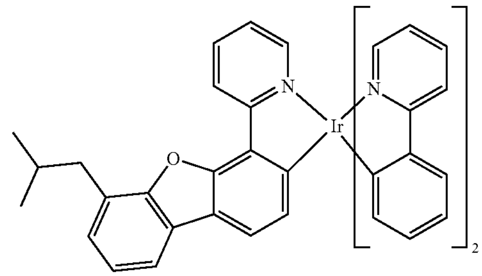
DD-63
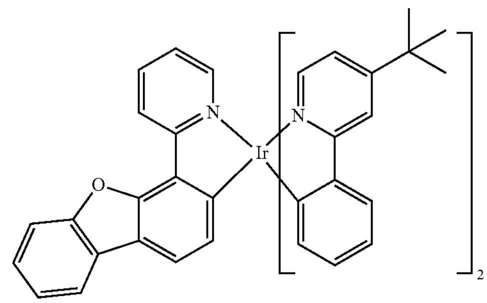
D-64
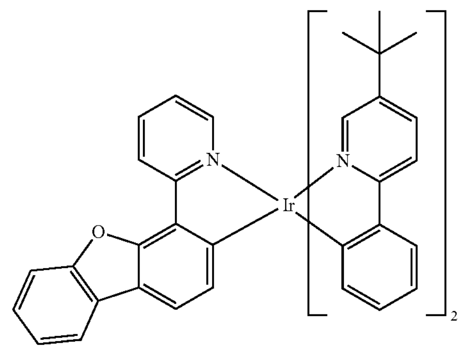
D-65
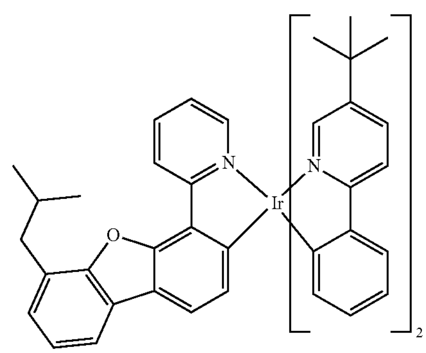
D-66
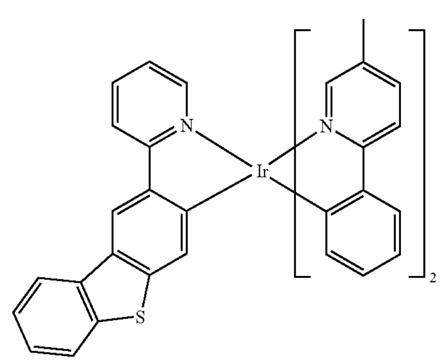

-continued
D-67
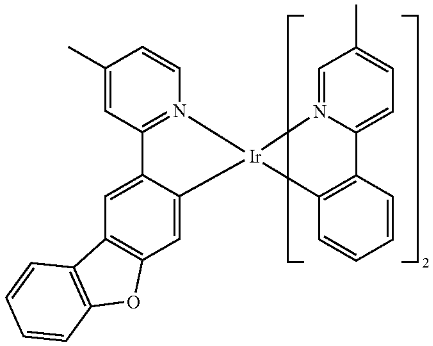
D-68
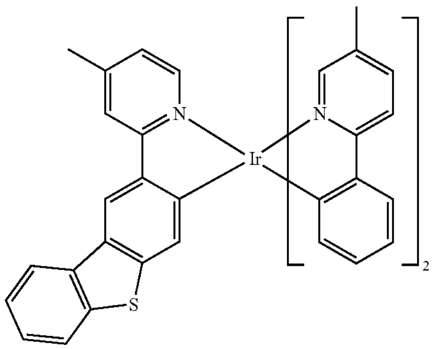
D-69
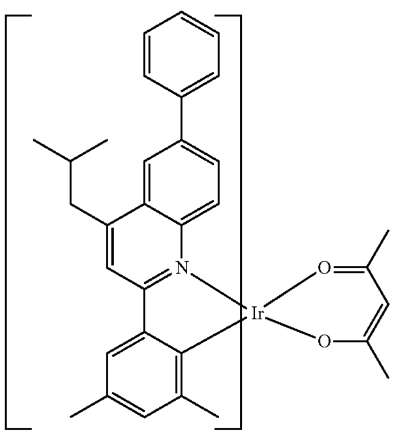
D-70
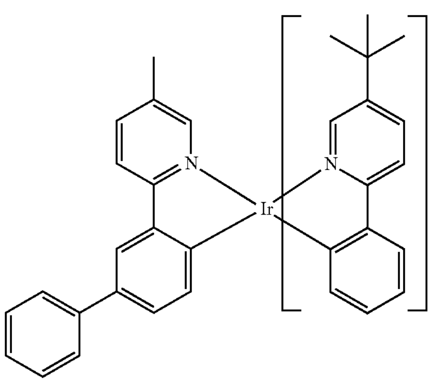
-continued
D-71
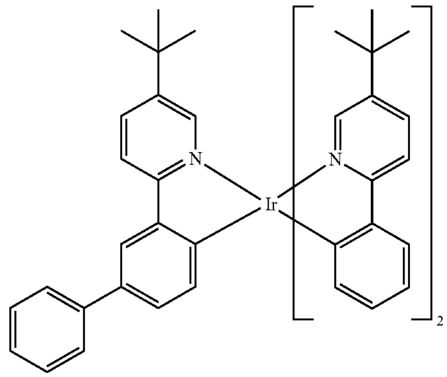
D-72
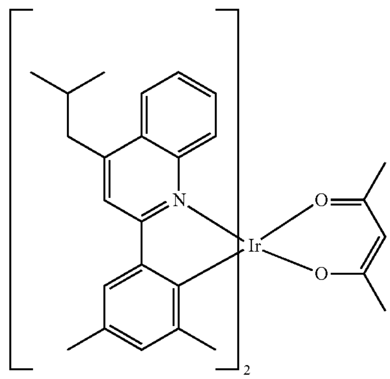
D-73
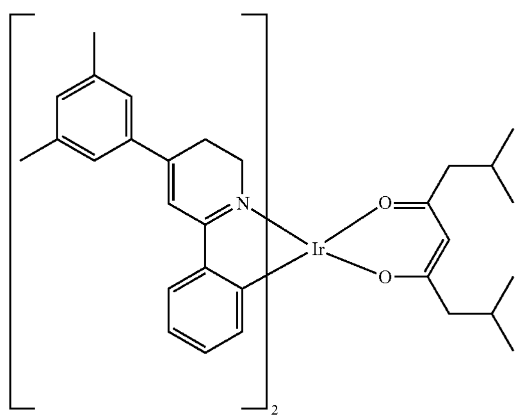
D-74
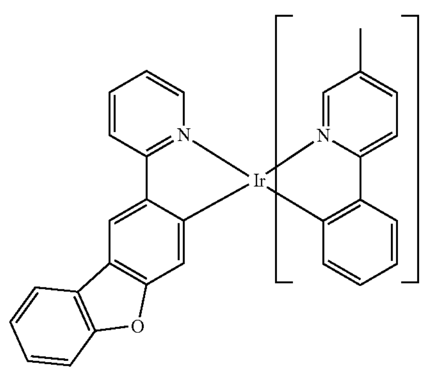

-continued
D-75
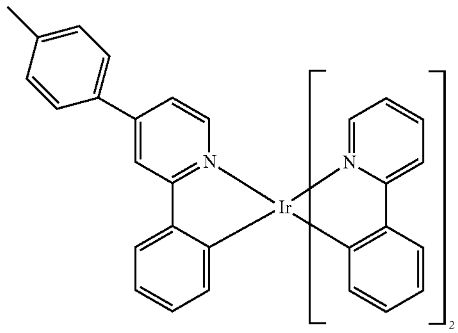
D-76
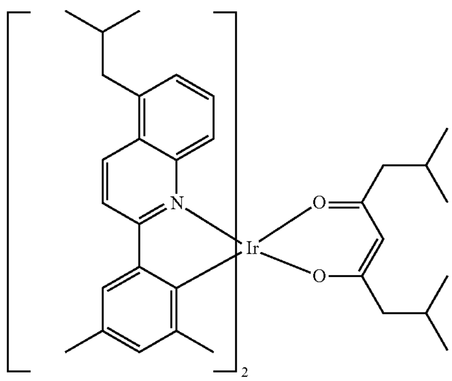
D-77
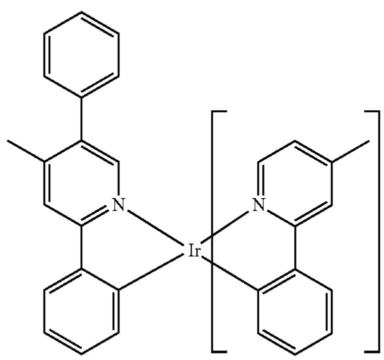
D-78
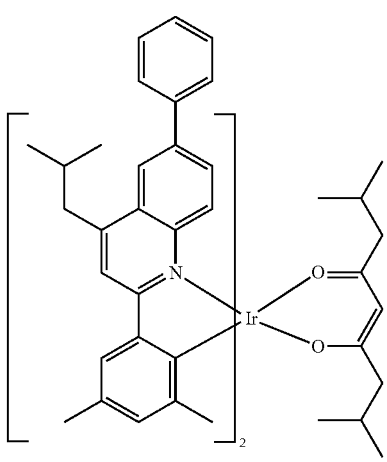
-continued
D-79
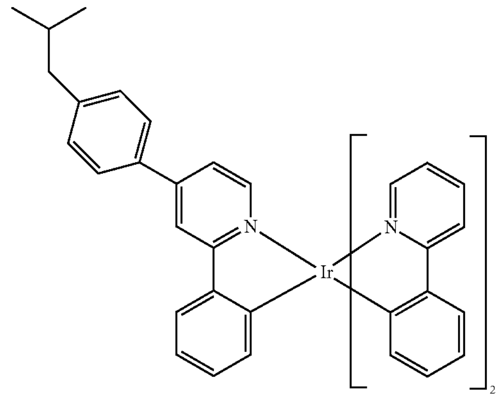
D-80
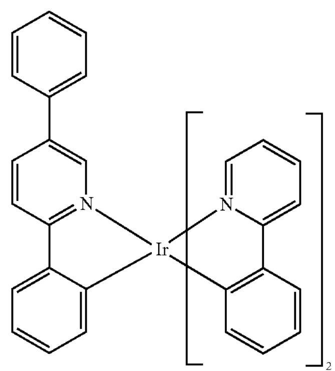
D-81
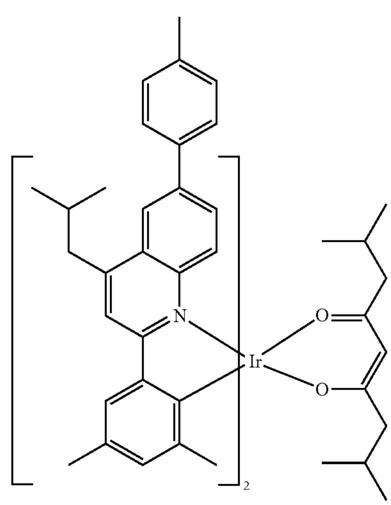

-continued
D-82
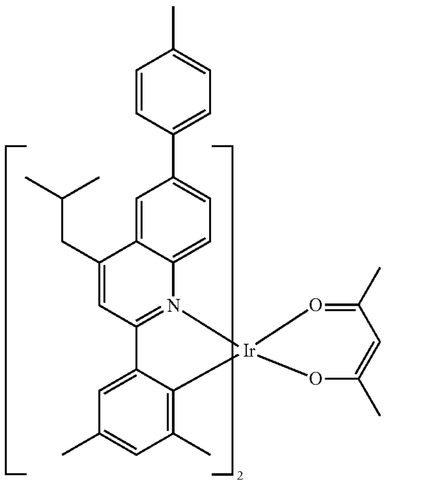
D-83
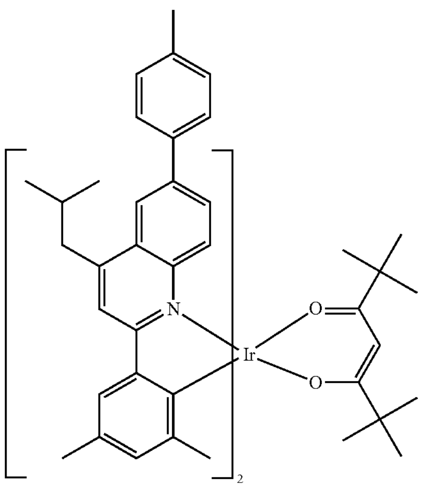
D-84
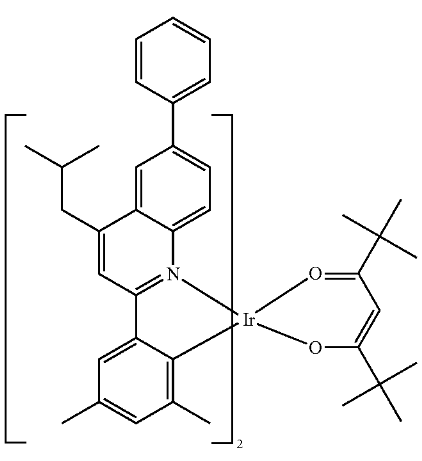
-continued
D-85
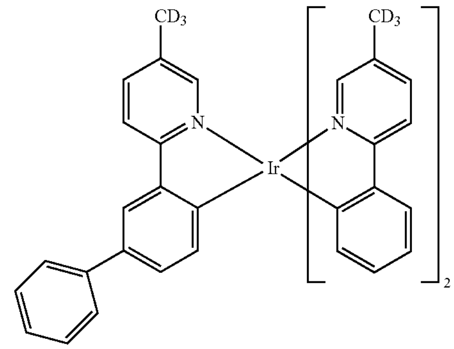
D-86
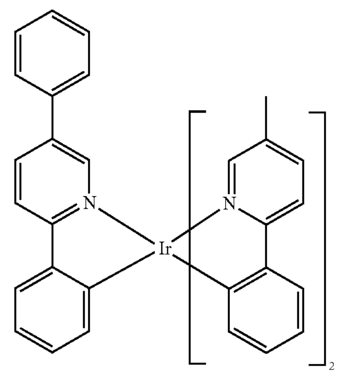
D-87
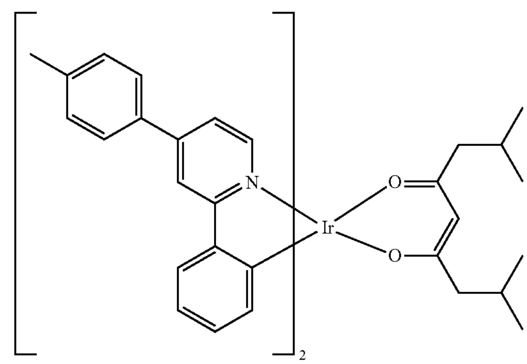
D-88
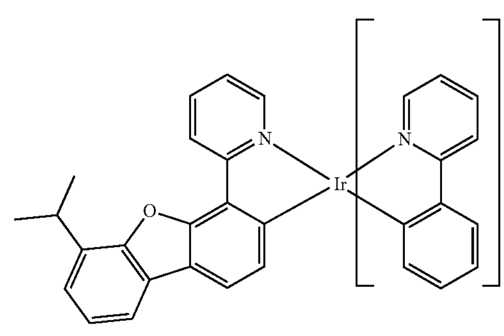

-continued
D-89
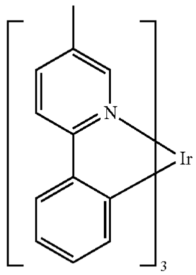
D-90
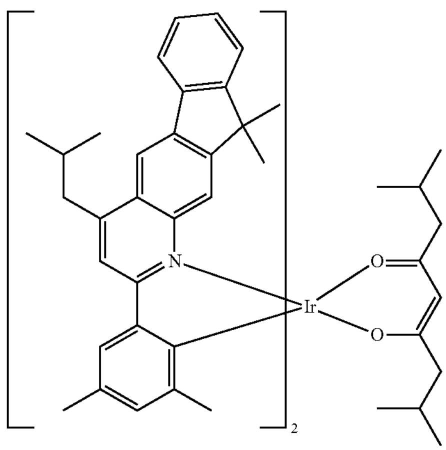
D-91
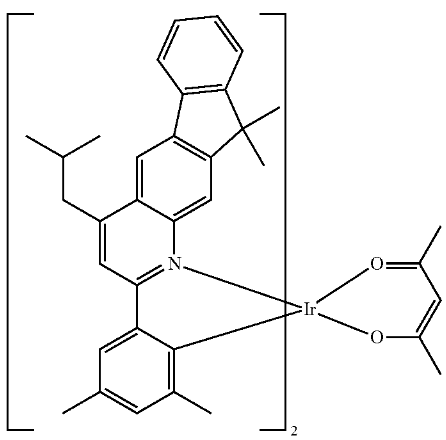
D-92
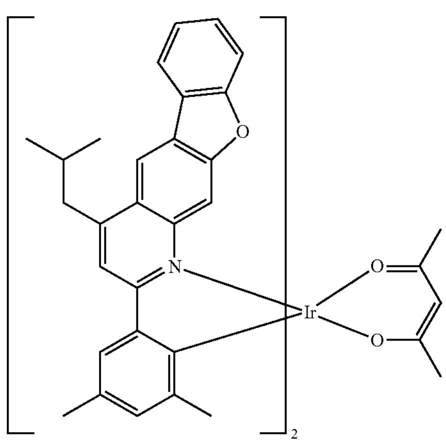
-continued
D-93
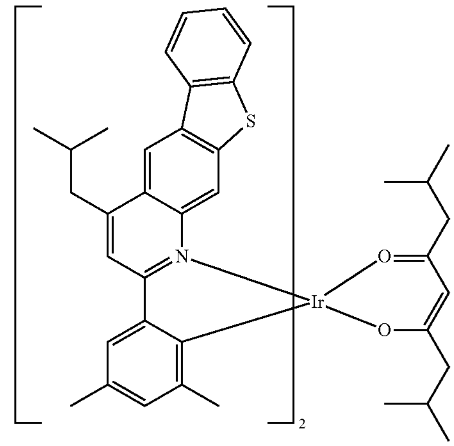
D-94
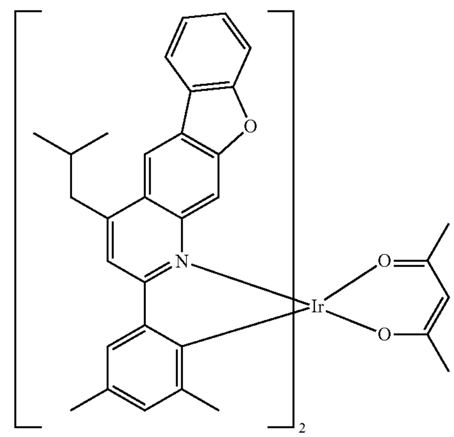
D-95
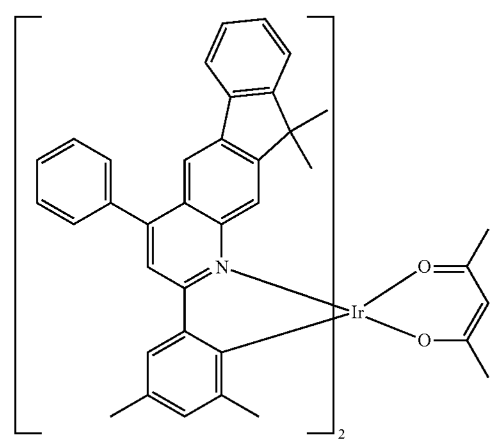

-continued
D-96
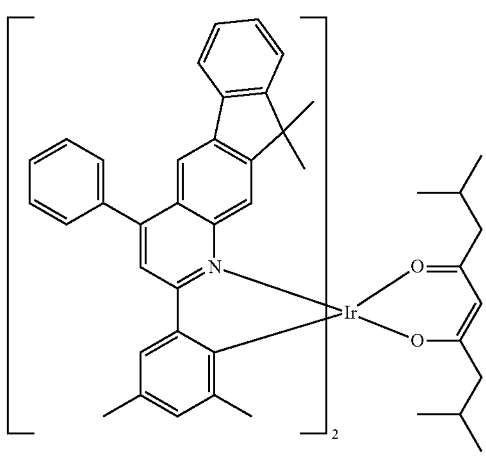
D-97
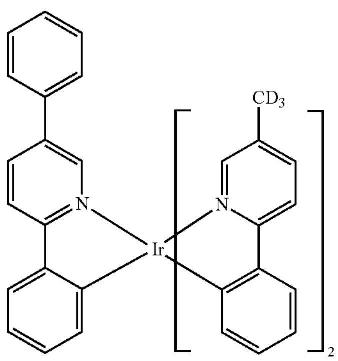
D-98
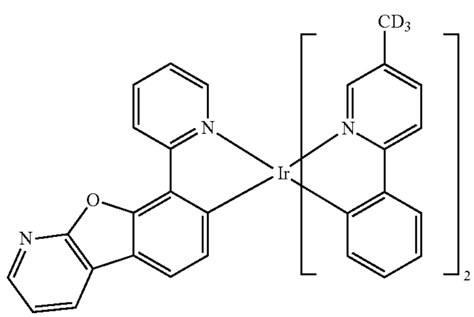
D-99
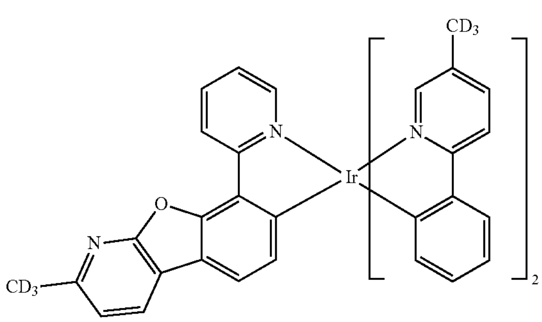
-continued
D-100
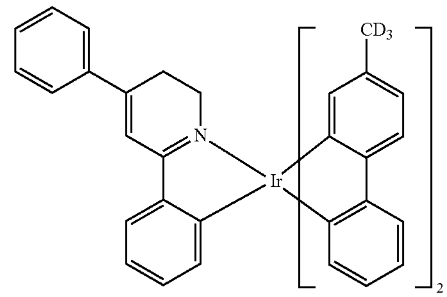
D-101
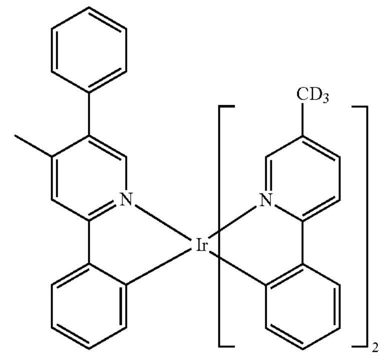
D-102
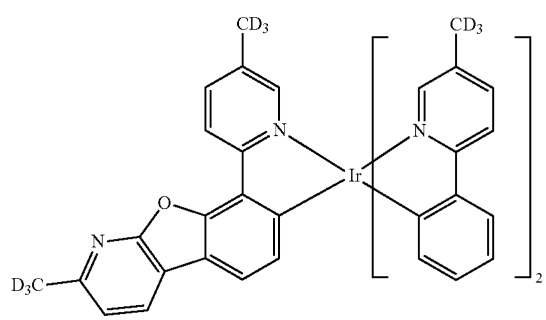
D1-103
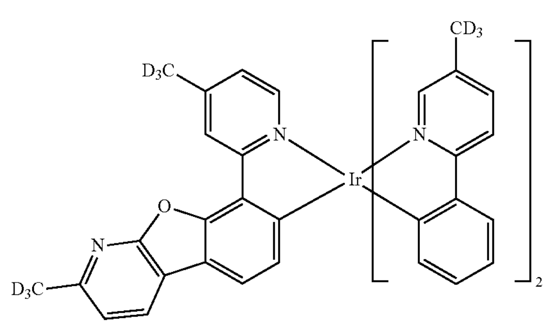

-continued
D-104
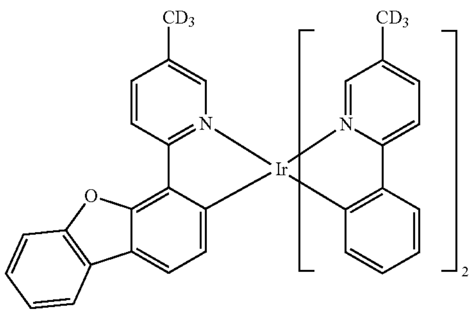
D-105
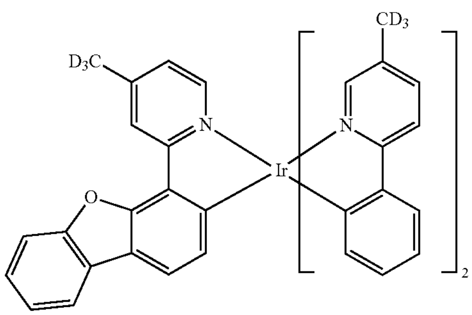
D-106
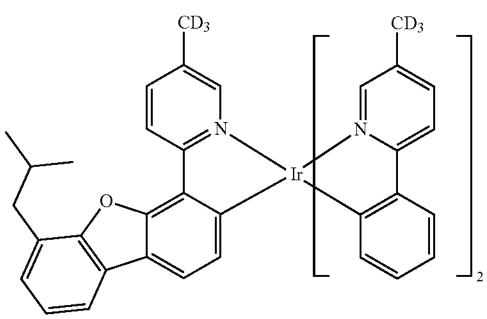
D-107
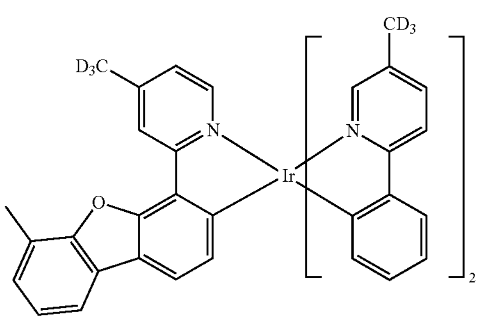
-continued
D-108
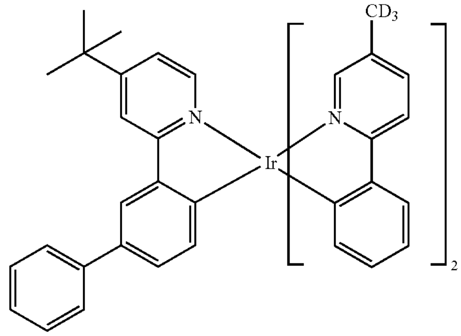
D-109
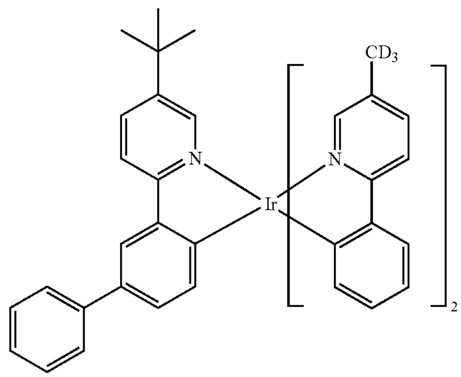
D-110
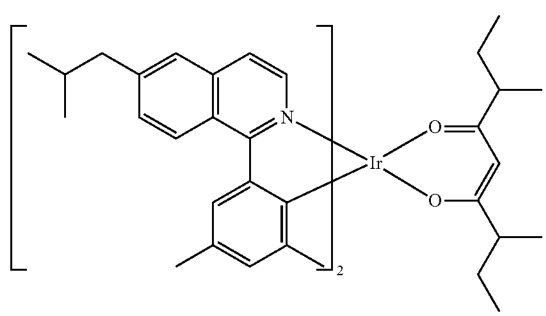
D-111
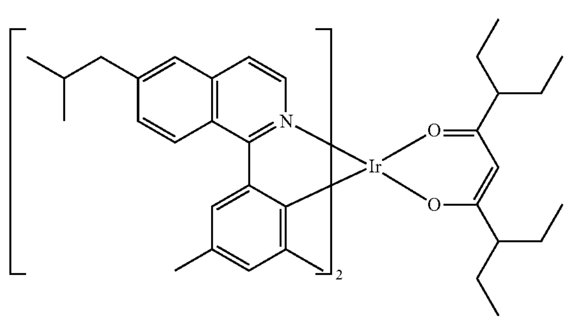

-continued
D-112
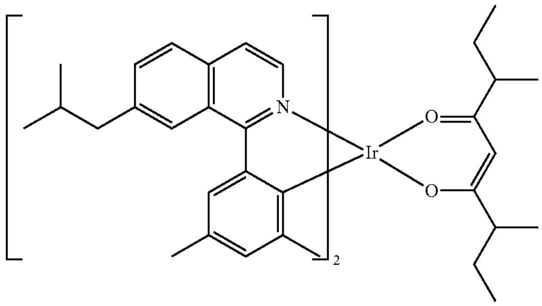
D-113
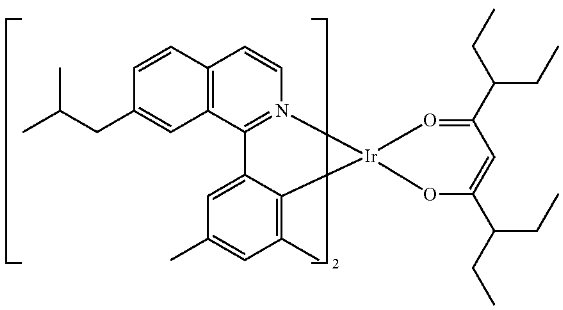
D-114
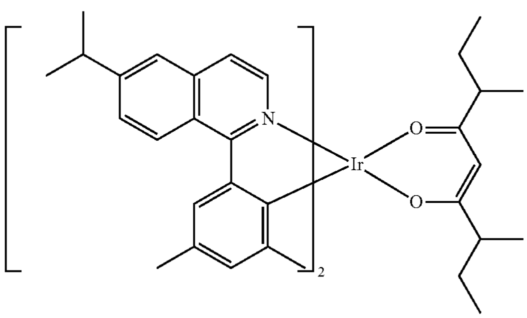
D-115
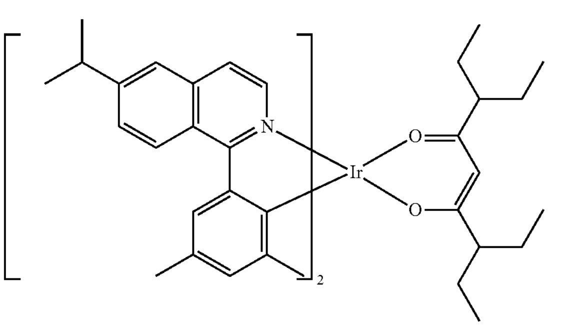
-continued
D-116
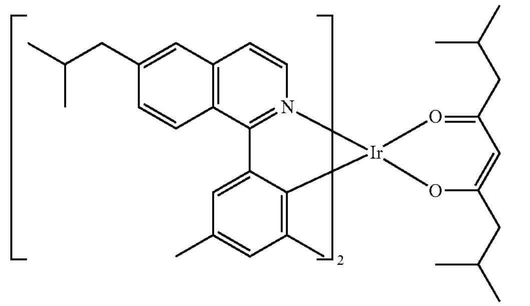
D-117
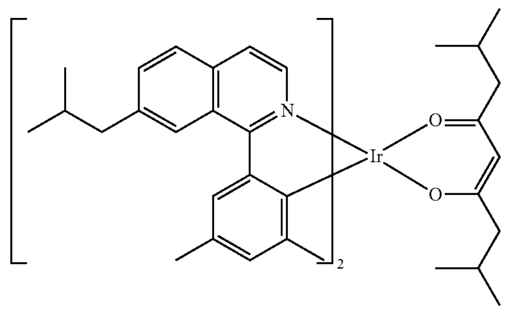
D-118
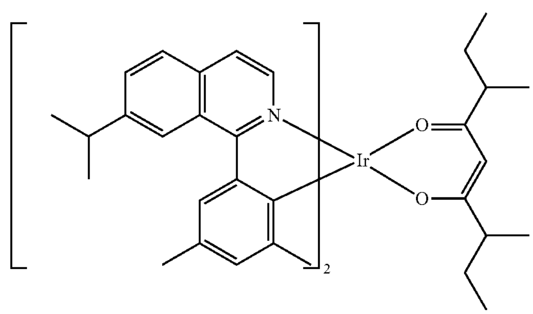
D-119
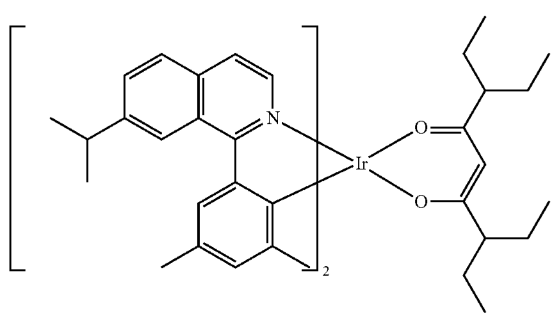

-continued
D-120
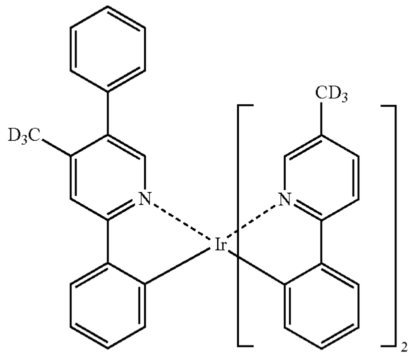
D-121
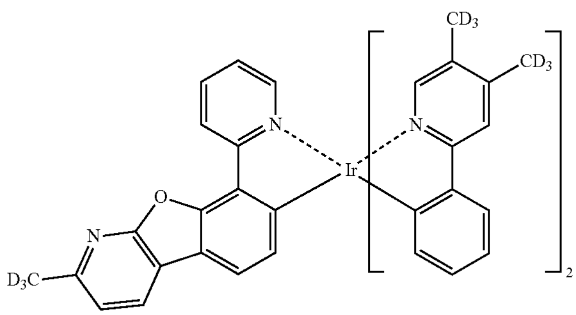
D-122
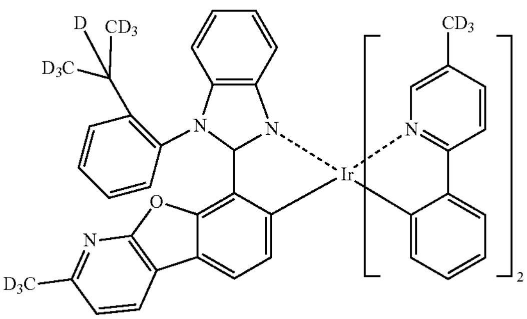
D-123
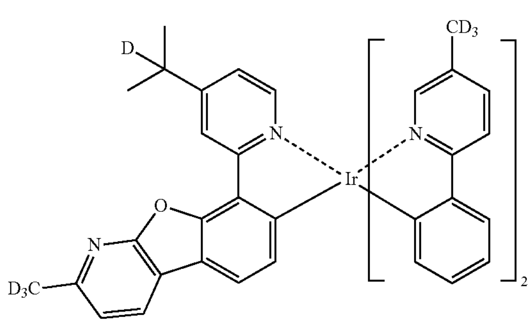
-continued
D-124
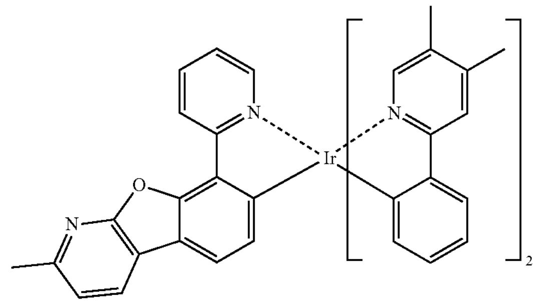
D-125
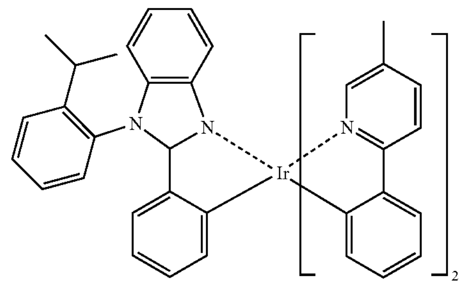
D-127
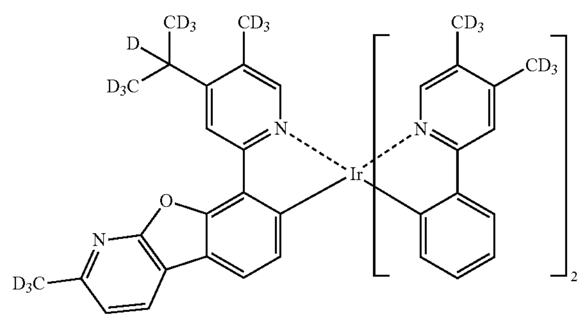
D-128
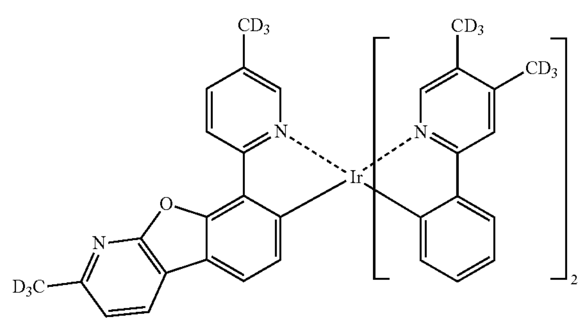
D-129
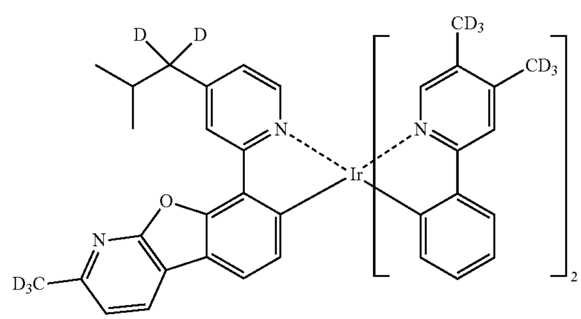

-continued
D-130
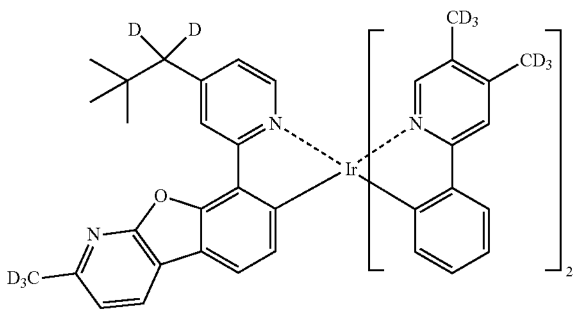
D-131
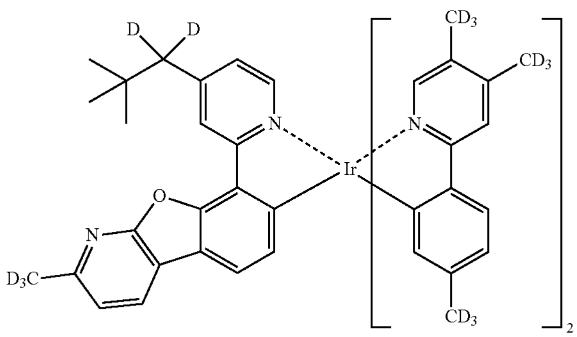
D-132
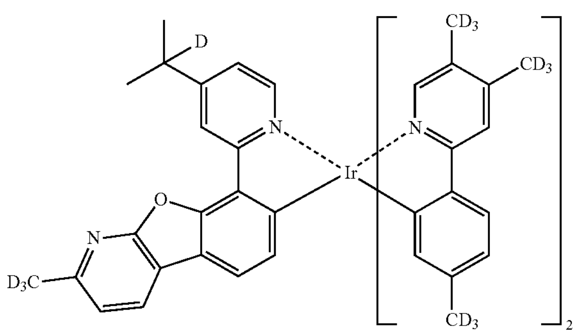
D-133
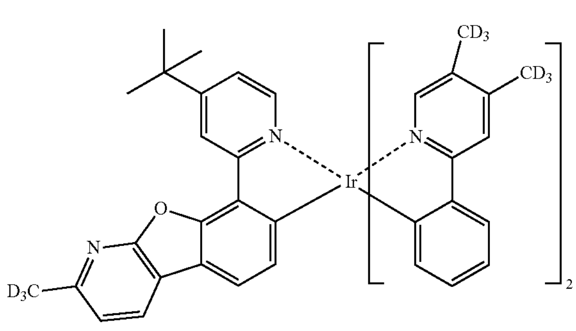
-continued
D-134
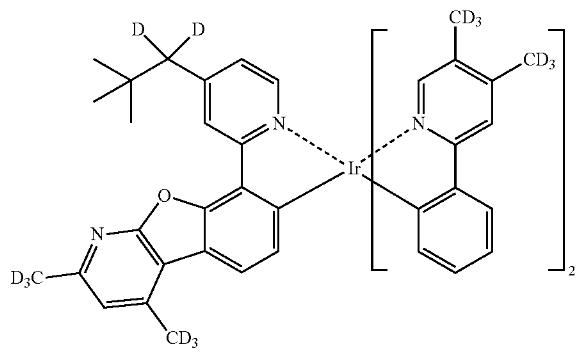
D-135
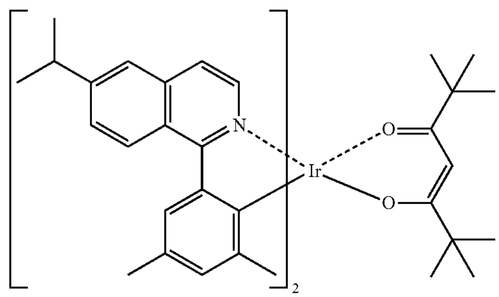
D-136
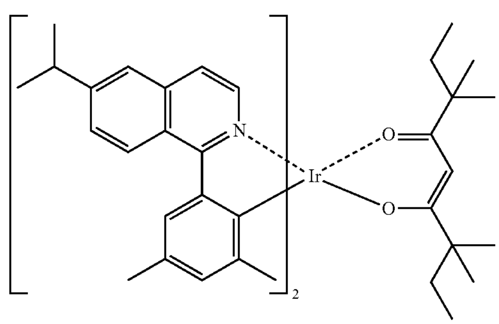
D-137
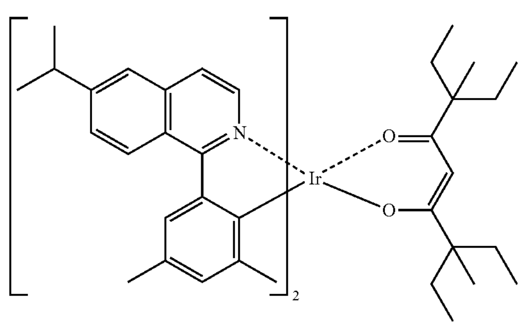

-continued
D-138
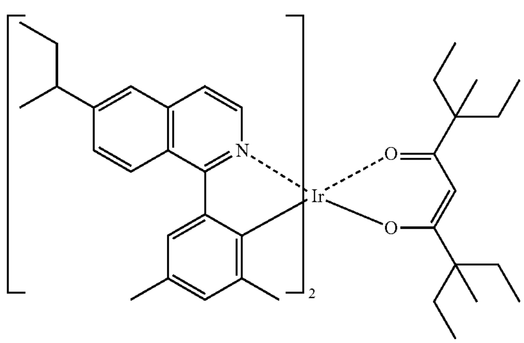
D-139
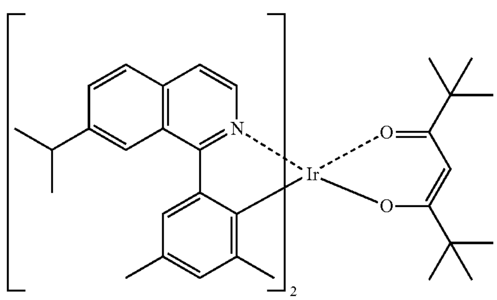
D-140
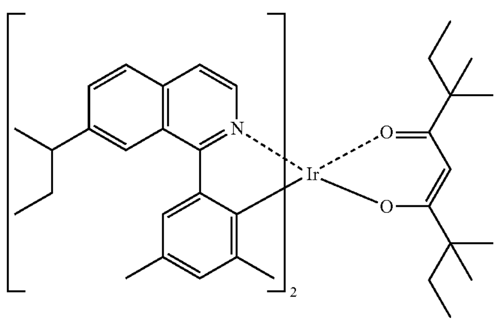
D-141
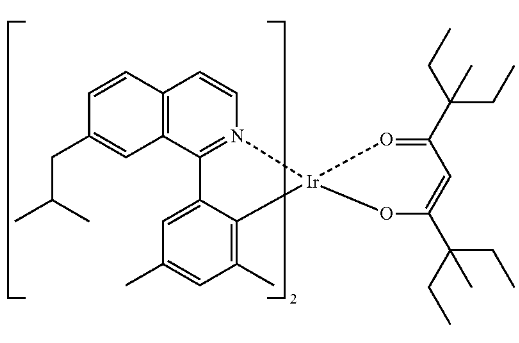
-continued
D-142
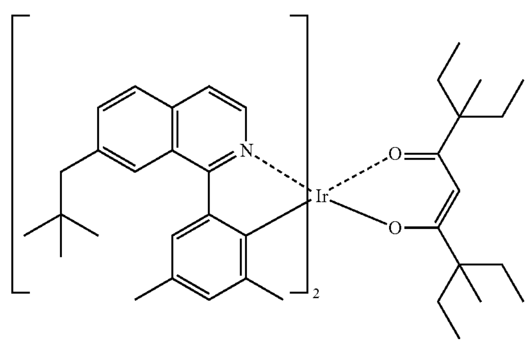
D-143
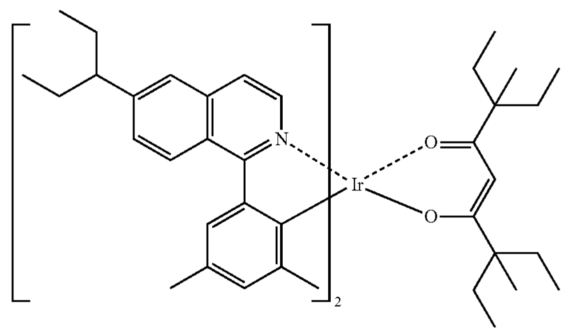
D-144
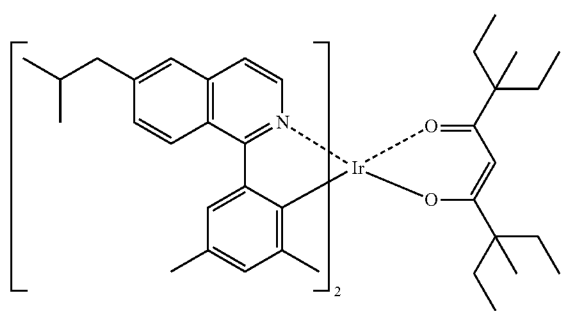
D-145
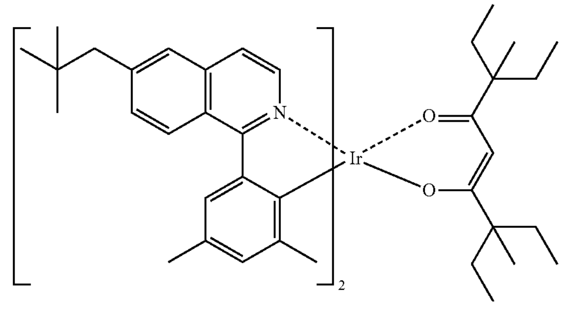

-continued

D-146

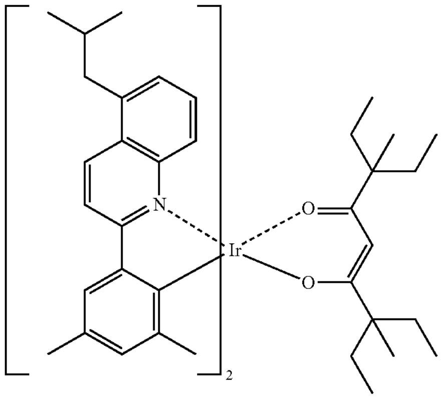

D-147

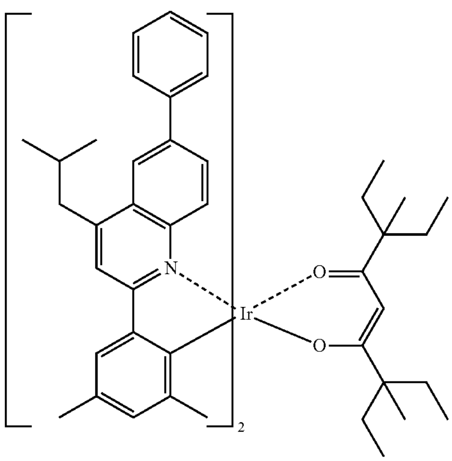

D-148

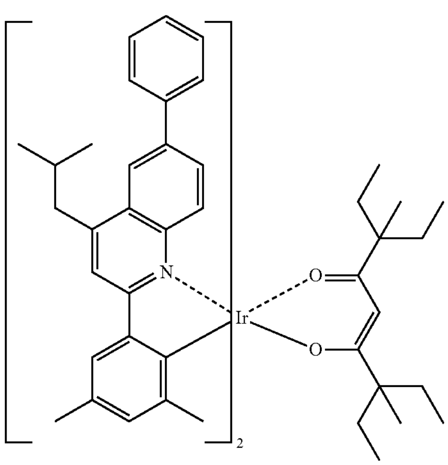

-continued

D-149

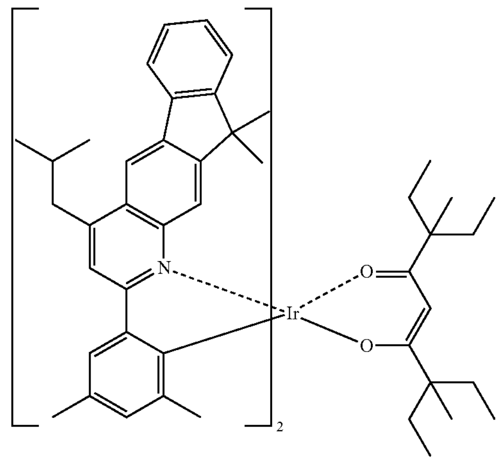

In an organic electroluminescent device of the present disclosure, a hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

In addition, an electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

The plurality of host materials according to the present disclosure may also be used in an organic electroluminescent device comprising a quantum dot (QD).

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film can be formed by dissolving or diffusing materials forming each layer into any suitable solvent such as ethanol, chloroform, tetrahydrofuran, dioxane, etc. The solvent can be any one where the materials forming each layer can be dissolved or diffused, and where there are no problems in film-formation capability.

The first, second and third host compounds of the present disclosure may be film-formed by the above-listed methods, commonly by a co-evaporation process or a mixture-evaporation process. The co-evaporation is a mixed deposition method in which two or more materials are placed in a respective individual crucible source and a current is applied to both cells simultaneously to evaporate the materials. The mixture-evaporation is a mixed deposition method in which two or more materials are mixed in one crucible source before evaporating them, and a current is applied to the cell to evaporate the materials. Further, if the first, second and third host compounds are present in the same layer or different layers in an organic electroluminescent device, the three host compounds may individually form films. For example, the second host compound may be deposited after depositing the first and third host compounds.

The present disclosure may provide a display system using at least three types of host materials comprising the compound represented by formula 1, the compound represented by any one of formulas 2 to 4, and the compound represented by any one of formulas 1 to 4. In other words, it is possible to produce a display system or lighting system by using the plurality of host materials of the present disclosure. To be specific, it is possible to produce a display system, e.g., a display system for smart phones, tablets, notebooks, PCs, TVs, or cars; or a lighting system, e.g., an outdoor or indoor lighting system, by using the plurality of host materials of the present disclosure.

Originally, LUMO (lowest unoccupied molecular orbital) energy and HOMO (highest occupied molecular orbital) energy levels have negative values. However, for convenience, LUMO energy level and HOMO energy level are expressed in absolute values in the present disclosure. In addition, the LUMO energy levels are compared based on absolute values.

The values calculated by density functional theory (DFT) are used for LUMO and HOMO energy levels in the present disclosure. HOMO and LUMO energy levels of the light-emitting layer, which will be described later, are defined as a first host HOMO ($A_{h1}$), a second host HOMO ($A_{h2}$) and a third host HOMO ($A_{h3}$), and a first host LUMO ($A_{l1}$), a second host LUMO ($A_{l2}$) and a third host LUMO ($A_{l3}$). The results are intended to explain the tendency of alternative devices according to the overall HOMO and LUMO energy groups, and the results different from the above may be obtained depending on the intrinsic properties of specific derivatives and the stability of materials.

In an organic electroluminescent device of the present disclosure, assuming that the first and third host materials having strong hole transport properties are used with the second host having strong electron transport properties, the HOMO energy level of the first host compound may be greater than that of the third host compound. The difference of the HOMO energy levels between the first host compound and the third host compound may be specifically about 0.5 eV or less, preferably about 0.3 eV or less. For example, the HOMO energy levels of the first and third host compounds may be about 5.1 eV and about 4.8 eV, respectively, and thus, the difference between their HOMO energy levels may be about 0.3 eV.

Figure 2:
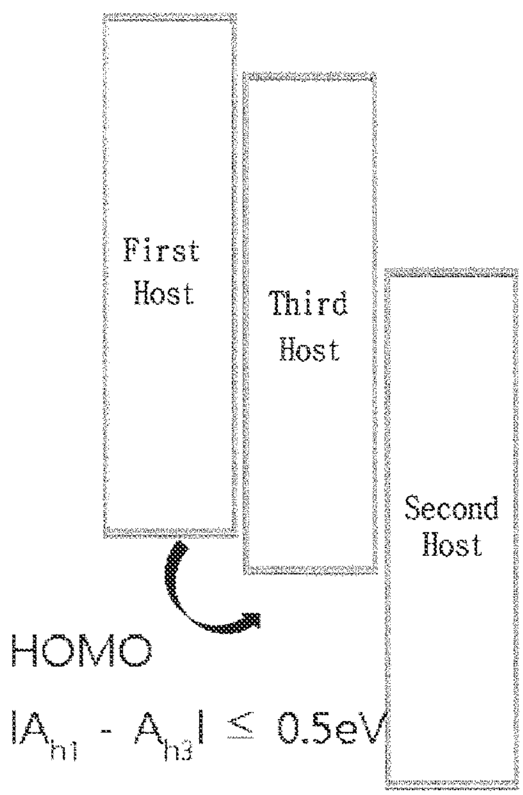
FIG. 2 illustrates a diagram schematically showing a HOMO energy diagram of a light-emitting layer of an organic electroluminescent device according to an embodiment of the present disclosure.

With reference to FIG. 2, when each of the first and third host materials has stronger hole transport properties than the second host material, the HOMO energy level of the light-emitting layer comprising the plurality of host materials may satisfy the following Equation 1, preferably, the following Equation 2.

$$|A_{h1}-A_{h3}|\leq 0.5\text{ eV} \quad \text{[Equation 1]}$$

$$|A_{h1}-A_{h3}|\leq 0.3\text{ eV} \quad \text{[Equation 2]}$$

In Equations 1 and 2, $A_{h1}$ represents the HOMO energy level of the first host material, and $A_{h3}$ represents the HOMO energy level of the third host material.

The HOMO barrier between the first host compound and the hole transport layer may be a factor in increasing the driving voltage, and there is almost no HOMO barrier between the third host compound and the hole transport layer, so the hole trap is not smooth, and thus there is a significant limitation in increasing the efficiency. However, when the third host compound comprises a compound having a low HOMO energy level among the compounds of formula 1 and a low barrier to the hole transport layer, transporting holes to the host compound becomes easier compared to each compound, and at the same time, efficiency and lifetime can be improved.

In addition, assuming that the first host material having strong hole transport properties are used with the second and third hosts having strong electron transport properties, the LUMO energy level of the second host compound may be greater than that of the third host compound. The difference between the LUMO energy levels of the second and third host compounds may be specifically about 0.5 eV or less, preferably about 0.3 eV or less. For example, the LUMO energy levels of the second and third host compounds may be about 1.8 eV and about 2.1 eV, respectively, and thus, the difference between their LUMO energy levels may be about 0.3 eV.

Figure 3:
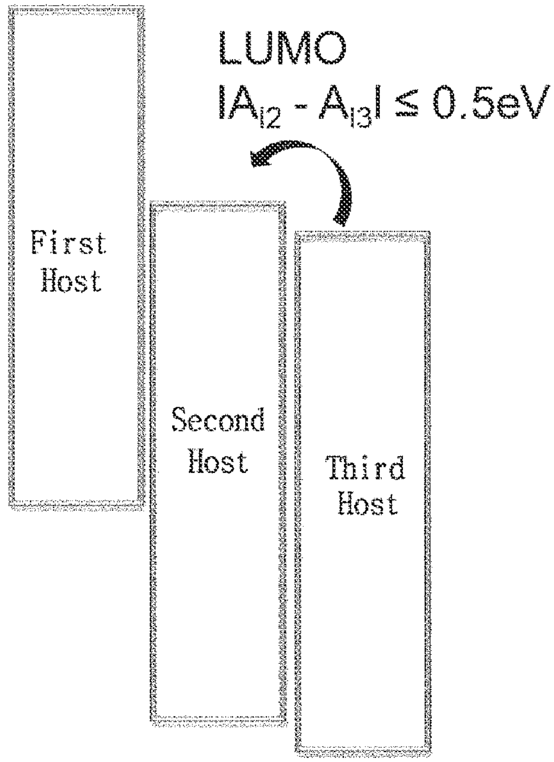
FIG. 3 illustrates a diagram schematically showing a LUMO energy diagram of a light-emitting layer of an organic electroluminescent device according to an embodiment of the present disclosure.

With reference to FIG. 3, when each of the second and third host materials has stronger electron transport properties than the first host material, the LUMO energy level of the light-emitting layer comprising the plurality of host materials may satisfy the following Equation 3, preferably, the following Equation 4.

$$|A_{l2}-A_{l3}|\leq 0.5\text{ eV} \quad \text{[Equation 3]}$$

$$|A_{l2}-A_{l3}|\leq 0.3\text{ eV} \quad \text{[Equation 4]}$$

In Equations 3 and 4, $A_{l2}$ represents the LUMO energy level of the second host material, and $A_{l3}$ represents the LUMO energy level of the third host material.

Since the second host compound has a high LUMO energy, transporting electrons is not easy, so there is a limitation in increasing efficiency properties. The third host compound has a significant limitation in increasing lifetime properties due to relatively fast electron transport. However, when the second and third host compounds are mixed, the efficiency and lifetime can be increased at the same time by maintaining the appropriate current properties and controlling the ratio of the hole and electrons in the light-emitting layer. Therefore, the organic electroluminescent device of the present disclosure may have a low driving voltage, excellent luminous efficiency, and a long lifetime.

Hereinafter, the preparation method of the compounds according to the present disclosure, the properties thereof, and the properties of the OLED comprising the plurality of host materials according to the present disclosure will be explained in detail with reference to the representative compounds of the present disclosure. The following examples only describe the properties of the OLED comprising the compound according to the present disclosure, but the present disclosure is not limited to the following examples.

Example 1: Preparation of Compound H1-222

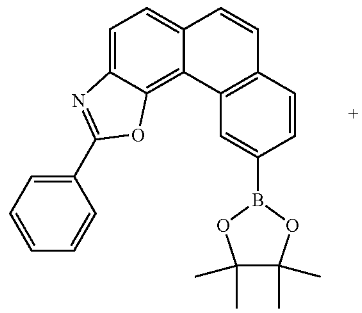

1-1

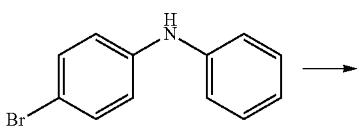

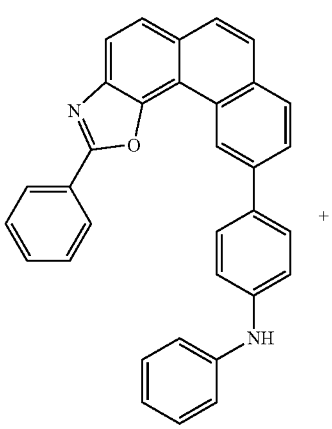

1-2

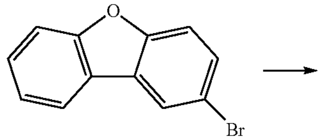

-continued

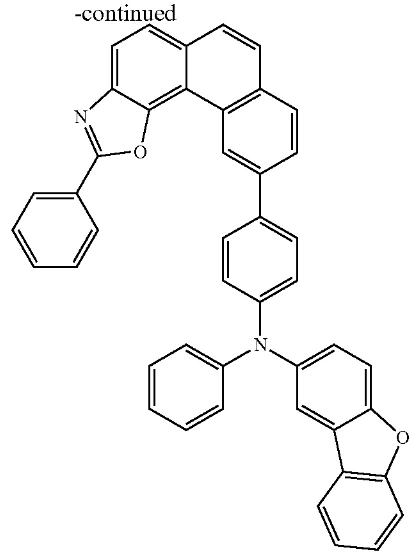

H1-222

Synthesis of Compound 1-2

Compound 1-1 (50 g, 118.6 mmol), 4-bromo-N-phenylaniline (29.5 g, 118.9 mmol), $Pd(OAc)_2$ (0.2664 g, 1.18 mmol), S-Phos (0.9744 g, 2.3 mmol), and $K_2CO_3$ (41 g, 296.6 mmol) were dissolved in 600 mL of toluene and 95.7 mL of $H_2O$, and the mixture was stirred under reflux for 2 hours. The mixture was cooled to room temperature, and filtered through Celite. The obtained solid was separated by column chromatography to obtain compound 1-2 (45 g, yield: 82%).

Synthesis of Compound H1-222

Compound 1-2 (45 g, 97.2 mmol), 2-bromobenzofuran (24 g, 97.1 mmol), $Pd(OAc)_2$ (0.2183 g, 0.97 mmol), S-Phos (0.7887 g, 1.92 mmol), and NaOt-Bu (23.4 g, 243.4 mmol) were dissolved in 450 mL of o-xylene, and the mixture was stirred under reflux for 3 hours. The mixture was cooled to room temperature, and filtered through Celite. The obtained solid was separated by column chromatography to obtain compound H1-222 (18 g, yield: 29%).

| | MW | M.P. |
|---|---|---|
| H1-222 | 628.73 | 252° C. |

Example 2: Preparation of Compound H1-221

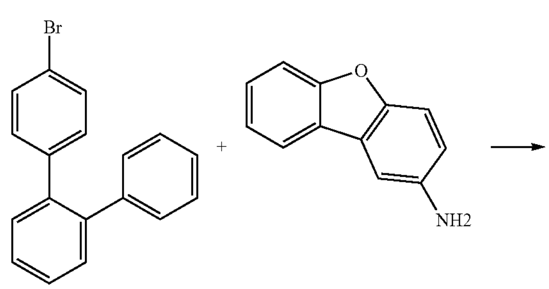

-continued

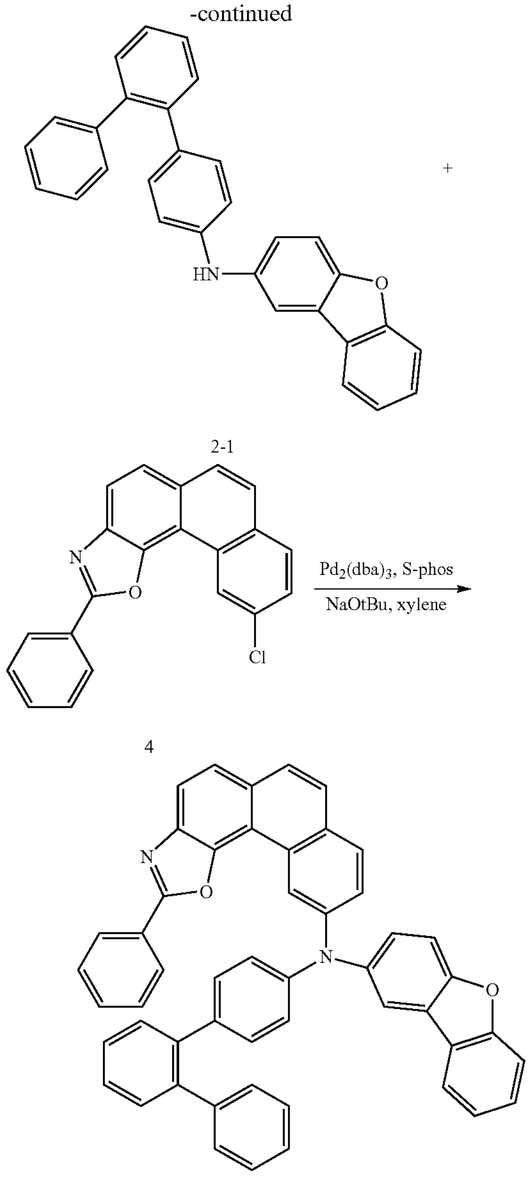

2-1

4

H1-221

Synthesis of Compound 2-1

4-bromo-1,1':2',1"-terphenyl (10.0 g, 32.34 mmol), 8-aminodibenzo[b,d]furan-2-yl (8.8 g, 48.51 mmol), $PdCl_2(Amphos)_2$ (2.3 g, 3.23 mmol), and NaOt-Bu (4.6 g, 48.51 mmol) were dissolved in 161 mL of o-xylene, and the mixture was stirred under reflux for 2 hours. The mixture was cooled to room temperature, and filtered through Celite. The obtained solid was separated by column chromatography to obtain compound 2-1 (8.6 g, yield: 64.6%).

Synthesis of Compound H1-221

Compound 2-1 (8.6 g, 20.90 mmol), compound 4 (8.3 g, 25.08 mmol), $Pd_2(dba)_3$ (1.0 g, 1.05 mmol), S-Phos (900 mg, 2.09 mmol), and NaOt-Bu (5.0 g, 52.25 mmol) were dissolved in 140 mL of o-xylene, and the mixture was stirred under reflux for 3 hours. The mixture was cooled to room temperature, and filtered through Celite. The obtained solid was separated by column chromatography to obtain compound H1-221 (5.8 g, yield: 39.4%).

| | MW | M.P. |
|---|---|---|
| H1-221 | 704.83 | 168° C. |

Example 3: Preparation of Compound H2-745

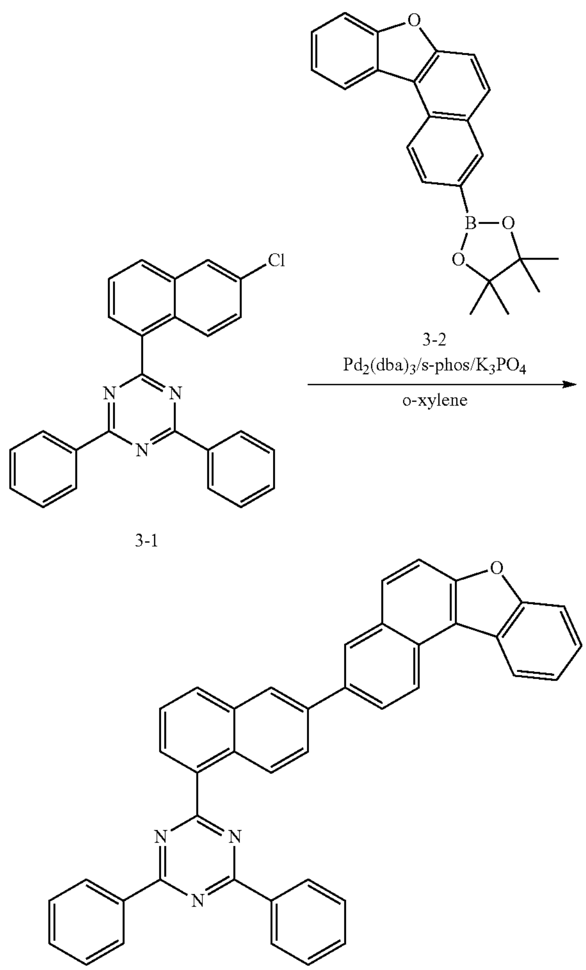

3-2

3-1

H2-745

In a flask, compound 3-1 (5 g, 12.69 mmol), compound 3-2 (8.7 g, 25.38 mmol), $Pd_2(dba)_3$ (0.58 g, 0.634 mmol), s-phos (0.52 g, 1.269 mmol), and $K_3PO_4$ (6.7 g, 31.73 mmol) were dissolved in 65 mL of o-xylene, and the mixture was stirred under reflux for 15 hours. After completion of the reaction, the mixture was cooled to room temperature, and methanol was added, and then the solid was filtered. Thereafter, the resulting solid was dissolved in chlorobenzene, and separated by silica filter to obtain compound H2-745 (3.3 g, yield: 45%).

| | MW | M.P. |
|---|---|---|
| H2-745 | 575.6 | 250.9° C. |

Device Examples 1 to 16: Producing a Red OLED Deposited with a Plurality of Host Materials According to the Present Disclosure as Hosts OLEDs according to the present disclosure were produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 was introduced into a cell of the vacuum vapor deposition apparatus, and compound HT-1 was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm on the ITO substrate. Next, compound HT-1 was deposited on the hole injection layer to form a first hole transport layer having a thickness of 80 nm. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: The first host compound, the second host compound, and the third host compound shown in Table 1 below were introduced into three cells of the vacuum vapor deposition apparatus as hosts, and compound D-39 was introduced into another cell as a dopant. The three host materials were evaporated at a rate of 0.25:0.5:0.25 (the first host: the second host the third host) and the dopant material was simultaneously evaporated at a different rate, and the dopant was deposited in a doping amount of 3 wt % based on the total amount of the hosts and the dopant to form a light-emitting layer having a thickness of 40 nm on the second hole transport layer. Thereafter, compound ETL-1 and compound EIL-1 as electron transport materials were evaporated in a weight ratio of 50:50 to deposit an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Comparative Examples 1 to 27: Producing an OLED Comprising Comparative Compounds as Hosts OLEDs were produced in the same manner as in Device Example 1, except that the first host compound, the second host compound, or the third host compound shown in Table 1 below was used as the single host of the light-emitting layer.

The driving voltage, luminous efficiency, and light-emitting color at a luminance of 1,000 nit, and the time taken for luminance to decrease from 100% to 95% (lifetime; T95) at a luminance of 10,000 nit of the OLEDs produced in Device Examples 1 to 15, and Comparative Examples 1 to 27 are provided in Table 1 below.

TABLE 1

| | First Host | Second Host | Third Host | Driving Voltage M | Luminous Efficiency [cd/A] | Light-Emitting Color | Lifetime (T95) [hr] |
|---|---|---|---|---|---|---|---|
| Device Example 1 | H1-222 | H2-745 | H1-221 | 3.1 | 36.4 | Red | 121 |
| Device Example 2 | H1-226 | H2-745 | H1-221 | 3.1 | 35.8 | Red | 184 |
| Device Example 3 | H1-227 | H2-746 | H1-228 | 3.0 | 34.5 | Red | 318 |
| Device Example 4 | H1-227 | H2-746 | H1-229 | 3.1 | 34.4 | Red | 210 |
| Device Example 5 | H1-227 | H2-746 | H1-226 | 3.0 | 34.1 | Red | 246 |
| Device Example 6 | H1-230 | H2-712 | H1-225 | 2.9 | 36.8 | Red | 260 |
| Device Example 7 | H1-230 | H2-712 | H1-231 | 3.1 | 36.4 | Red | 167 |
| Device Example 8 | H1-233 | H2-751 | H1-234 | 3.1 | 35.6 | Red | 140 |
| Device Example 9 | H1-232 | H2-146 | H1-235 | 3.2 | 36.5 | Red | 188 |
| Device Example 10 | H1-200 | H2-858 | H2-859 | 3.0 | 35.7 | Red | 164 |
| Device Example 11 | H1-234 | H2-746 | H2-860 | 3.0 | 36.5 | Red | 184 |
| Device Example 12 | H1-200 | H2-858 | H2-861 | 3.0 | 35.5 | Red | 190 |
| Device Example 13 | H1-21 | H2-864 | H2-332 | 2.9 | 31.3 | Red | 84 |
| Device Example 14 | H1-282 | H2-864 | H2-332 | 3.0 | 33.9 | Red | 196 |
| Device Example 15 | H1-227 | H2-746 | H1-185 | 3.1 | 34.5 | Red | 178 |

TABLE 1-continued

| | First Host | Second Host | Third Host | Driving Voltage M | Luminous Efficiency [cd/A] | Light-Emitting Color | Lifetime (T95) [hr] |
|---|---|---|---|---|---|---|---|
| Comparative Example 1 | H1-222 | — | — | 4.2 | 9.3 | Red | 4.2 |
| Comparative Example 2 | — | — | H1-221 | 3.8 | 7.5 | Red | 2.0 |
| Comparative Example 3 | — | H2-745 | | 3.5 | 28.8 | Red | 13.7 |
| Comparative Example 4 | H1-226 | — | — | 3.7 | 10.2 | Red | 1.6 |
| Comparative Example 5 | H1-227 | — | — | 4.1 | 9.6 | Red | 4.3 |
| Comparative Example 6 | — | — | H1-228 | 3.8 | 10.3 | Red | 2.4 |
| Comparative Example 7 | — | — | H1-229 | 4.5 | 8.1 | Red | 6.2 |
| Comparative Example 8 | — | H2-746 | — | 3.0 | 24.6 | Red | 15.3 |
| Comparative Example 9 | — | H2-747 | — | 3.1 | 24.6 | Red | 8.1 |
| Comparative Example 10 | H1-230 | — | — | 4.3 | 6.5 | Red | 2.0 |
| Comparative Example 11 | — | — | H1-225 | 3.7 | 9.5 | Red | 3.3 |
| Comparative Example 12 | — | — | H1-231 | 4.7 | 8.0 | Red | 2.0 |
| Comparative Example 13 | — | H2-712 | — | 3.6 | 30.4 | Red | 11.3 |
| Comparative Example 14 | H1-232 | — | — | 4.3 | 7.8 | Red | 2.3 |
| Comparative Example 15 | — | H2-751 | — | 3.6 | 29.4 | Red | 9.9 |
| Comparative Example 16 | — | H2-146 | — | 3.5 | 31.8 | Red | 17.5 |
| Comparative Example 17 | — | — | H1-234 | 4.3 | 7.4 | Red | 3.4 |
| Comparative Example 18 | — | H2-858 | — | 3.7 | 3.7 | Red | 30 |
| Comparative Example 19 | — | H2-860 | — | 3.5 | 31.5 | Red | 23 |
| Comparative Example 20 | — | H2-859 | — | 3.2 | 30.1 | Red | 6 |
| Comparative Example 21 | — | H2-861 | — | 3.2 | 29.0 | Red | 0 |
| Comparative Example 22 | — | H2-863 | — | 3.6 | 29.9 | Red | 24 |
| Comparative Example 23 | H1-21 | — | — | 6.1 | 3.3 | Red | 1.7 |
| Comparative Example 24 | H1-282 | — | — | 4.3 | 7.8 | Red | 7.2 |
| Comparative Example 25 | — | H2-864 | — | 3.7 | 28.0 | Red | 9.0 |
| Comparative Example 26 | — | — | H2-332 | 3.1 | 26.6 | Red | 6.7 |
| Comparative Example 27 | — | — | H1-185 | 4.4 | 9.2 | Red | 8.3 |

From Table r above, it can be confirmed that the OLED comprising the compound according to the present disclosure as the three types of host materials exhibits lower driving voltage and/or higher luminous efficiency, in particular, significantly improved lifetime properties, compared to the conventional OLED using a single host material (Comparative Examples 1 to 27).

FIG. 1 illustrates a graph showing luminous properties according to wavelengths of the host material of the combination of three host compounds according to Device Example 1, and the host material according to Comparative Examples 1 to 3. The wavelength values corresponding to PL max are described in Table 2 below.

TABLE 2

| | Host | PL max |
|---|---|---|
| Comparative Example 1 | H1-222 | 450 |
| Comparative Example 2 | H1-221 | 456 |
| Comparative Example 3 | H2-745 | 461 |
| Device Example 1 | H1-222:H2-745:H1-221 (2.5:5.0:2.5, wt %) | 513 |

With Reference to the results of FIG. 1 and Table 2, it can be seen that the combination of the organic compounds according to Device Example 1 exhibits relatively long wavelength properties compared to the organic materials according to Comparative Examples 1 to 3, which is evidence of the formation of an exciplex of the organic light-emitting material. In addition, it can be confirmed that a PL peak in a new wavelength band is formed due to a combination of three types of hosts.

That is, without being limited by theory, the three types of host materials comprising a specific combination of the compounds of the present disclosure can facilitate the control of the energy level and mobility of the phosphorescent host material to improve the charge balance in the light-emitting layer, and thereby an organic electroluminescent device having high luminous efficiency and/or improved lifetime properties can be provided.

The compounds used in the Device Examples and the Comparative Examples are shown in Table 3 below.

TABLE 3

| | |
|---|---|
| Hole Injection Layer/ Hole Transport Layer | 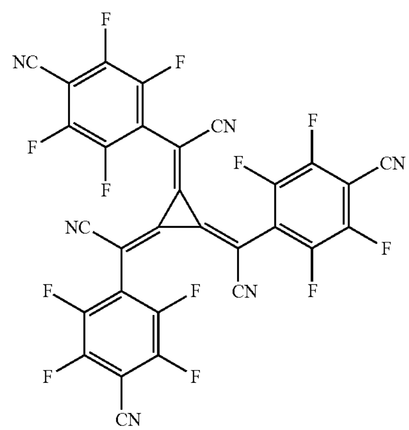 HI-1 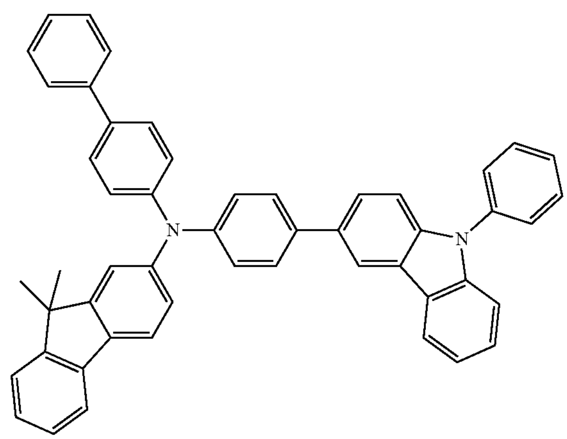 HT-1 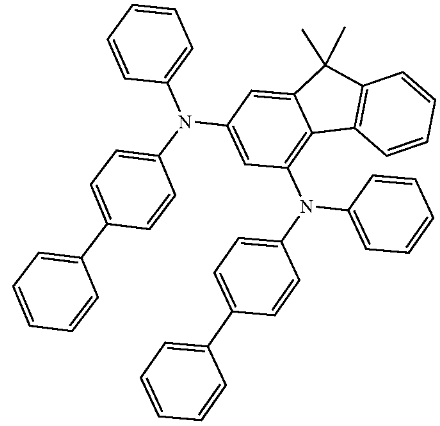 HT-2 |

TABLE 3-continued
Light Emitting Layer
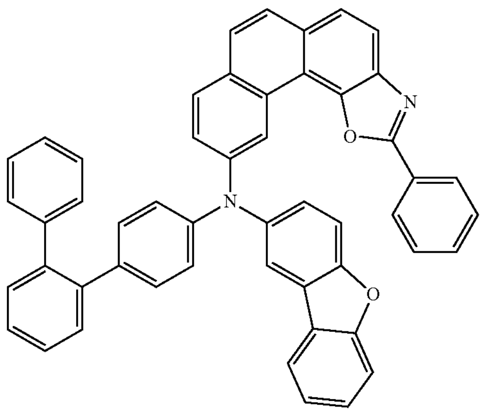
H1-221
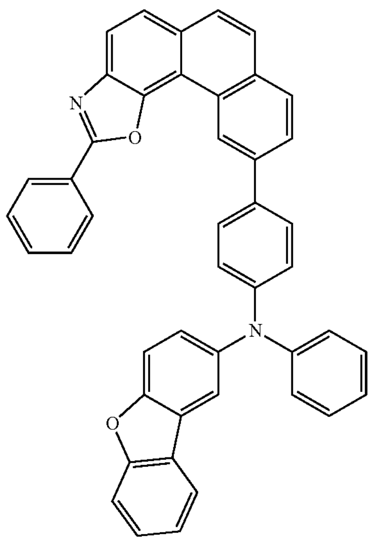
H1-222
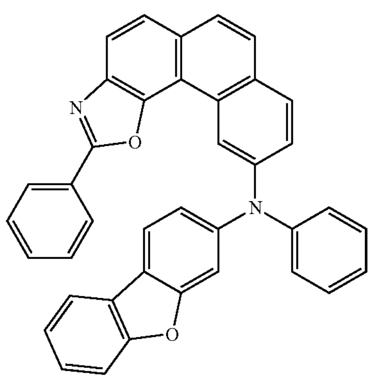
H1-225

TABLE 3-continued
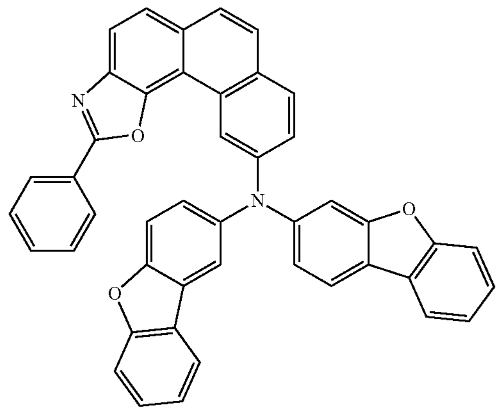
H1-226
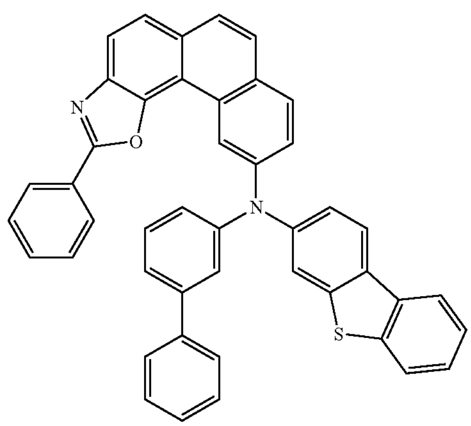
H1-227
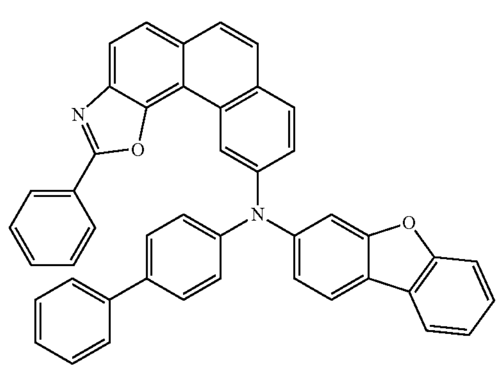
H1-228

TABLE 3-continued
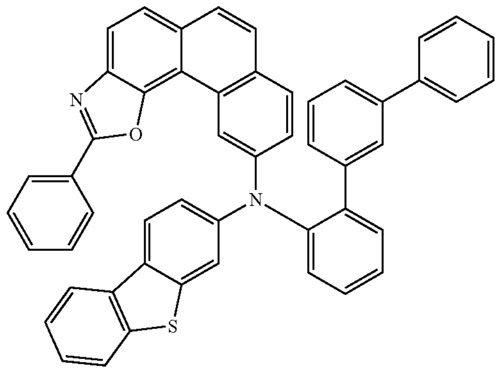
H1-229
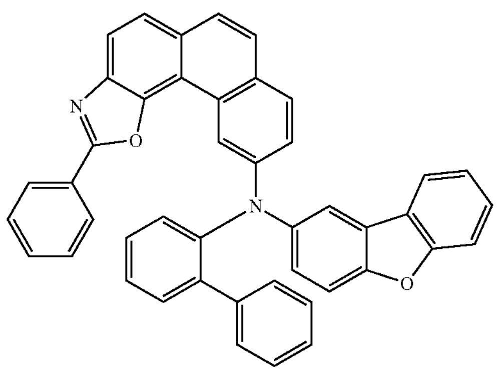
H1-230
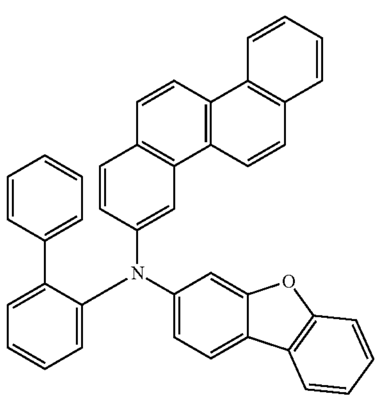
H1-231

TABLE 3-continued
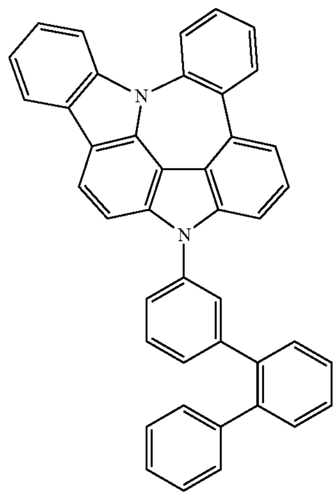
H1-282
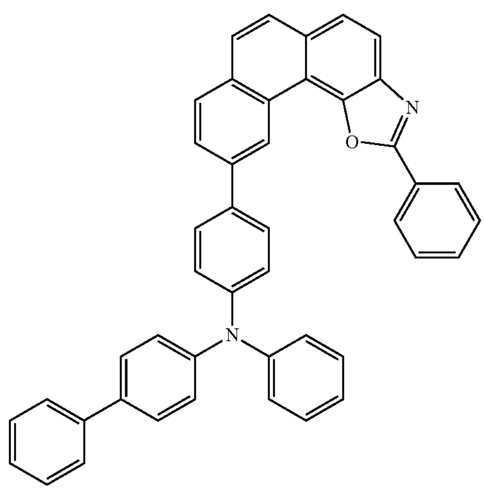
H1-185
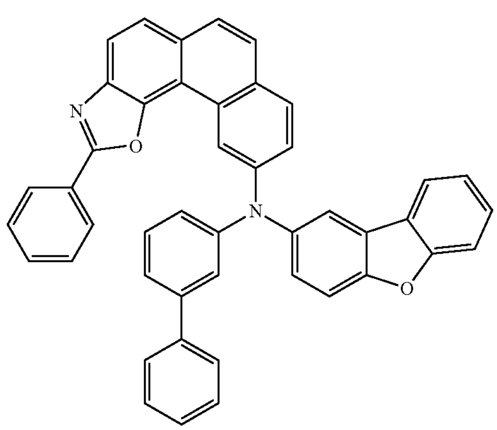
H1-232

TABLE 3-continued
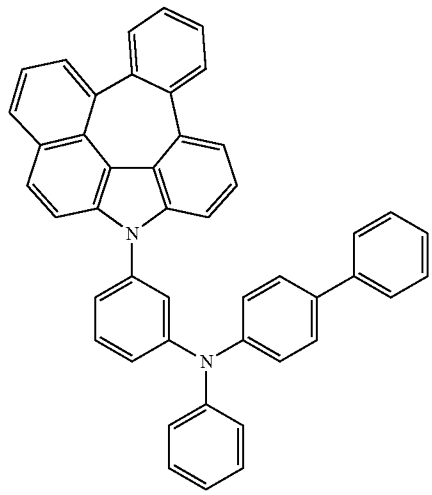
H1-233
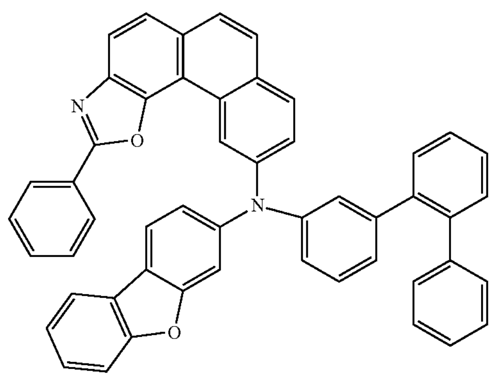
H1-234
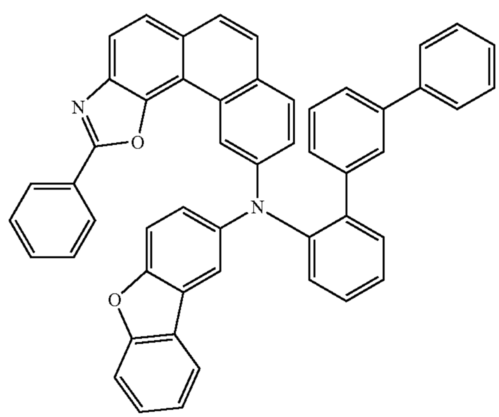
H1-235

TABLE 3-continued
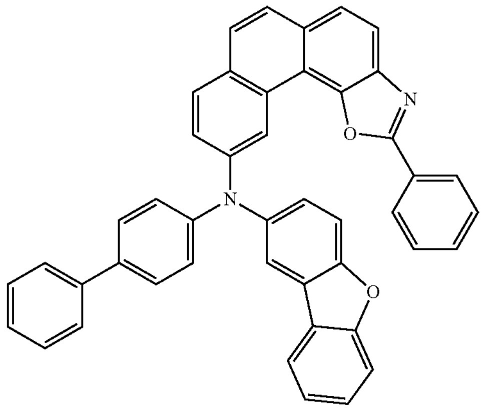
H1-200
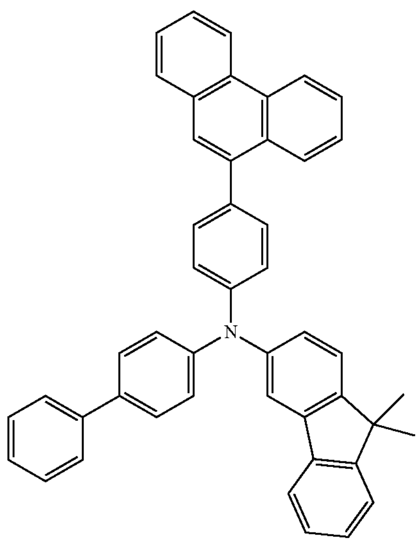
H1-21
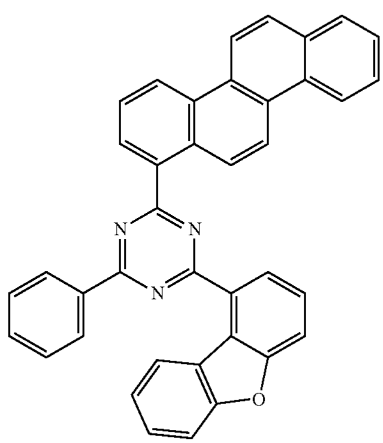
H2-146

TABLE 3-continued
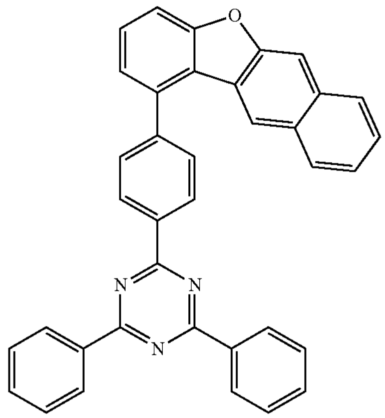
H2-712
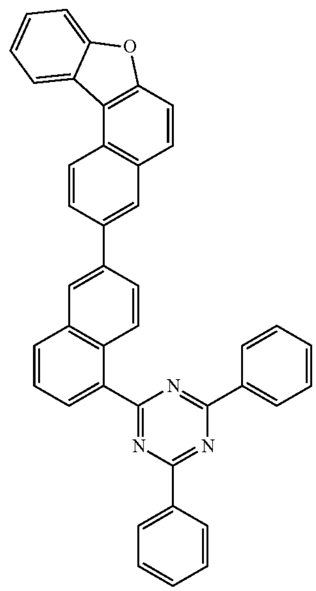
H2-745
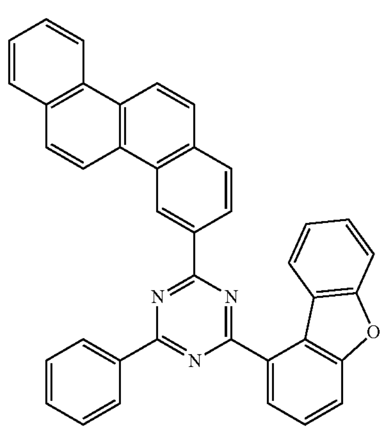
H2-858

TABLE 3-continued
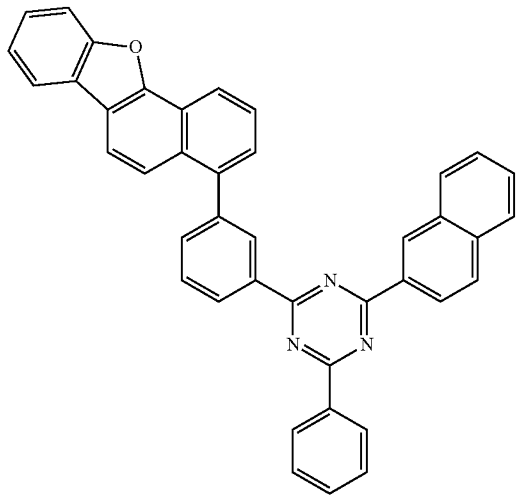
H2-859
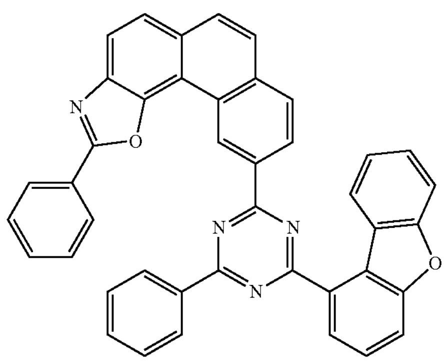
H2-860
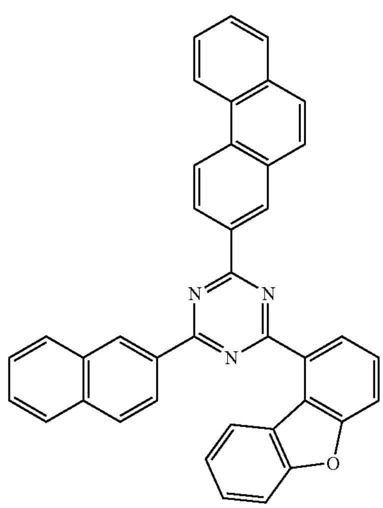
H2-861

TABLE 3-continued
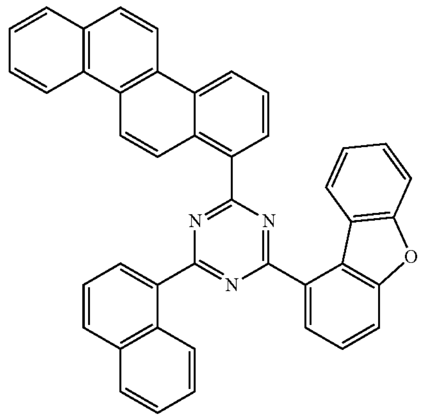
H2-862
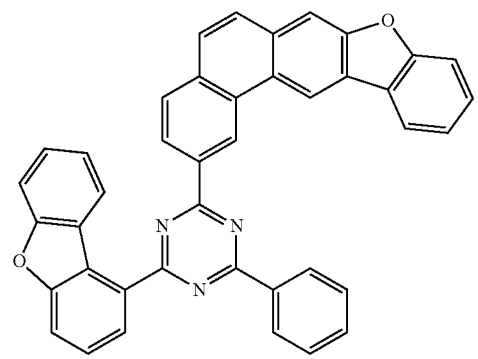
H2-863
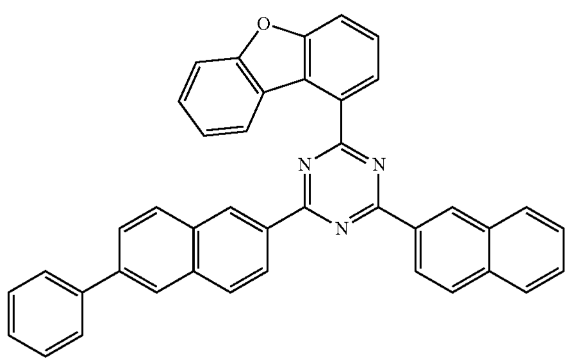
H2-746

TABLE 3-continued
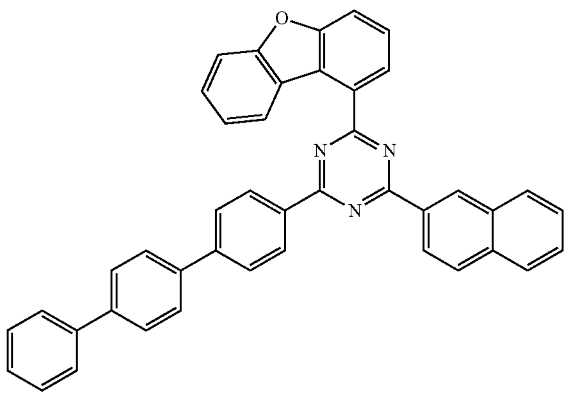
H2-747
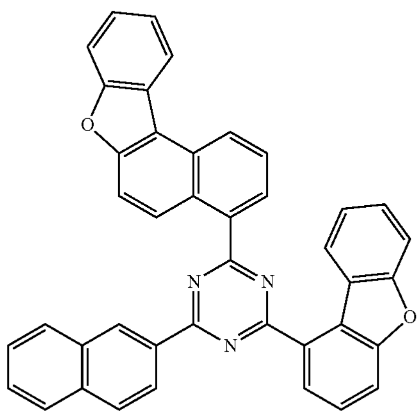
H2-751
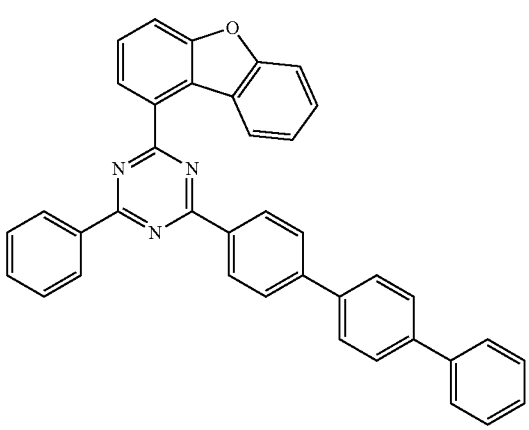
H2-864

TABLE 3-continued

| | |
|---|---|
| | 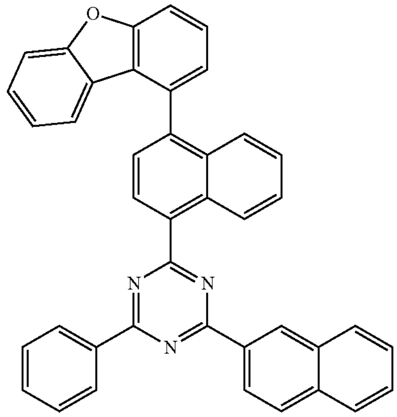 H2-332 |
| | 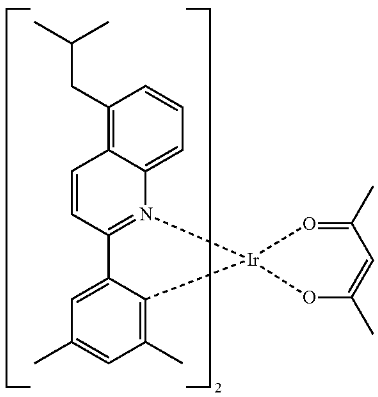 D-39 |
| Electron Transport Layer/ Electron Injection Layer | 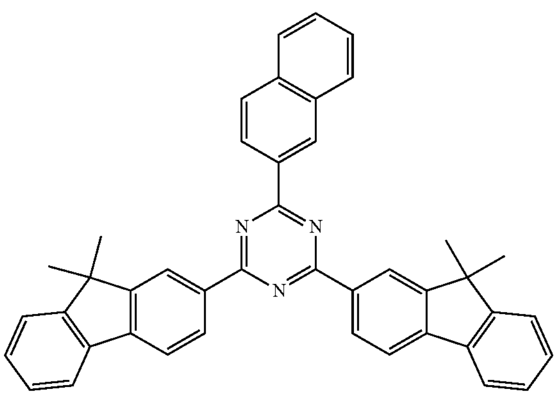 ETL-1 |
| | 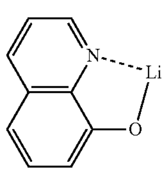 EIL-1 |

The invention claimed is:

1. A plurality of host materials comprising a first host material, a second host material, and a third host material, wherein each of the first host material, the second host material, and the third host material does not comprise a carbazole or fused carbazole structure, and the first host material, the second host material, and the third host material are different from each other; wherein the first host material comprises a compound represented by the following formula 1, the second host material comprises a compound represented by any one of the following formulas 2 to 4, and the third host material comprises a compound represented by any one of the following formulas 1 to 4, wherein the third host material is different from the first host material and the second host material:

$$T\text{-}L_1\text{-}Ar_1 \quad (1)$$

in formula 1,

T represents any one selected from the group consisting of the following formulas 1-1 to 1-5:

(1-1)

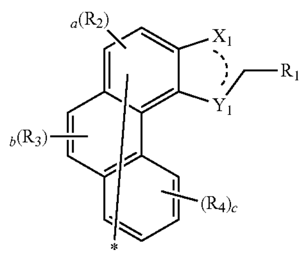

(1-2)

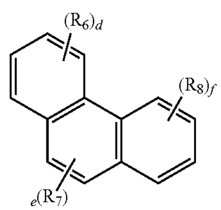

(1-3)

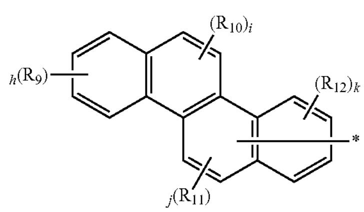

(1-4)

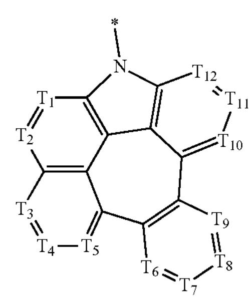

(1-5)

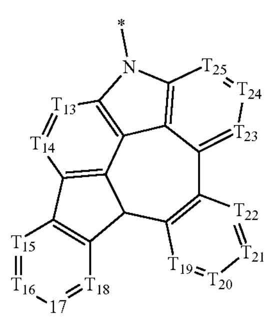

wherein, $X_1$ and $Y_1$, each independently, represent-N=, —$NR_5$-, —O—, or —S—, with the proviso that any one of $X_1$ and $Y_1$ represents-N=, and the other of $X_1$ and $Y_1$ represents —$NR_5$-, —O—, or —S—;

$R_1$ represents a substituted or unsubstituted (C6-C30)aryl, or a substituted or unsubstituted (3- to 30-membered) heteroaryl;

$R_2$ to $R_5$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C6-C30) aryl(3- to 30-membered)heteroarylamino, or a substituted or unsubstituted (C1-C30)alkyl(C6-C30) arylamino; or may be linked to an adjacent substituent (s) to form a ring(s);

a and b, each independently, represent 1 or 2; c represents an integer of 1 to 4; where if each of a to c is an integer of 2 or more, each of $R_2$ to each of $R_4$ may be the same or different;

$R_6$ to $R_{12}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

$T_1$ to $T_{25}$, each independently, represent N or $CV_1$;

$V_1$, each independently, represents hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30)

cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)aryldiyl, a substituted or unsubstituted mono- or di-(C1-C30)alkylamino, a substituted or unsubstituted mono- or di-(C2-C30)alkenylamino, a substituted or unsubstituted (C1-C30) alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, or a substituted or unsubstituted (C6-C30)aryl(3- to 30-membered)heteroarylamino; or may be linked to an adjacent substituent(s) to form a ring(s);

d, f, h, and k, each independently, represent an integer of 1 to 4; e, i, and i, each independently, represent an integer of 1 or 2; where if each of d to f and h to k is an integer of 2 or more, each of $R_6$ to each of $R_{11}$ may be the same or different;

$Ar_1$ represents a substituted or unsubstituted (C6-C30) aryl, a substituted or unsubstituted (3- to 30-membered) heteroaryl, or

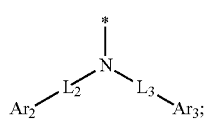

$Ar_2$ and $Ar_3$, each independently, represent a substituted or unsubstituted (C6-C30)aryl, a substituted or unsubstituted (3- to 30-membered)heteroaryl, or a substituted or unsubstituted (C3-C30)cycloalkyl; and $L_1$ to $L_3$, each independently, represent a single bond, a substituted or unsubstituted (C6-C30)arylene, or a substituted or unsubstituted (3- to 30-membered)heteroarylene;

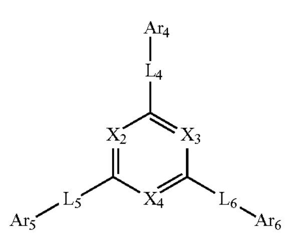

(2)

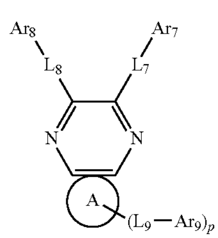

(3)

-continued

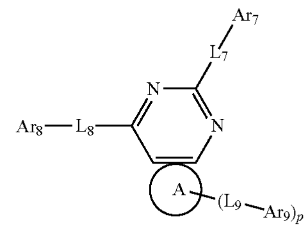

(4)

in formulas 2 to 4, $X_2$ to $X_4$, each independently, represent $CR_{13}$ or N, with the proviso that at least one of $X_2$ to $X_4$ represents N;

$R_{13}$, each independently, represents hydrogen, deuterium, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30) aryl, or a substituted or unsubstituted (3-to 30-membered)heteroaryl; or may be linked to an adjacent substituent(s) to form a ring(s);

$L_4$ to $L_9$, each independently, represent a single bond, a substituted or unsubstituted (C6-C30)arylene, or a substituted or unsubstituted (3- to 30-membered)heteroarylene;

ring A represents a benzene ring or a naphthalene ring;

$Ar_4$ to $Ar_9$, each independently, represent a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi (C6-C30)arylsilyl, or a substituted or unsubstituted tri(C6-C30)arylsilyl; or may be linked to an adjacent substituent(s) to form a ring(s); and p represents an integer of 0 to 6; where if p is an integer of 2 or more, each of $L_9$ and each of $Ar_9$ may be the same or different; and wherein the maximum emission wavelength of the plurality of host materials is shifted by at least 20 nm from the maximum emission wavelength of each of the first host material, the second host material, and the third host material.

2. The plurality of host materials according to claim 1, wherein the substituent(s) of the substituted (C1-C30)alkyl, the substituted (C3-C30)cycloalkyl, the substituted (3- to 7-membered)heterocycloalkyl, the substituted fused ring group, the substituted (C6-C30)aryl, the substituted (C6-C30)arylene, the substituted (3- to 30-membered)heteroaryl, the substituted (3- to 30-membered)heteroarylene, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C2-C30)alkenylamino, the substituted (C1-C30)alkyl(C2-C30) alkenylamino, the substituted mono- or di-(C6-C30) arylamino, the substituted (C1-C30)alkyl(C6-C30)

arylamino, the substituted mono- or di-(3- to 30-membered) heteroarylamino, the substituted (C1-C30)alkyl(3- to 30-membered)heteroarylamino, the substituted (C2-C30) alkenyl(C6-C30)arylamino, the substituted (C2-C30)alkenyl(3- to 30-membered)heteroarylamino, and the substituted (C6-C30)aryl(3- to 30-membered)heteroarylamino, each independently, are at least one selected from the group consisting of deuterium; a halogen; a cyano; a carboxyl; a nitro; a hydroxyl; a phosphine oxide; a (C1-C30)alkyl; a halo(C1-C30)alkyl; a (C2-C30)alkenyl unsubstituted or substituted with a (C6-C30)aryl(s); a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30)alkyl(s) and a (3- to 30-membered)heteroaryl(s); a tri(C1-C30)alkylsilyl; a tri (C6-C30)arylsilyl; a di(C1-C30)alkyl(C6-C30)arylsilyl; a (C1-C30)alkyldi(C6-C30)arylsilyl; a fused ring group of a (C3-C30) aliphatic ring(s) and a (C6-C30) aromatic ring(s); an amino; a mono- or di-(C1-C30)alkylamino; a mono- or di-(C2-C30)alkenylamino; a mono- or di-(C6-C30)arylamino unsubstituted or substituted with a (C1-C30)alkyl(s); a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30) arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The plurality of host materials according to claim 1, wherein the formula 1 is represented by any one of the following formulas 1-11 to 1-16:

(1-11)

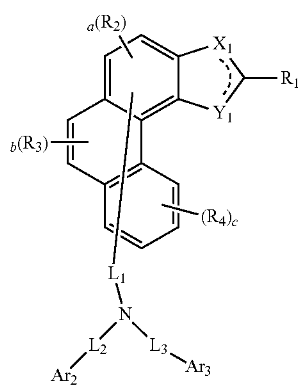

(1-12)

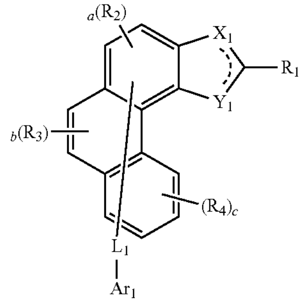

-continued (1-13)

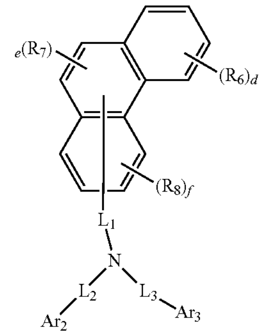

(1-14)

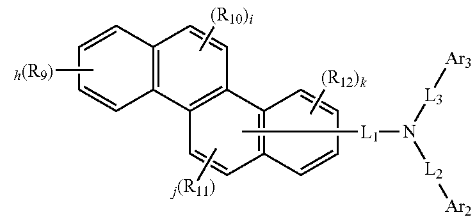

(1-15)

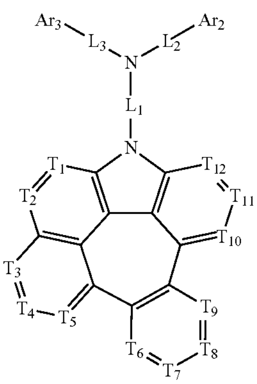

(1-16)

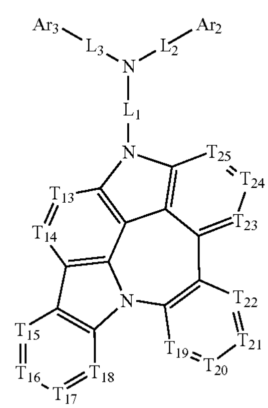

in formulas 1-11 to 1-16, $Ar_1$ represents a substituted or unsubstituted (C6-C30) aryl, or a substituted or unsubstituted (3- to 30-membered)heteroaryl; and $X_1$, $Y_1$, $R_1$ to $R_4$, $R_6$ to $R_{12}$, $T_1$ to $T_{25}$, $L_1$ to $L_3$, $Ar_2$, $Ar_3$, a to f, and h to k are as defined in claim 1.

4. The plurality of host materials according to claim 1, wherein in formulas 2 to 4, at least one of $Ar_4$ to $Ar_9$ is selected from the group consisting of the following formulas a-1 to a-7:

(a-1)

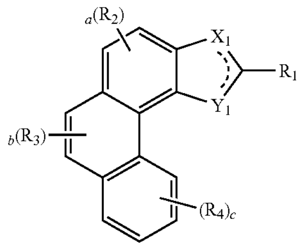

(a-2)

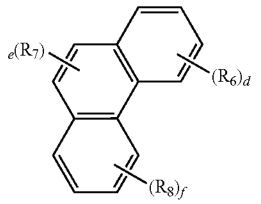

(a-3)

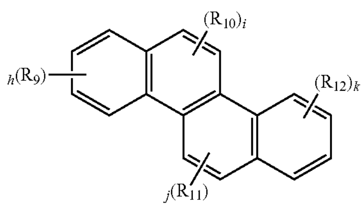

(a-4)

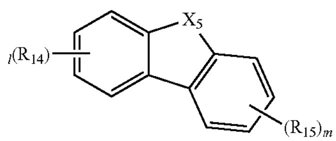

(a-5)

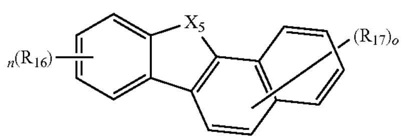

(a-6)

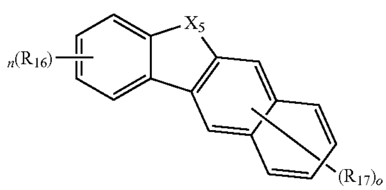

(a-7)

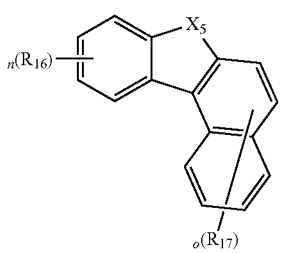

in formulas a-1 to a-7, $X_5$, each independently, represents O, S, or $CR_{18}R_{19}$;

$R_{18}$ and $R_{19}$, each independently, represent a substituted or unsubstituted (C1-C30)alkyl, a substituted or unsubstituted (C3-C30)cycloalkyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl; or $R_{18}$ and $R_{19}$ may be linked to each other to form a spiro ring;

$R_{14}$ and $R_{15}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

l to n, each independently, represent an integer of 1 to 4; o represents an integer of 1 to 6; where if each of I to o is an integer of 2 or more, each of $R_{14}$ to each of $R_{17}$ may be the same or different;

$R_6$ to $R_8$, $R_{16}$, and $R_{17}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi (C6-C30)arylsilyl, a substituted or unsubstituted tri (C6-C30)arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30) arylamino, a substituted or unsubstituted (C1-C30) alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to an adjacent substituent(s) to form a ring(s); and $X_1$, $Y_1$, $R_1$ to $R_4$, $R_9$ to $R_{12}$, a to f, and h to k are as defined in claim 1.

5. The plurality of host materials according to claim 1, wherein any two of the first host material, the second host material and the third host material have a difference in deposition temperature of between 0° C. and 20° C. at $10^{-3}$ torr or less.

6. A plurality of host materials comprising a first host material, a second host material, and a third host material, wherein each of the first host material, the second host material, and the third host material does not comprise a carbazole or fused carbazole structure, and the first host material, the second host material, and the third host material are different from each other; wherein the first host material comprises a compound represented by the following formula 1, the second host material comprises a compound represented by any one of the following formulas 2 to 4, and the third host material comprises a compound represented by any one of the following formulas 1 to 4, wherein the third host material is different from the first host material and the second host material:

$$T\text{-}L_1\text{-}Ar_1 \quad (1)$$

in formula 1,

T represents any one selected from the group consisting of the following formulas 1-1 to 1-5:

(1-1)

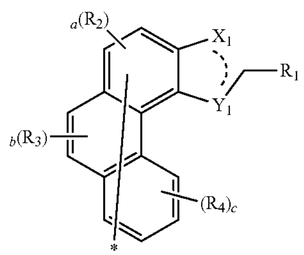

(1-2)

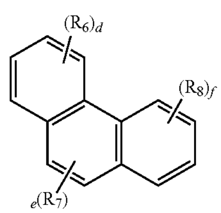

(1-3)

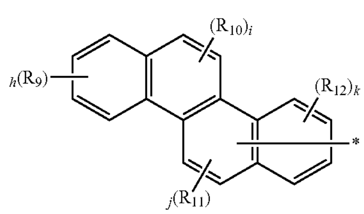

(1-4)

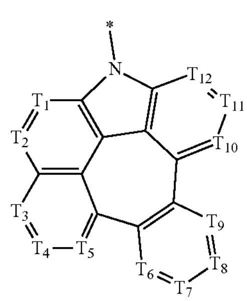

-continued (1-5)

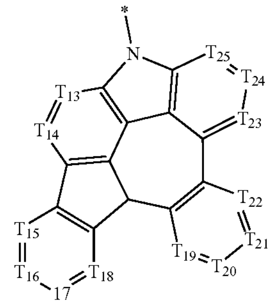

wherein, $X_1$ and $Y_1$, each independently, represent-N=, —$NR_5$-, —O—, or —S—, with the proviso that any one of $X_1$ and $Y_1$ represents-N=, and the other of $X_1$ and $Y_1$ represents —$NR_5$-, —O—, or —S—;

$R_1$ represents a substituted or unsubstituted (C6-C30)aryl, or a substituted or unsubstituted (3- to 30-membered) heteroaryl;

$R_2$ to $R_5$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C6-C30) aryl(3- to 30-membered)heteroarylamino, or a substituted or unsubstituted (C1-C30)alkyl(C6-C30) arylamino; or may be linked to an adjacent substituent (s) to form a ring(s);

a and b, each independently, represent 1 or 2; c represents an integer of 1 to 4; where if each of a to c is an integer of 2 or more, each of $R_2$ to each of $R_4$ may be the same or different;

$R_6$ to $R_{12}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

$T_1$ to $T_{25}$, each independently, represent N or $CV_1$;

$V_1$, each independently, represents hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted (C1-C30) alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, or a substituted or unsubstituted (C6-C30)aryl(3- to 30-membered)heteroarylamino; or may be linked to an adjacent substituent(s) to form a ring(s);

d, f, h, and k, each independently, represent an integer of 1 to 4; e, i, and i, each independently, represent an integer of 1 or 2; where if each of d to f and h to k is an integer of 2 or more, each of $R_6$ to each of $R_{11}$ may be the same or different;

$Ar_1$ represents a substituted or unsubstituted (C6-C30) aryl, a substituted or unsubstituted (3- to 30-membered) heteroaryl, or (2)

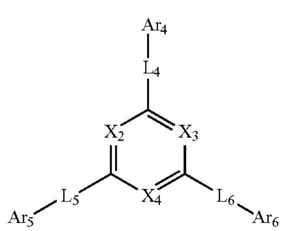

(3)

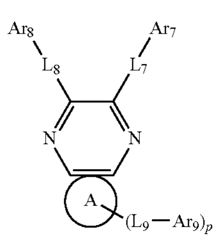

-continued (4)

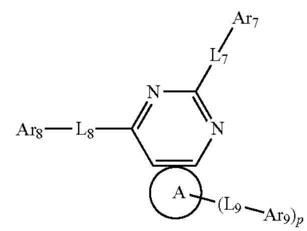

$Ar_2$ and $Ar_3$, each independently, represent a substituted or unsubstituted (C6-C30)aryl, a substituted or unsubstituted (3- to 30-membered)heteroaryl, or a substituted or unsubstituted (C3-C30)cycloalkyl; and $L_1$ to $L_3$, each independently, represent a single bond, a substituted or unsubstituted (C6-C30)arylene, or a substituted or unsubstituted (3- to 30-membered)heteroarylene;

(2)

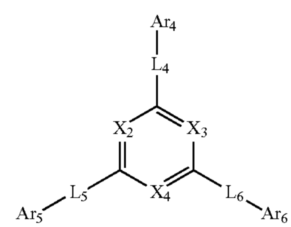

(3)

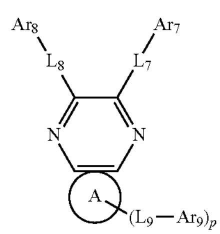

(4)

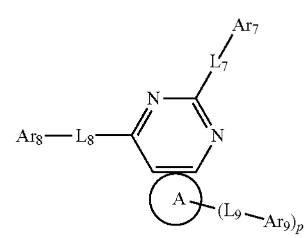

in formulas 2 to 4, $X_2$ to $X_4$, each independently, represent $CR_{13}$ or N, with the proviso that at least one of $X_2$ to $X_4$ represents N;

$R_{13}$, each independently, represents hydrogen, deuterium, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30) aryl, or a substituted or unsubstituted (3-to 30-membered)heteroaryl; or may be linked to an adjacent substituent(s) to form a ring(s);

$L_4$ to $L_9$, each independently, represent a single bond, a substituted or unsubstituted (C6-C30)arylene, or a substituted or unsubstituted (3- to 30-membered)heteroarylene;

ring A represents a benzene ring or a naphthalene ring;

$Ar_4$ to $Ar_9$, each independently, represent a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri(C6-C30)arylsilyl; or may be linked to an adjacent substituent(s) to form a ring(s); and p represents an integer of 0 to 6; where if p is an integer of 2 or more, each of $L_9$ and each of $Ar_9$ may be the same or different; and wherein each of the first host material and the third host material has stronger hole transport properties than the second host material; and the HOMO energy level of a light-emitting layer comprising the plurality of host materials satisfies the following Equation 1 or 2:

$$|A_{h1}-A_{h3}| \leq 0.5 \text{ eV} \quad \text{[Equation 1]}$$

$$|A_{h1}-A_{h3}| \leq 0.3 \text{ eV} \quad \text{[Equation 2]}$$

in Equations 1 and 2, $A_{h1}$ represents the HOMO energy level of the first host material, and $A_{h3}$ represents the HOMO energy level of the third host material.

7. A plurality of host materials comprising a first host material, a second host material, and a third host material, wherein each of the first host material, the second host material, and the third host material does not comprise a carbazole or fused carbazole structure, and the first host material, the second host material, and the third host material are different from each other; wherein the first host material comprises a compound represented by the following formula 1, the second host material comprises a compound represented by any one of the following formulas 2 to 4, and the third host material comprises a compound represented by any one of the following formulas 1 to 4, wherein the third host material is different from the first host material and the second host material:

$$T\text{-}L_1\text{-}Ar_1 \quad (1)$$

in formula 1,

T represents any one selected from the group consisting of the following formulas 1-1 to 1-5:

(1-1)

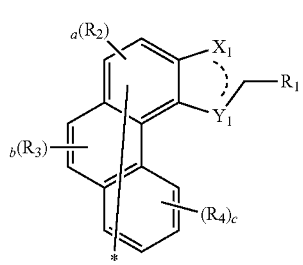

-continued (1-2)

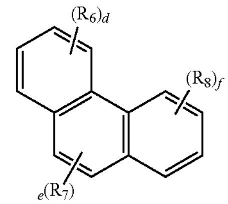

(1-3)

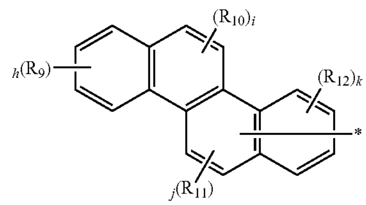

(1-4)

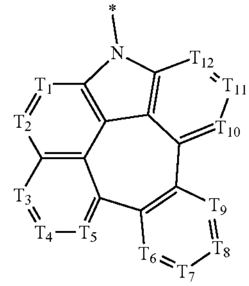

(1-5)

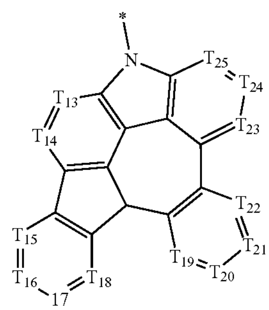

wherein, $X_1$ and $Y_1$, each independently, represent-N=, —$NR_5$-, —O—, or —S—, with the proviso that any one of $X_1$ and $Y_1$ represents-N=, and the other of $X_1$ and $Y_1$ represents —$NR_5$-, —O—, or —S—;

$R_1$ represents a substituted or unsubstituted (C6-C30)aryl, or a substituted or unsubstituted (3- to 30-membered) heteroaryl;

$R_2$ to $R_5$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C6-C30) aryl(3- to 30-membered)heteroarylamino, or a substituted or unsubstituted (C1-C30)alkyl(C6-C30) arylamino; or may be linked to an adjacent substituent (s) to form a ring(s);

a and b, each independently, represent 1 or 2; c represents an integer of 1 to 4; where if each of a to c is an integer of 2 or more, each of $R_2$ to each of $R_4$ may be the same or different;

$R_6$ to $R_{12}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

$T_1$ to $T_{25}$, each independently, represent N or $CV_1$;

$V_1$, each independently, represents hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted (C1-C30) alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, or a substituted or unsubstituted (C6-C30)aryl(3- to 30-membered)heteroarylamino; or may be linked to an adjacent substituent(s) to form a ring(s);

d, f, h, and k, each independently, represent an integer of 1 to 4; e, i, and i, each independently, represent an integer of 1 or 2; where if each of d to f and h to k is an integer of 2 or more, each of $R_6$ to each of $R_{11}$ may be the same or different;

$Ar_1$ represents a substituted or unsubstituted (C6-C30) aryl, a substituted or unsubstituted (3- to 30-membered) heteroaryl, or

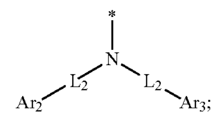

$Ar_2$ and $Ar_3$, each independently, represent a substituted or unsubstituted (C6-C30)aryl, a substituted or unsubstituted (3- to 30-membered)heteroaryl, or a substituted or unsubstituted (C3-C30)cycloalkyl; and $L_1$ to $L_3$, each independently, represent a single bond, a substituted or unsubstituted (C6-C30)arylene, or a substituted or unsubstituted (3- to 30-membered)heteroarylene;

(2)

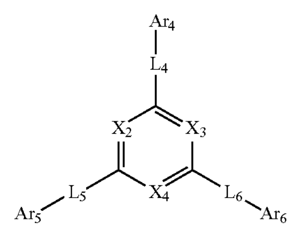

(3)

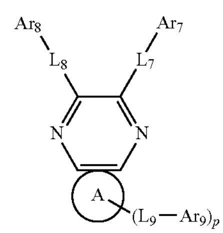

(4)

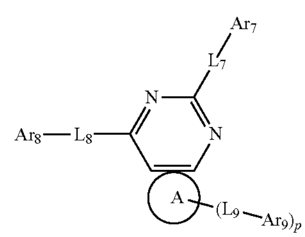

in formulas 2 to 4, $X_2$ to $X_4$, each independently, represent $CR_{13}$ or N, with the proviso that at least one of $X_2$ to $X_4$ represents N;

$R_{13}$, each independently, represents hydrogen, deuterium, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30) aryl, or a substituted or unsubstituted (3-to 30-membered)heteroaryl; or may be linked to an adjacent substituent(s) to form a ring(s);

$L_4$ to $L_9$, each independently, represent a single bond, a substituted or unsubstituted (C6-C30)arylene, or a substituted or unsubstituted (3- to 30-membered)heteroarylene;

ring A represents a benzene ring or a naphthalene ring;

$Ar_4$ to $Ar_9$, each independently, represent a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring group of a (C3-C30) aliphatic ring(s) and a (C6-C30) aromatic ring(s), a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri(C6-C30)arylsilyl; or may be linked to an adjacent substituent(s) to form a ring(s); and p represents an integer of 0 to 6; where if p is an integer of 2 or more, each of $L_9$ and each of $Ar_9$ may be the same or different; and wherein each of the second host material and the third host material has stronger electron transport properties than the first host material; and the LUMO energy level of a light-emitting layer comprising the plurality of host materials satisfies the following Equation 3 or 4:

$$|A_{l2}-A_{l3}| \leq 0.5\text{ eV} \quad \text{[Equation 3]}$$

$$|A_{l2}-A_{l3}| \leq 0.3\text{ eV} \quad \text{[Equation 4]}$$

in Equations 3 and 4, $A_{l2}$ represents the LUMO energy level of the second host material, and $A_{l3}$ represents the LUMO energy level of the third host material.

8. The plurality of host materials according to claim 1, wherein the plurality of host materials comprise 5 wt % to 70 wt % of the first host material, 5 wt % to 70 wt % of the second host material, and 10 wt % to 90 wt % of the third host material.

9. The plurality of host materials according to claim 1, wherein the compound represented by formula 1 is at least one selected from the group consisting of the following compounds:

H1-1

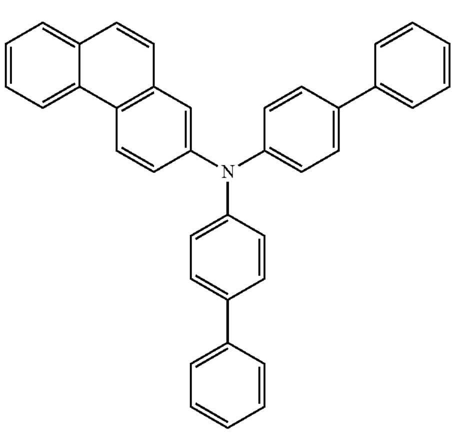

-continued

H1-2

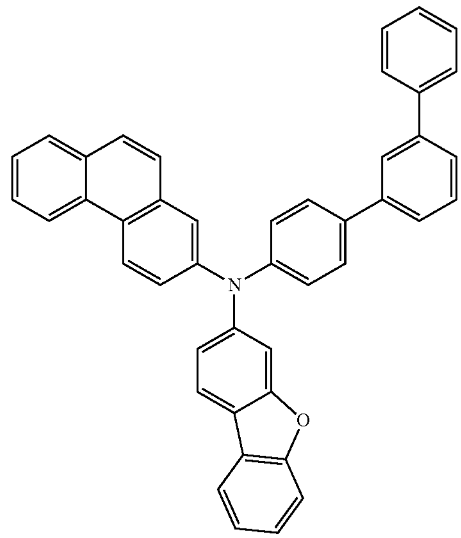

H1-3

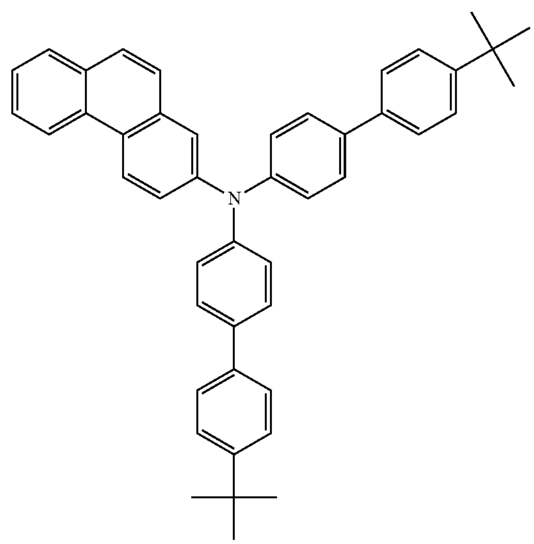

H1-4

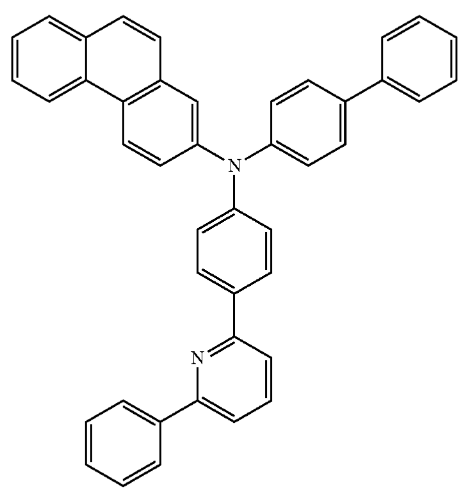

-continued
H1-5
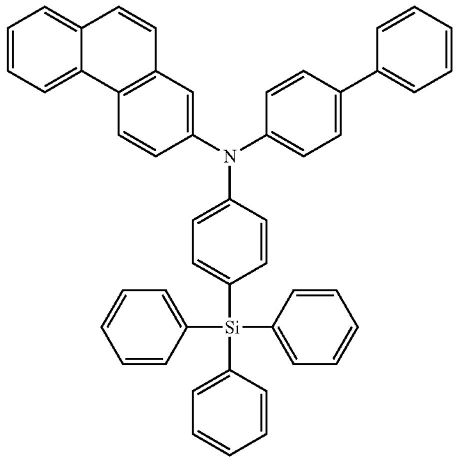
H1-6
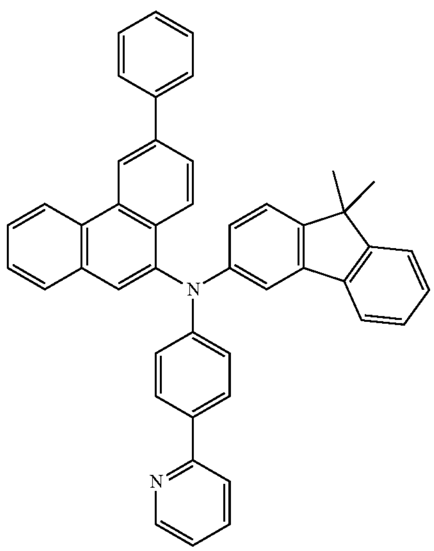
H1-7
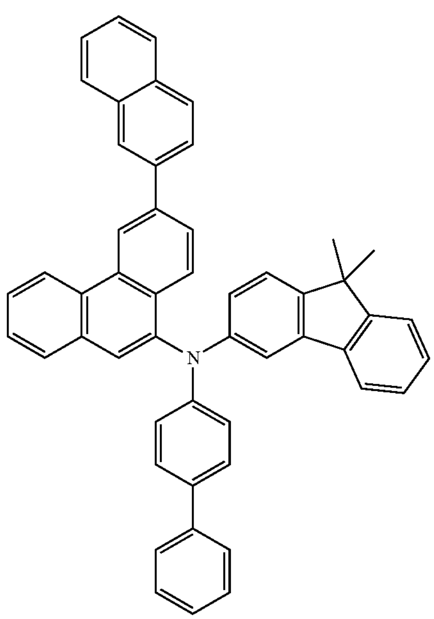
-continued
H1-8
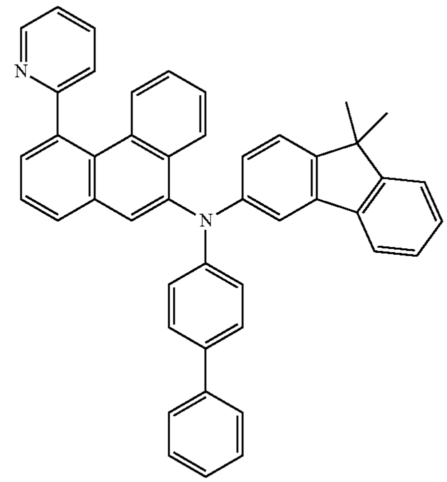
H1-9
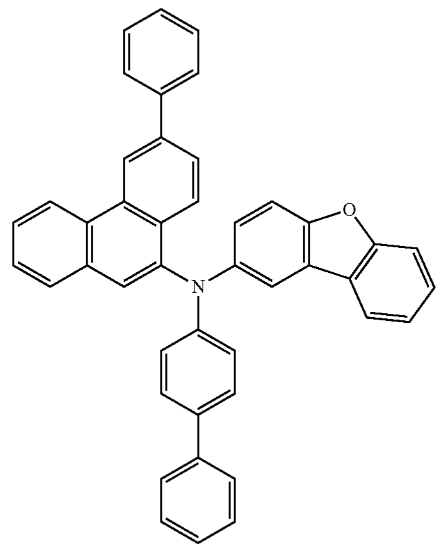
H1-10
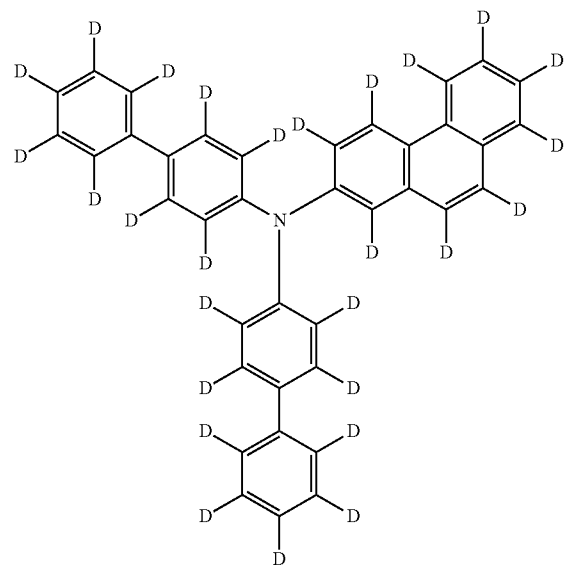

-continued
H1-11
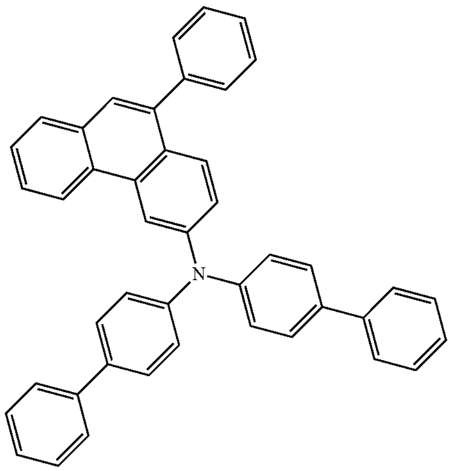
H1-12
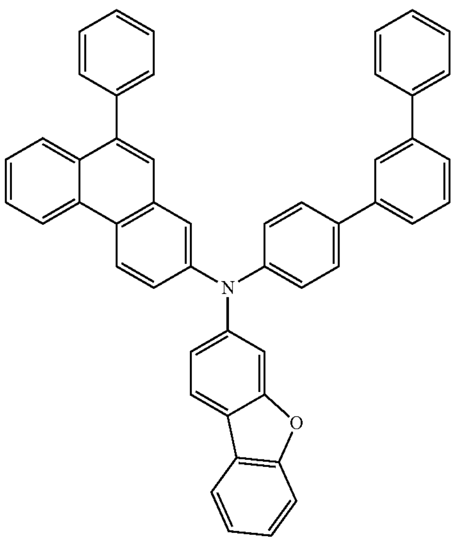
H1-13
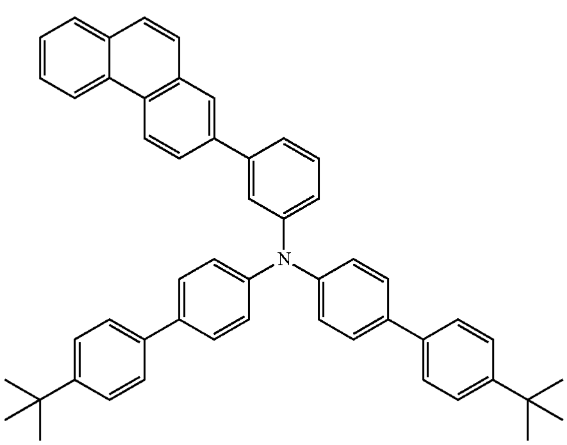
-continued
H1-14
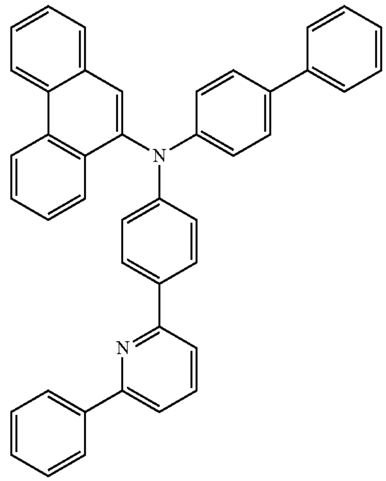
H1-15
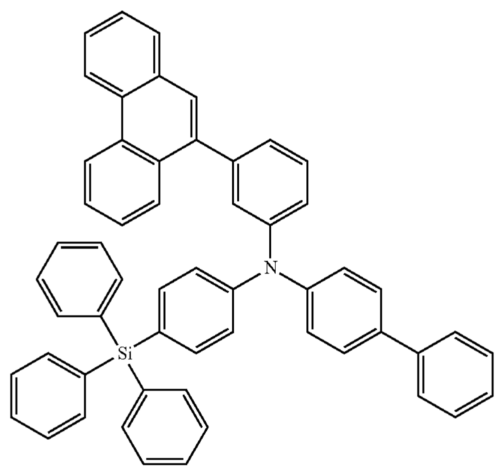
H1-16
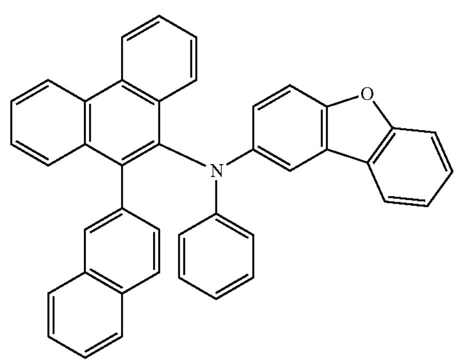

-continued
H1-17
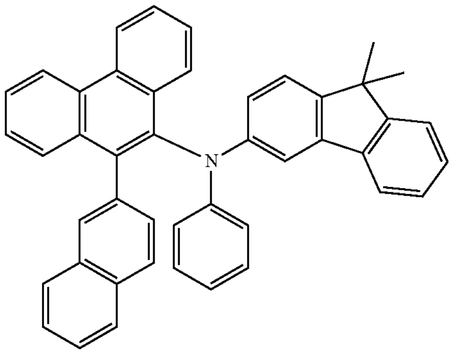
H1-18
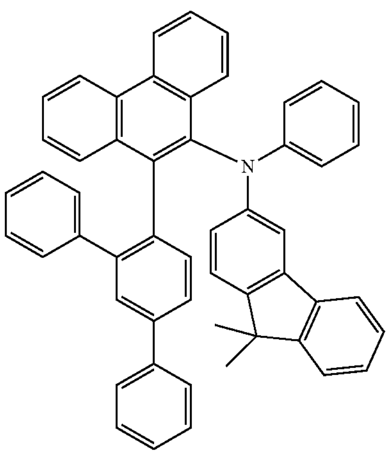
H1-19
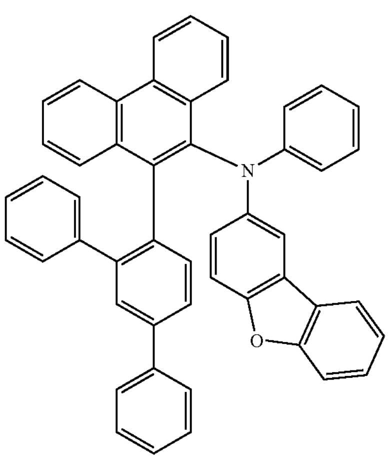
-continued
H1-20
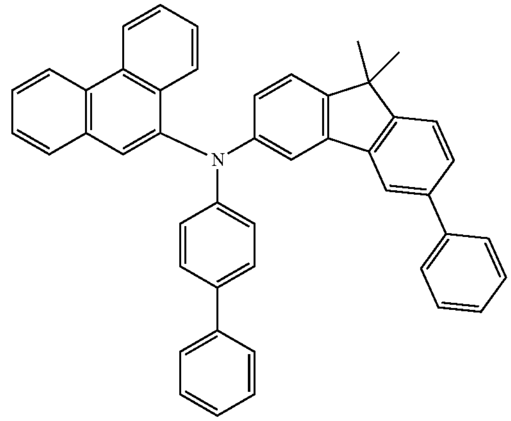
H1-21
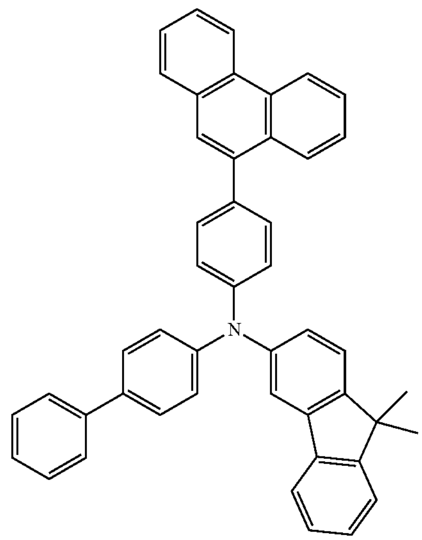
H1-22
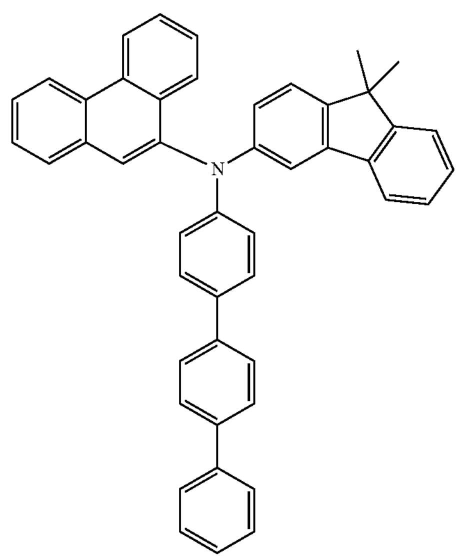

-continued
H1-23
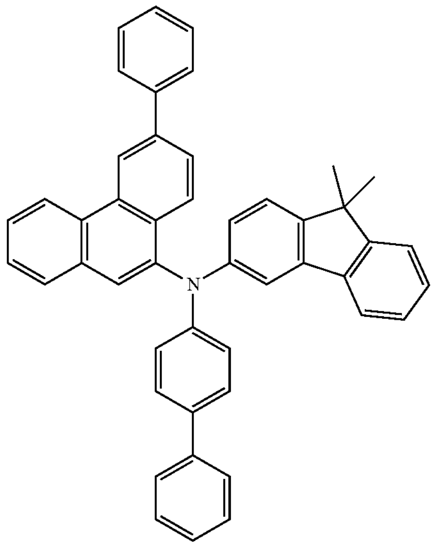
H1-24
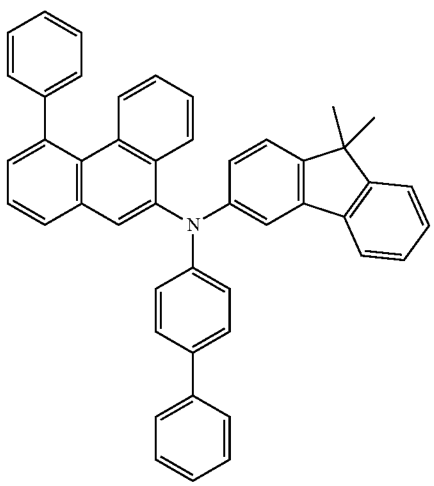
H1-25
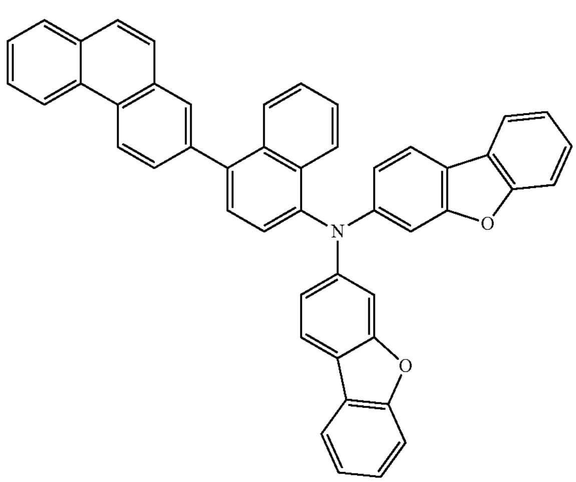
-continued
H1-26
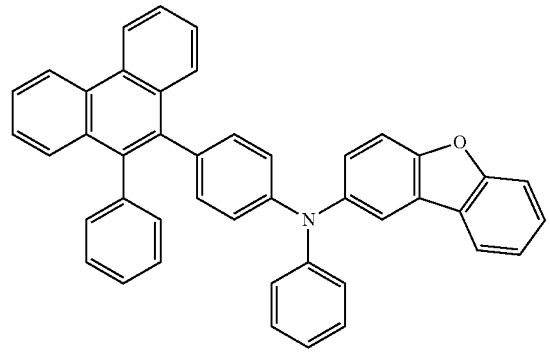
H1-27
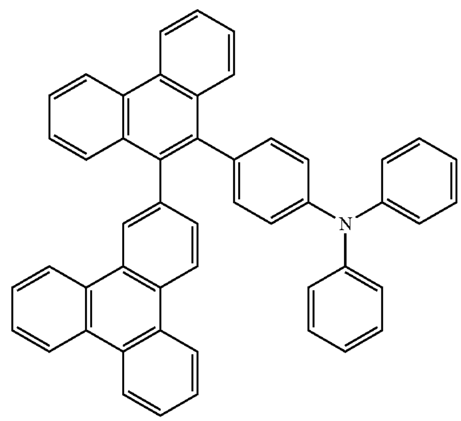
H1-28
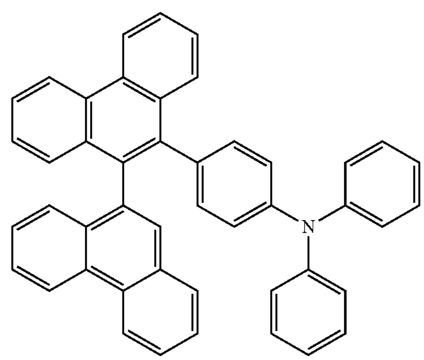
H1-29
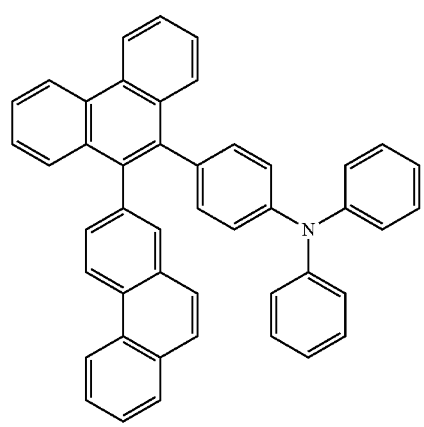

-continued
H1-30
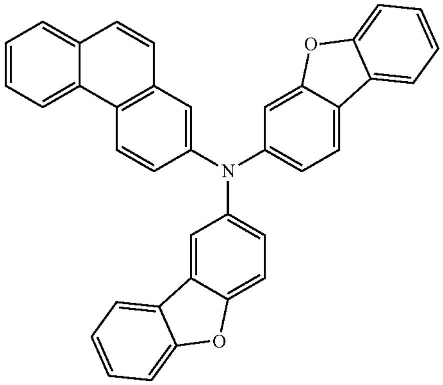
H1-31
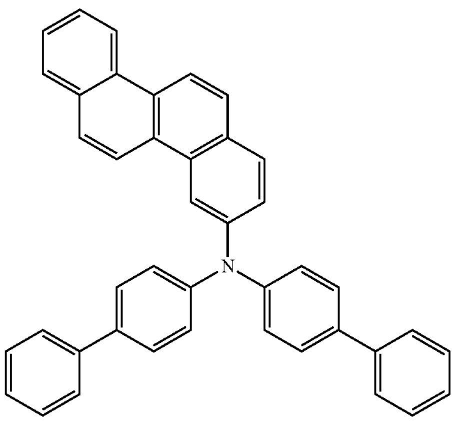
H1-32
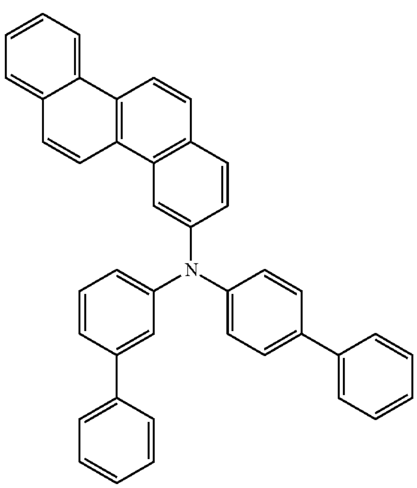
-continued
H1-33
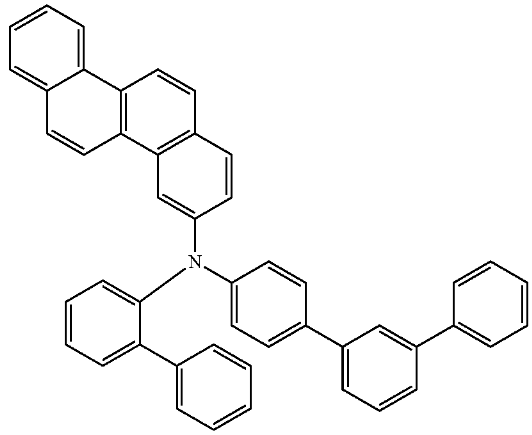
H1-34
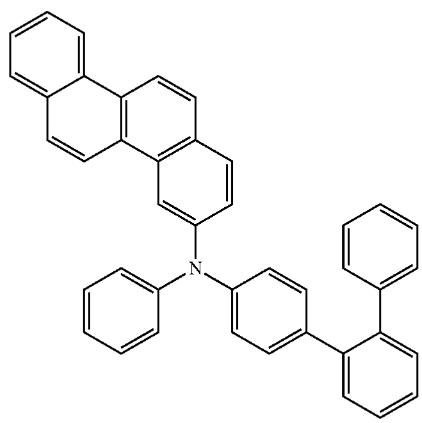
H1-35
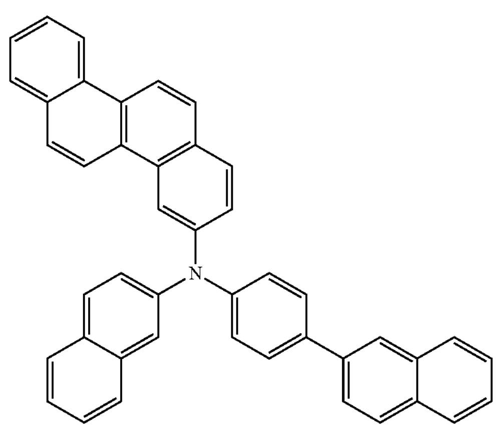

-continued
H1-36
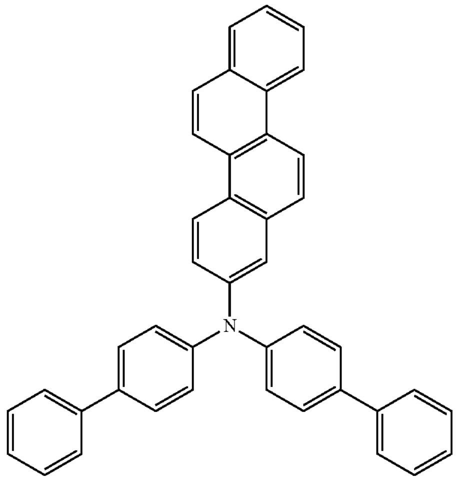
H1-37
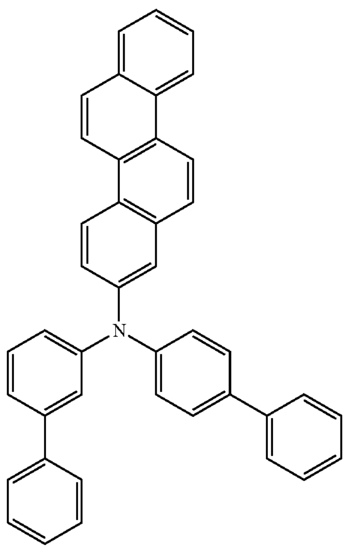
H1-38
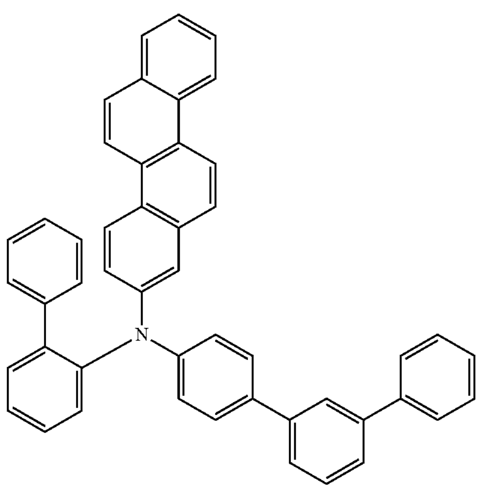
-continued
H1-39
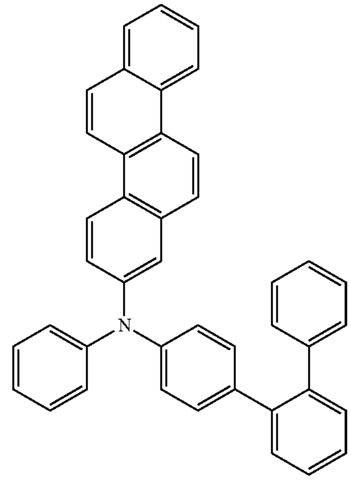
H1-40
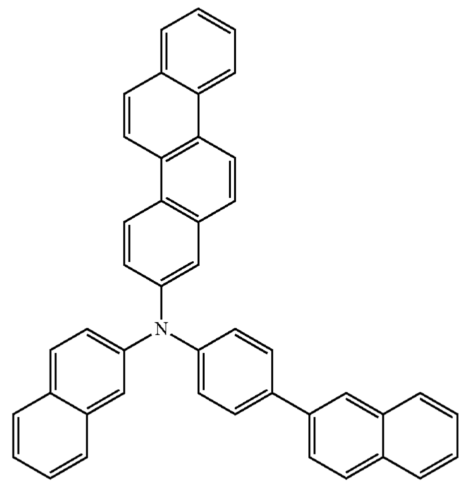
H1-41
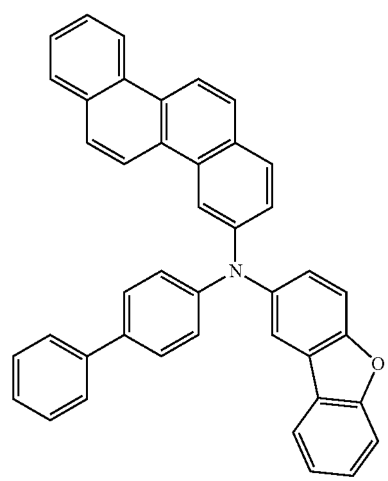

-continued
H1-42
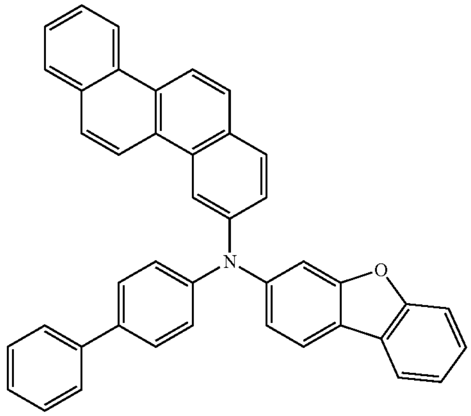
H1-43
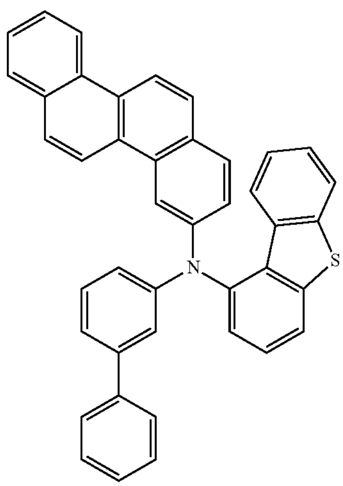
H1-44
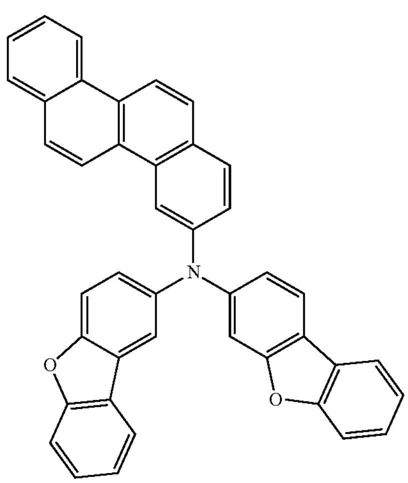
-continued
H1-45
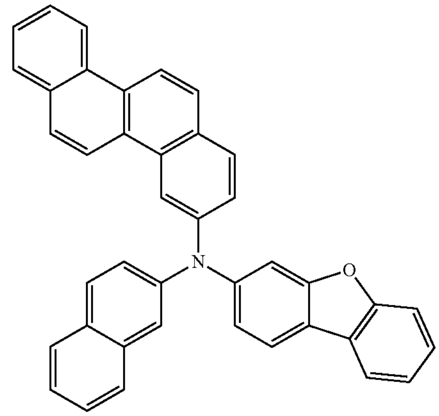
H1-46
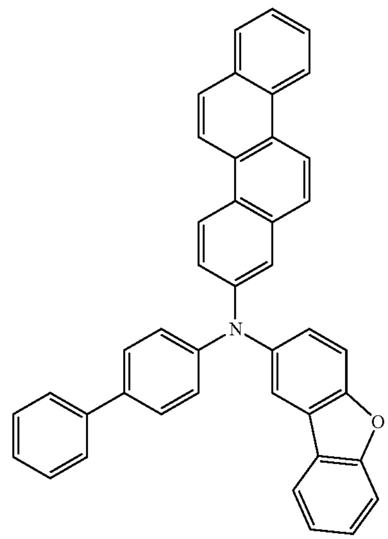
H1-47
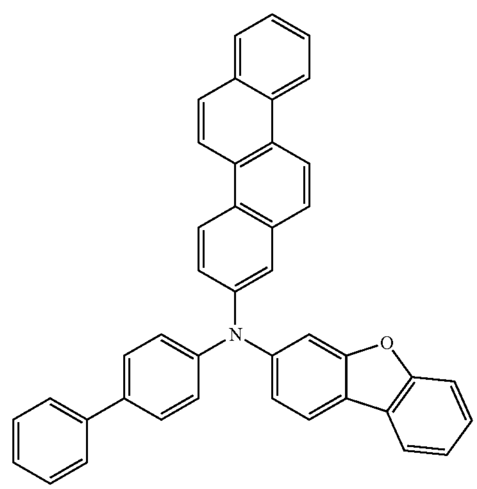

-continued
H1-48
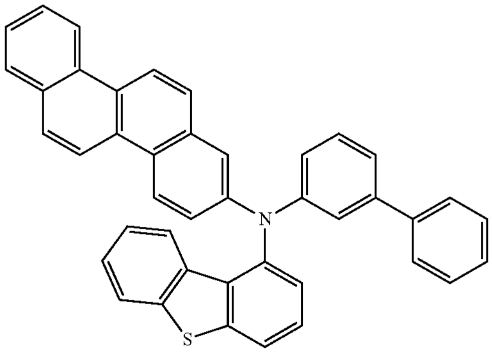
H1-49
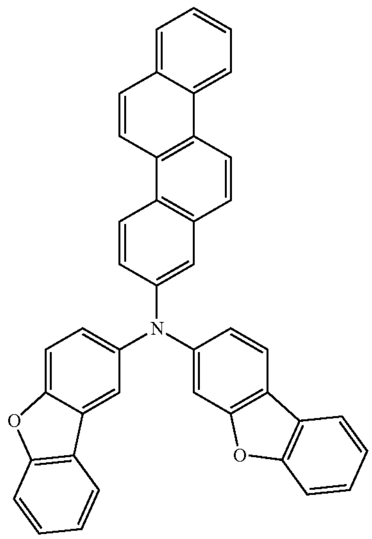
H1-50
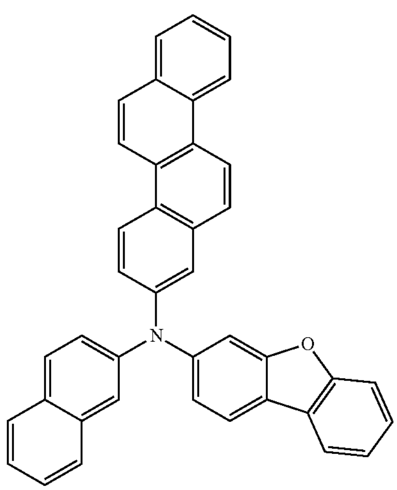
-continued
H1-51
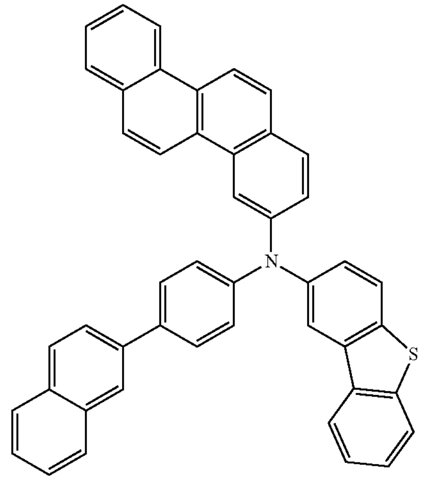
H1-52
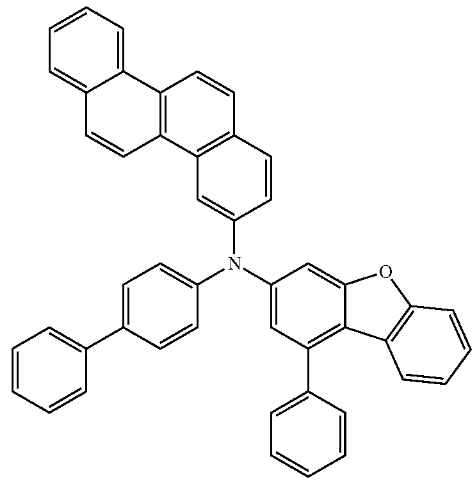
H1-53
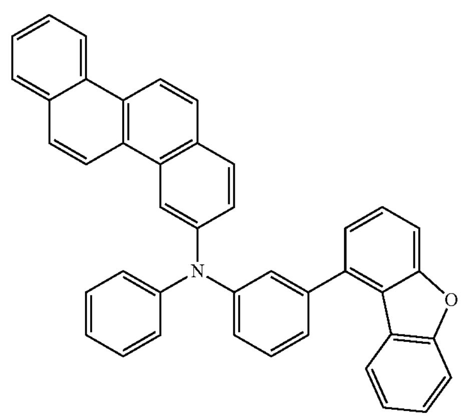

-continued
H1-54
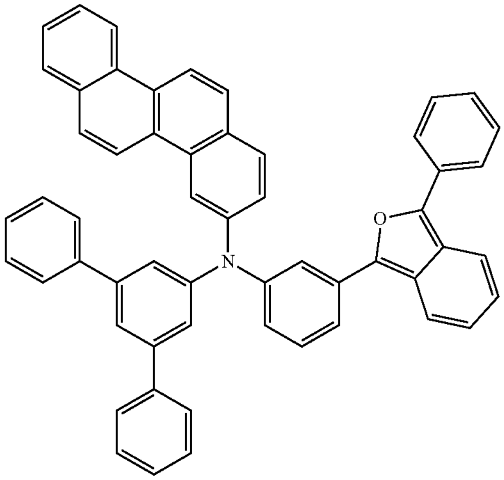
H1-55
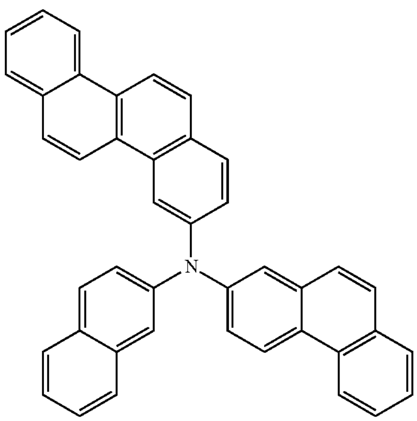
H1-56
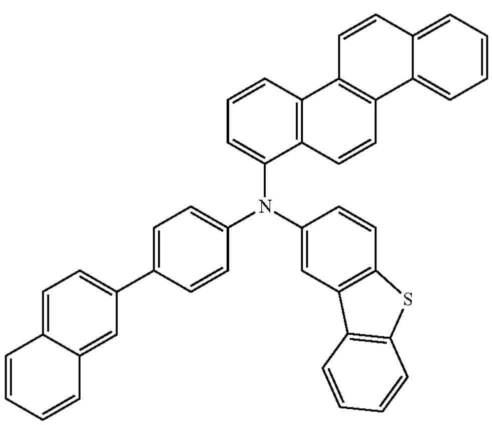
-continued
H1-57
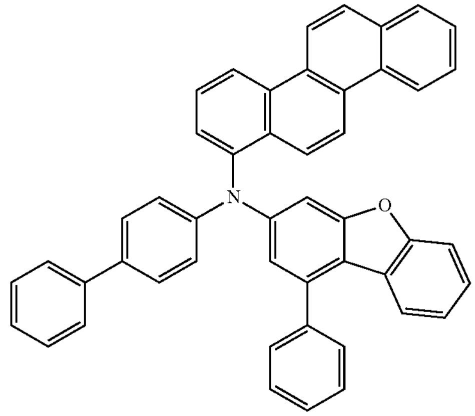
H1-58
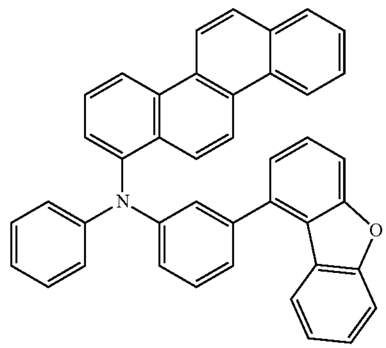
H1-59
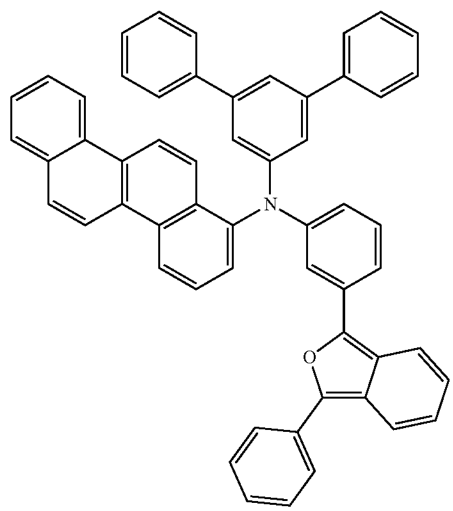
H1-60
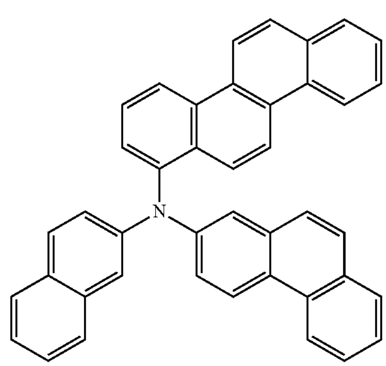

-continued
H1-61
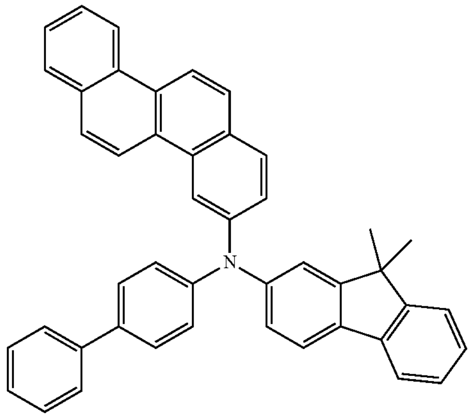
H1-62
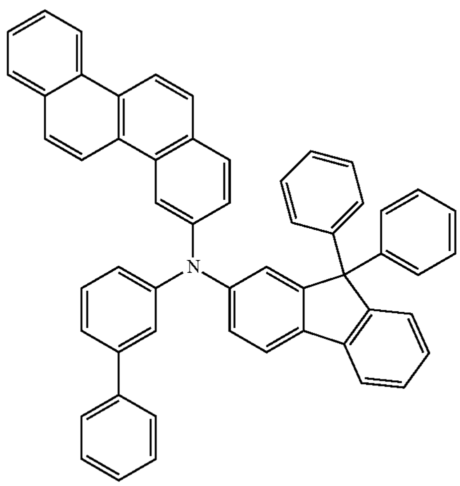
H1-63
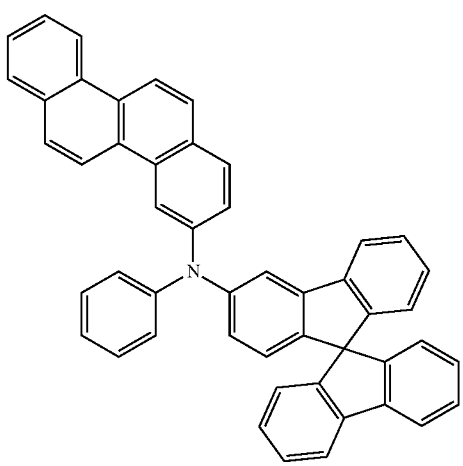
-continued
H1-64
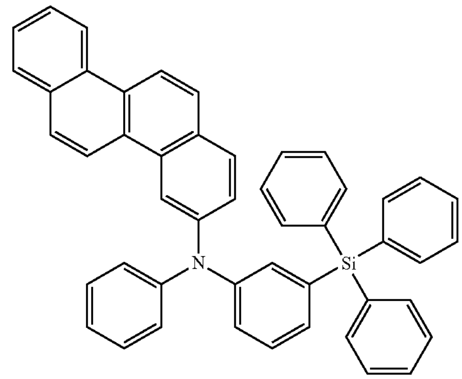
H1-65
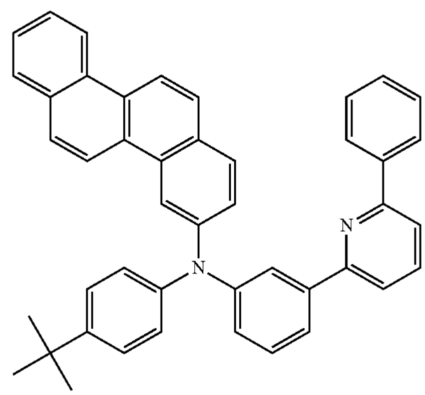
H1-66
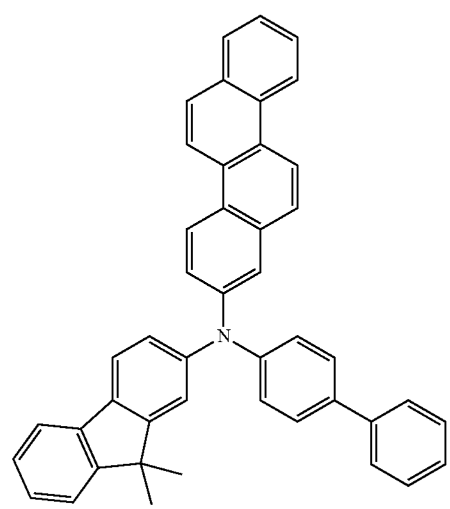

-continued
H1-67
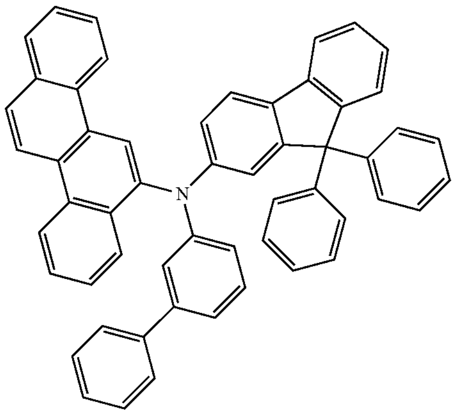
H1-68
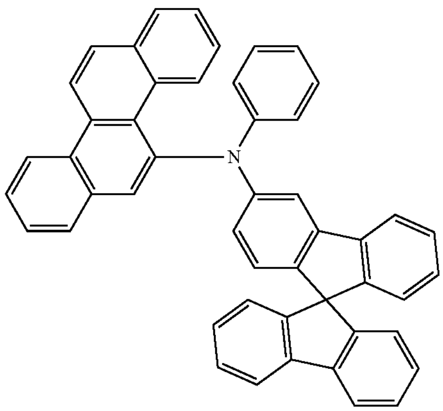
H1-69
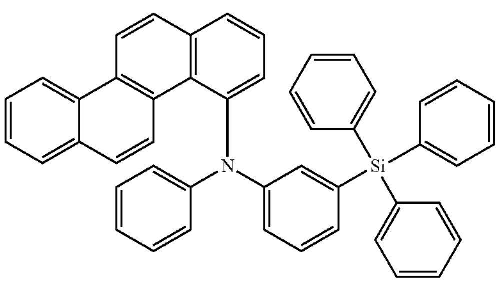
H1-70
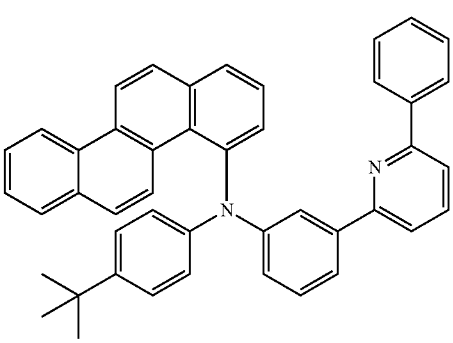
-continued
H1-71
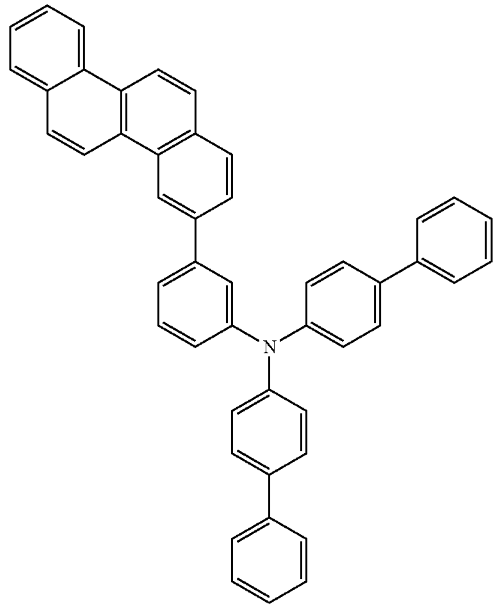
H1-72
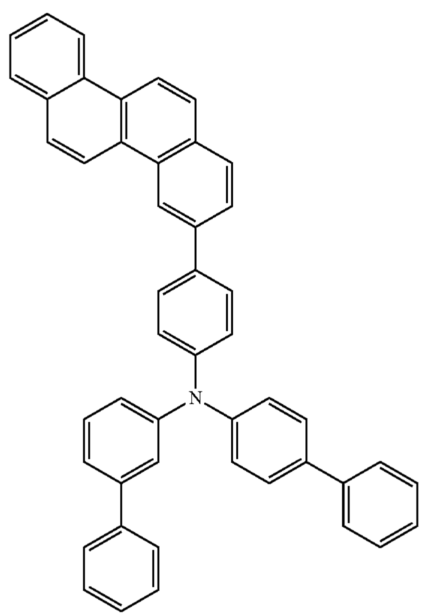

-continued
H1-73
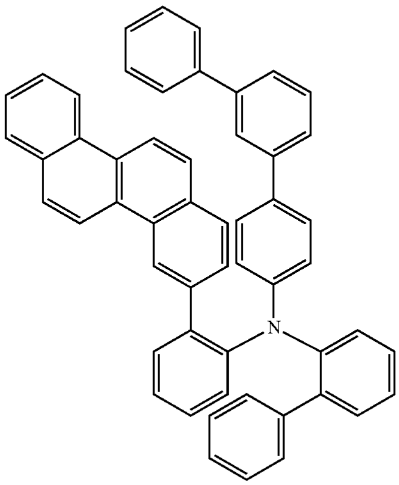
H1-74
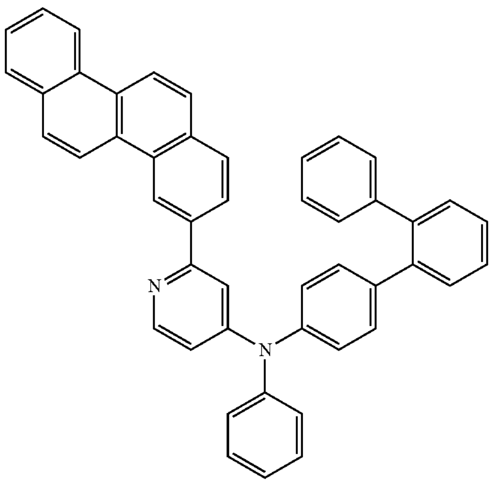
H1-75
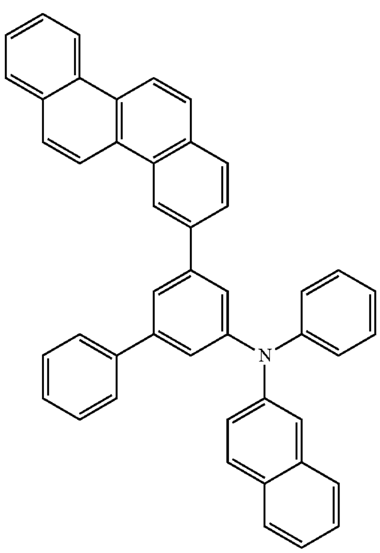
-continued
H1-76
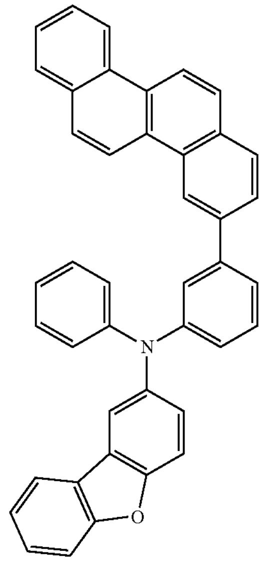
H1-77
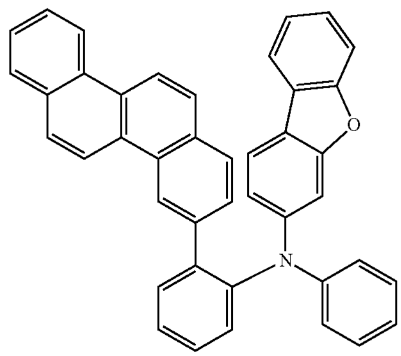
H1-78
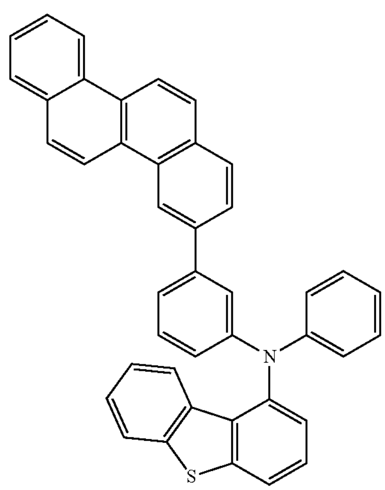

-continued
H1-79
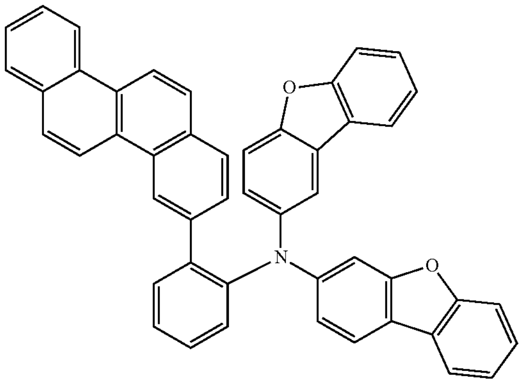
H1-80
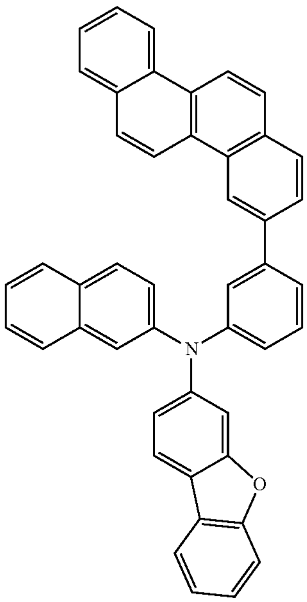
H1-81
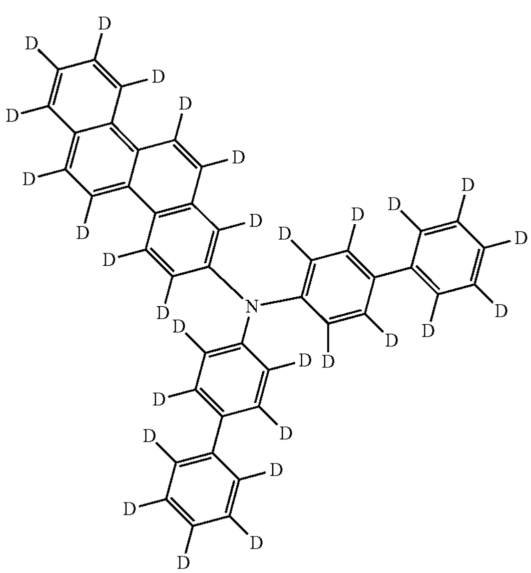
-continued
H1-82
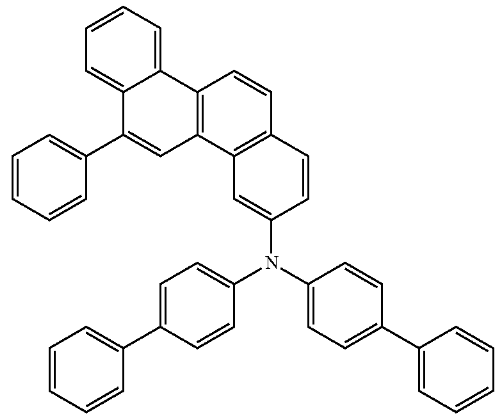
H1-83
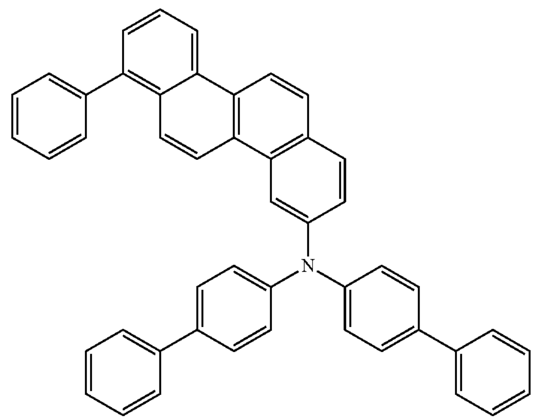
H1-84
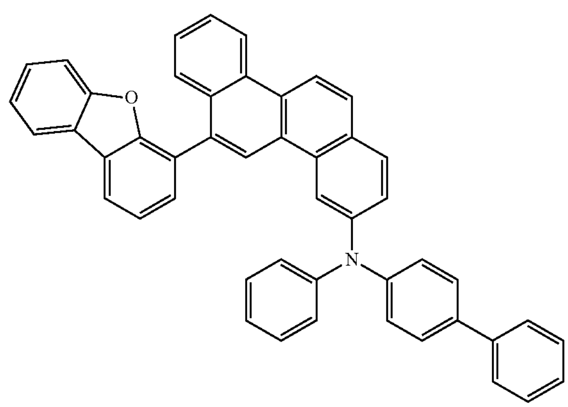
H1-85
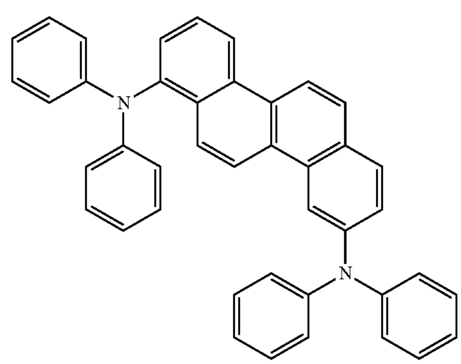

-continued
H1-86
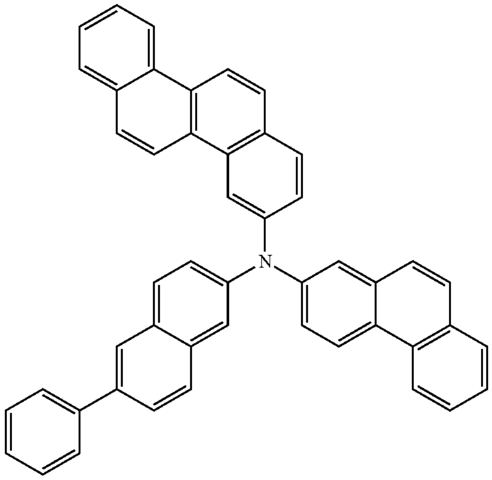
H1-87
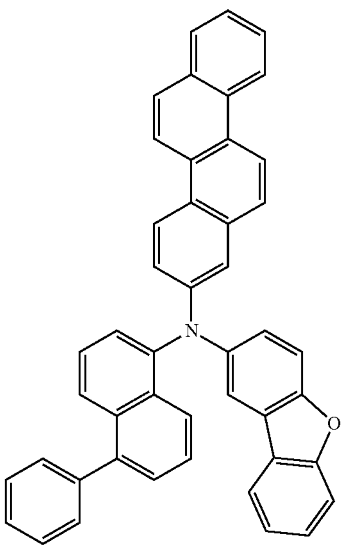
H1-88
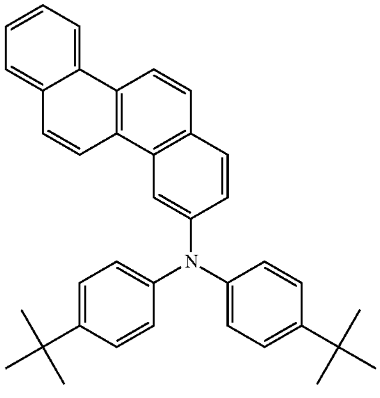
-continued
H1-89
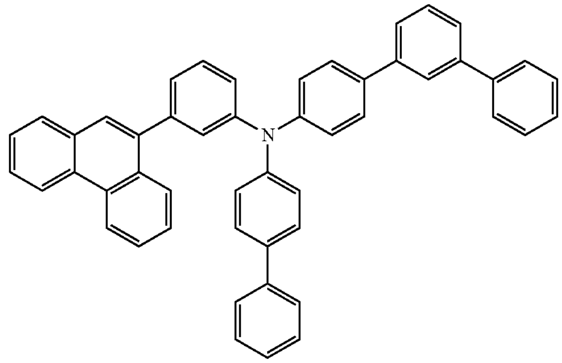
H1-90
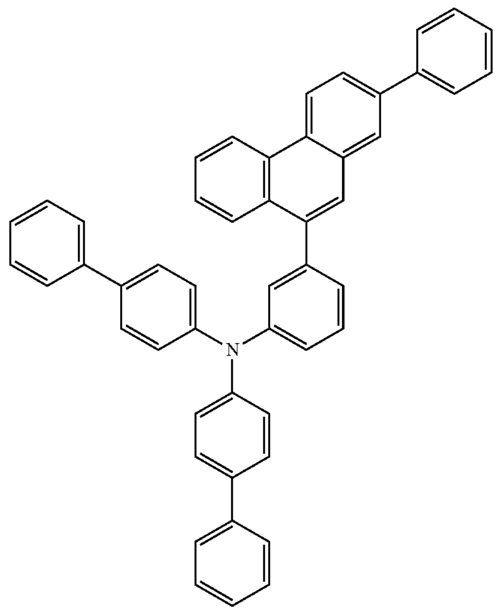
H1-91
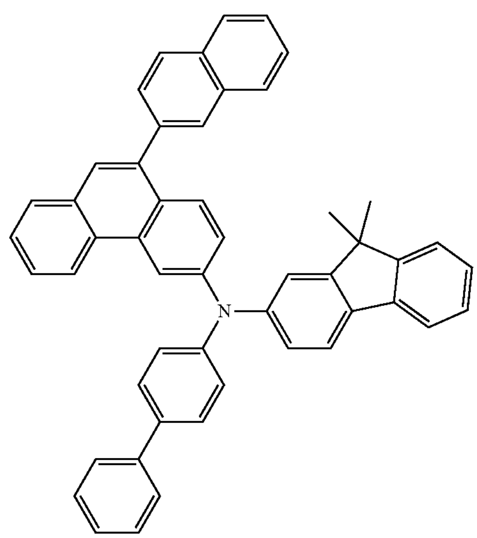

-continued
H1-92
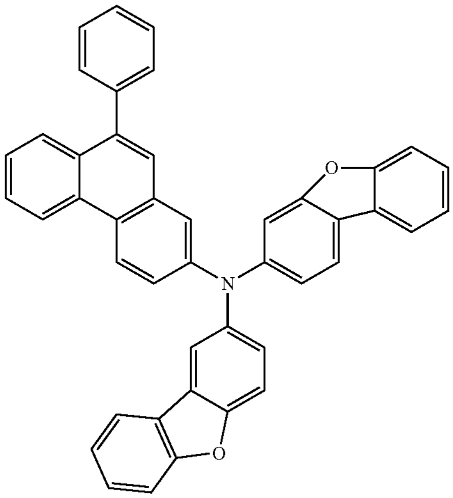
H1-93
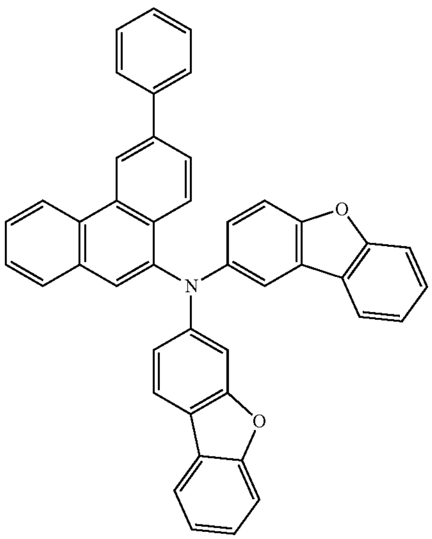
H1-94
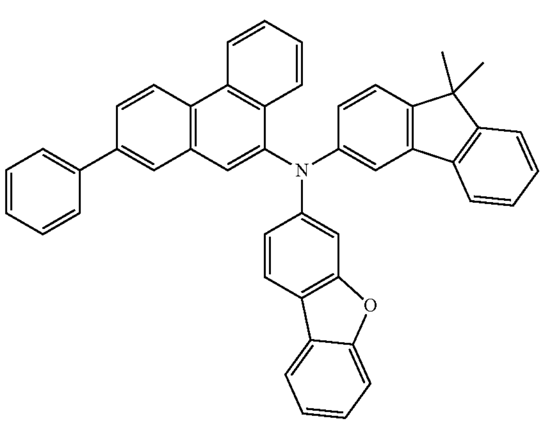
-continued
H1-95
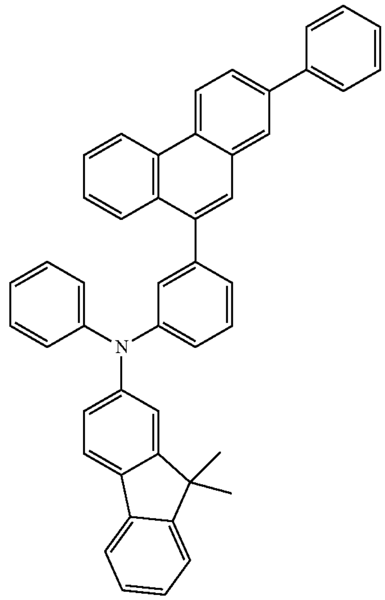
H1-96
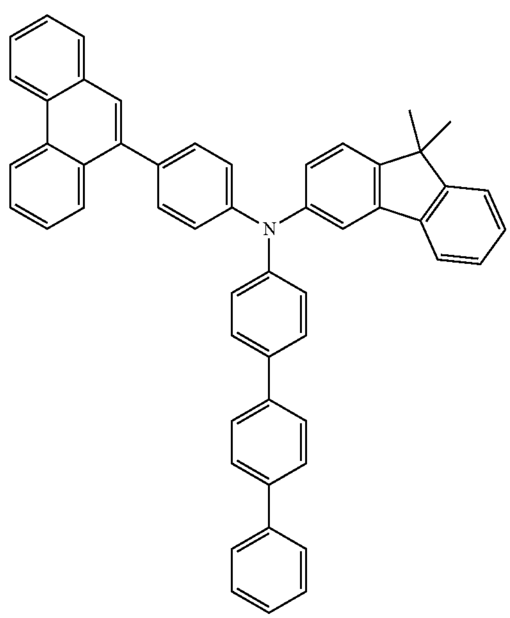

-continued
H1-97
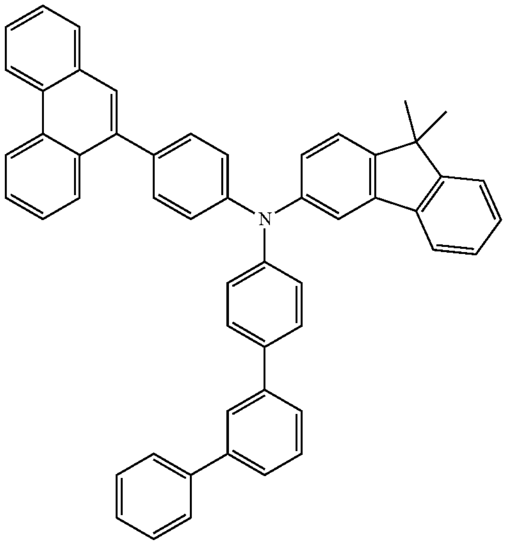
H1-98
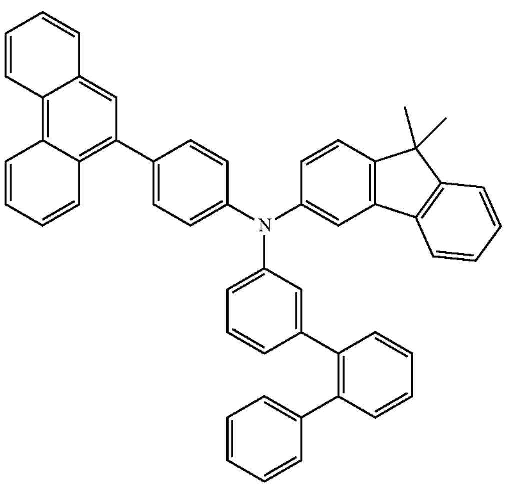
H1-99
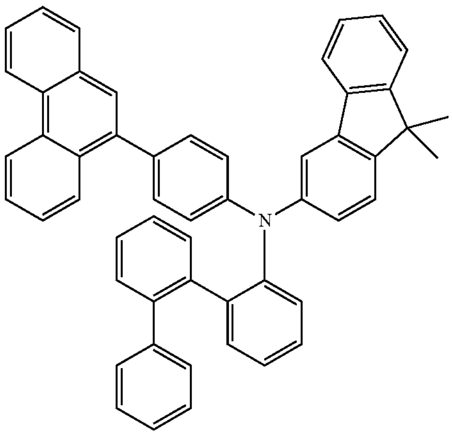
-continued
H1-100
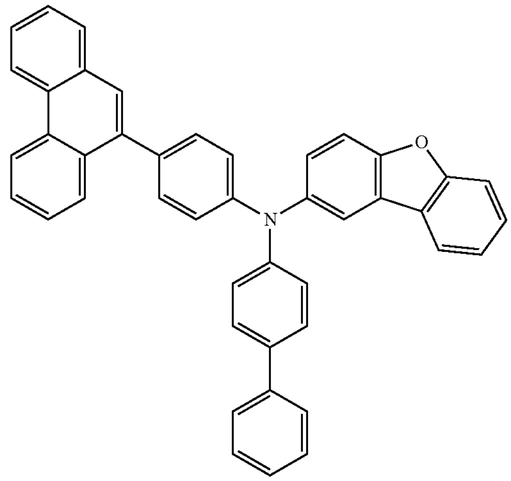
H1-101
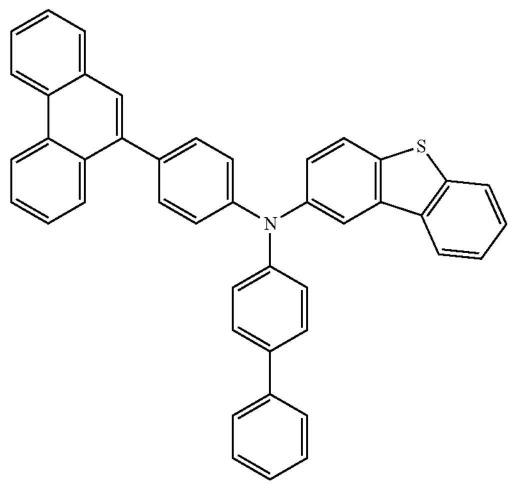
H1-102
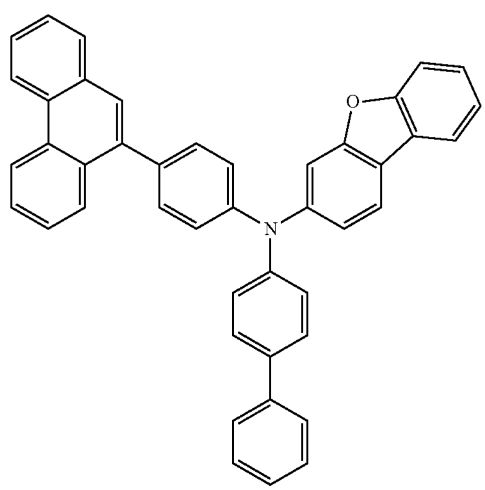

H1-103
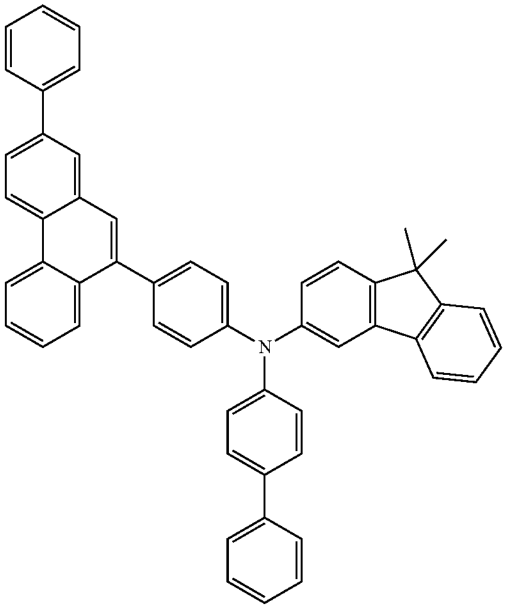
H1-104
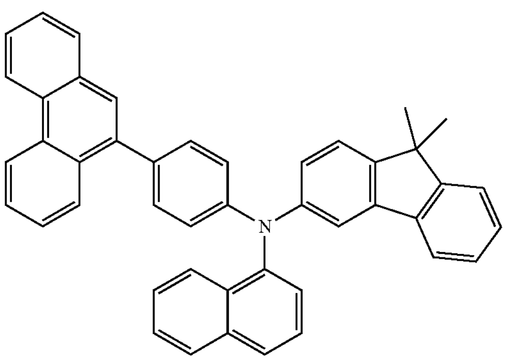
H1-105
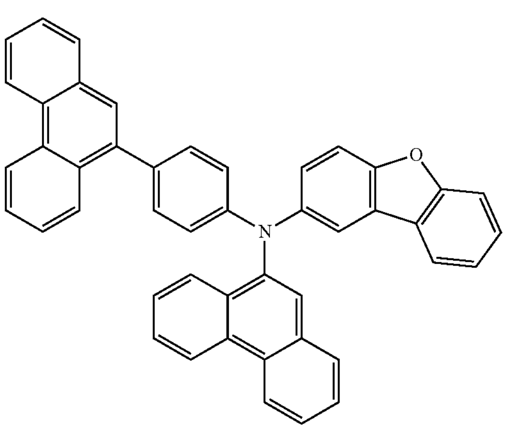
H1-106
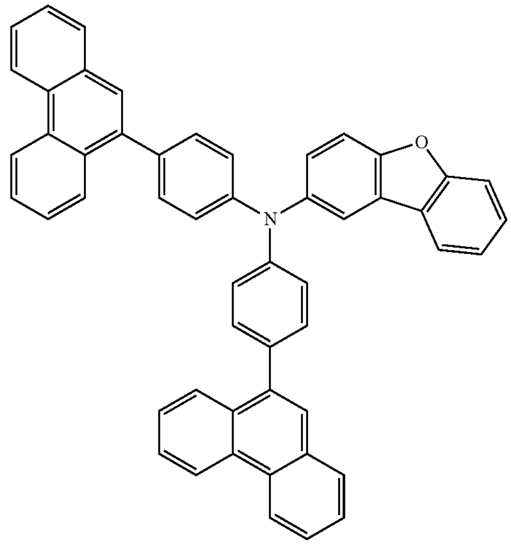
H1-107
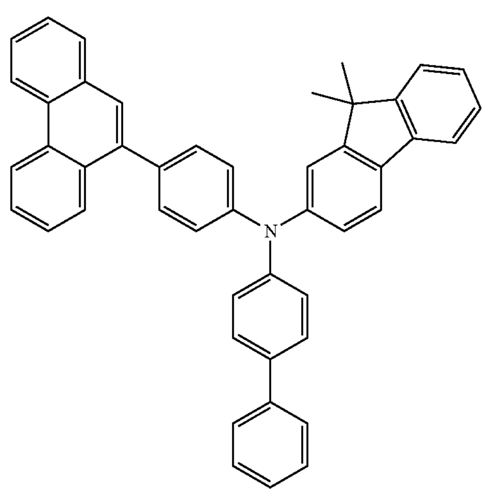

-continued
H1-108
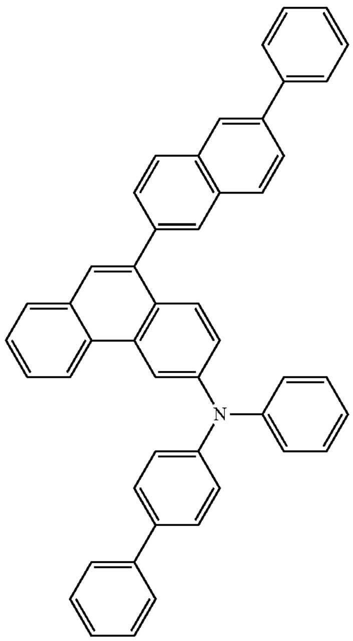
H1-109
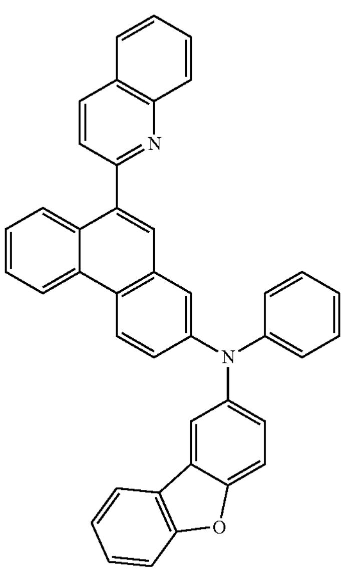
-continued
H1-110
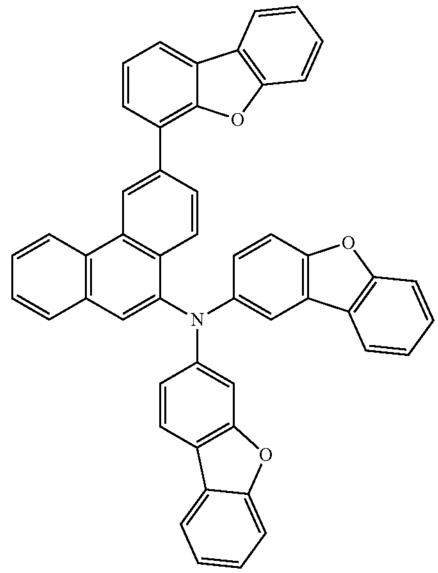
H1-111
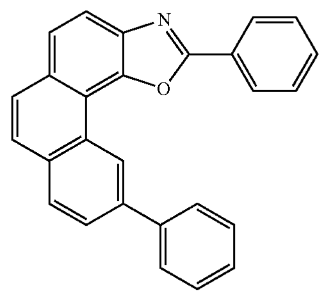
H1-112
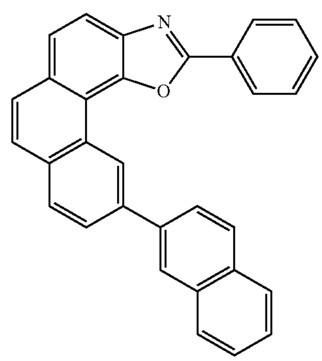
H1-113
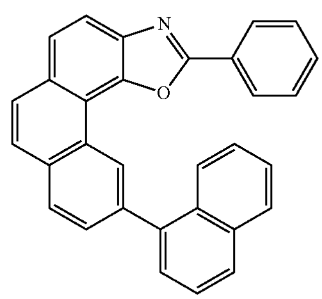

-continued
H1-114
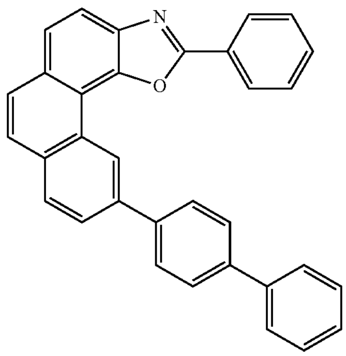
H1-115
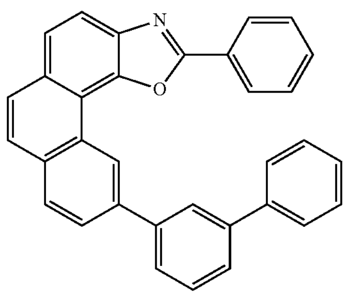
H1-116
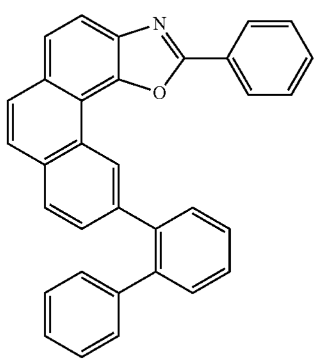
H1-117
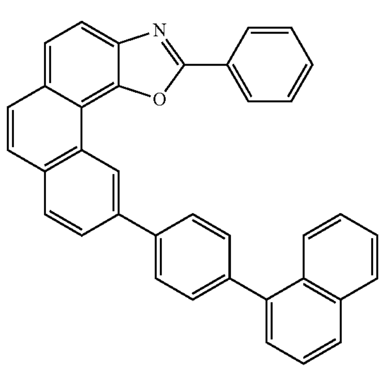
-continued
H1-118
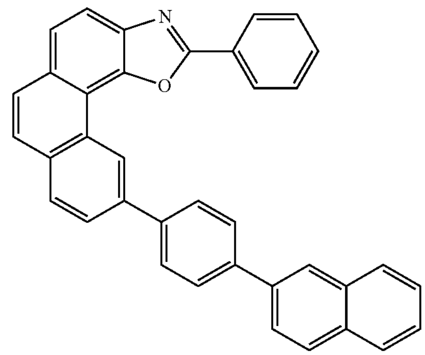
H1-119
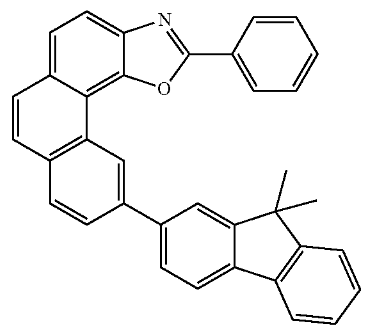
H1-120
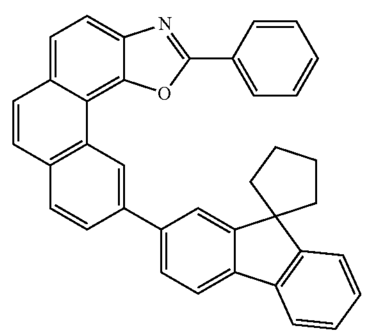
H1-121
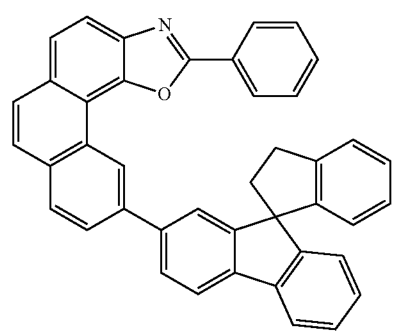

H1-122
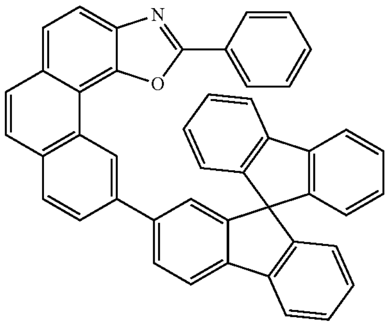
H1-123
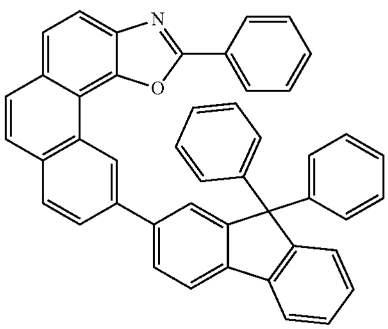
H1-124
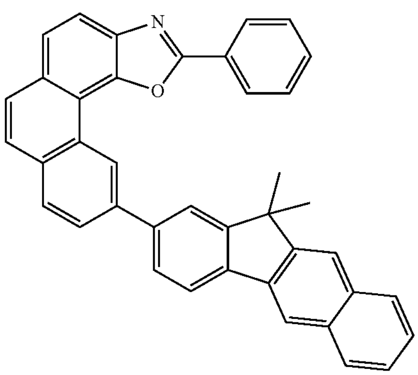
H1-125
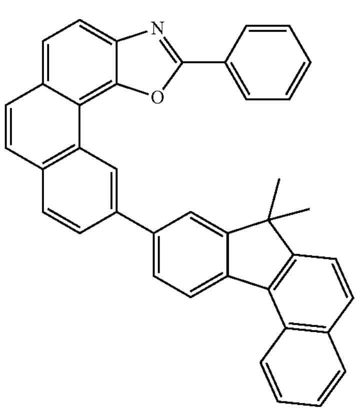
H1-126
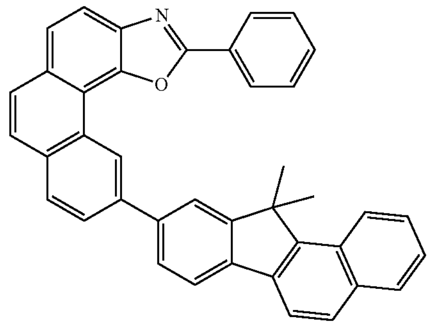
H1-127
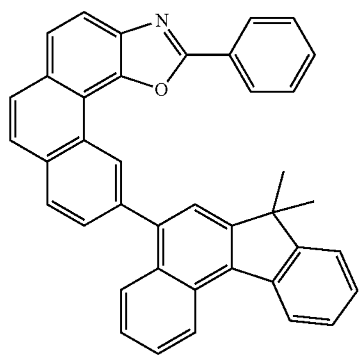
H1-128
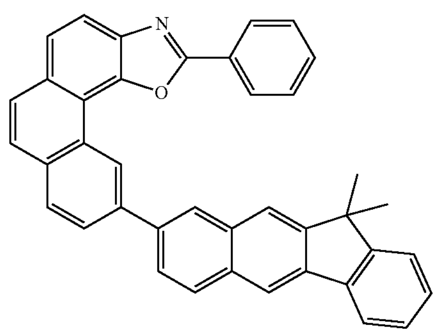
H1-129
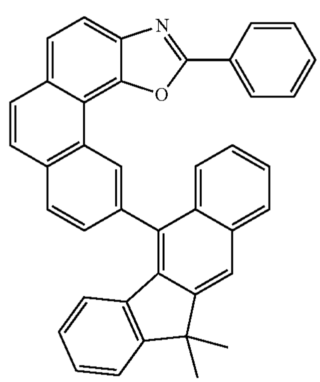

-continued
H1-130
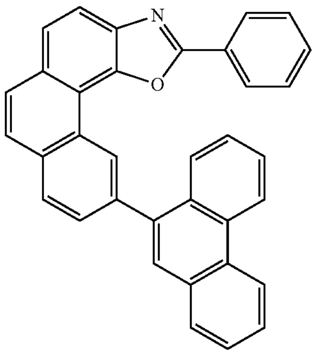
H1-131
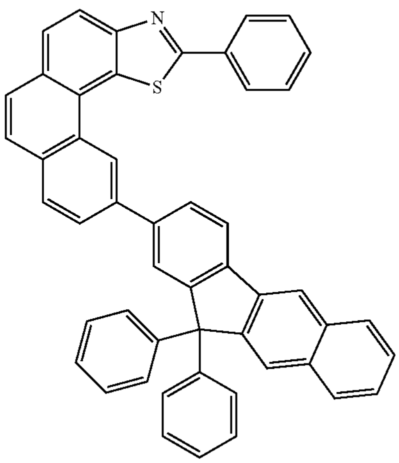
H1-132
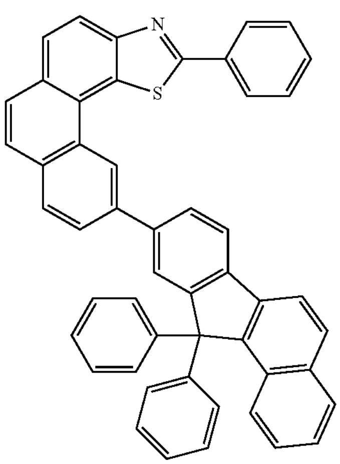
-continued
H1-133
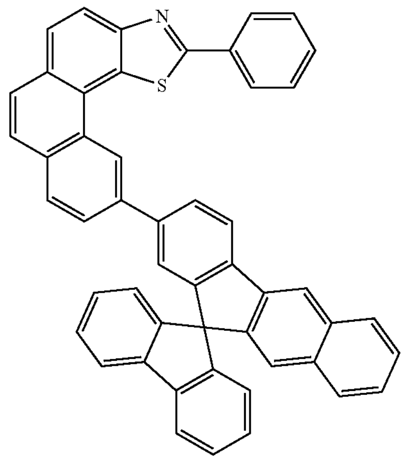
H1-134
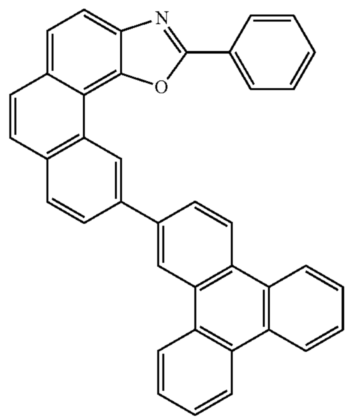
H1-135
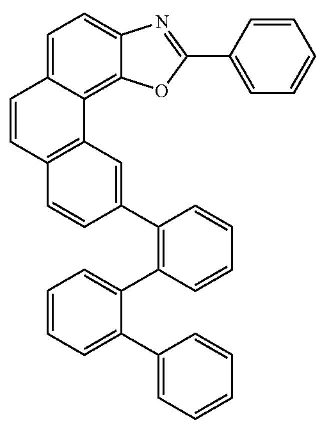
H1-136
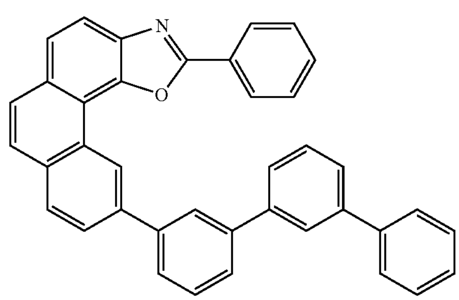

-continued
H1-137
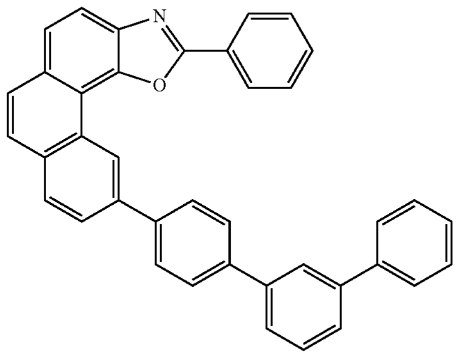
H1-138
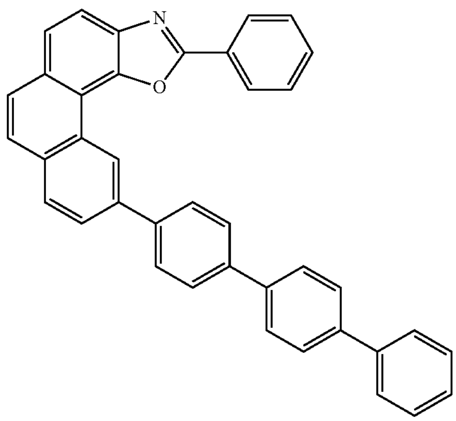
H1-139
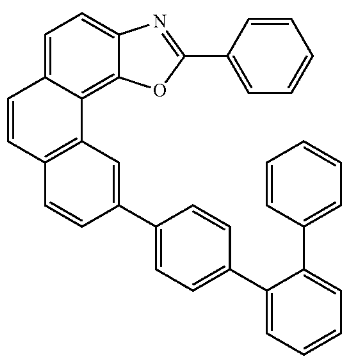
H1-140
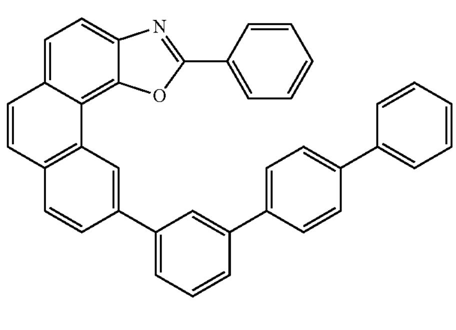
-continued
H1-141
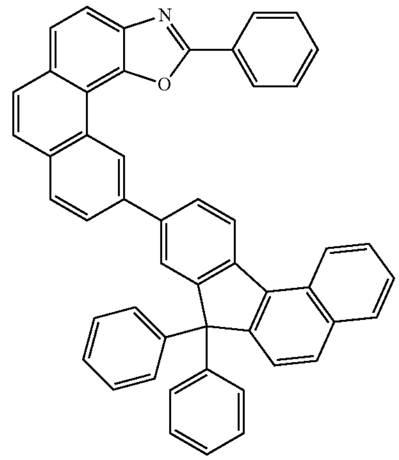
H1-142
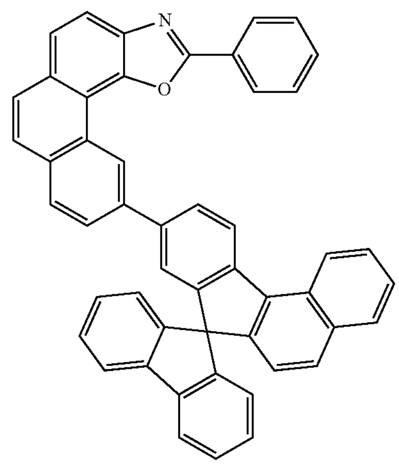
H1-143
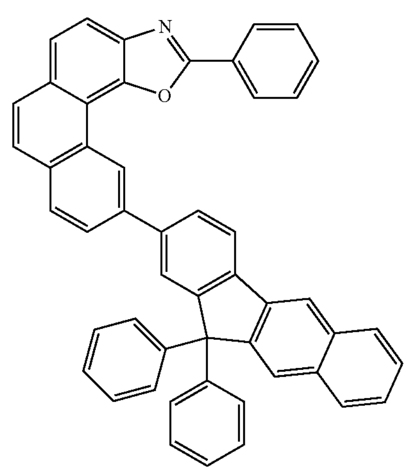

-continued
H1-144
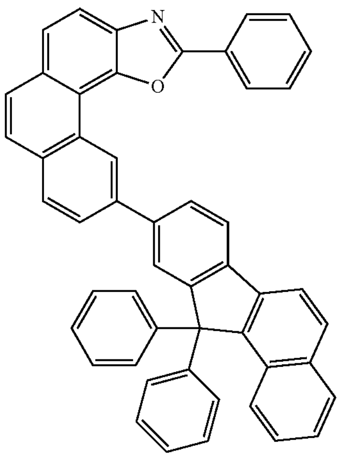
H1-145
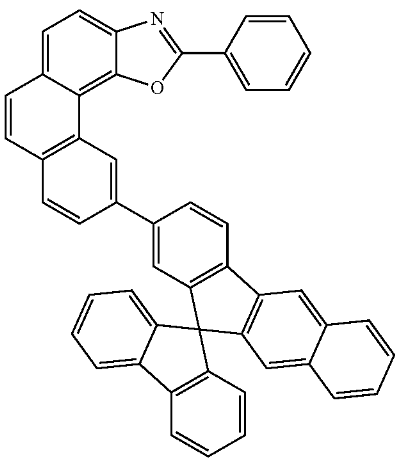
H1-146
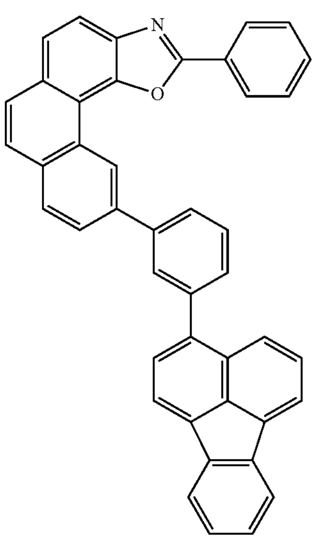
-continued
H1-147
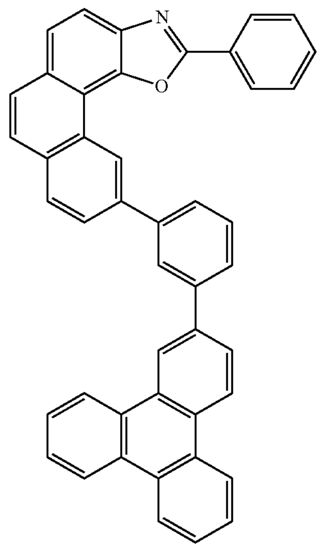
H1-148
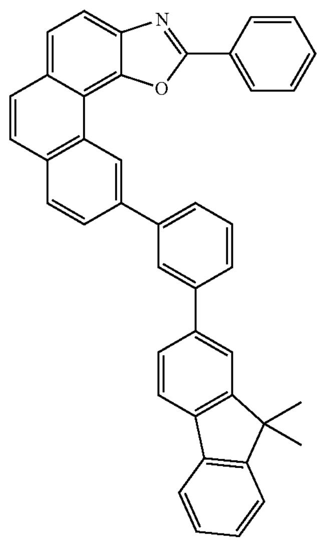
H1-149
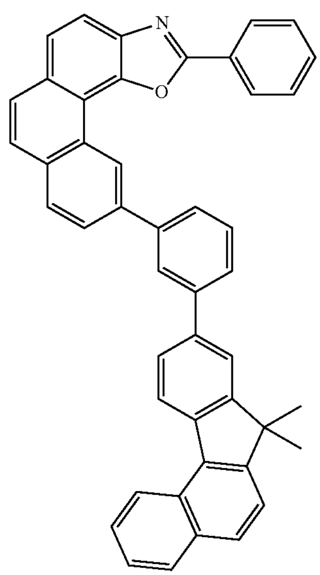

H1-150
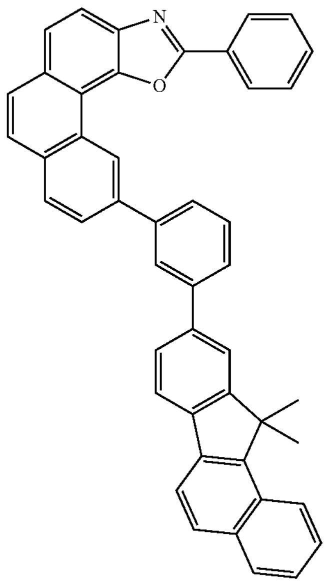
H1-151
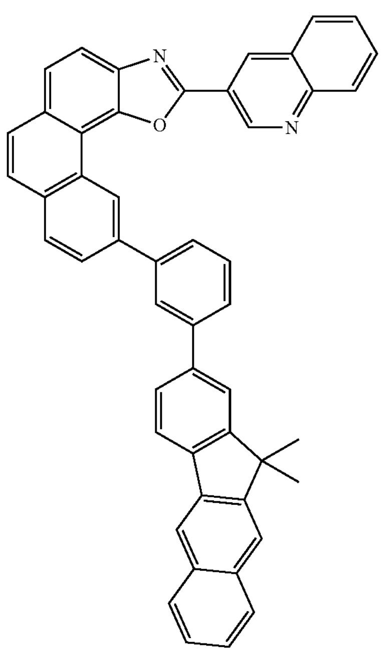
H1-152
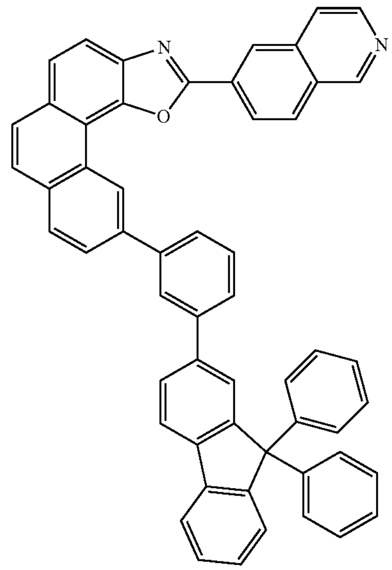
H1-153
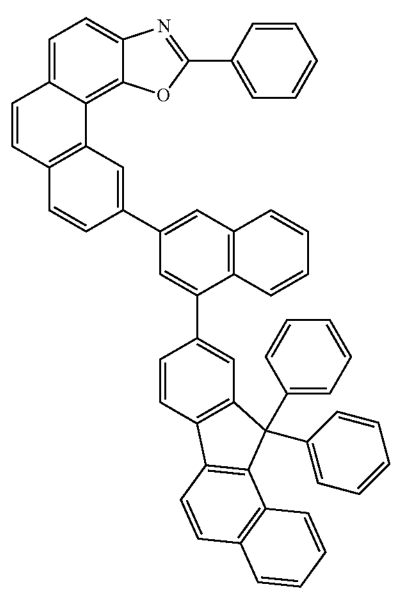

-continued
H1-154
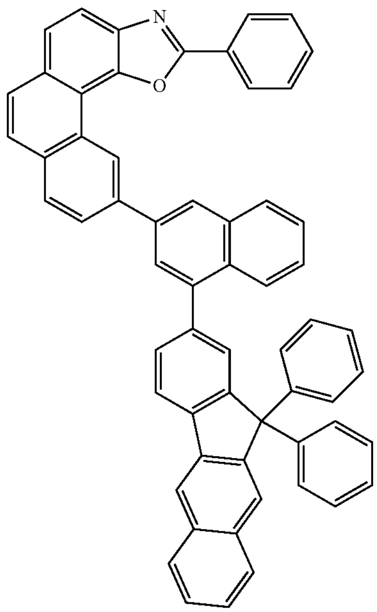
H1-155
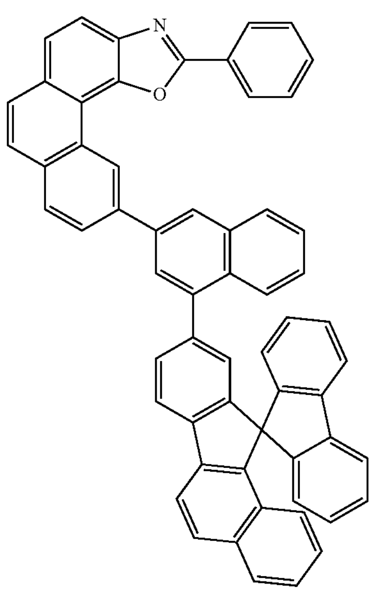
-continued
H1-156
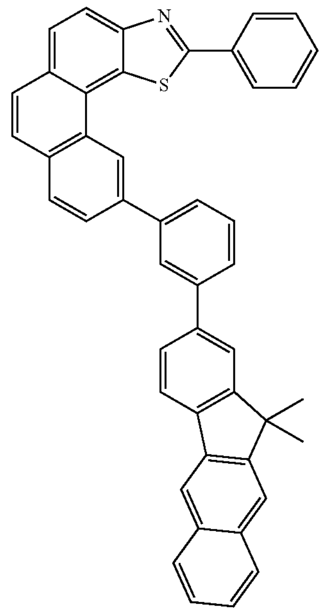
H1-157
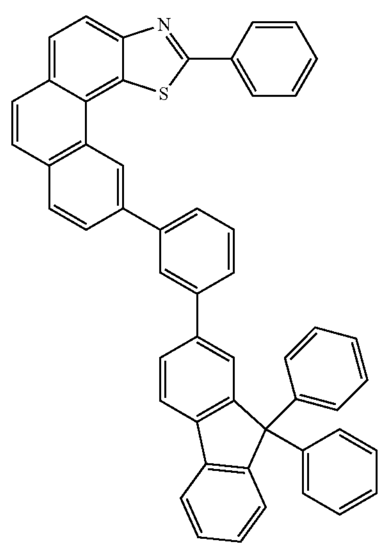

-continued
H1-158
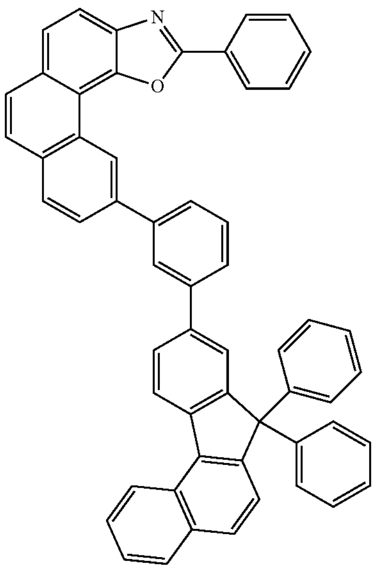
H1-159
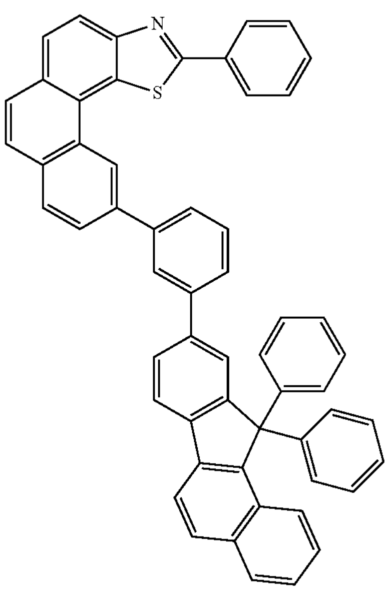
H1-160
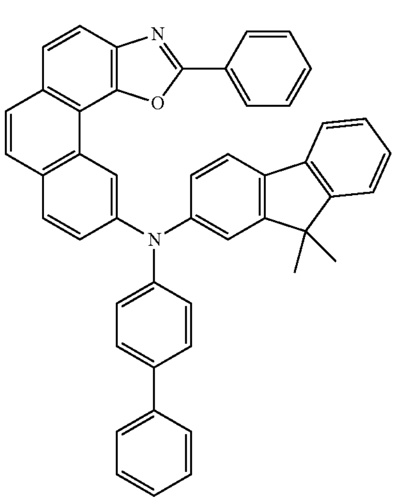
-continued
H1-161
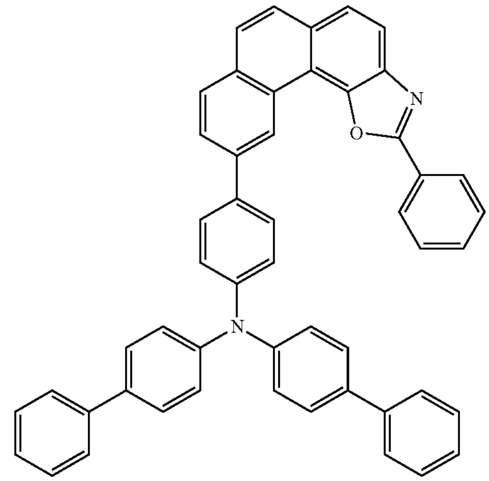
H1-162
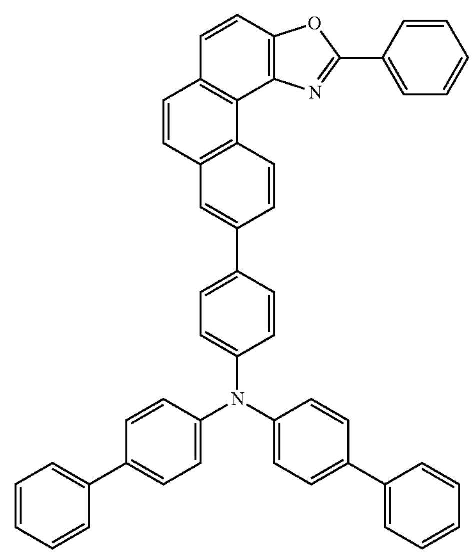
H1-163
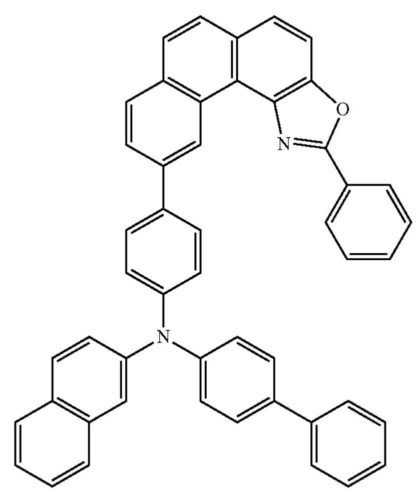

-continued
H1-164
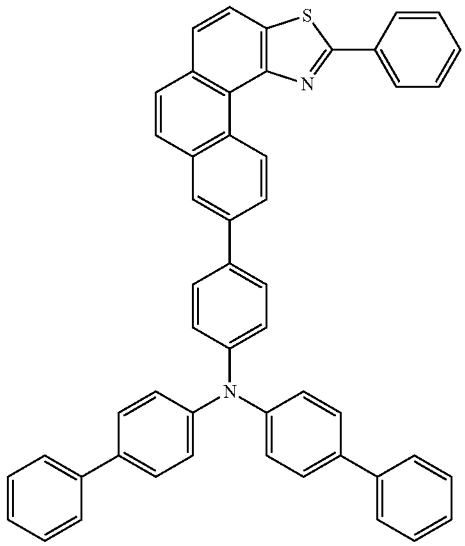
H1-165
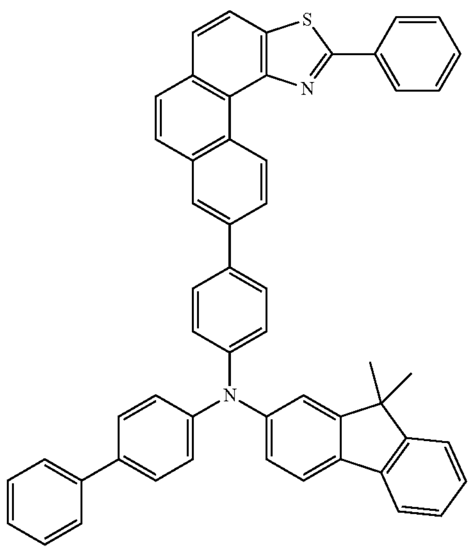
H1-166
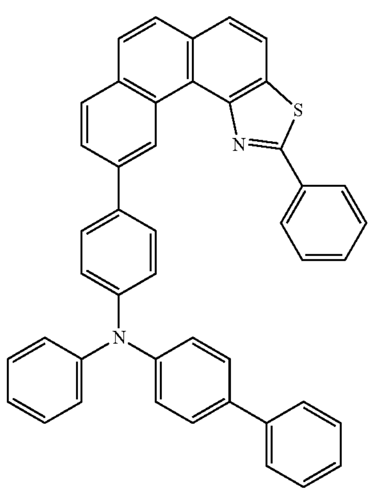
-continued
H1-167
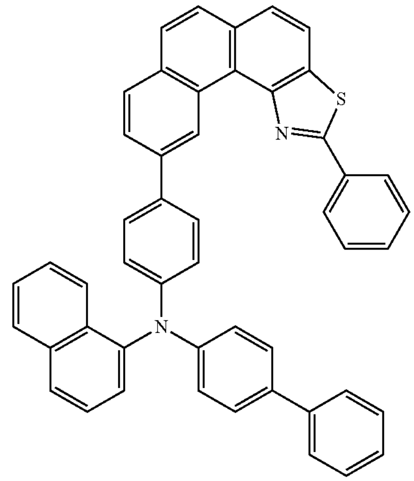
H1-168
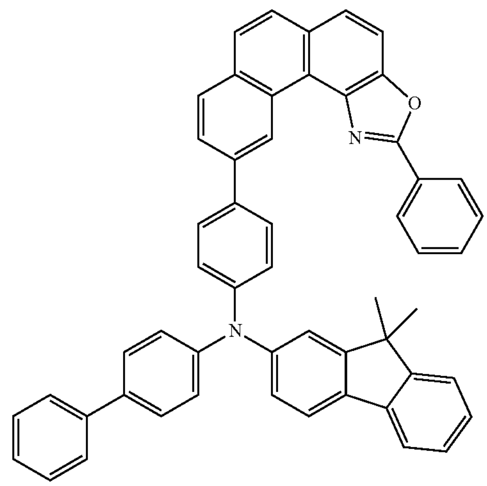
H1-169
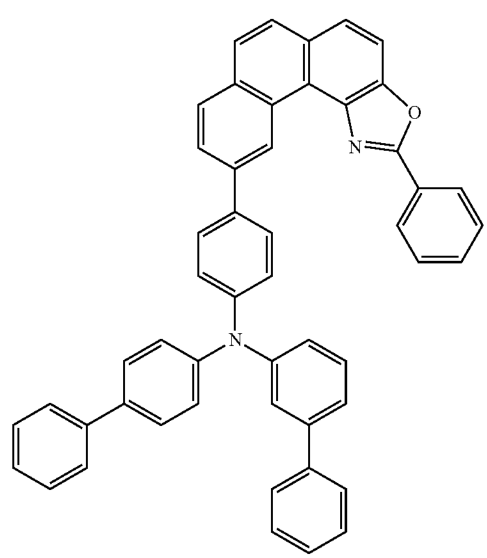

-continued
H1-170
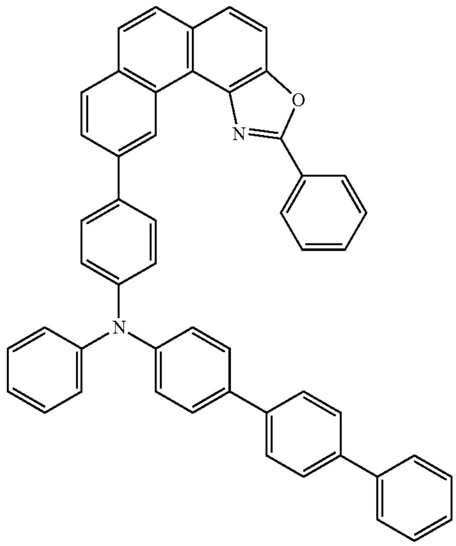
H1-171
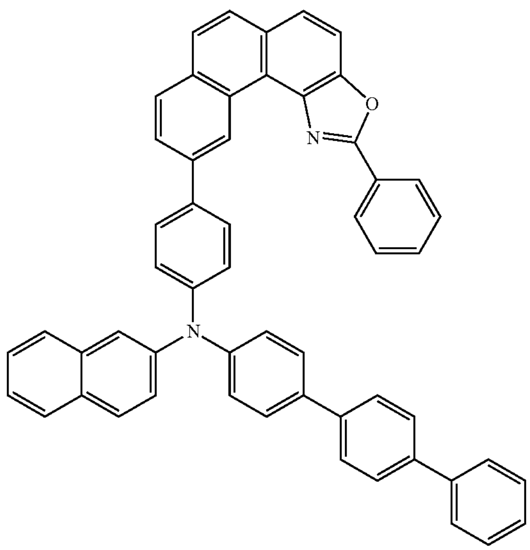
H1-172
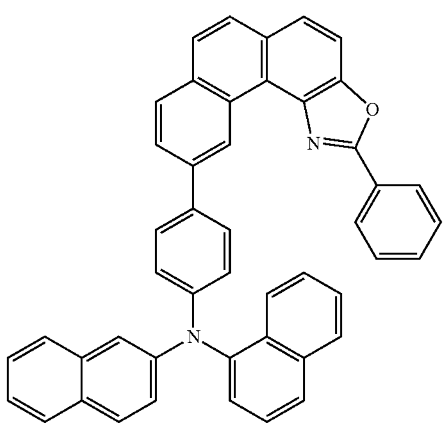
-continued
H1-173
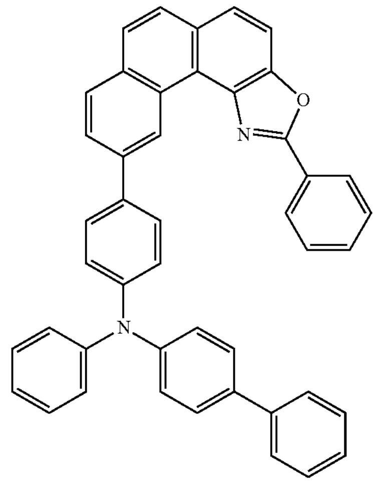
H1-174
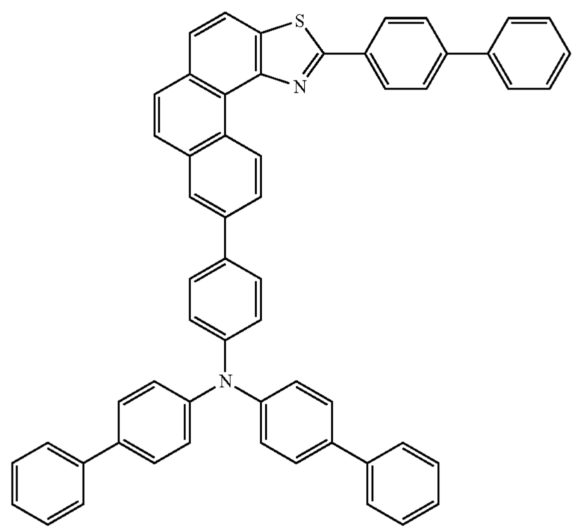
H1-175
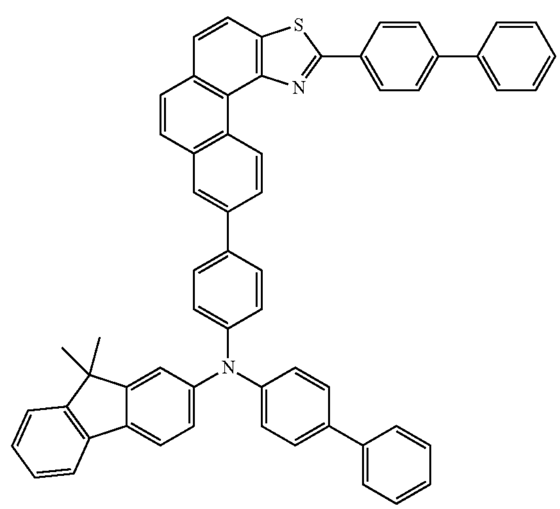

-continued
H1-176
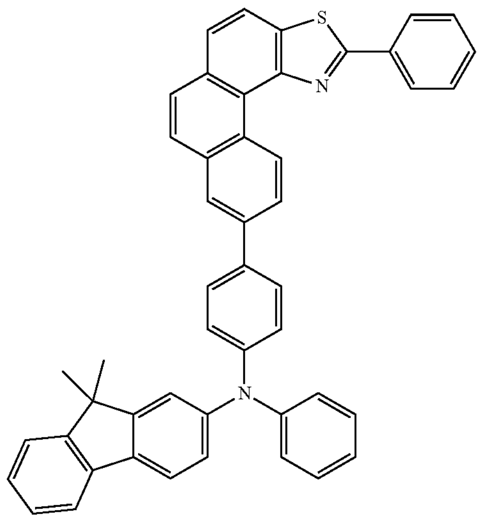
H1-177
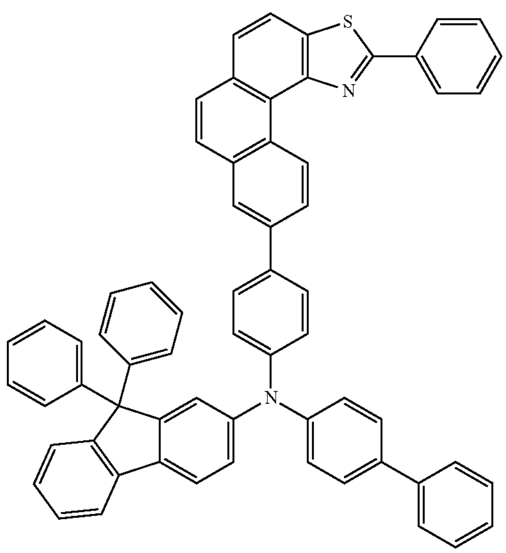
H1-178
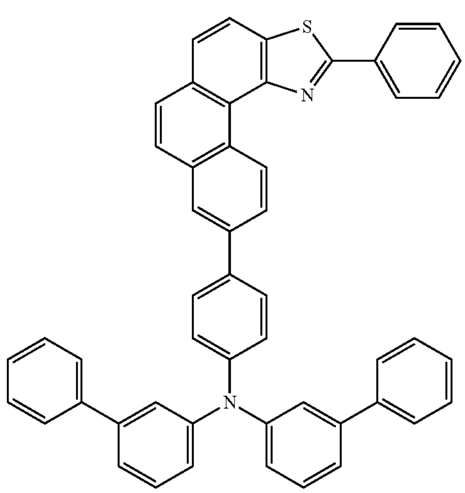
-continued
H1-179
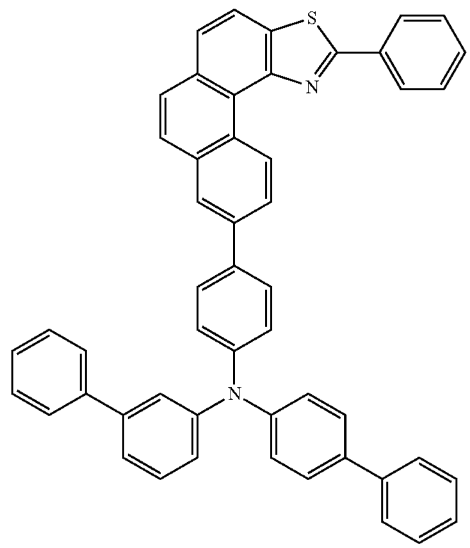
H1-180
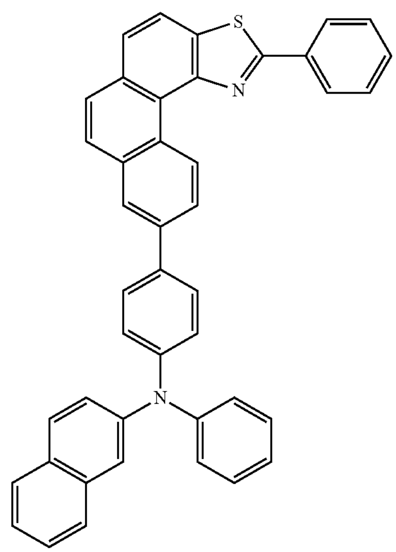
H1-181
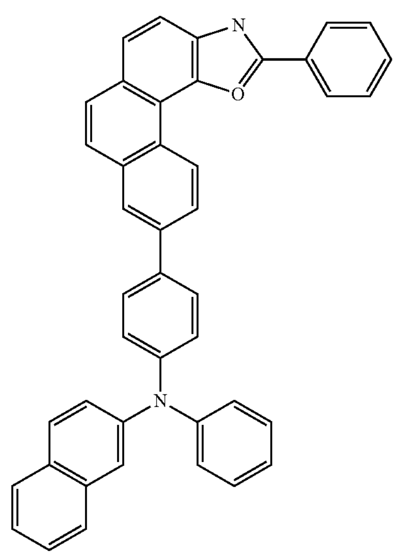

-continued
H1-182
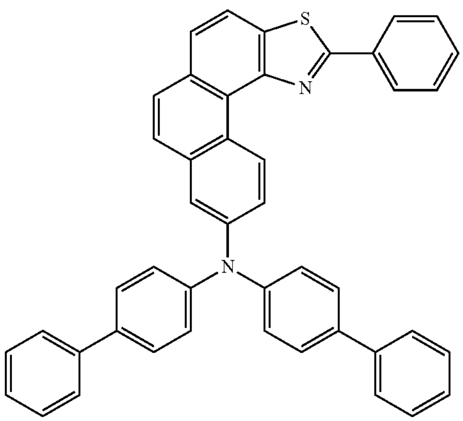
H1-183
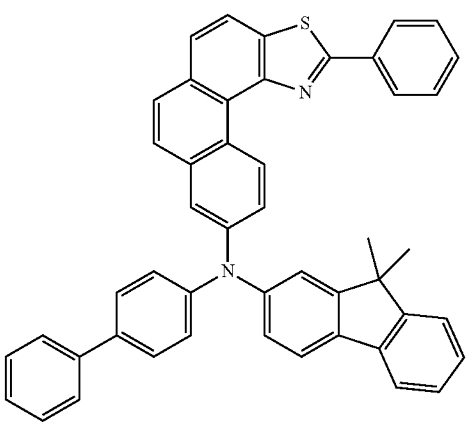
H1-184
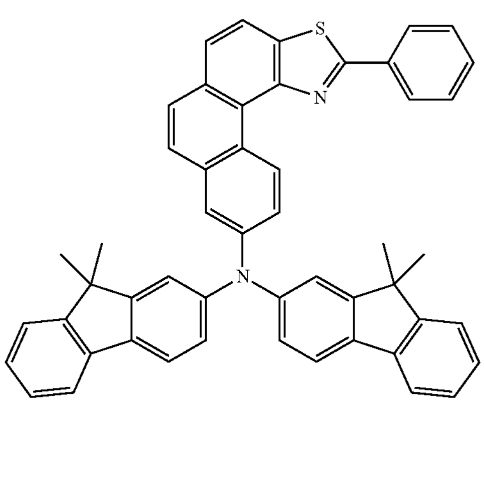
-continued
H1-185
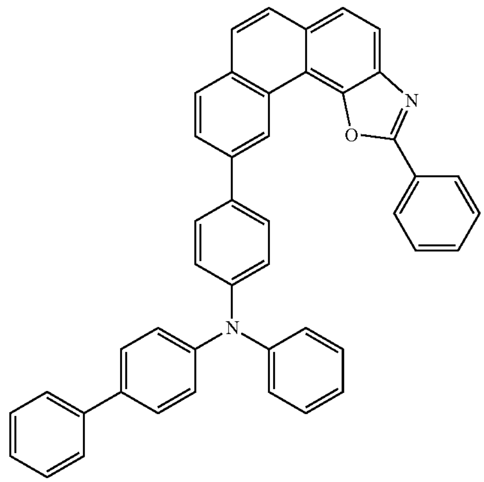
H1-186
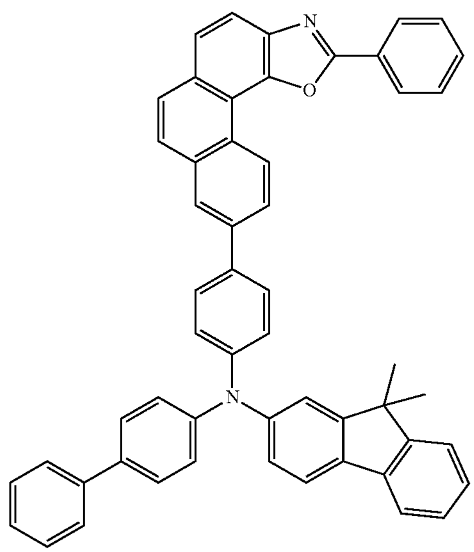
H1-187
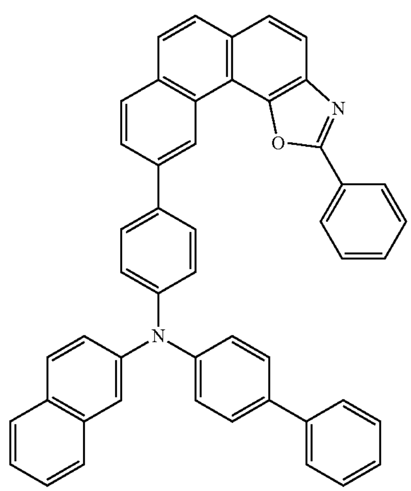

-continued
H1-188
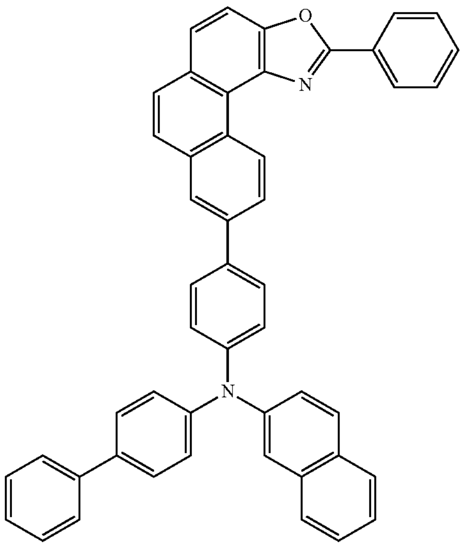
H1-189
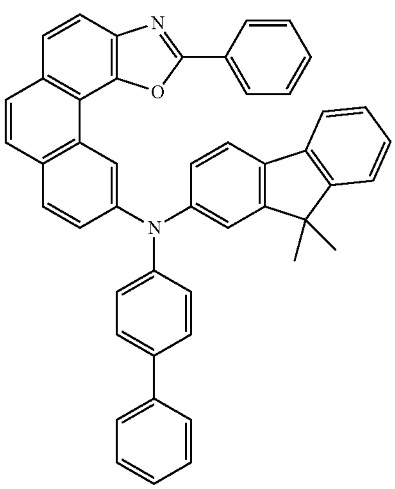
H1-190
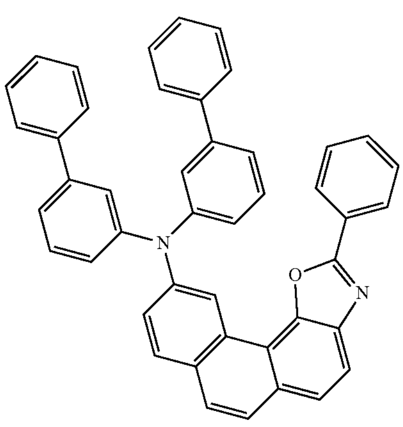
-continued
H1-191
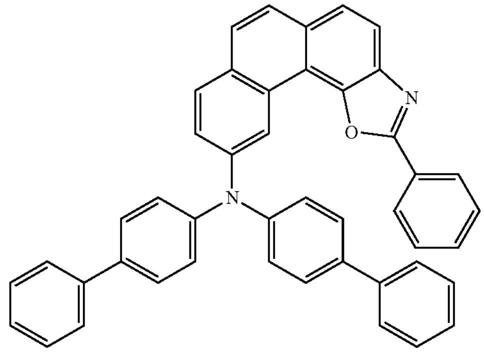
H1-192
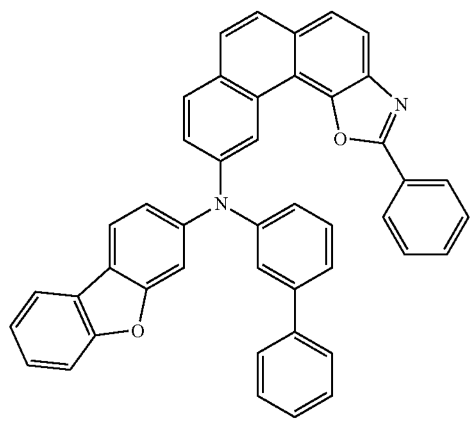
H1-193
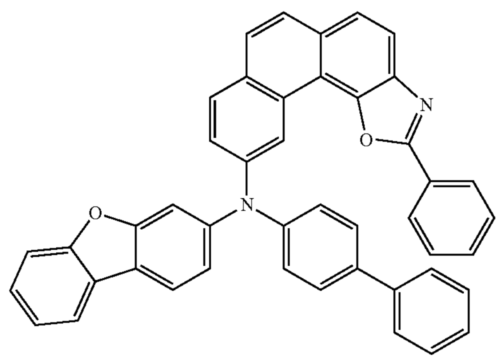
H1-194
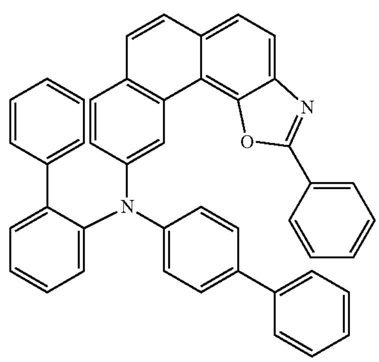

-continued
H1-195
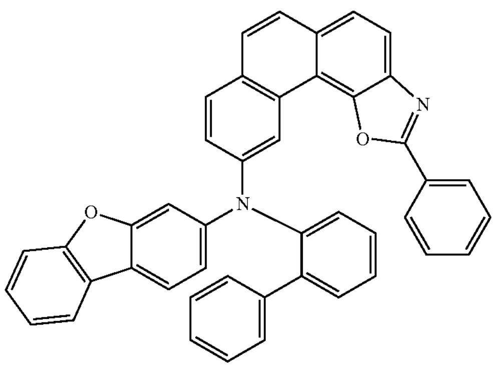
H1-196
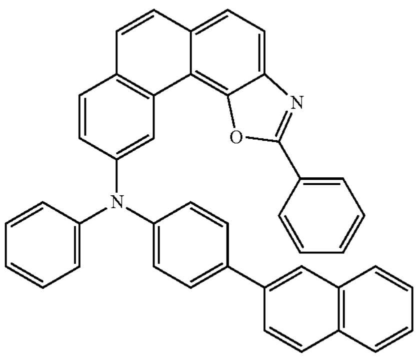
H1-197
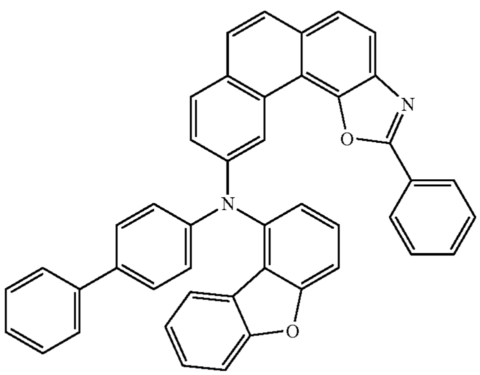
H1-198
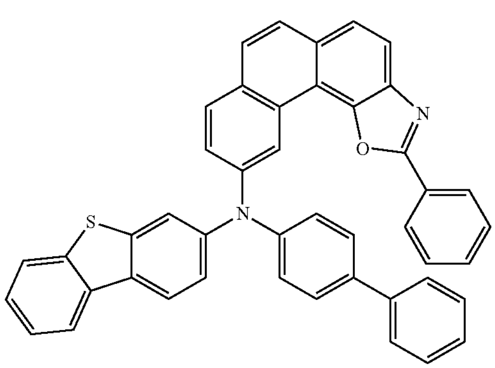
-continued
H1-199
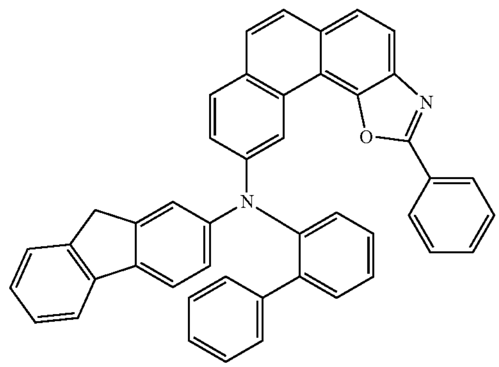
H1-200
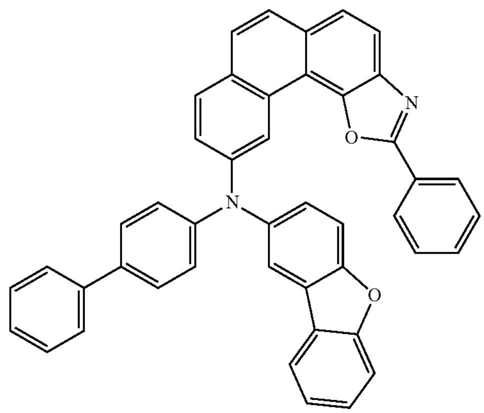
H1-201
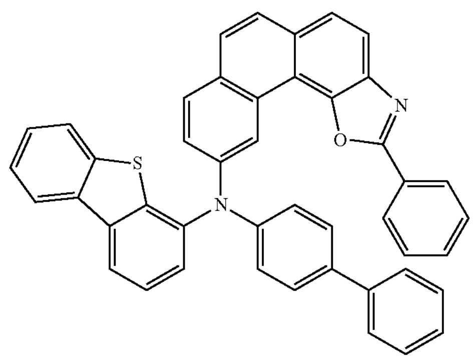
H1-202
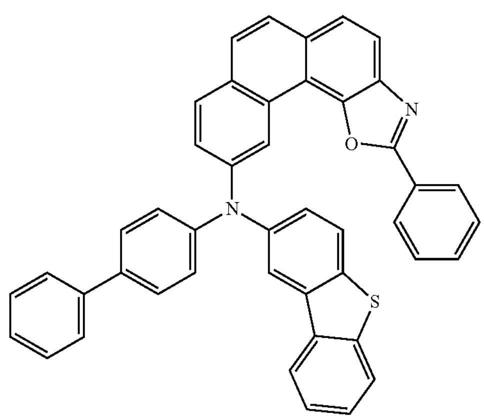

-continued
H1-203
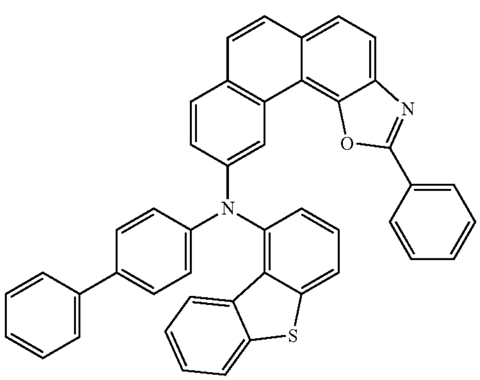
H1-204
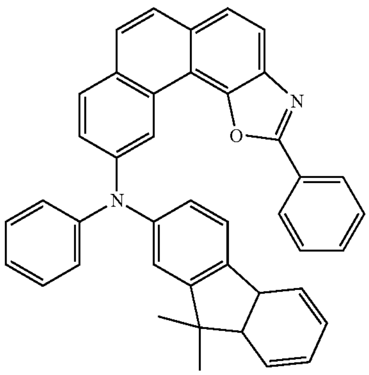
H1-205
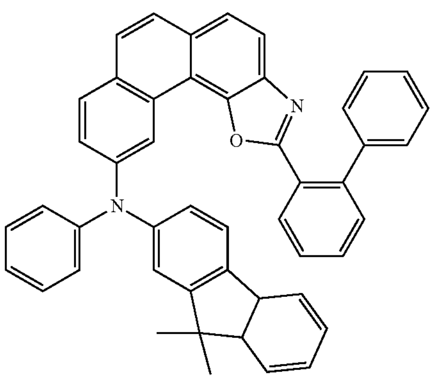
H1-206
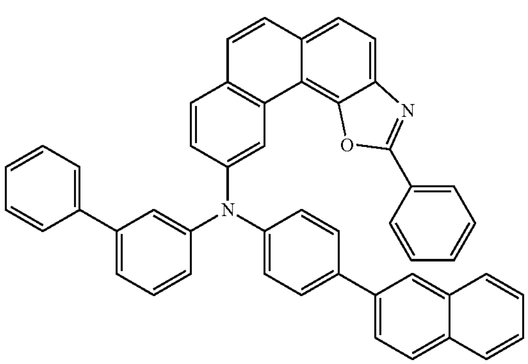
-continued
H1-207
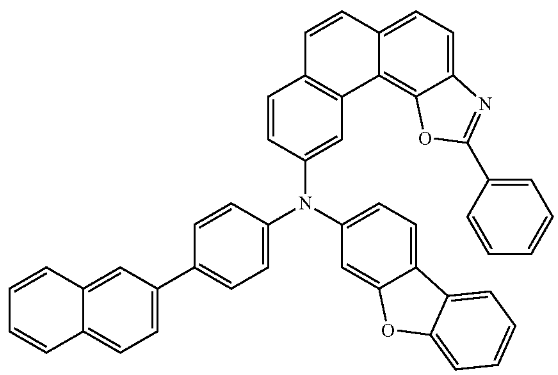
H1-208
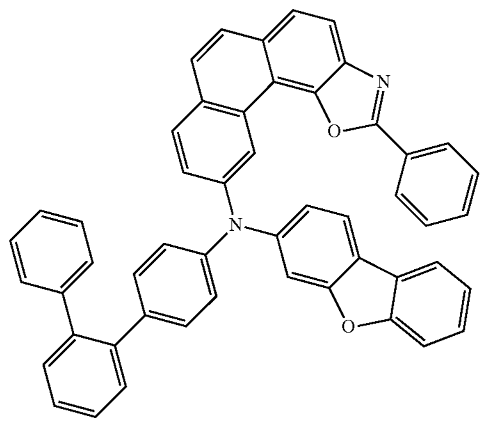
H1-209
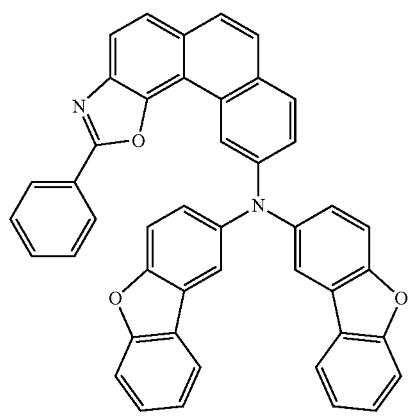
H1-210
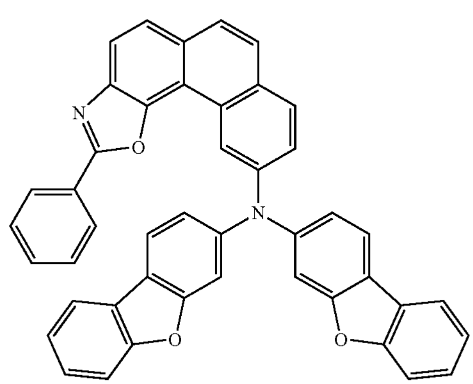

-continued
H1-211
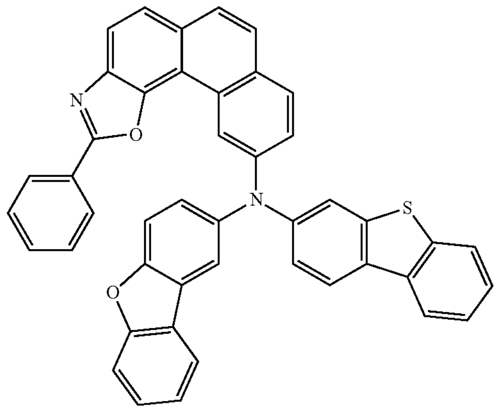
H1-212
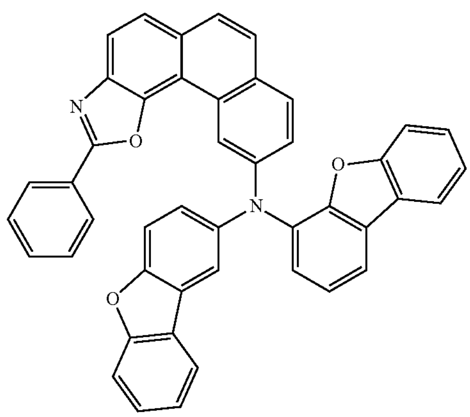
H1-213
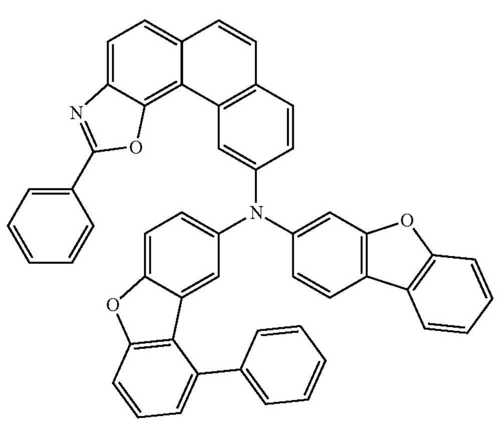
-continued
H1-214
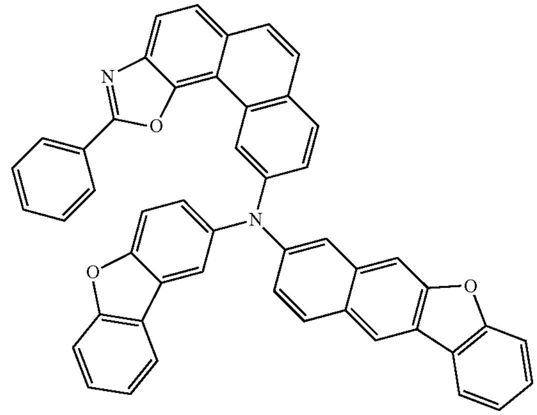
H1-215
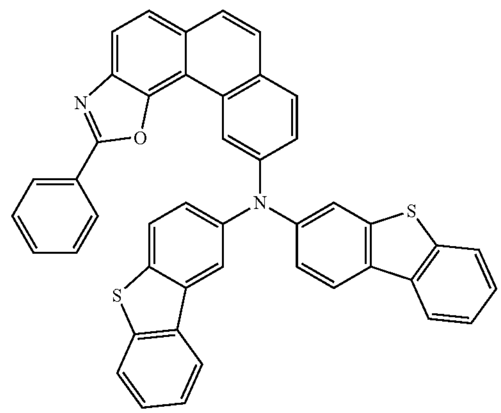
H1-216
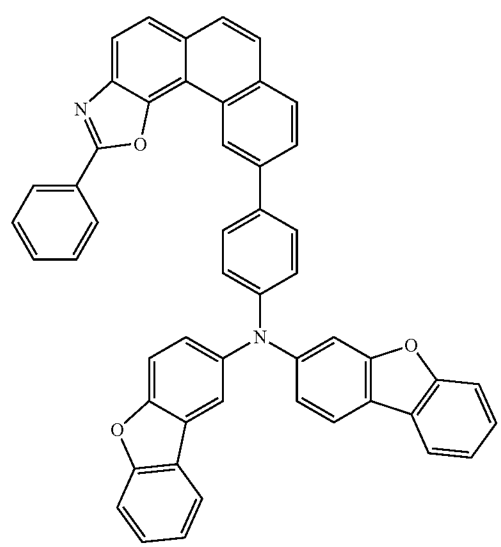

-continued
H1-217
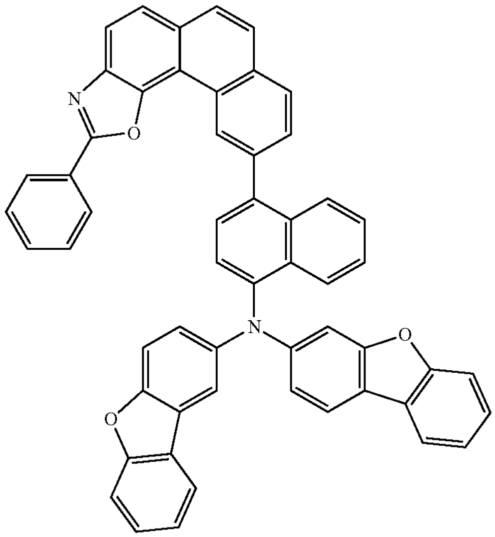
H1-218
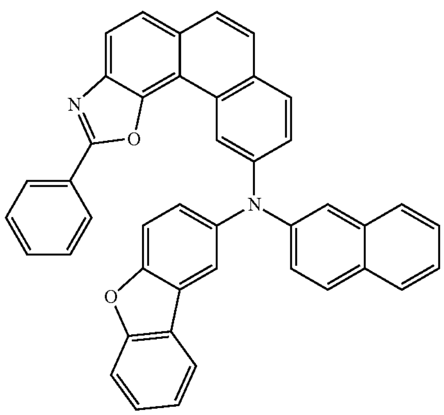
H1-219
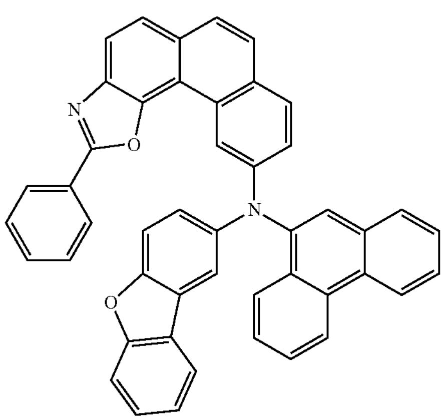
-continued
H1-220
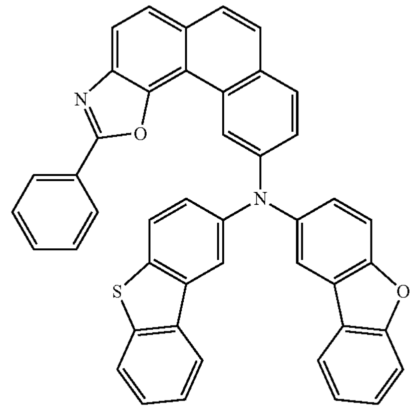
H1-221
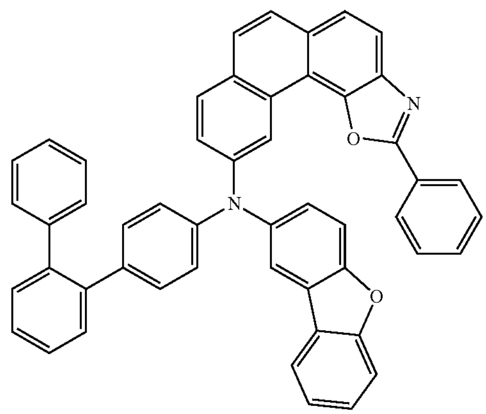
H1-222
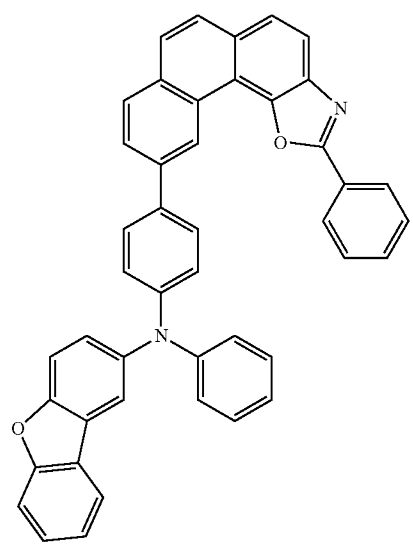

-continued
H1-223
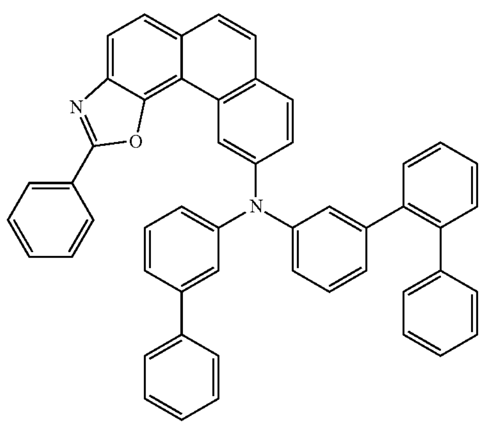
H1-224
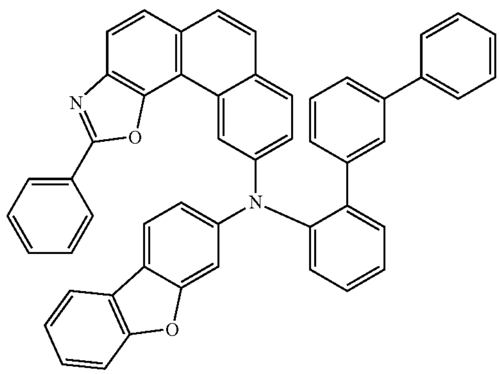
H1-225
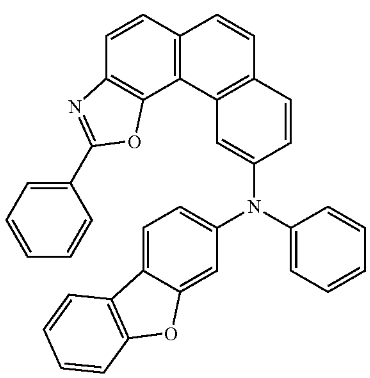
H1-226
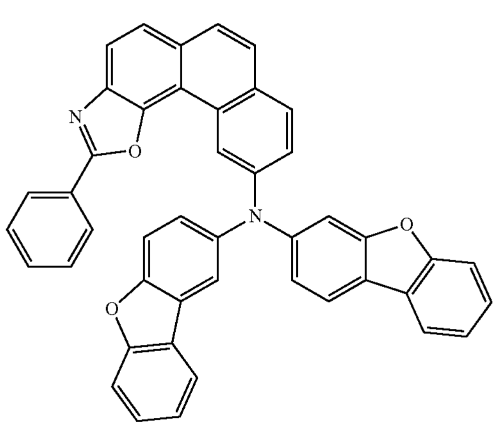
-continued
H1-227
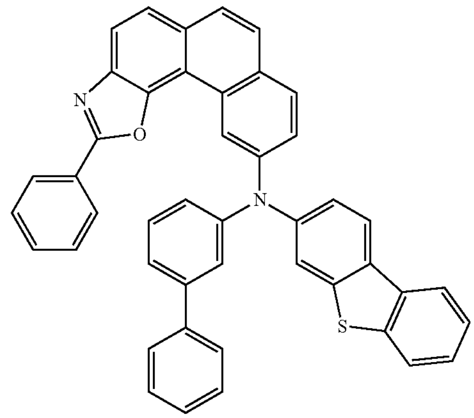
H1-228
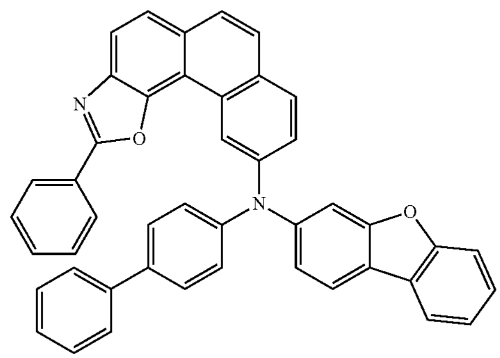
H1-229
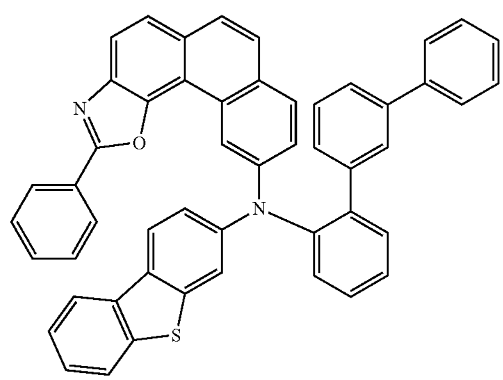
H1-230
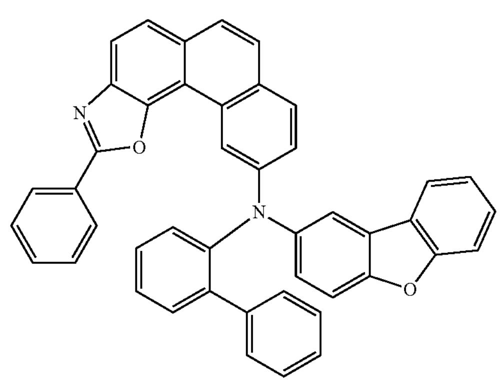

-continued
H1-231
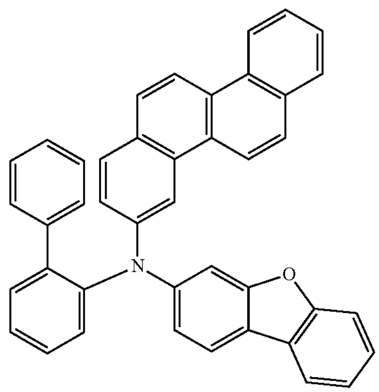
H1-232
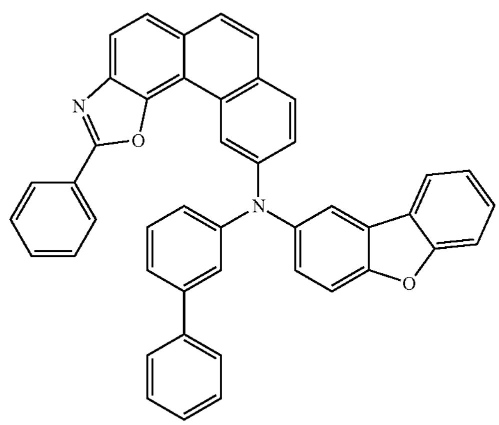
H1-233
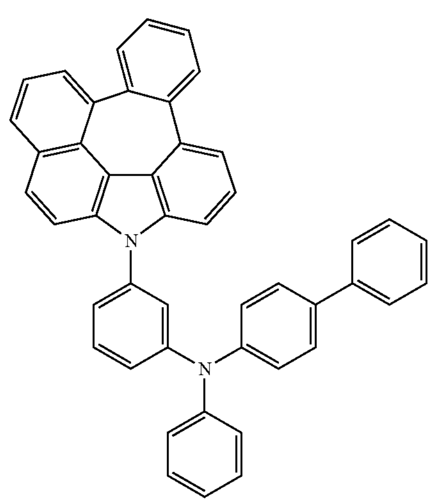
-continued
H1-234
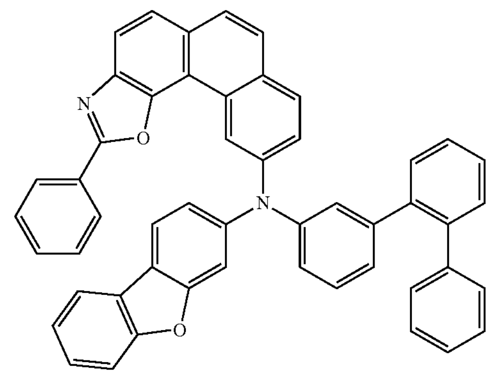
H1-235
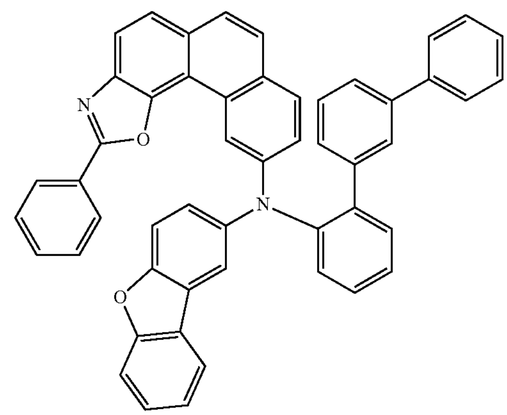
H1-236
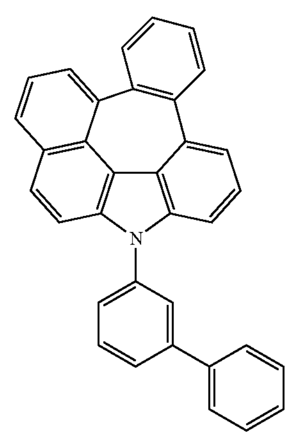

-continued
H1-237
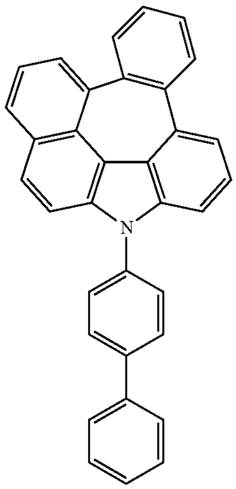
H1-238
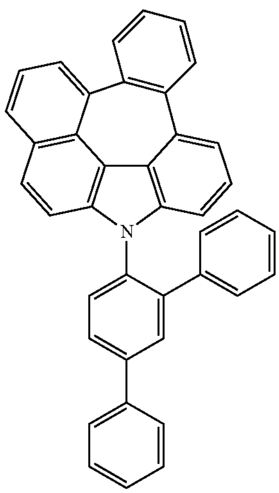
H1-239
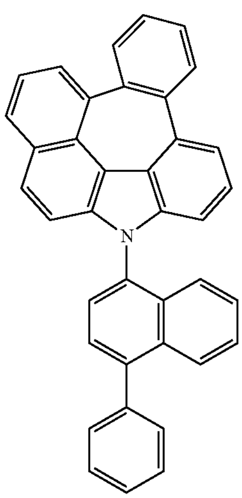
-continued
H1-240
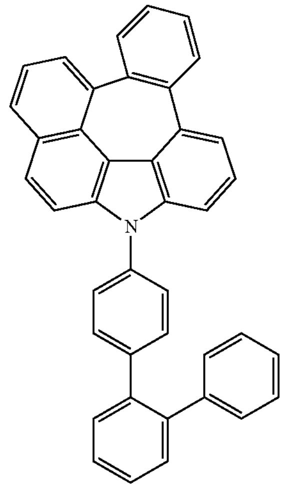
H1-241
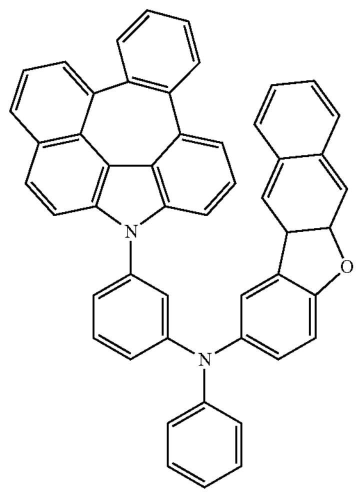
H1-242
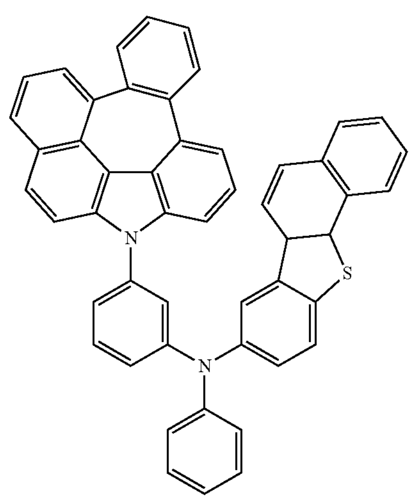

-continued
H1-243
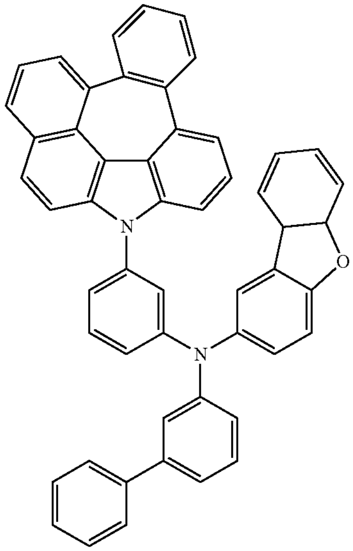
H1-244
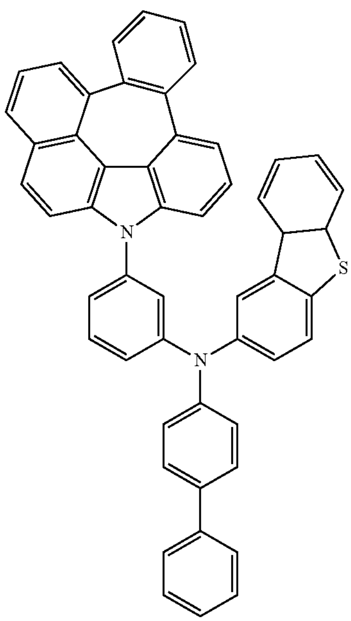
H1-245
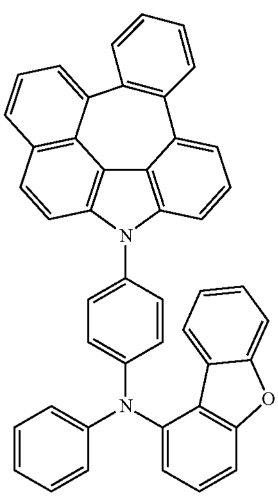
-continued
H1-246
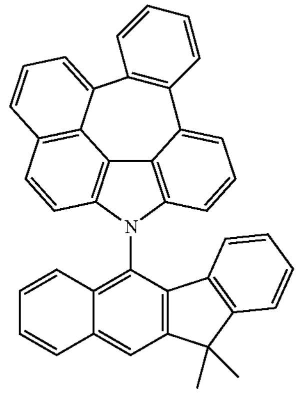
H1-247
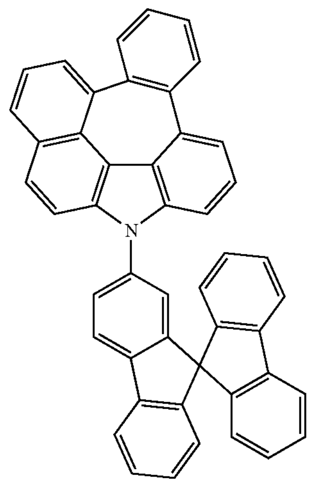
H1-248
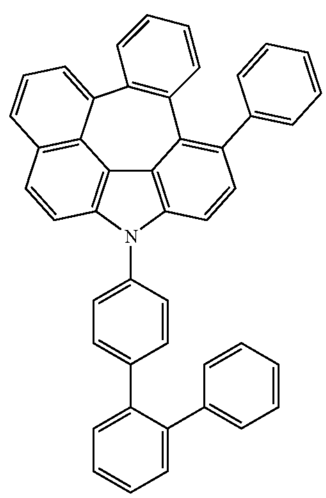

-continued
H1-249
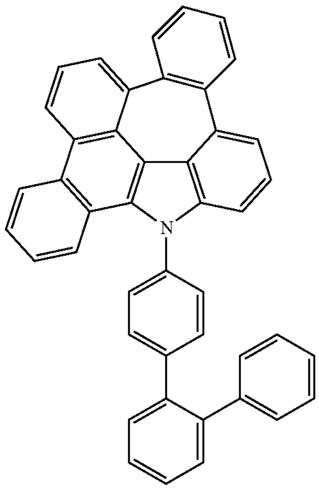
H1-250
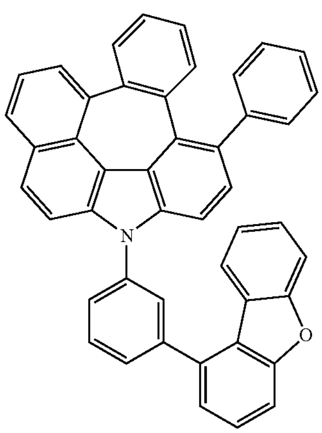
H1-251
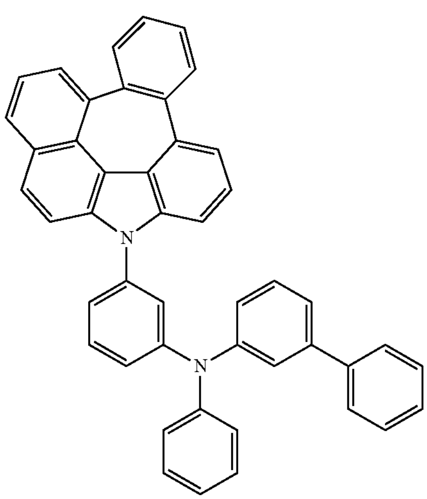
-continued
H1-252
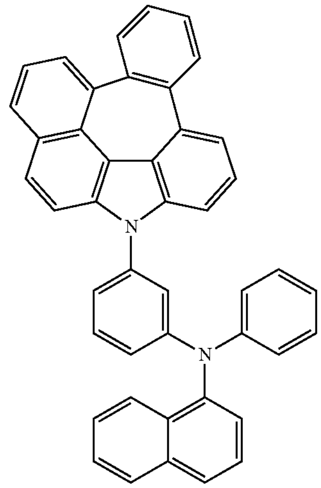
H1-253
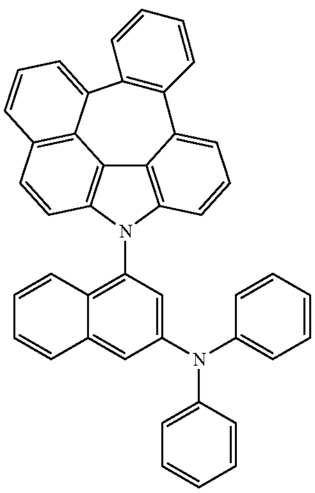
H1-254
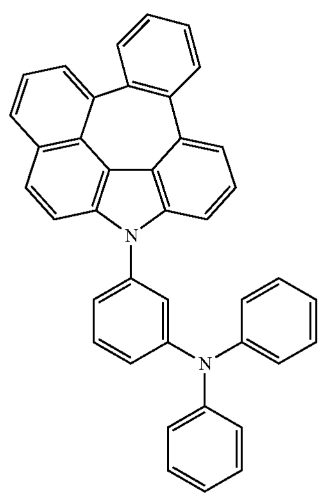

-continued
H1-255
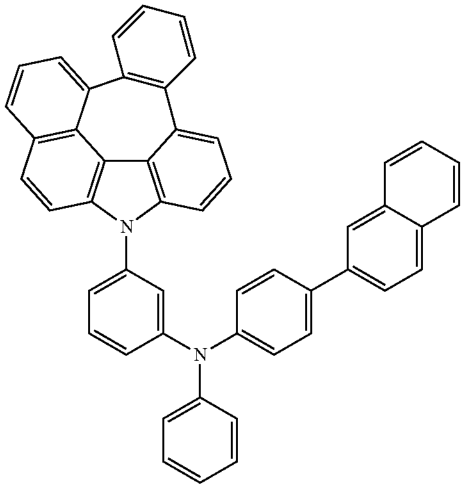
H1-256
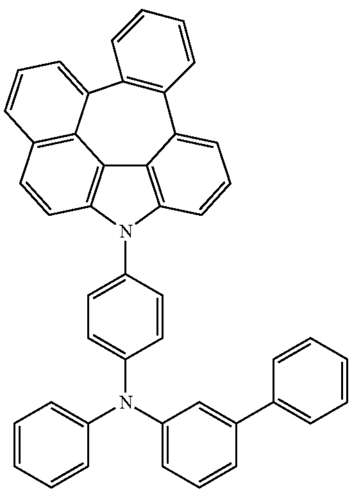
H1-257
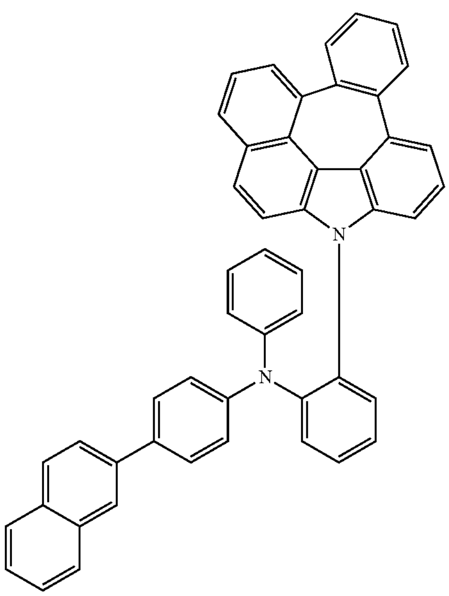
-continued
H1-258
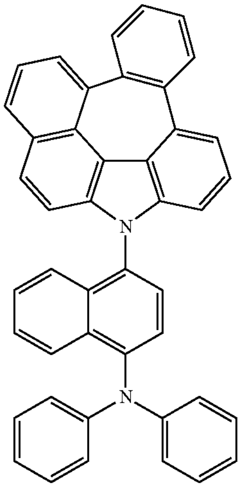
H1-259
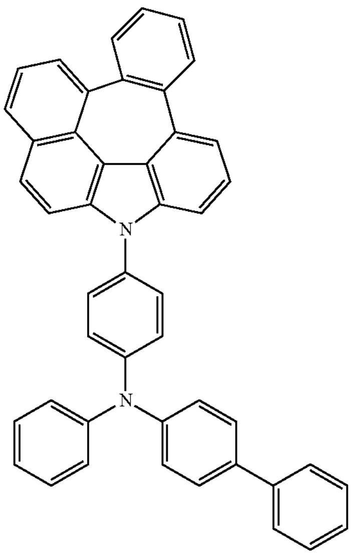
H1-260
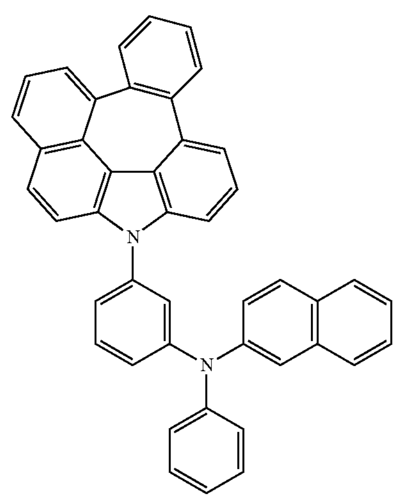

-continued
H1-261
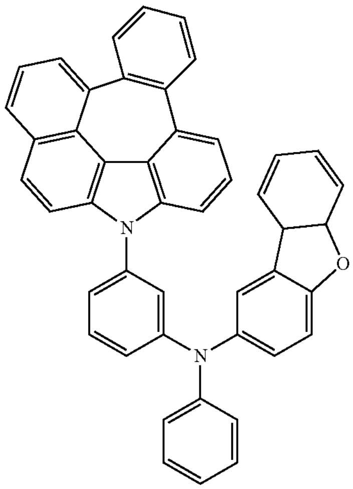
H1-262
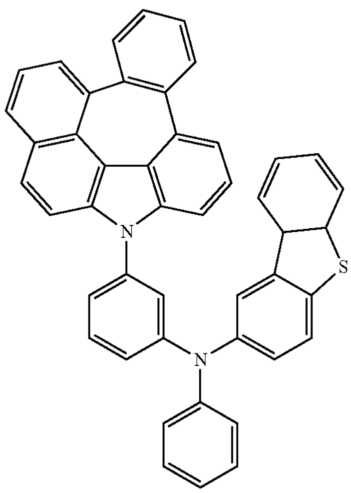
H1-263
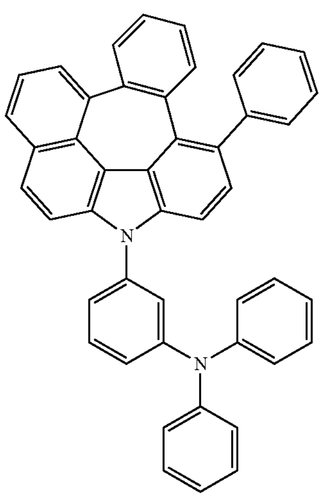
-continued
H1-264
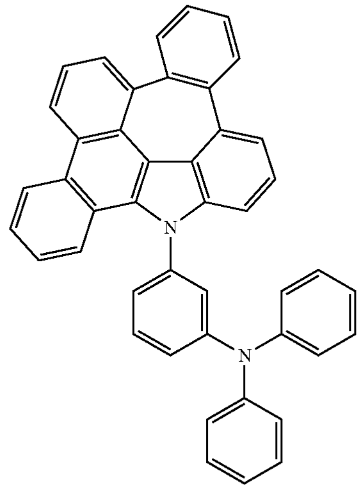
H1-265
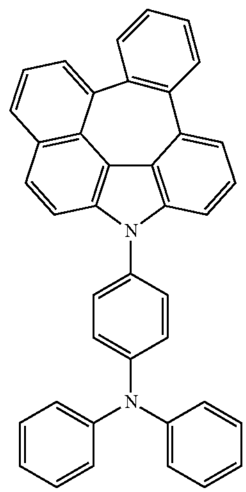
H1-266
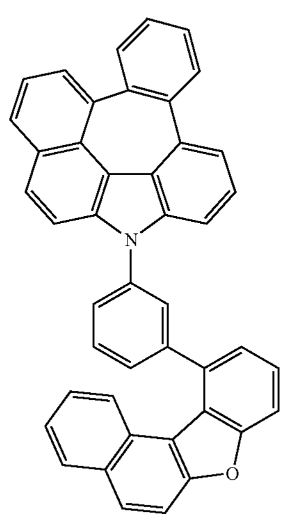

-continued
H1-267
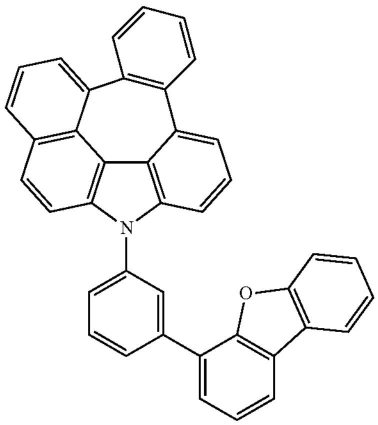
H1-268
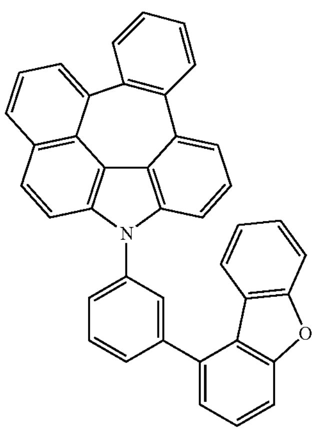
H1-269
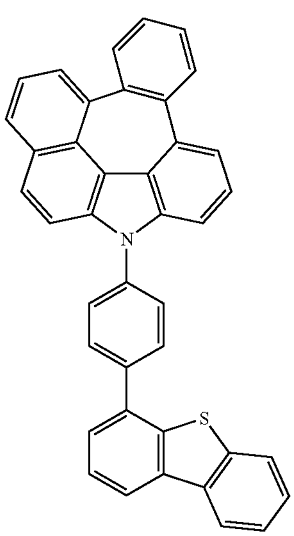
-continued
H1-270
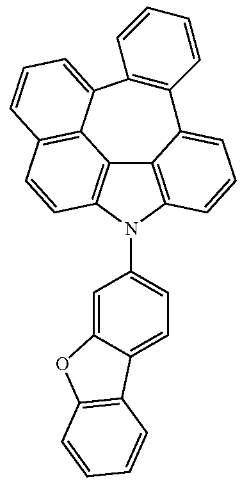
H1-271
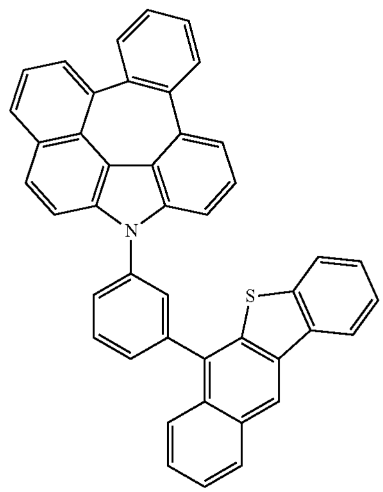
H1-272
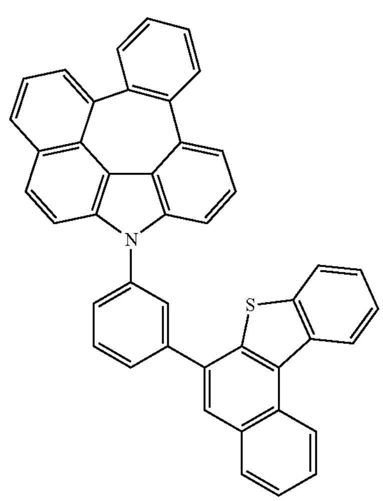

-continued
H1-273
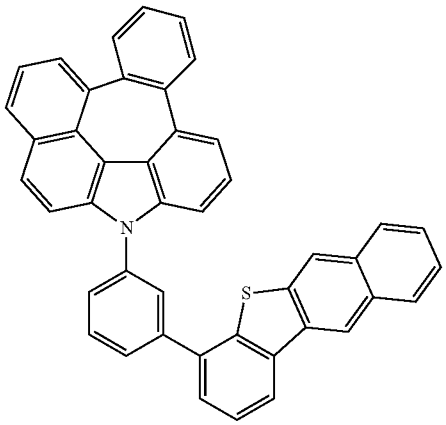
H1-274
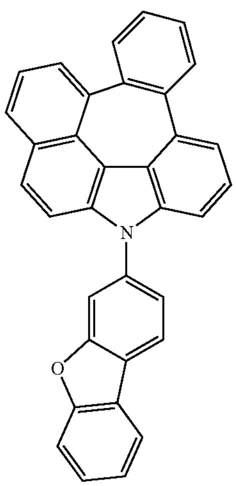
H1-275
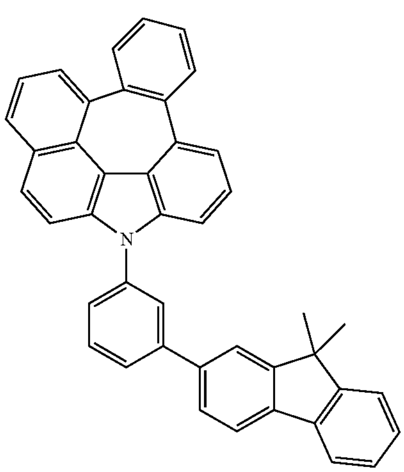
-continued
H1-276
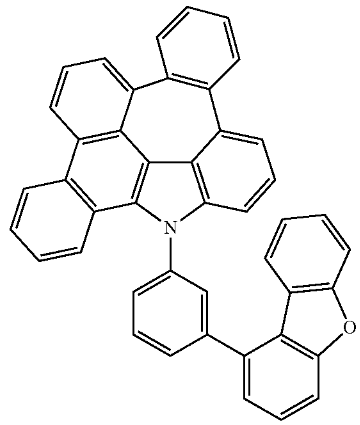
H1-277
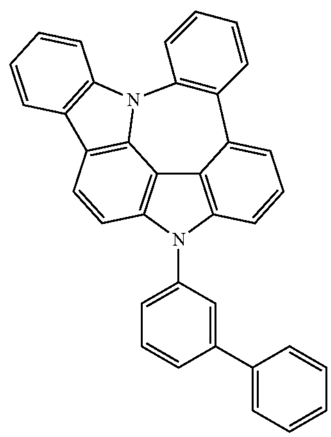
H1-278
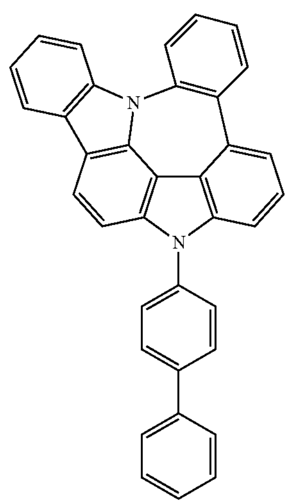

-continued
H1-279
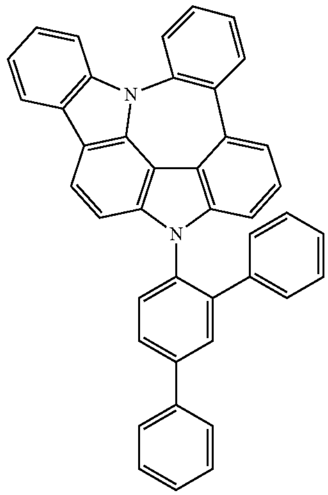
H1-280
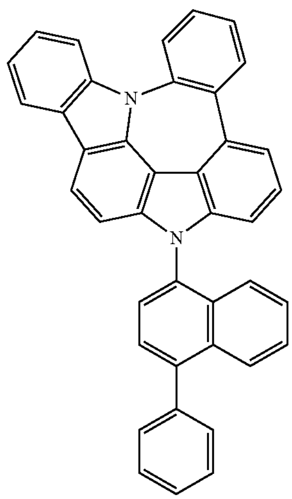
H1-281
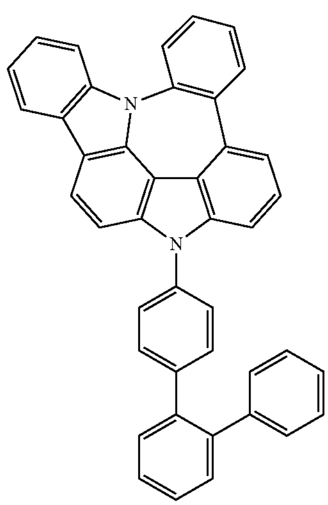
-continued
H1-282
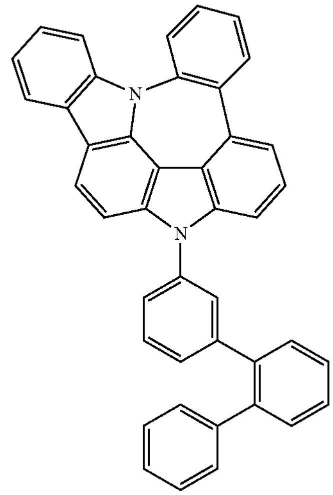
H1-283
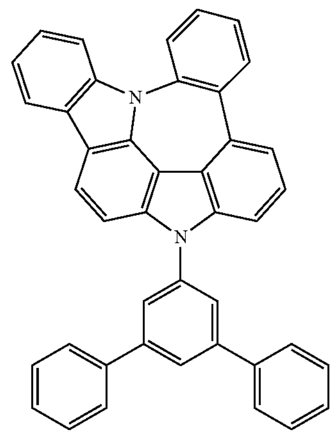
H1-284
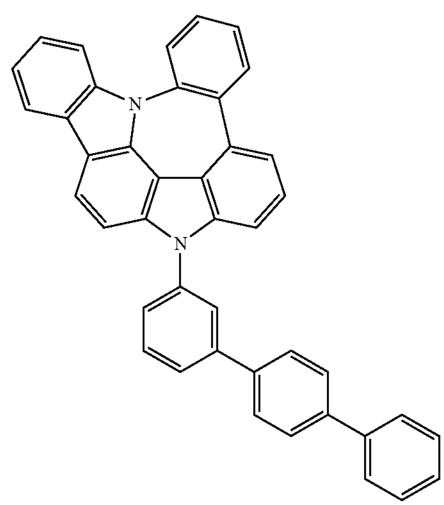

-continued
H1-285
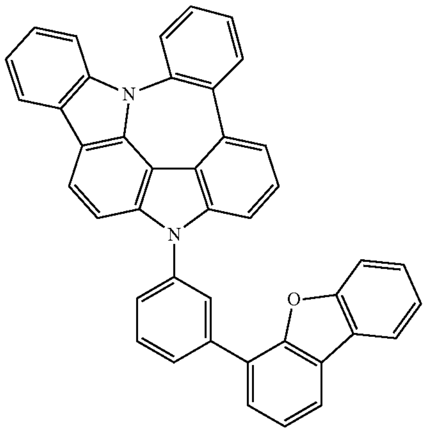
H1-286
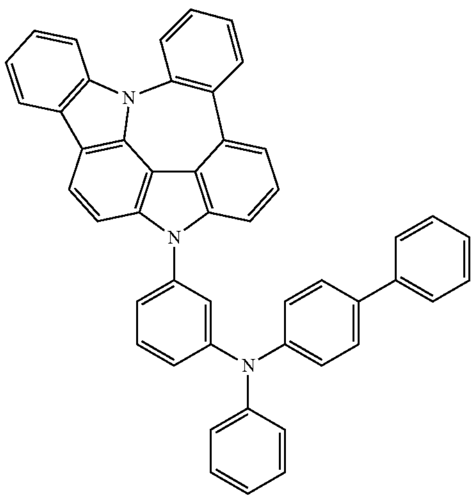
H1-287
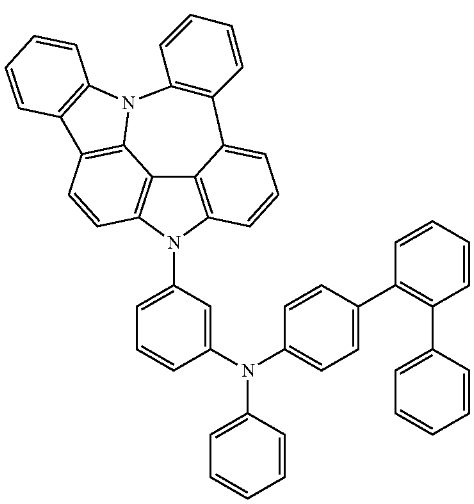
-continued
H1-288
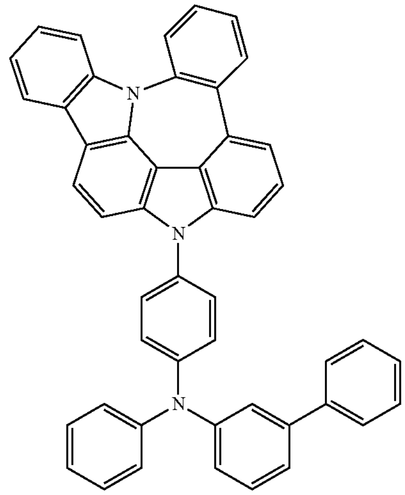
H1-289
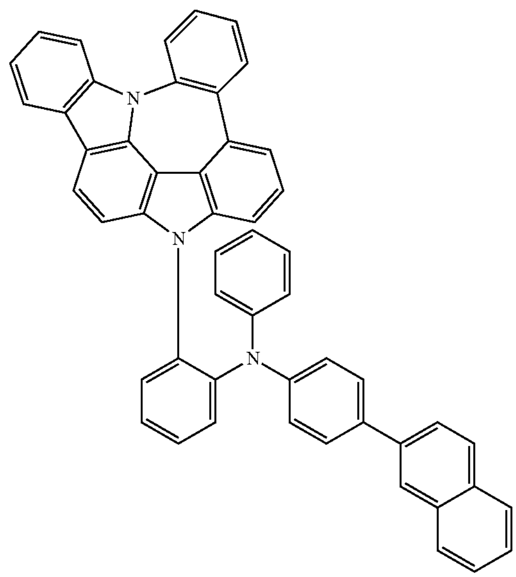
H1-290
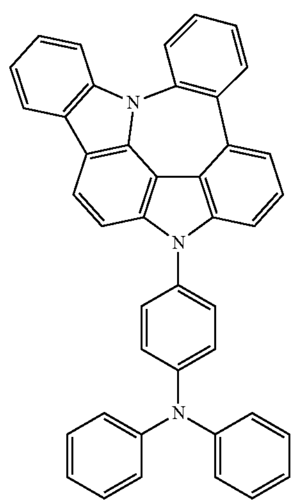

-continued
H1-291
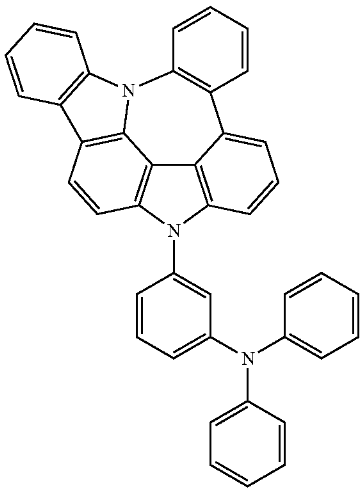
H1-292
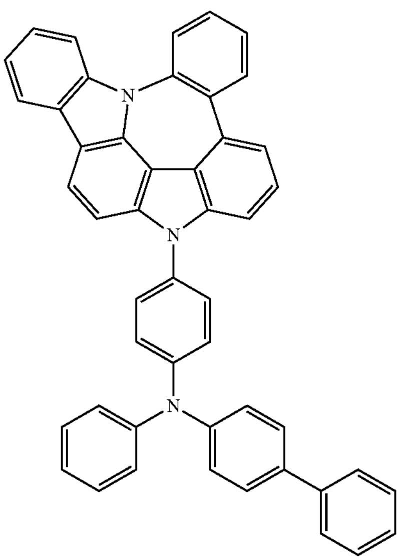
H1-293
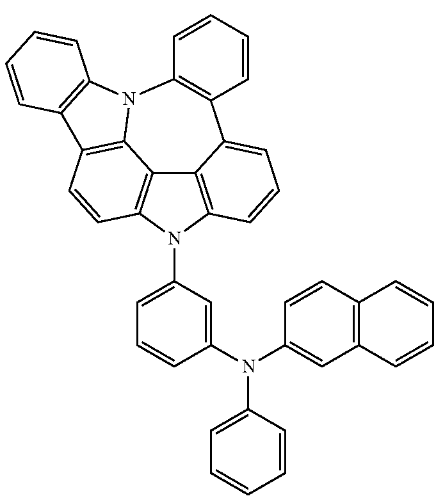
H1-294
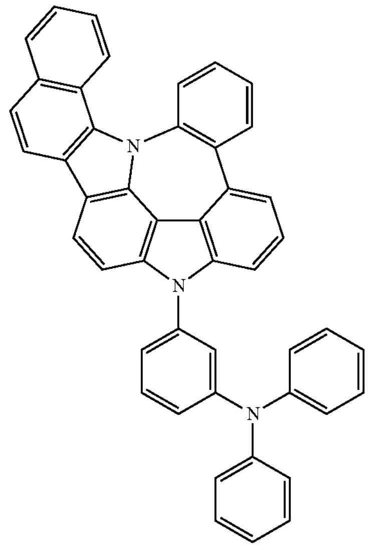
H1-295
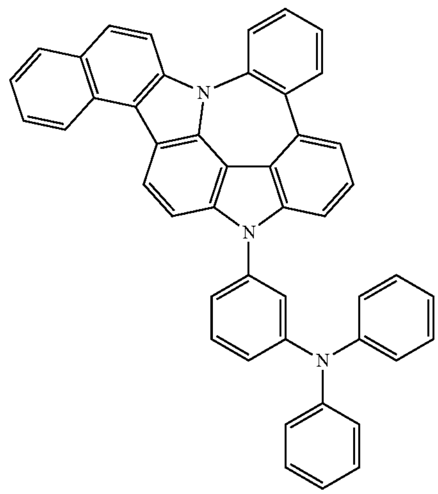
H1-296
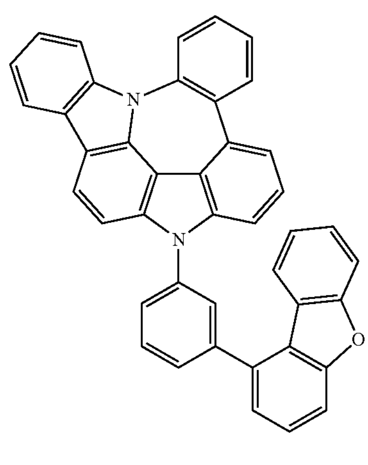

-continued
H1-297
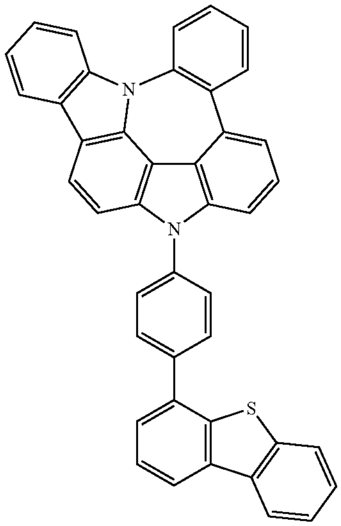
H1-298
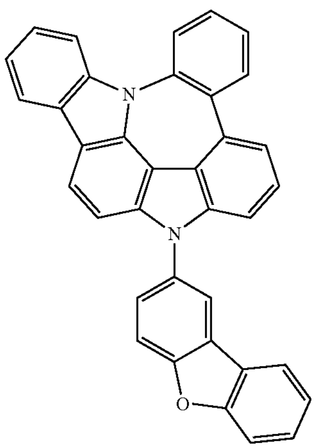
H1-299
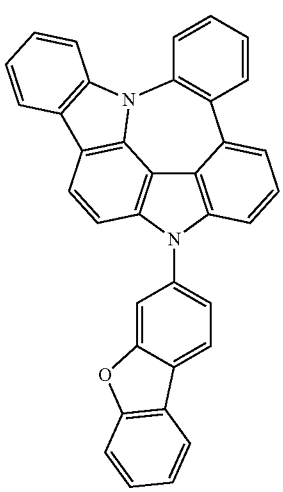
-continued
H1-300
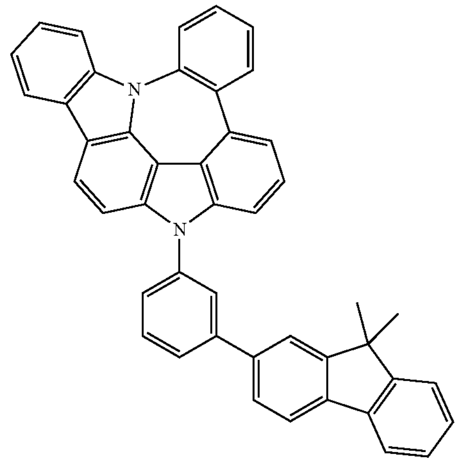
H1-301
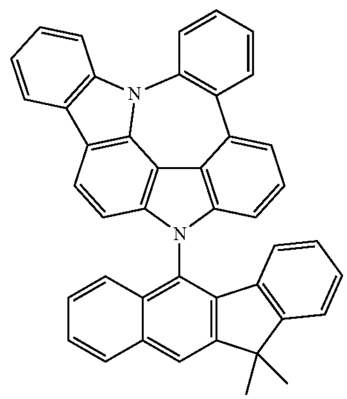
H1-302
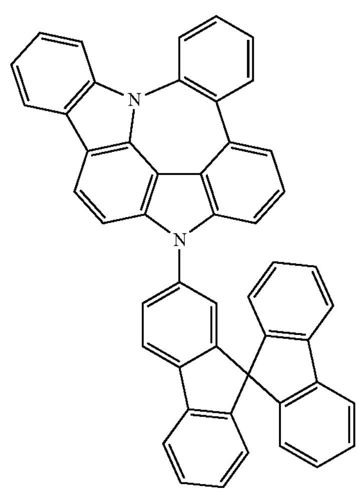

-continued
H1-303
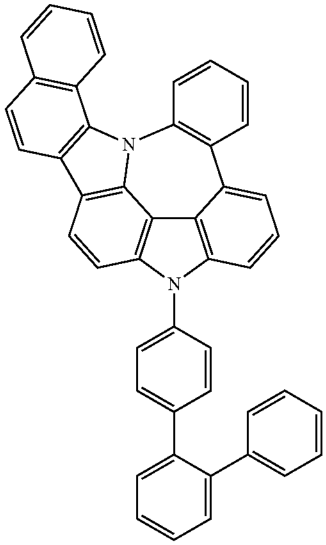
H1-304
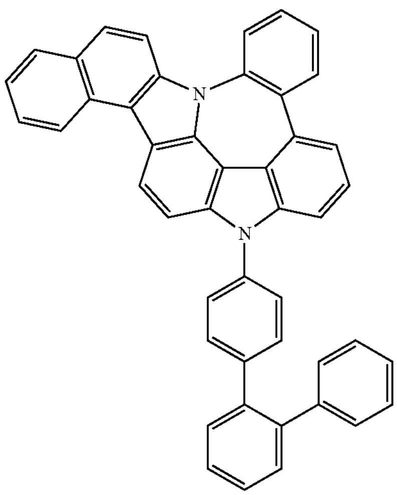
H1-305
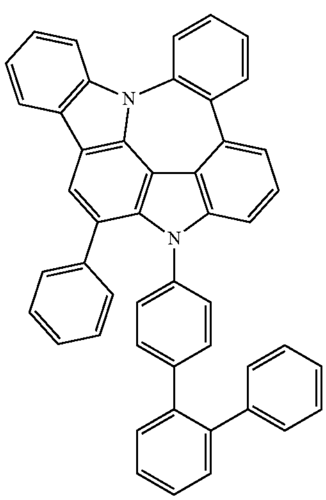
-continued
H1-306
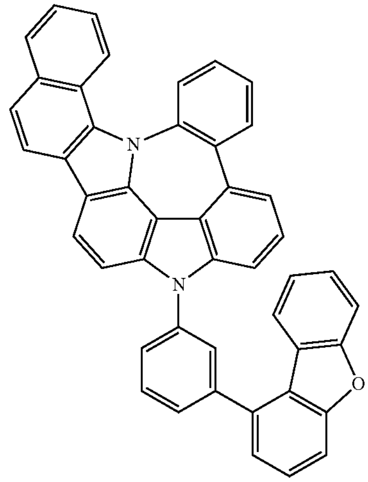
H1-307
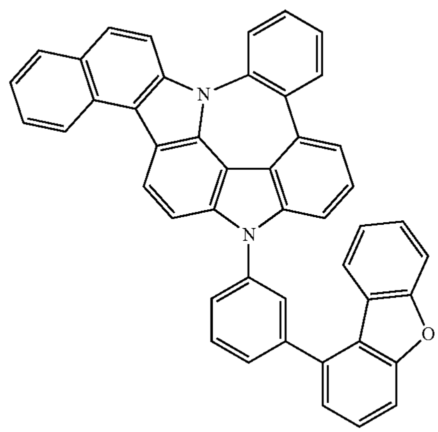
H1-308
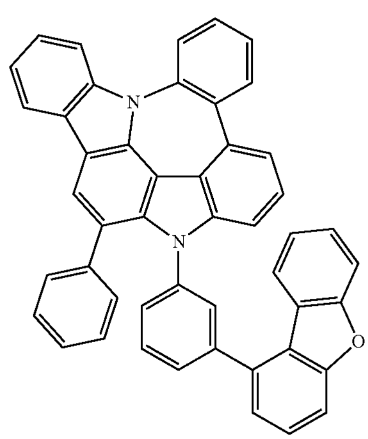

-continued
H1-309
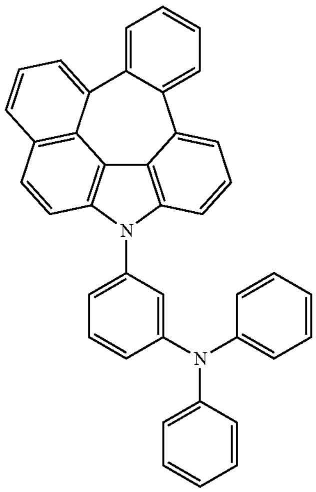
and
H1-310
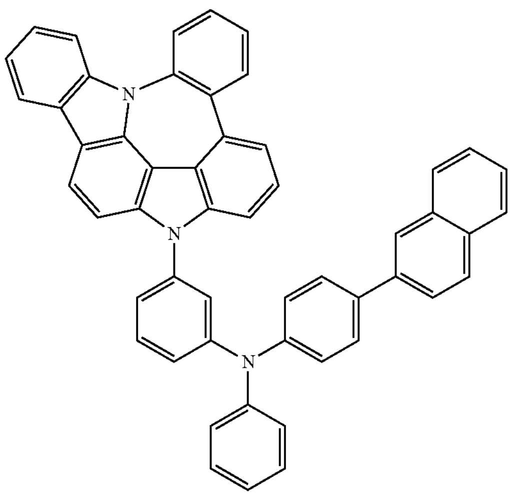
.
10. The plurality of host materials according to claim 1, wherein the compound represented by any one of the formulas 2 to 4 is at least one selected from the group consisting of the following compounds:
H2-1
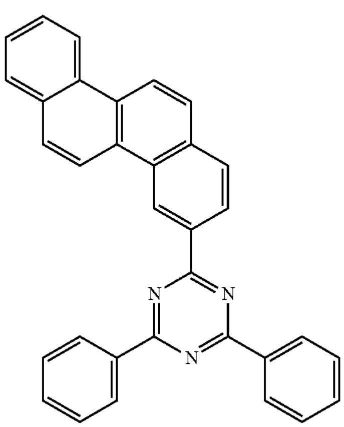
-continued
H2-2
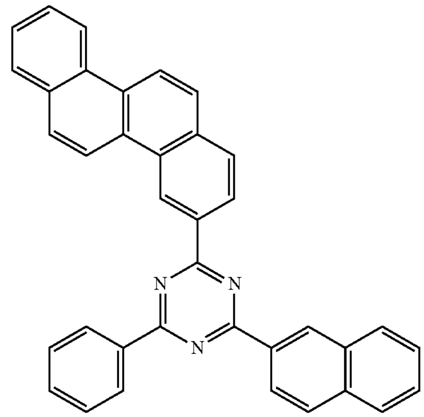
H2-3
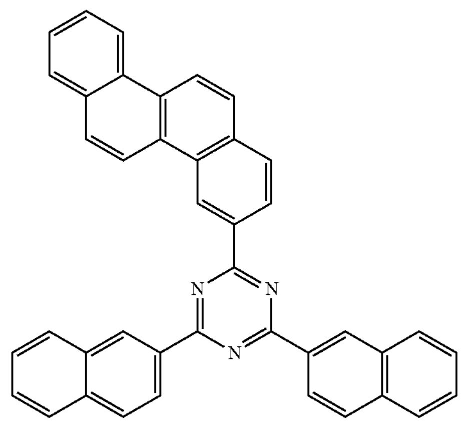
H2-4
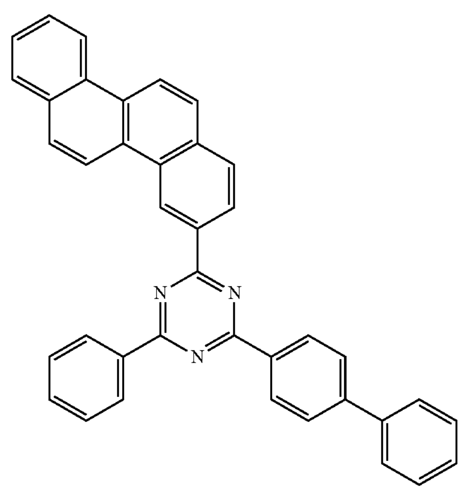

-continued
H2-5
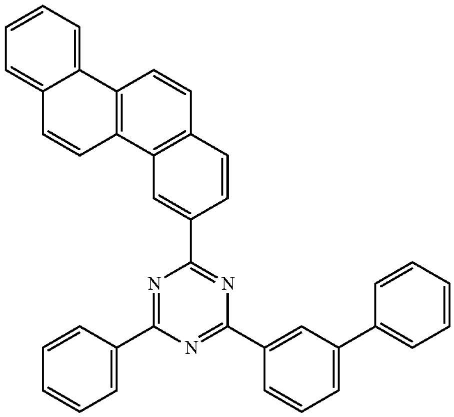
H2-6
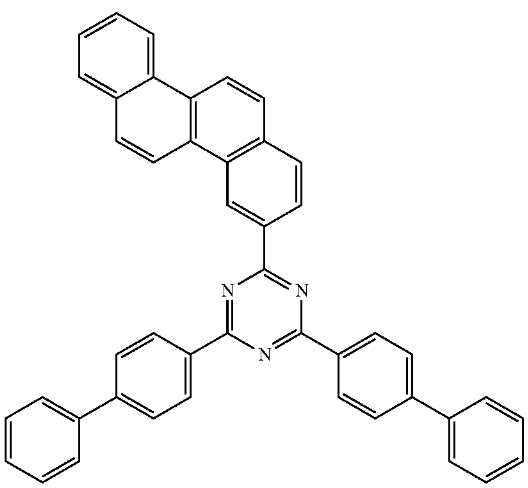
H2-7
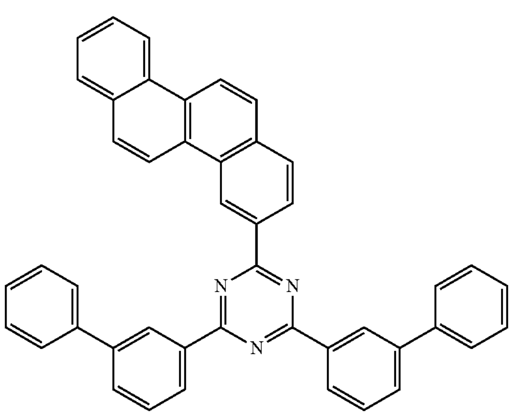
-continued
H2-8
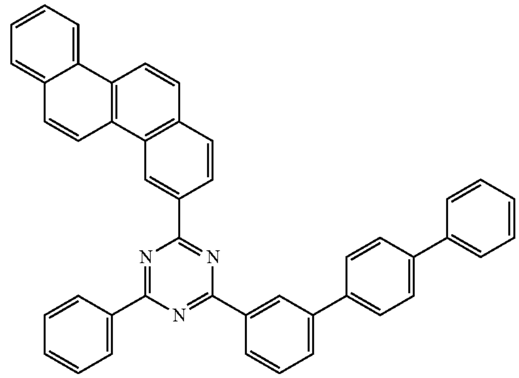
H2-9
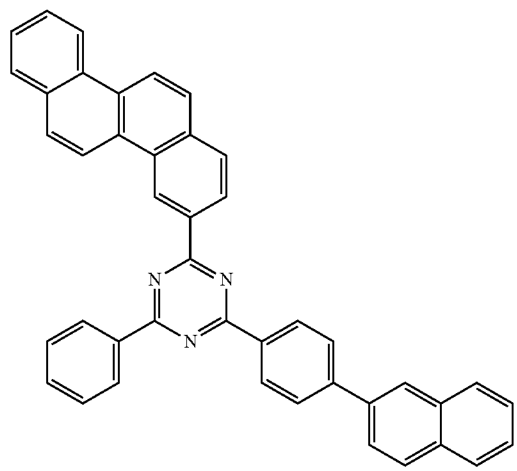
H2-10
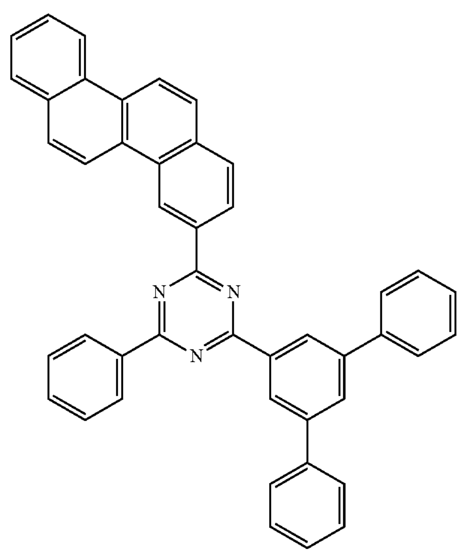

-continued
H2-11
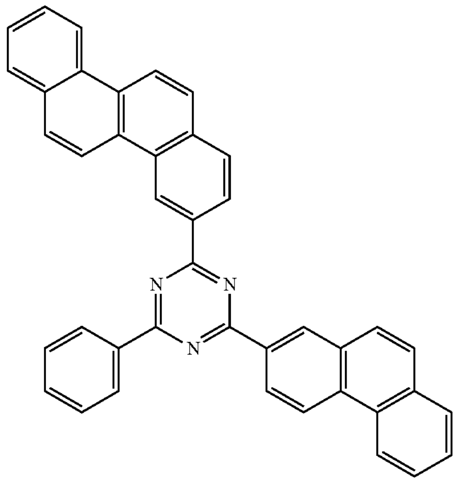
H2-12
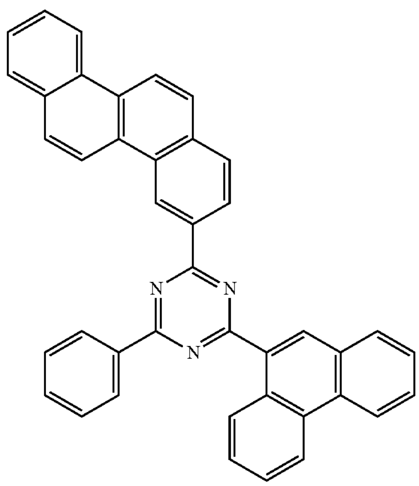
H2-13
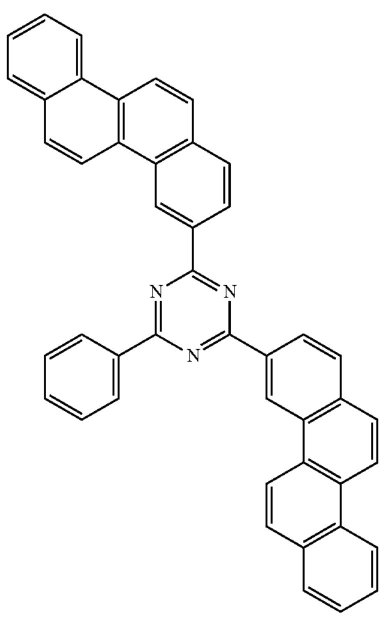
-continued
H2-14
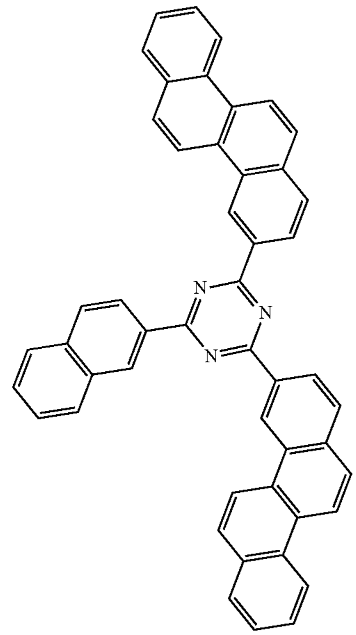
H2-15
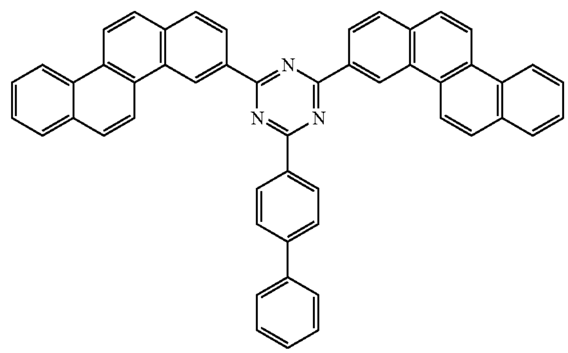
H2-16
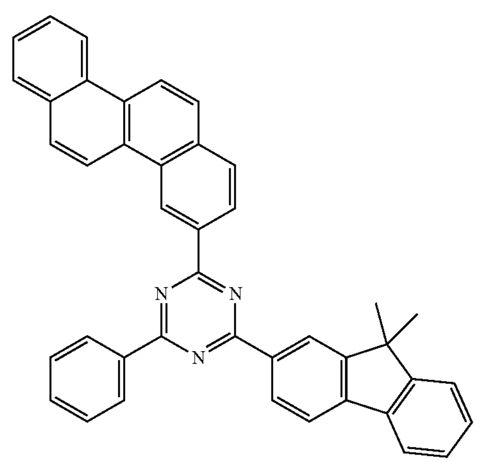

-continued
H2-17
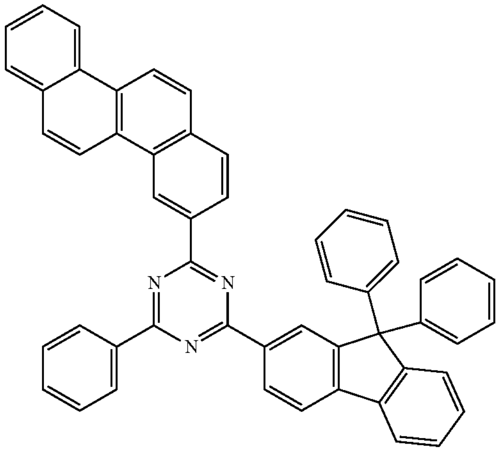
H2-18
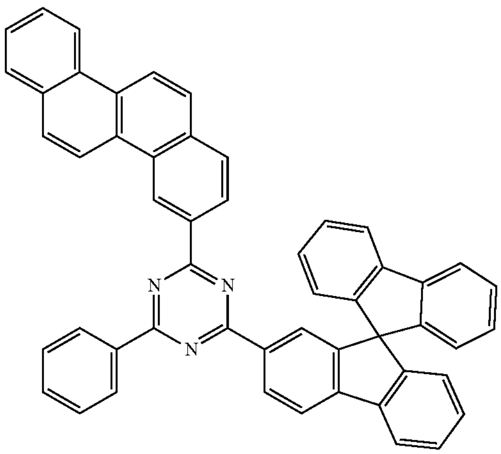
H2-19
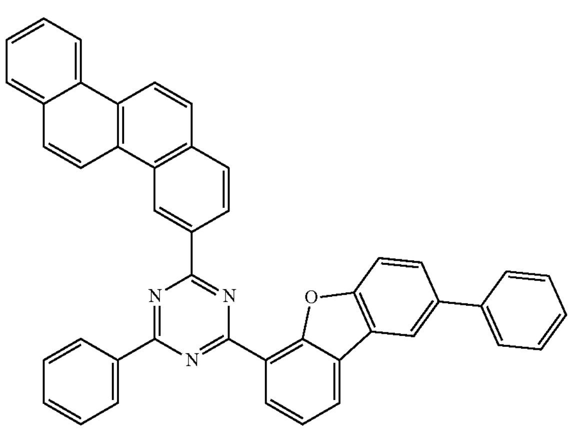
-continued
H2-20
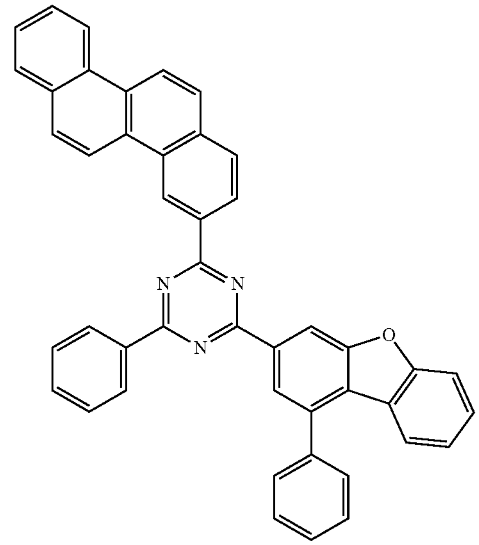
H2-21
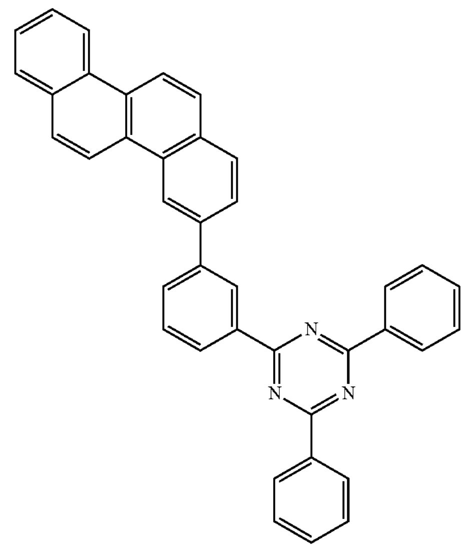
H2-22
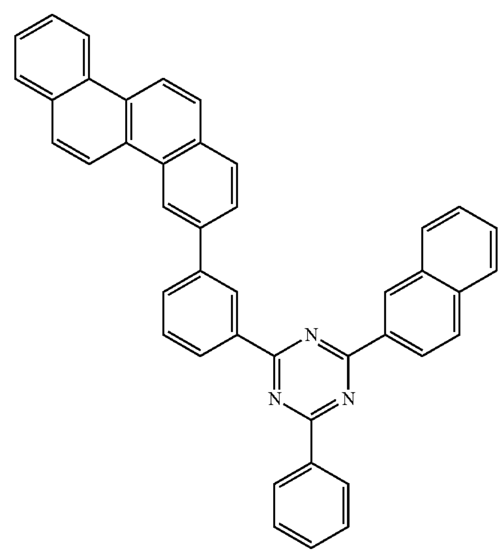

-continued
H2-23
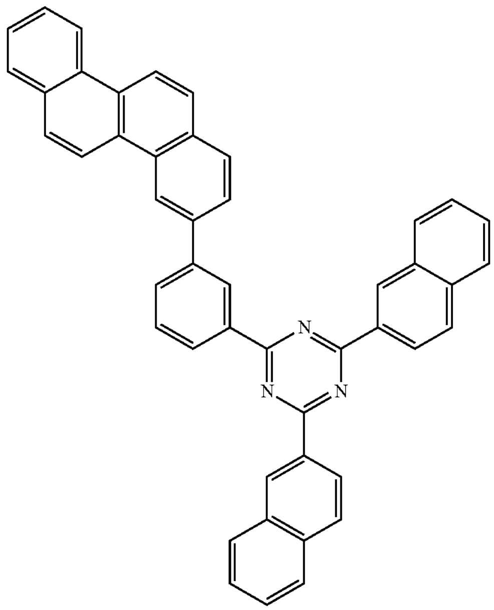
H2-24
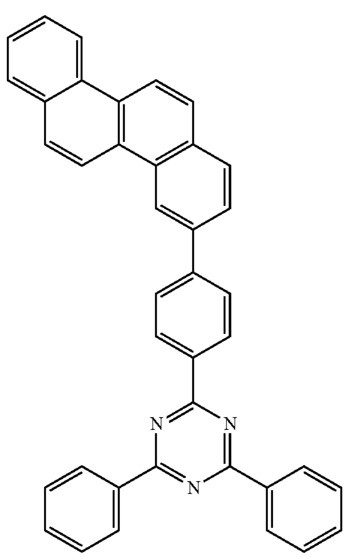
-continued
H2-25
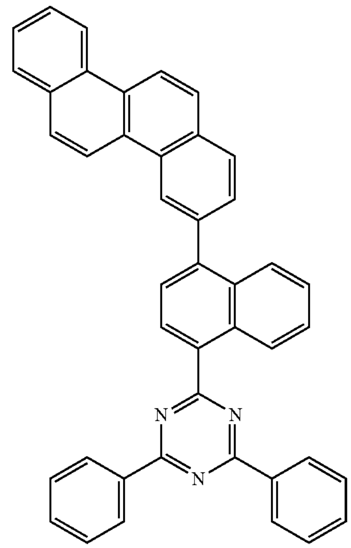
H2-26
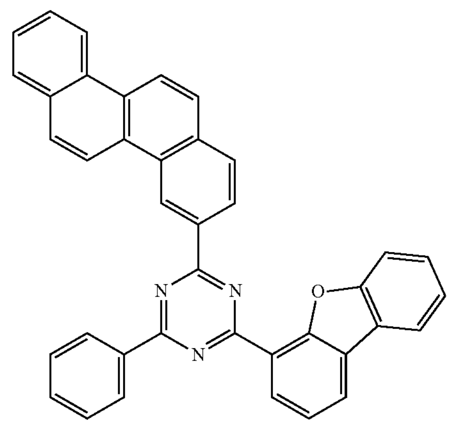
H2-27
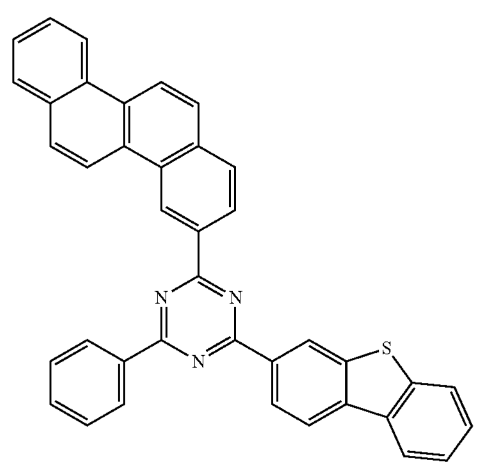

-continued
H2-28
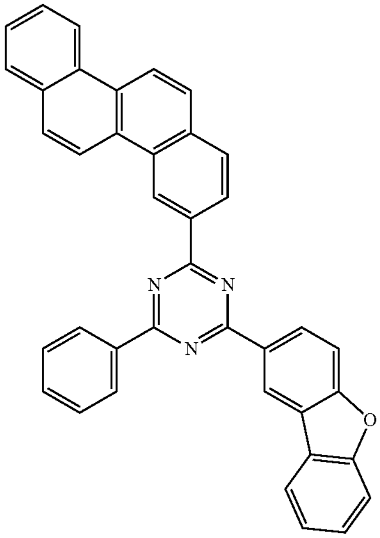
H2-29
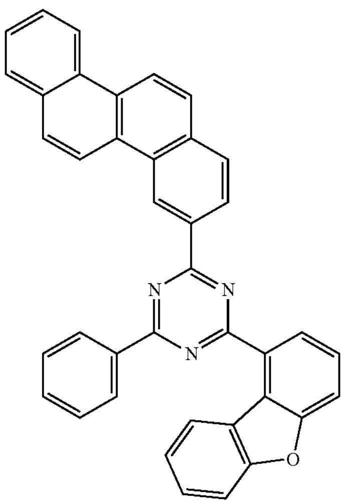
H2-30
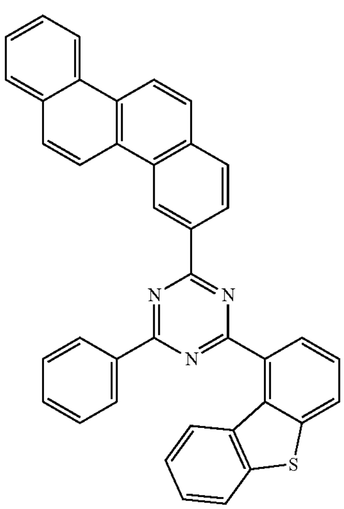
-continued
H2-31
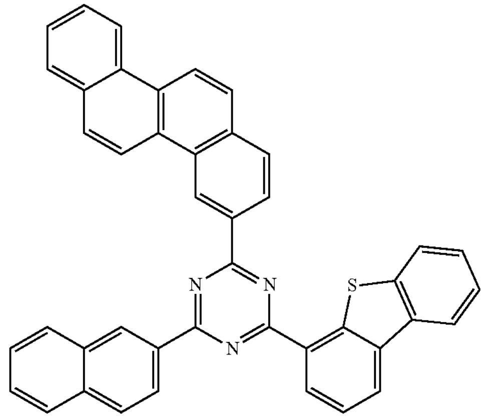
H2-32
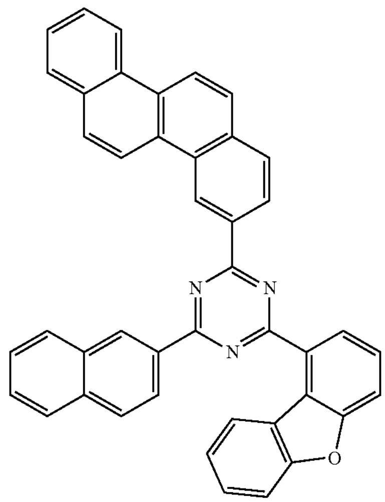
H2-33
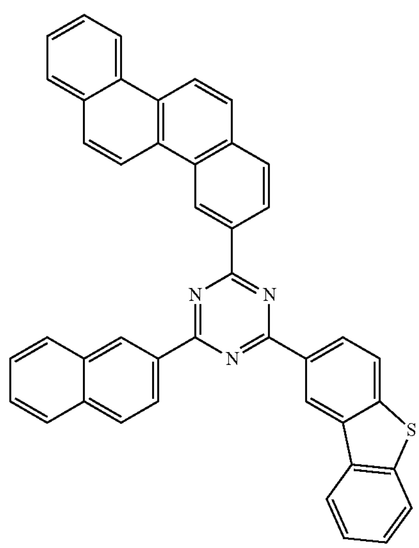

H2-34
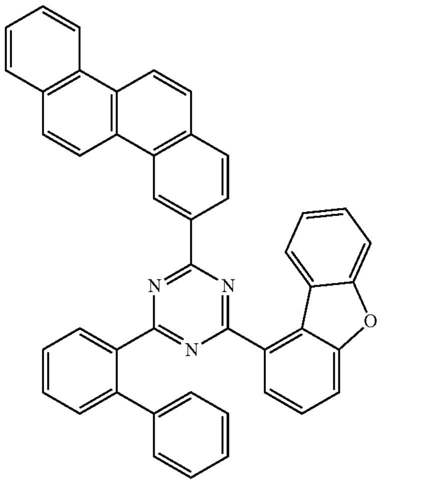
H2-35
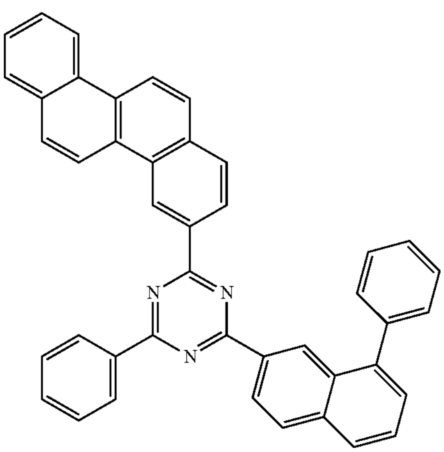
H2-36
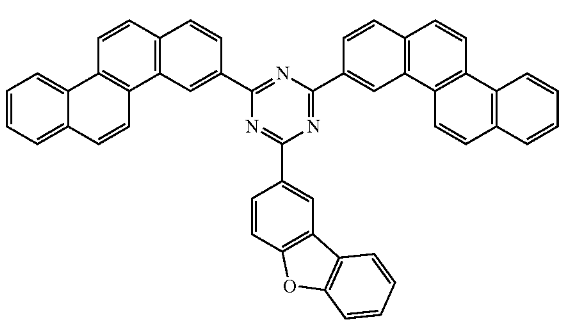
H2-37
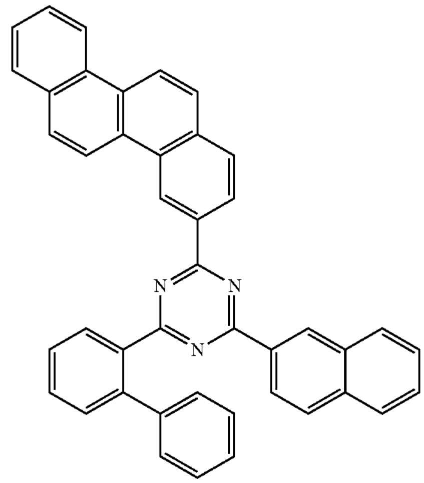
H2-38
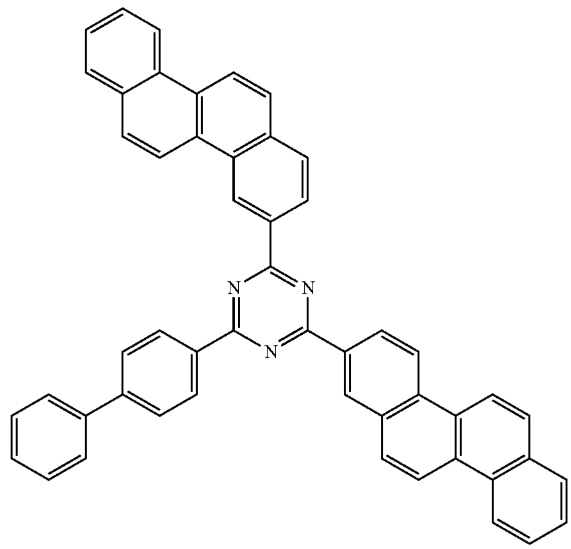
H2-39
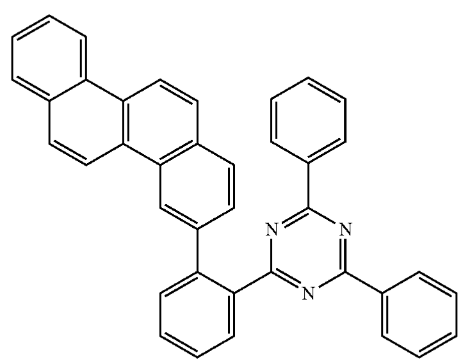

-continued
H2-40
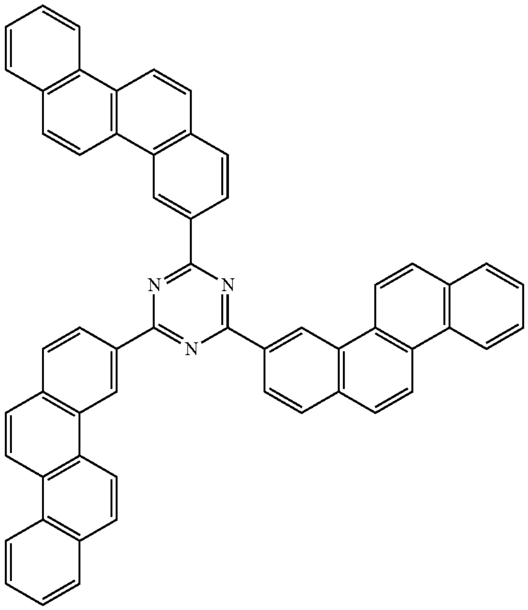
H2-41
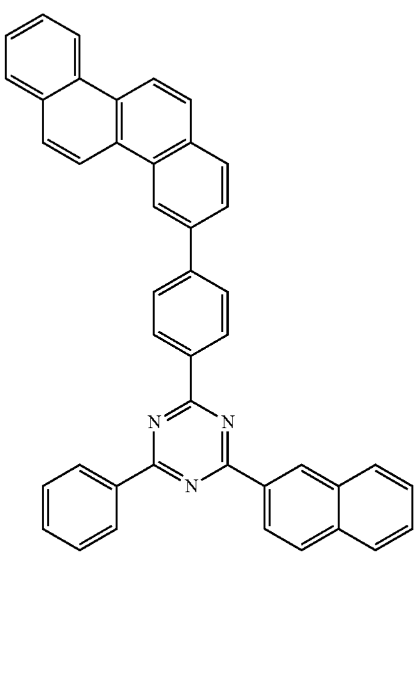
-continued
H2-42
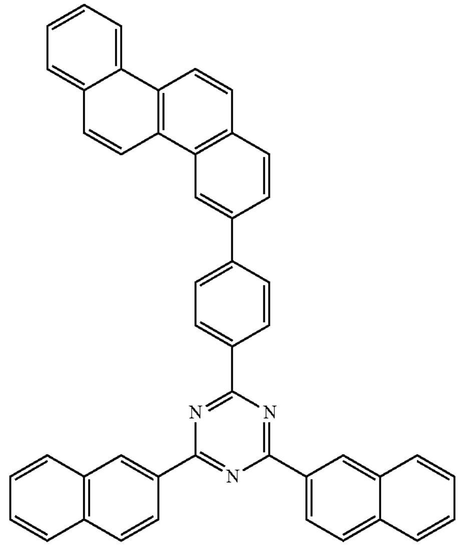
H2-43
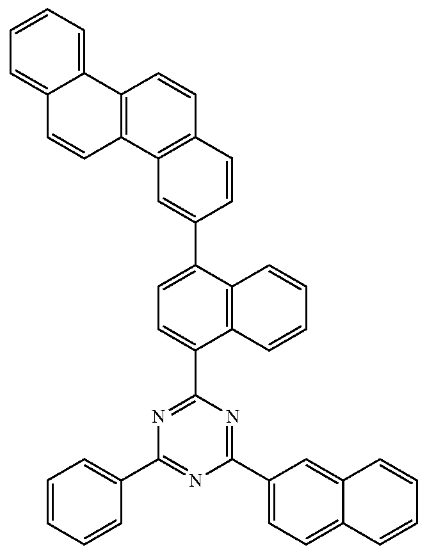
H2-44
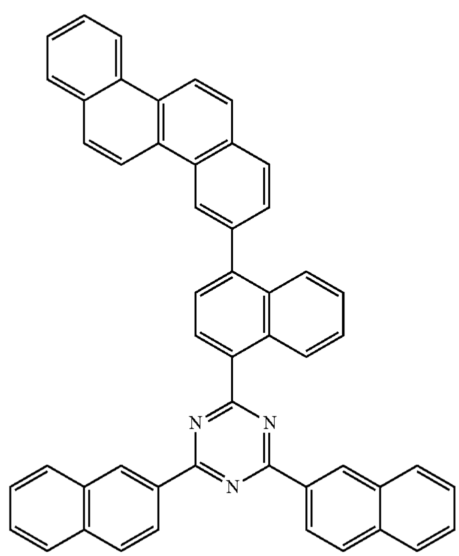

-continued
H2-45
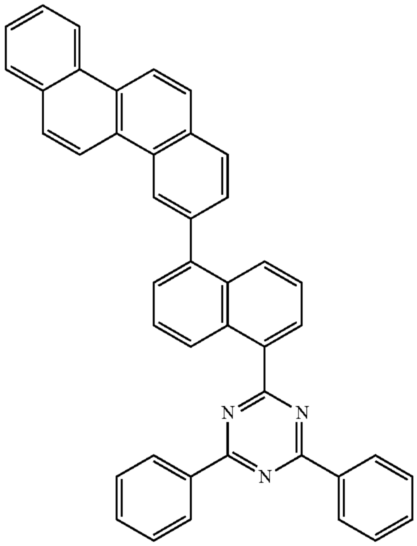
H2-46
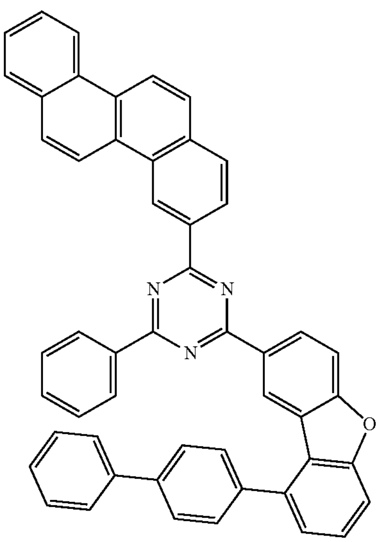
H2-47
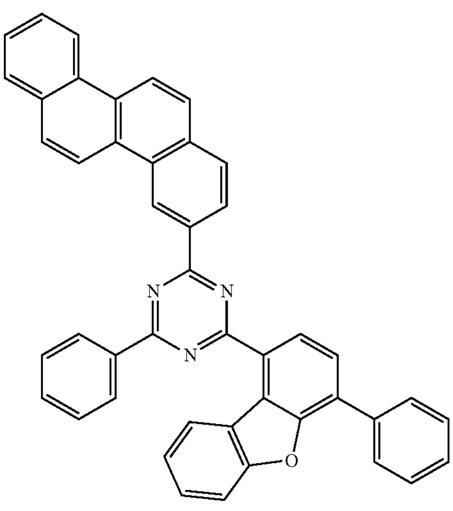
-continued
H2-48
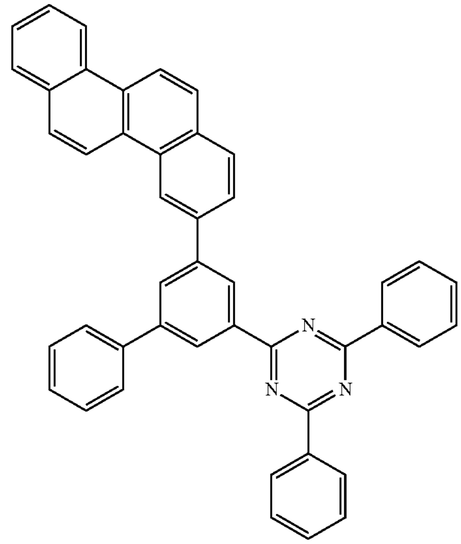
H2-49
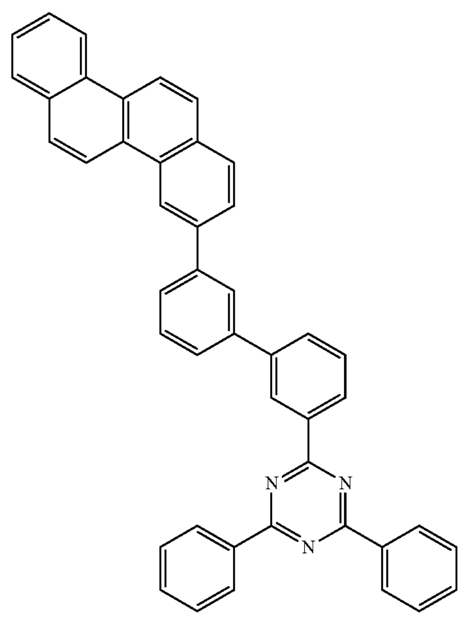

-continued
H2-50
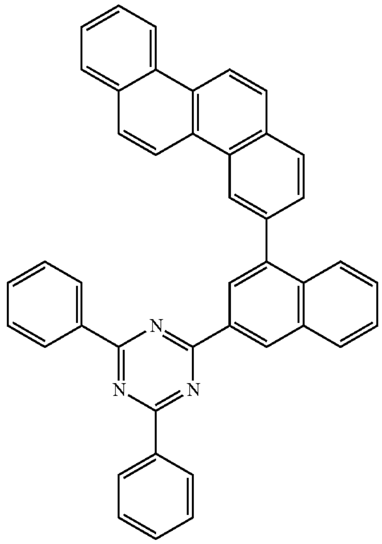
H2-51
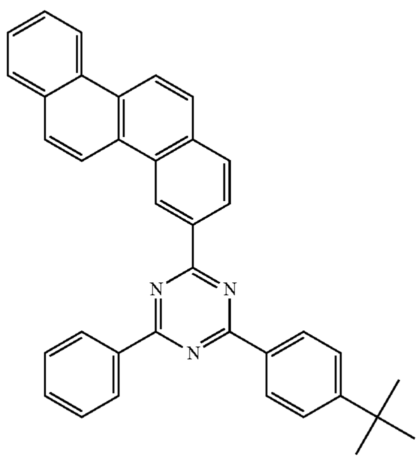
H2-52
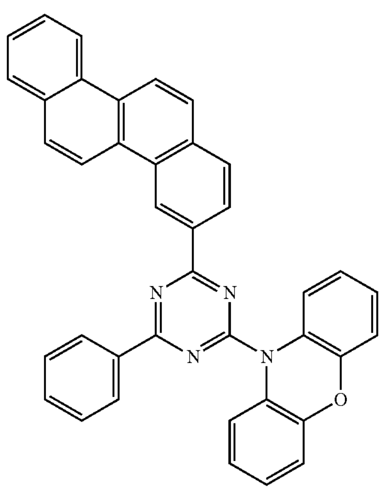
-continued
H2-53
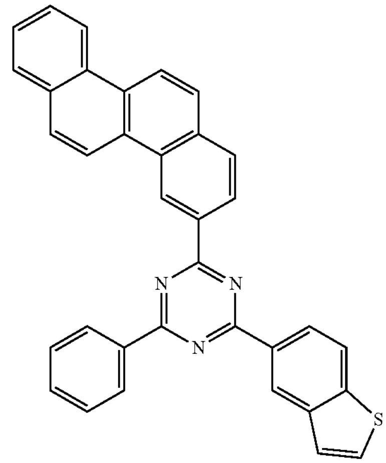
H2-54
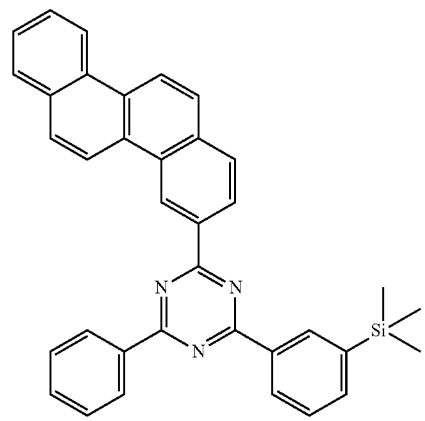
H2-55
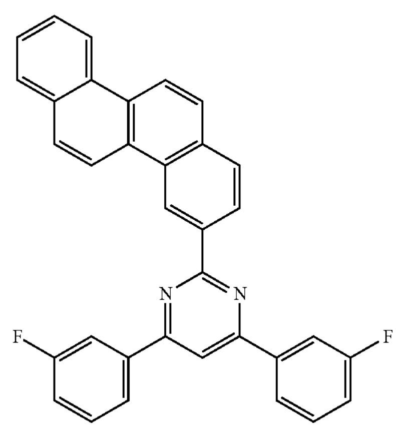

-continued
H2-56
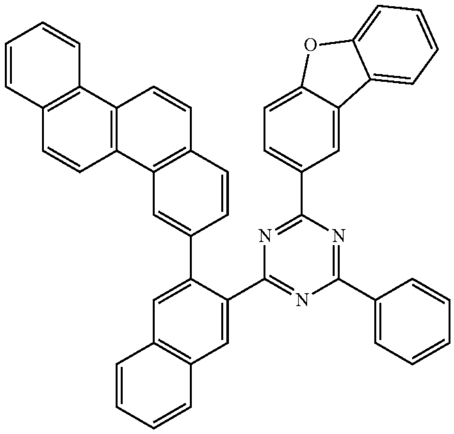
H2-57
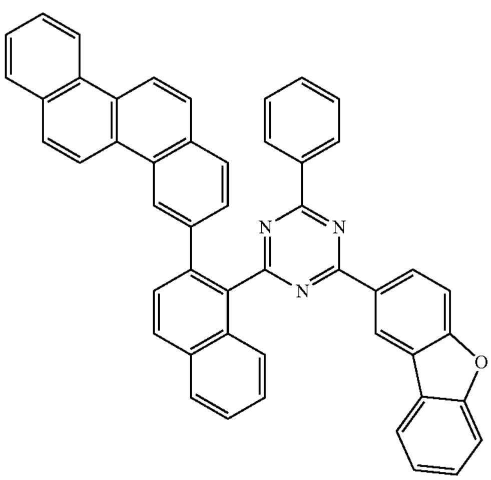
H2-58
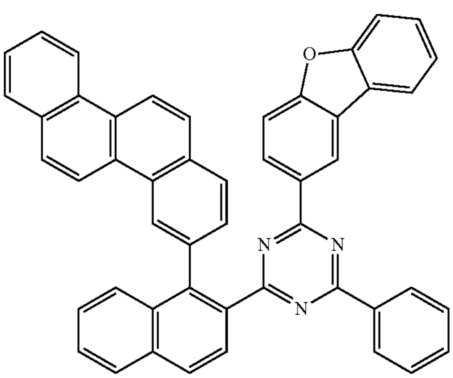
-continued
H2-59
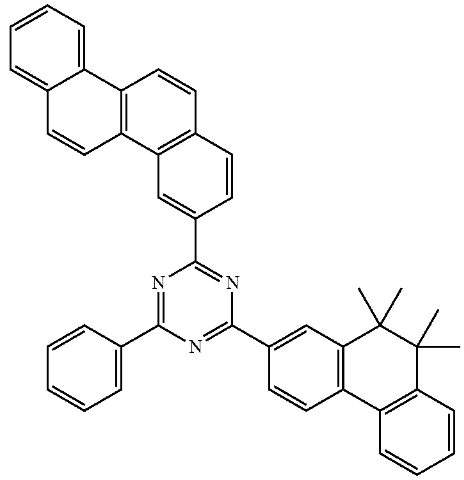
H2-60
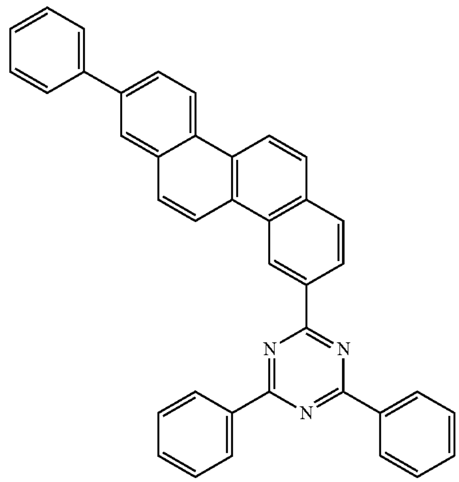
H2-61
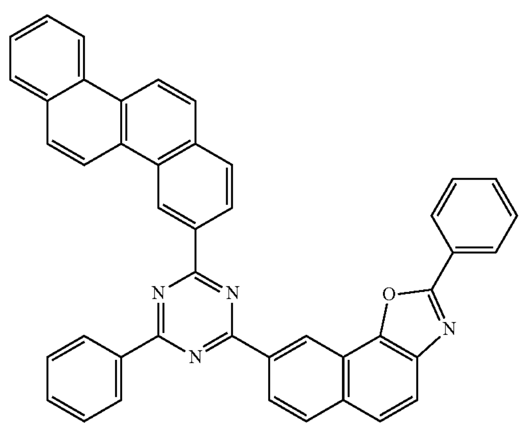

-continued
H2-62
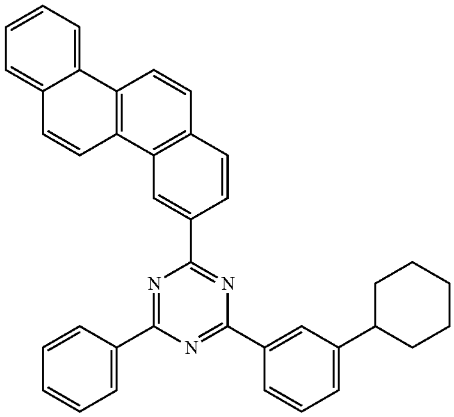
H2-63
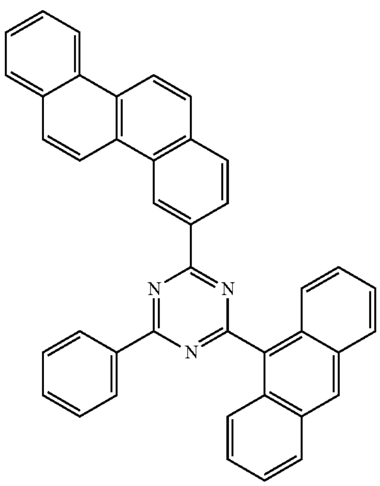
H2-64
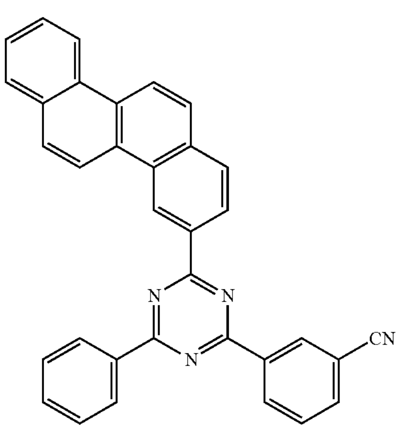
-continued
H2-65
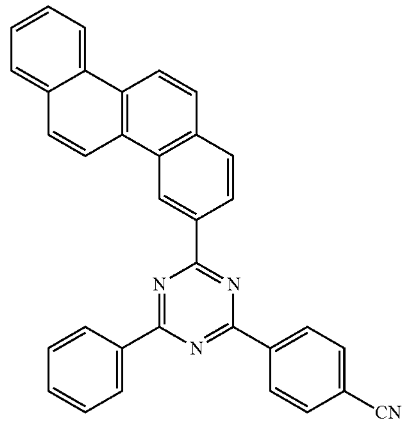
H2-66
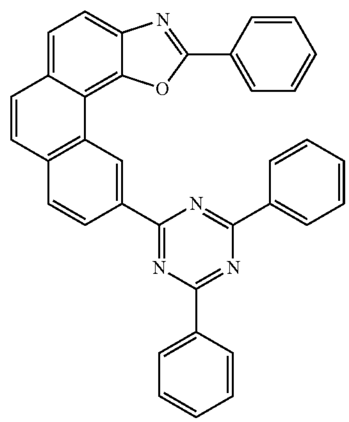
H2-67
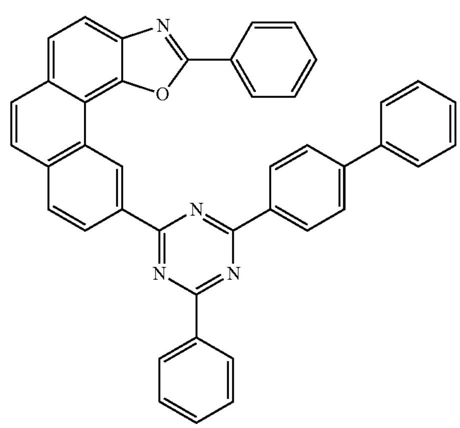

-continued
H2-68
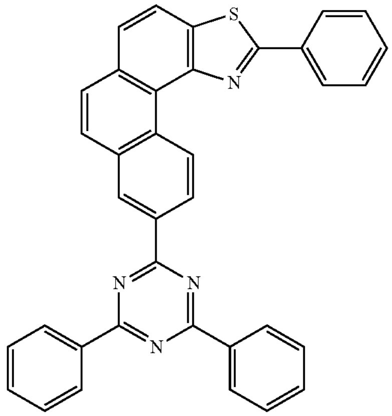
H2-69
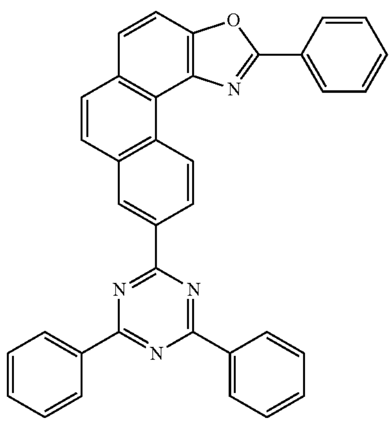
H2-70
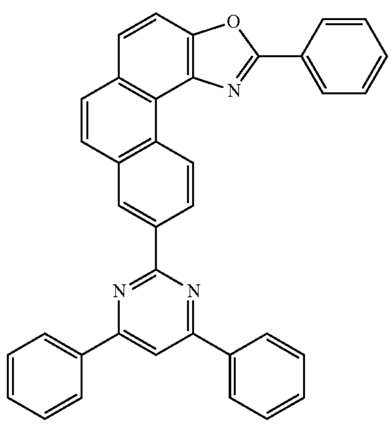
H2-71
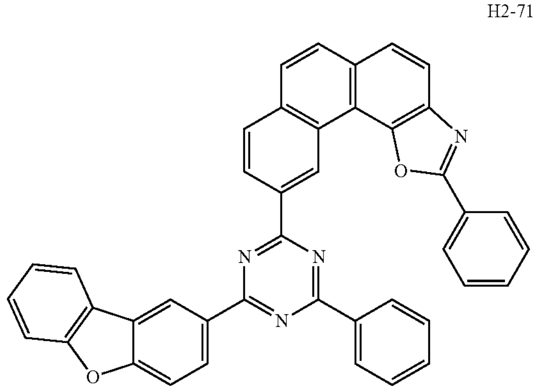
-continued
H2-72
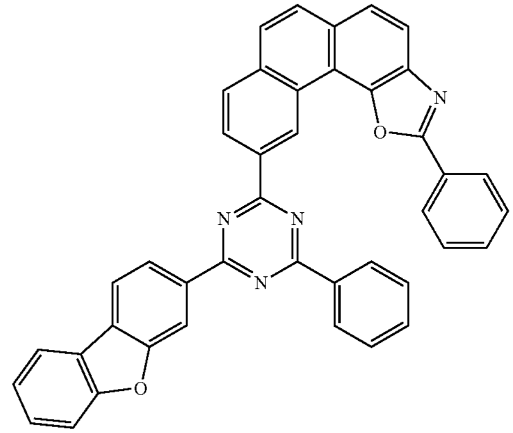
H2-73
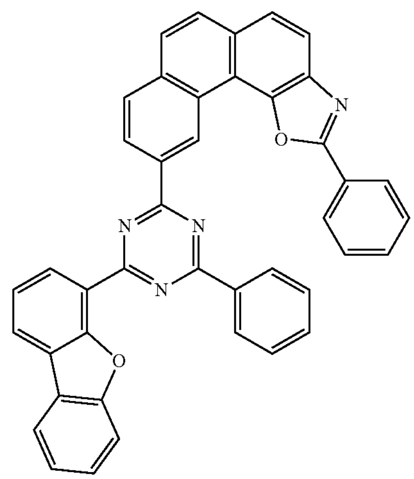
H2-74
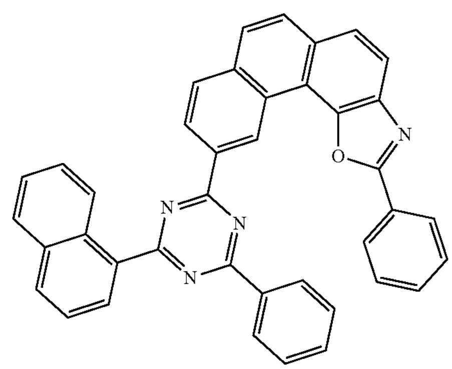

-continued
H2-75
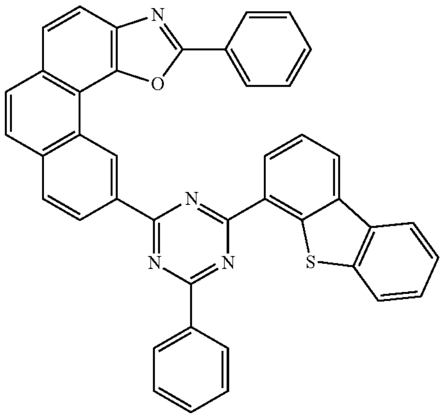
H2-76
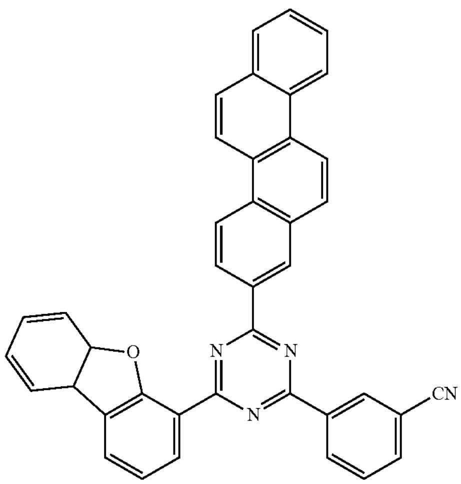
H2-77
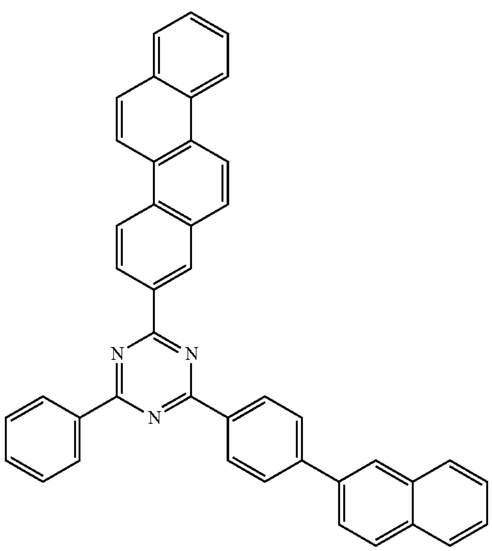
-continued
H2-78
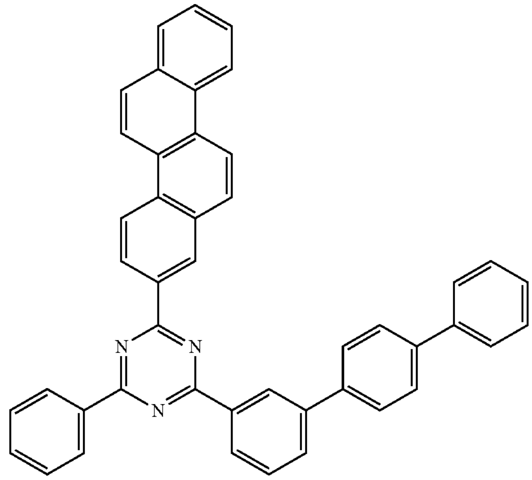
H2-79
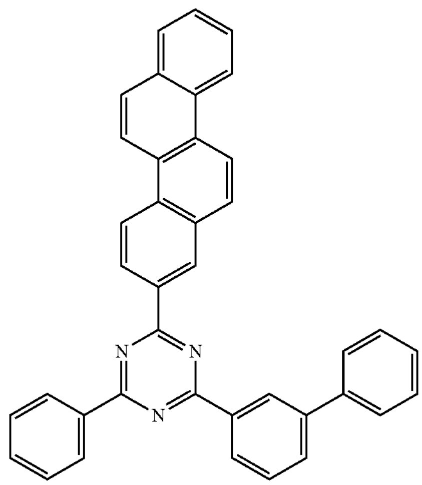
H2-80
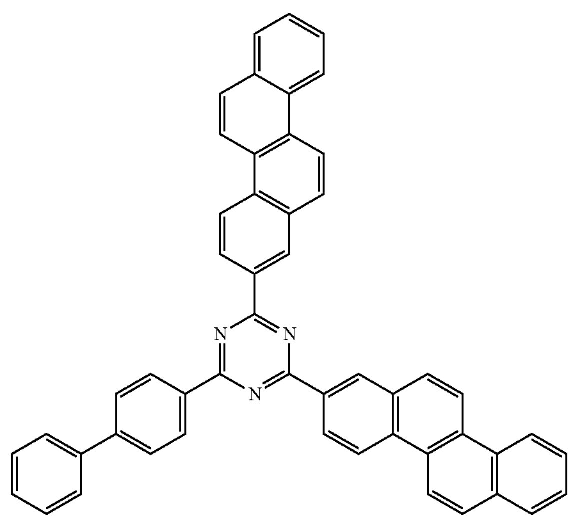

-continued
H2-81
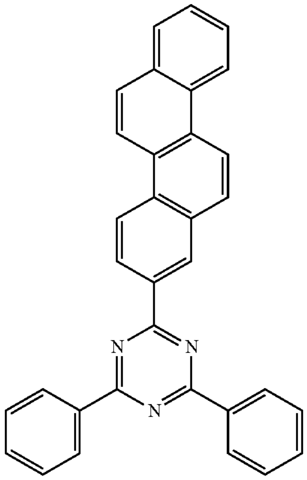
H2-82
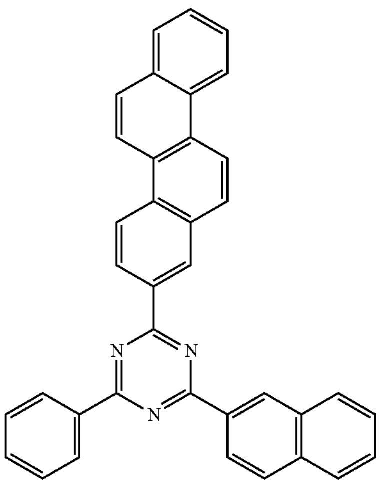
H2-83
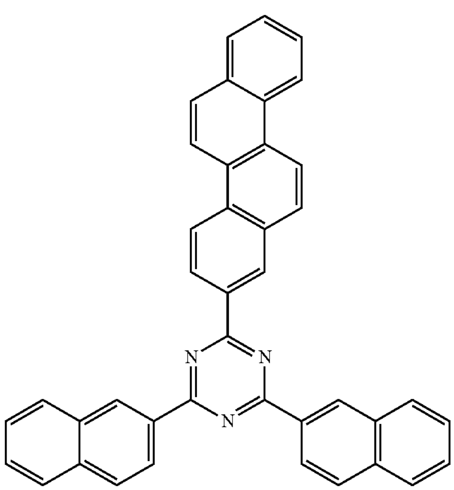
-continued
H2-84
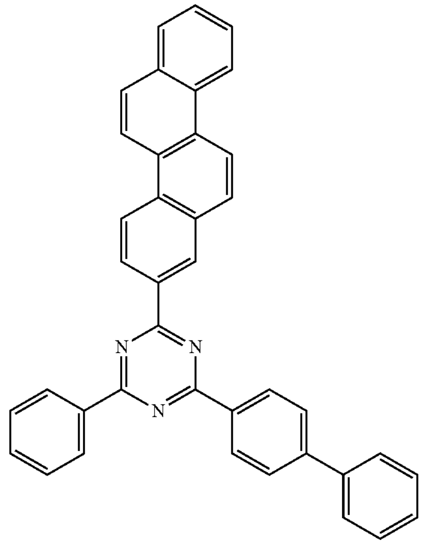
H2-85
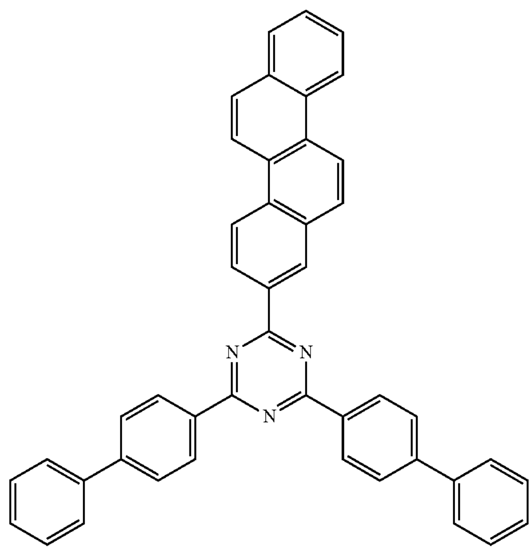
H2-86
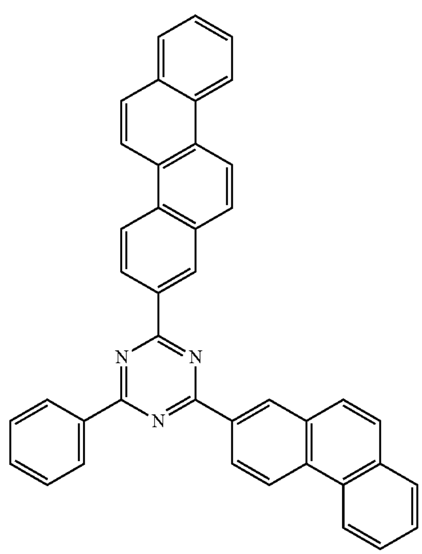

-continued
H2-87
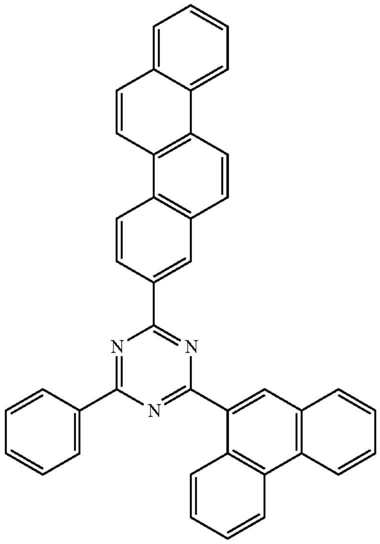
H2-88
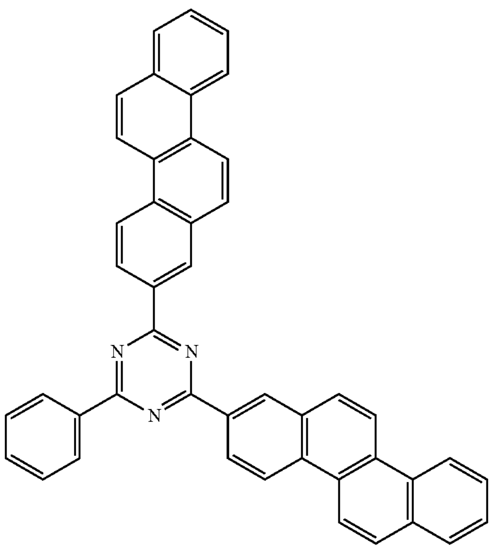
H2-89
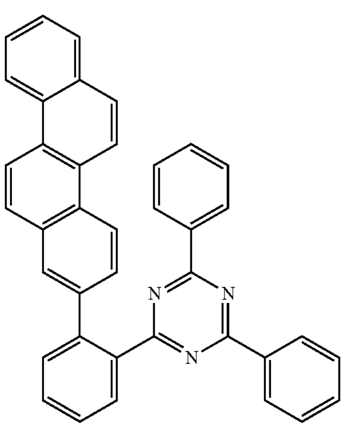
-continued
H2-90
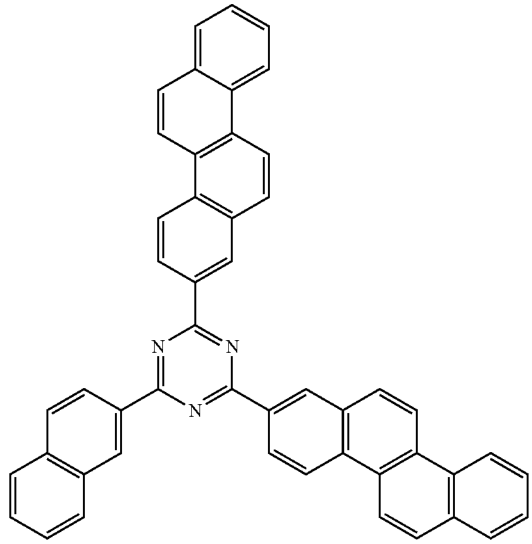
H2-91
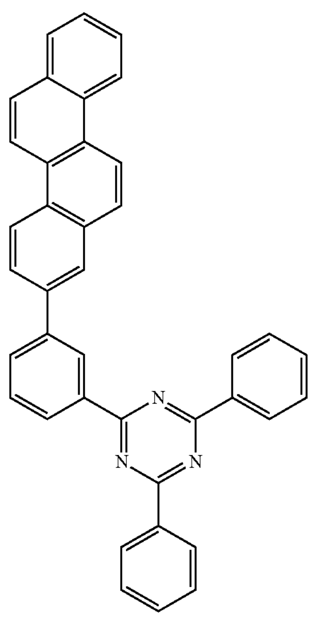

-continued
H2-92
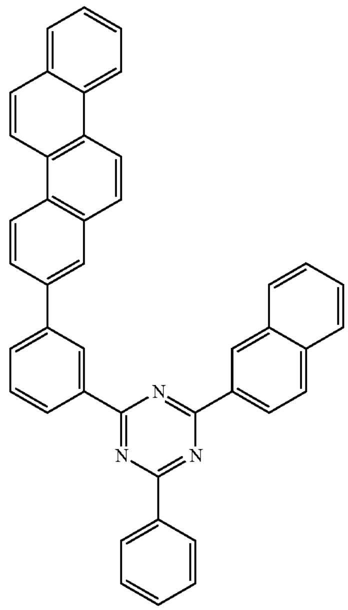
H2-93
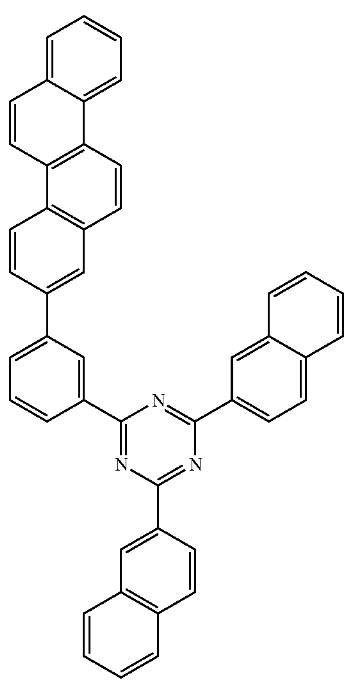
-continued
H2-94
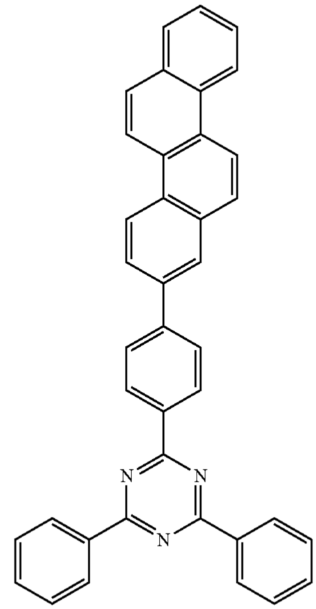
H2-95
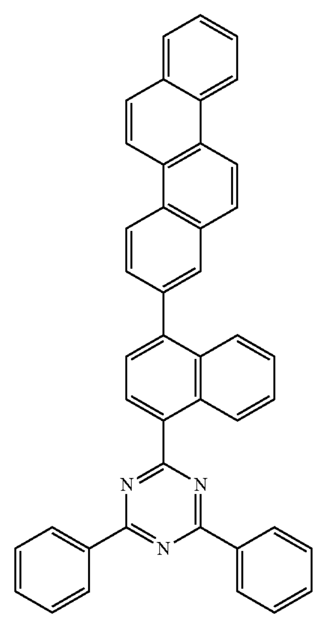

-continued
H2-96
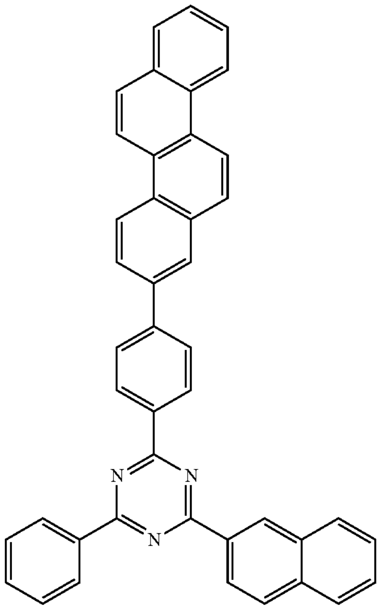
H2-97
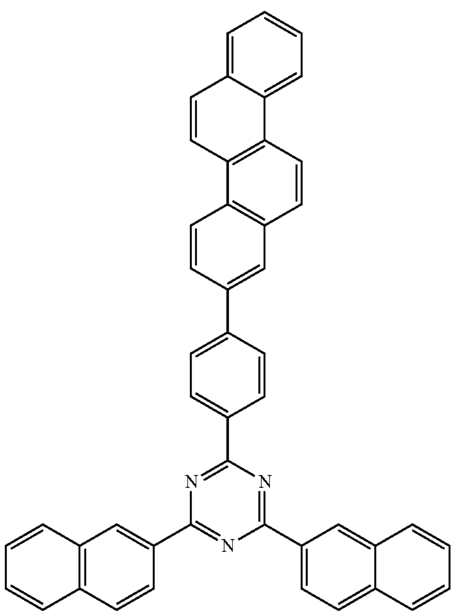
-continued
H2-98
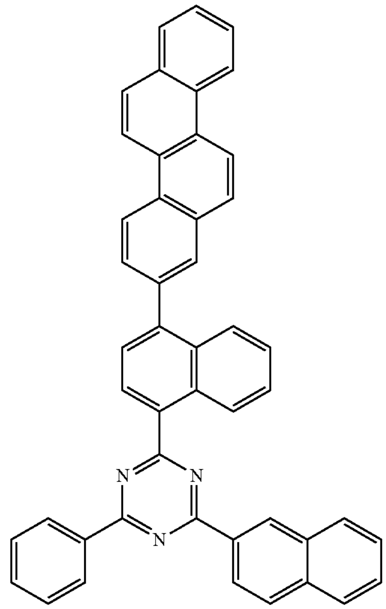
H2-99
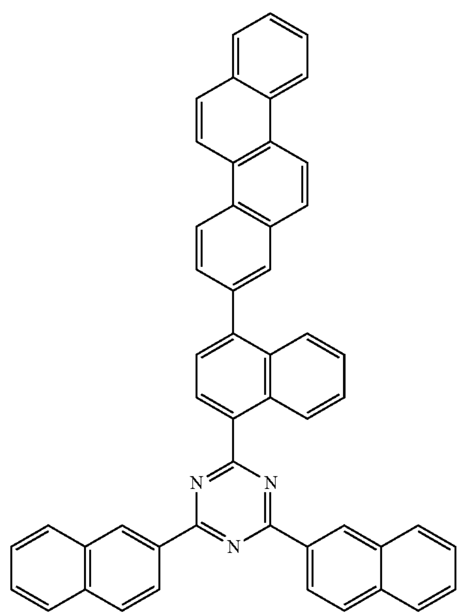

-continued
H2-100
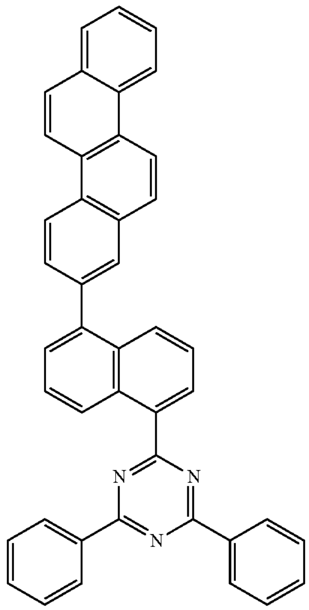
H2-101
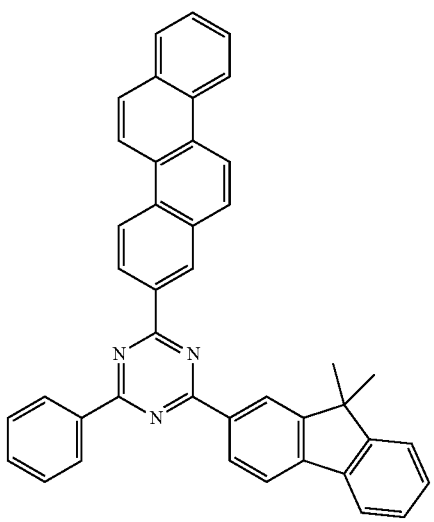
H2-102
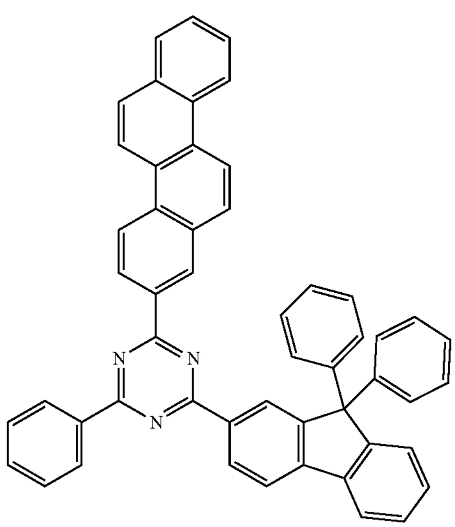
-continued
H2-103
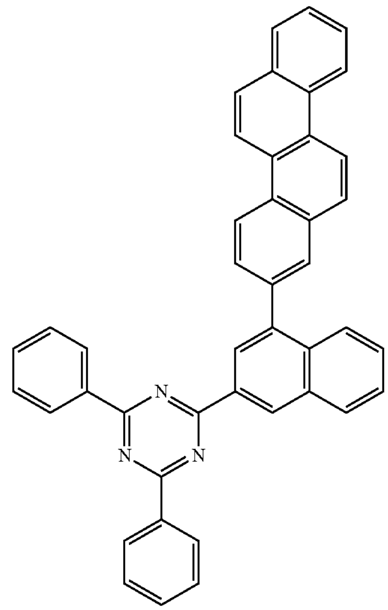
H2-104
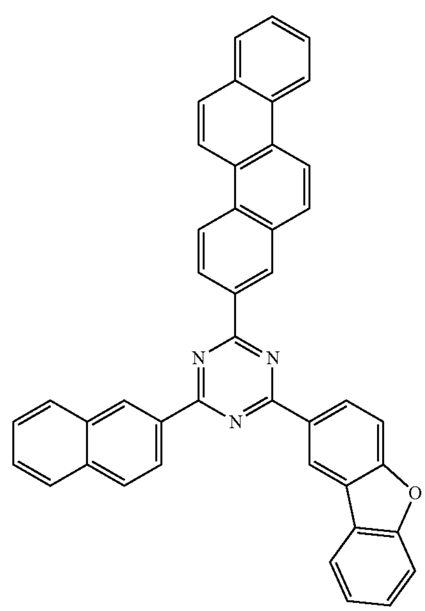

-continued
H2-105
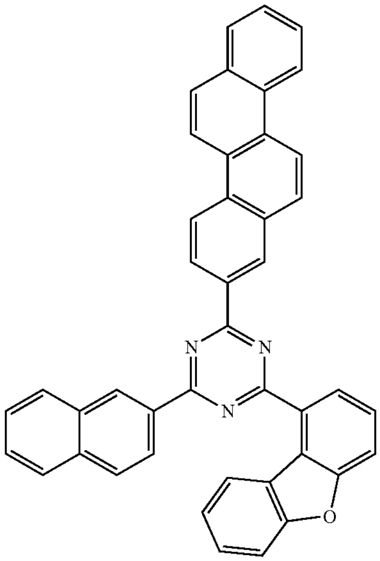
H2-106
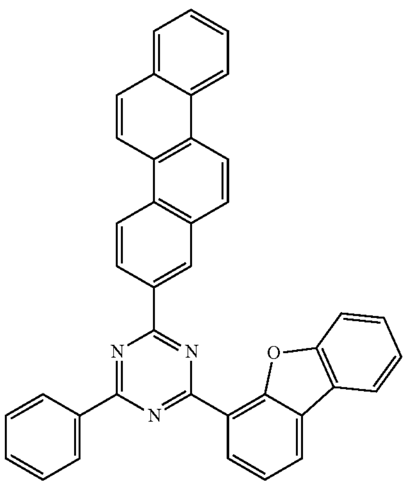
H2-107
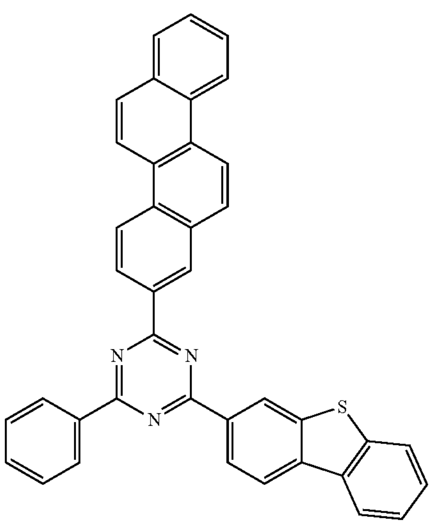
-continued
H2-108
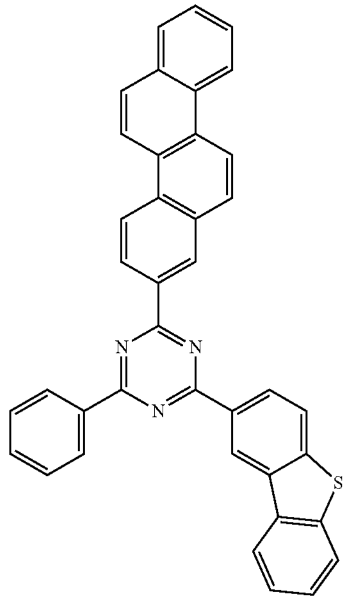
H2-109
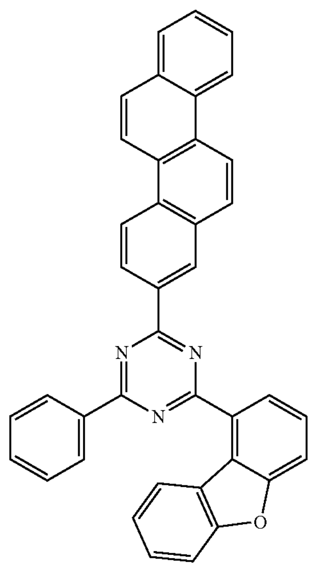
H2-110
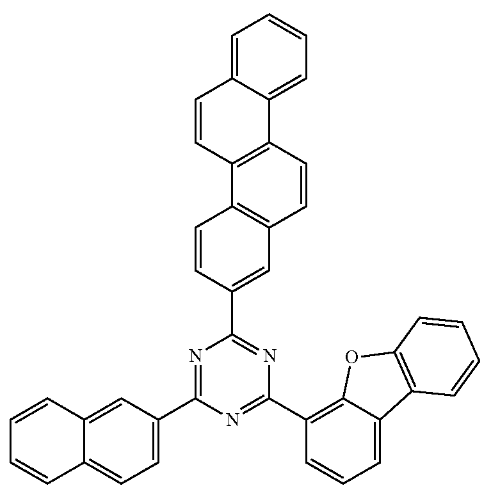

-continued
H2-111
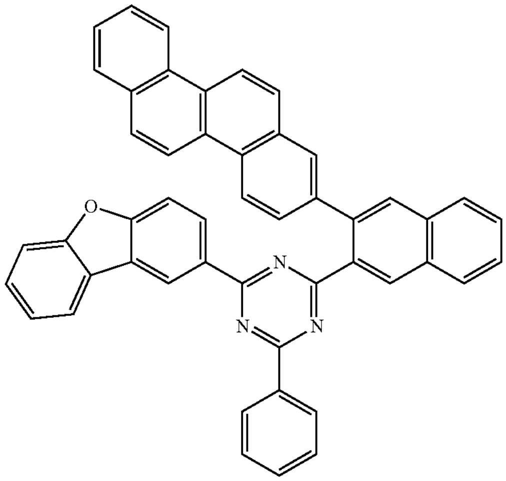
H2-112
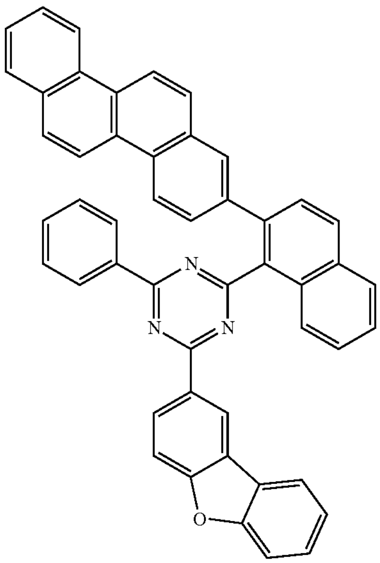
H2-113
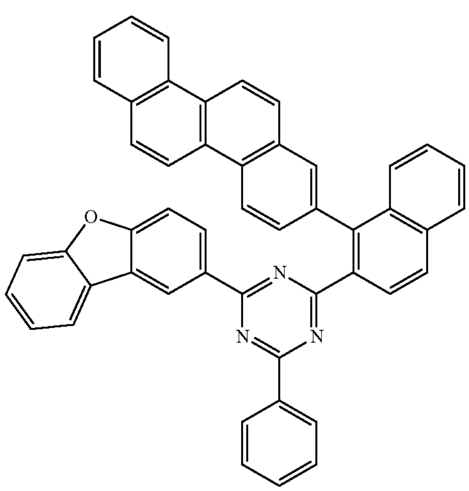
-continued
H2-114
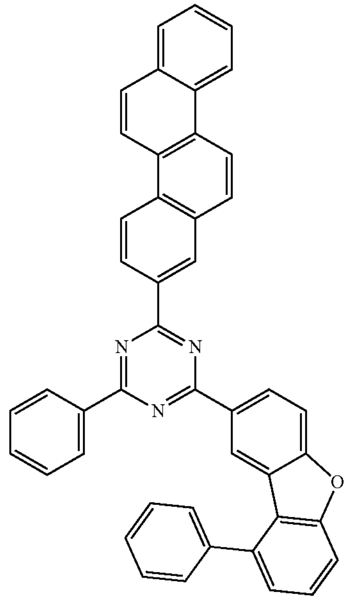
H2-115
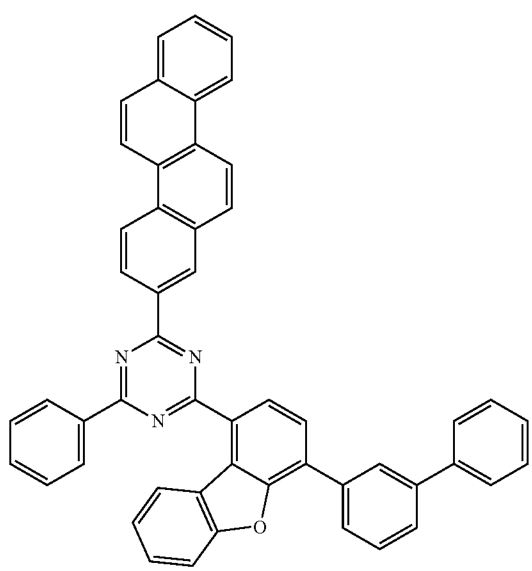

-continued
H2-116
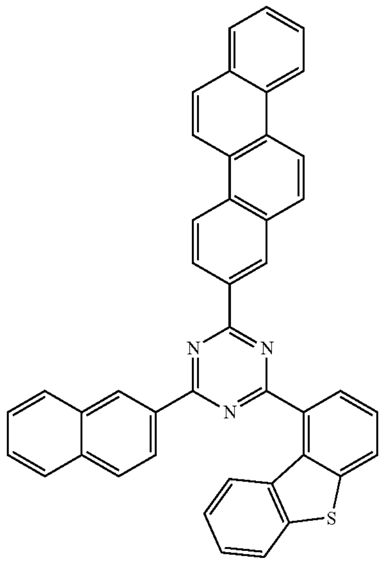
H2-117
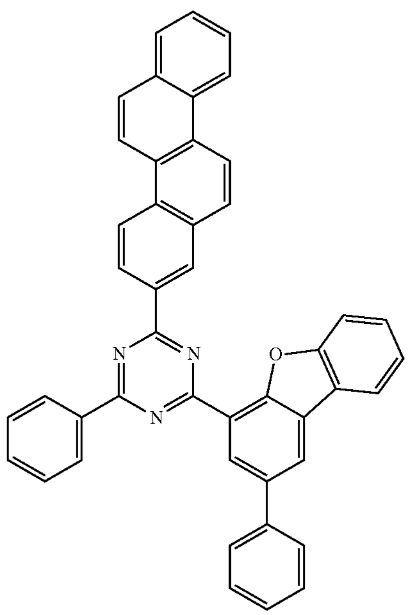
H2-118
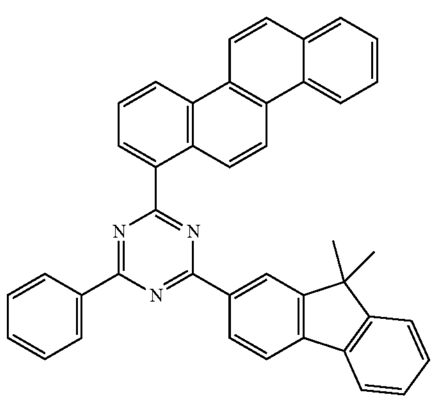
-continued
H2-119
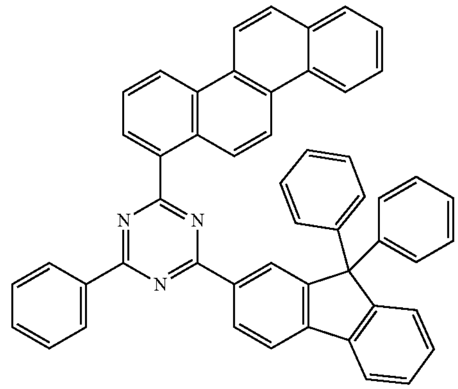
H2-120
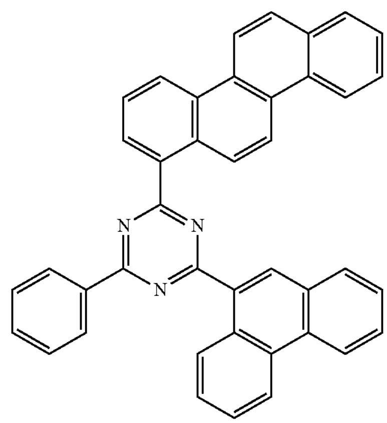
H2-121
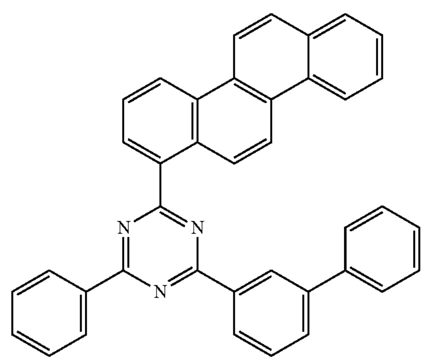
H2-122
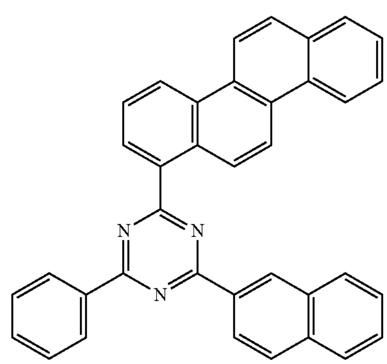

-continued
H2-123
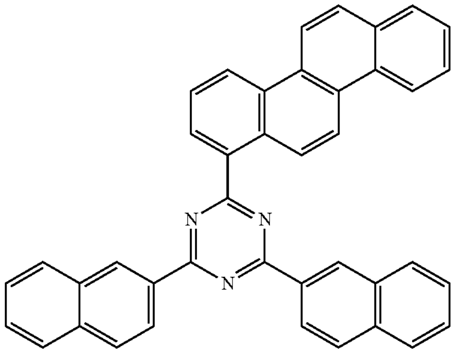
H2-124
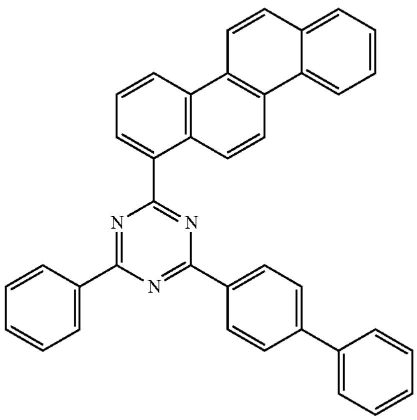
H2-125
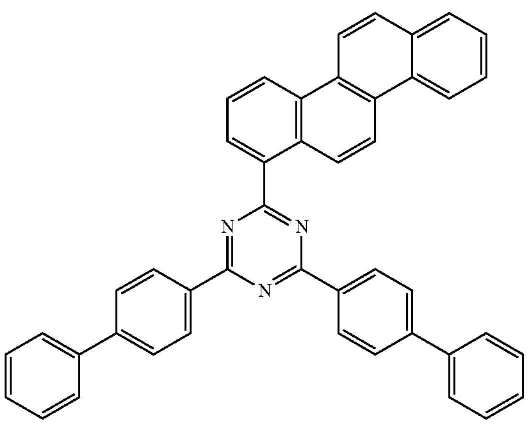
H2-126
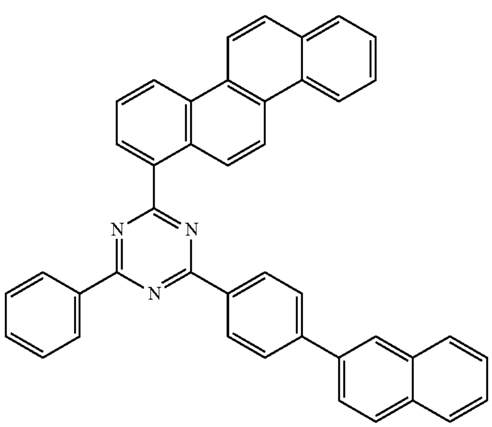
-continued
H2-127
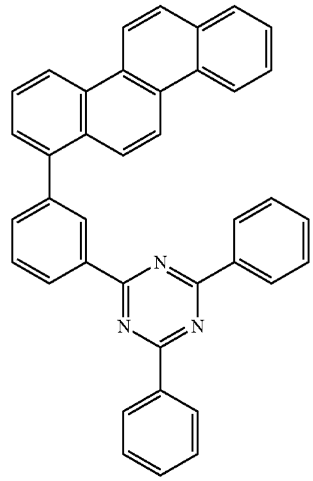
H2-128
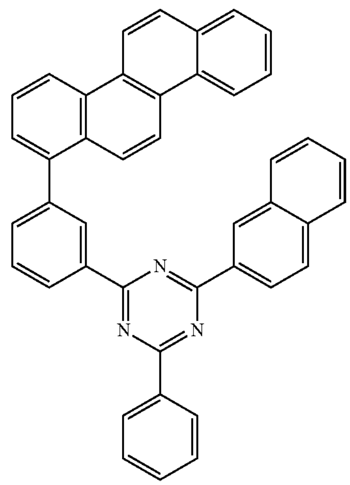
H2-129
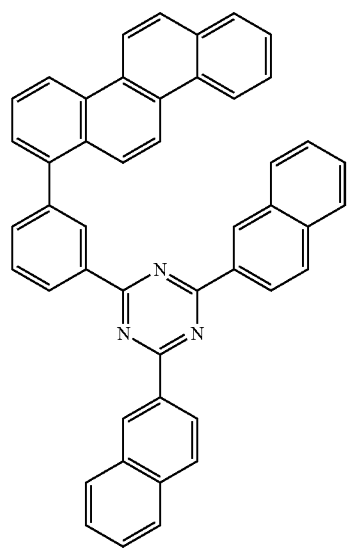

-continued
H2-130
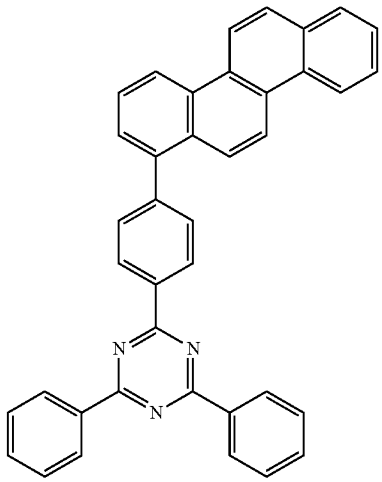
H2-131
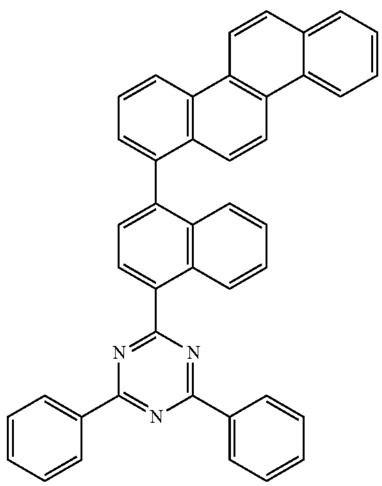
H2-132
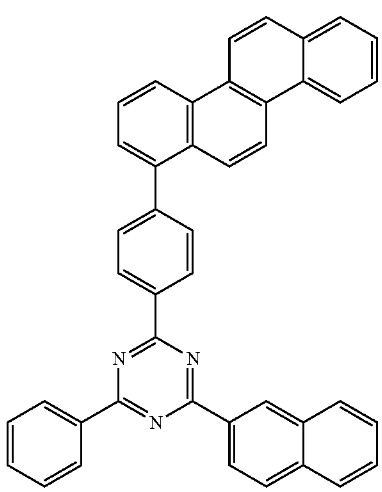
-continued
H2-133
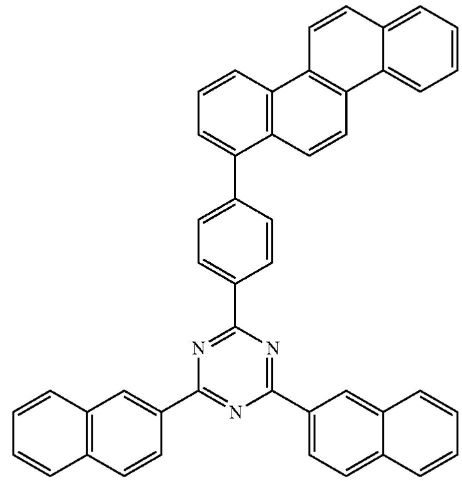
H2-134
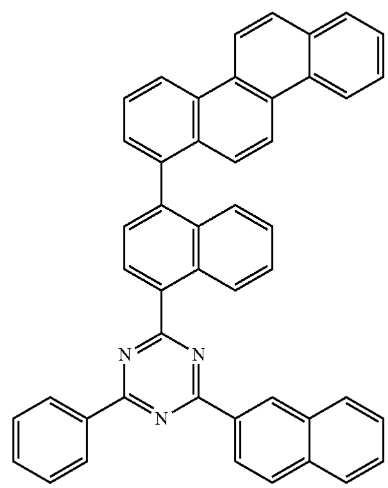
H2-135
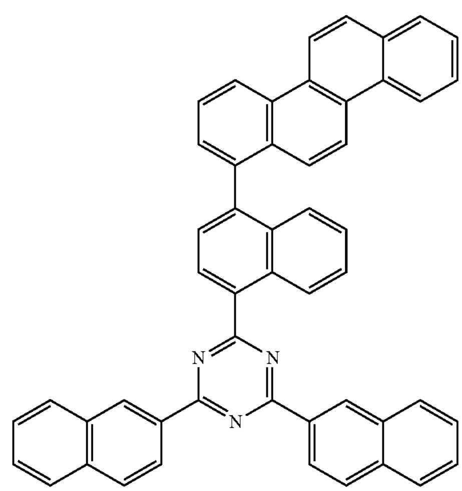

-continued
H2-136
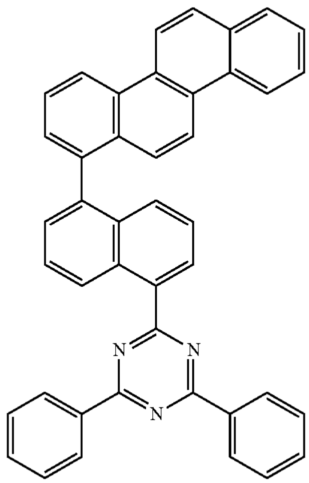
H2-137
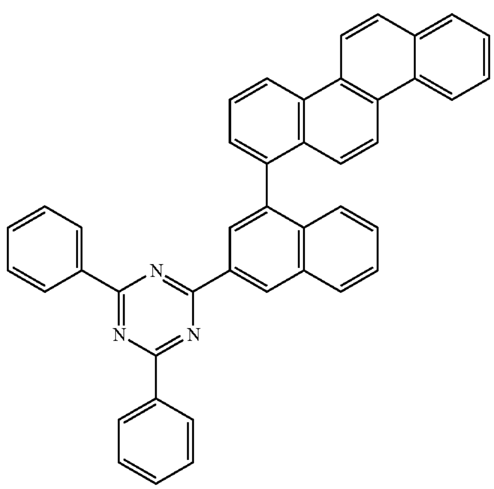
H2-138
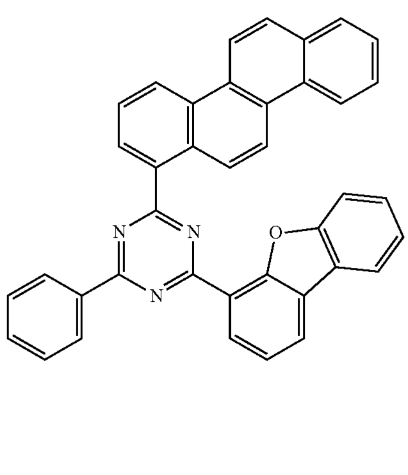
-continued
H2-139
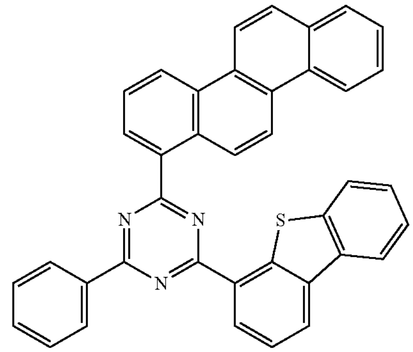
H2-140
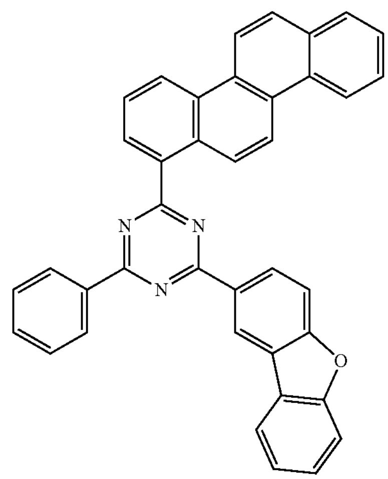
H2-141
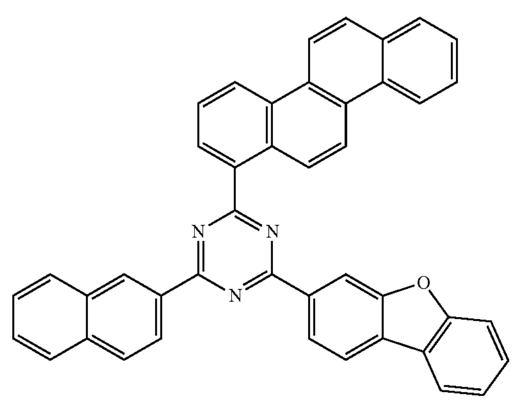

-continued
H2-142
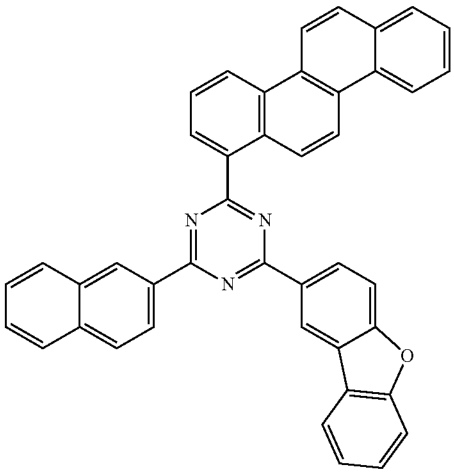
H2-143
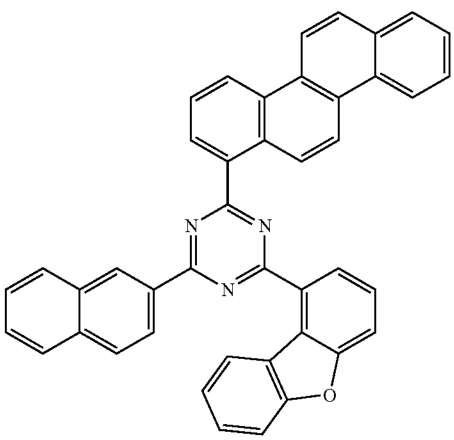
H2-144
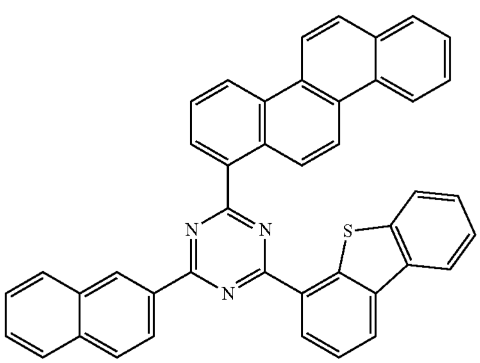
-continued
H2-145
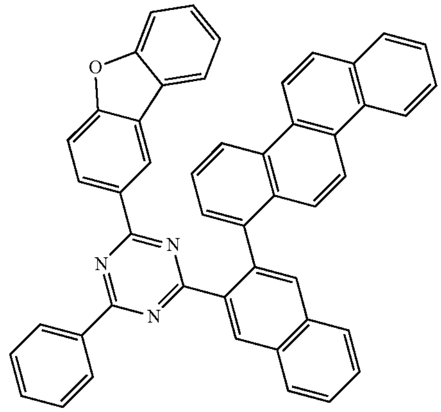
H2-146
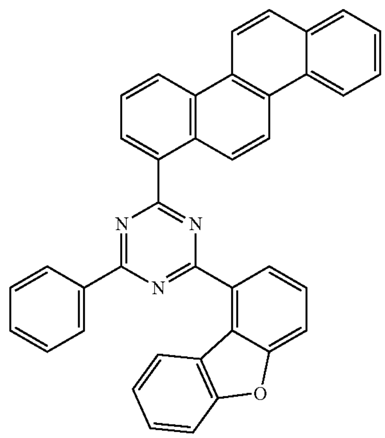
H2-147
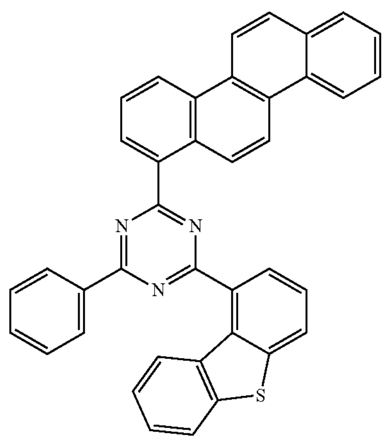
H2-148
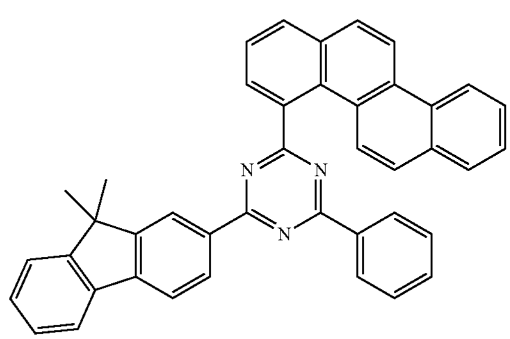

-continued
H2-149
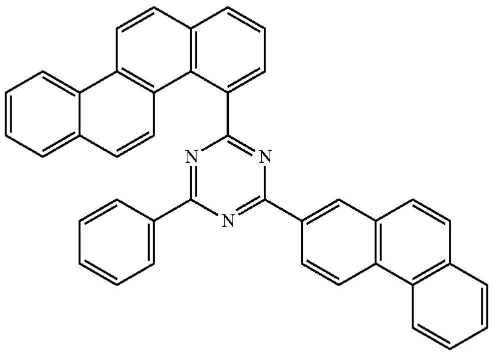
H2-150
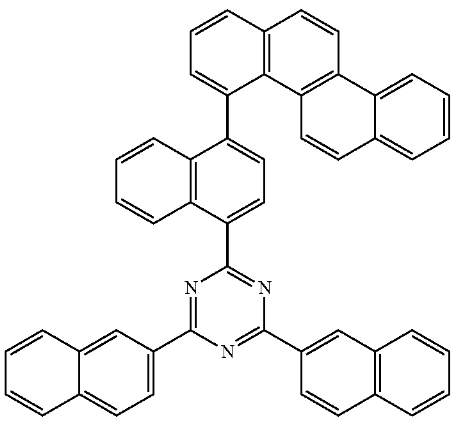
H2-151
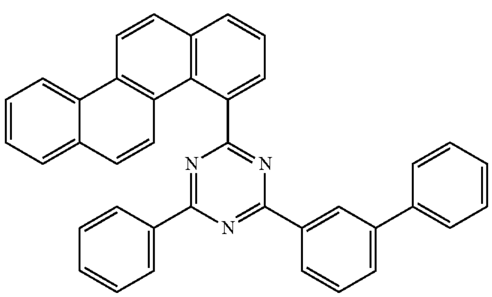
H2-152
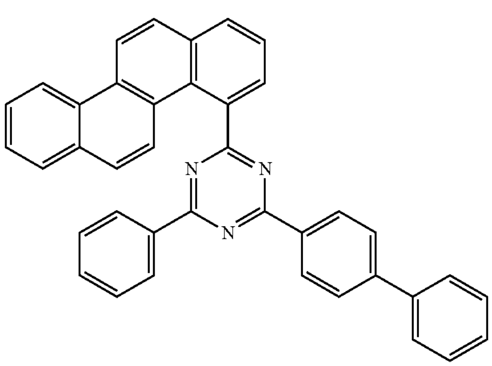
-continued
H2-153
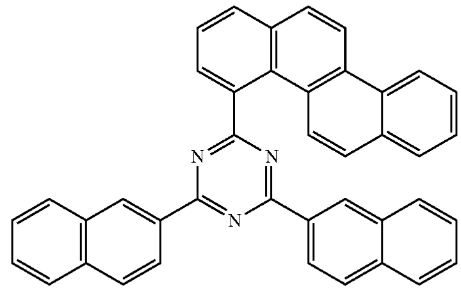
H2-154
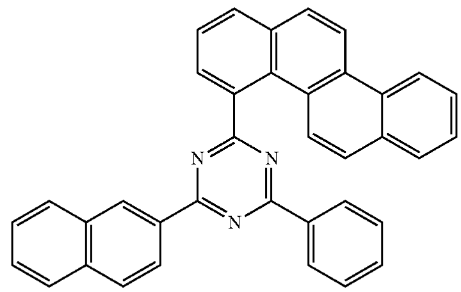
H2-155
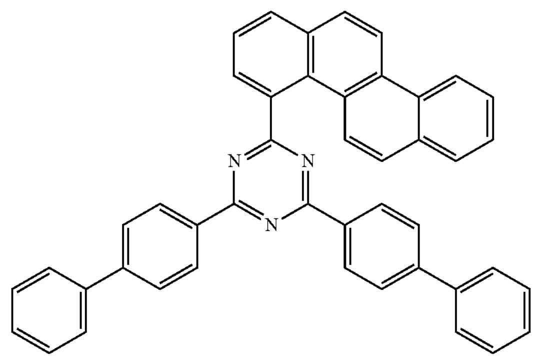
H2-156
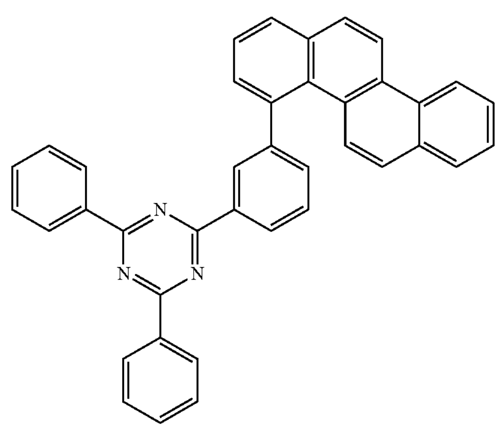

-continued
H2-157
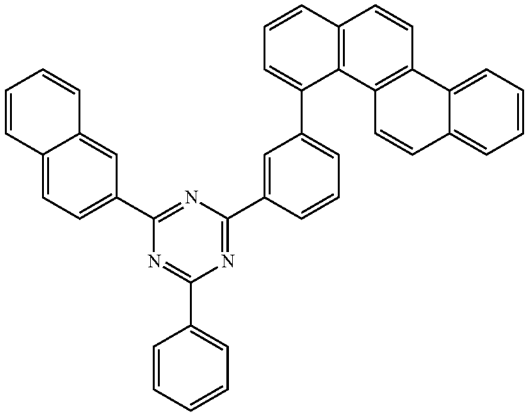
H2-158
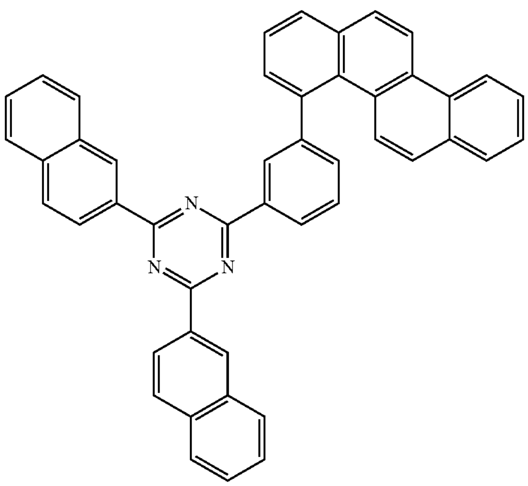
H2-159
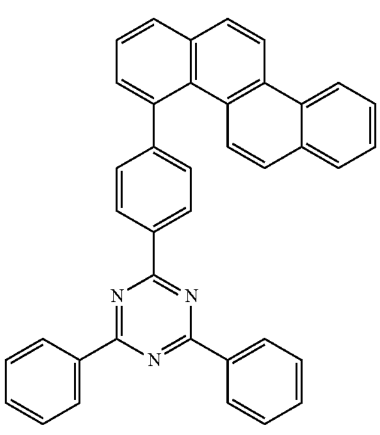
-continued
H2-160
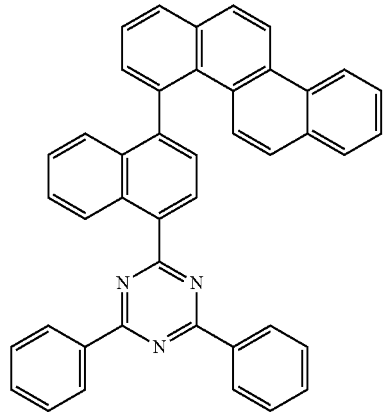
H2-161
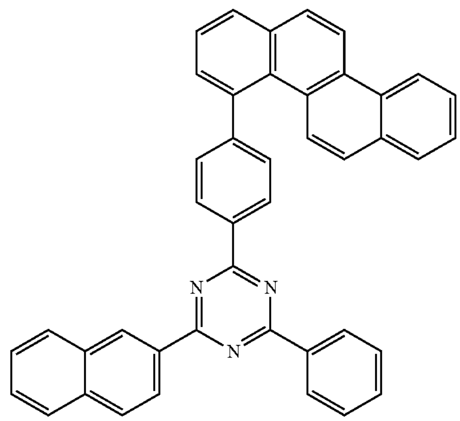
H2-162
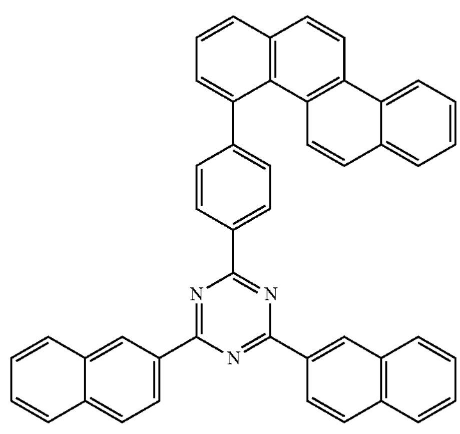

-continued
H2-163
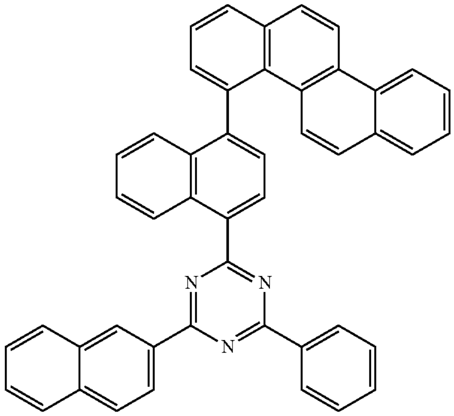
H2-164
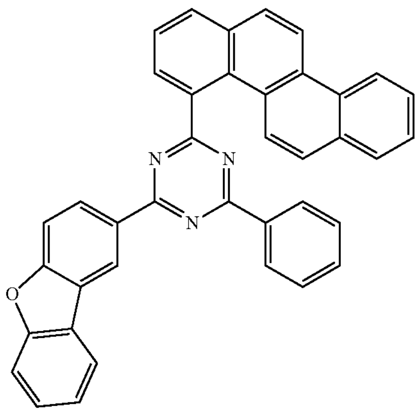
H2-165
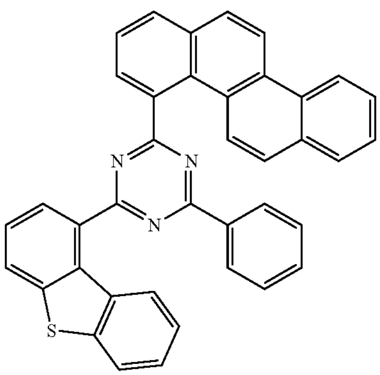
H2-166
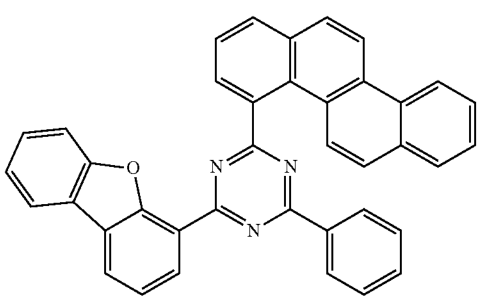
-continued
H2-167
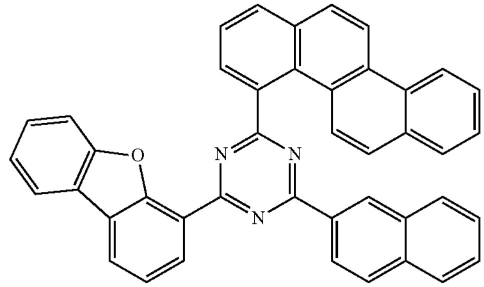
H2-168
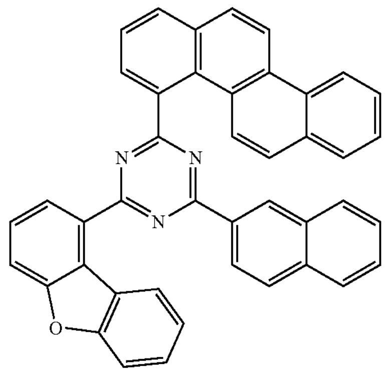
H2-169
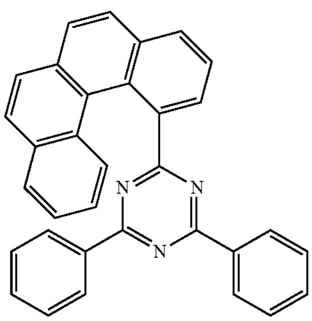
H2-170
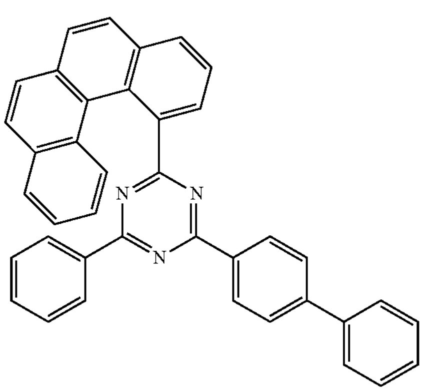

-continued
H2-171
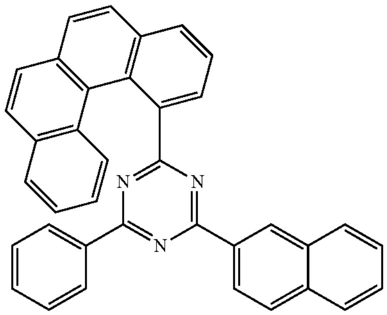
H2-172
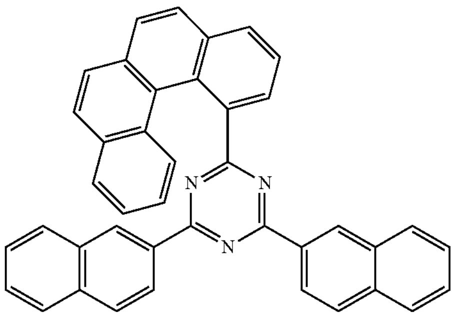
H2-173
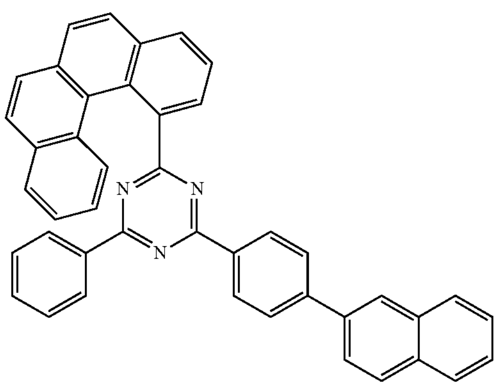
H2-174
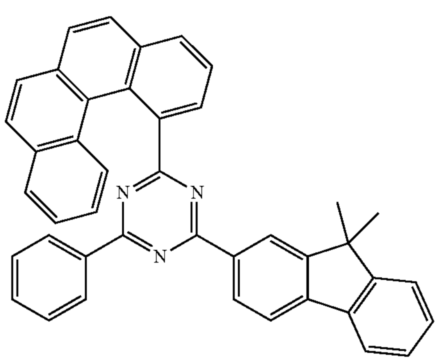
-continued
H2-175
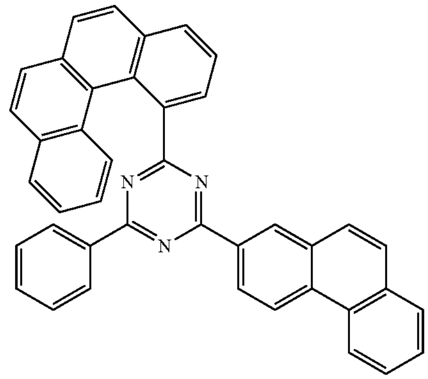
H2-176
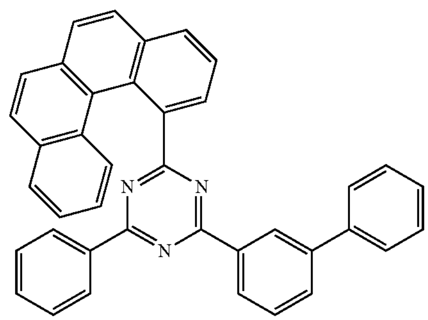
H2-177
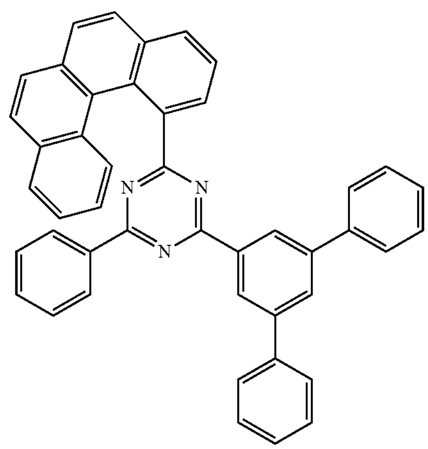
H2-178
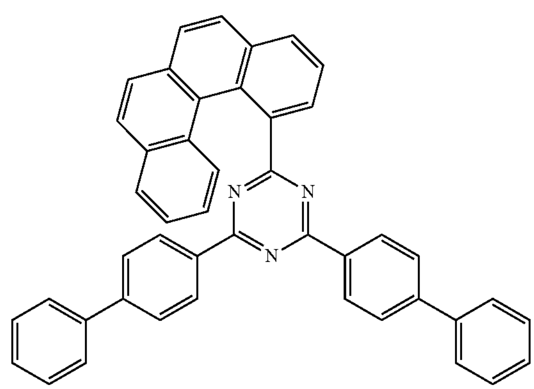

-continued
H2-179
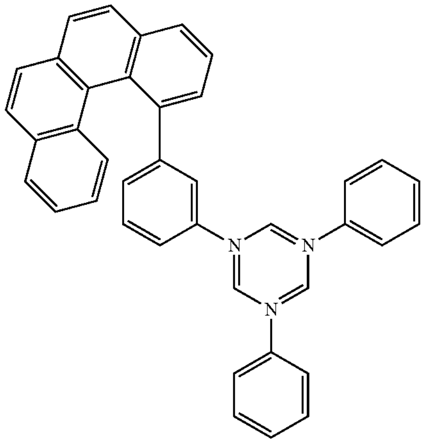
H2-180
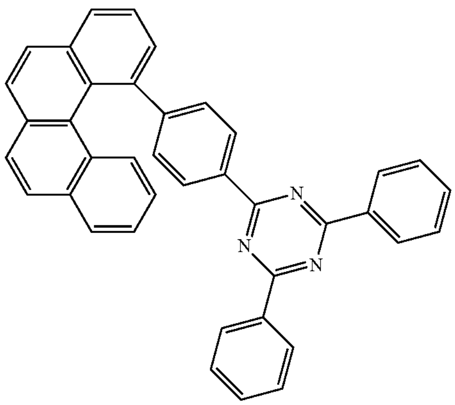
H2-181
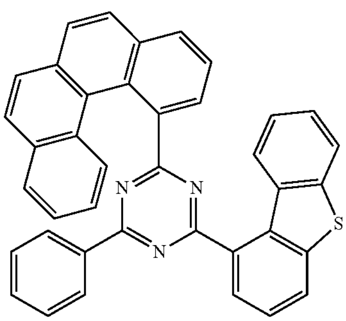
H2-182
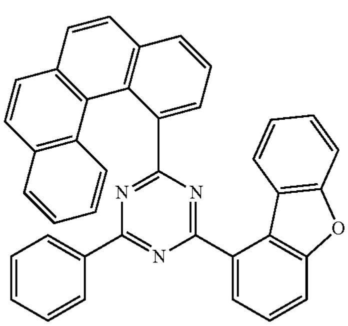
-continued
H2-183
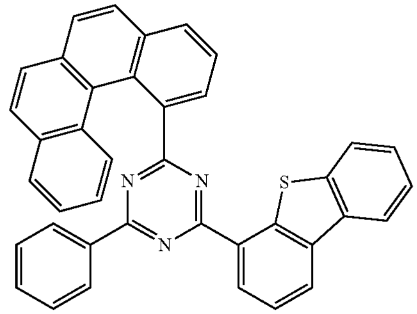
H2-184
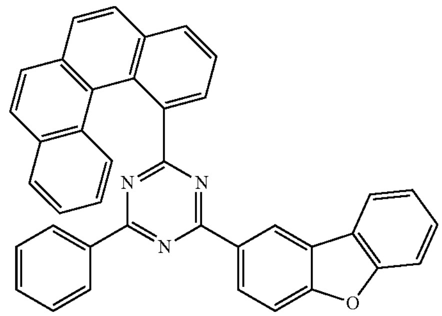
H2-185
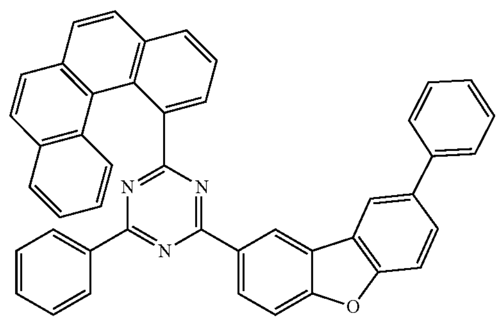
H2-186
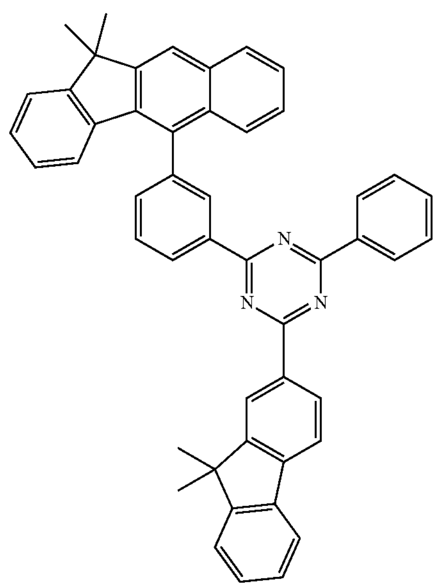

-continued
H2-187
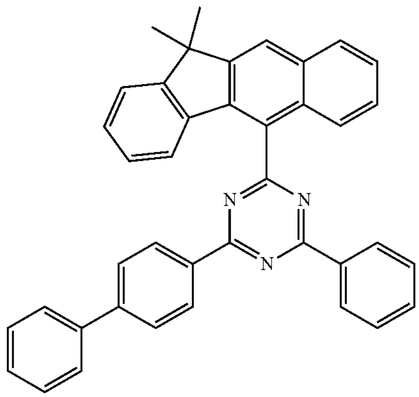
H2-188
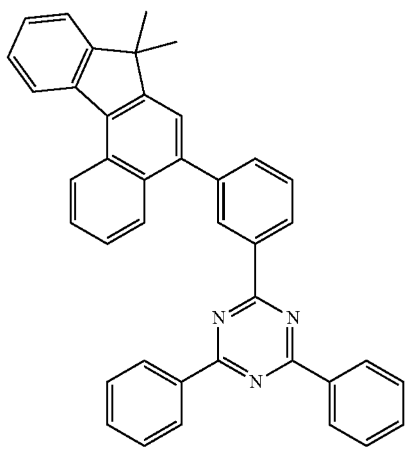
H2-189
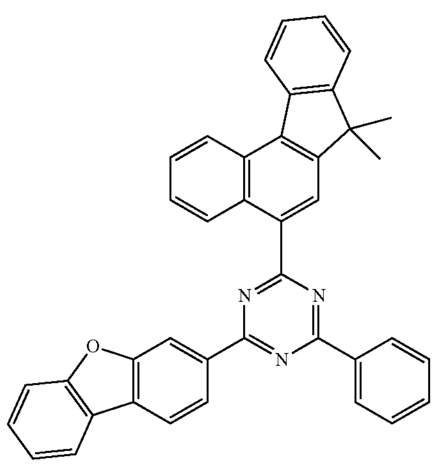
-continued
H2-190
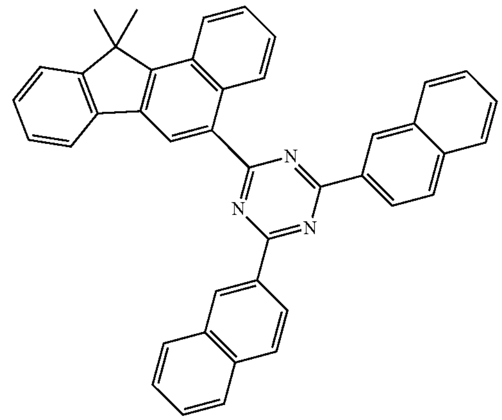
H2-191
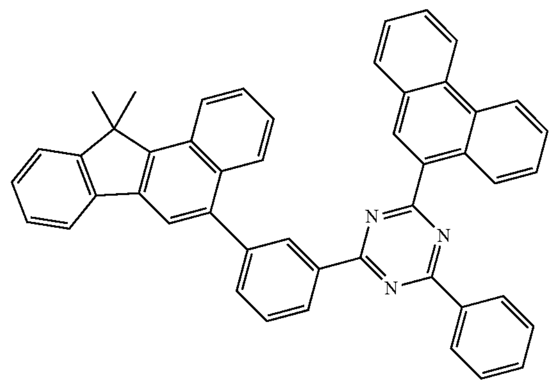
H2-192
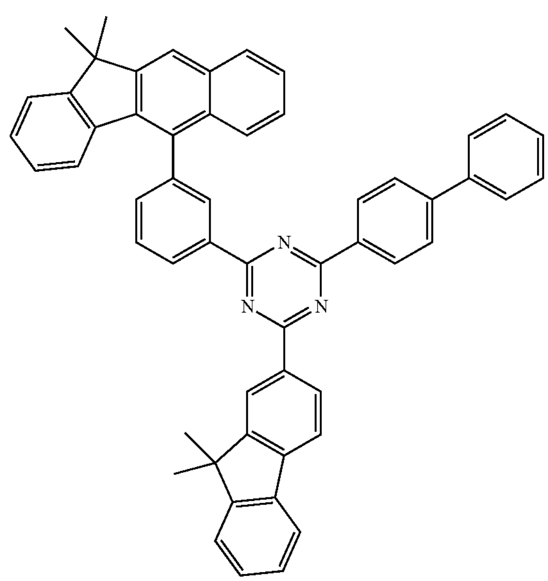

-continued
H2-193
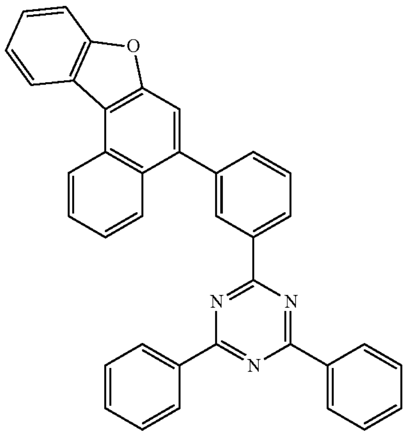
H2-194
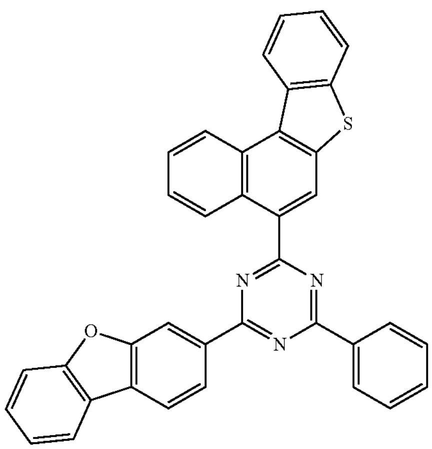
H2-195
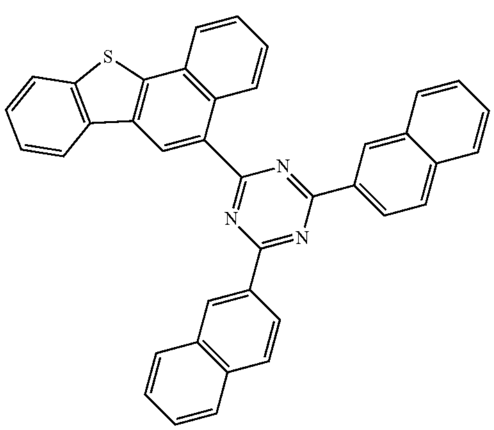
-continued
H2-196
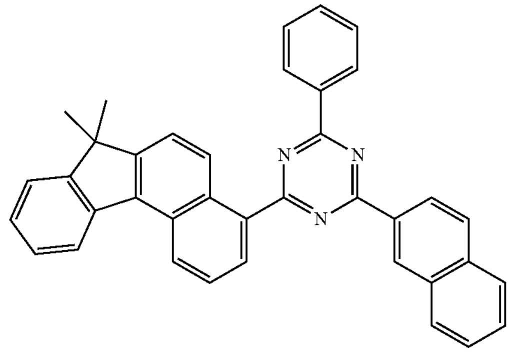
H2-197
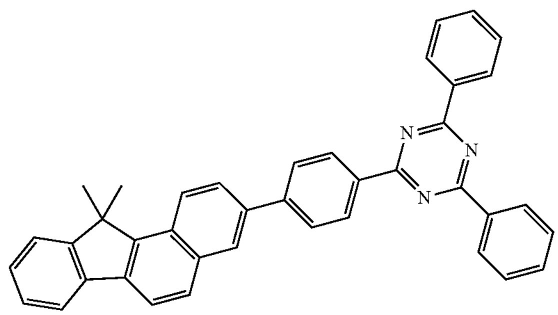
H2-198
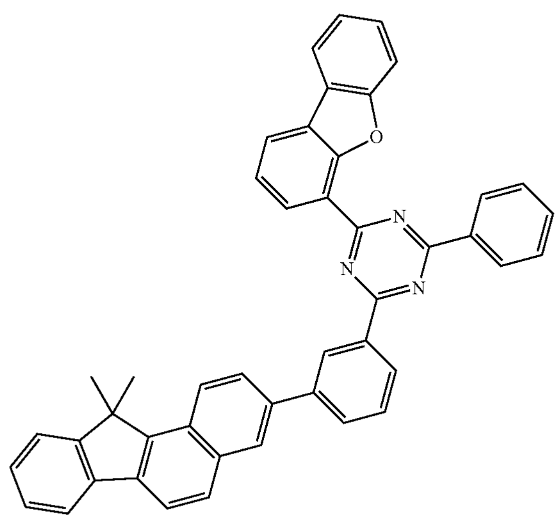

-continued
H2-199
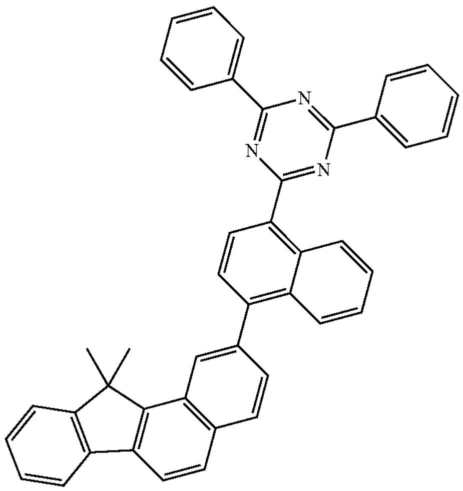
H2-200
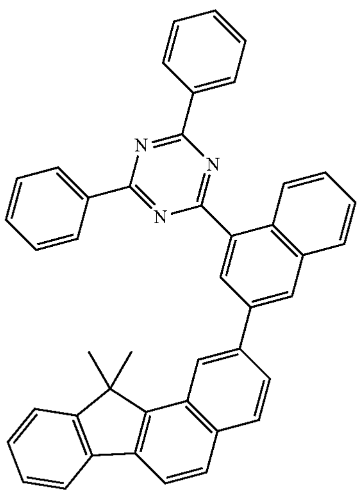
H2-201
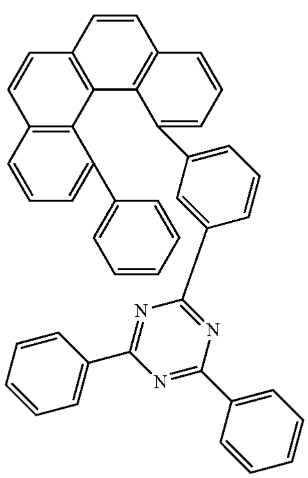
-continued
H2-202
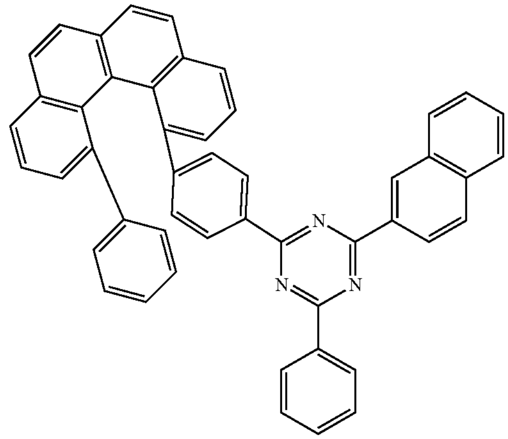
H2-203
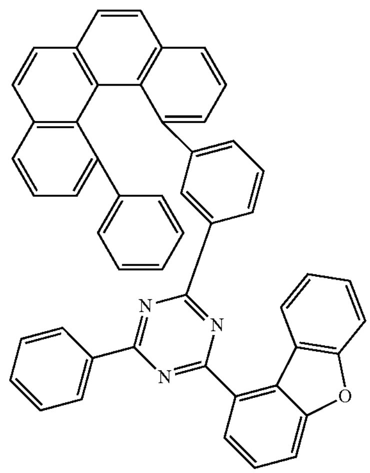
H2-204
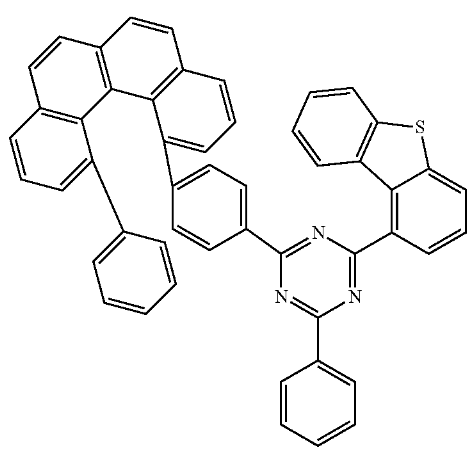

-continued
H2-205
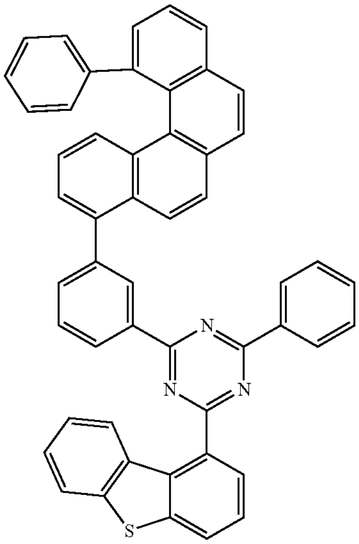
H2-206
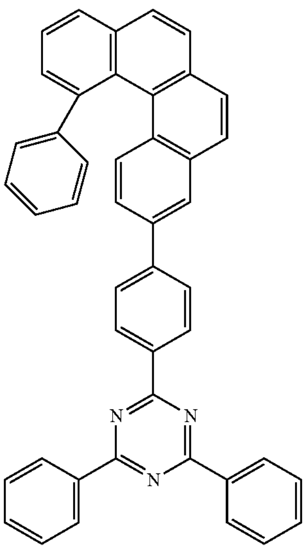
H2-207
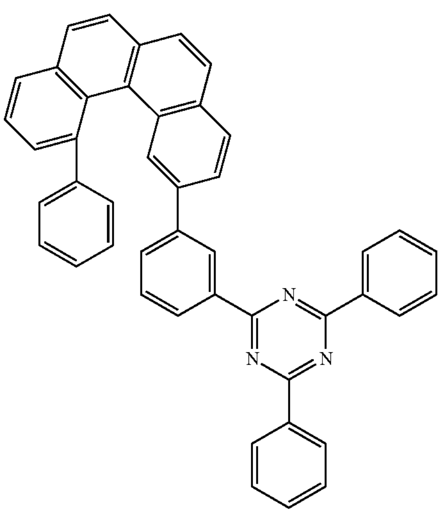
-continued
H2-208
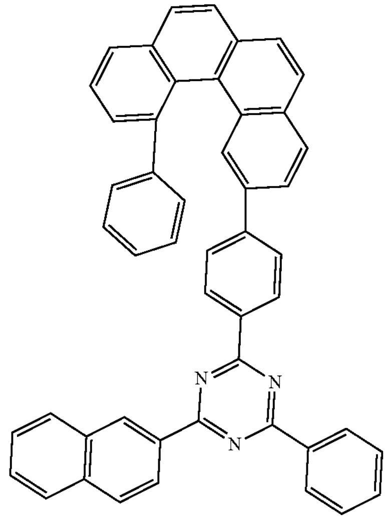
H2-209
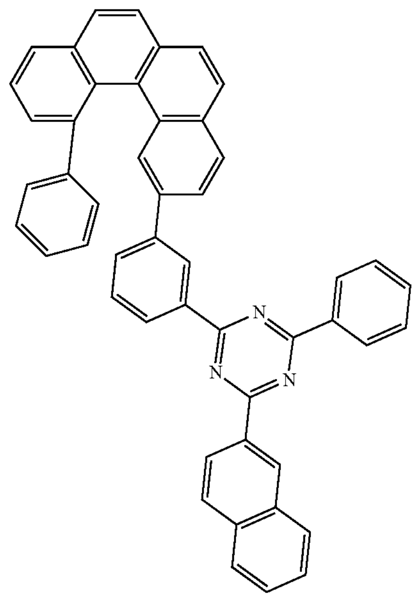
H2-210
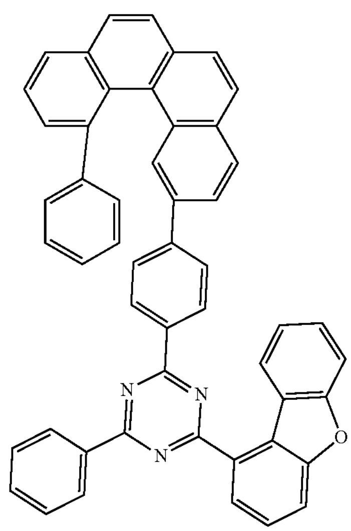

-continued
H2-211
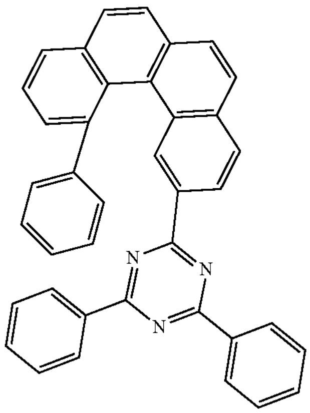
H2-212
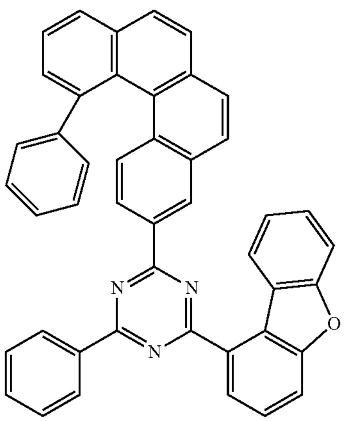
H2-213
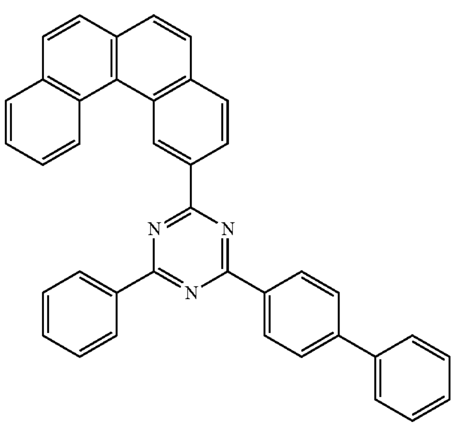
H2-214
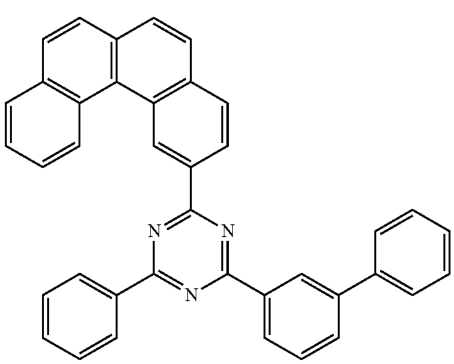
-continued
H2-215
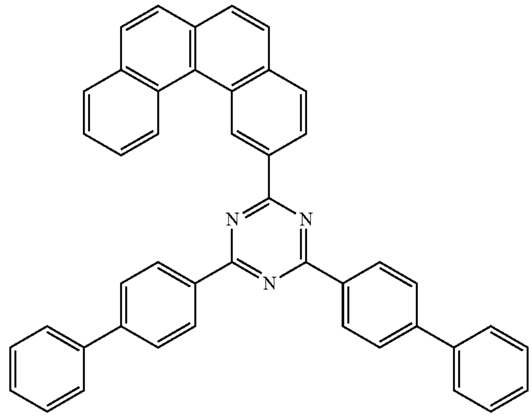
H2-216
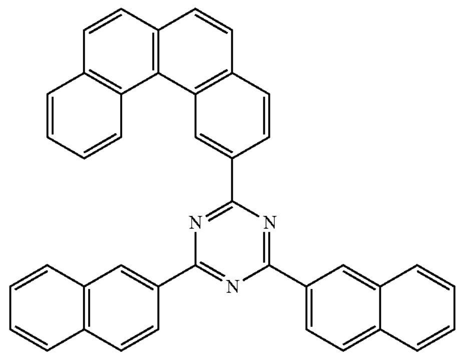
H2-217
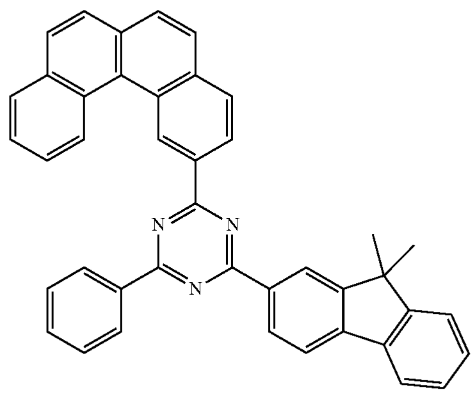
H2-218
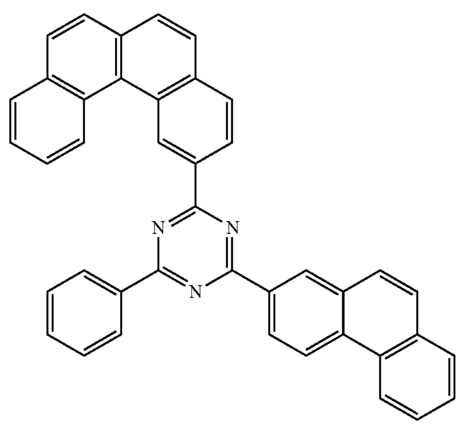

-continued
H2-219
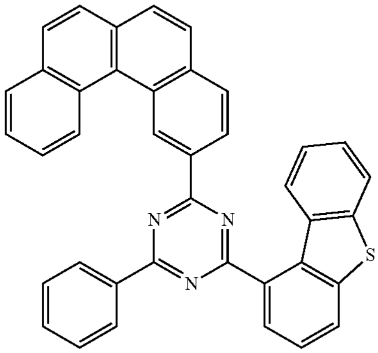
H2-220
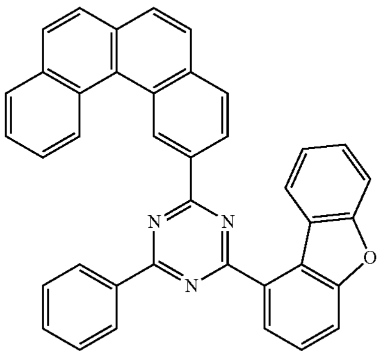
H2-221
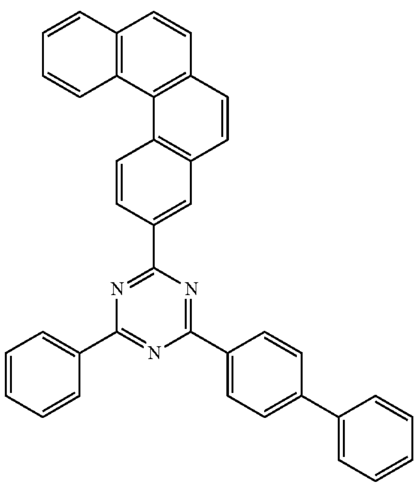
H2-222
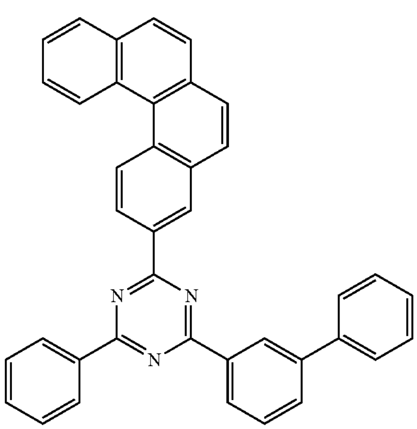
-continued
H2-223
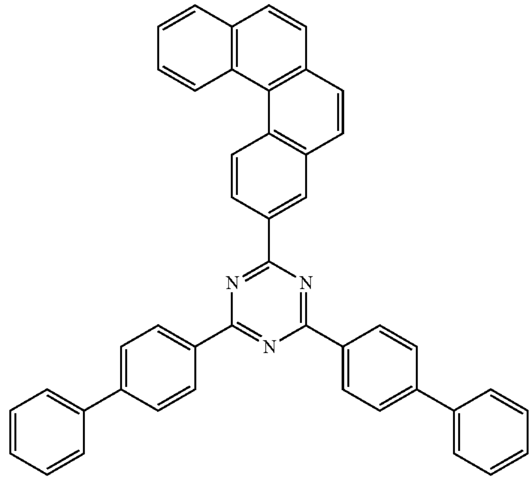
H2-224
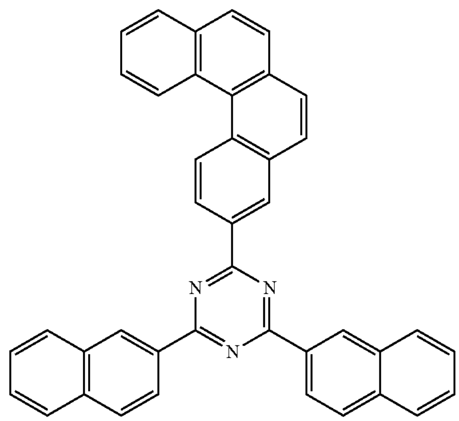
H2-225
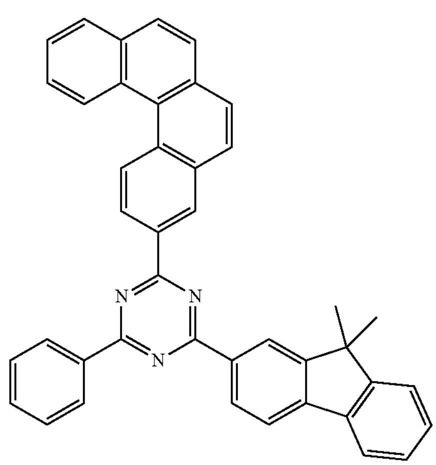

-continued
H2-226
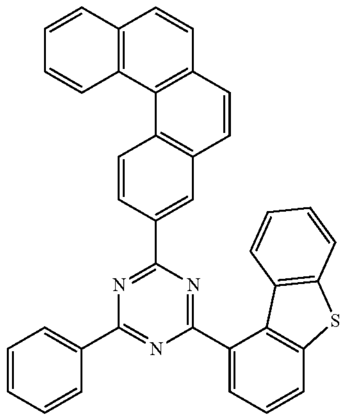
H2-227
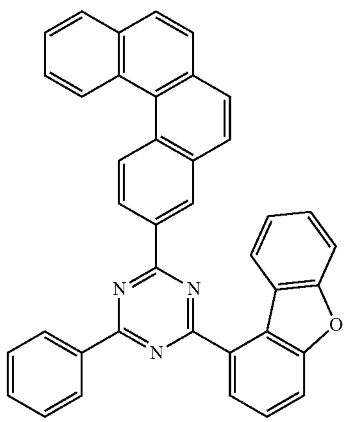
H2-228
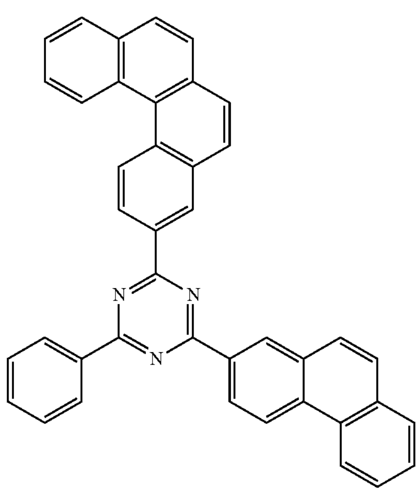
-continued
H2-229
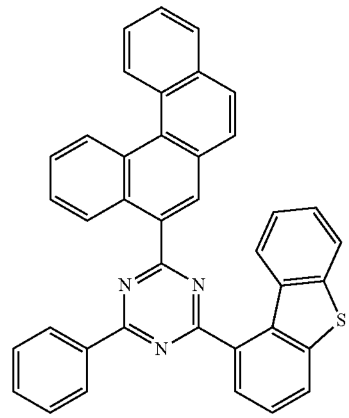
H2-230
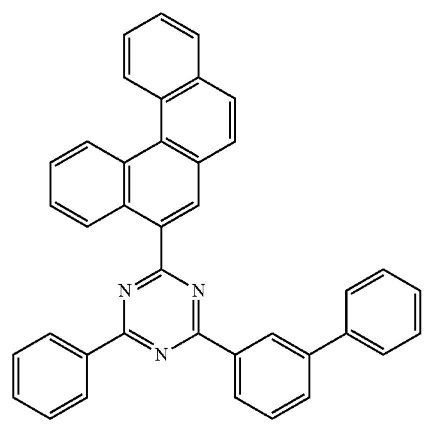
H2-231
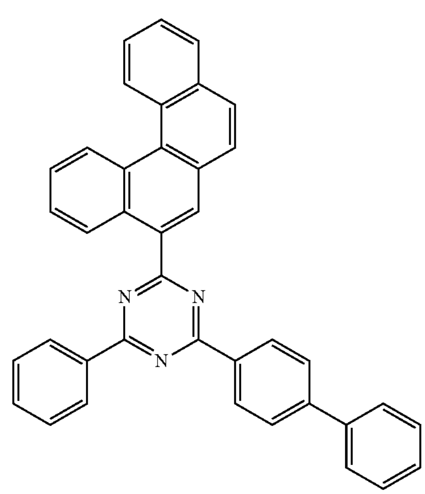

-continued
H2-232
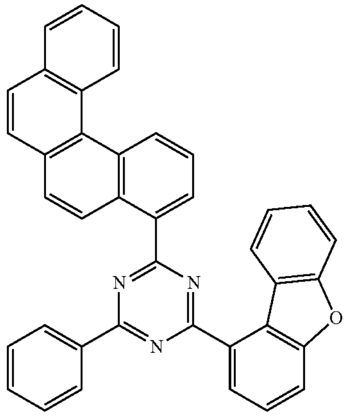
H2-233
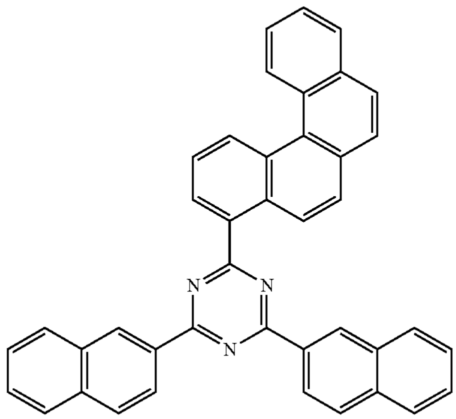
H2-234
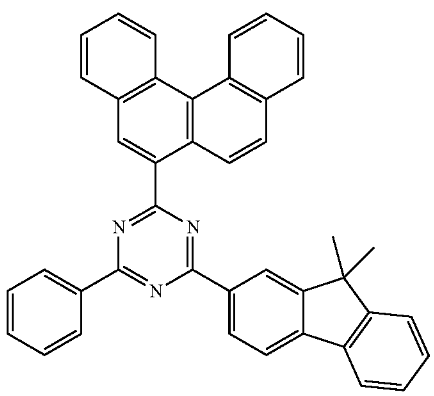
H2-235
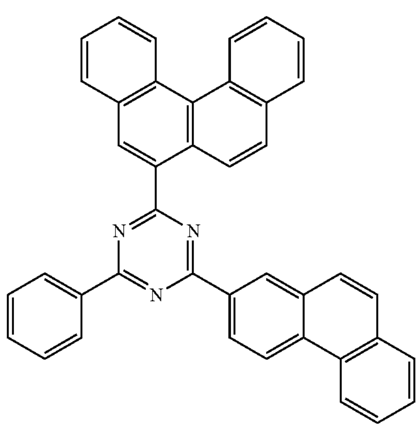
-continued
H2-236
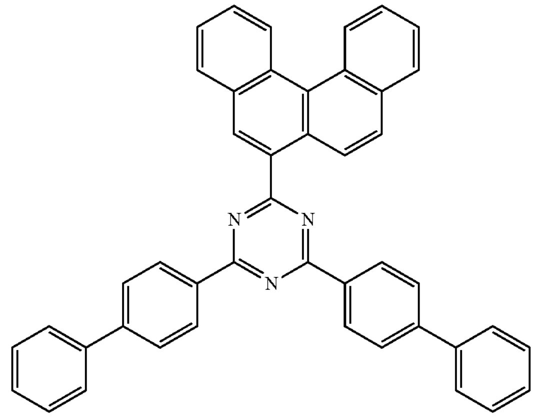
H2-237
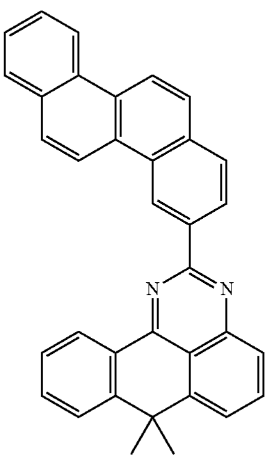
H2-238
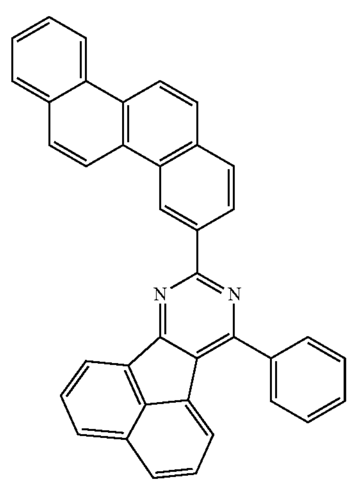

-continued
H2-239
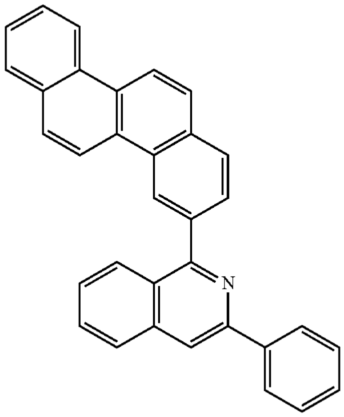
H2-240
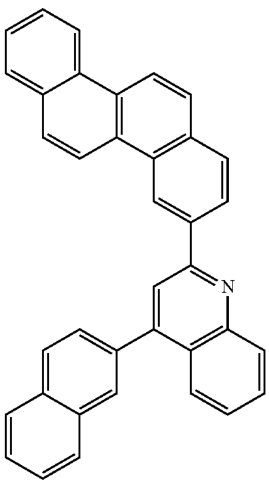
H2-241
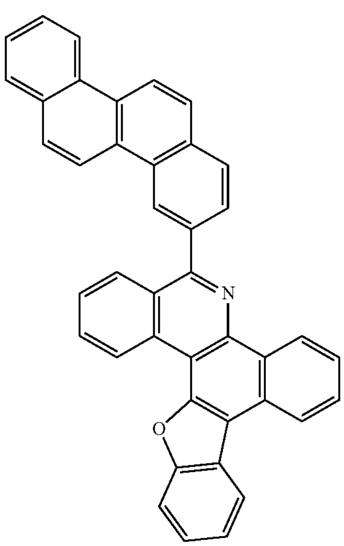
-continued
H2-242
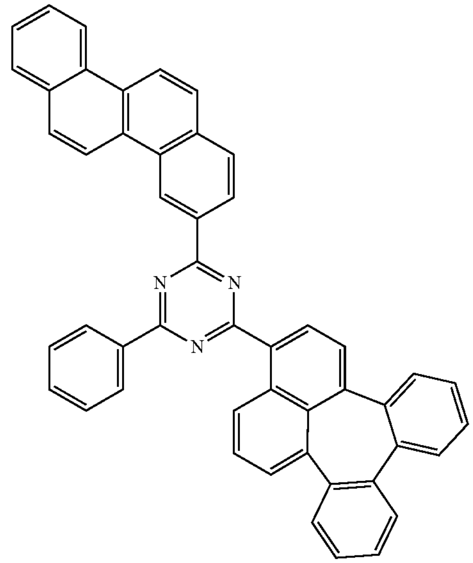
H2-243
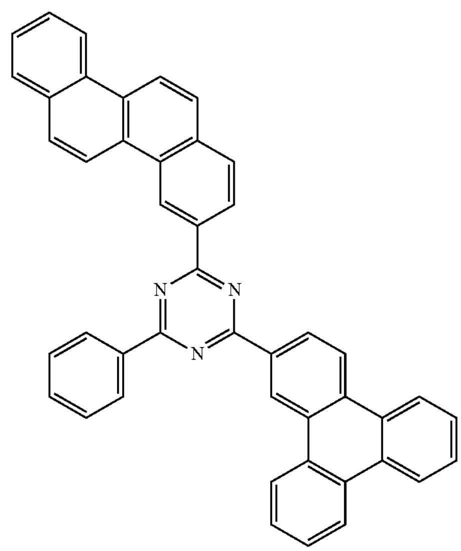

-continued
H2-244
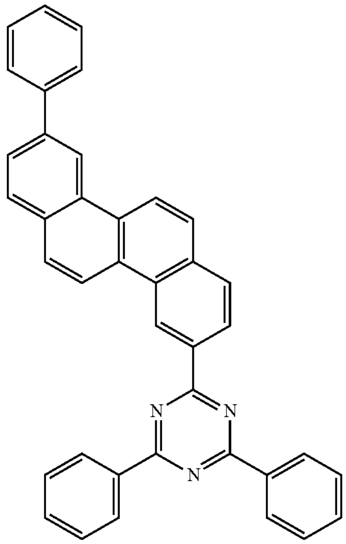
H2-245
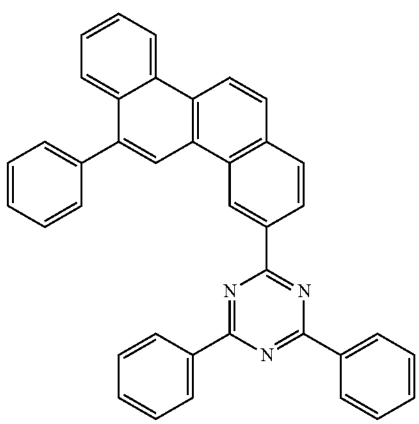
H2-246
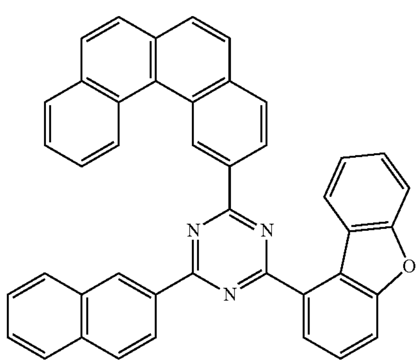
-continued
H2-247
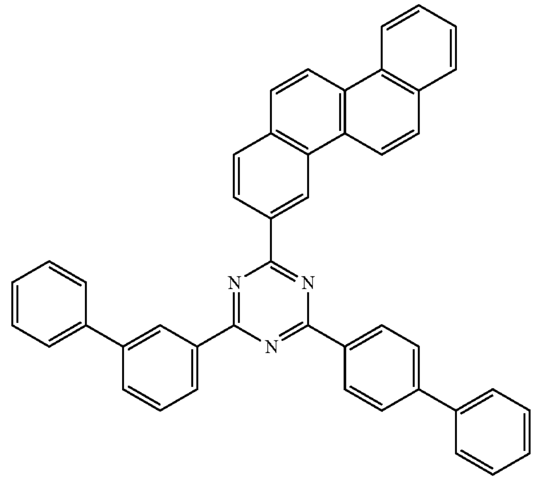
H2-248
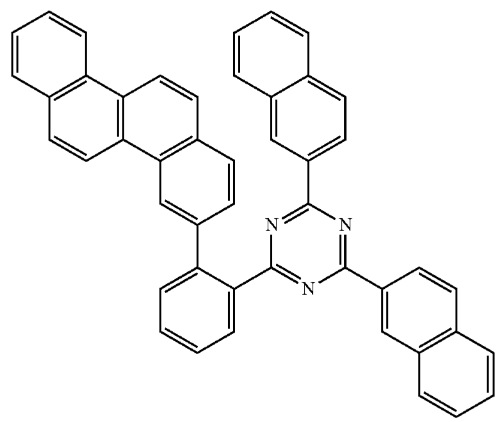
H2-249
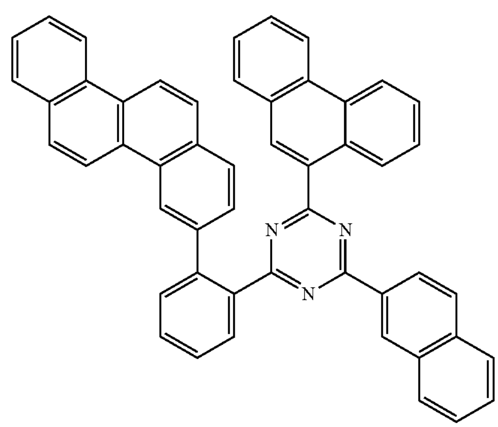

-continued
H2-250
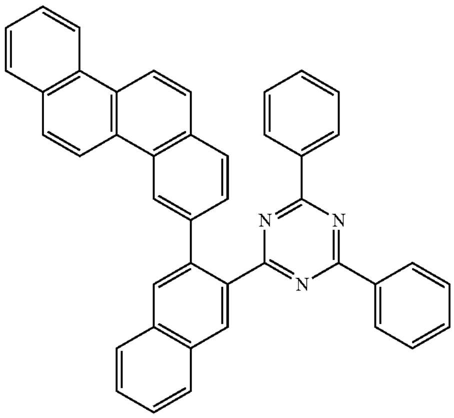
H2-251
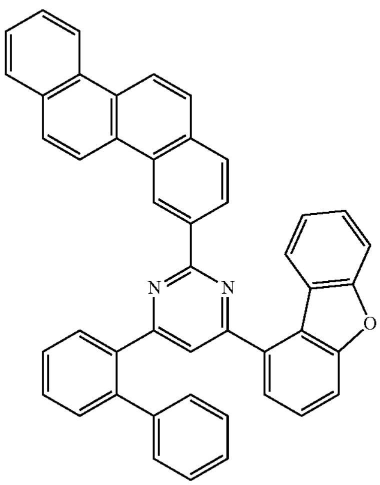
H2-252
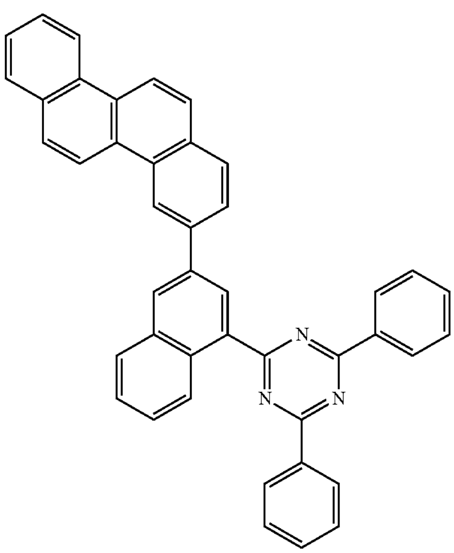
-continued
H2-253
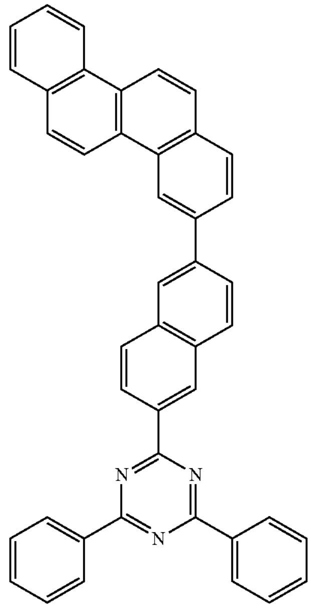
H2-254
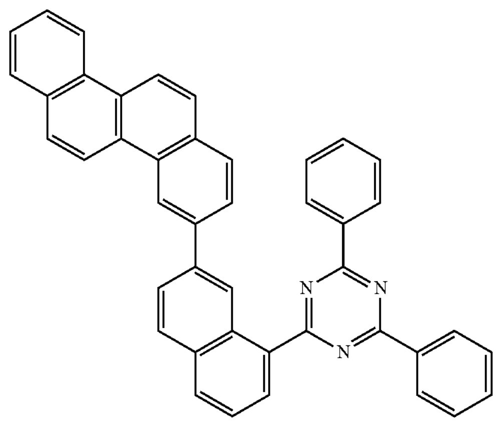
H2-255
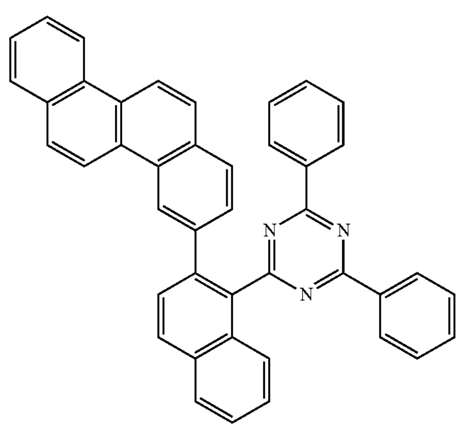

-continued
H2-256
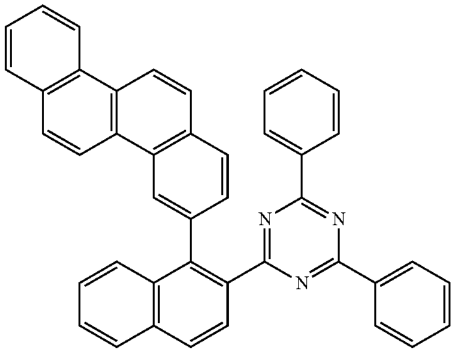
H2-257
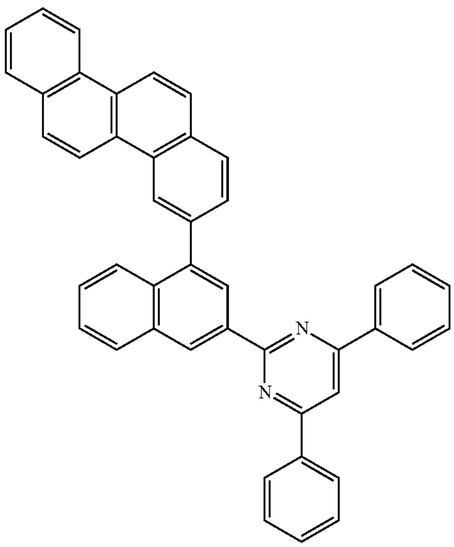
H2-258
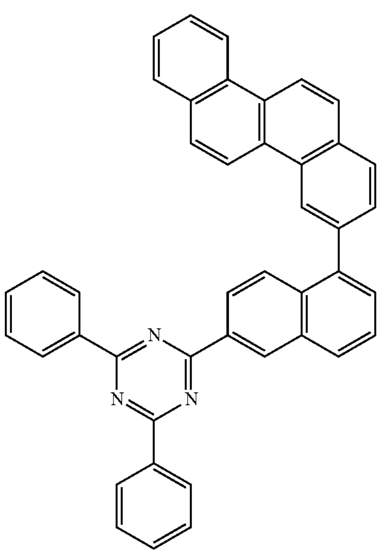
-continued
H2-259
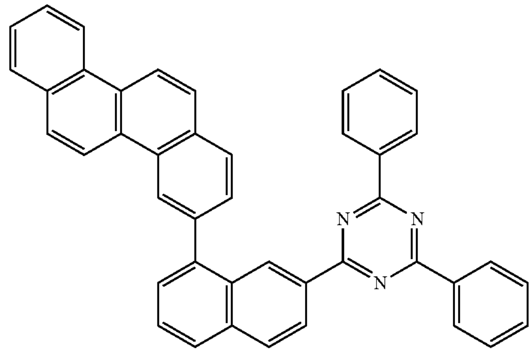
H2-260
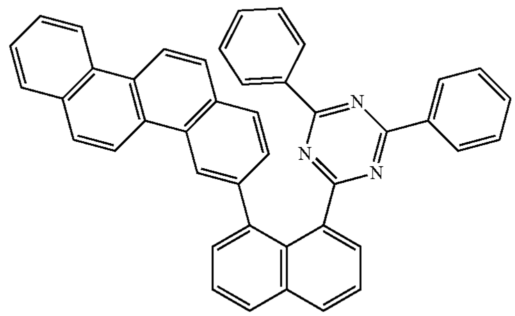
H2-261
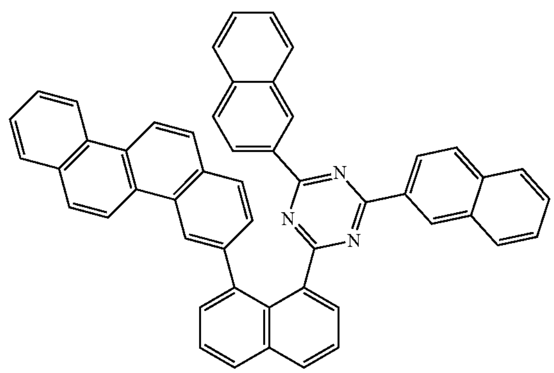
H2-262
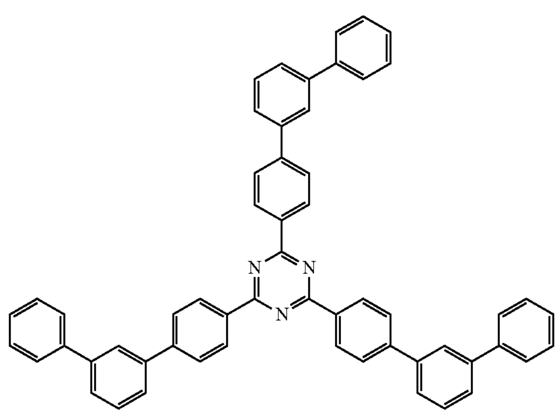

-continued
H2-263
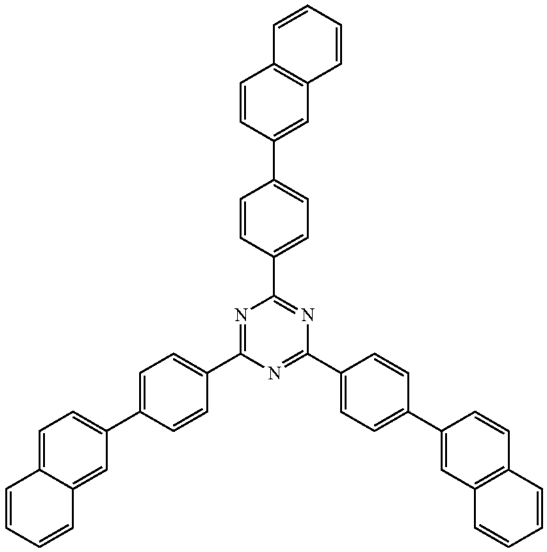
H2-264
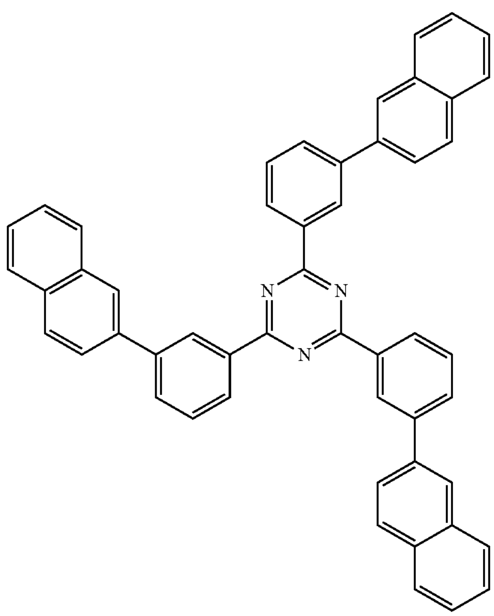
-continued
H2-265
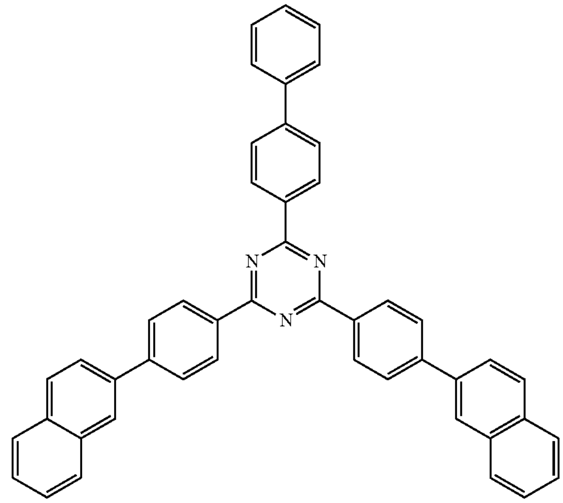
H2-266
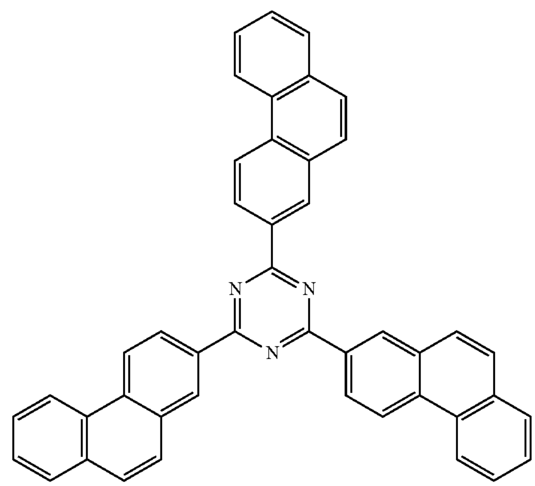
H2-267
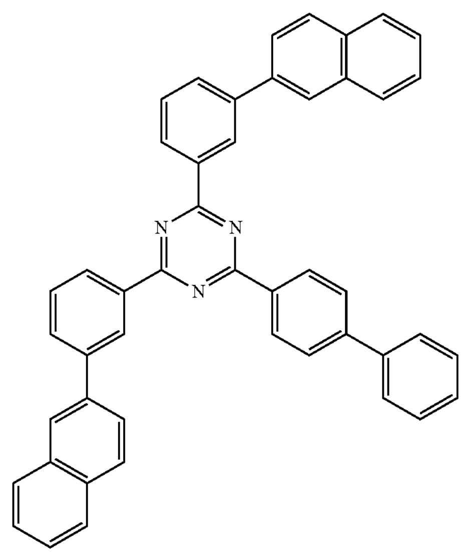

-continued
H2-268
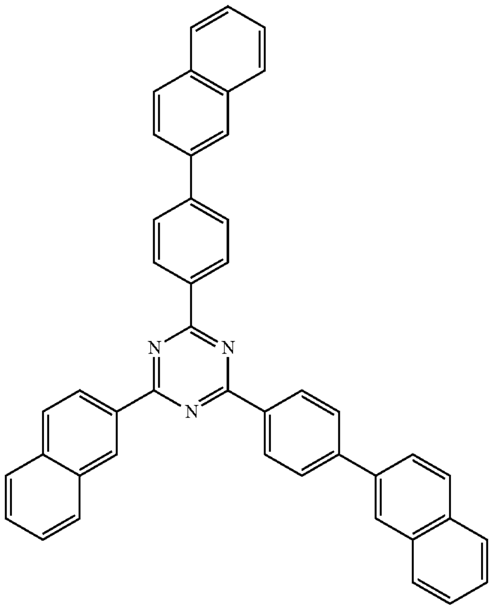
H2-269
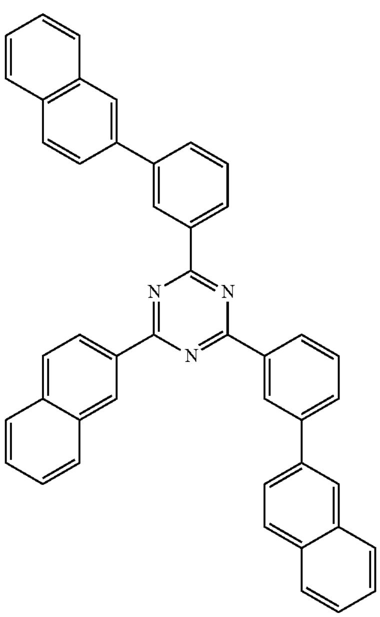
-continued
H2-270
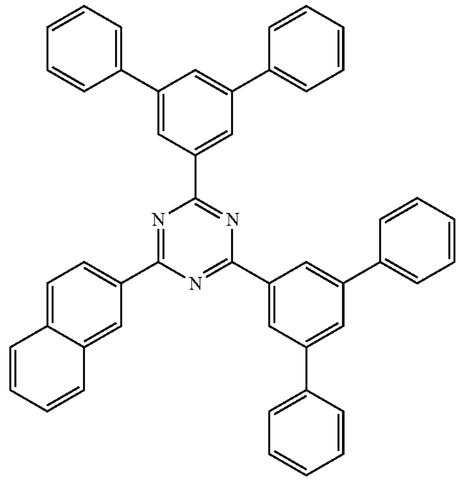
H2-271
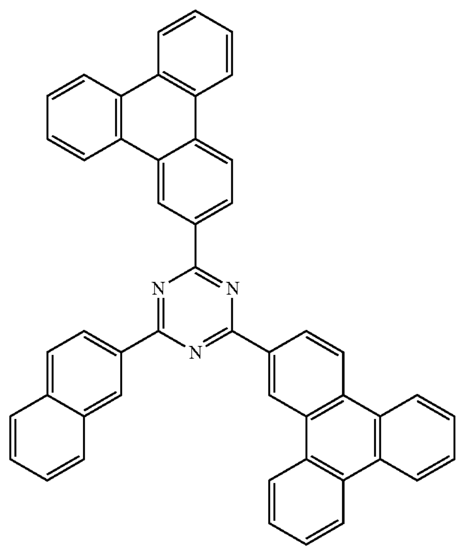
H2-272
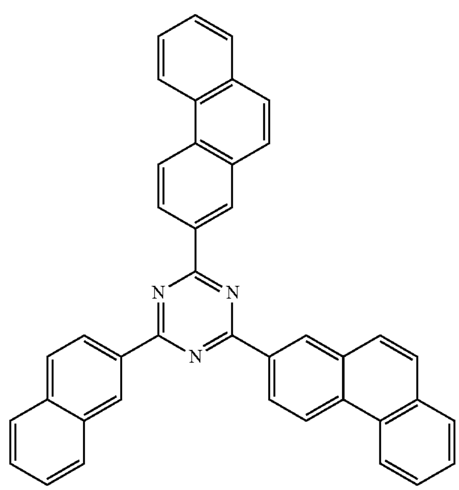

-continued
H2-273
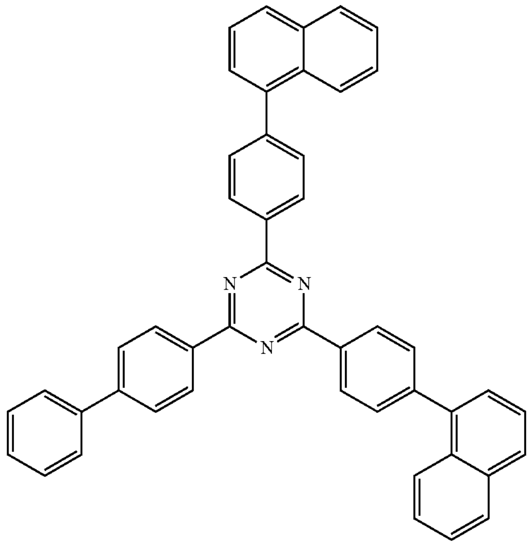
H2-274
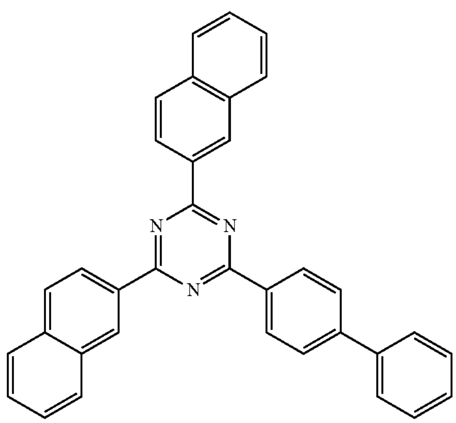
H2-275
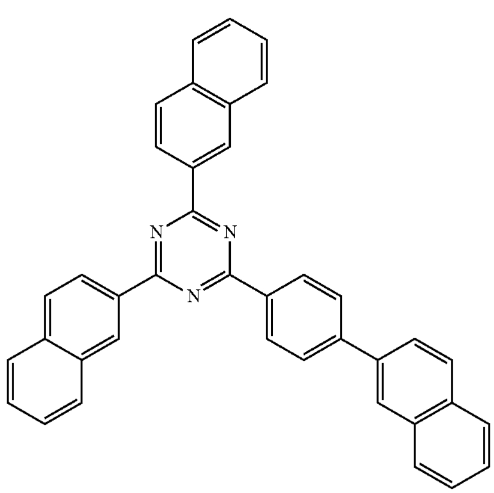
-continued
H2-276
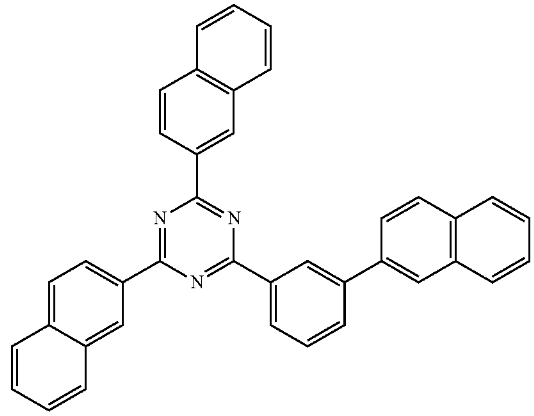
H2-277
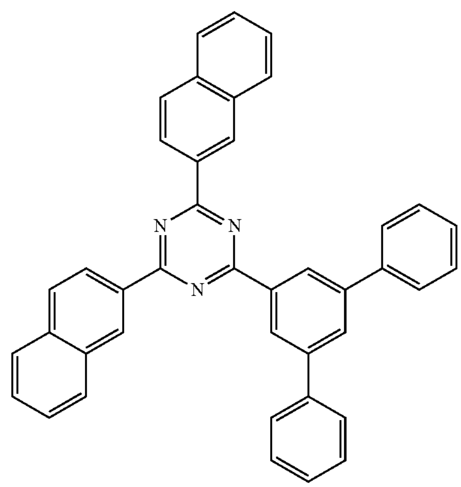
H2-278
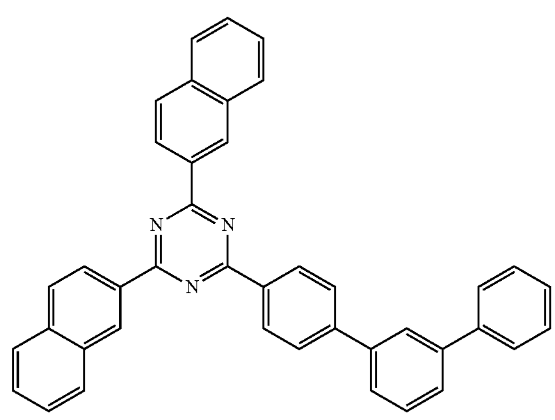

H2-279
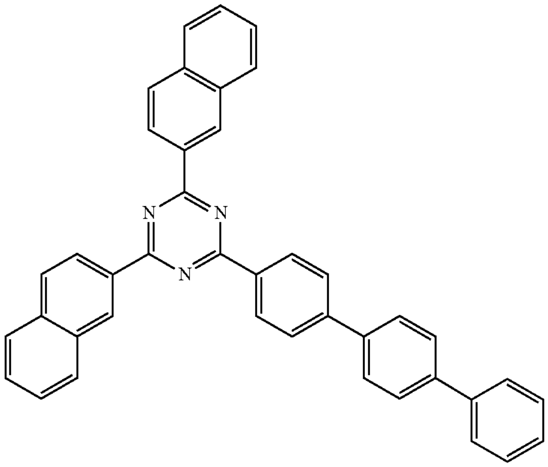
H2-280
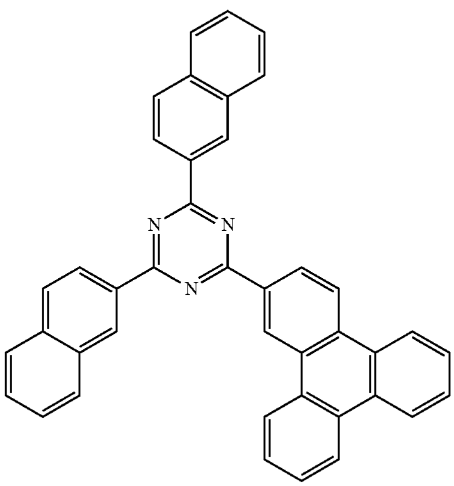
H2-281
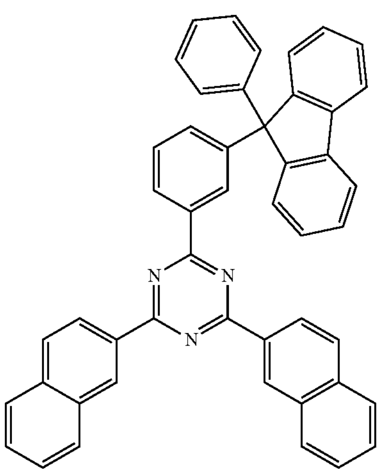
H2-282
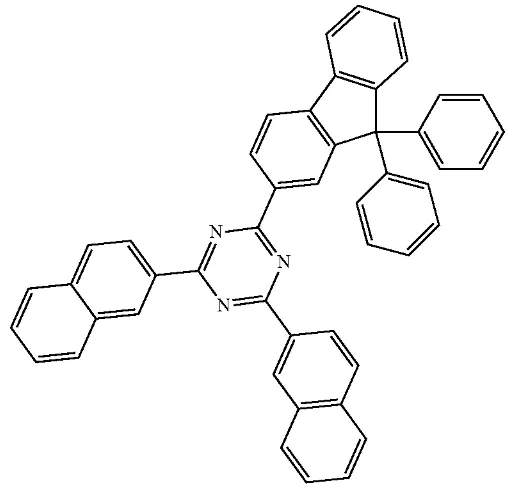
H2-283
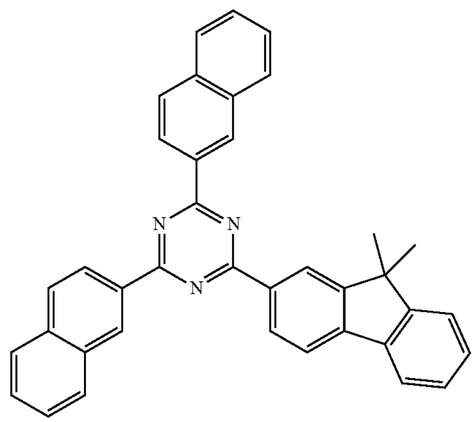
H2-284
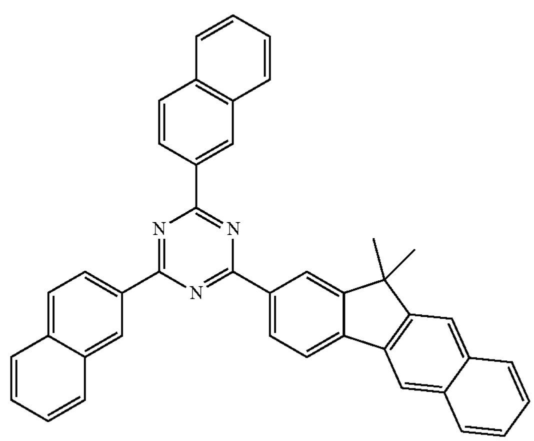

-continued
H2-285
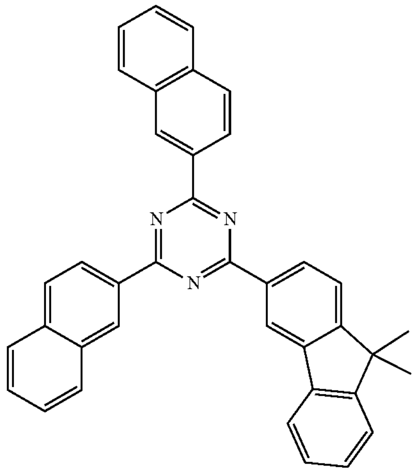
H2-286
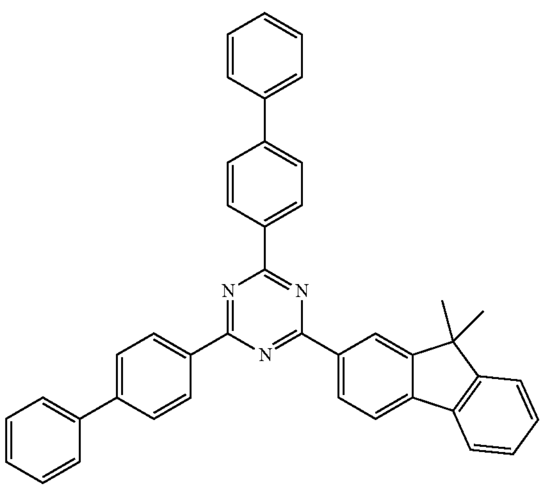
H2-287
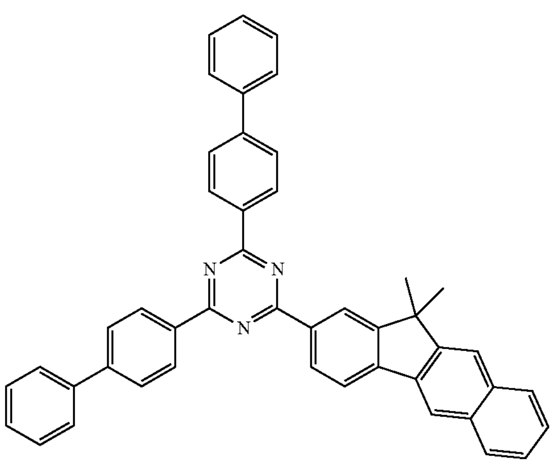
-continued
H2-288
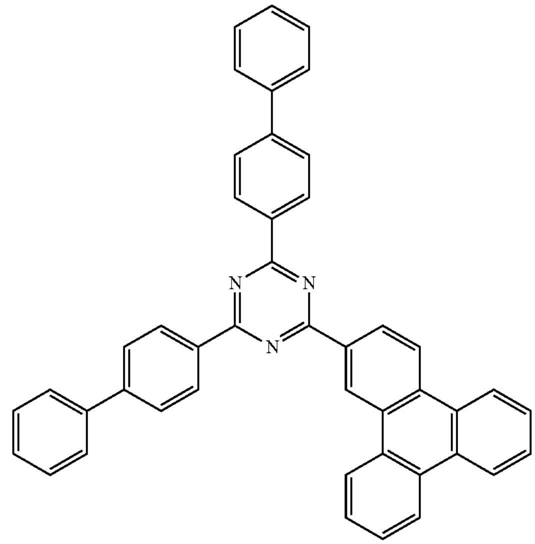
H2-289
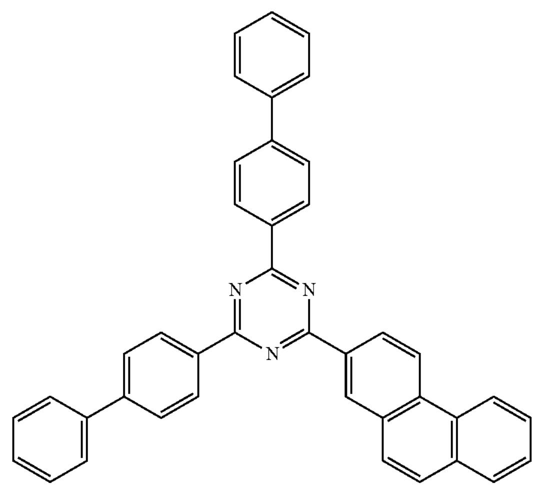
H2-290
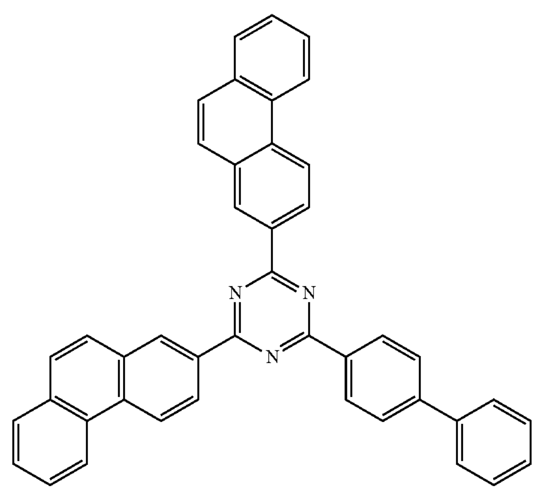

-continued
H2-291
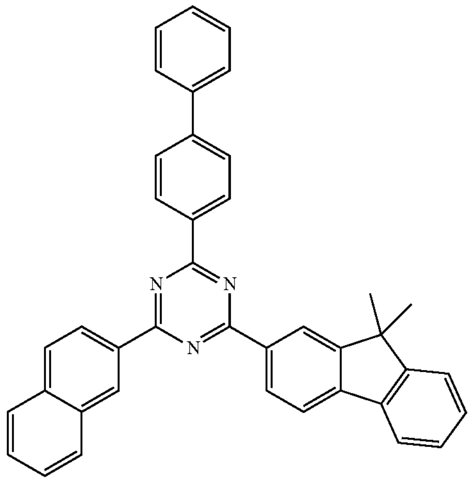
H2-292
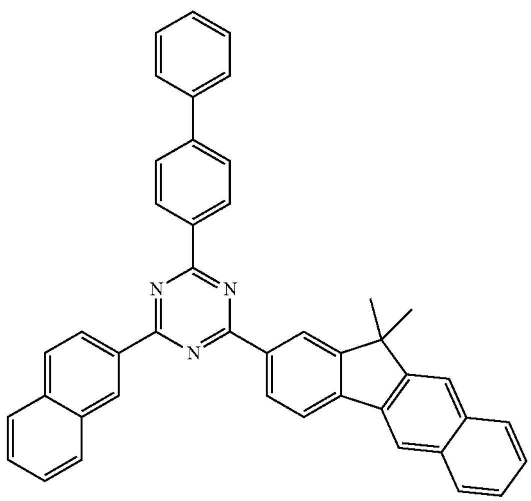
H2-293
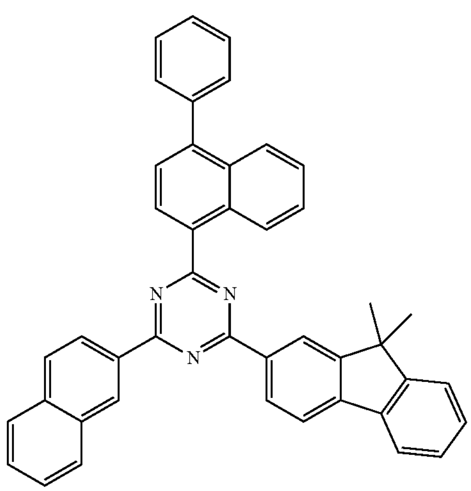
-continued
H2-294
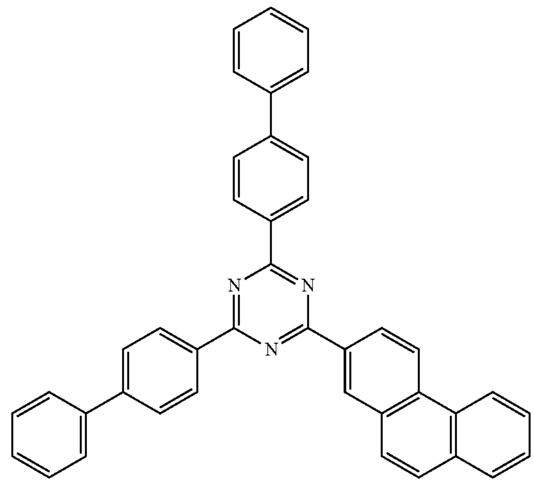
H2-295
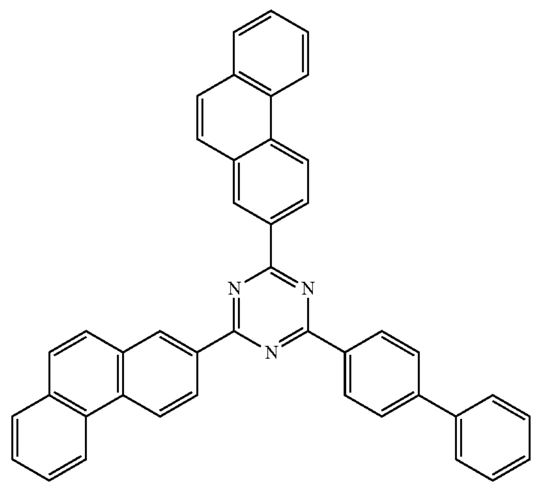
H2-296
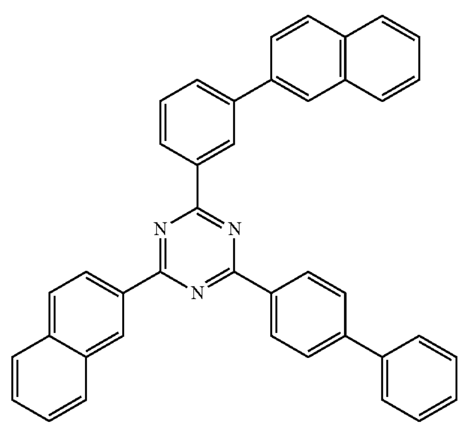

-continued
H2-297
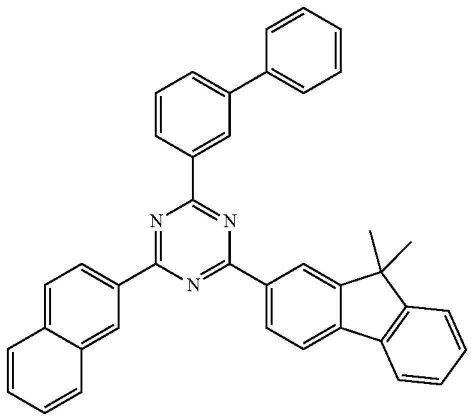
H2-298
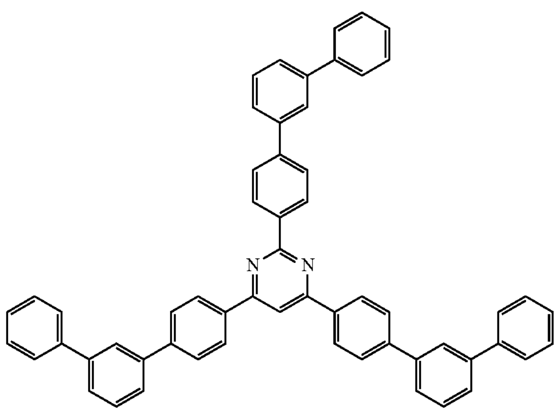
H2-299
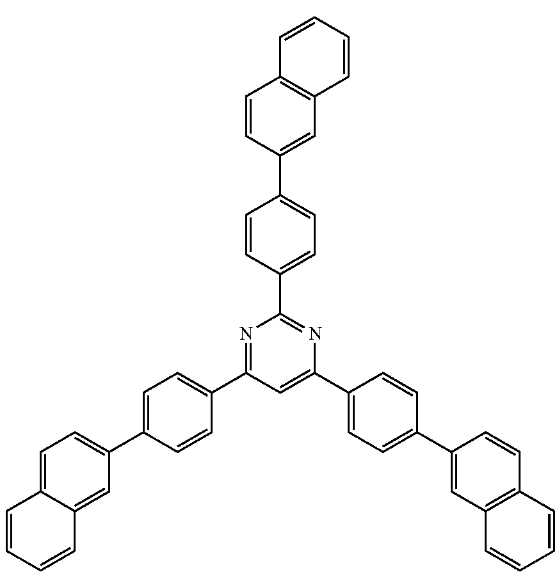
-continued
H2-300
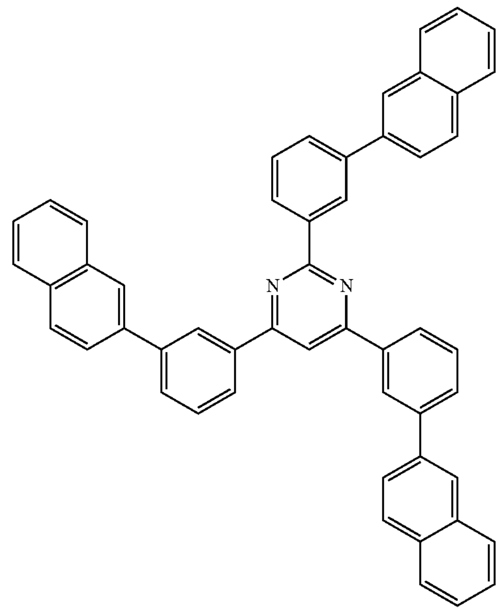
H2-301
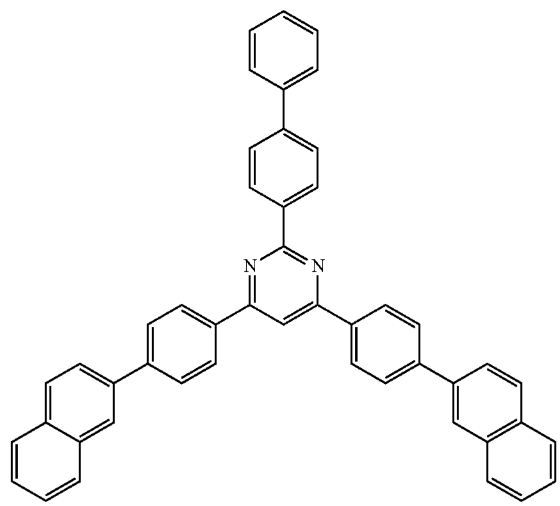
H2-302
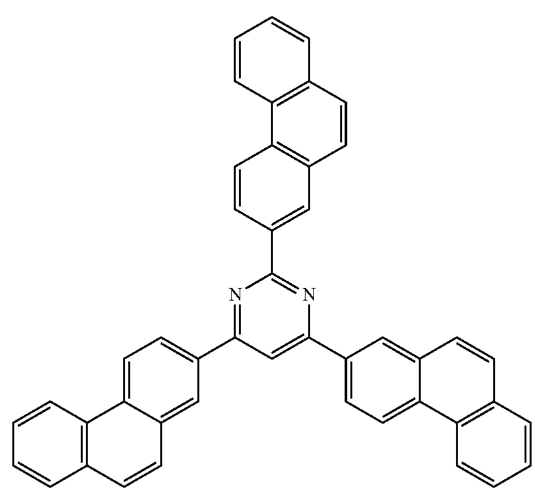

-continued
H2-303
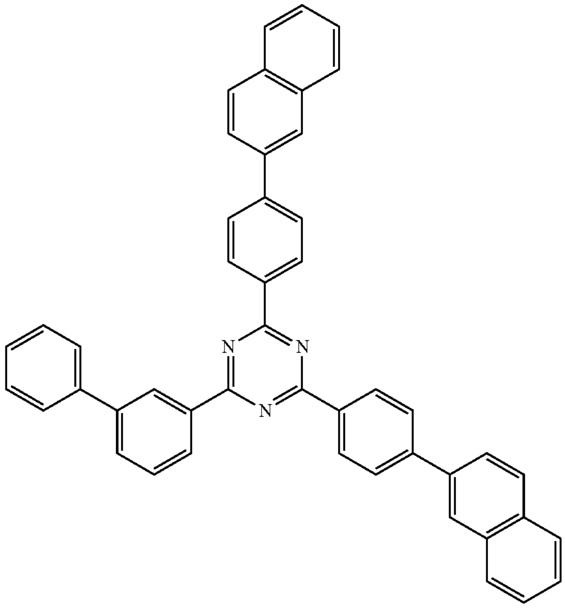
H2-304
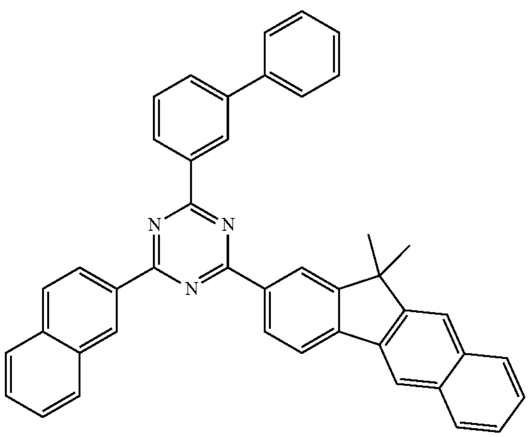
H2-305
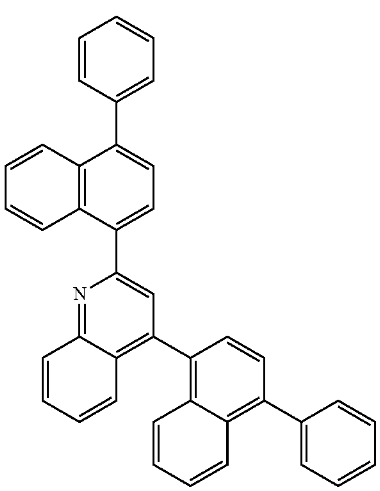
-continued
H2-306
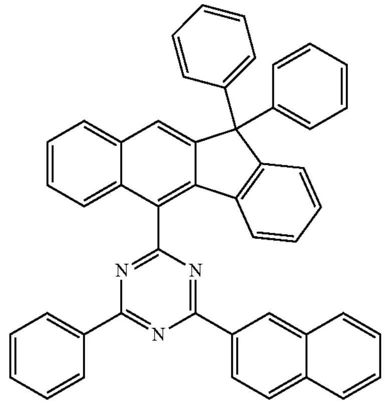
H2-307
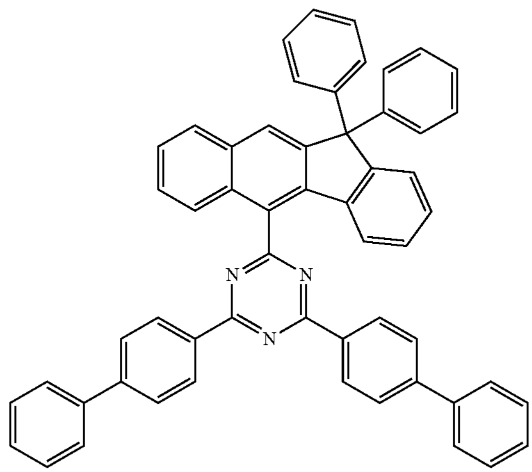
H2-308
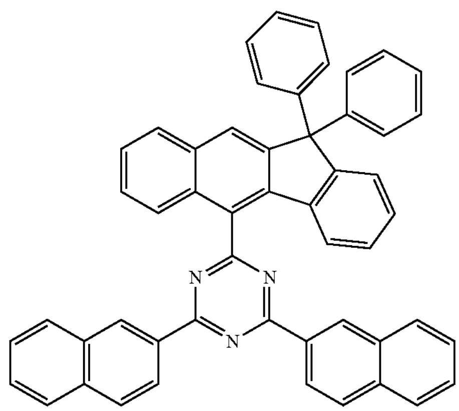
H2-309
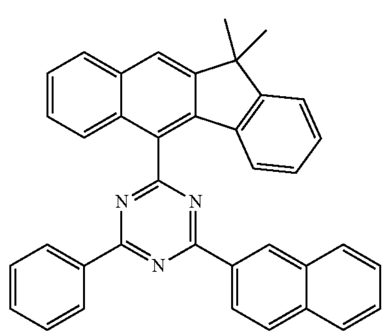

-continued
H2-10
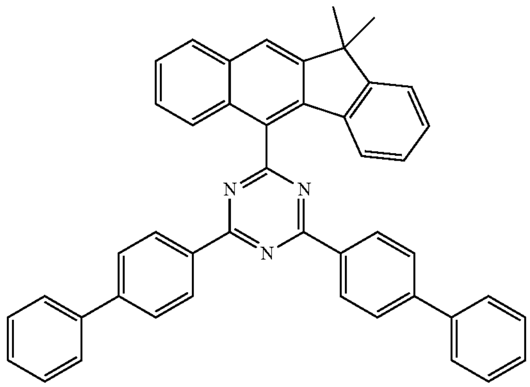
H2-311
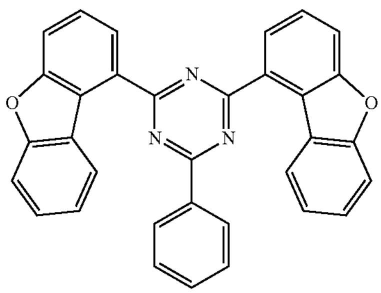
H2-312
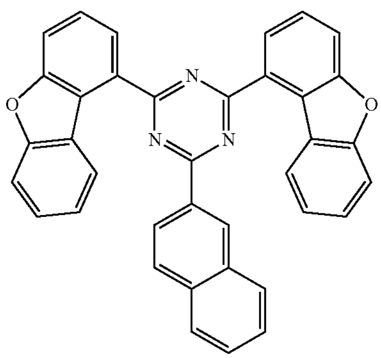
H2-313
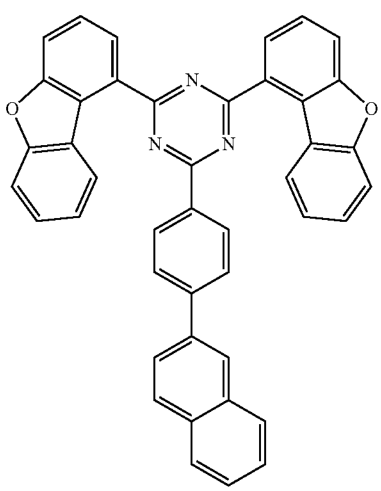
-continued
H2-314
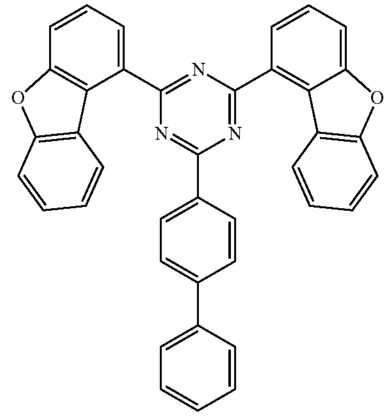
H2-315
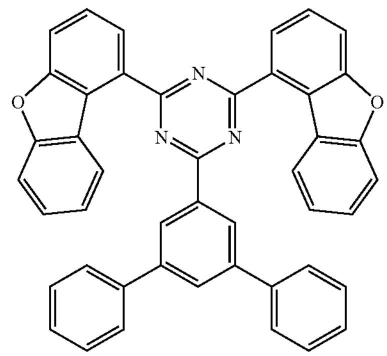
H2-316
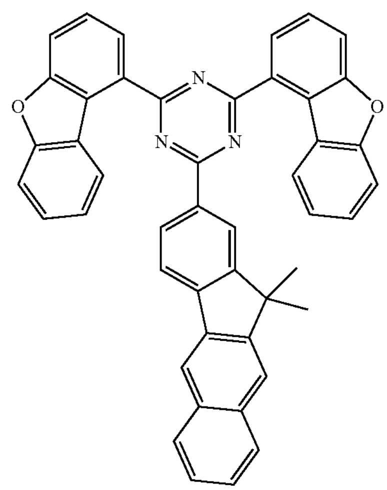
H2-317
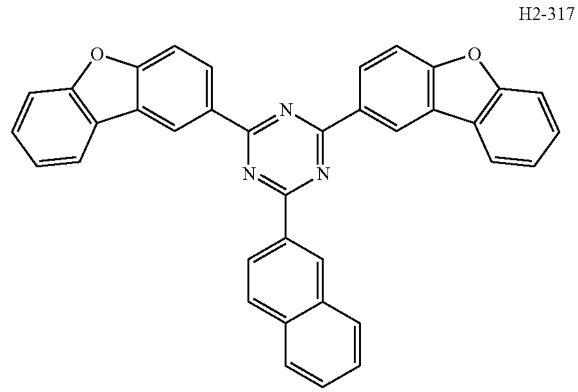

-continued
H2-318
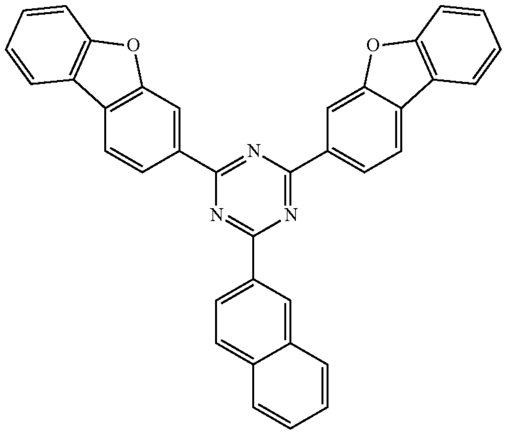
H2-319
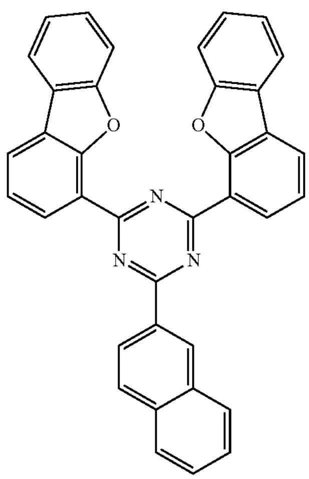
H2-320
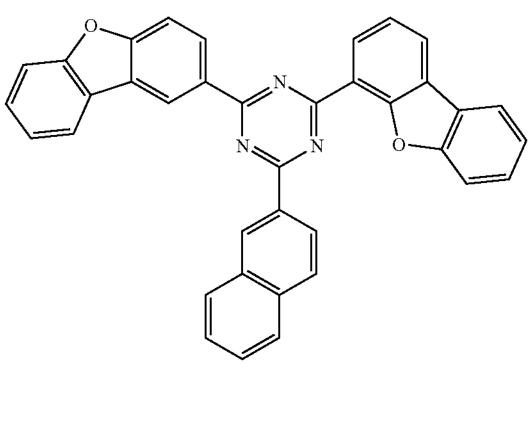
-continued
H2-321
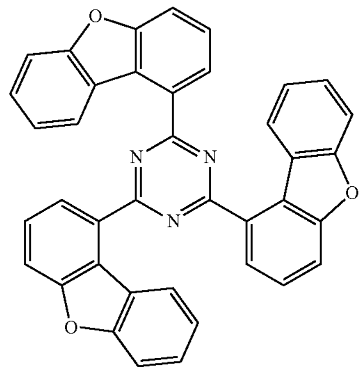
H2-322
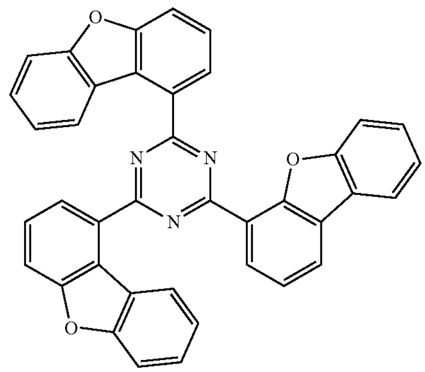
H2-323
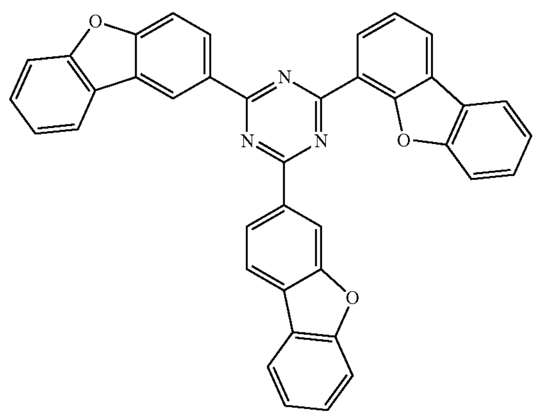
H2-324
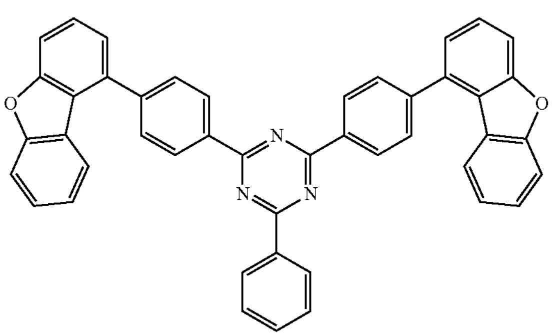

-continued
H2-325
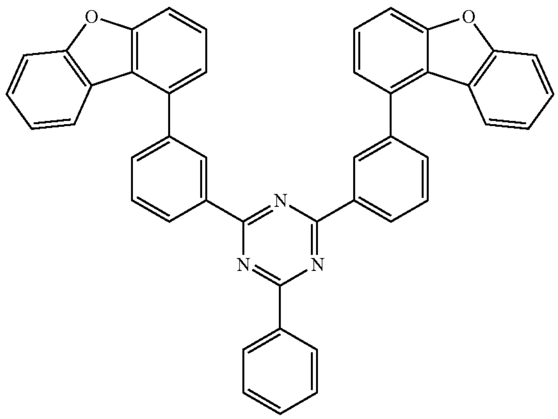
H2-326
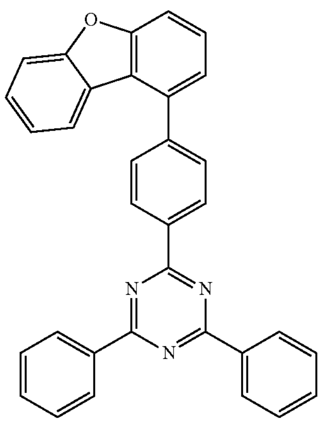
H2-327
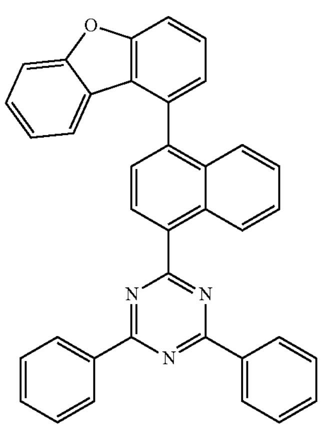
-continued
H2-328
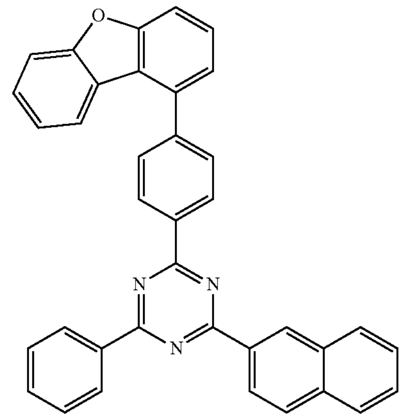
H2-329
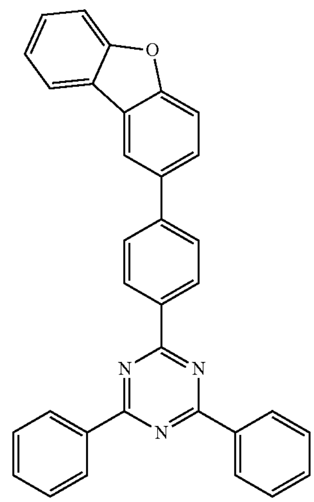
H2-330
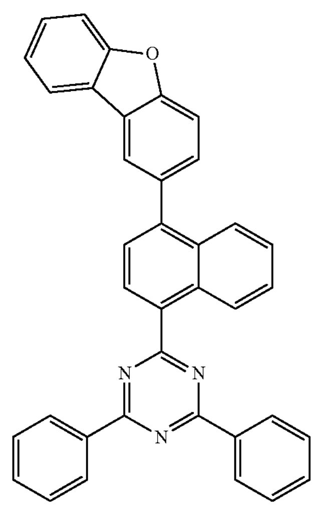

-continued
H2-331
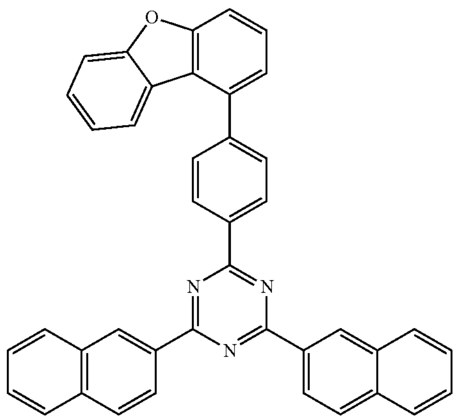
H2-332
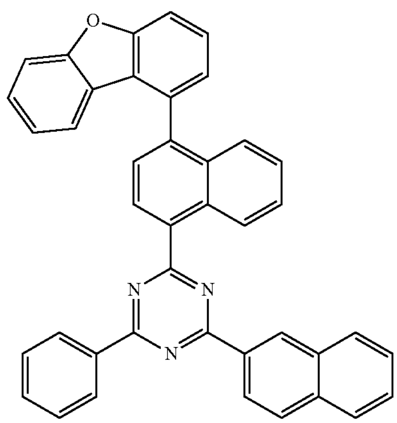
H2-333
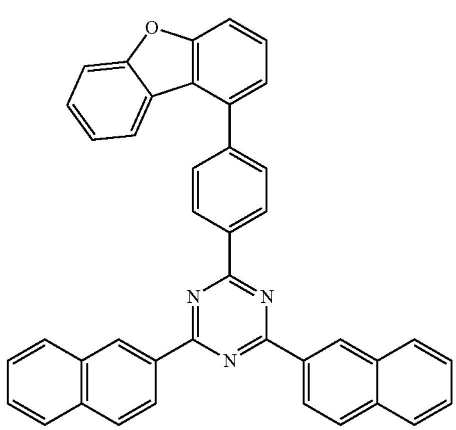
-continued
H2-334
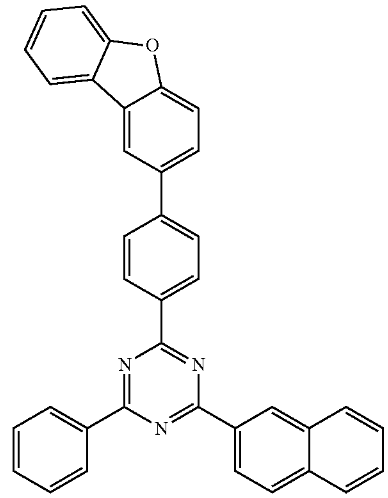
H2-335
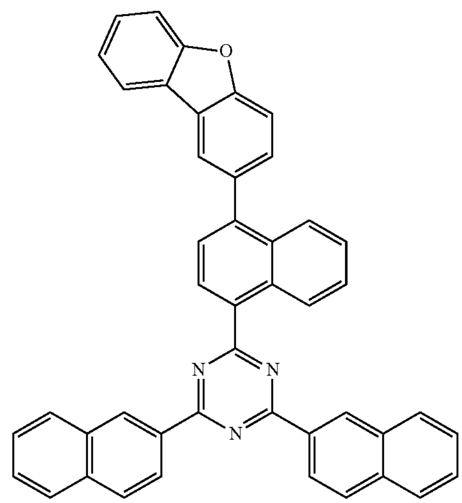
H2-336
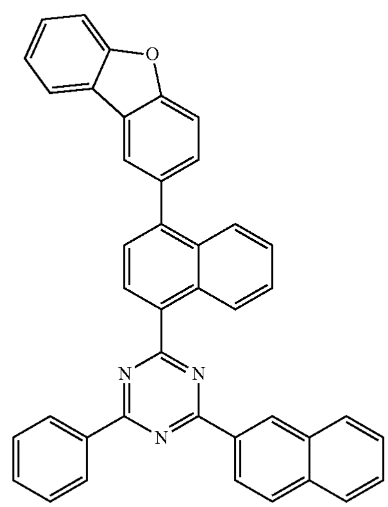

H2-337
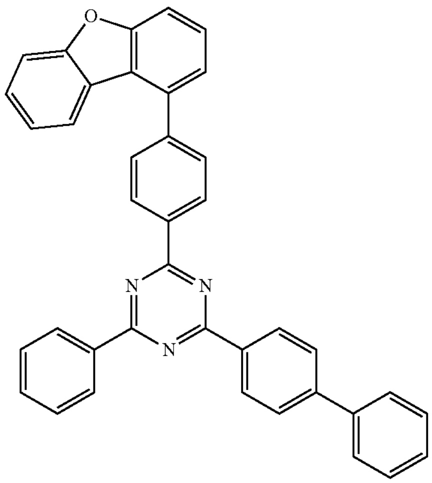
H2-338
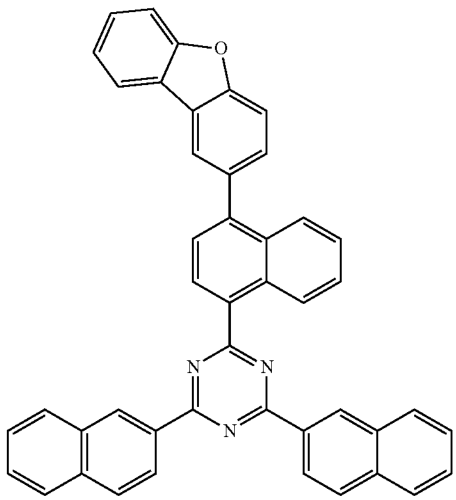
H2-339
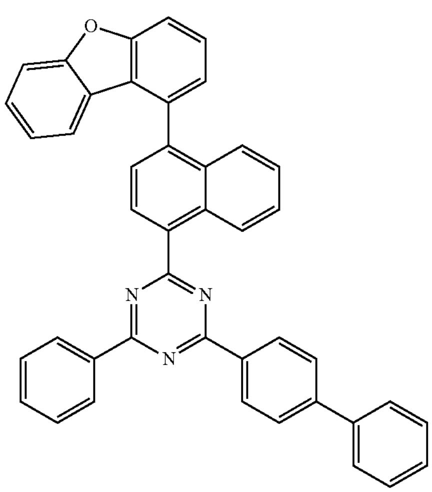
H2-340
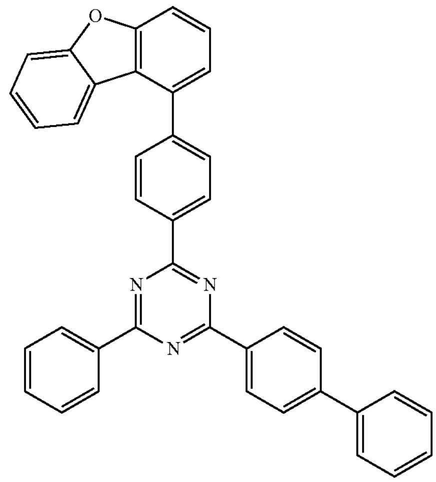
H2-341
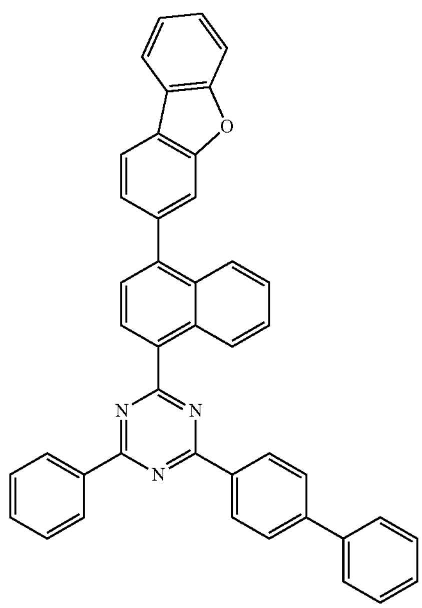

-continued
H2-342
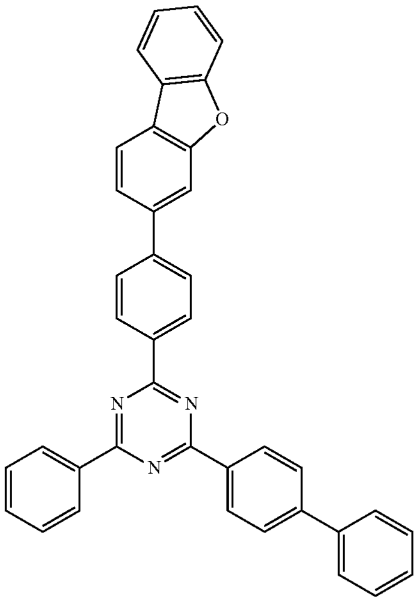
H2-343
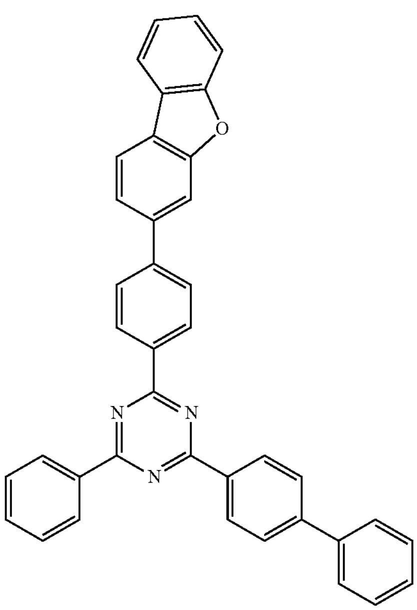
-continued
H2-344
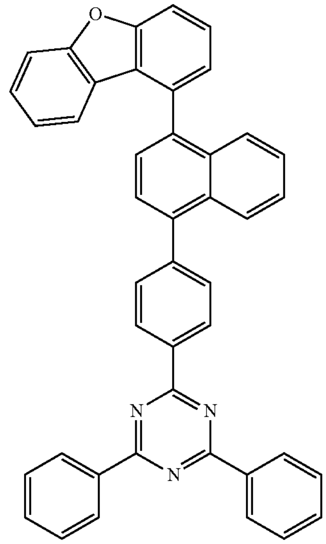
H2-345
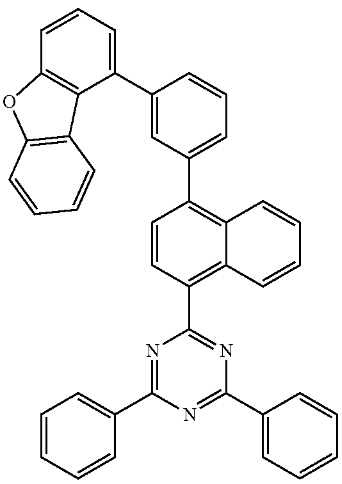
H2-346
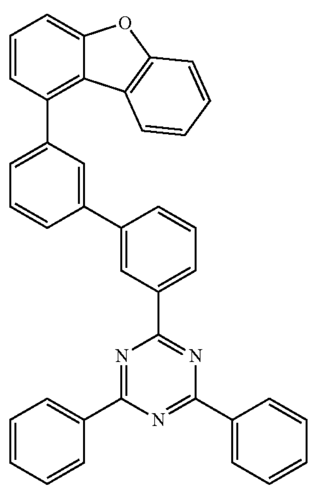

-continued
H2-347
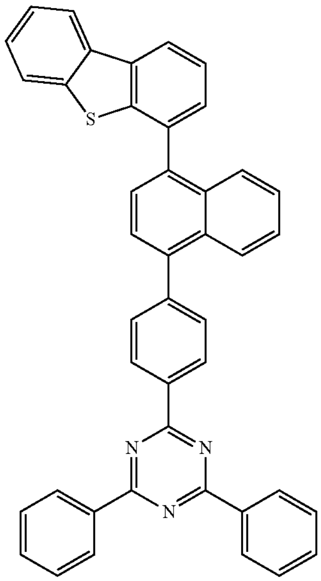
H2-348
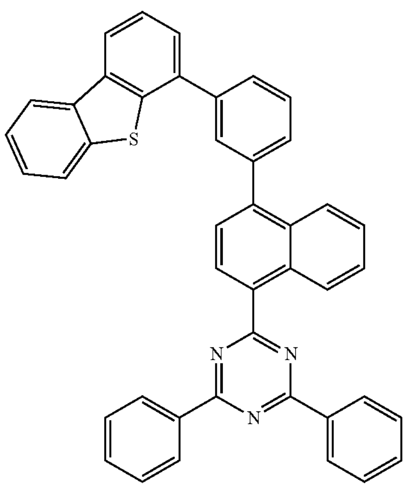
H2-349
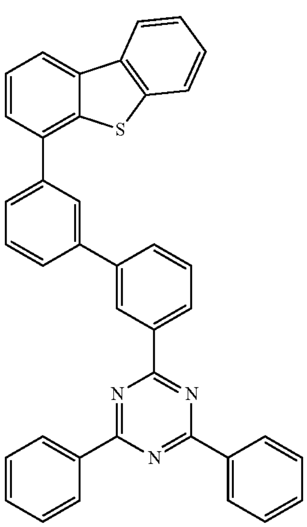
-continued
H2-350
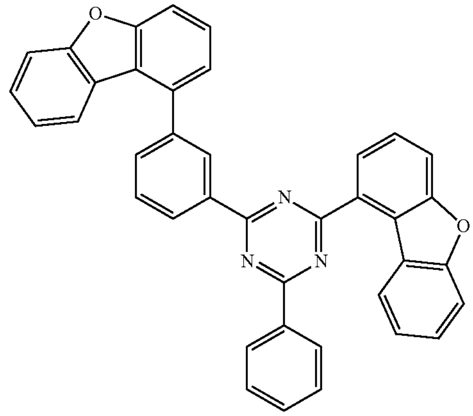
H2-351
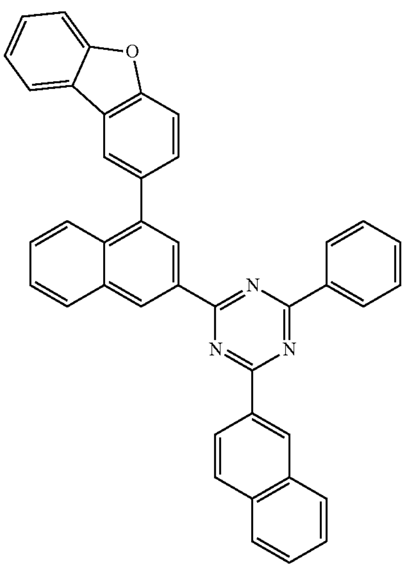
H2-352
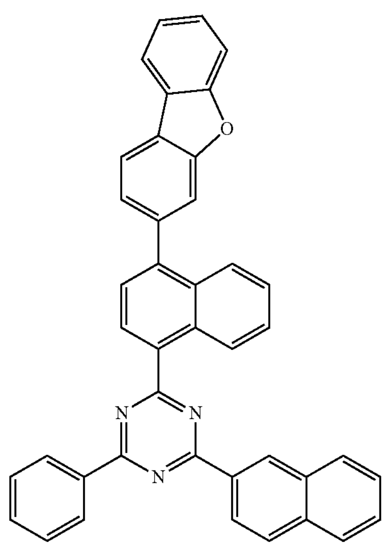

-continued
H2-353
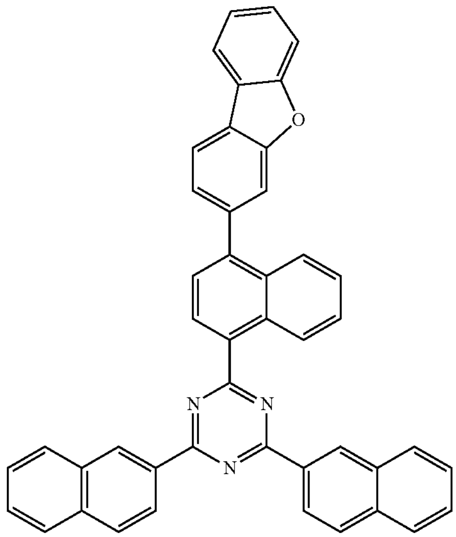
H2-354
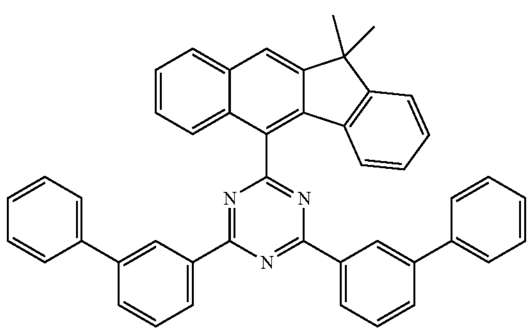
H2-355
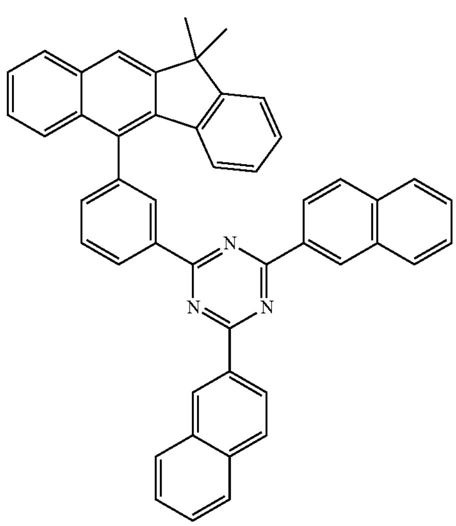
-continued
H2-356
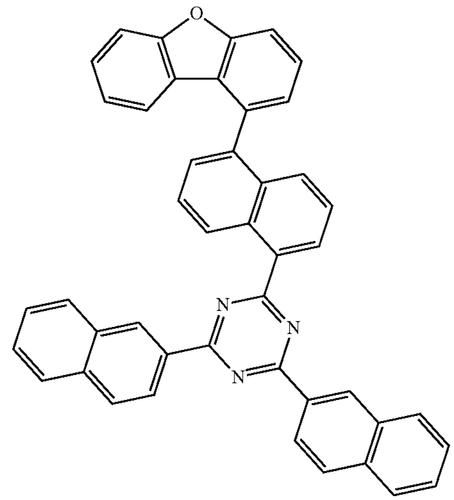
H-357
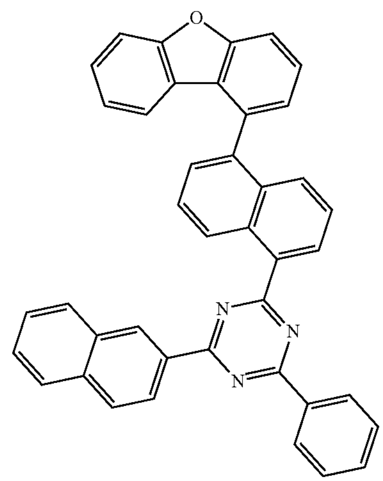
H2-358
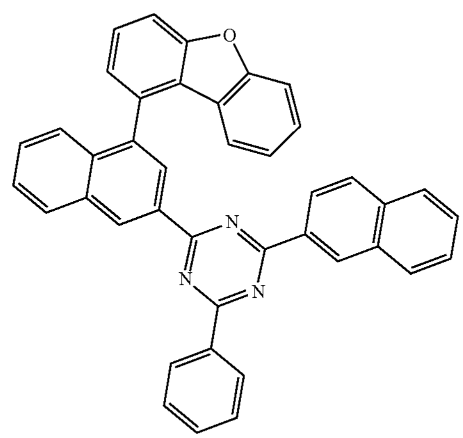

-continued
H2-359
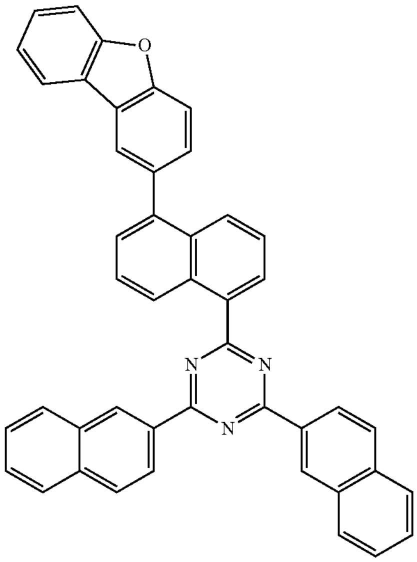
H2-360
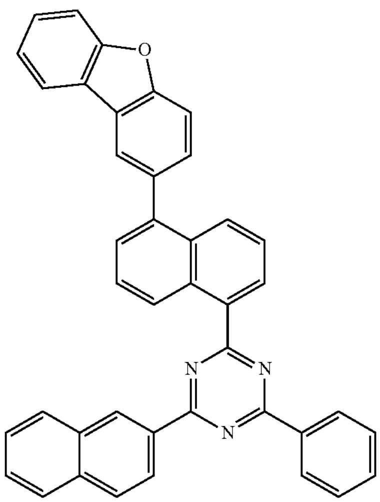
H2-361
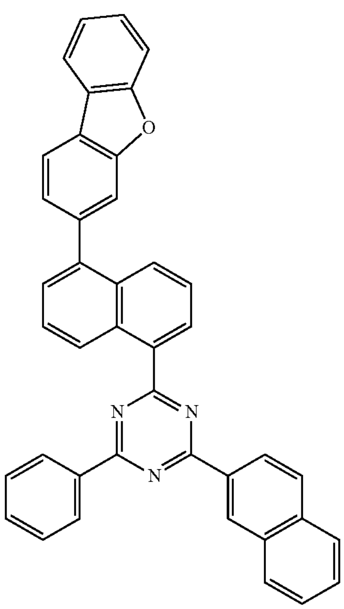
-continued
H2-363
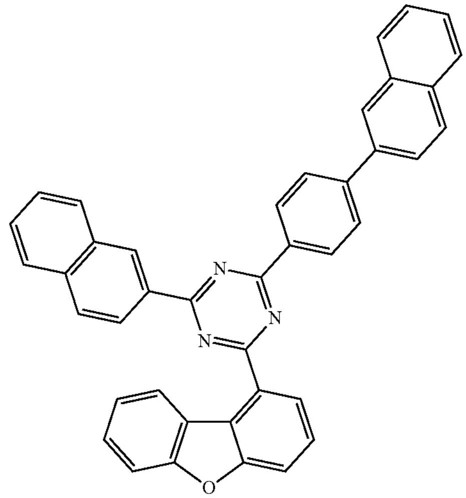
H2-363
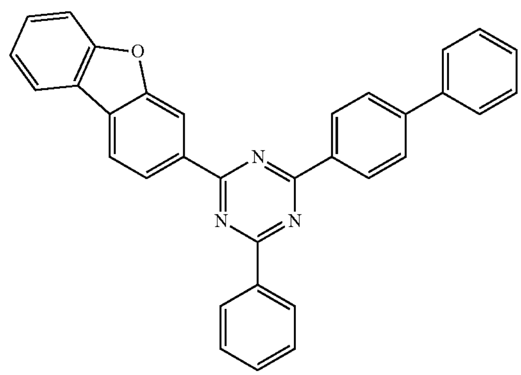
H2-364
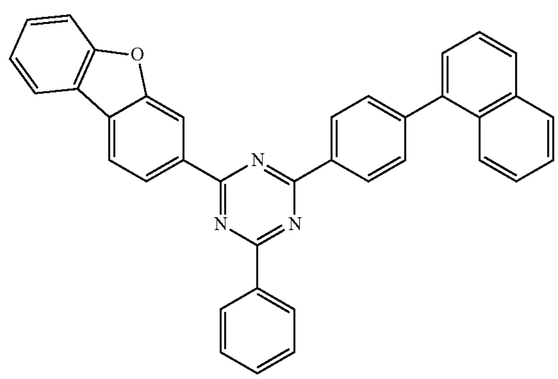

-continued
H2-365
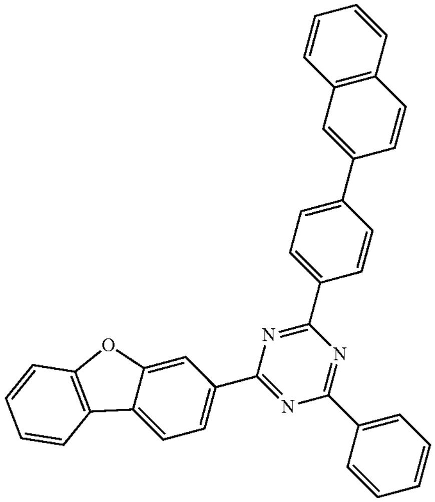
H2-366
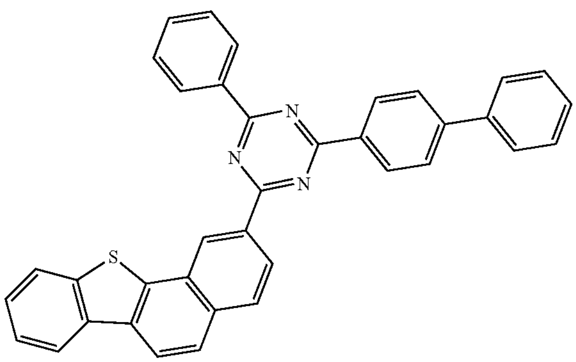
H2-367
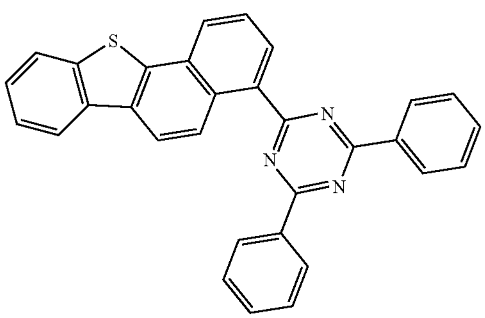
-continued
H2-368
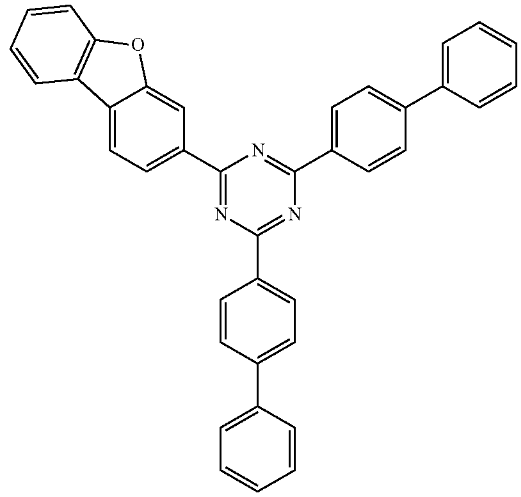
H2-369
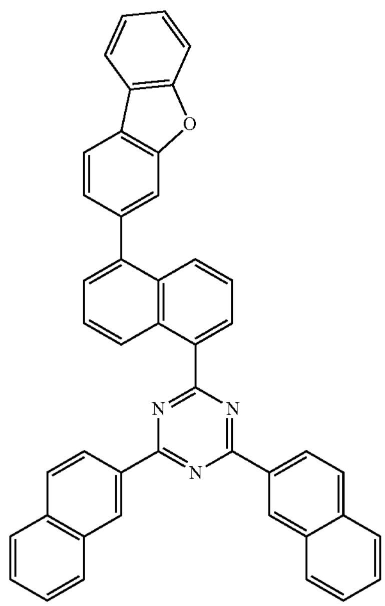
H2-370
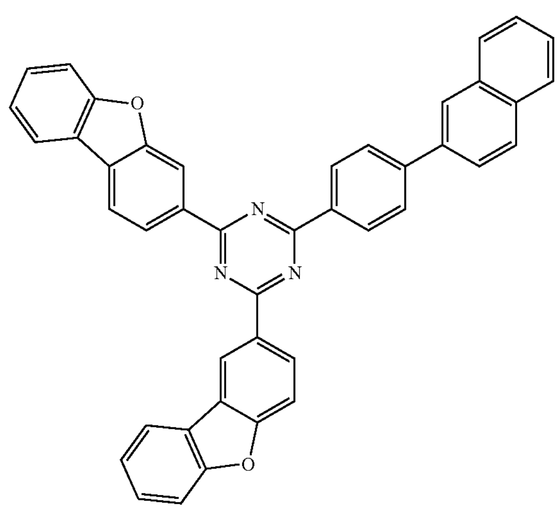

-continued
H2-371
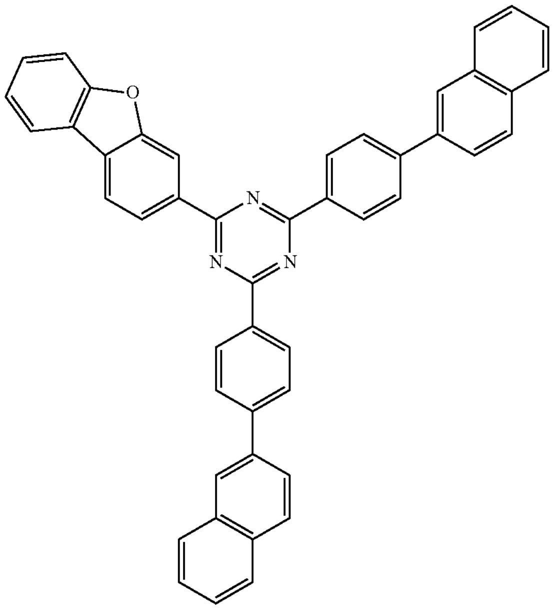
H2-372
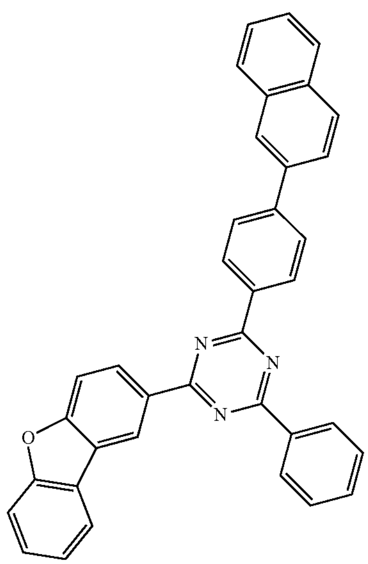
H2-373
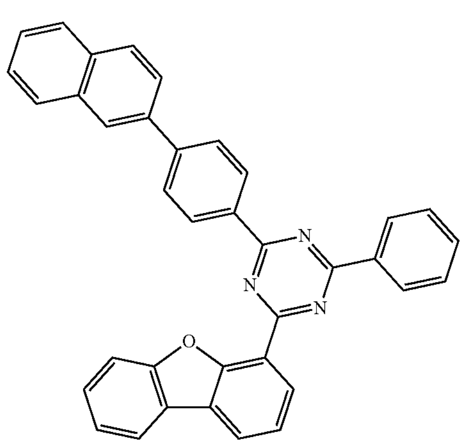
-continued
H2-374
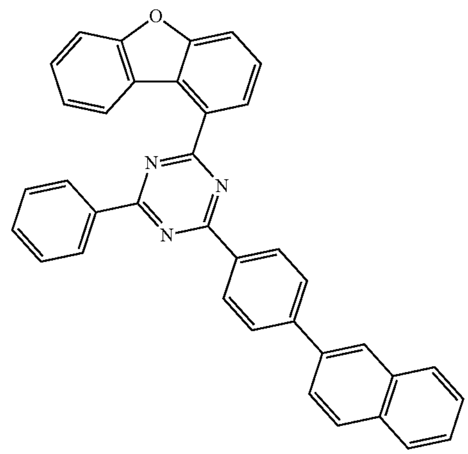
H2-375
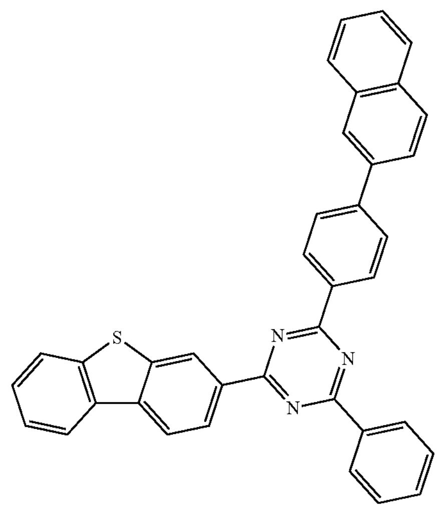
H2-376
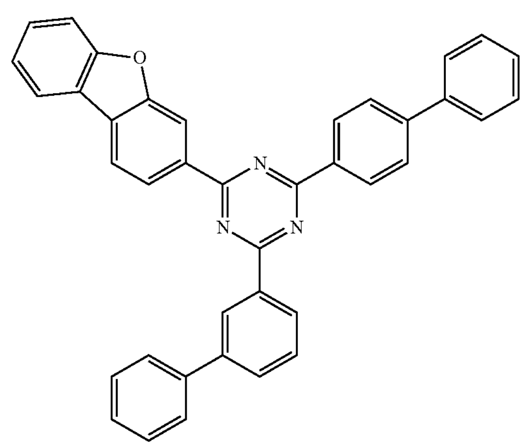

-continued
H2-377
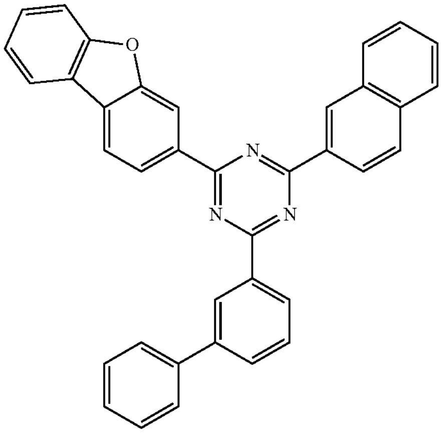
H2-378
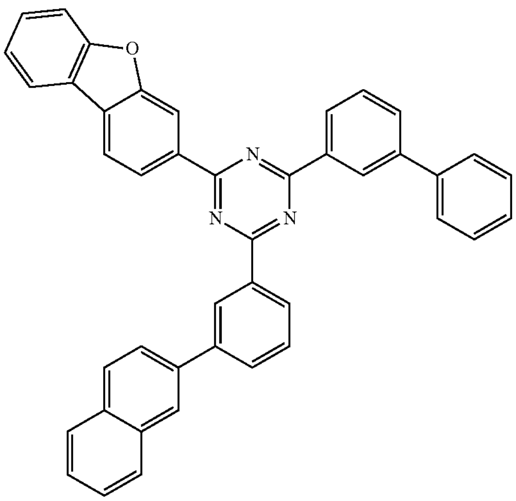
H2-379
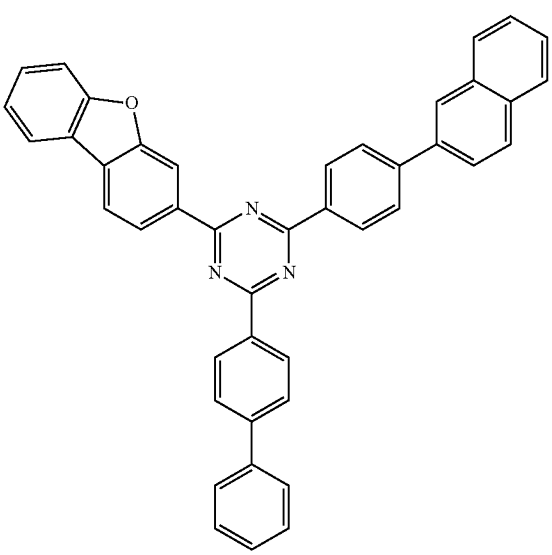
-continued
H2-380
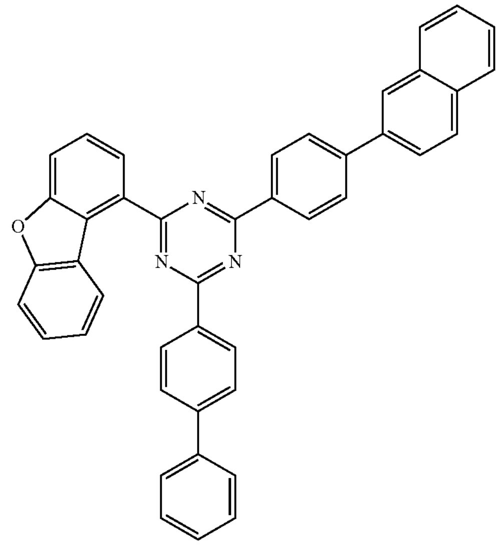
H2-381
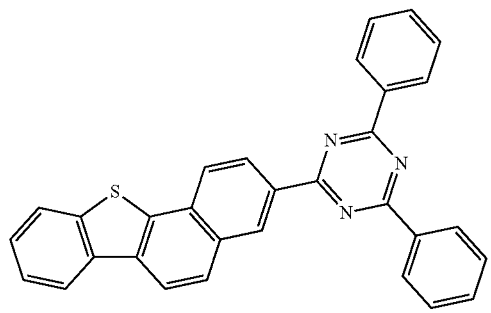
H2-382
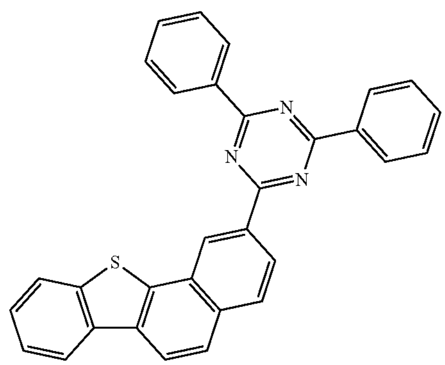
H2-383
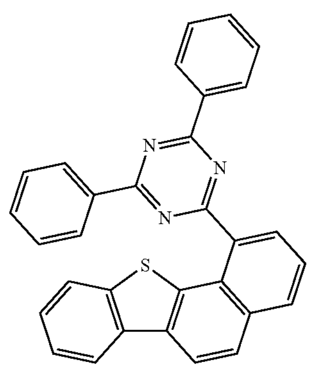

-continued
H2-384
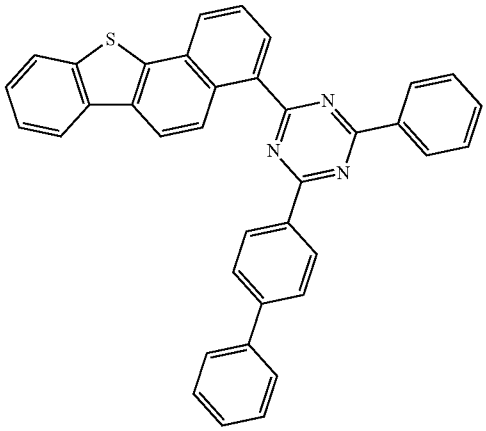
H2-385
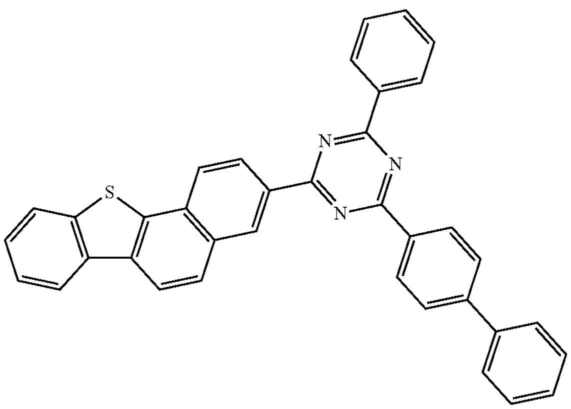
H2-386
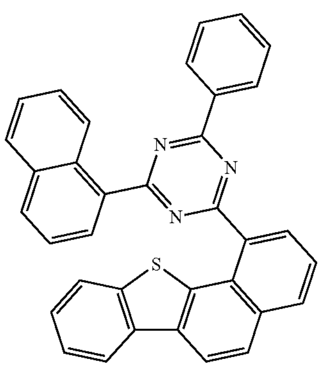
H2-387
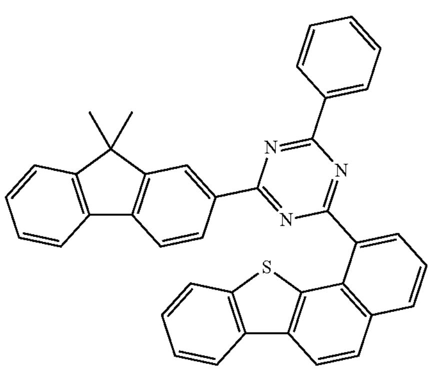
-continued
H2-388
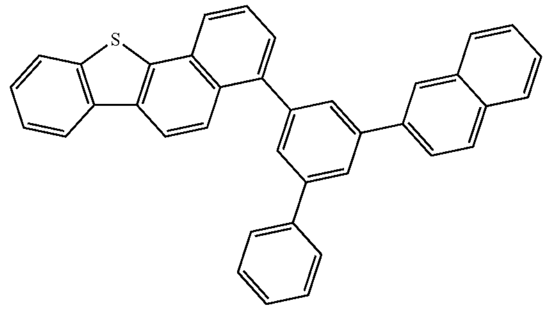
H2-389
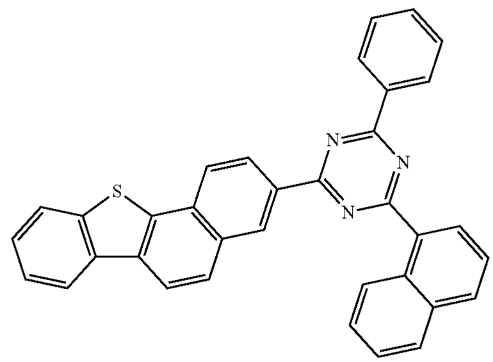
H2-390
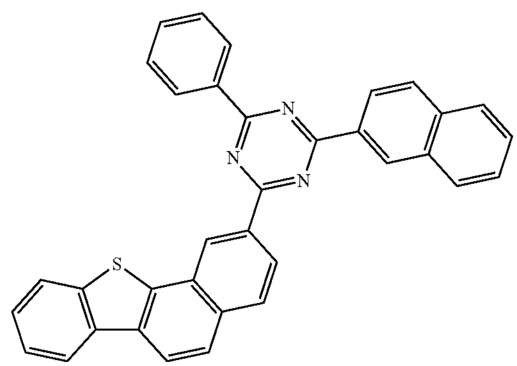
H2-391
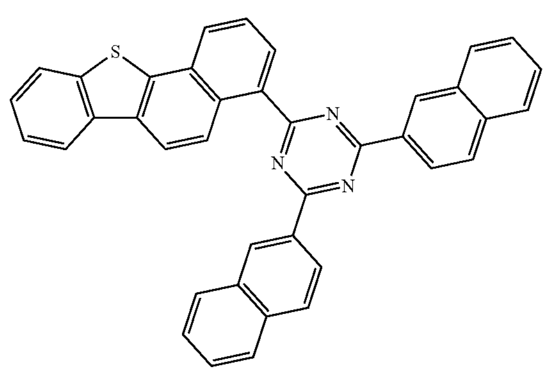

-continued
H2-392
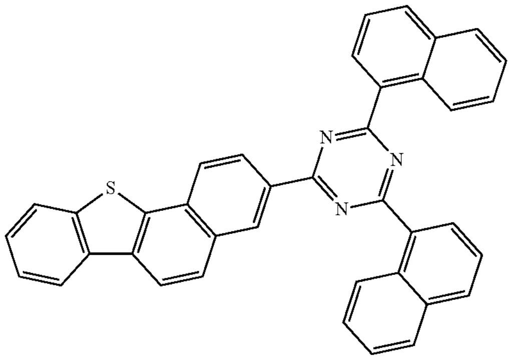
H2-393
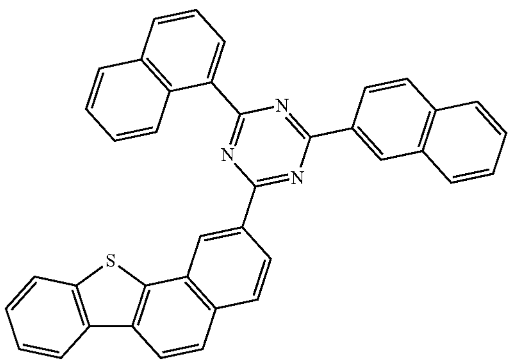
H2-394
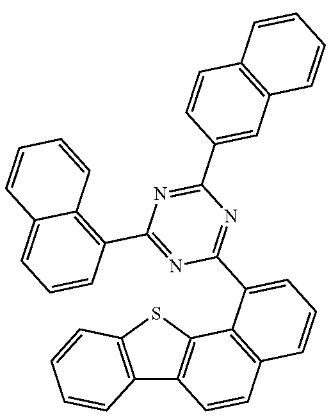
H2-395
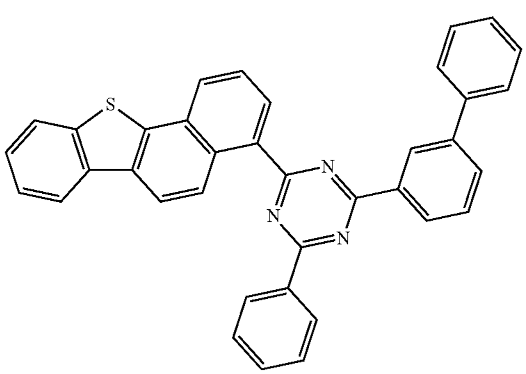
-continued
H2-396
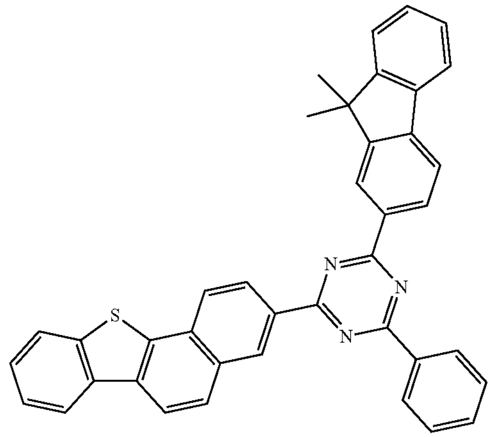
H2-397
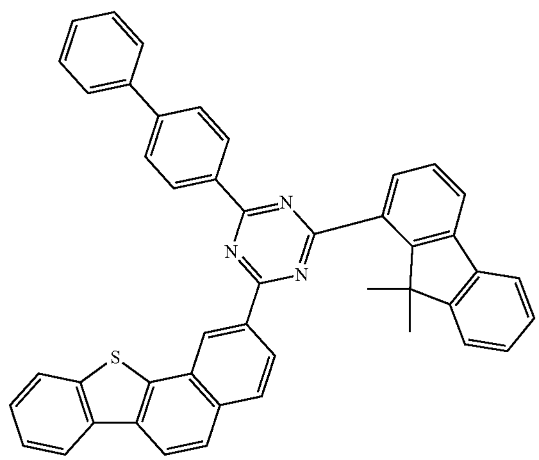
H2-398
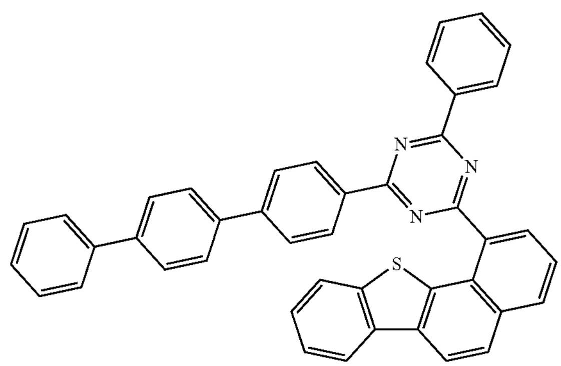

-continued
H2-399
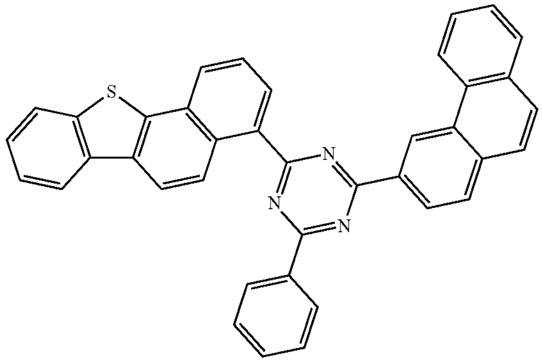
H2-400
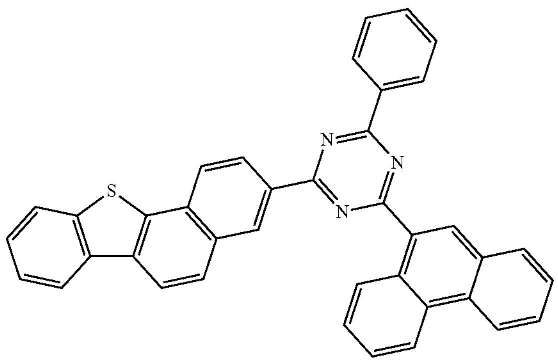
H2-401
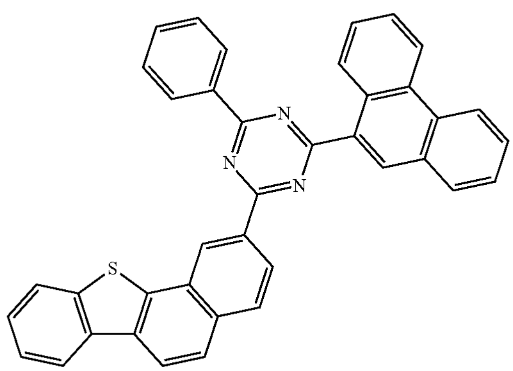
H2-402
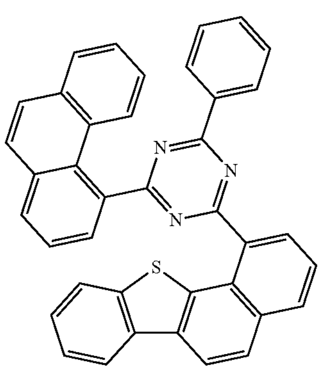
-continued
H2-403
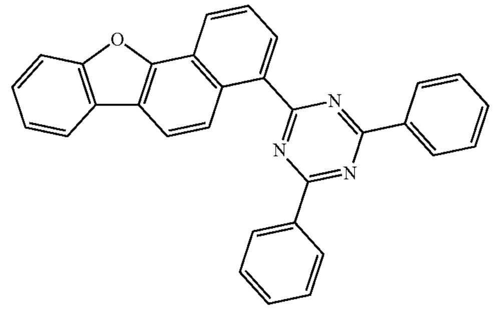
H2-404
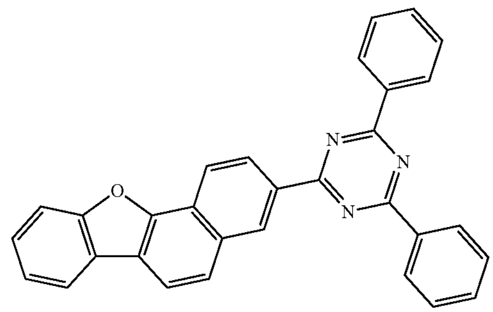
H2-405
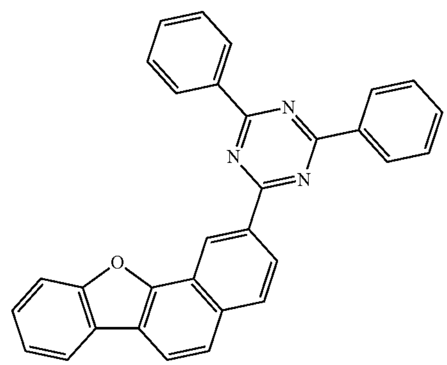
H2-406
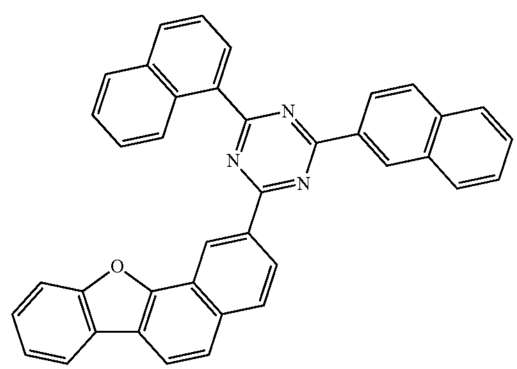

-continued
H2-407
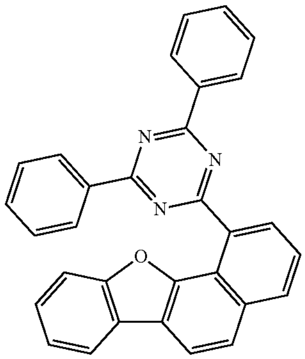
H2-408
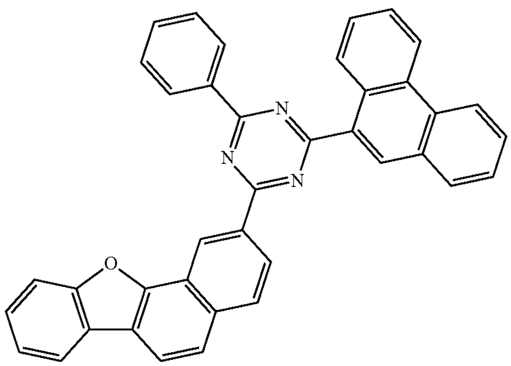
H2-409
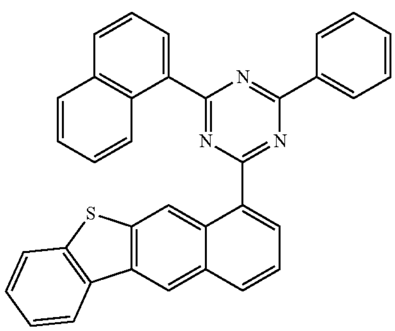
H2-410
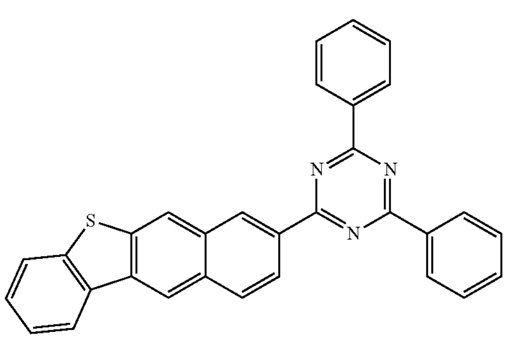
-continued
H2-411
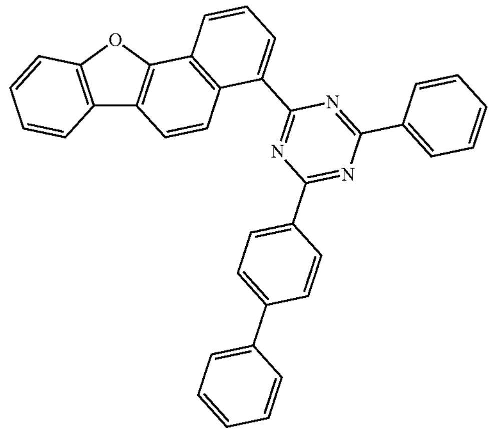
H2-412
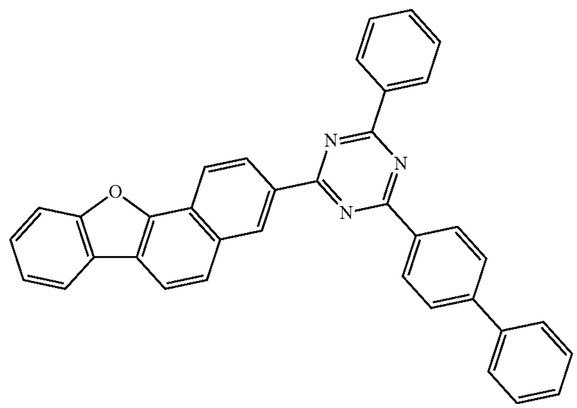
H2-413
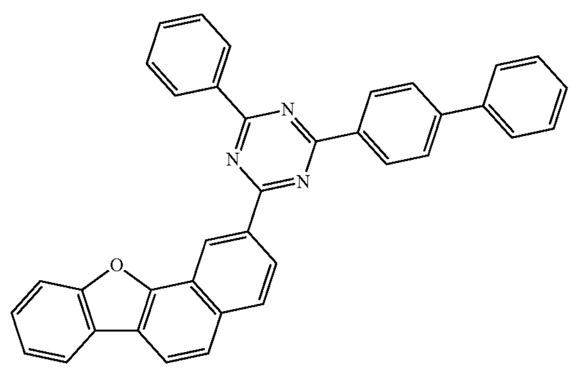
H2-414
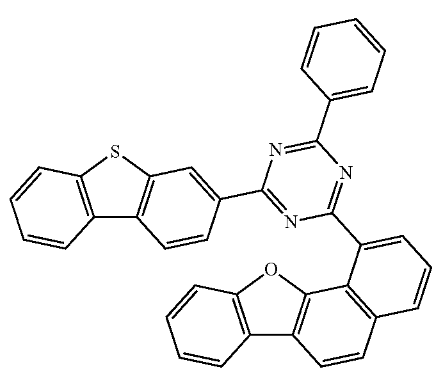

-continued
H2-415
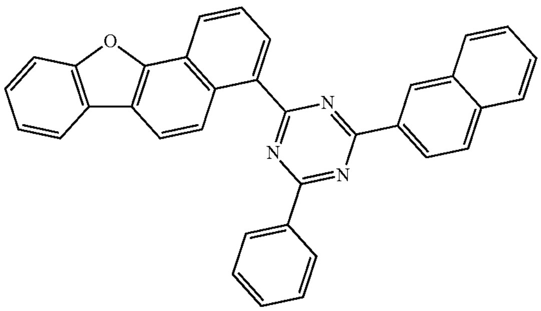
H2-416
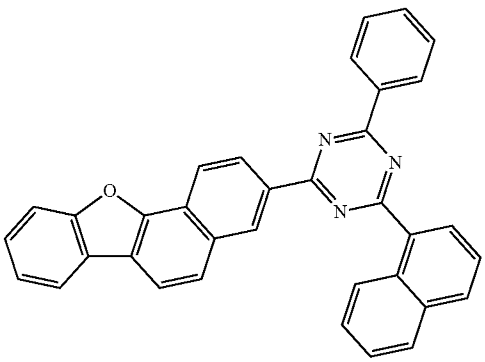
H2-417
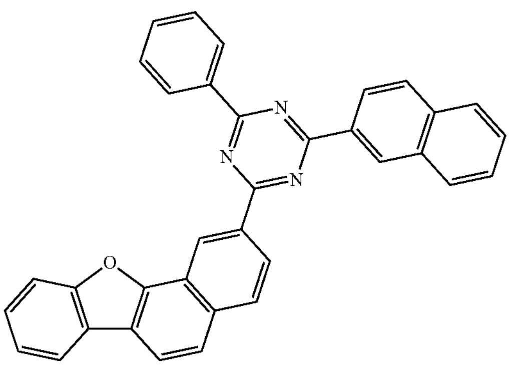
H2-418
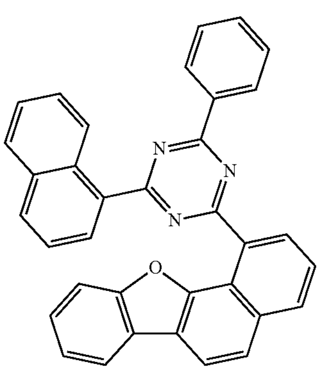
-continued
H2-419
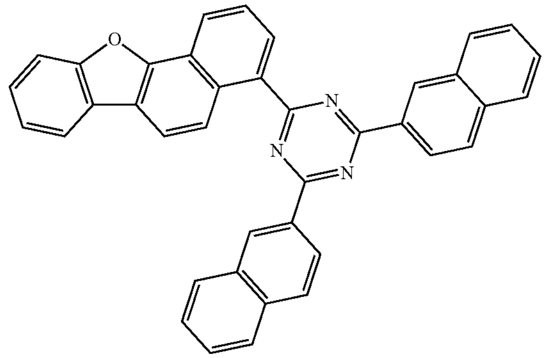
H2-420
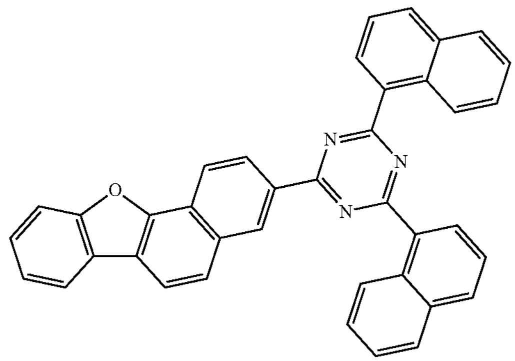
H2-421
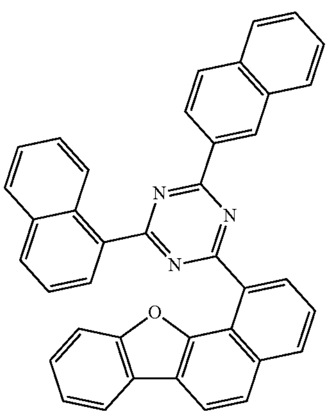
H2-422
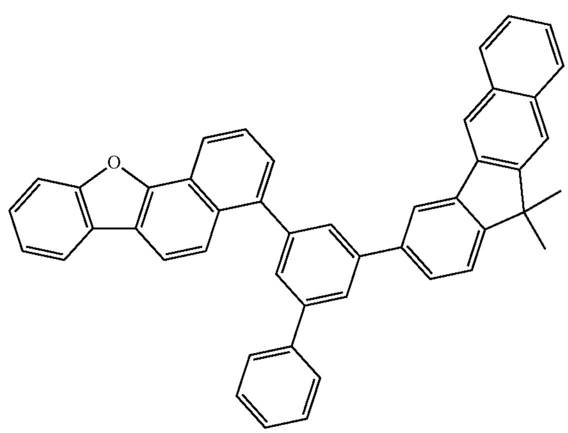

-continued
H2-423
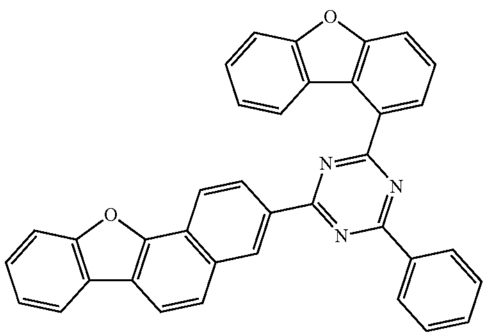
H2-424
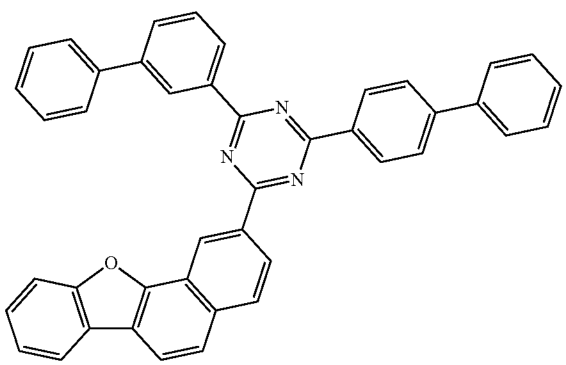
H2-425
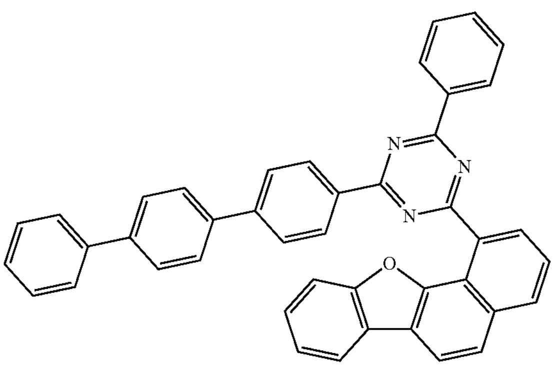
H2-426
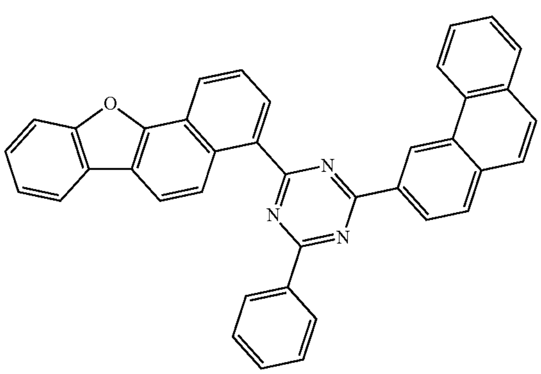
-continued
H2-427
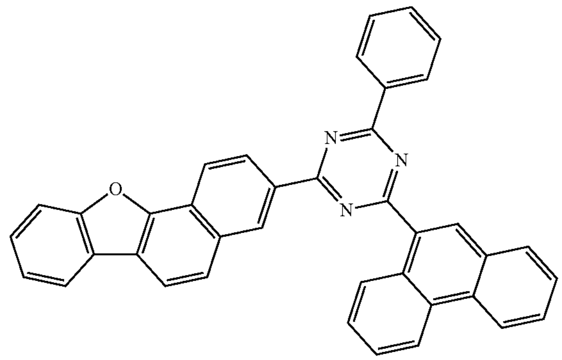
H2-428
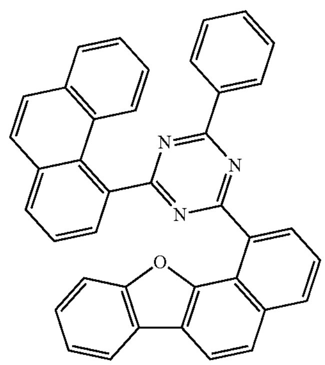
H2-429
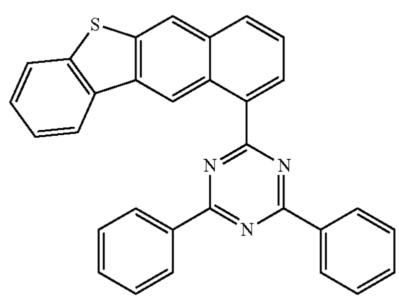
H2-430
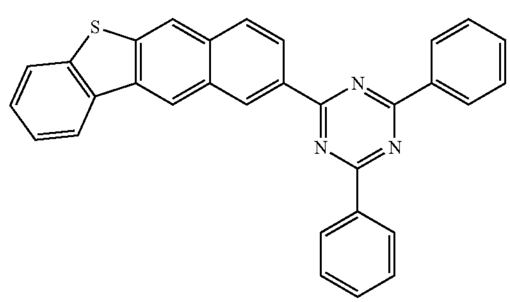

-continued
H2-431
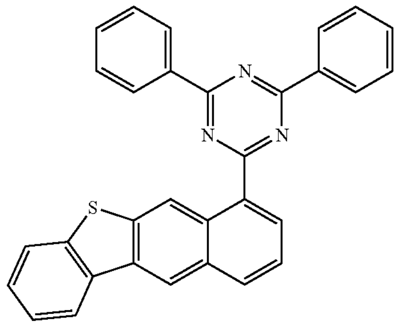
H2-432
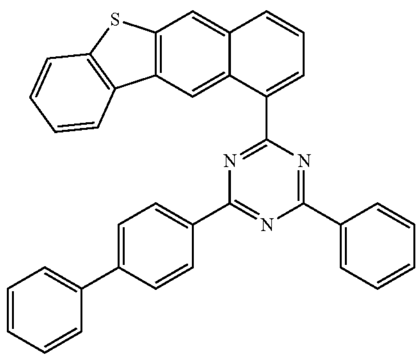
H2433
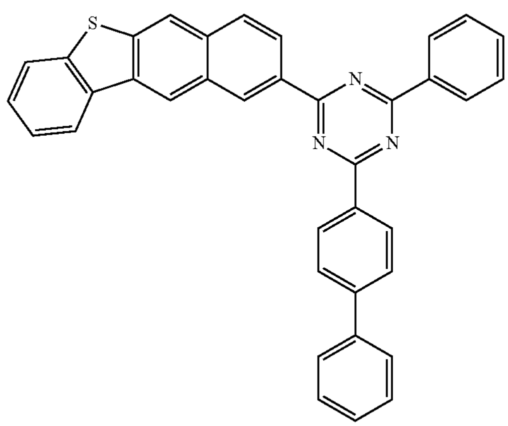
H2-434
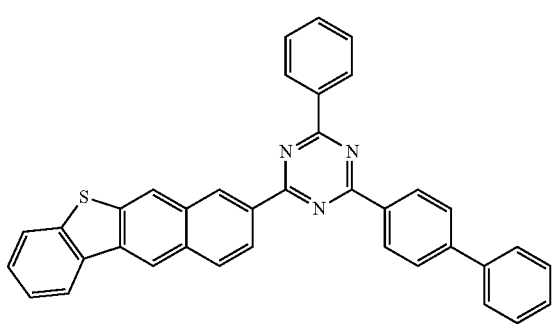
-continued
H2-435
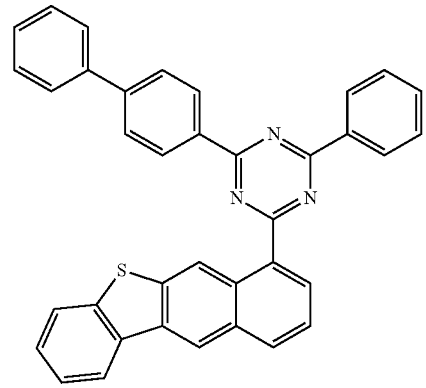
H2-436
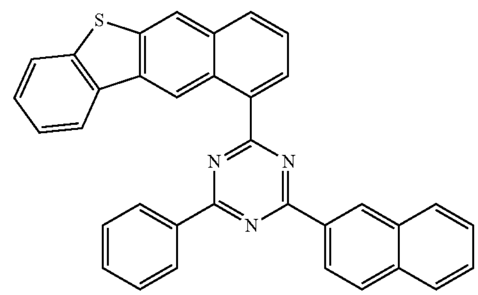
H2-437
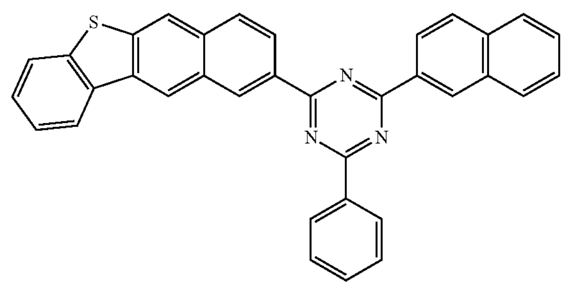
H2-438
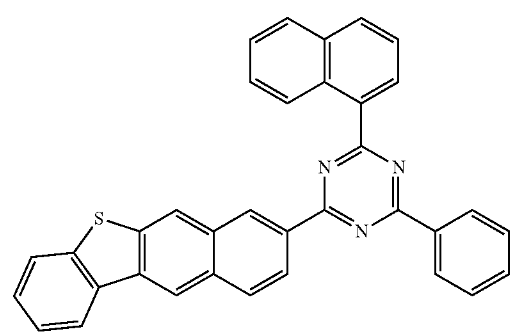

-continued
H2-439
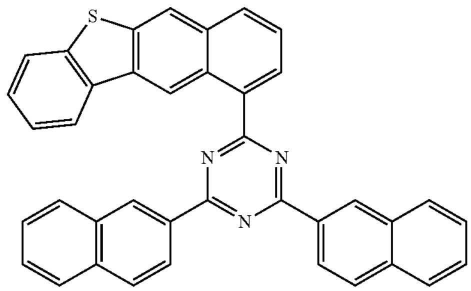
H2-440
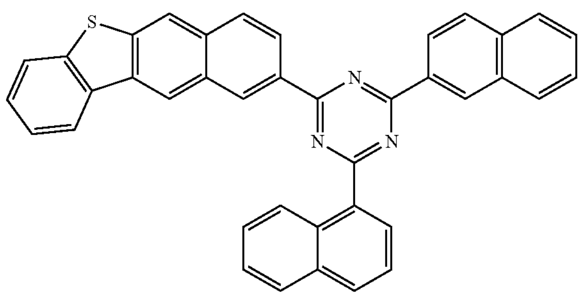
H2-441
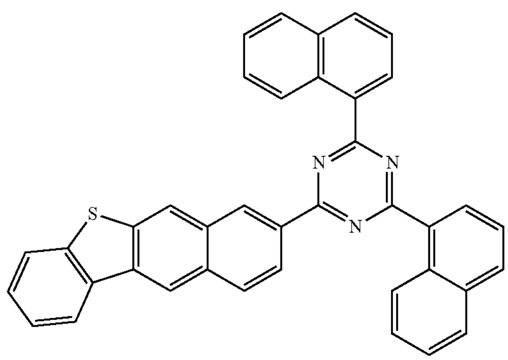
H2-442
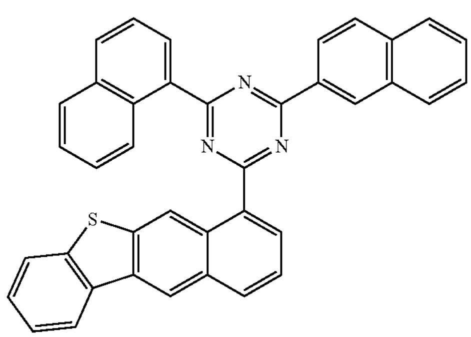
-continued
H2-443
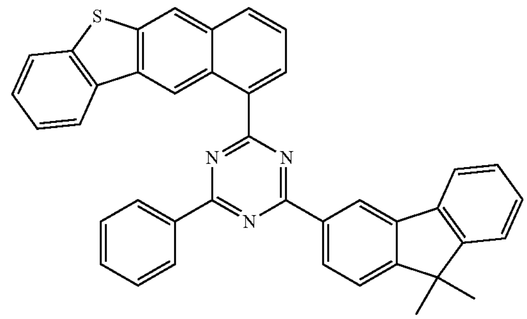
H2-444
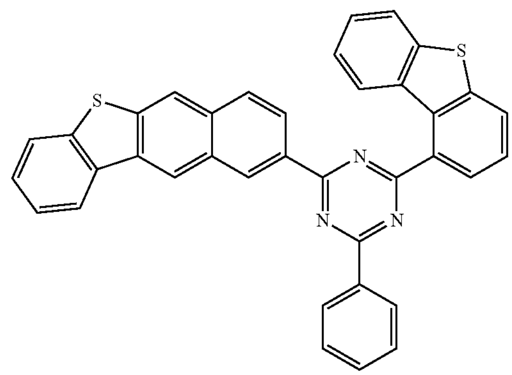
H2-445
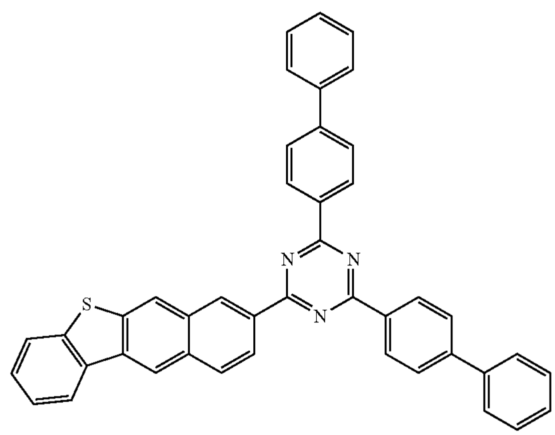
H2-446
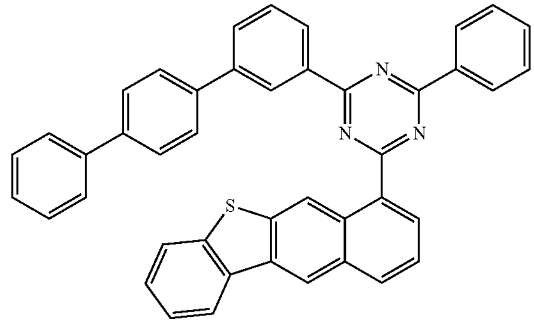

-continued
H2-447
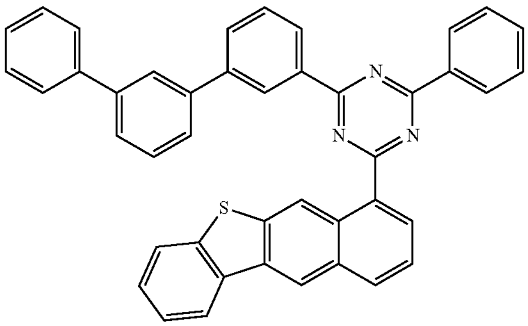
H2-448
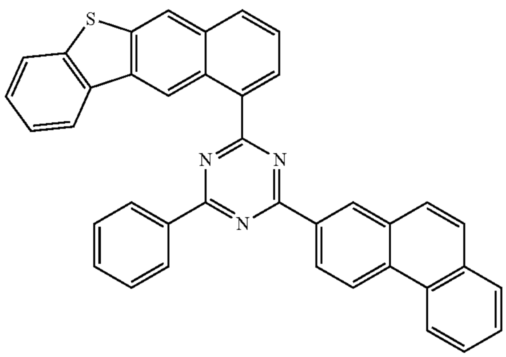
H2-449
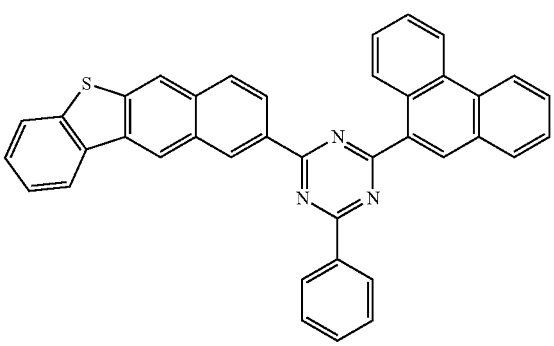
H2-450
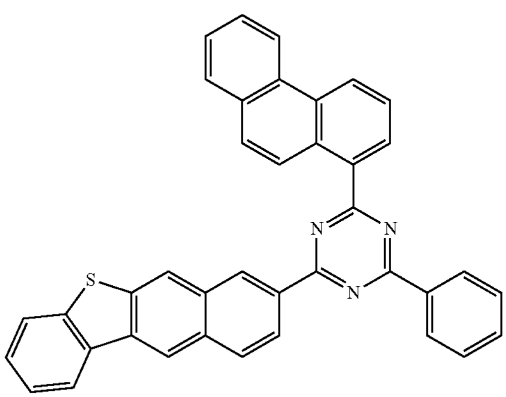
-continued
H2-451
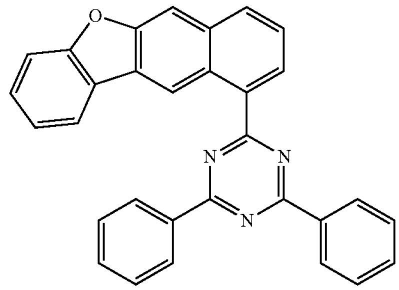
H2-452
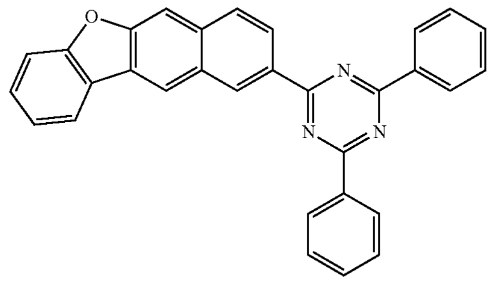
H2-453
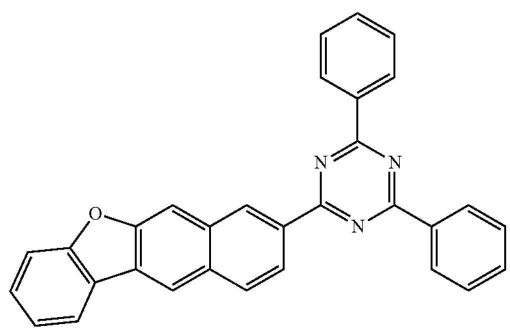
H2-454
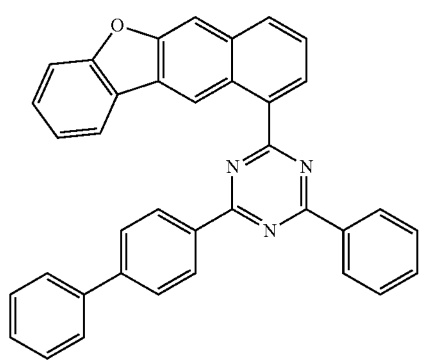

-continued
H2-455
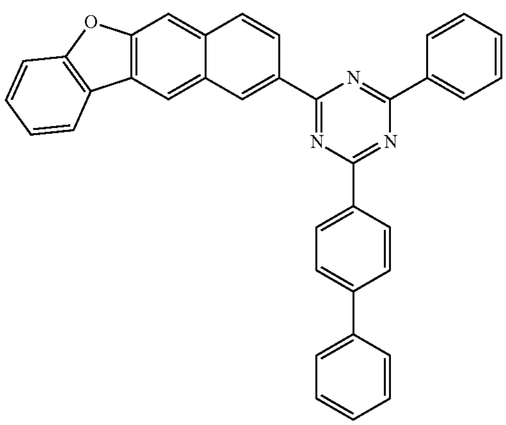
H2-456
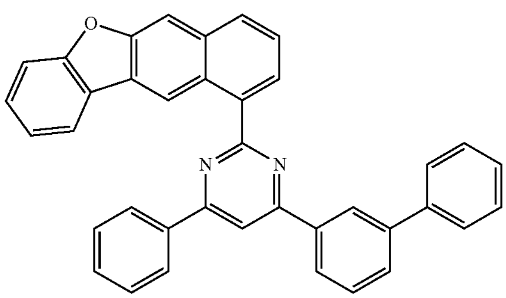
H2-457
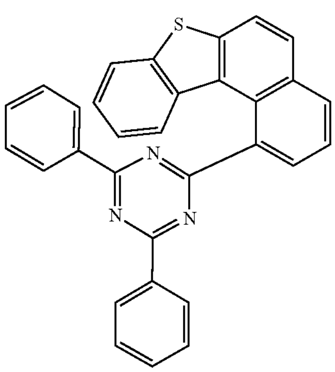
H2-458
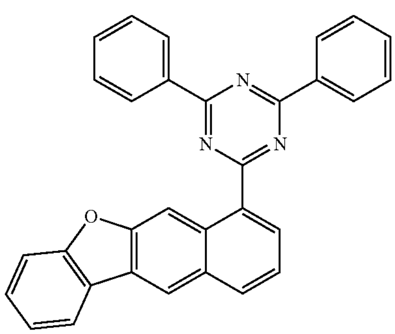
-continued
H2-459
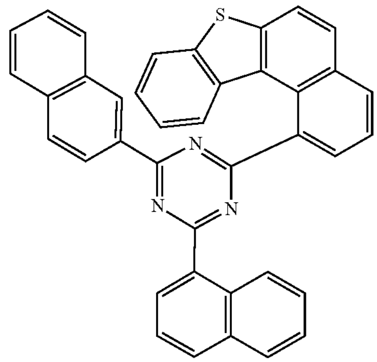
H2-460
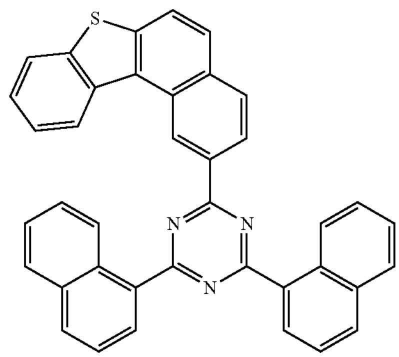
H2-461
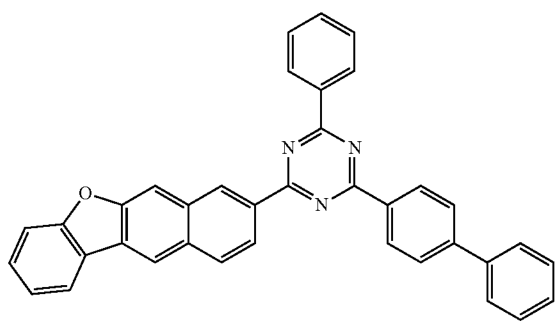
H2-462
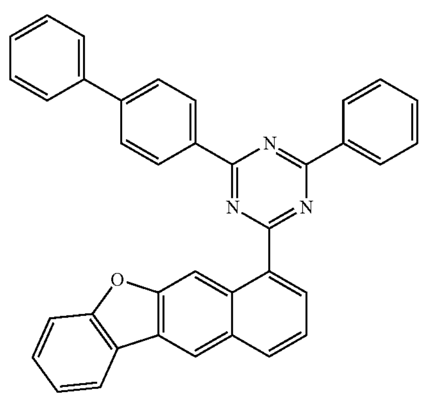

-continued
H2-463
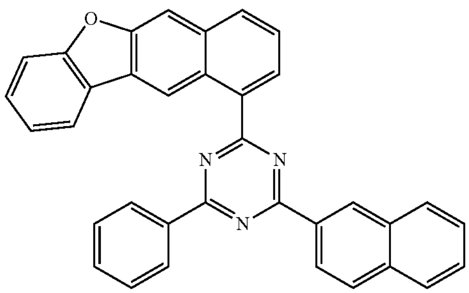
H2-464
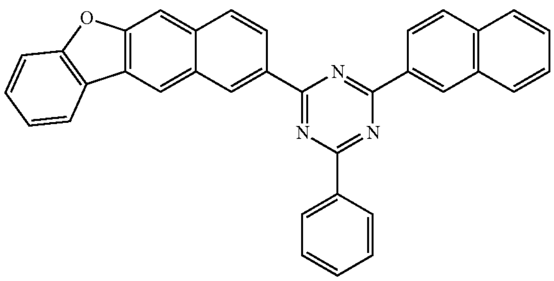
H2-465
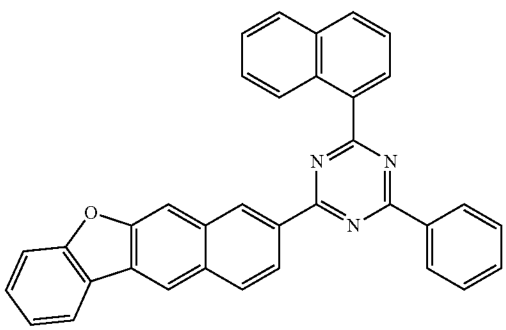
H2-466
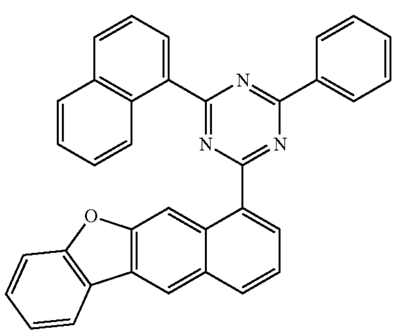
H2-467
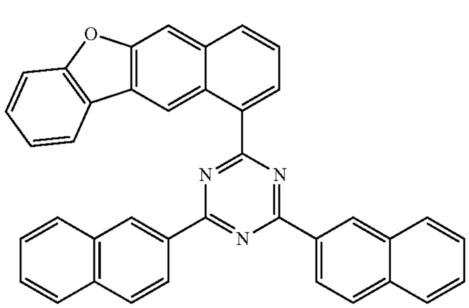
-continued
H2-468
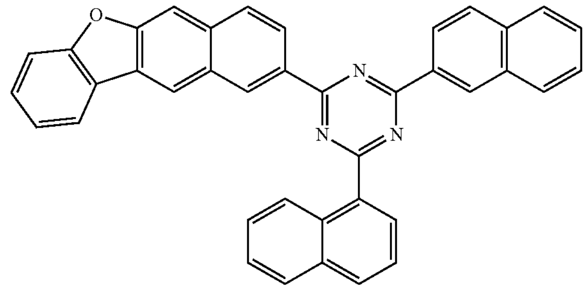
H2-469
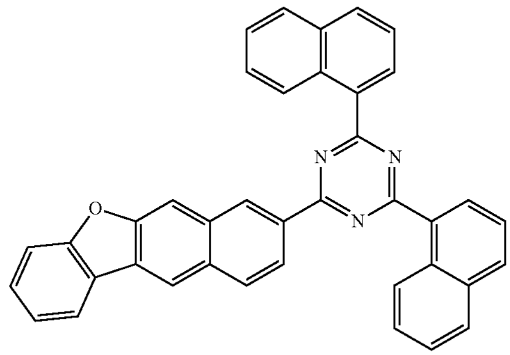
H2-470
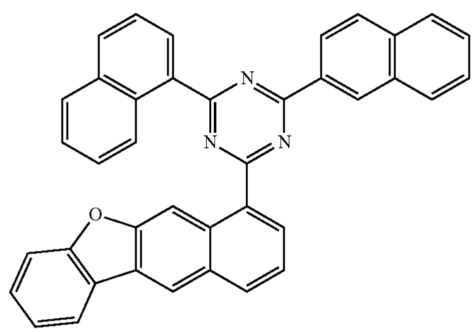
H2-471
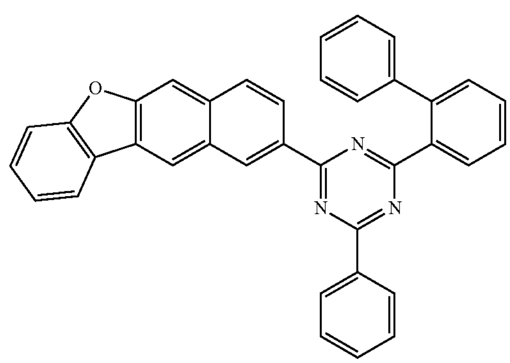

-continued
H2-472
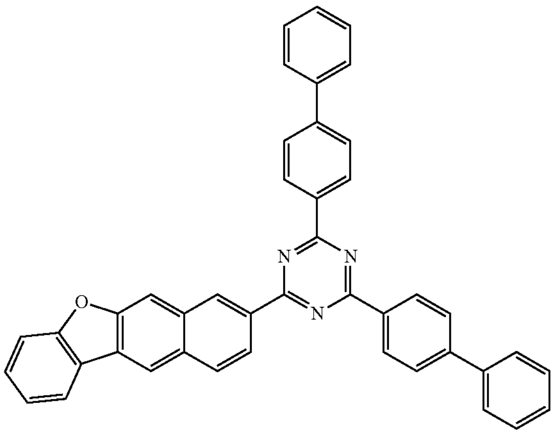
H2-473
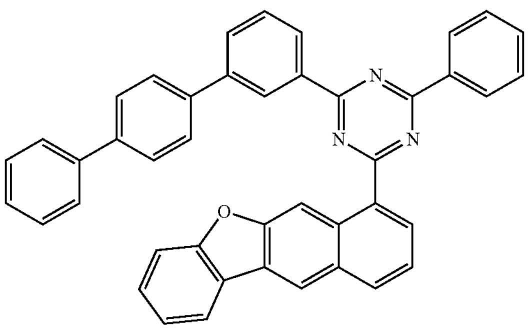
H2-474
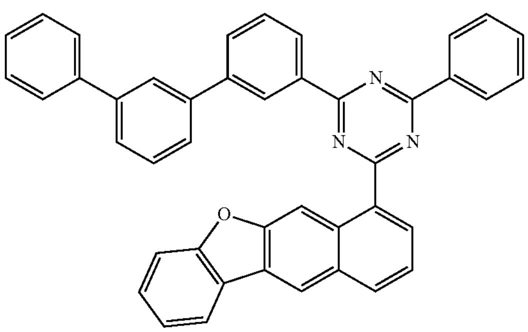
H2-475
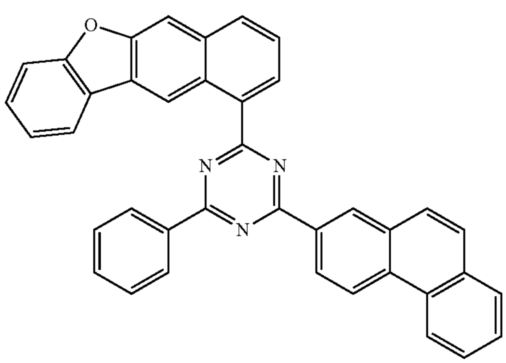
-continued
H2-476
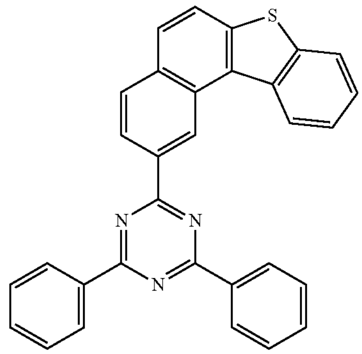
H2-477
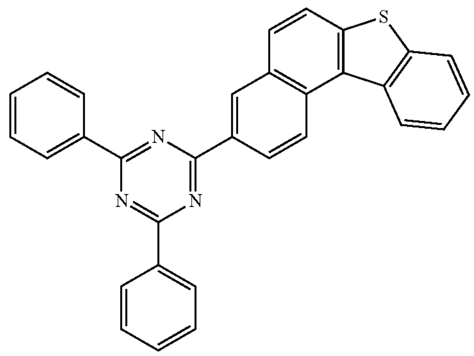
H2-478
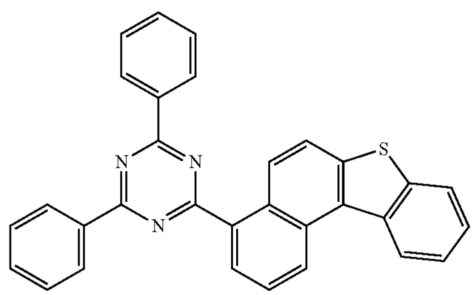
H2-479
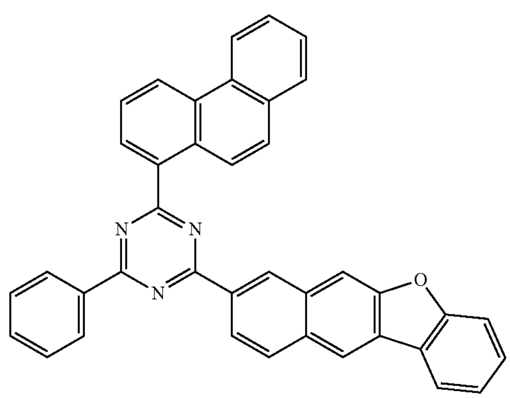

-continued
H2-480
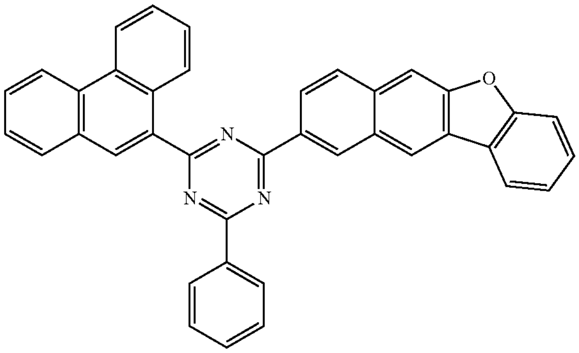
H2-481
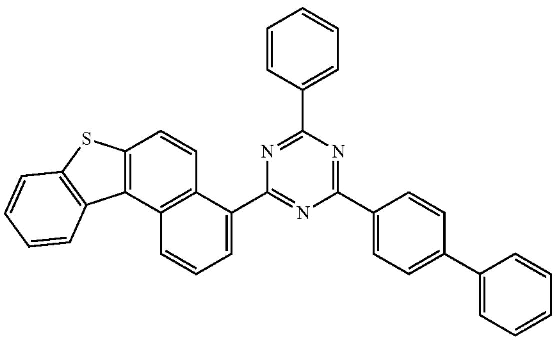
H2-482
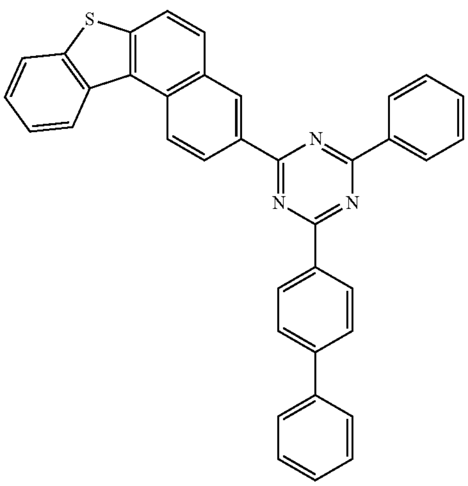
H2-483
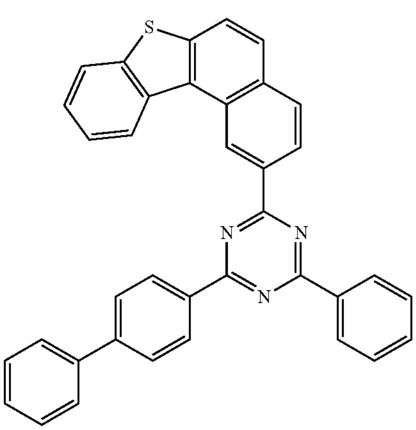
-continued
H2-484
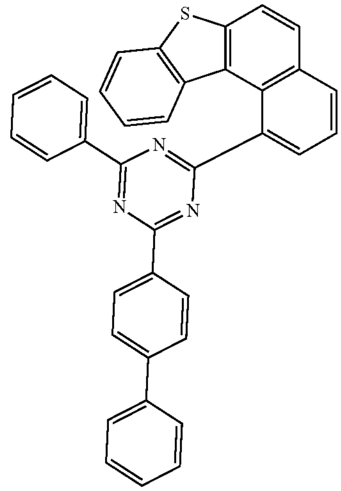
H2-485
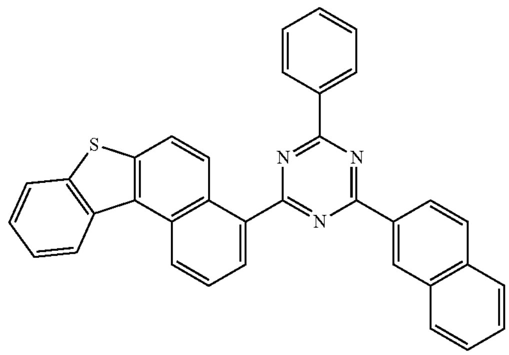
H2-486
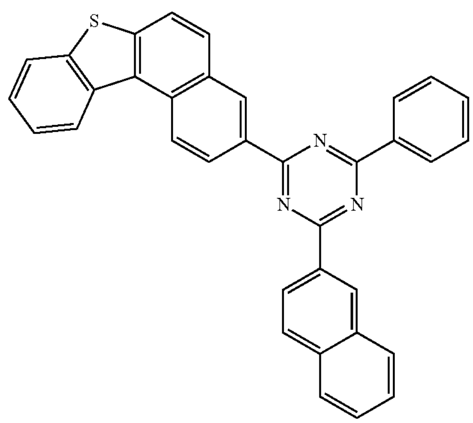
H2-487
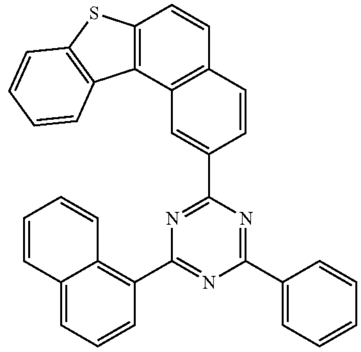

H2-488
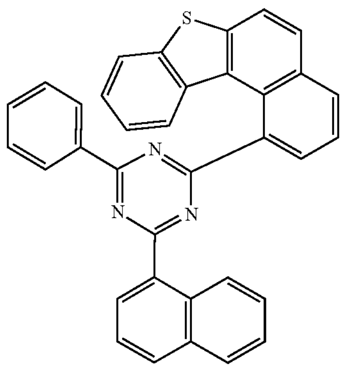
H2-489
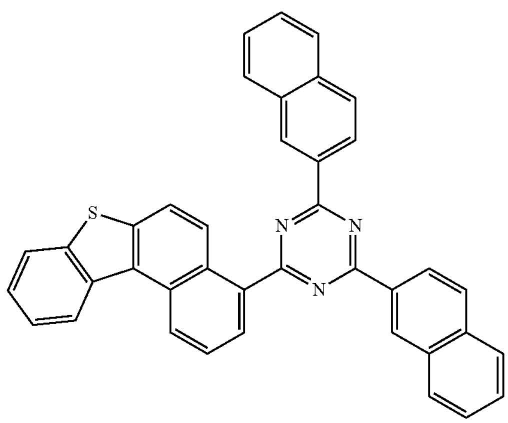
H2-490
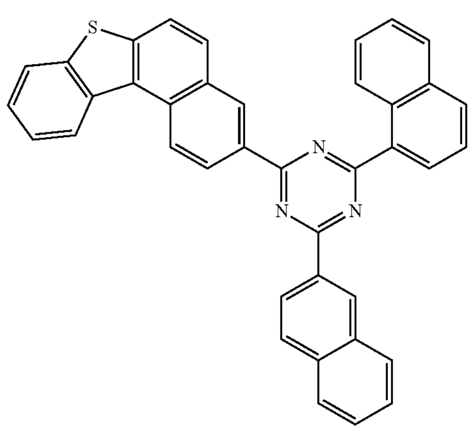
H2-491
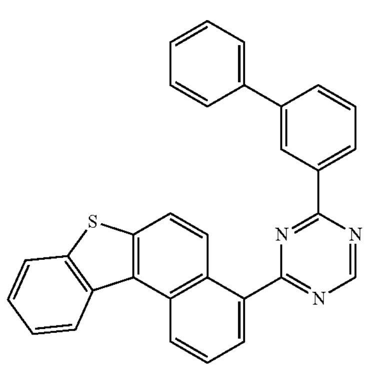
H2-494
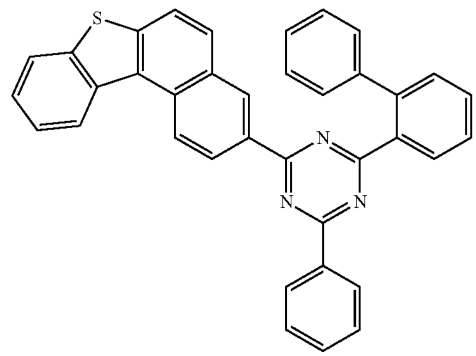
H2-493
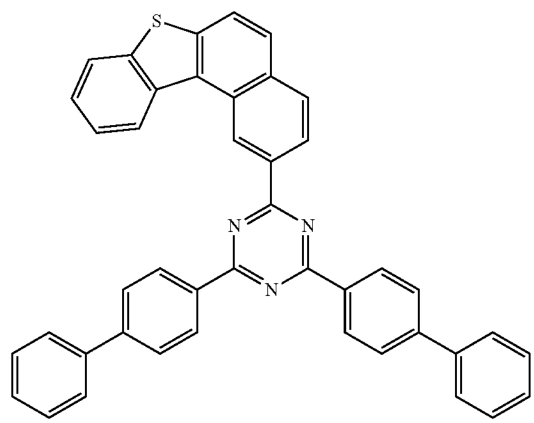
H2-494
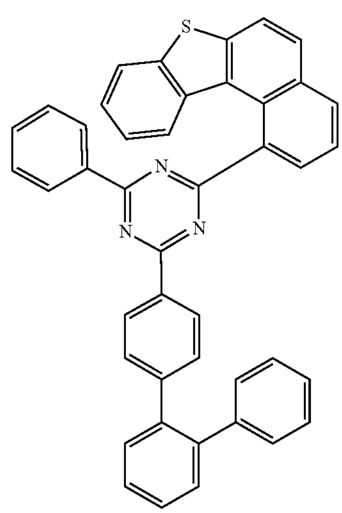

-continued
H2-495
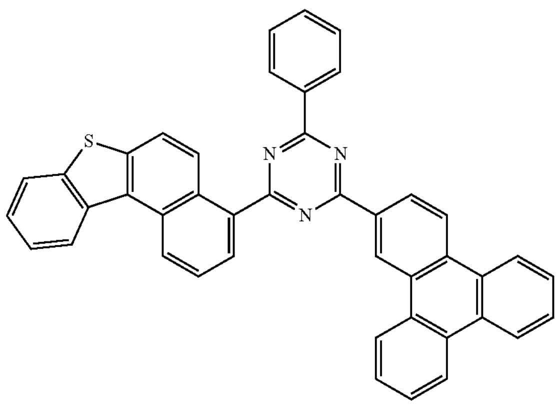
H2-496
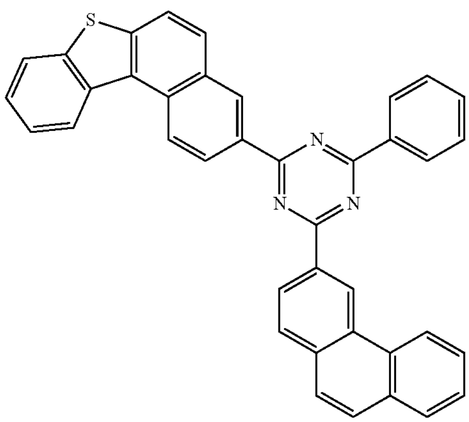
H2-497
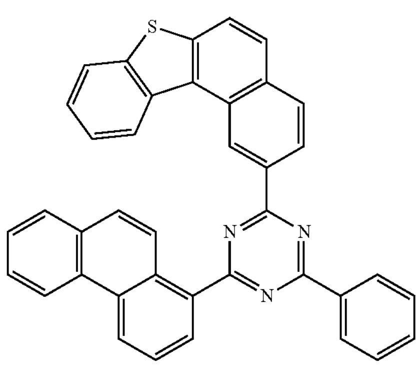
H2-498
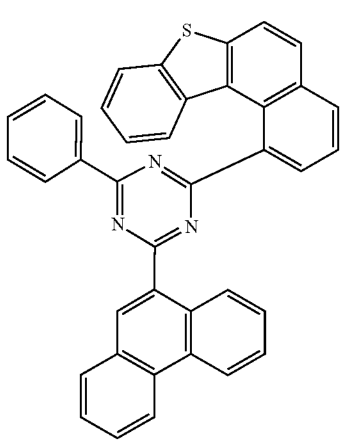
-continued
H2-499
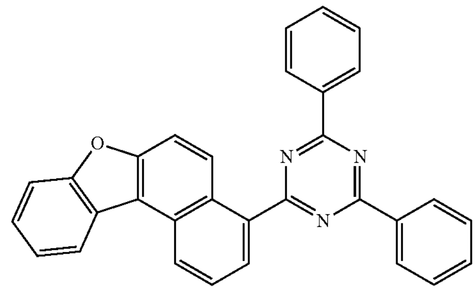
H2-500
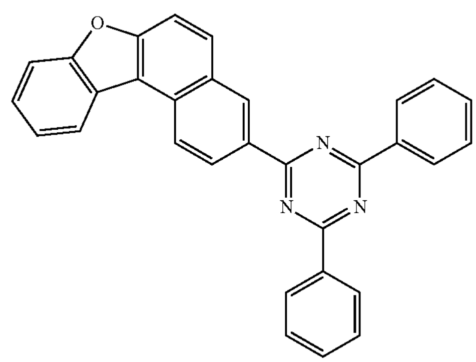
H2-501
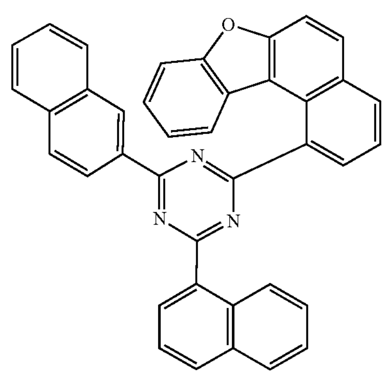
H2-502
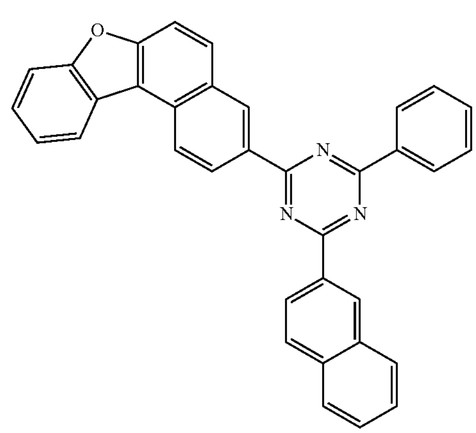

-continued
H2-503
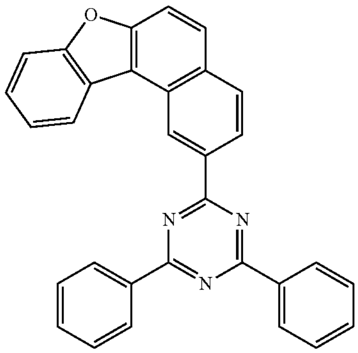
H2-504
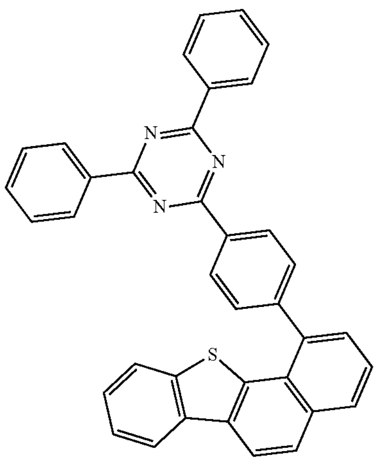
H2-505
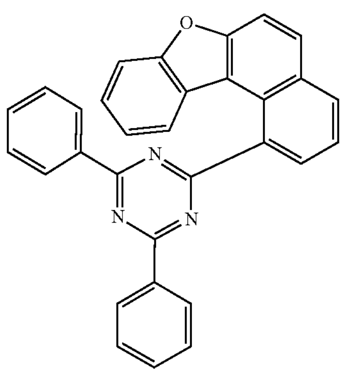
H2-506
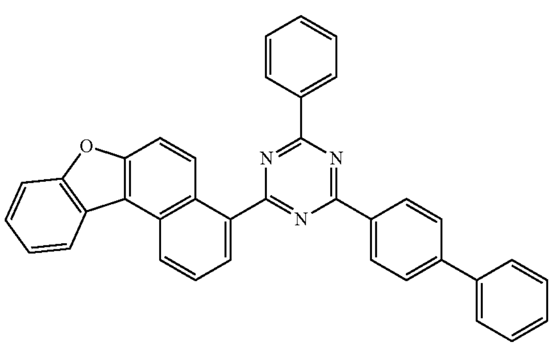
-continued
H2-507
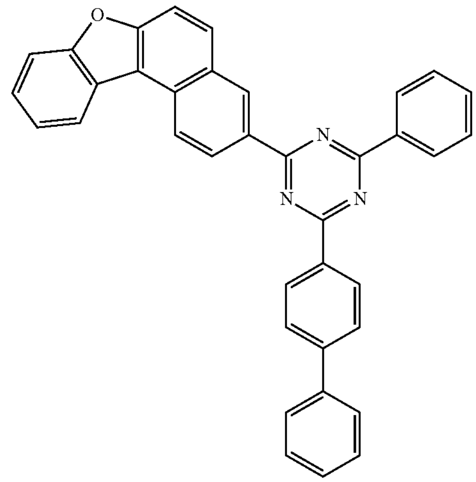
H2-508
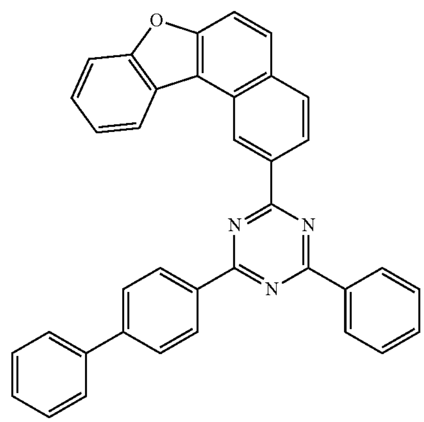
H2-509
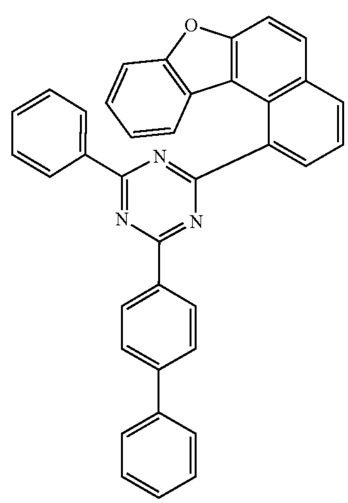

-continued
H2-510
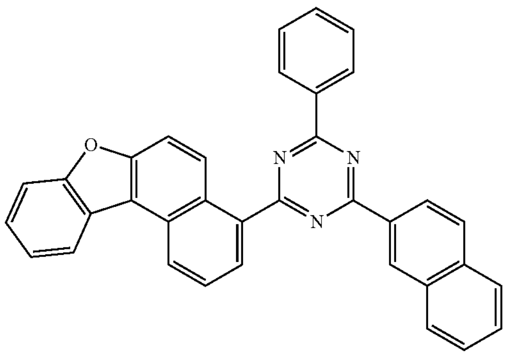
H2-511
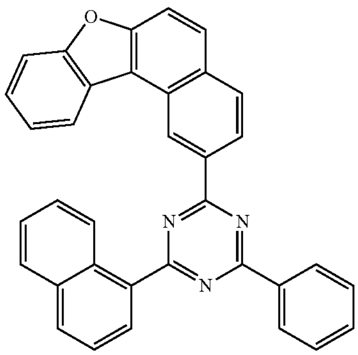
H2-512
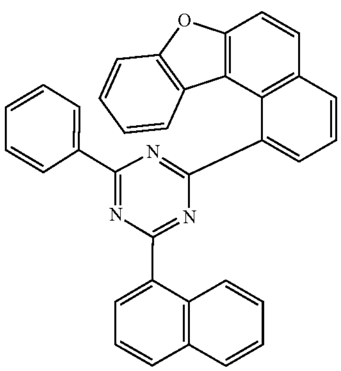
H2-513
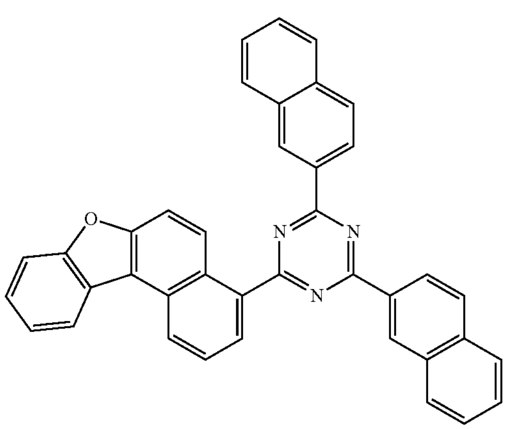
-continued
H2-514
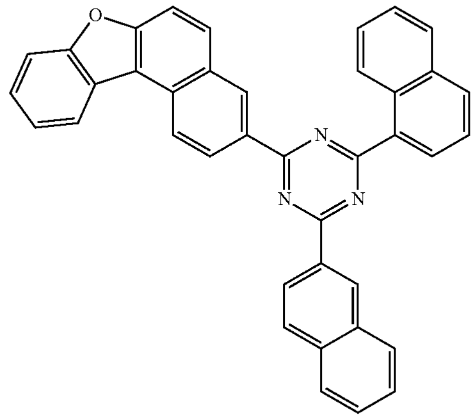
H2-515
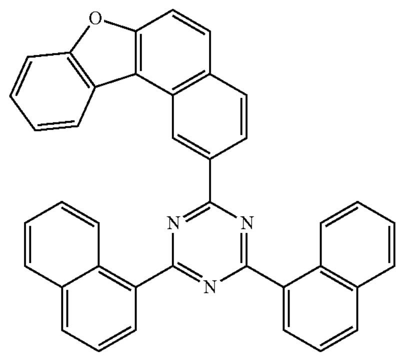
H2-516
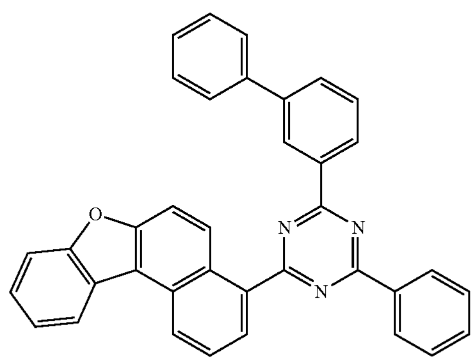
H2-517
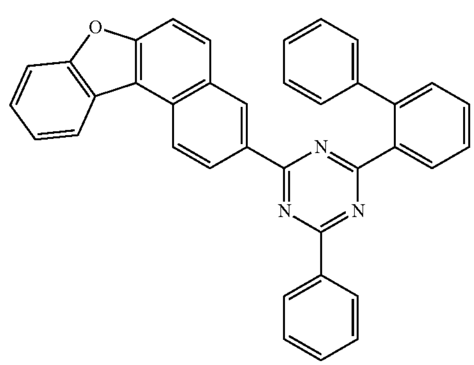

-continued
H2-518
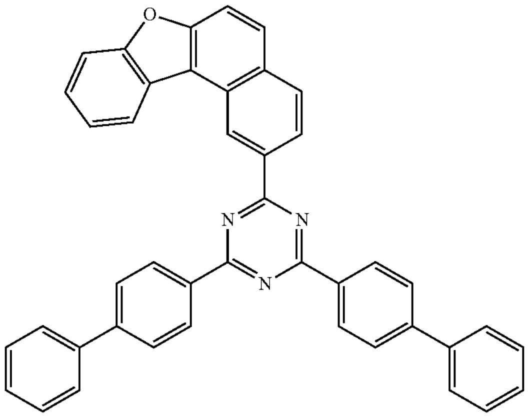
H2-519
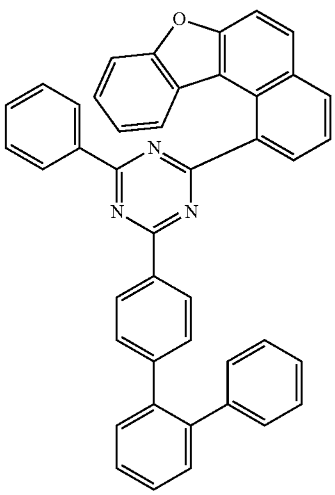
H2-520
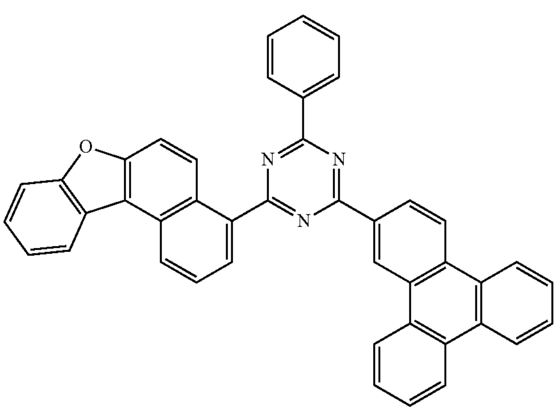
-continued
H2-521
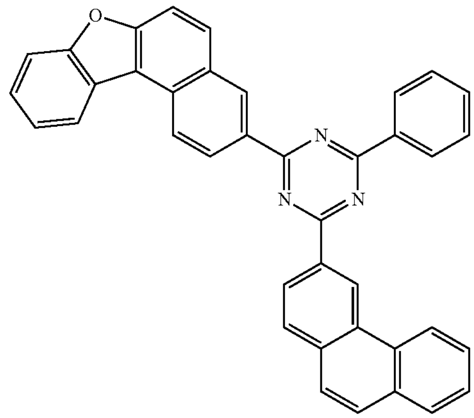
H2-522
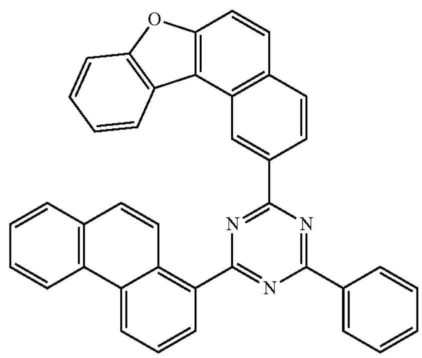
H2-523
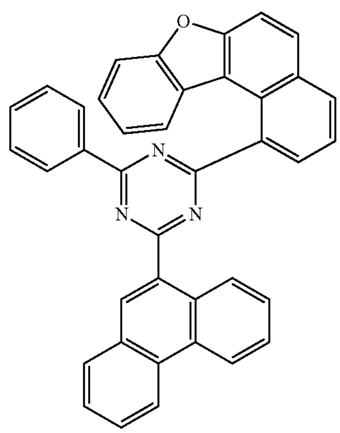
H2-524
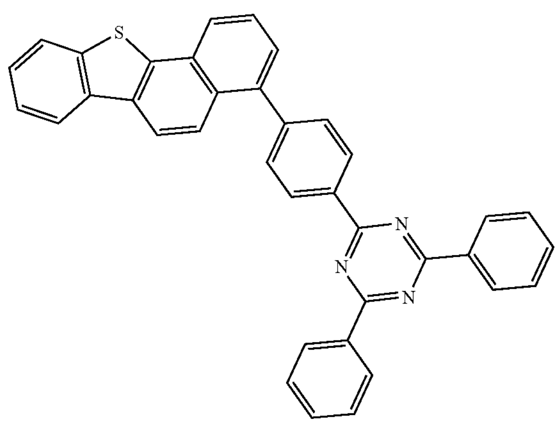

-continued
H2-525
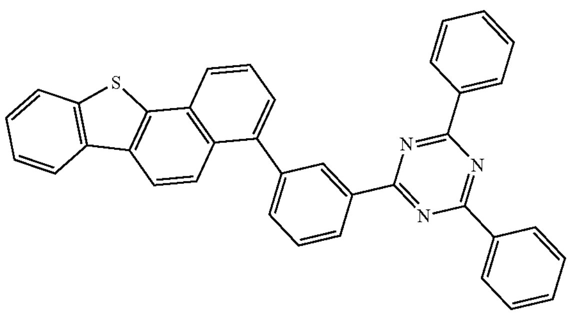
H2-526
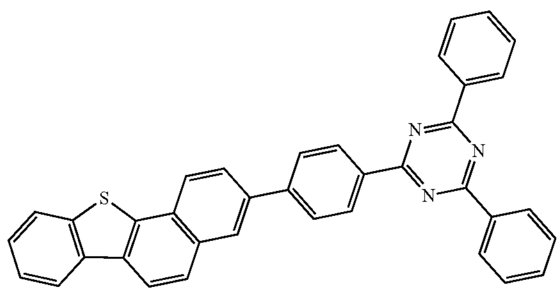
H2-527
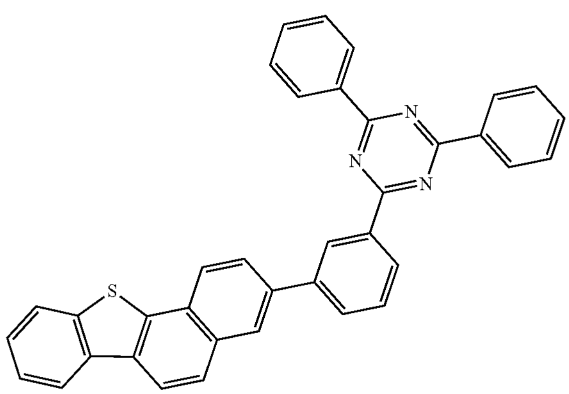
H2-528
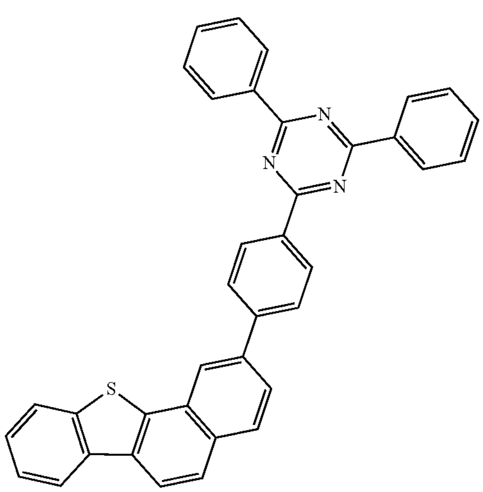
-continued
H2-529
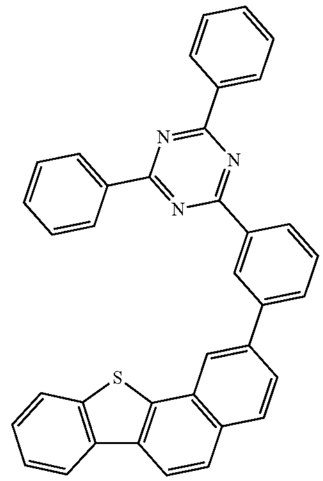
H2-530
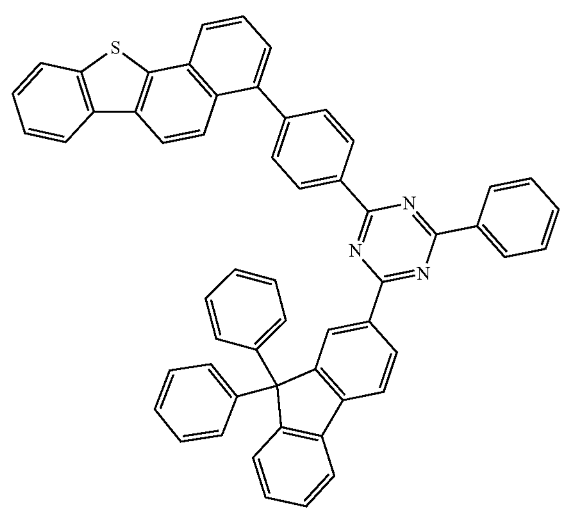
H2-531
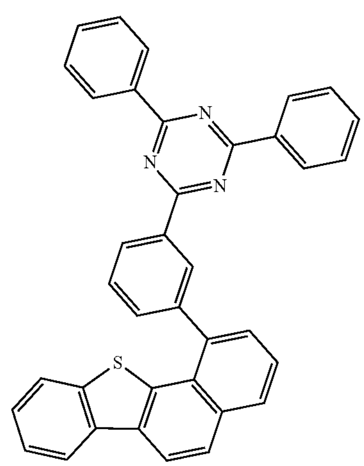

-continued
H2-532
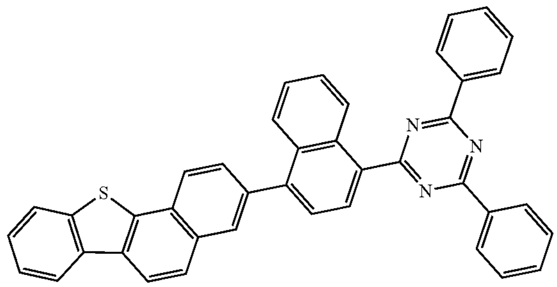
H2-533
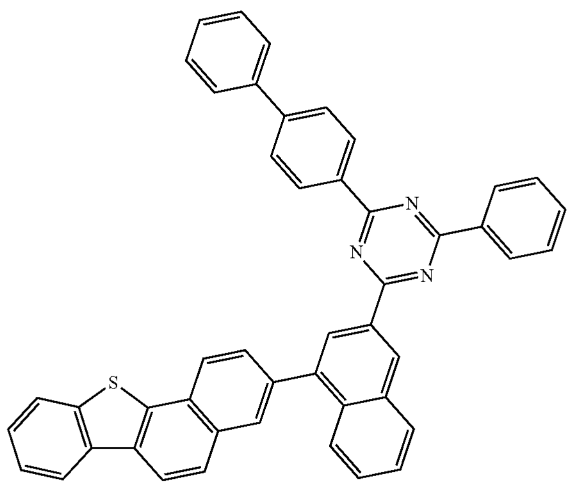
H2-534
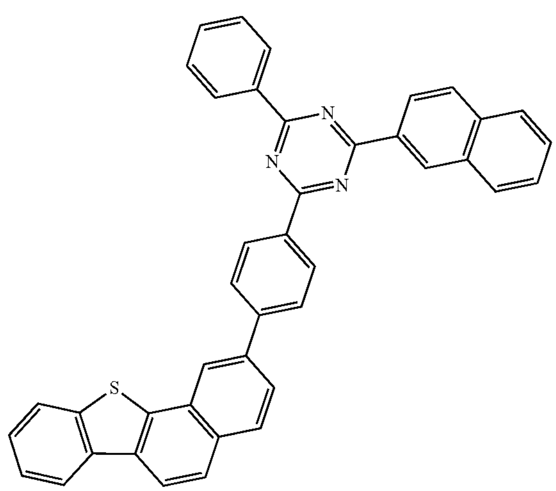
-continued
H2-535
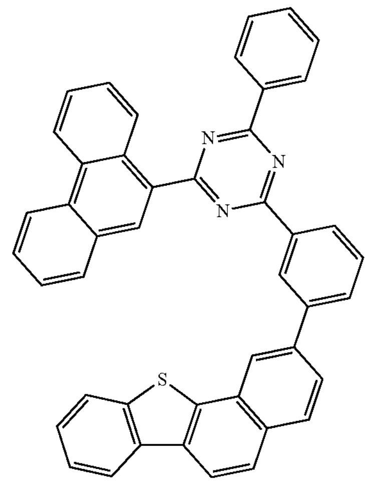
H2-536
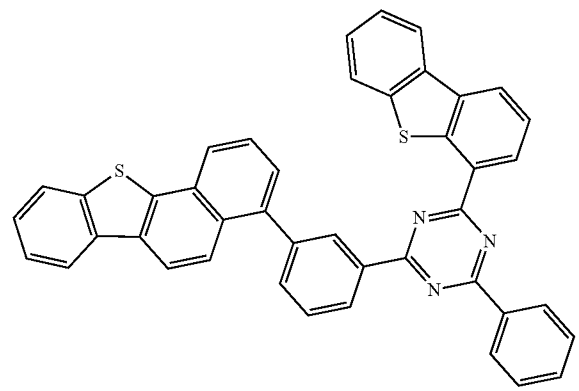
H2-537
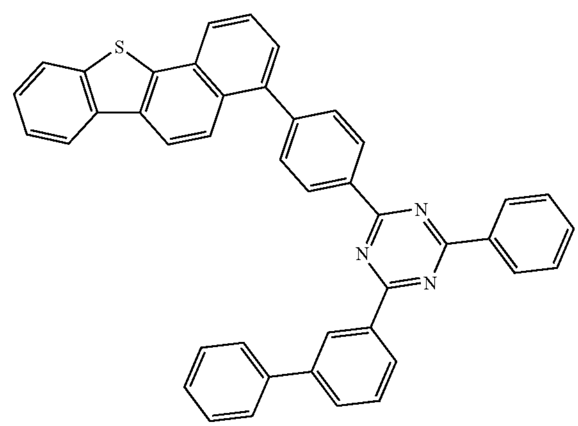
H2-538
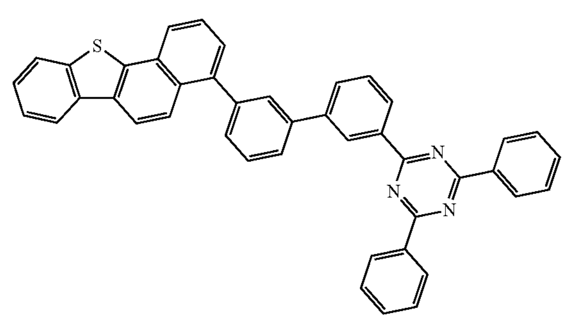

-continued
H2-539
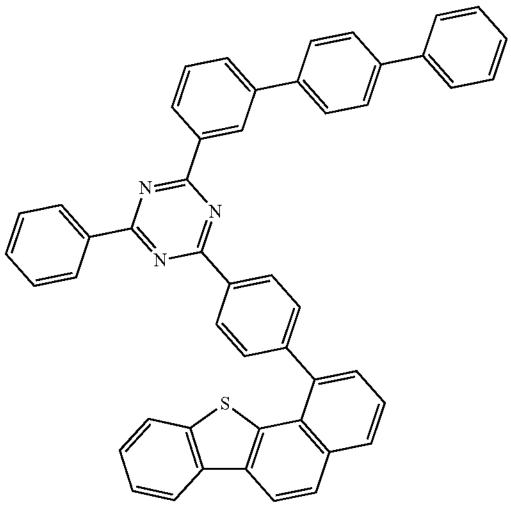
H2-540
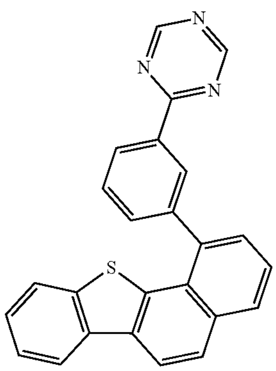
H2-541
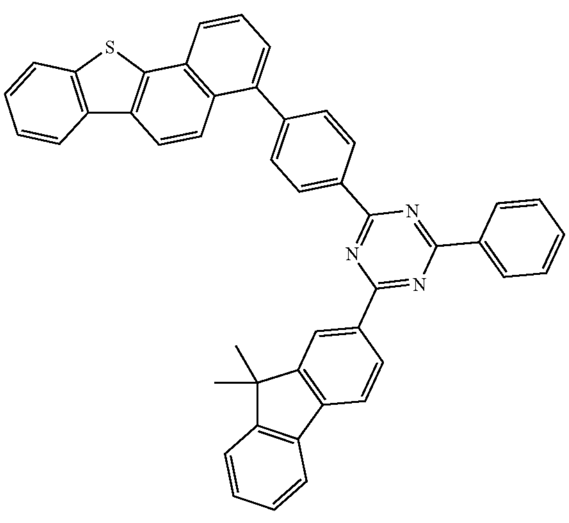
-continued
H2-542
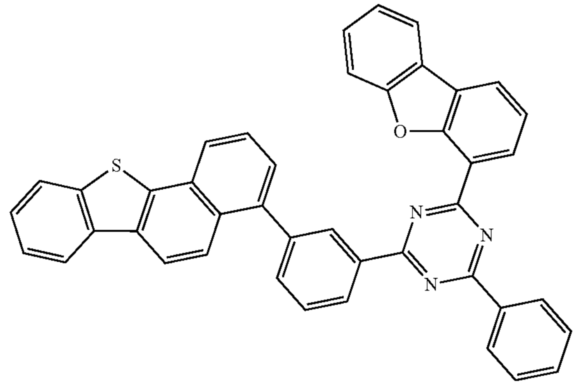
H2-543
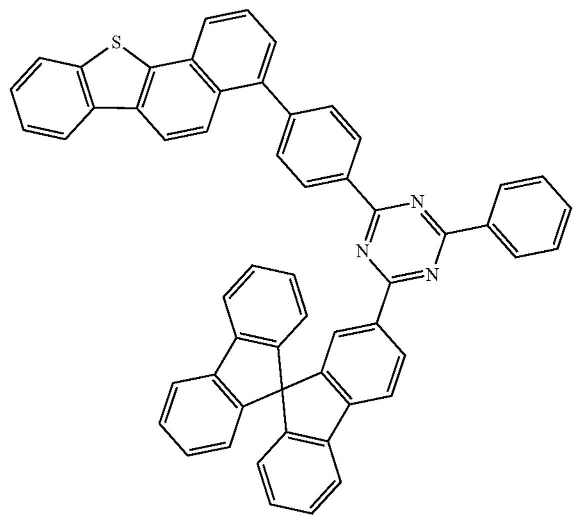
H2-544
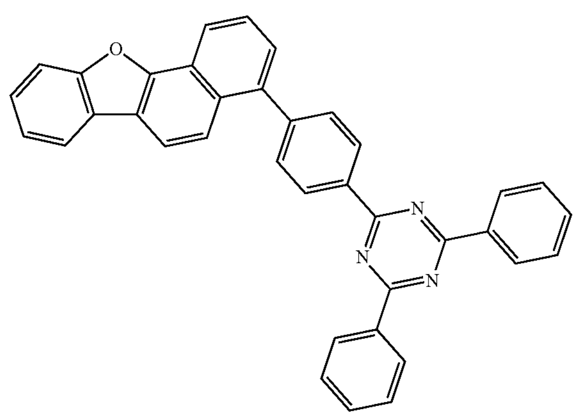

-continued
H2-545
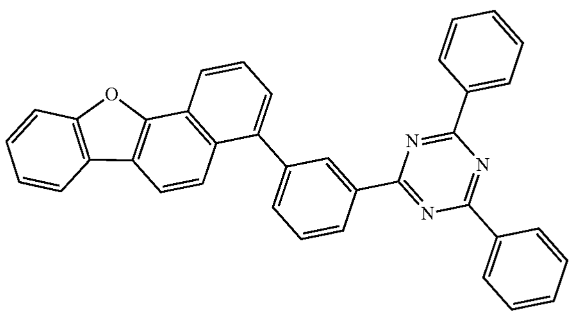
H2-546
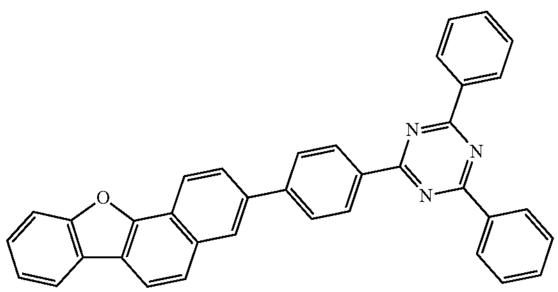
H2-547
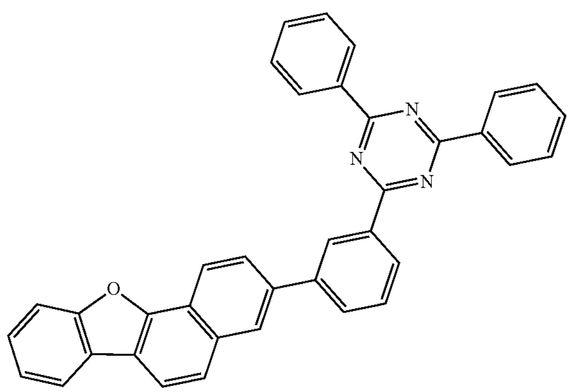
H2-548
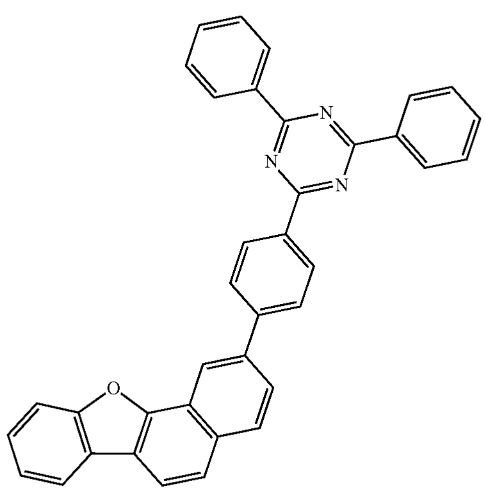
-continued
H2-549
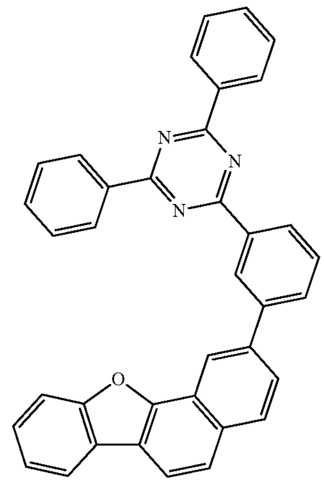
H2-550
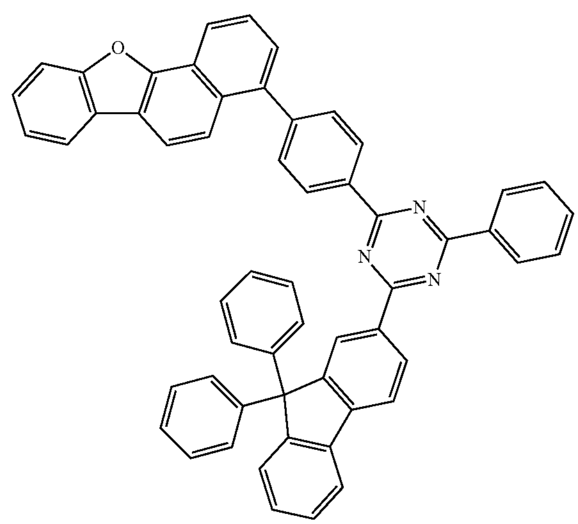
H2-551
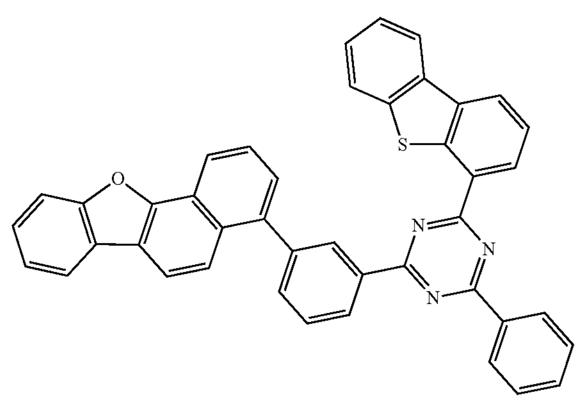

-continued
H2-552
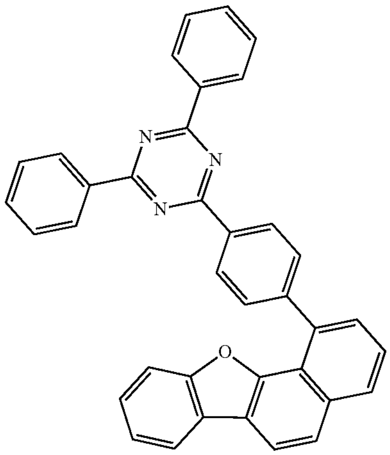
H2-553
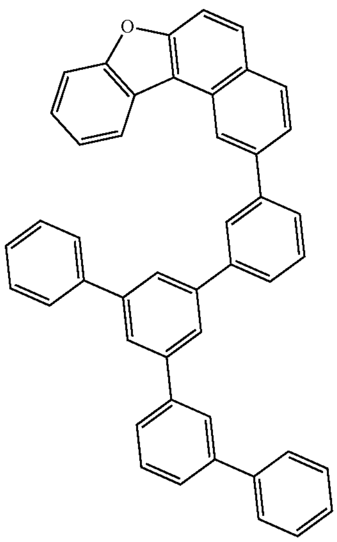
H2-554
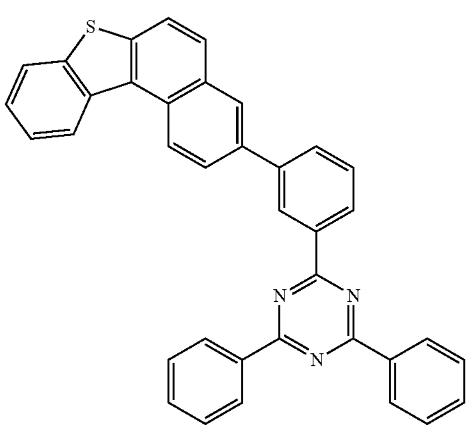
-continued
H2-555
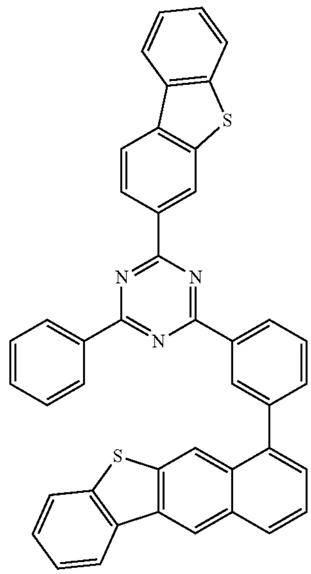
H2-556
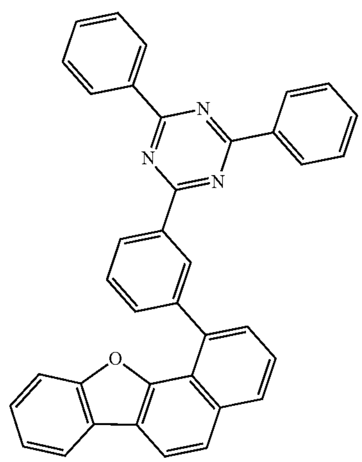
H2-557
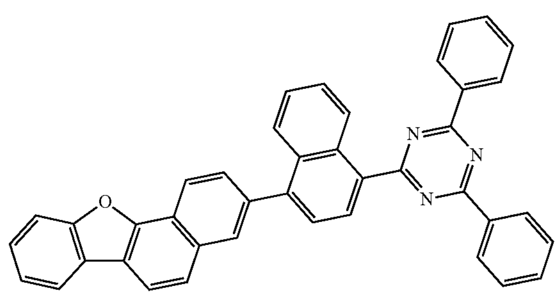

-continued
H2-558
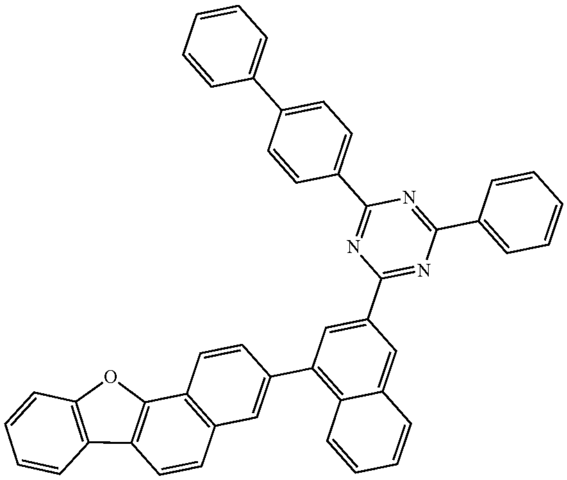
H2-559
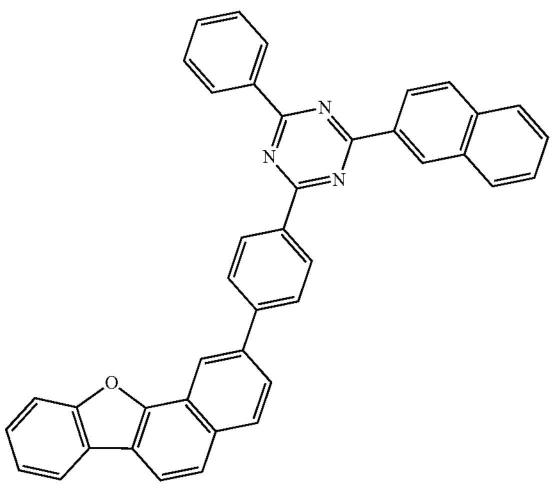
H2-560
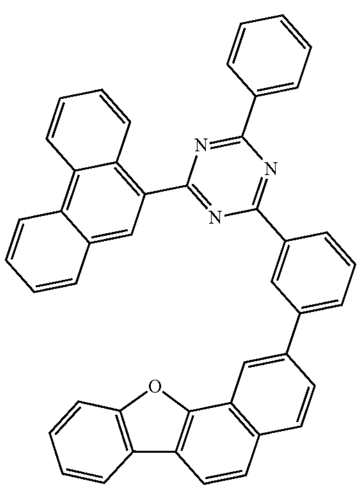
H2-561
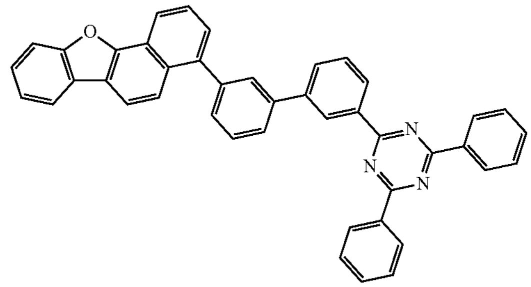
H2-562
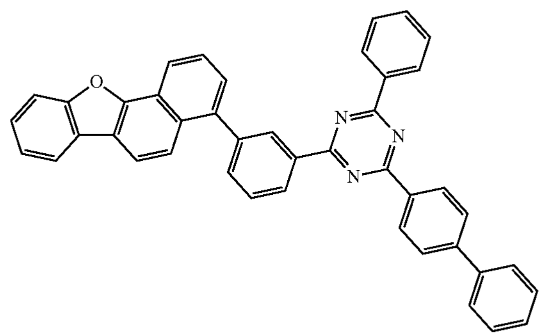
H2-563
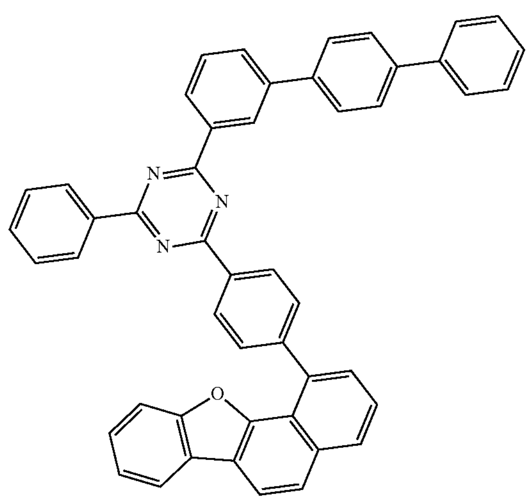

-continued
H2-564
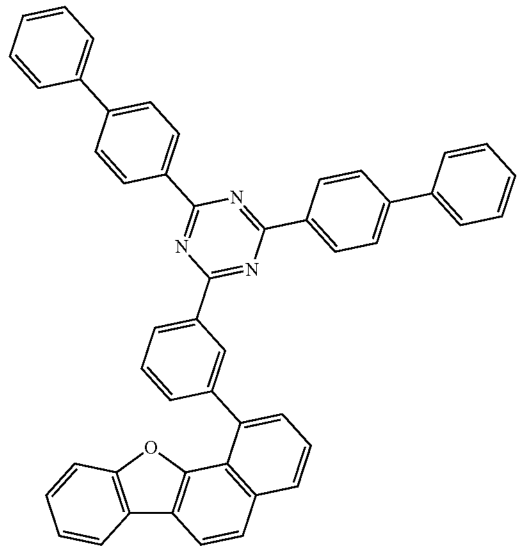
H2-565
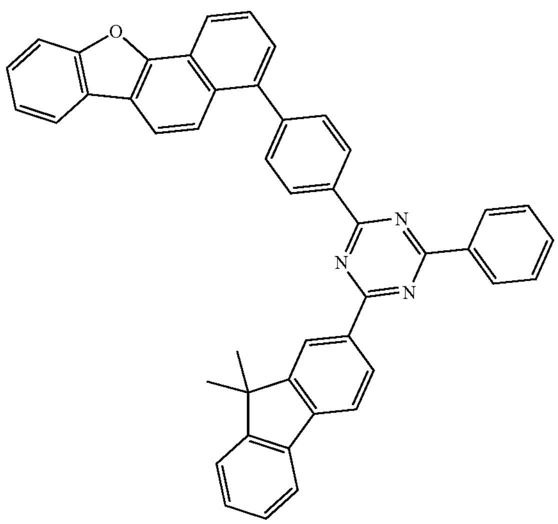
H2-566
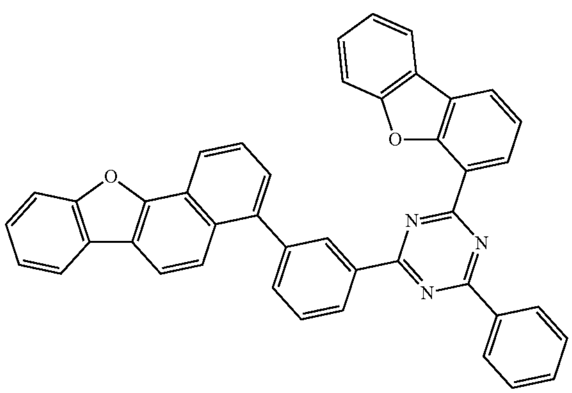
-continued
H2-567
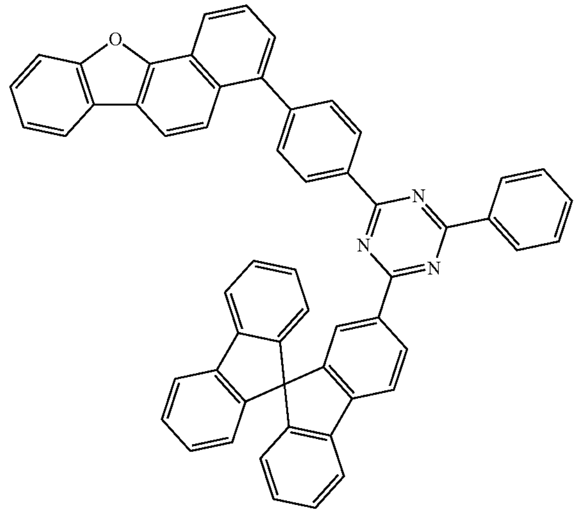
H2-568
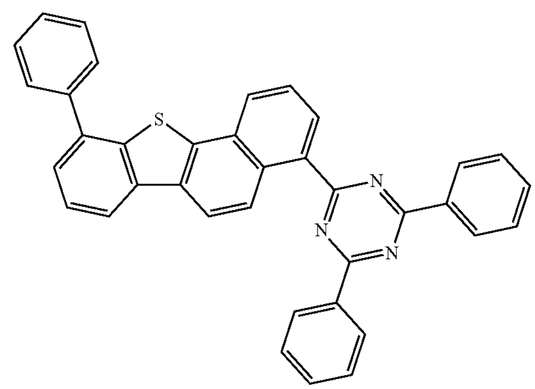
H2-569
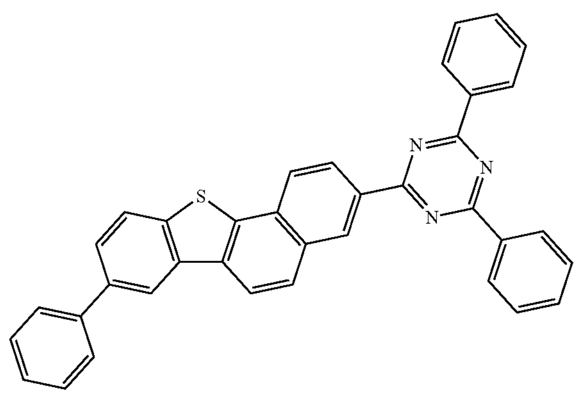

-continued
H2-570
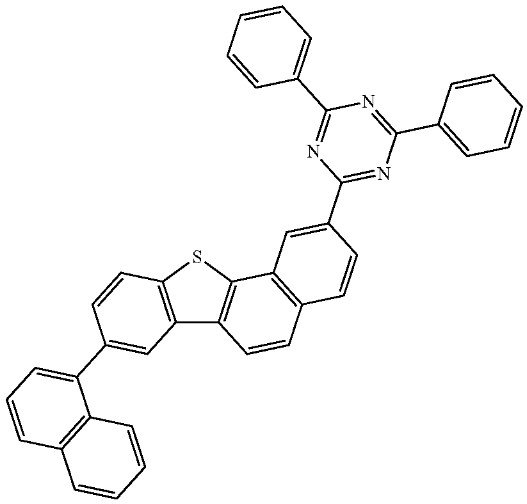
H2-571
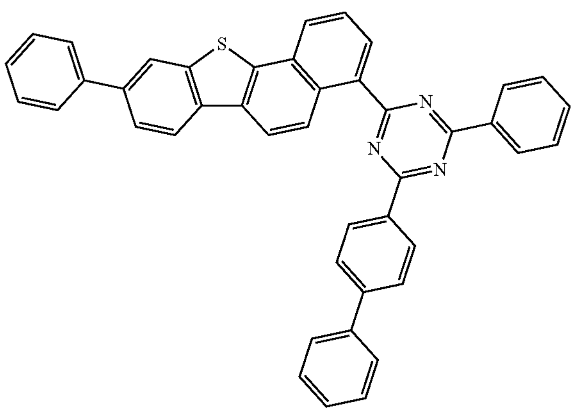
H2-572
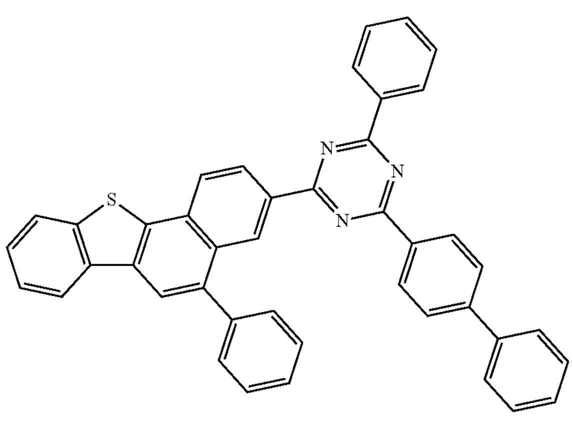
-continued
H2-573
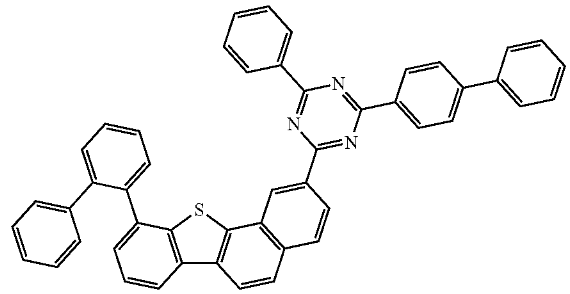
H2-574
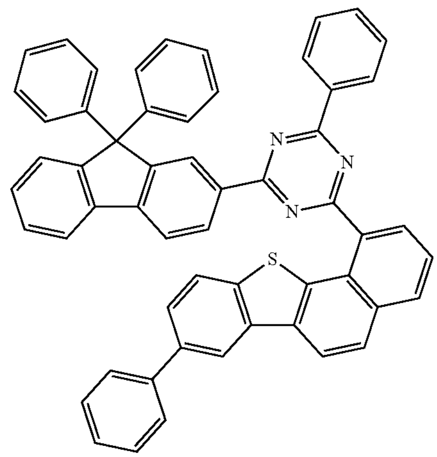
H2-575
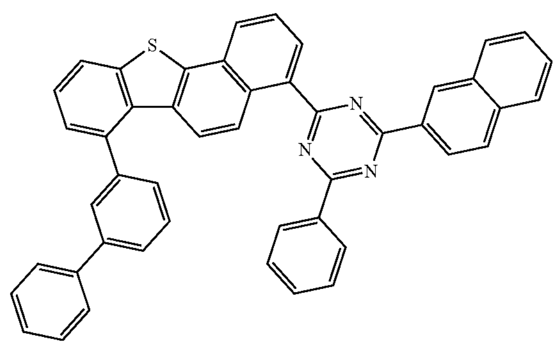
H2-576
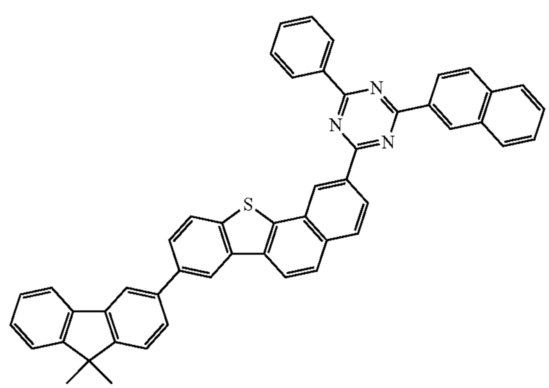

H2-577
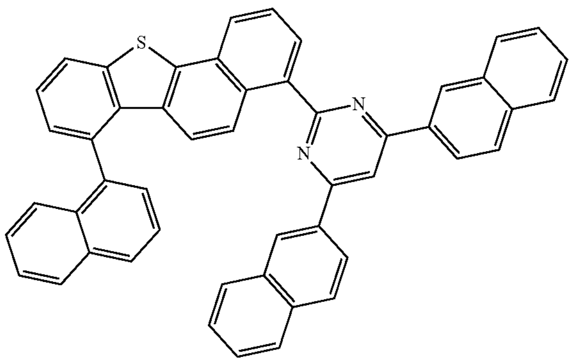
H2-578
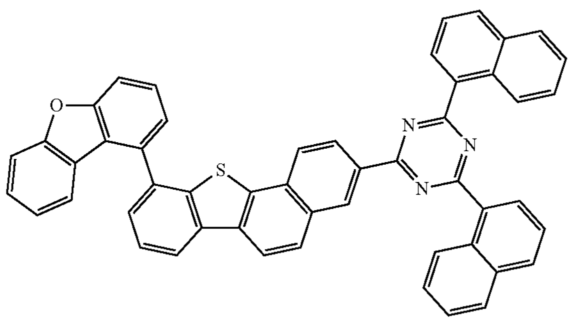
H2-579
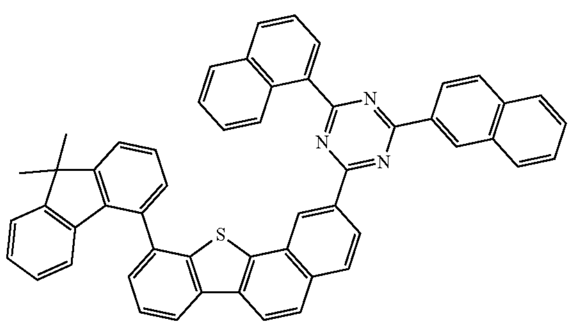
H2-580
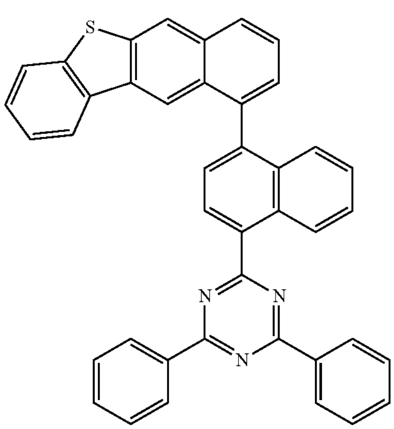
H2-581
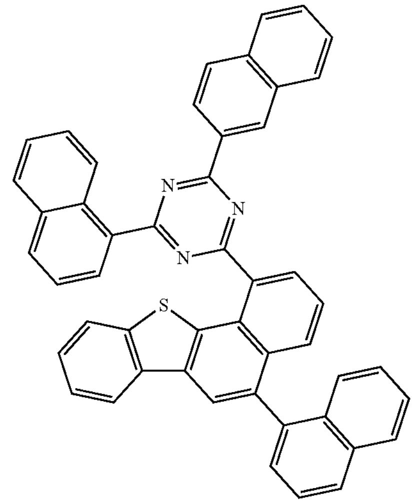
H2-582
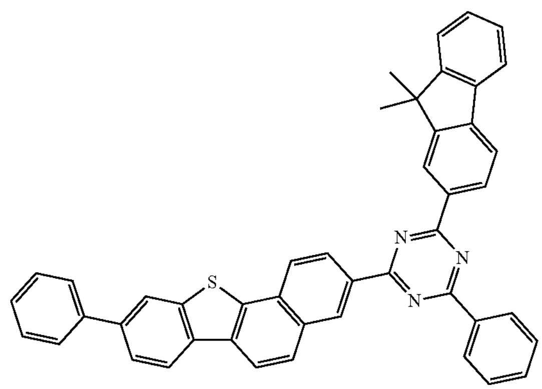
H2-583
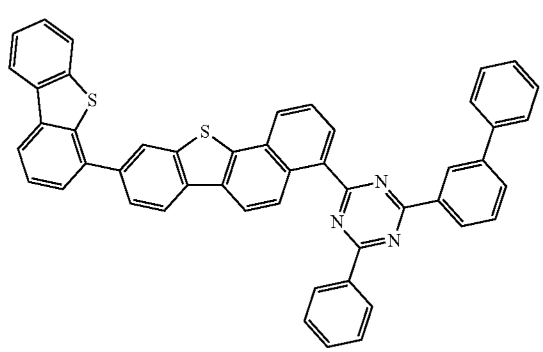

-continued
H2-584
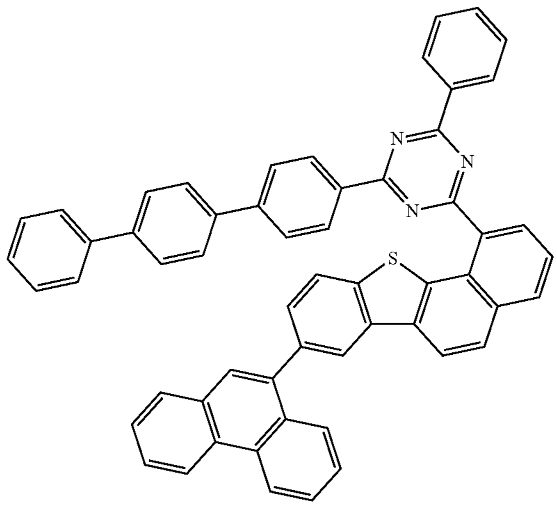
H2-585
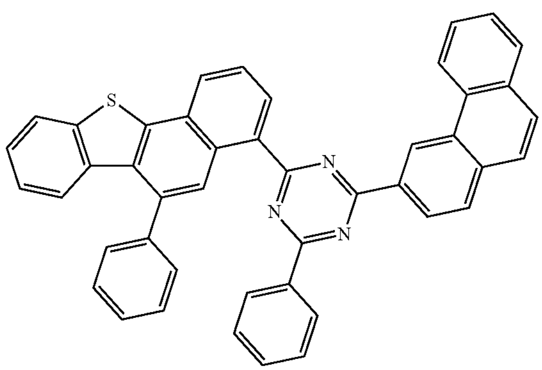
H2-586
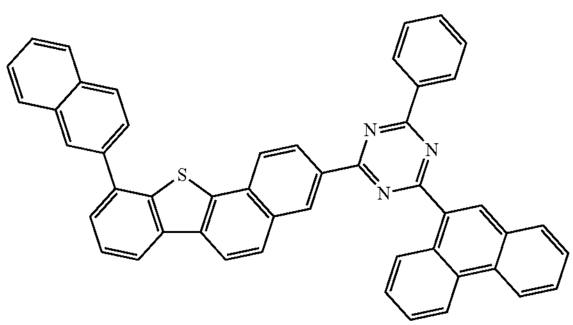
H2-587
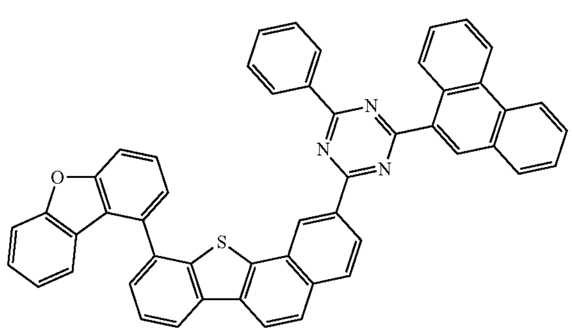
-continued
H2-588
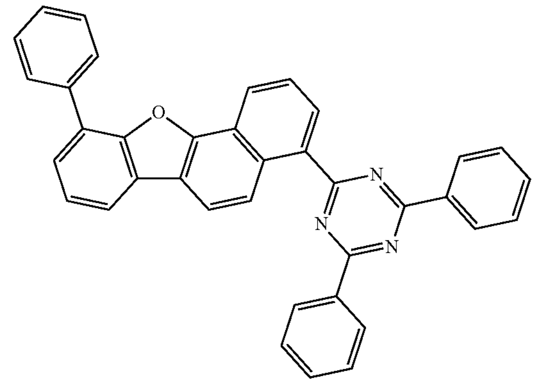
H2-589
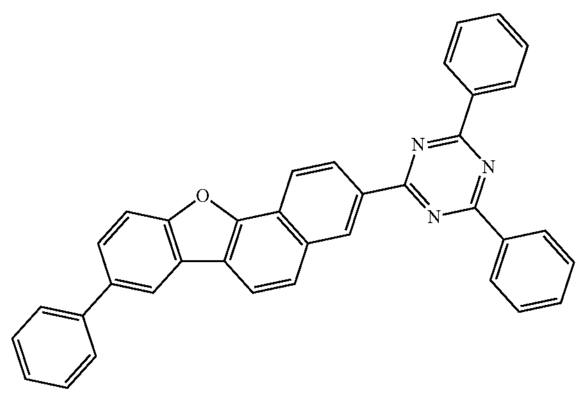
H2-590
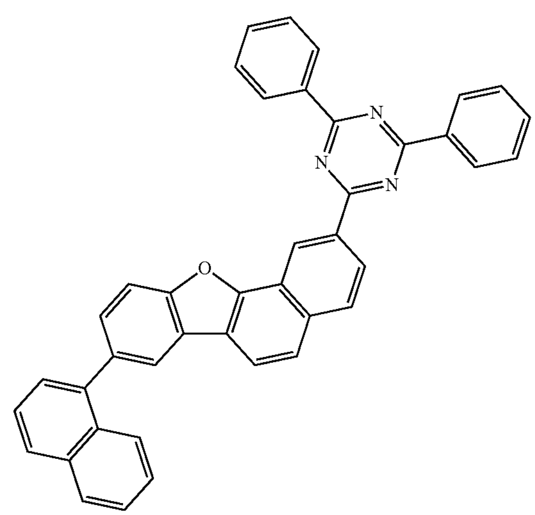

-continued
H2-591
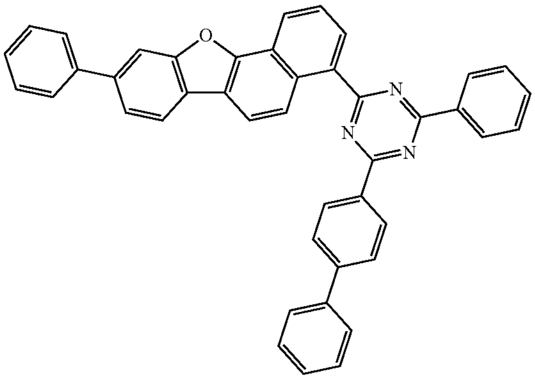
H2-592
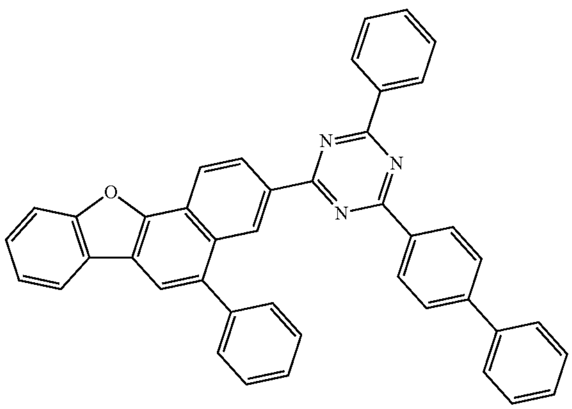
H2-593
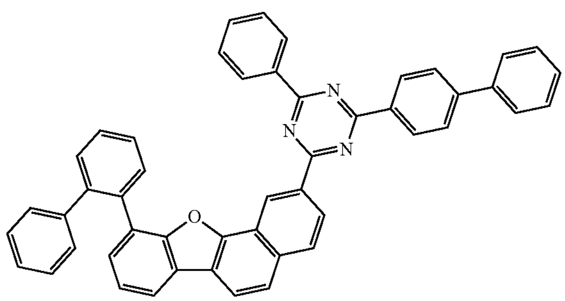
H2-594
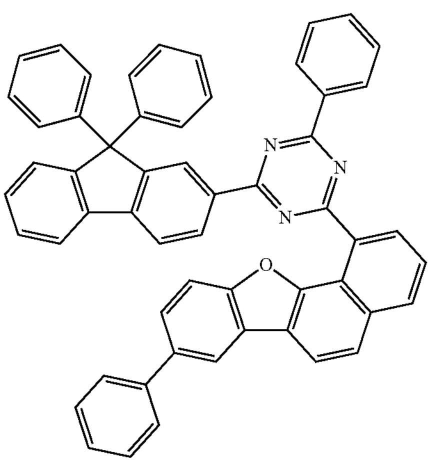
-continued
H2-595
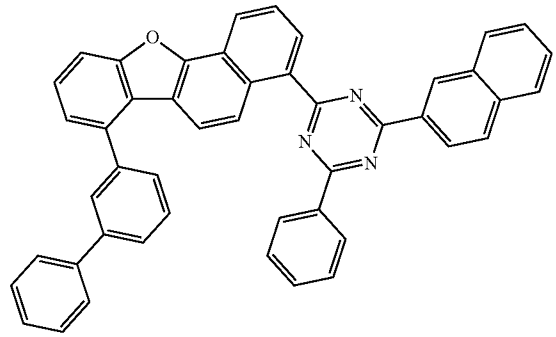
H2-596
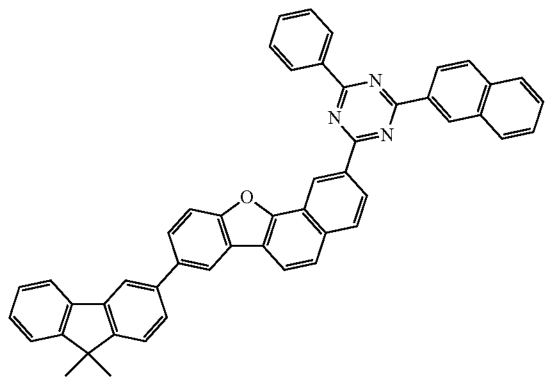
H2-597
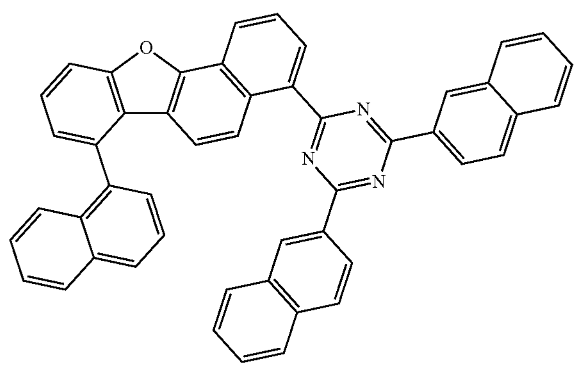
H2-598
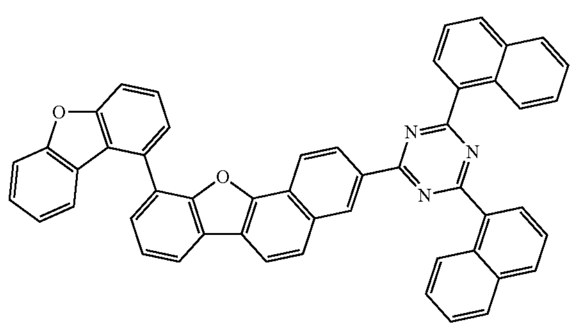

-continued
H2-599
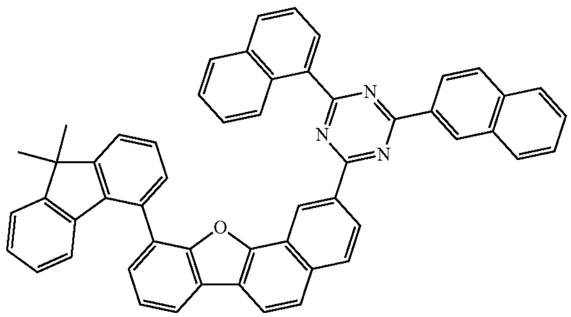
H2-600
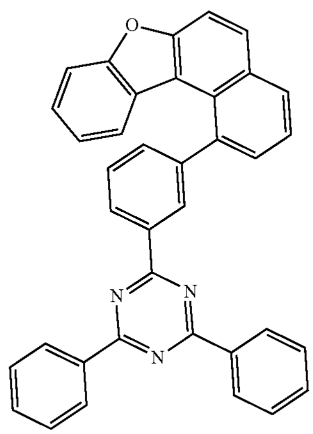
H2-601
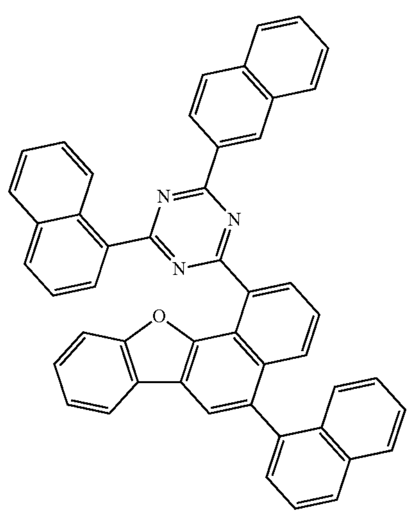
-continued
H2-602
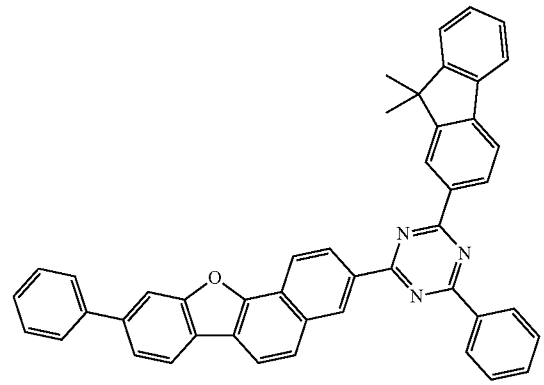
H2-603
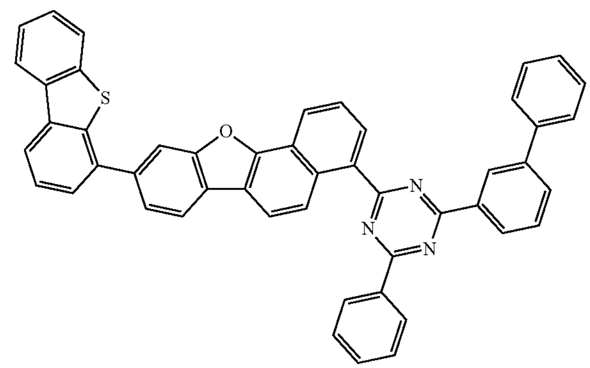
H2-604
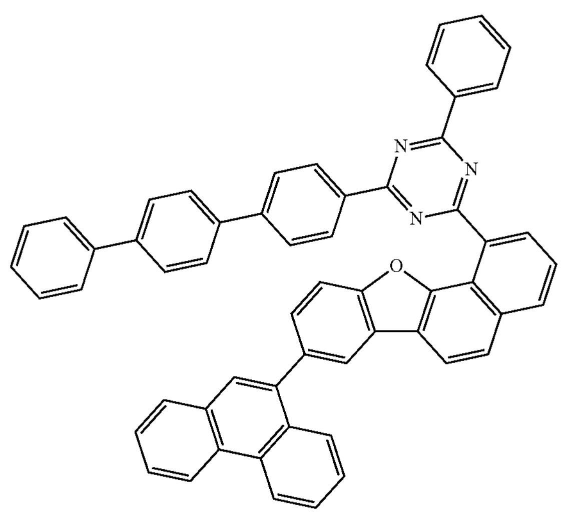

-continued
H2-605
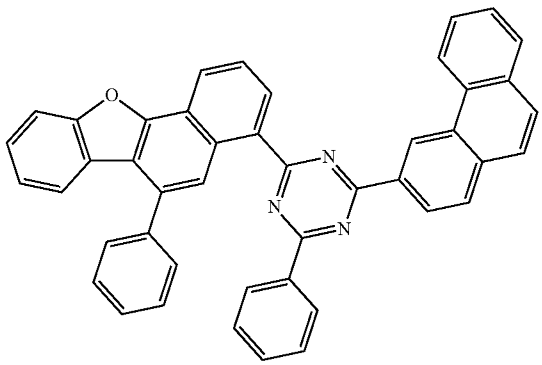
H2-606
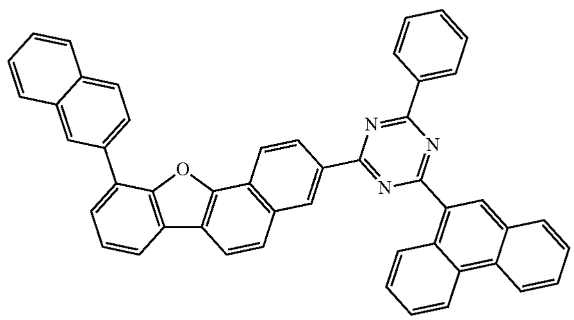
H2-607
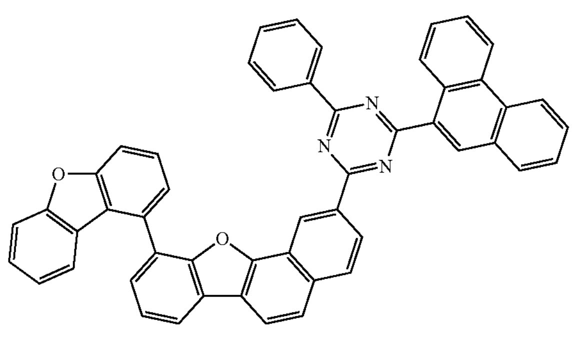
H2-608
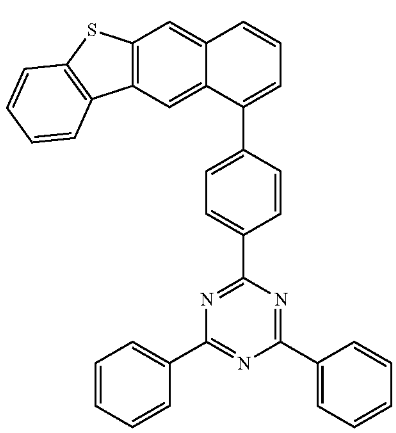
-continued
H2-609
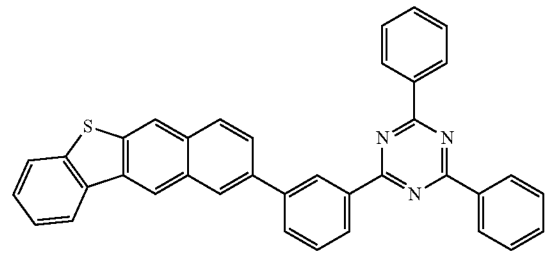
H2-610
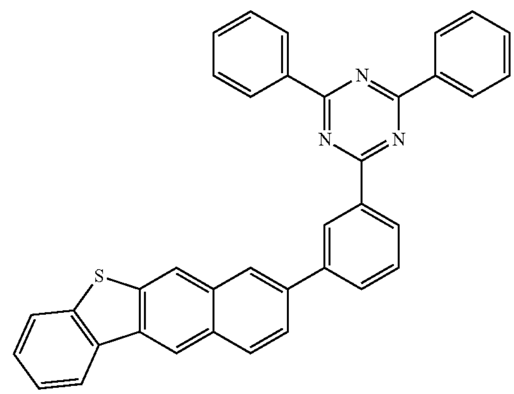
H2-611
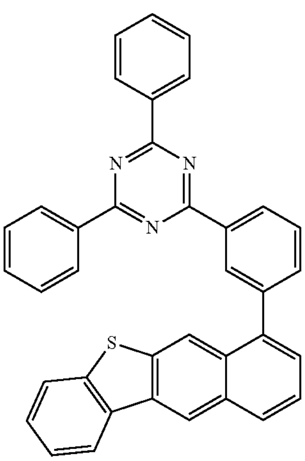
H2-612
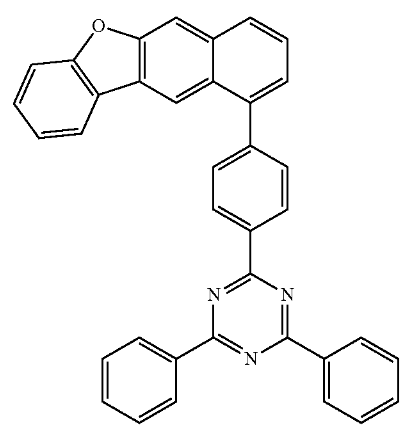

-continued
H2-613
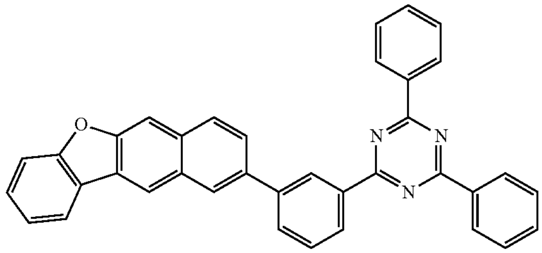
H2-614
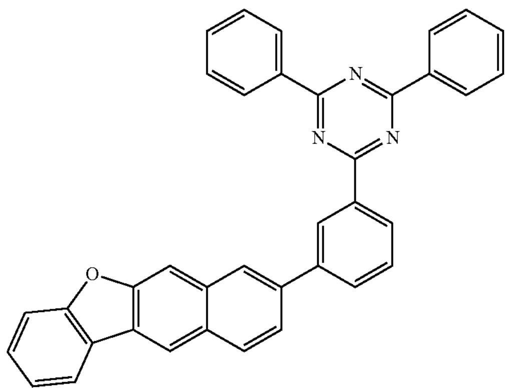
H2-615
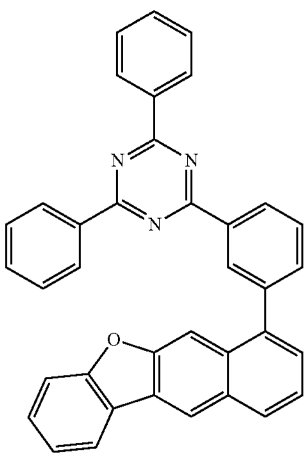
H2-616
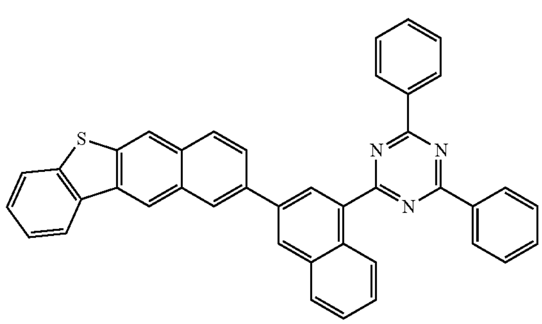
-continued
H2-617
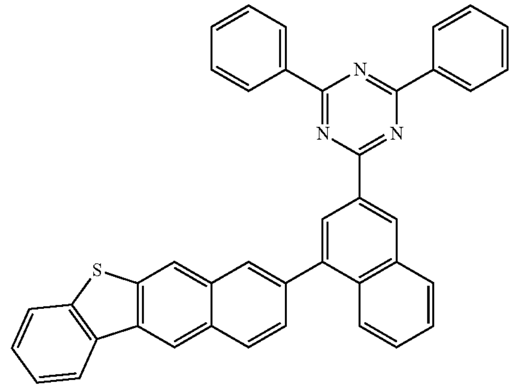
H2-618
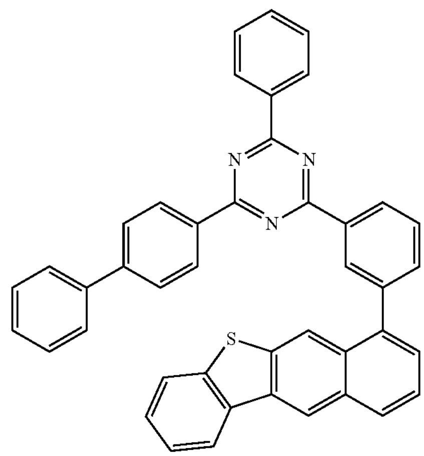
H2-619
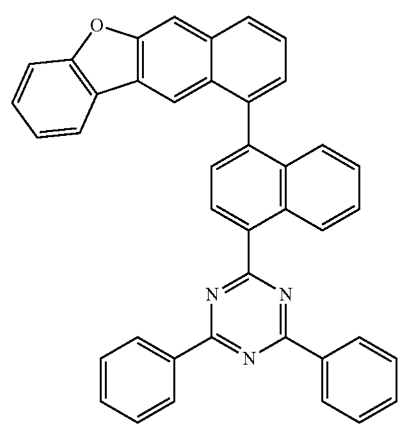
H2-620
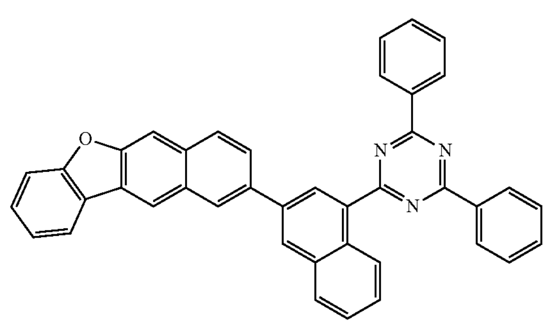

H2-621
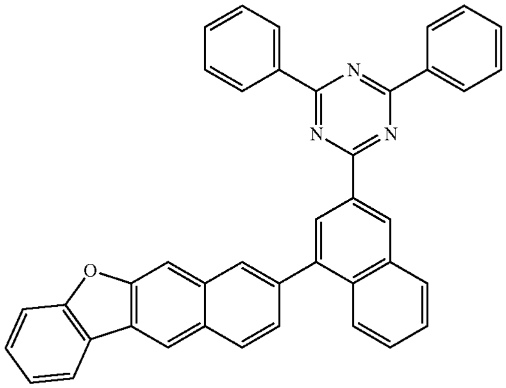
H2-622
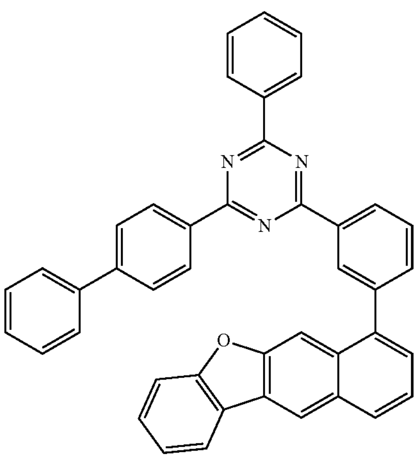
H2-623
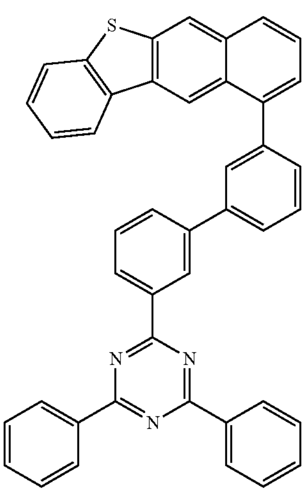
H2-624
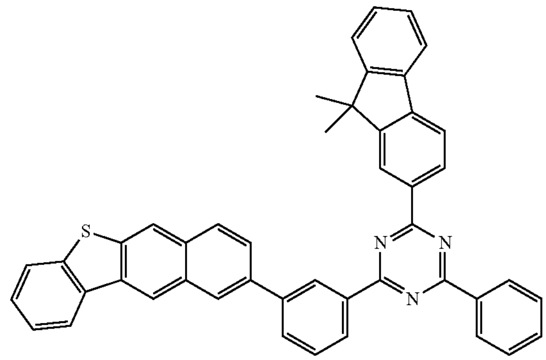
H2-625
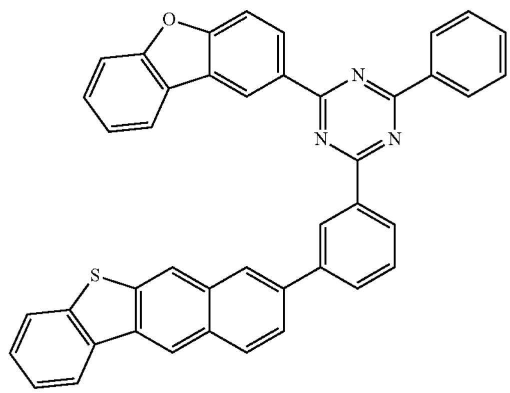
H2-626
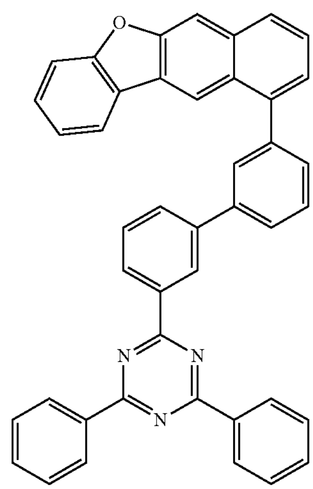
H2-627
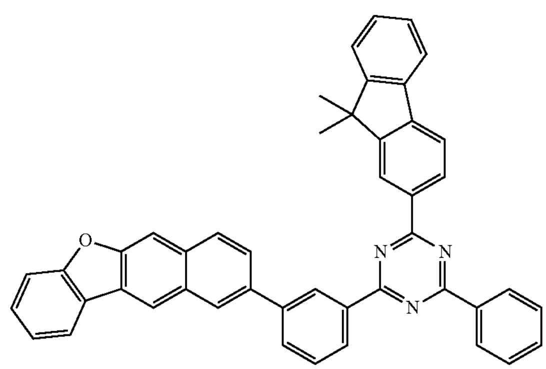

-continued
H2-628
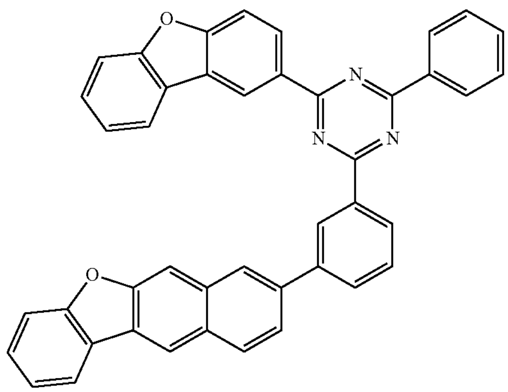
H2-629
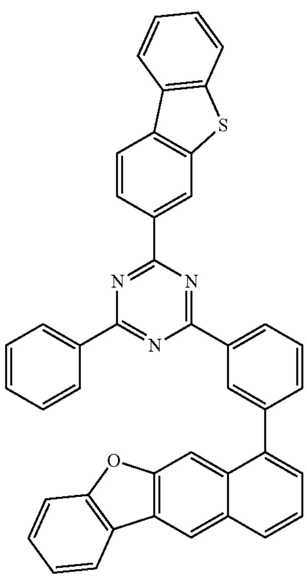
H2-630
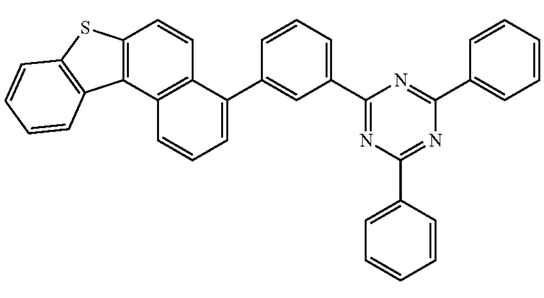
-continued
H2-631
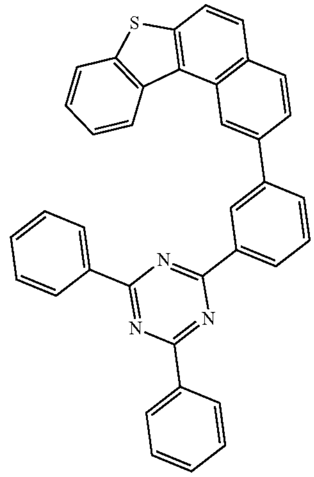
H2-632
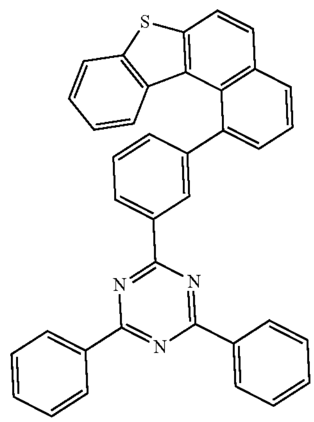
H2-633
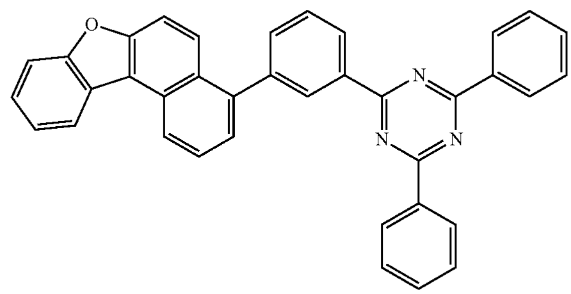
H2-634
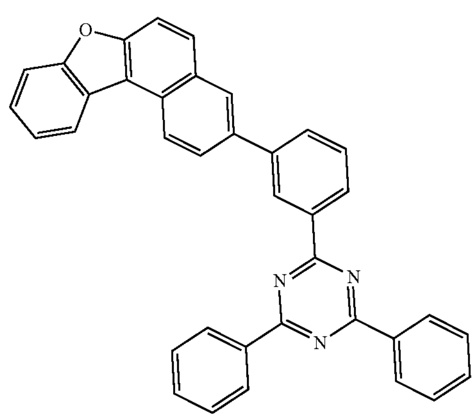

-continued
H2-635
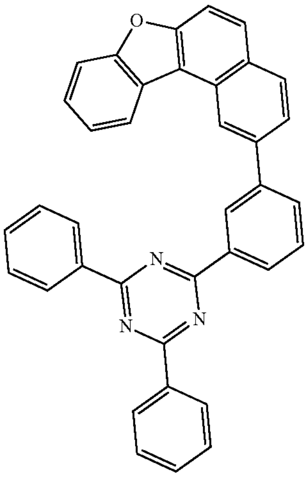
H2-636
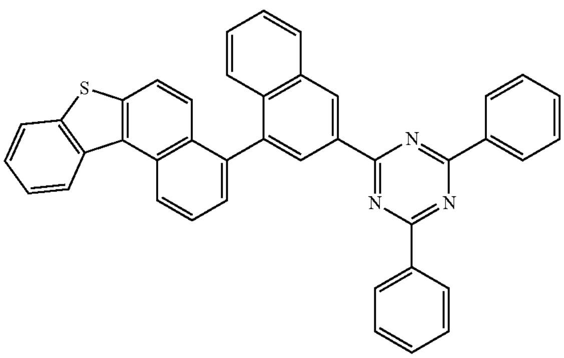
H2-637
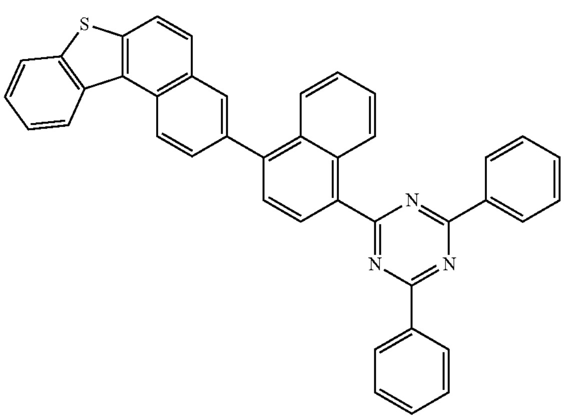
-continued
H2-638
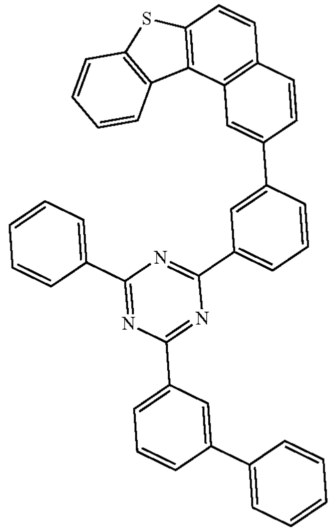
H2-639
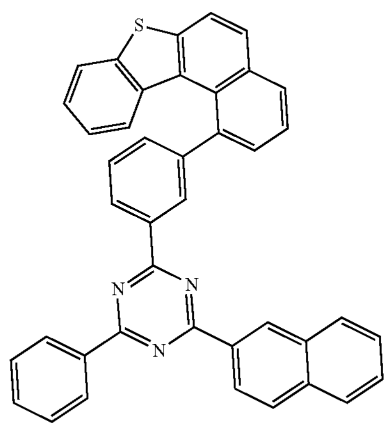
H2-640
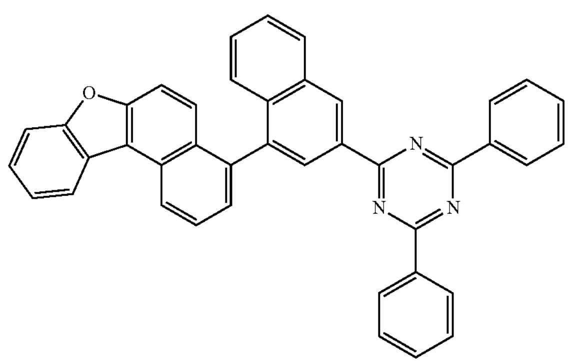

-continued
H2-641
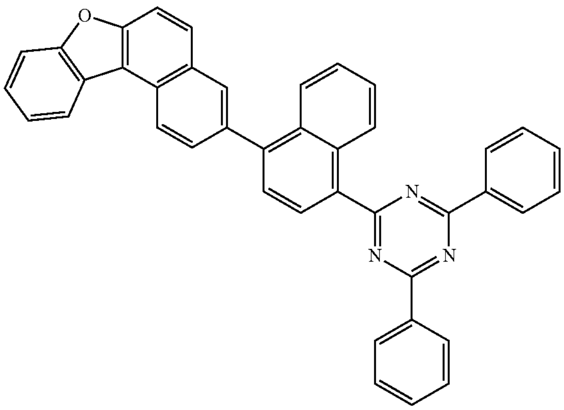
H2-642
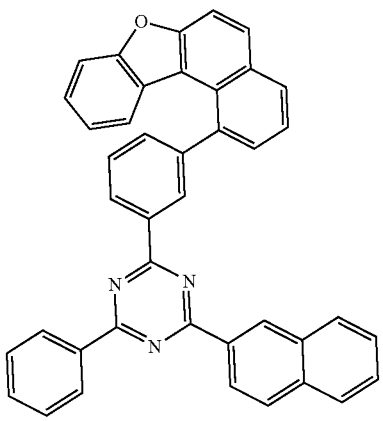
H2-643
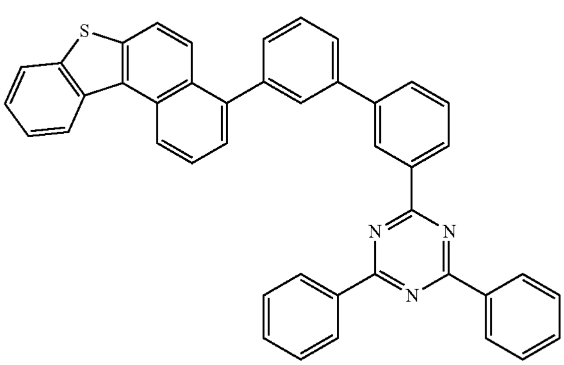
-continued
H2-644
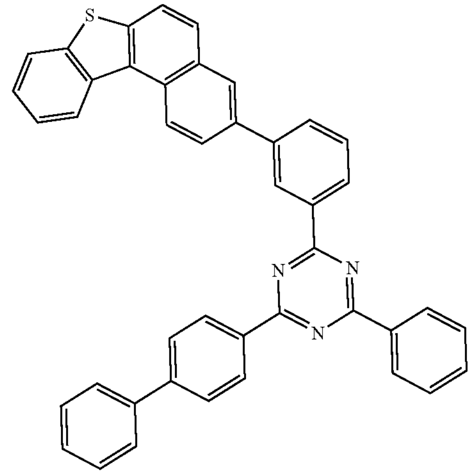
H2-645
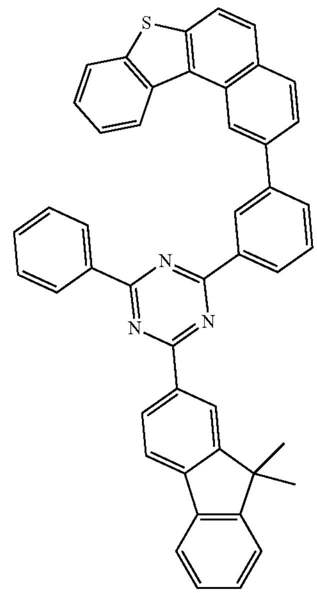
H2-646
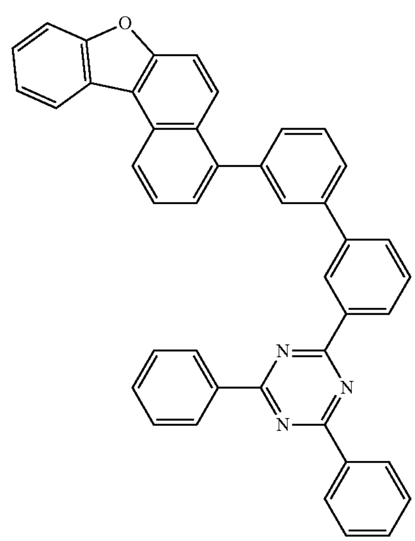

-continued
H2-647
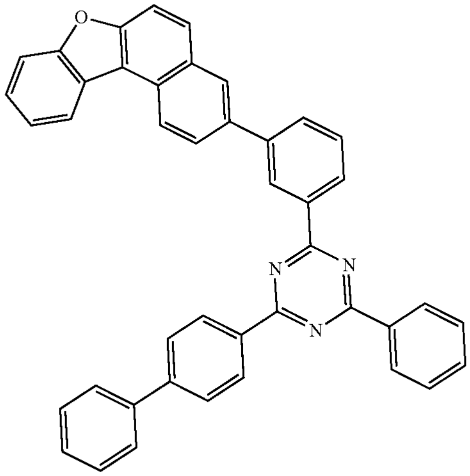
H2-648
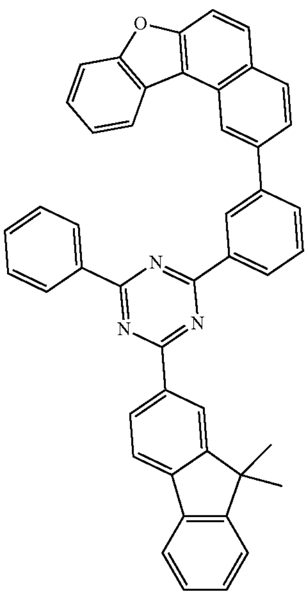
H2-649
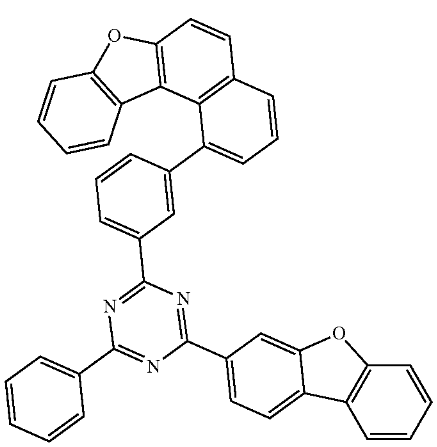
-continued
H2-650
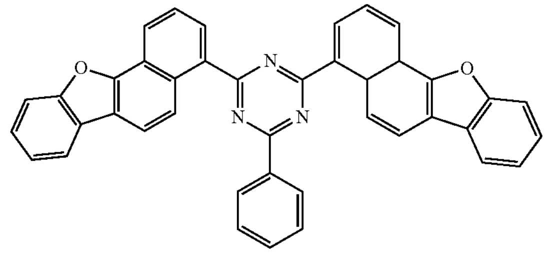
H2-651
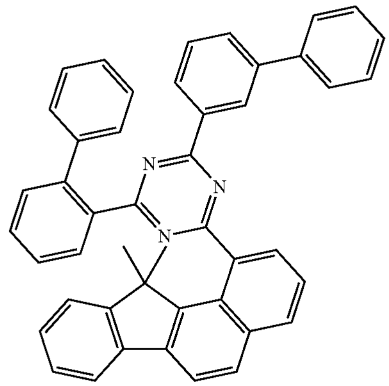
H2-625
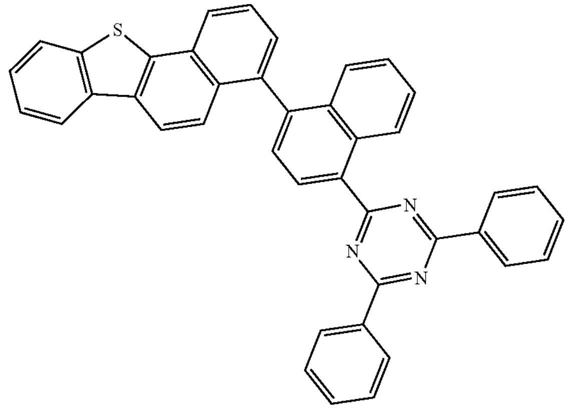
H2-653
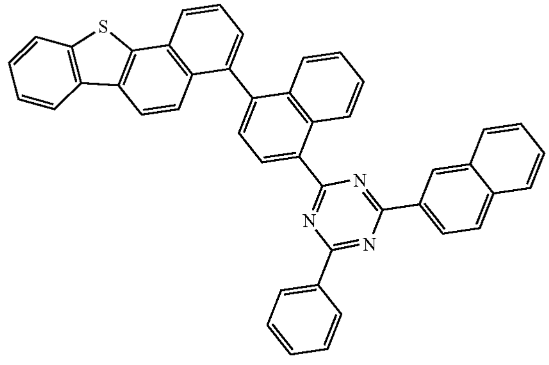

-continued
H2-654
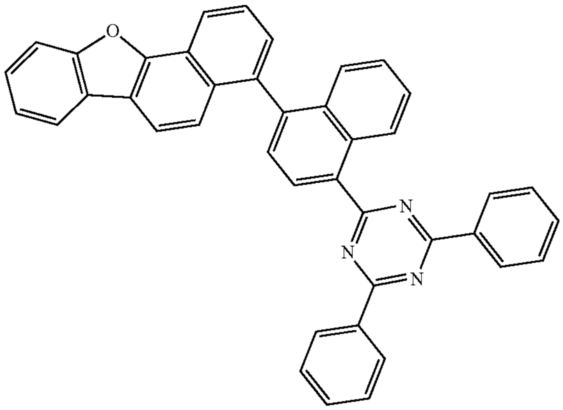
H2-655
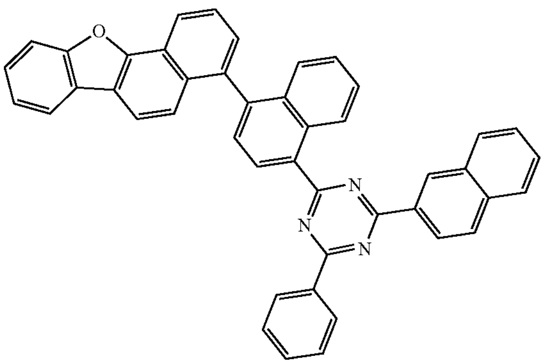
H2-656
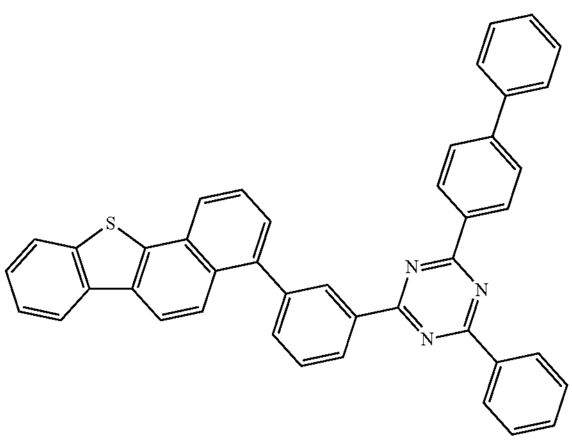
H2-657
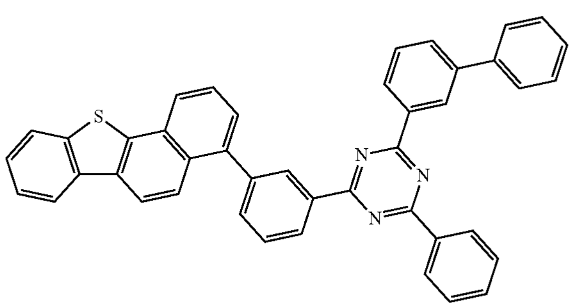
-continued
H2-658
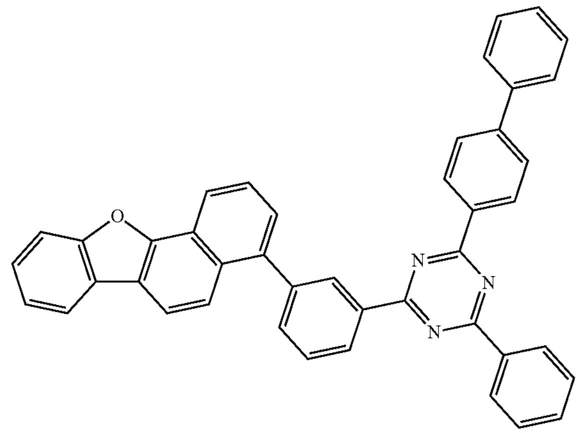
H2-659
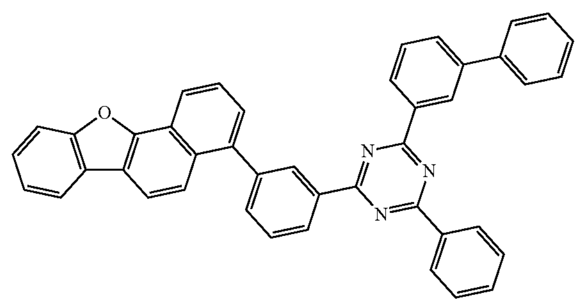
H2-660
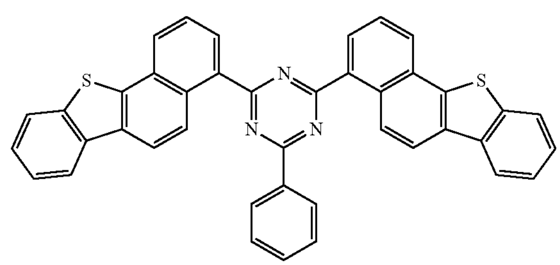
H2-661
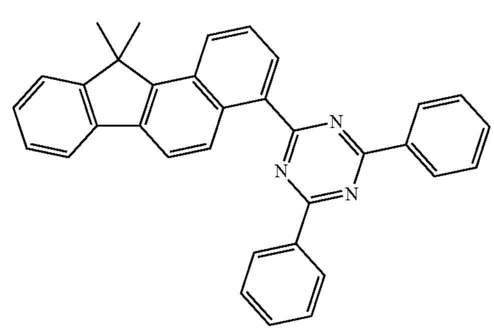

-continued
H2-662
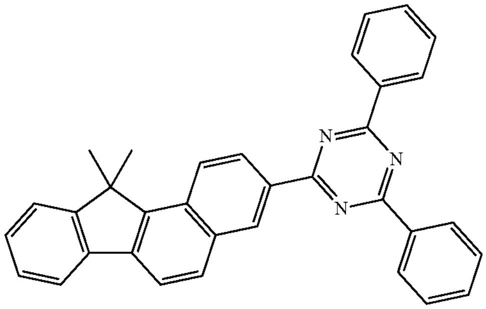
H2-663
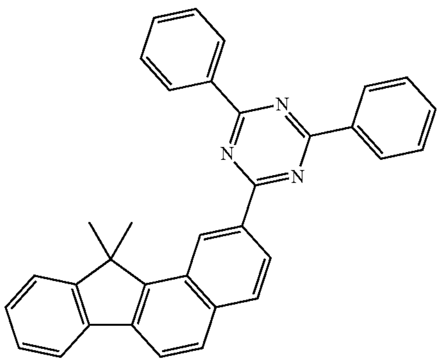
H2-664
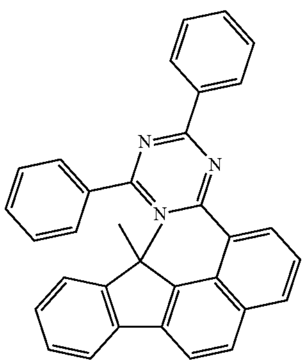
H2-665
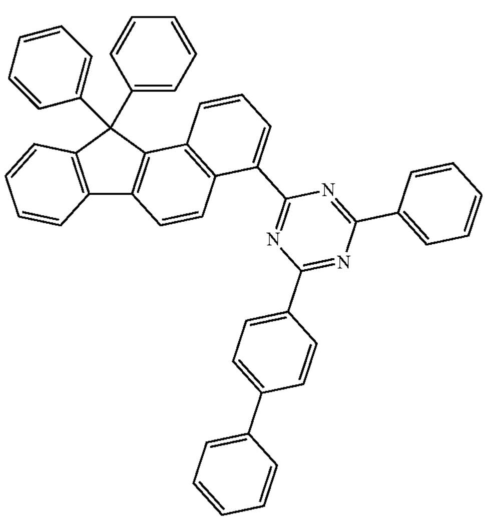
-continued
H2-666
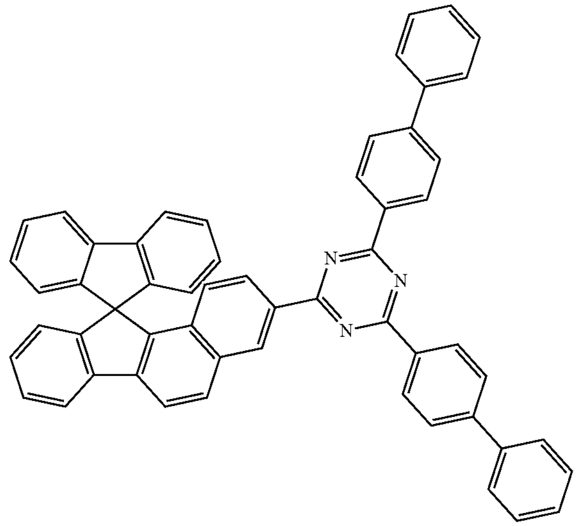
H2-667
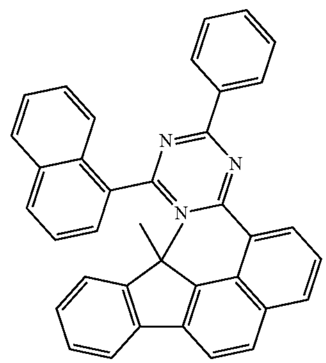
H2-668
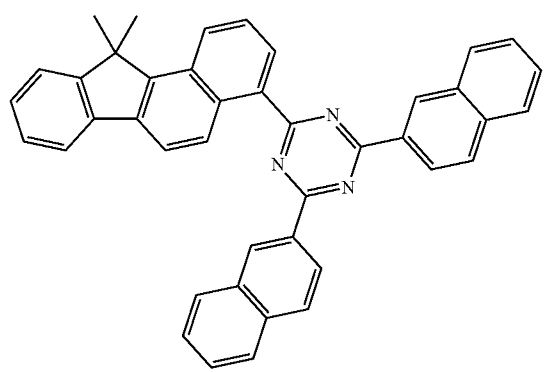

-continued
H2-669
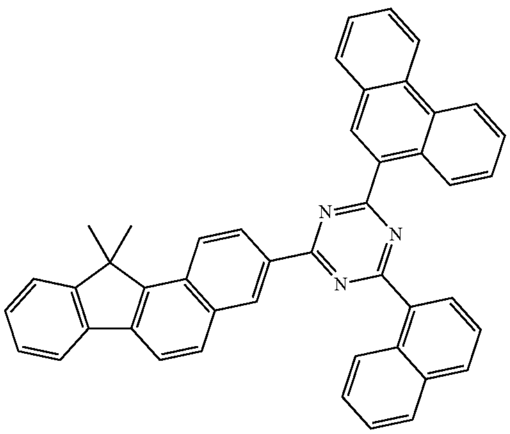
H2-670
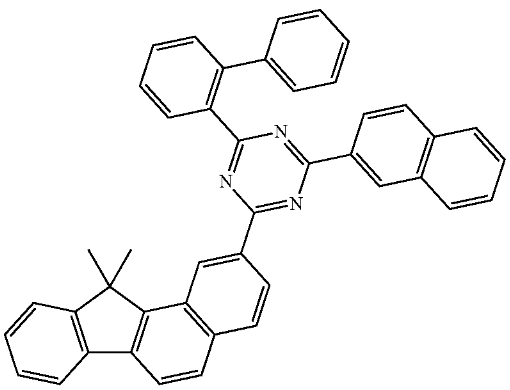
H2-671
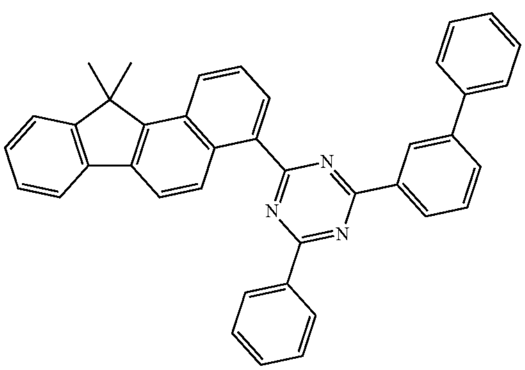
H2-672
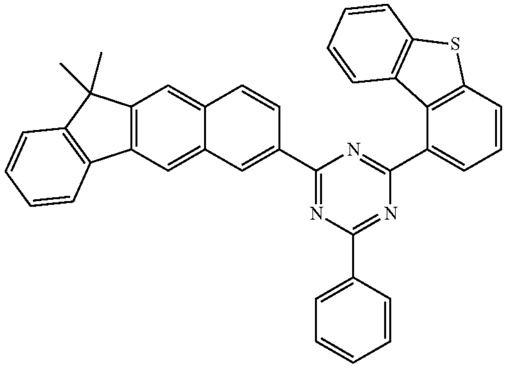
-continued
H2-673
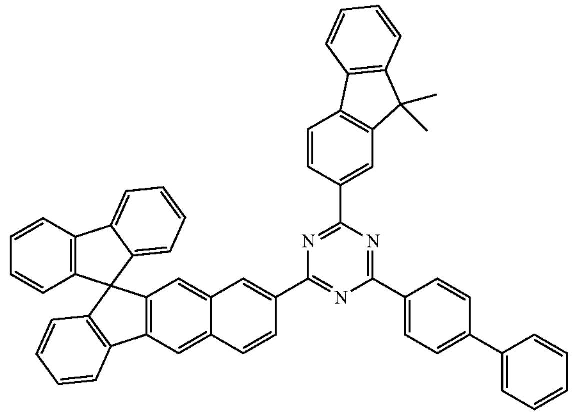
H2-674
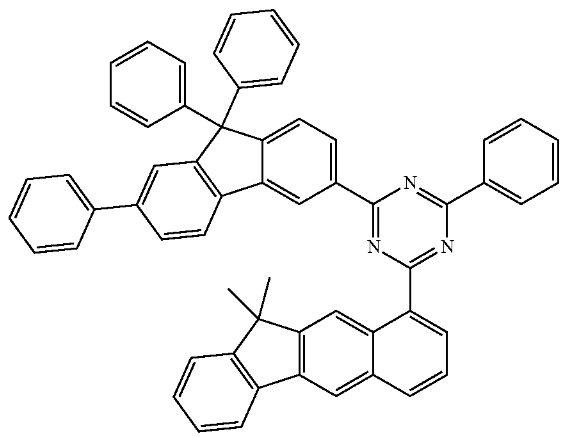
H2-675
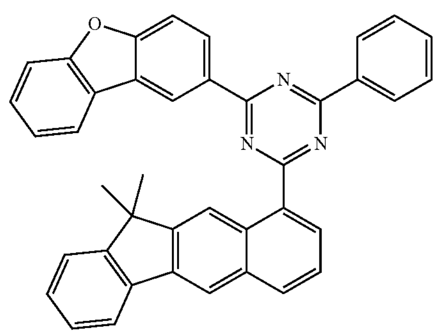

-continued
H2-676
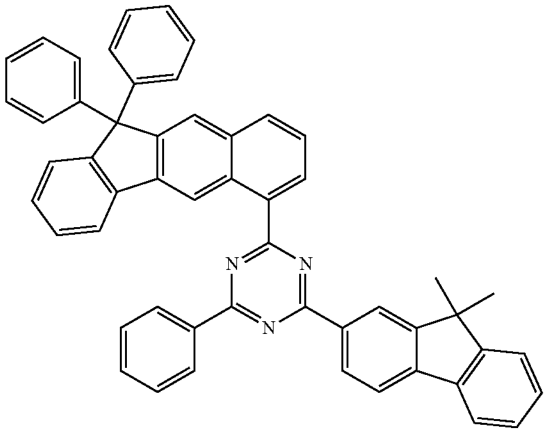
H2-677
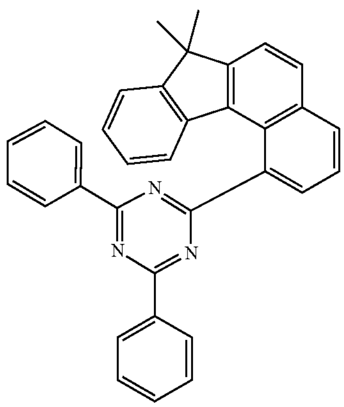
H2-678
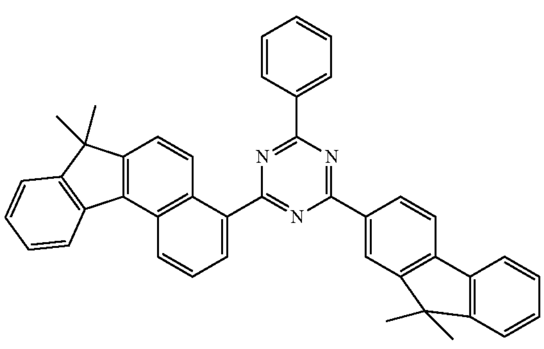
-continued
H2-679
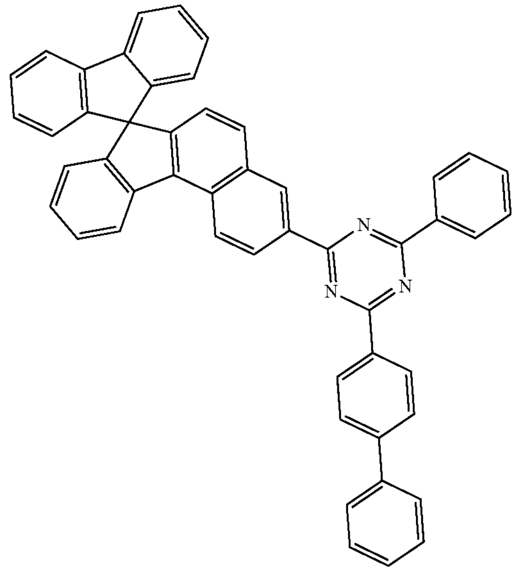
H2-680
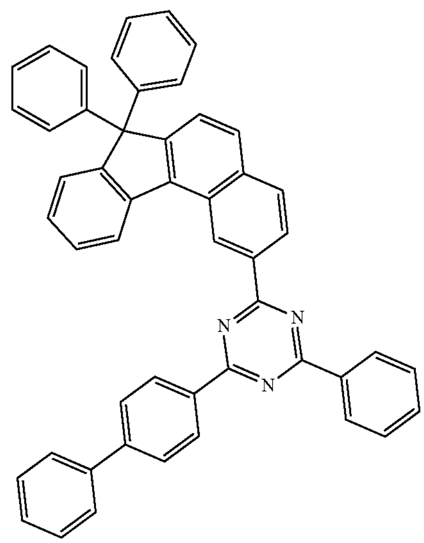
H2-681
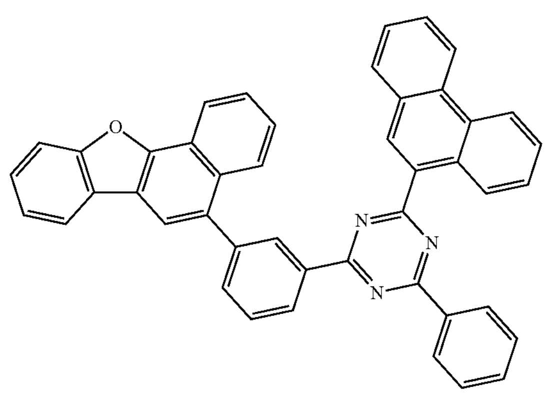

-continued
H2-682
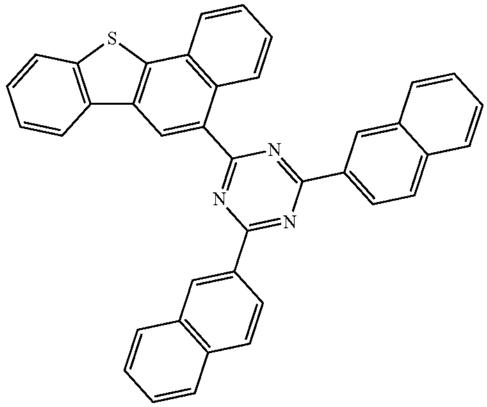
H2-683
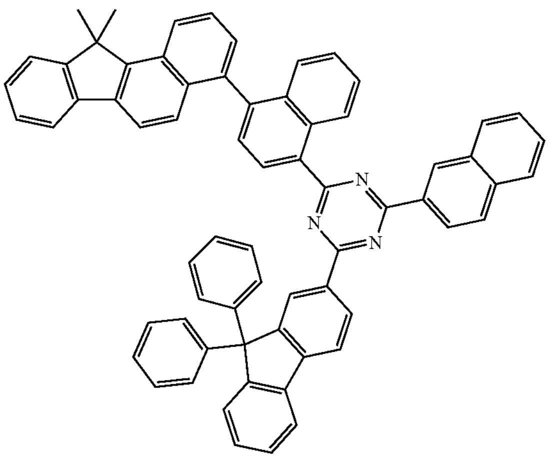
H2-684
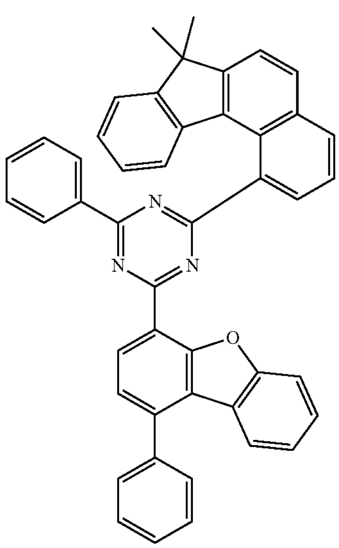
-continued
H2-685
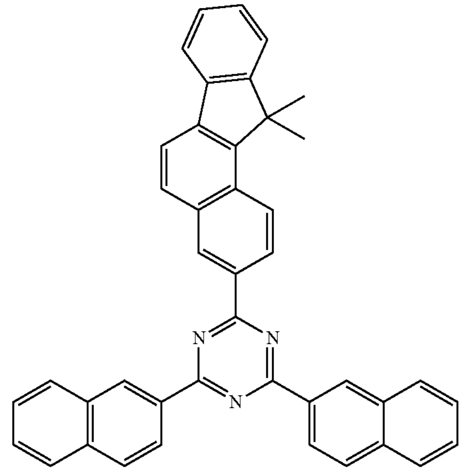
H2-686
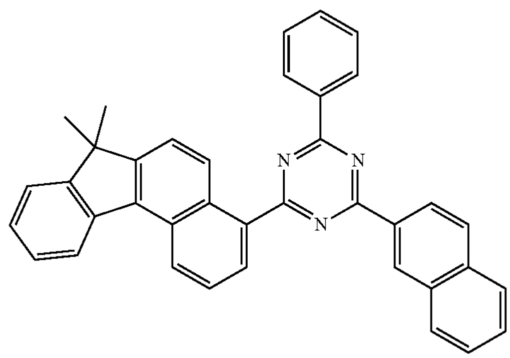
H2-687
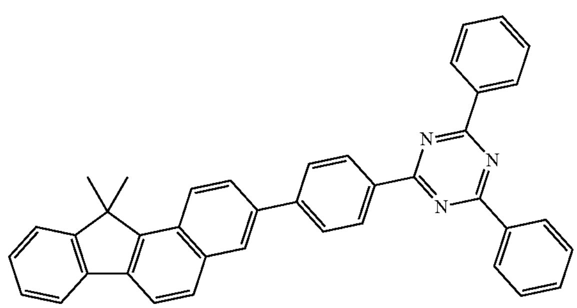

H2-688
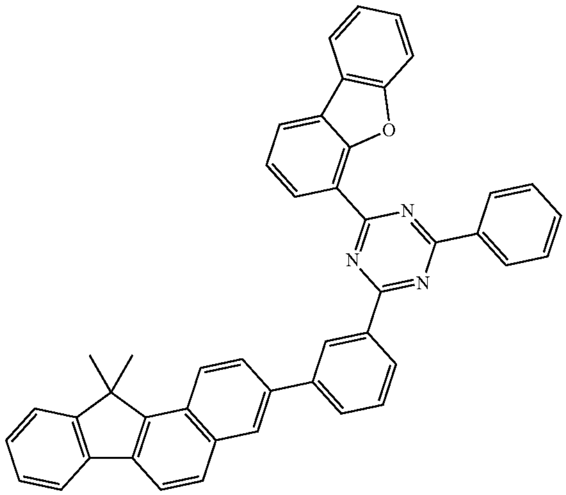
H2-689
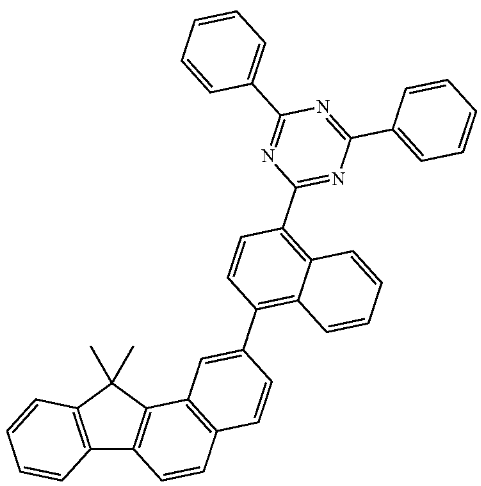
H2-690
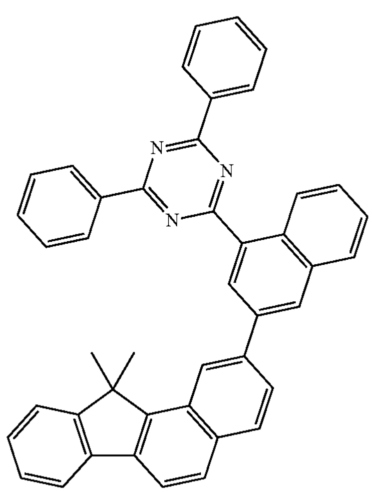
H2-691
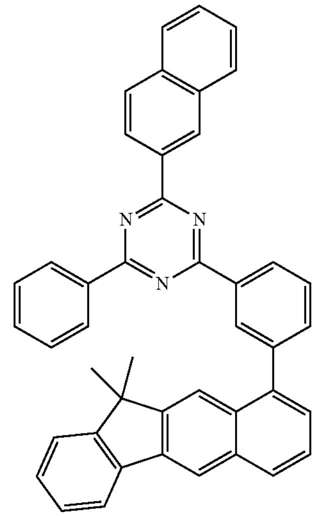
H2-692
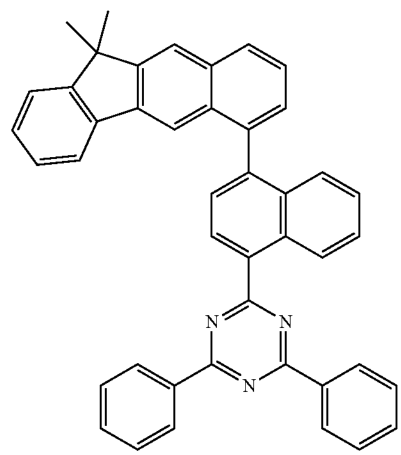
H2-693
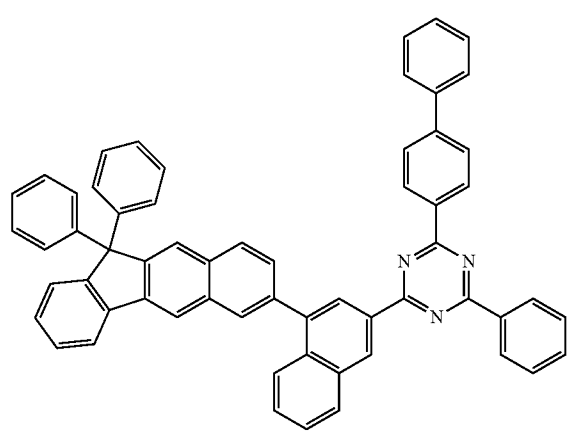

-continued
H2-694
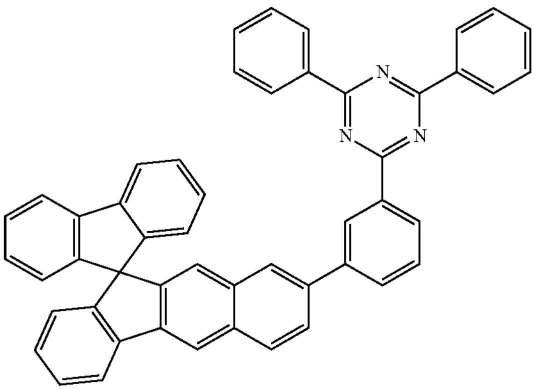
H2-695
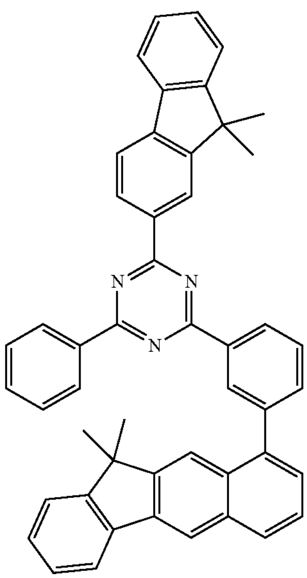
H2-696
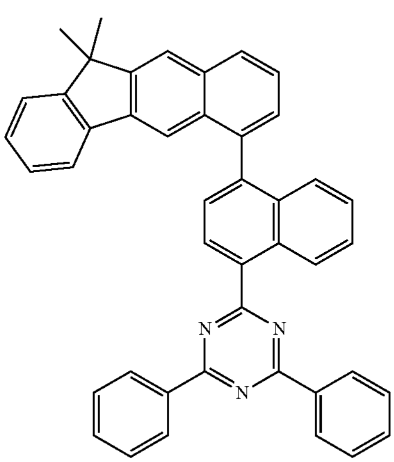
-continued
H2-697
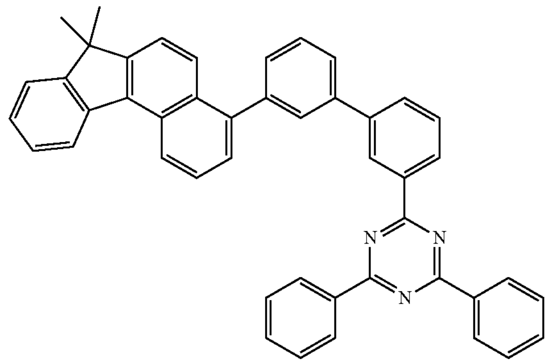
H2-698
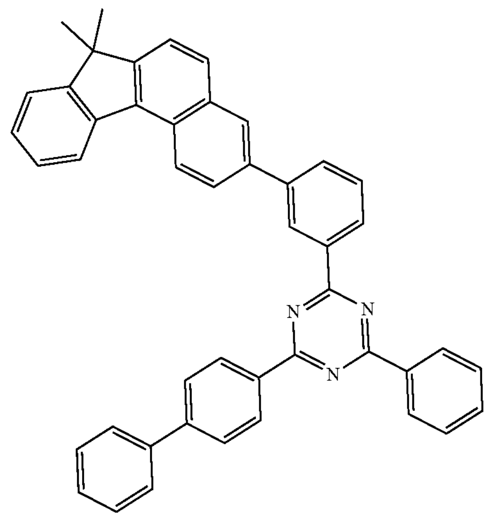
H2-699
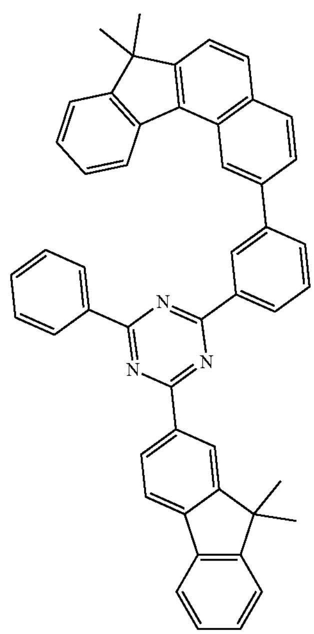

-continued
H2-700
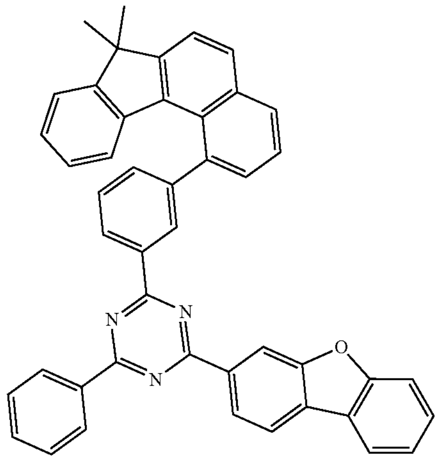
H2-701
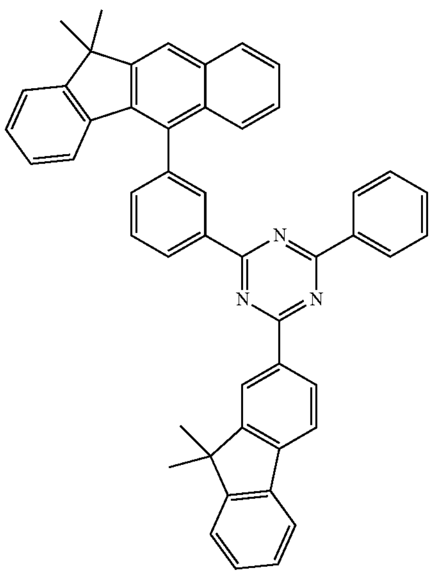
H2-702
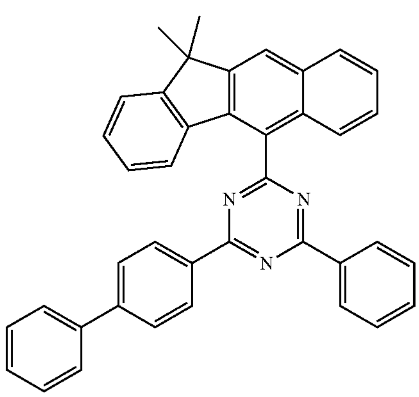
-continued
H2-703
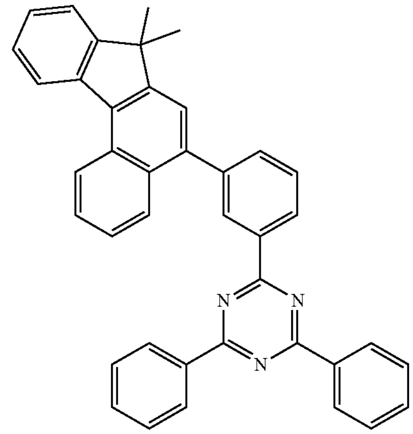
H2-704
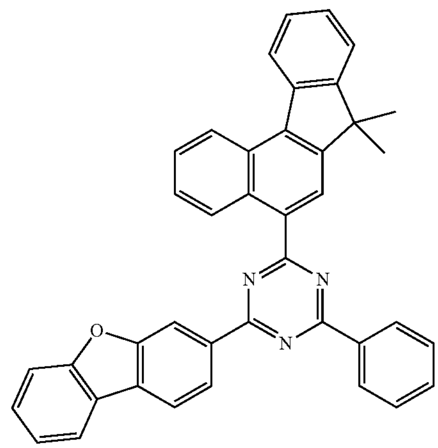
H2-705
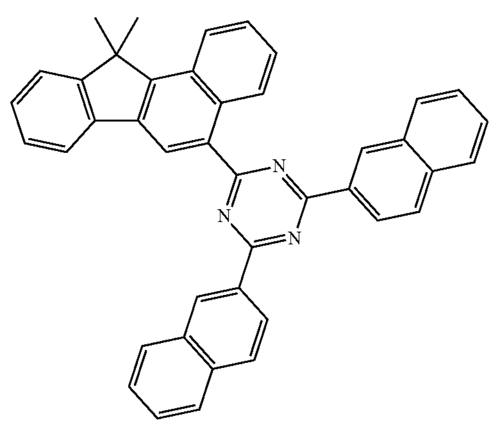

-continued
H2-706
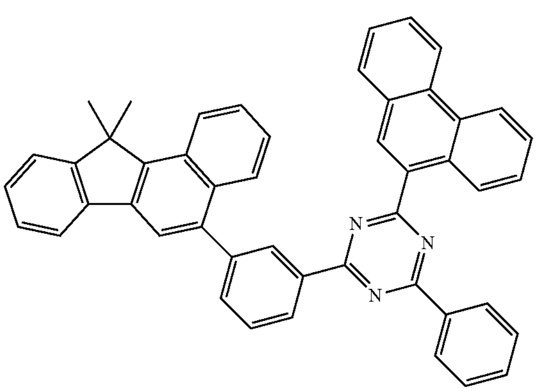
H2-707
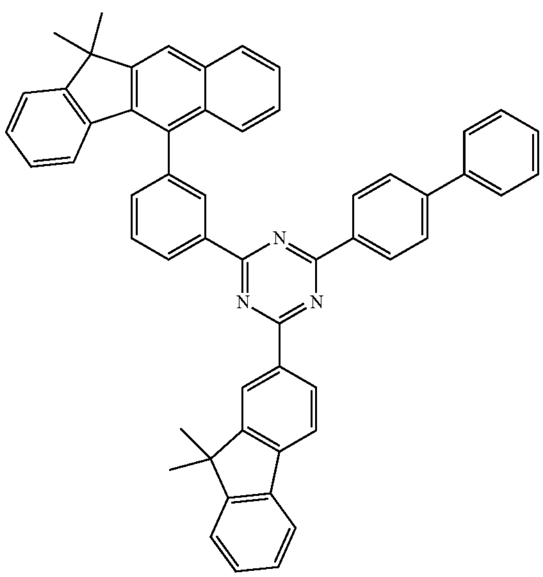
H2-708
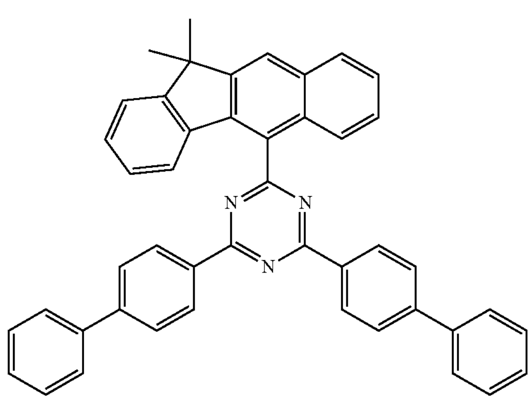
H2-709
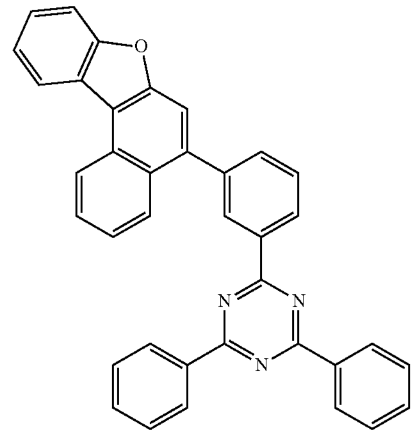
H2-710
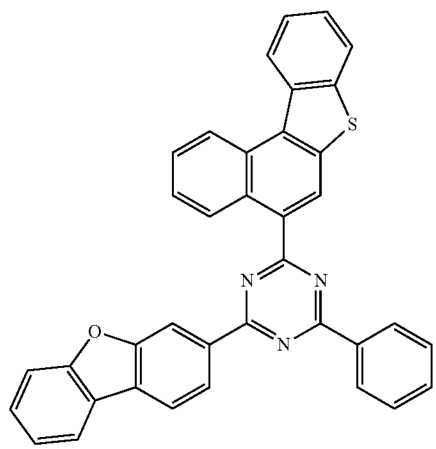
H2-711
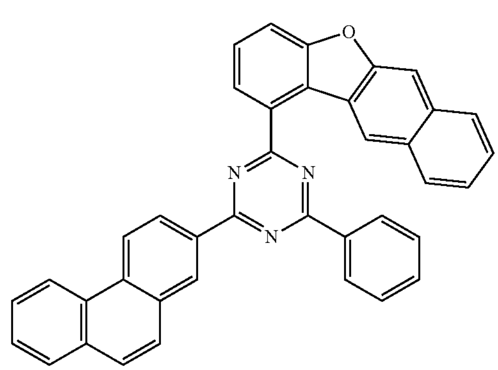

-continued
H2-712
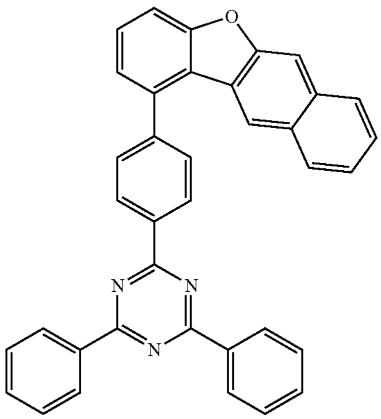
H2-713
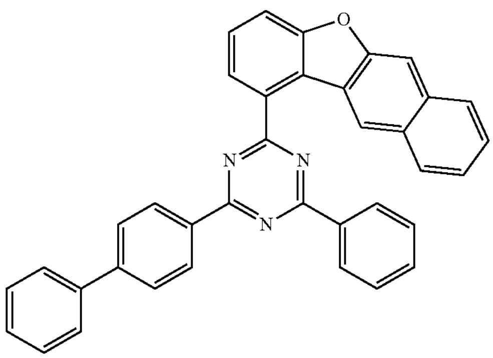
H2-714
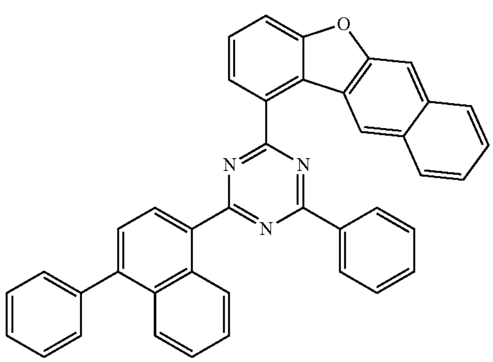
H2-715
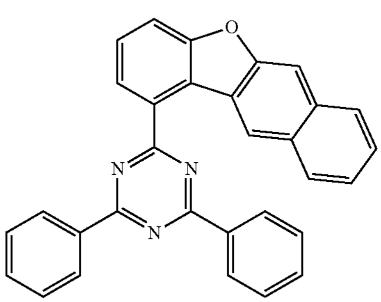
-continued
H2-716
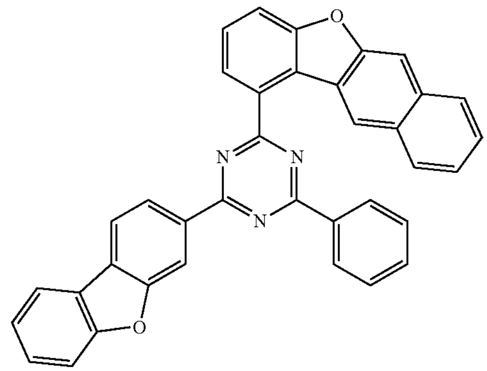
H2-717
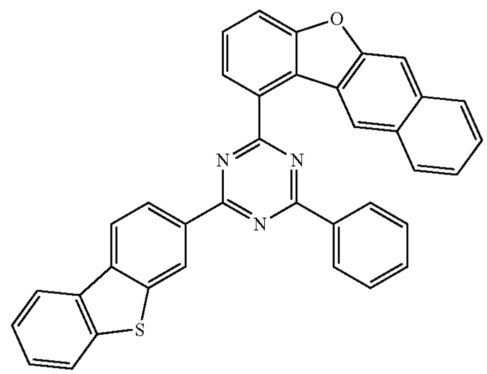
H2-718
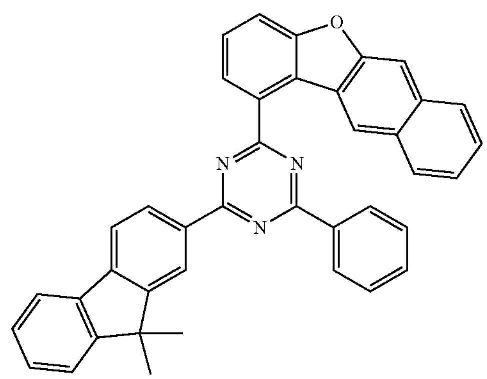
H2-719
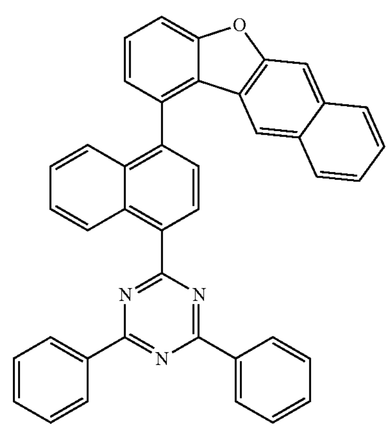

-continued
H2-720
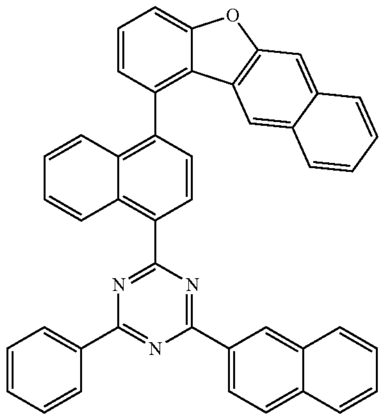
H2-721
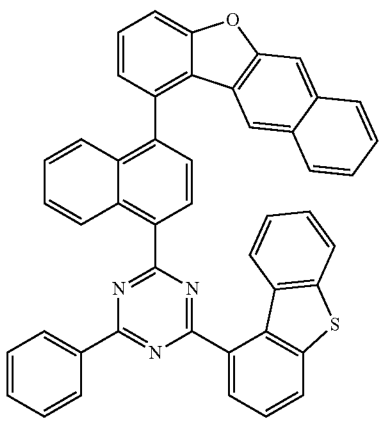
H2-722
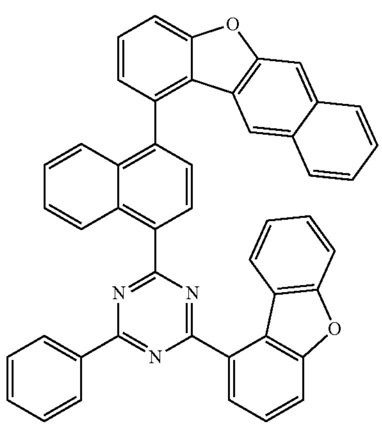
-continued
H2-723
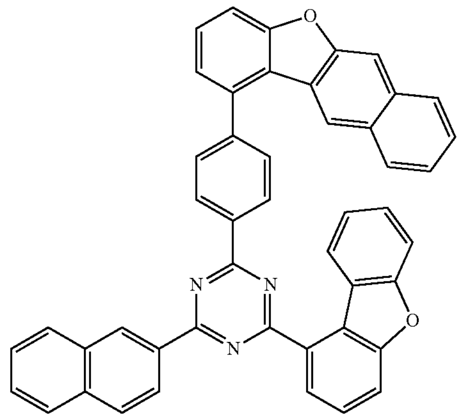
H2-724
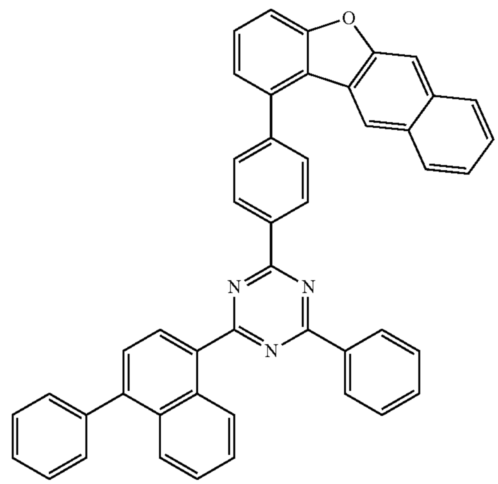
H2-725
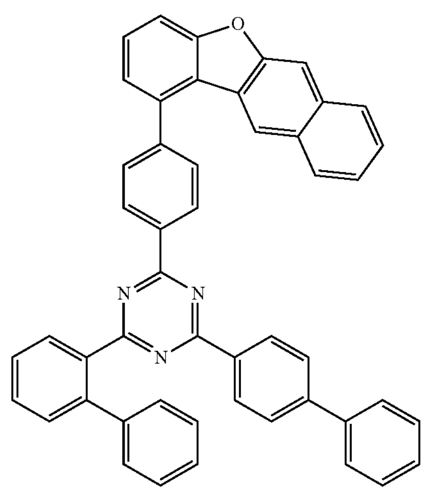

-continued
H2-726
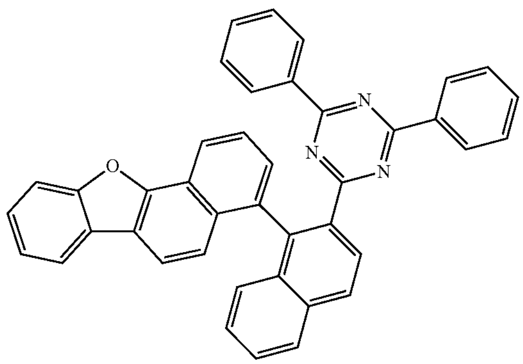
H2-727
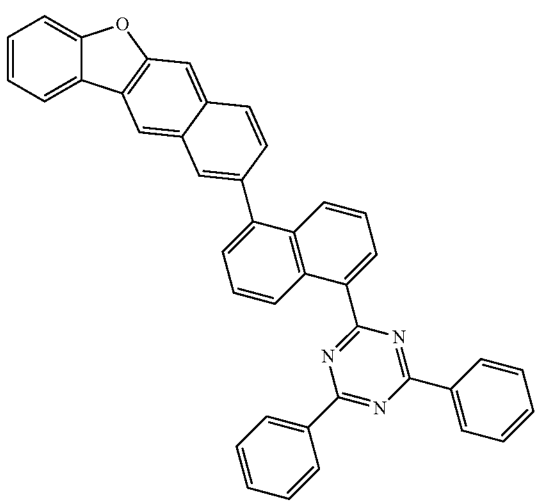
H2-728
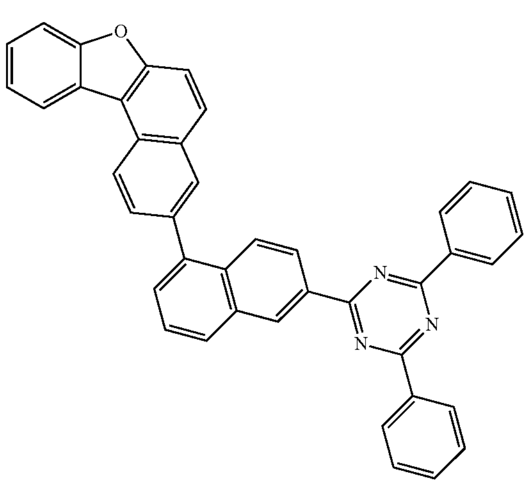
-continued
H2-729
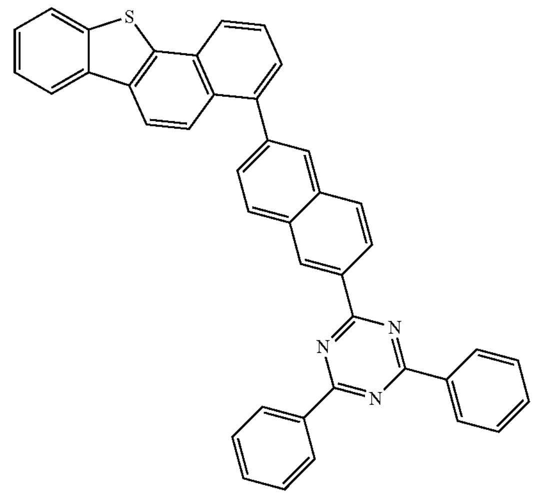
H2-730
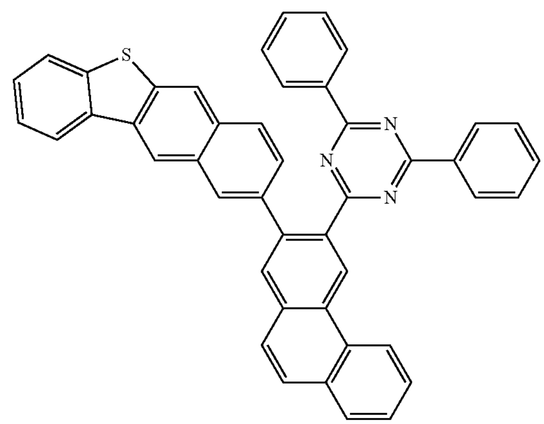
H2-731
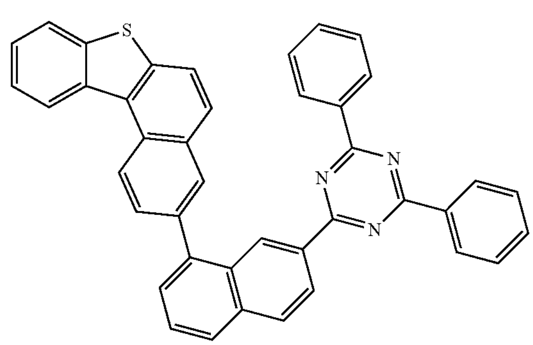

H2-732
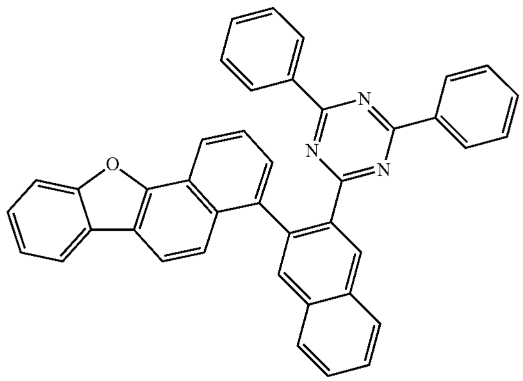
H2-733
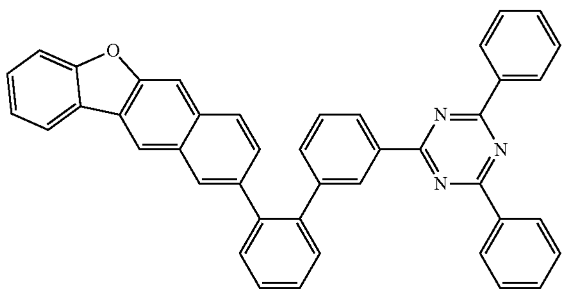
H2-734
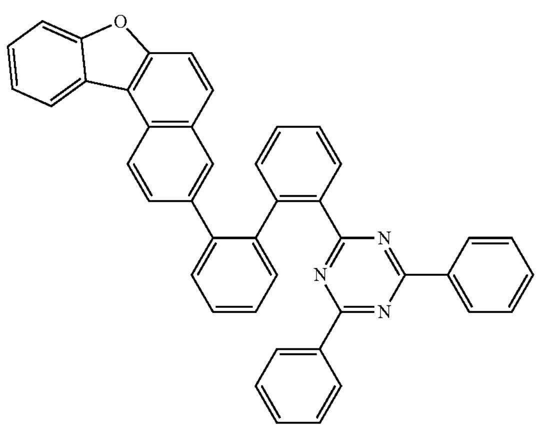
H2-735
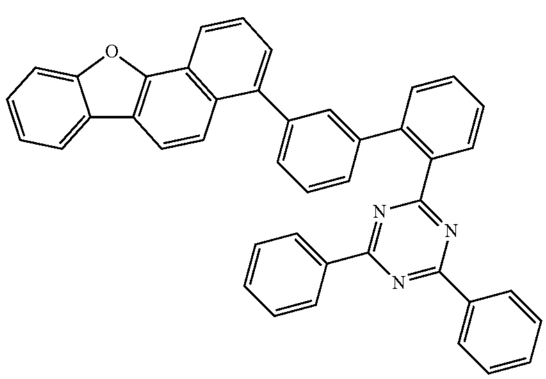
H2-736
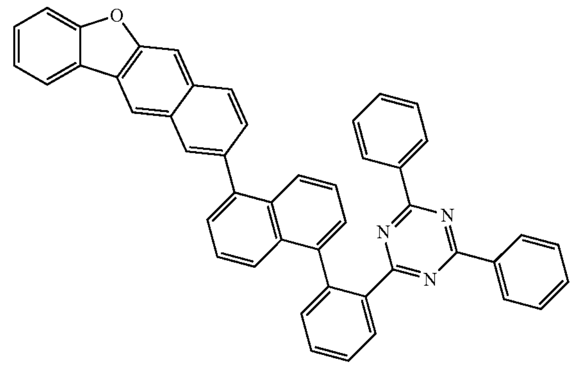
H2-737
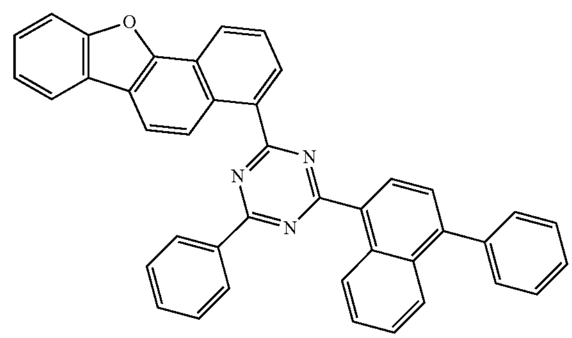
H2-738
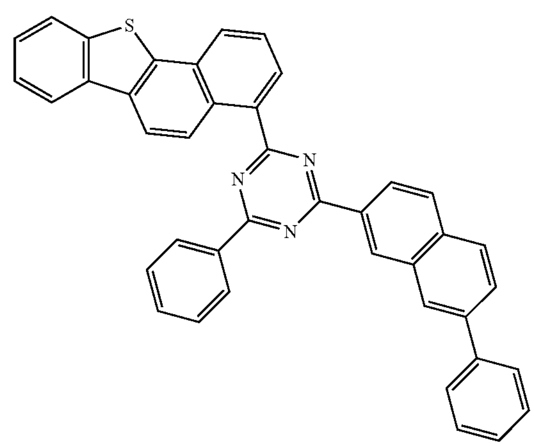

-continued
H2-739
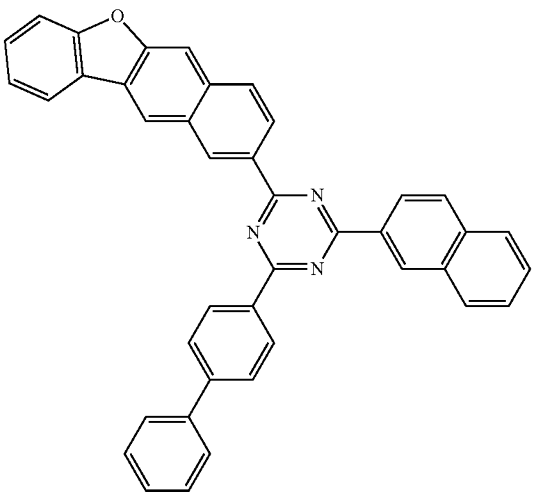
H2-740
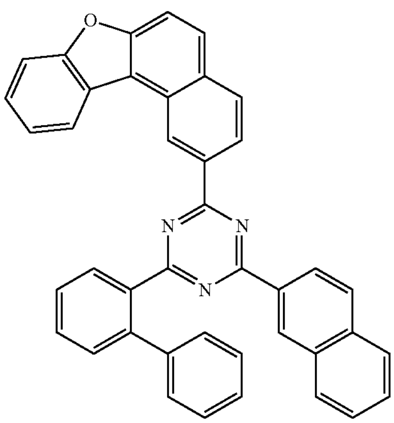
H2-741
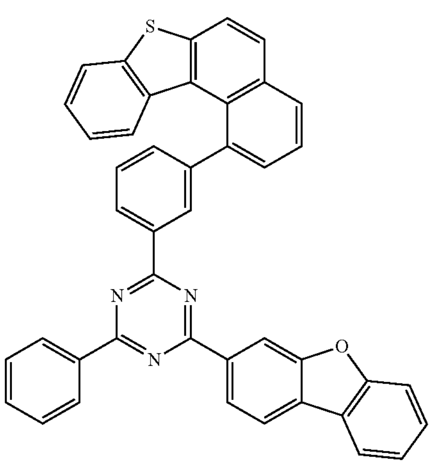
-continued
H2-742
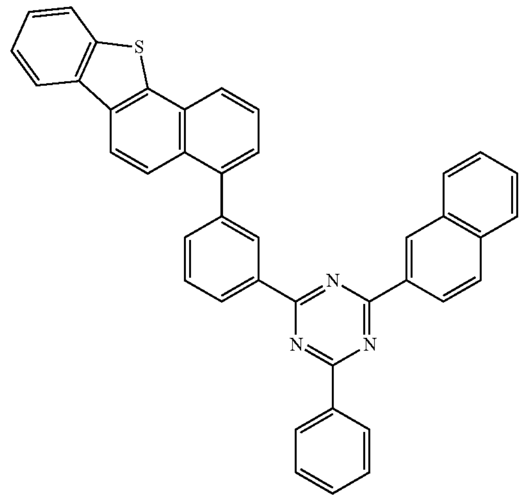
H2-743
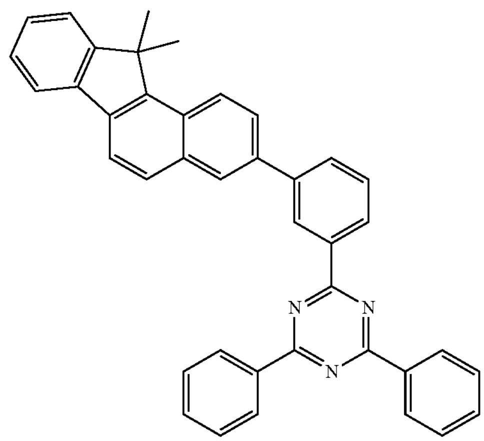
H2-744
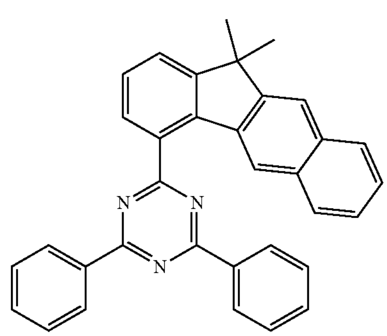

-continued
H2-745
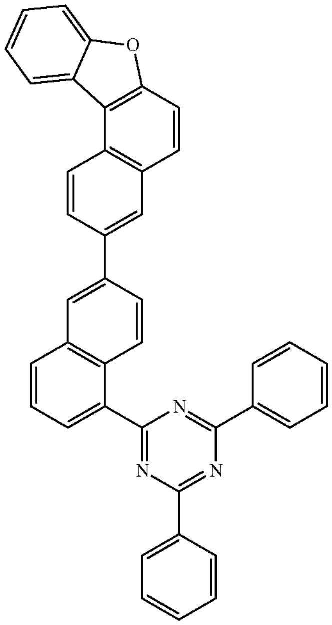
H2-746
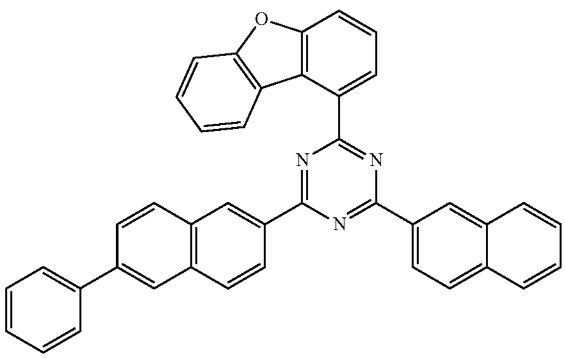
H2-747
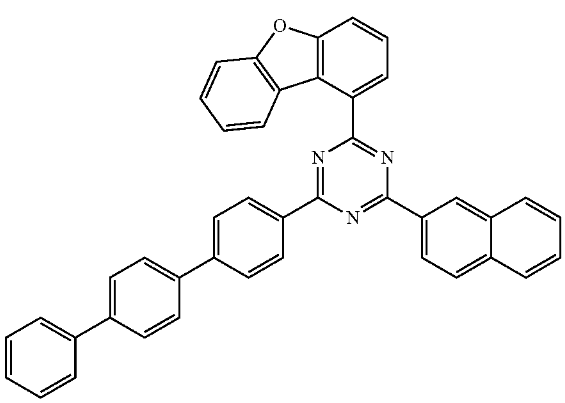
-continued
H2-748
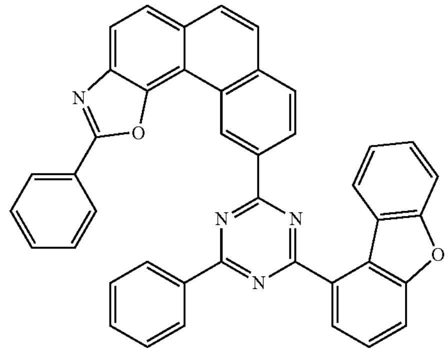
H2-749
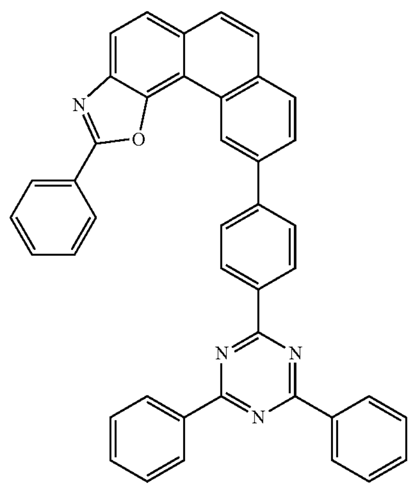
H2-750
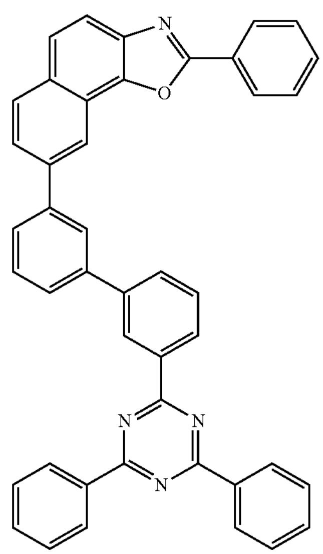

-continued
H2-751
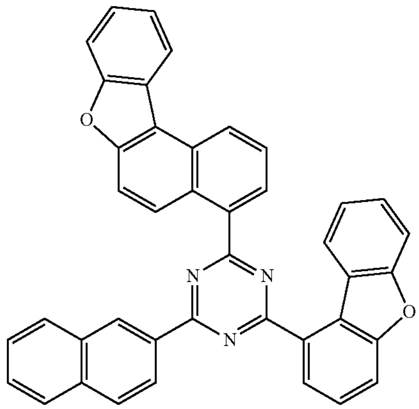
H2-752
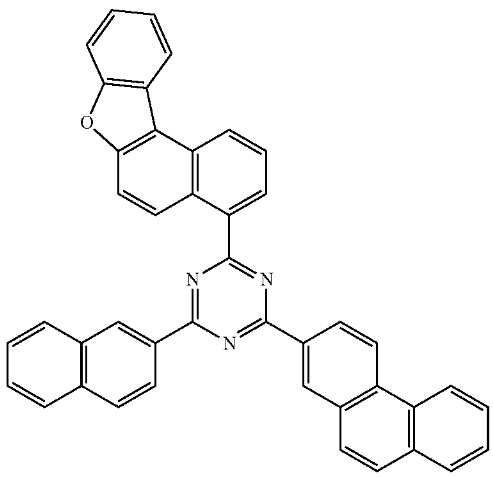
H2-753
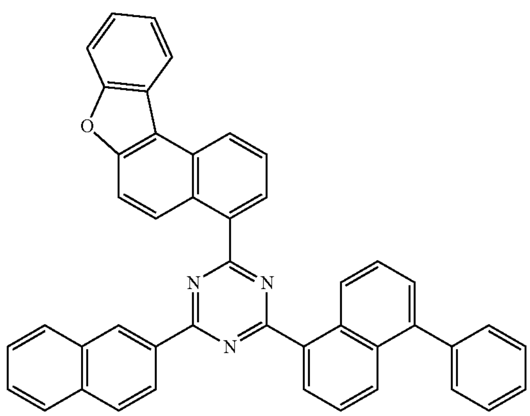
-continued
H2-754
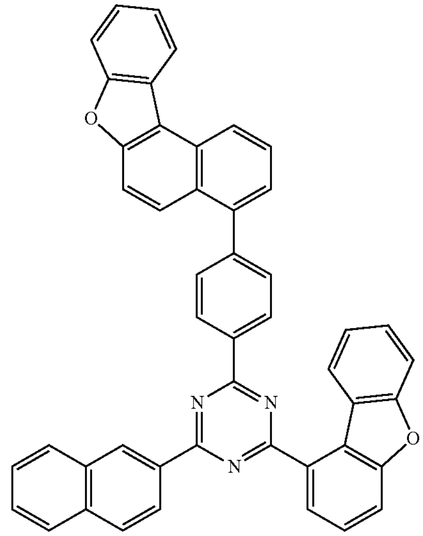
H2-755
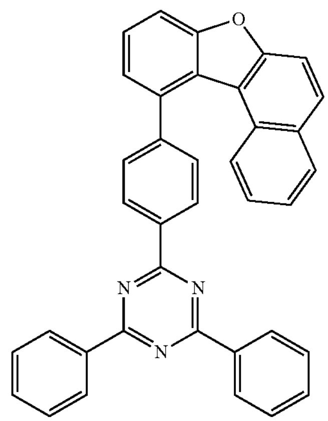
H2-756
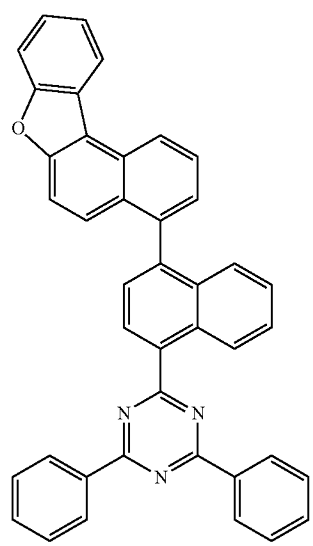

-continued
H2-757
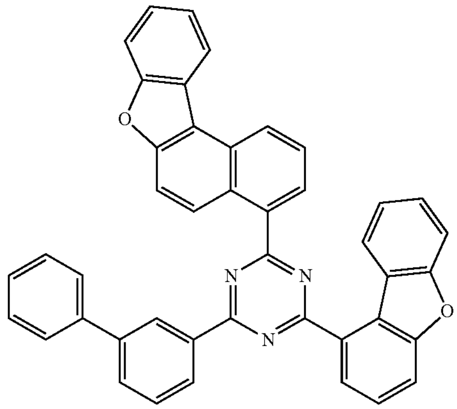
H2-758
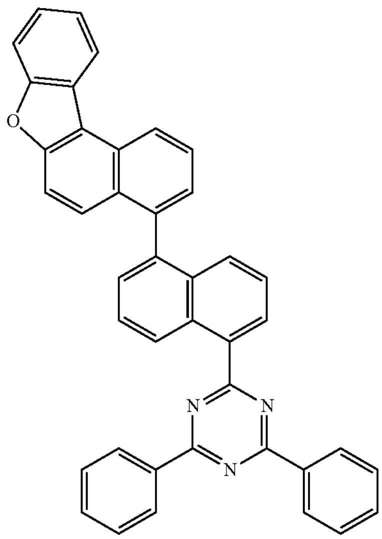
H2-759
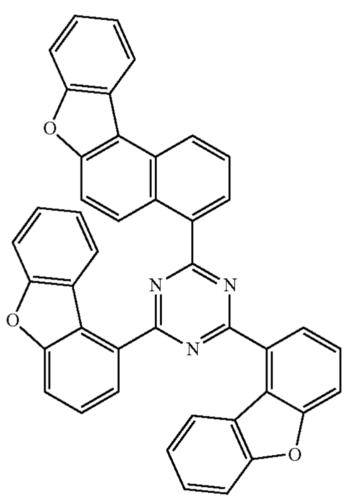
-continued
H2-760
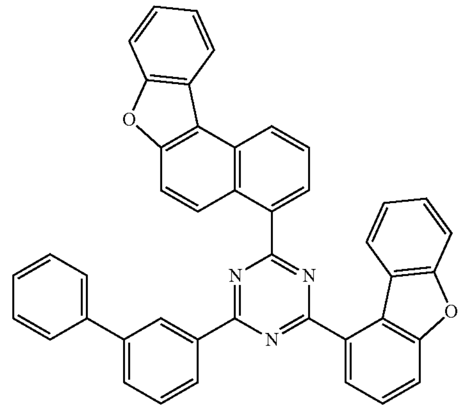
H2-761
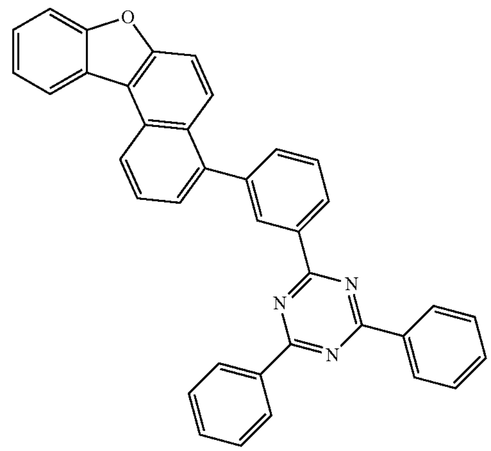
H2-762
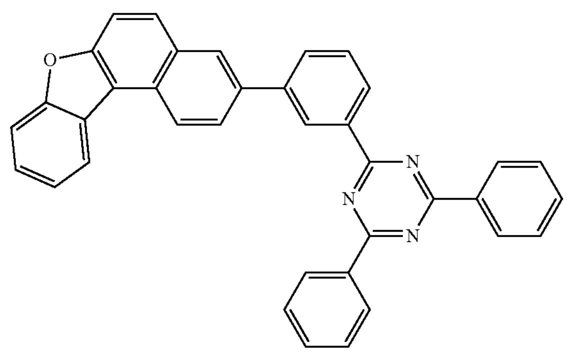
H2-763
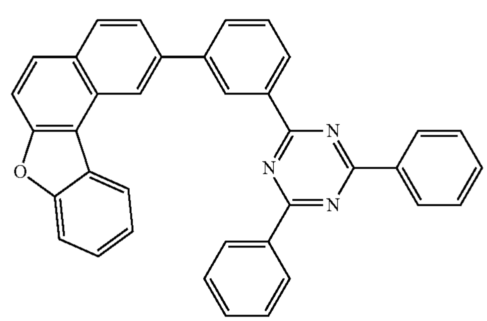

-continued
H2-764
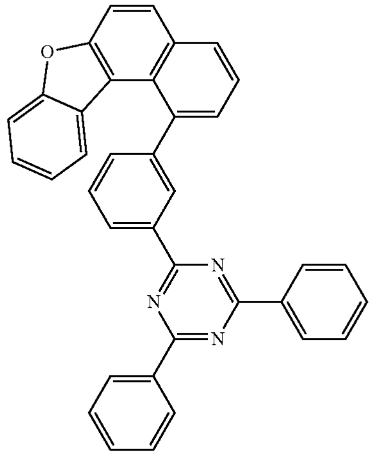
H2-765
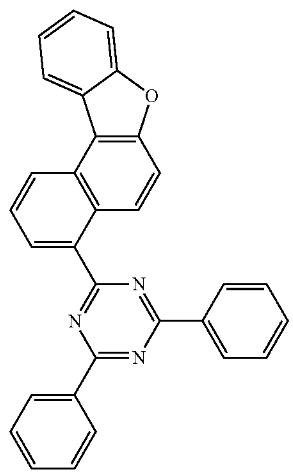
H2-766
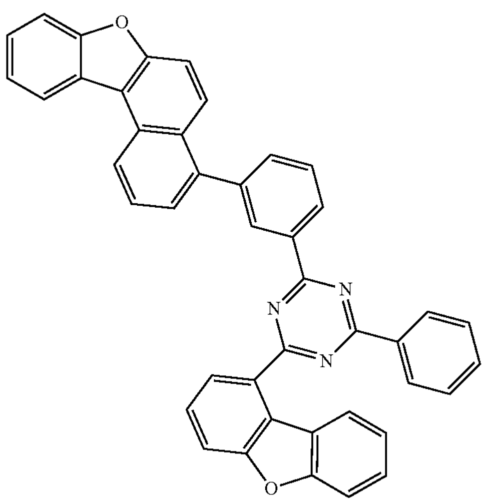
-continued
H2-767
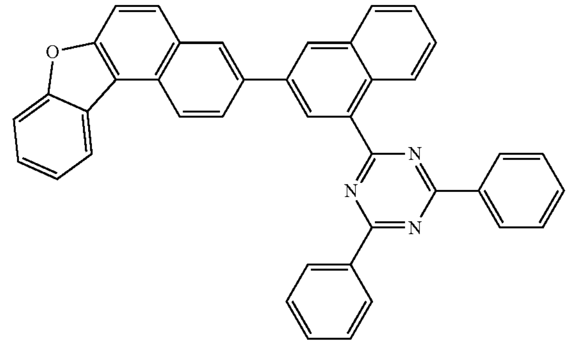
H2-768
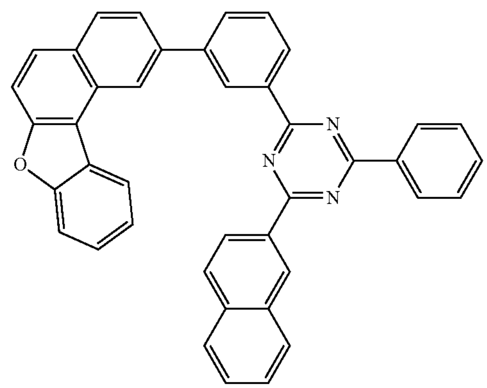
H2-769
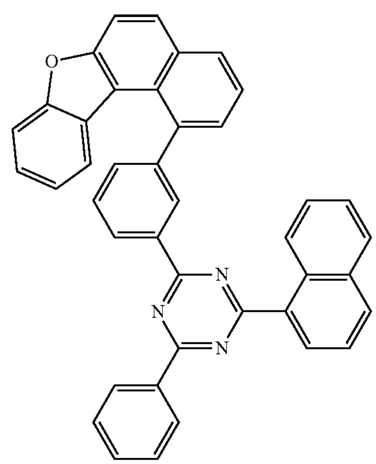

-continued
H2-770
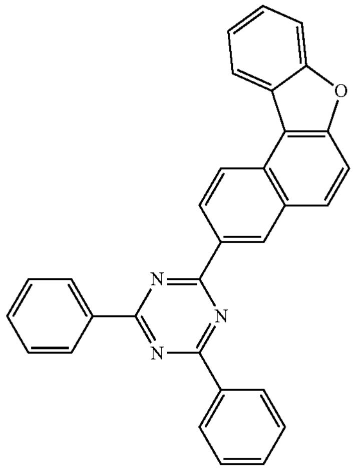
H2-771
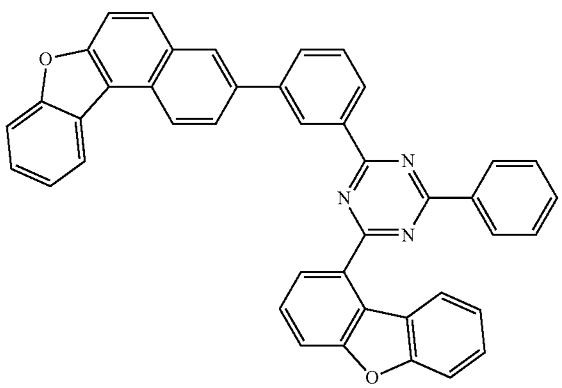
H2-772
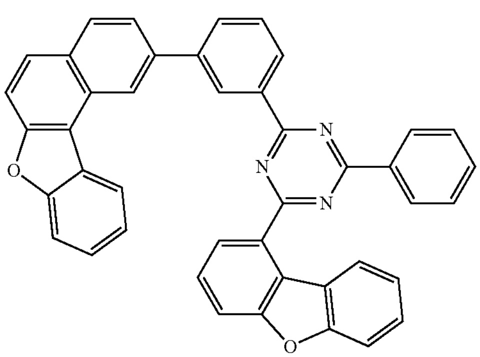
-continued
H2-773
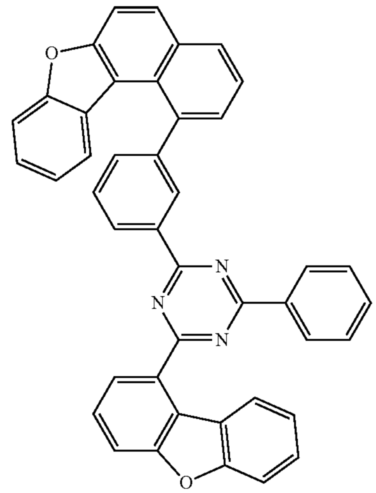
H2-774
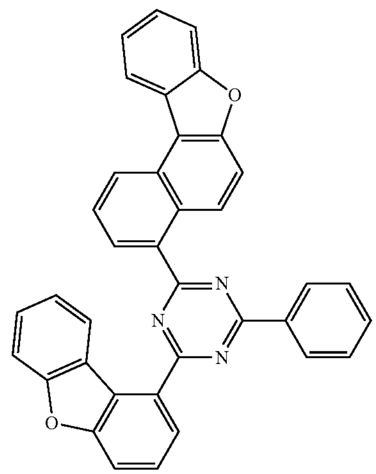
H2-775
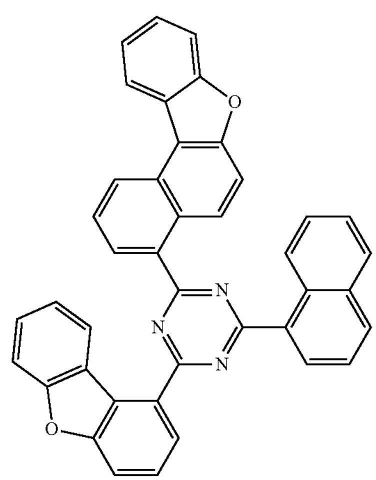

-continued
H2-776
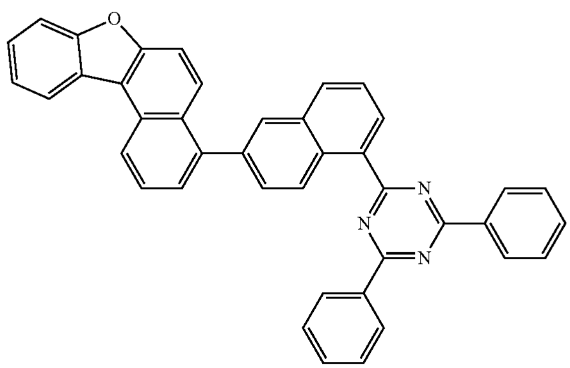
H2-777
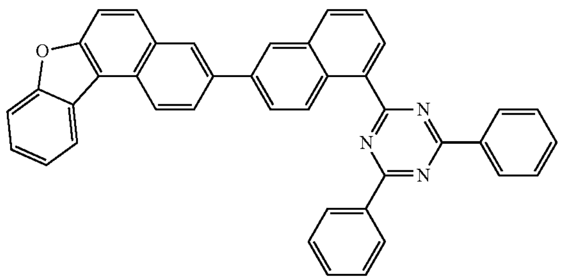
H2-778
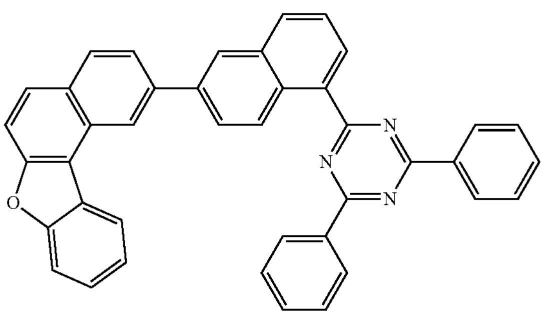
H2-779
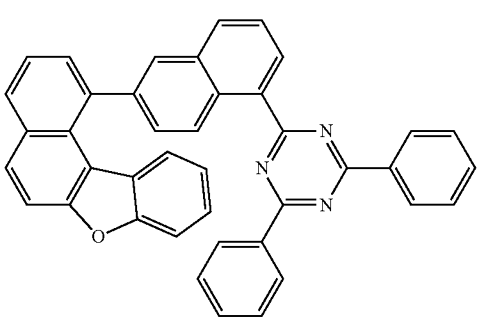
-continued
H2-780
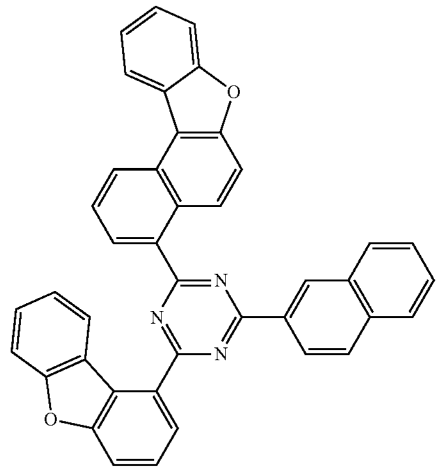
H2-781
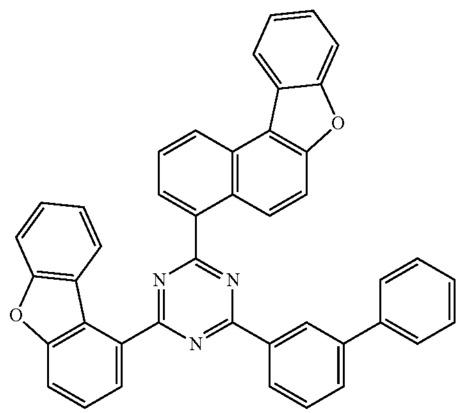
H2-782
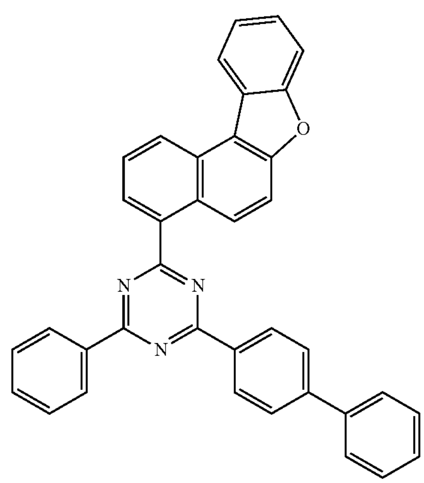

-continued
H2-783
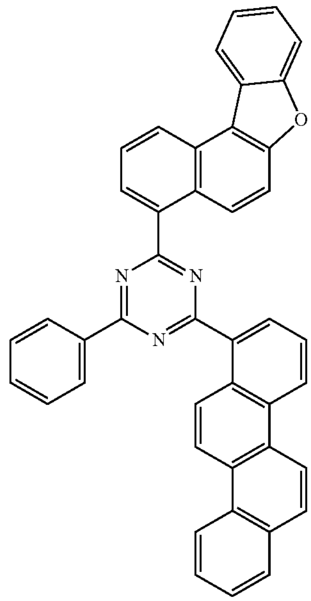
H2-784
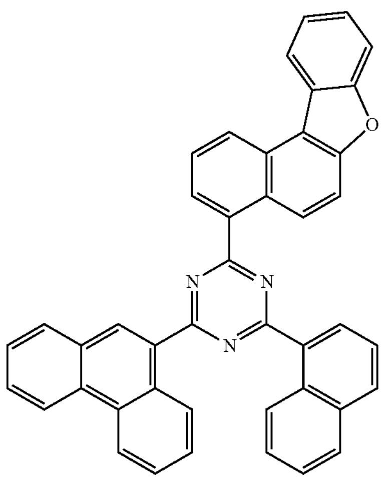
H2-785
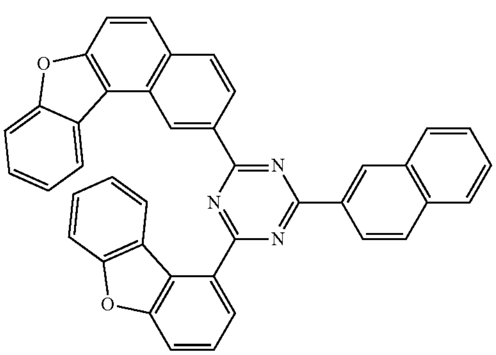
-continued
H2-786
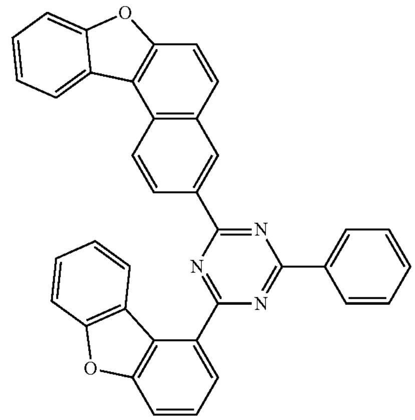
H2-787
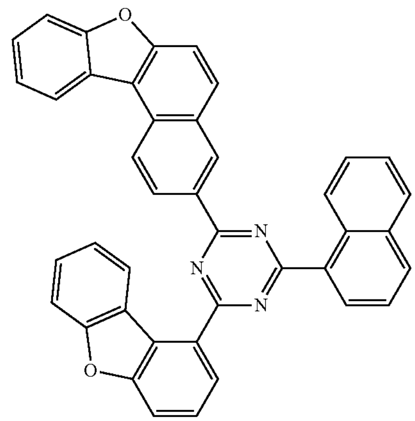
H2-788
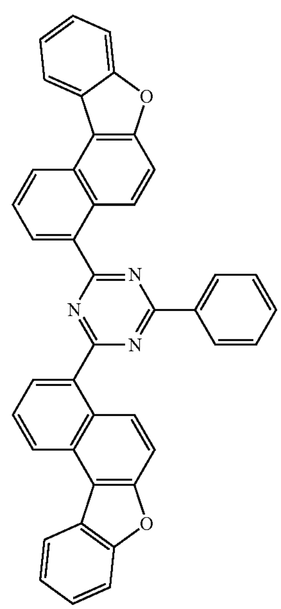

H2-789
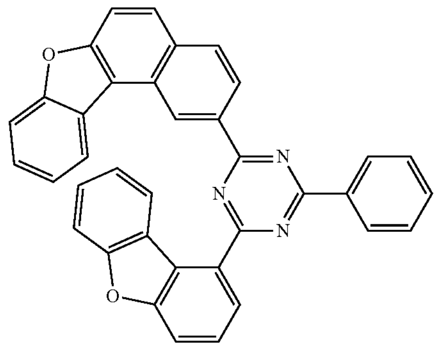
H2-790
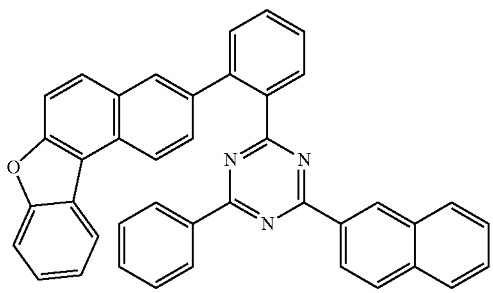
H2-791
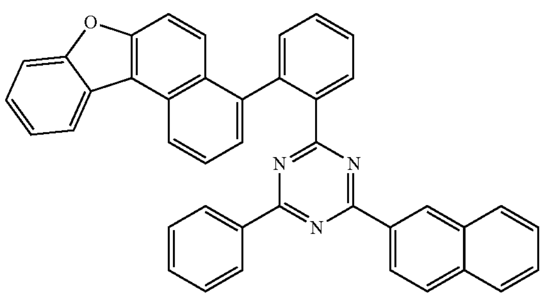
H2-792
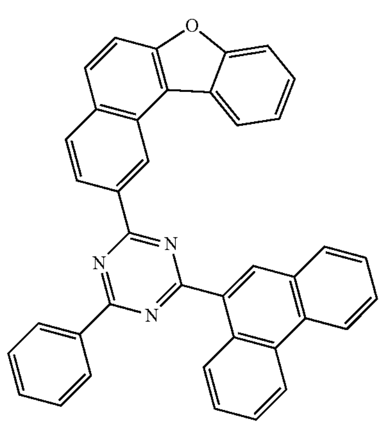
H2-793
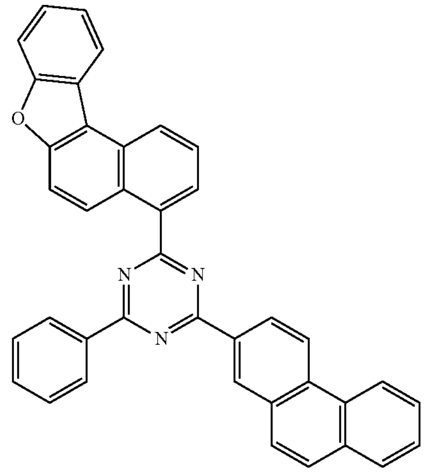
H2-794
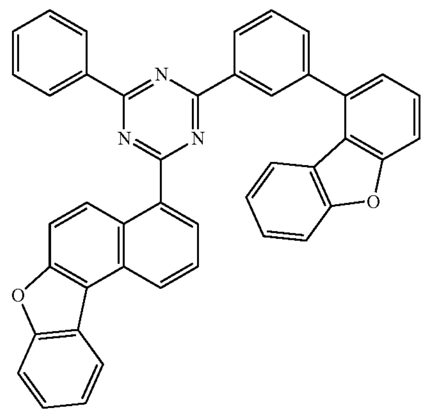
H2-795
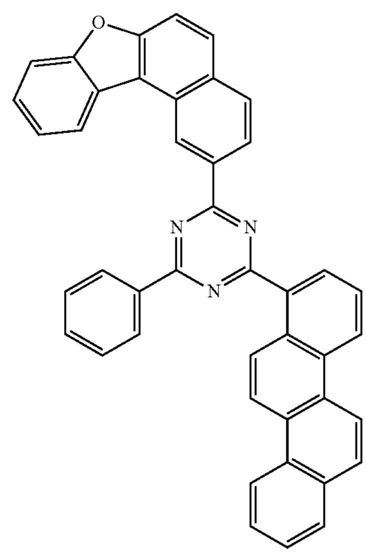

-continued
H2-796
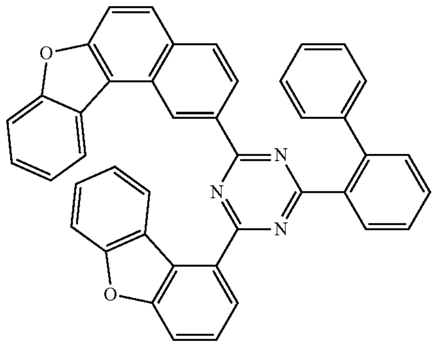
H2-797
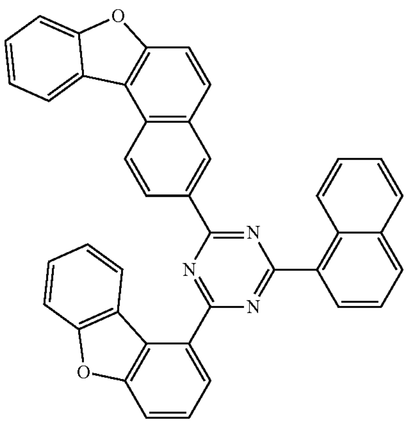
H2-798
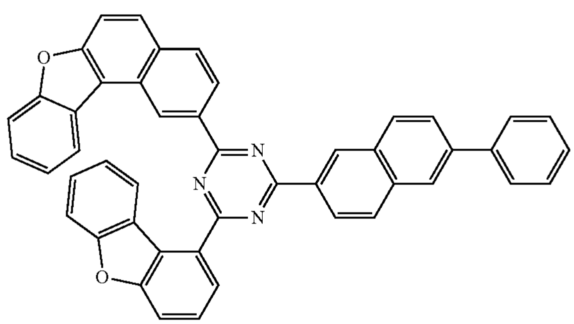
H2-799
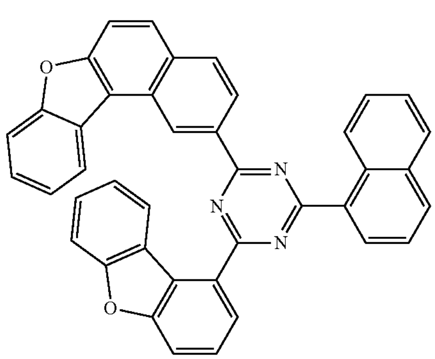
-continued
H2-800
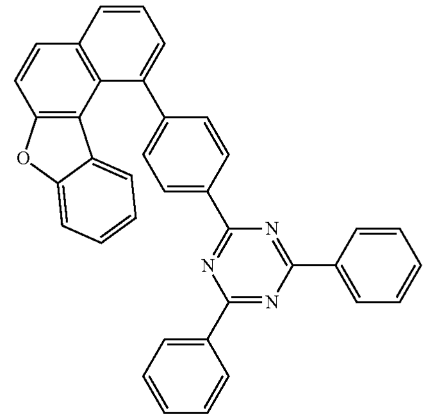
H2-801
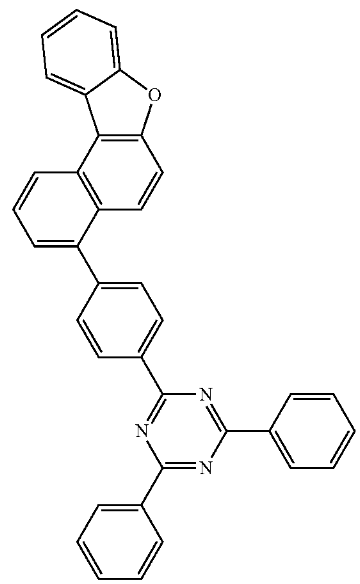
H2-802
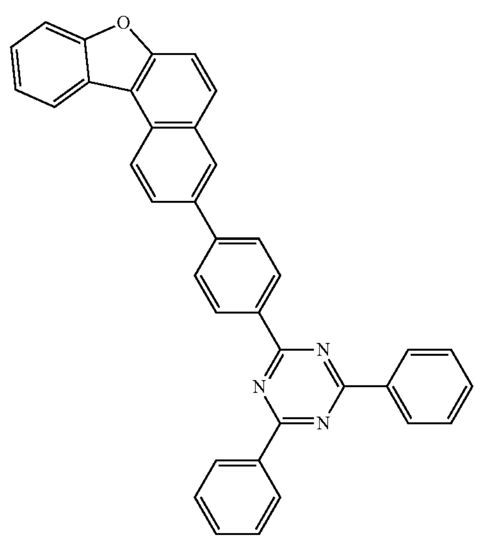

-continued
H2-803
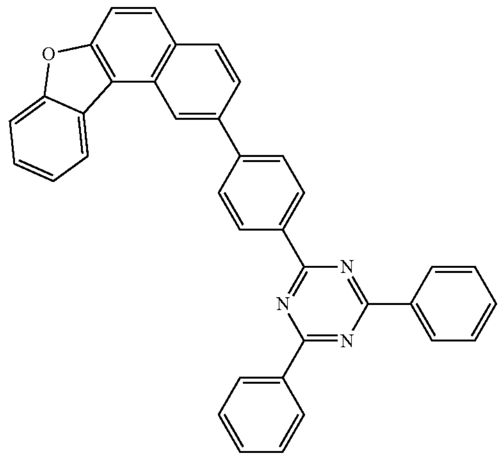
H2-804
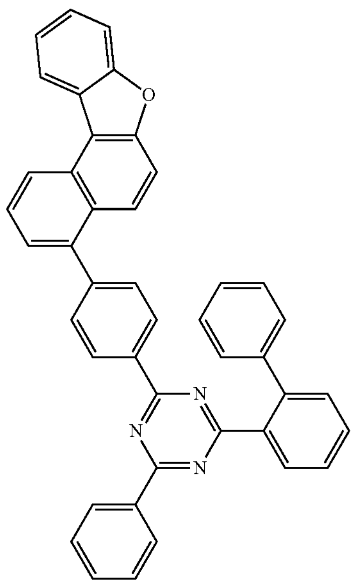
H2-805
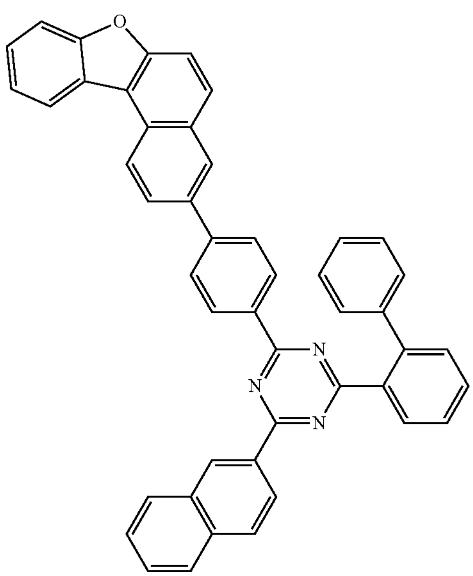
-continued
H2-806
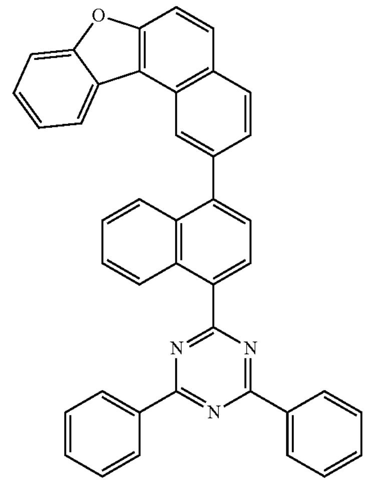
H2-807
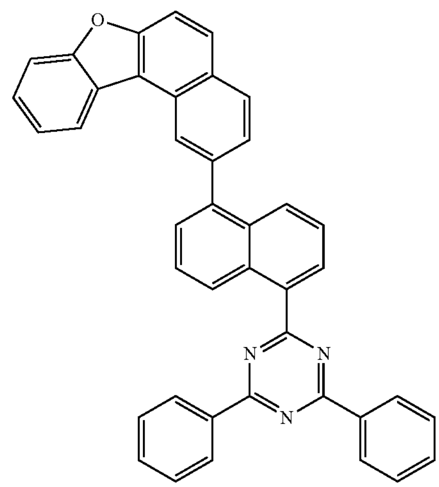
H2-808
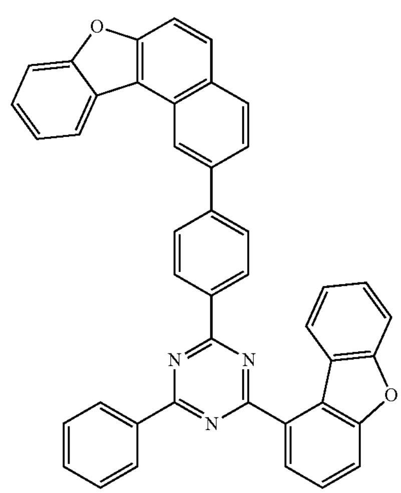

-continued
H2-809
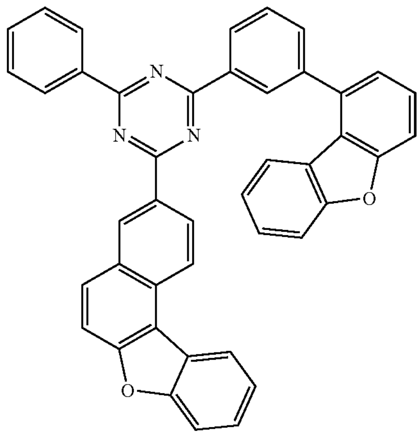
H2-810
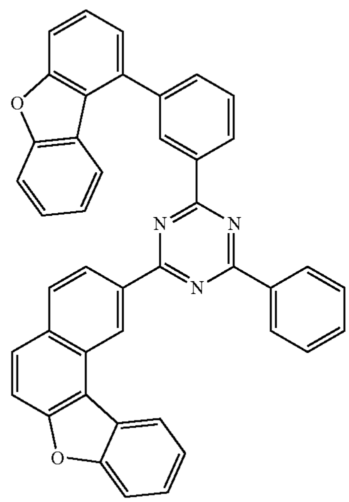
H2-811
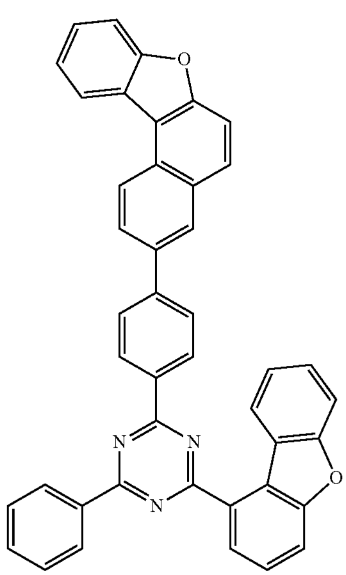
-continued
H2-812
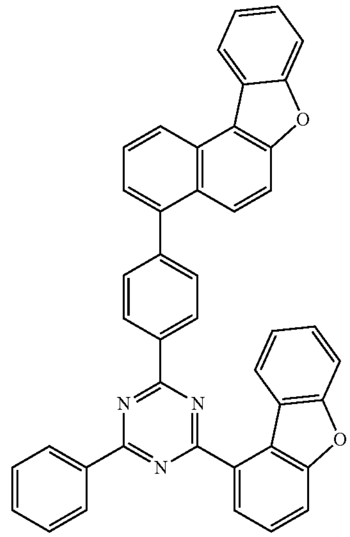
H2-813
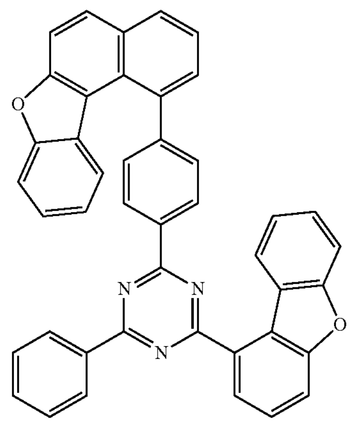
H2-814
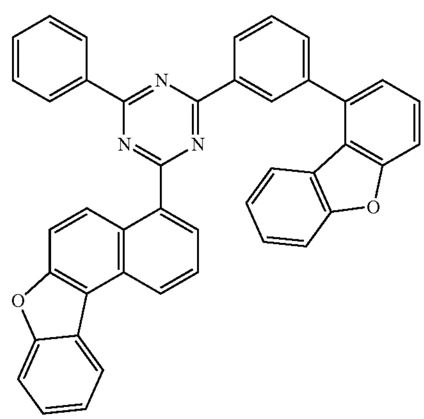

-continued
H2-815
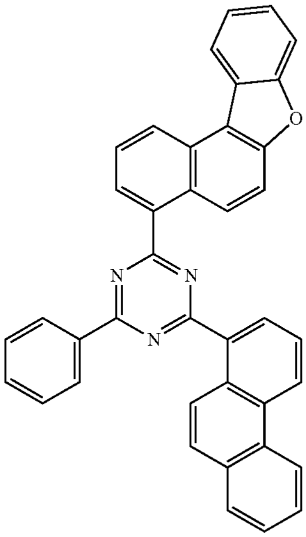
H2-816
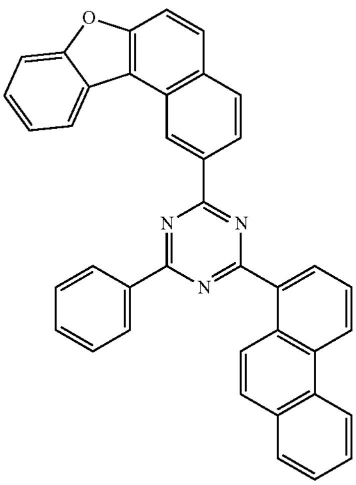
H2-817
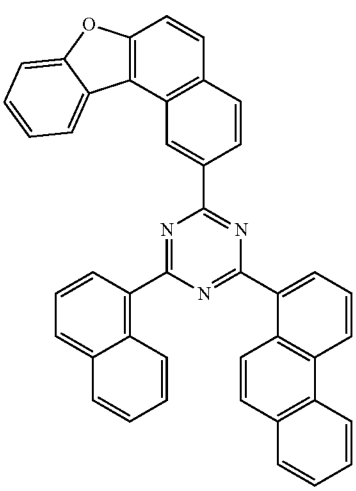
-continued
H2-818
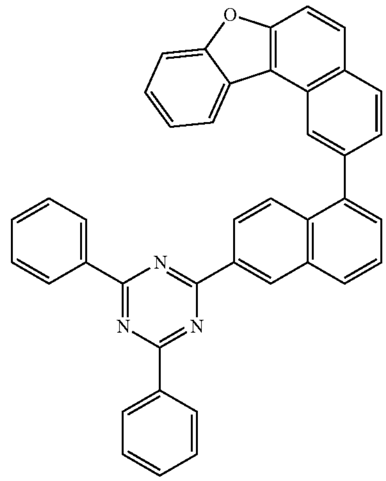
H2-819
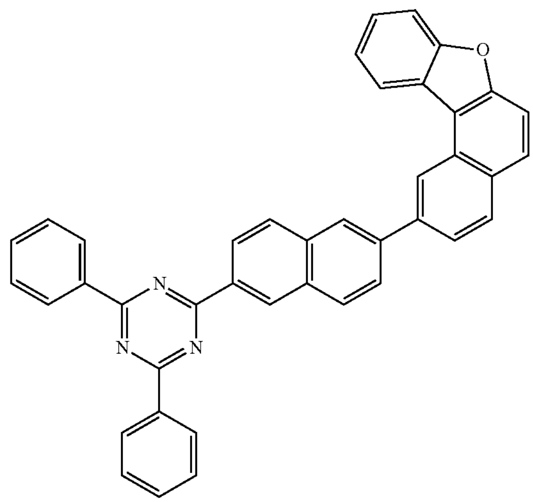
H2-820
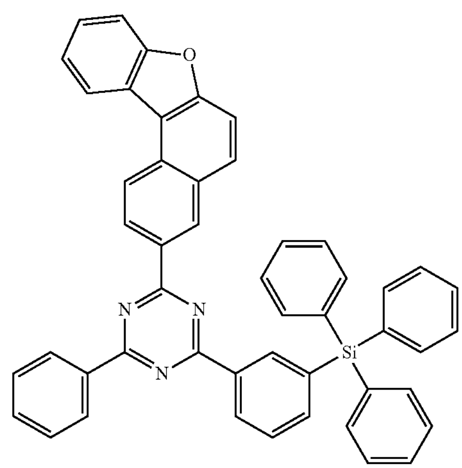

-continued
H2-821
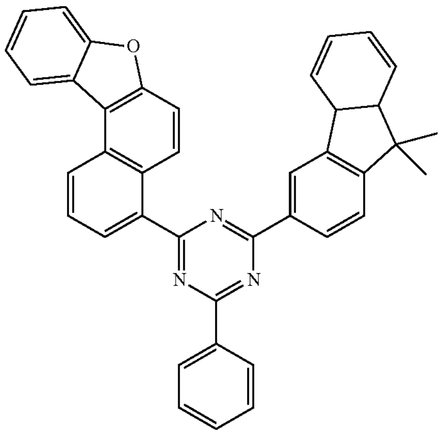
H2-822
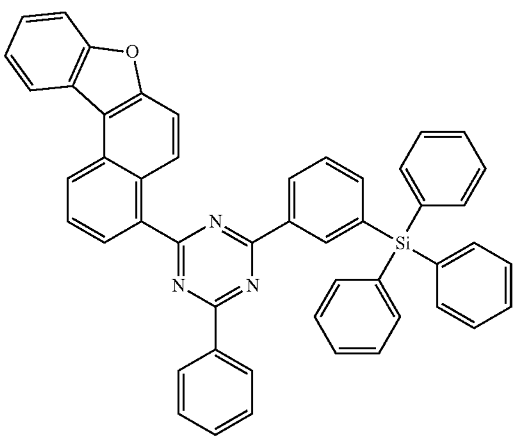
H2-823
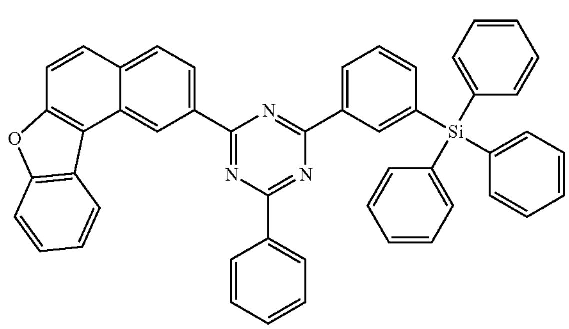
-continued
H2-824
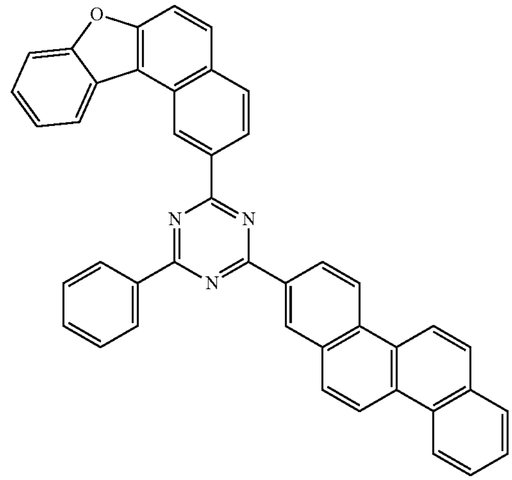
H2-825
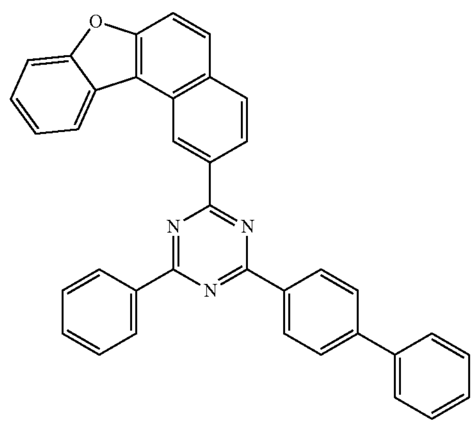
H2-826
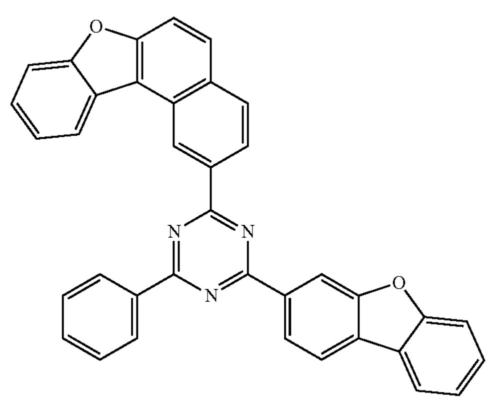

-continued
H2-827
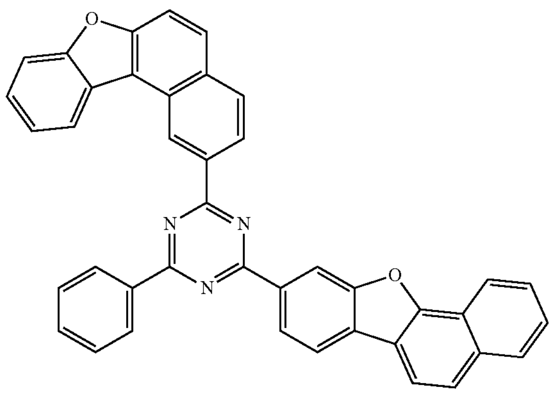
H2-828
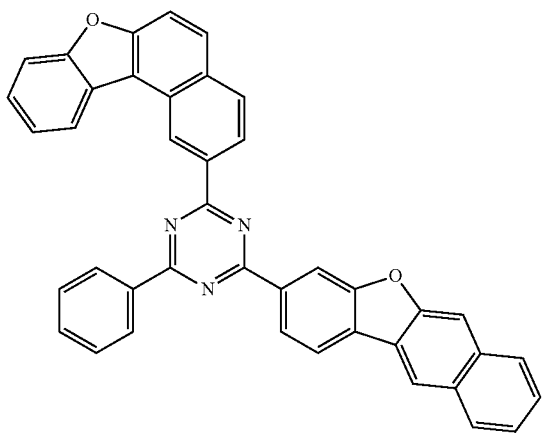
H2-829
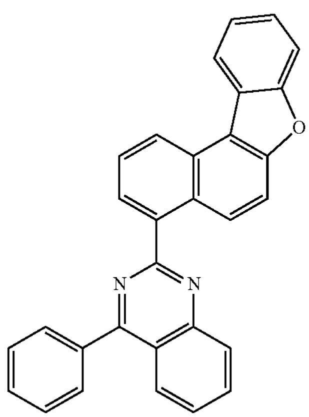
H2-830
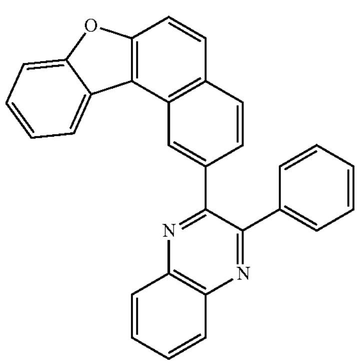
H2-831
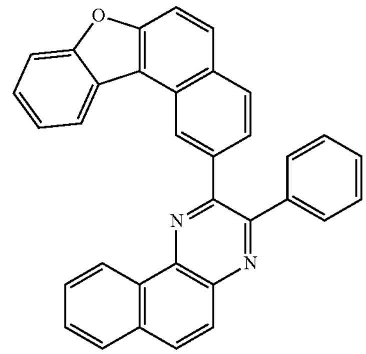
H2-832
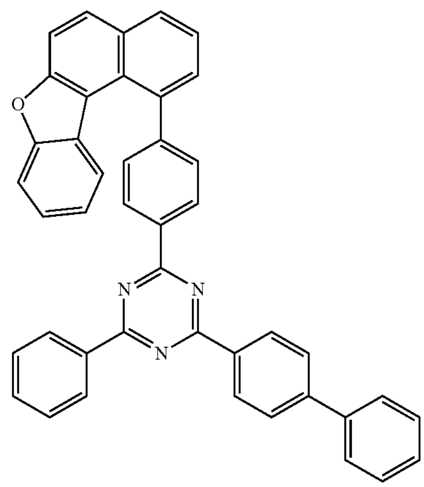
H2-833
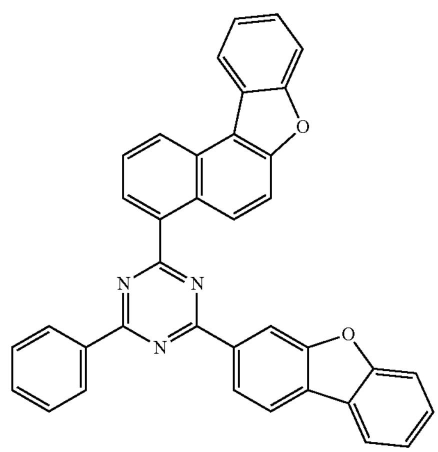

-continued
H2-834
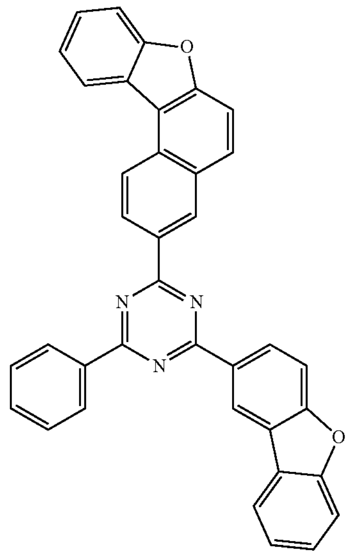
H2-835
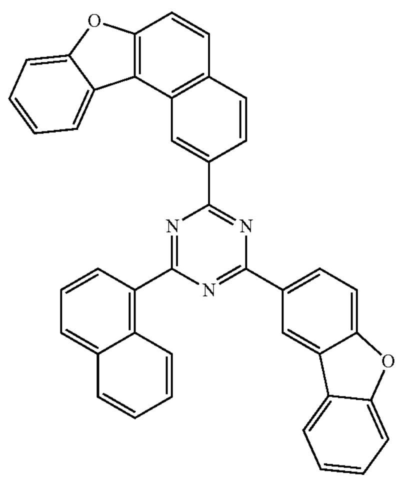
H2-836
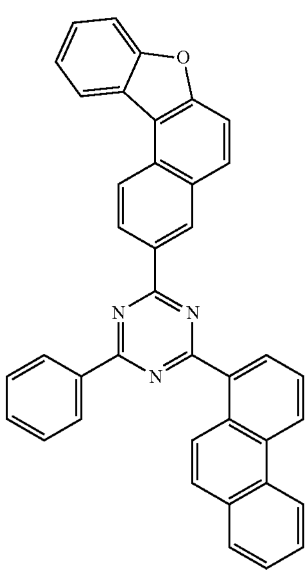
-continued
H2-837
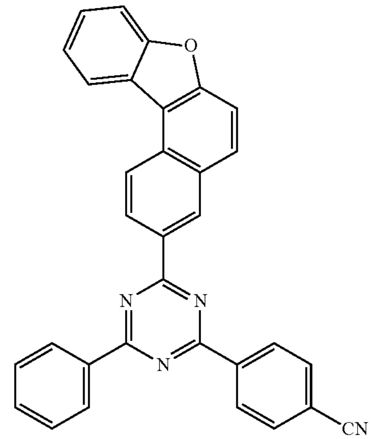
H2-838
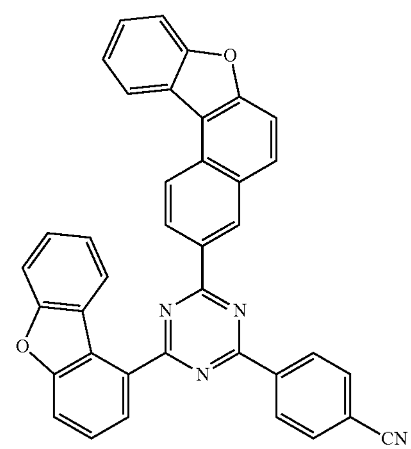

-continued
H2-839
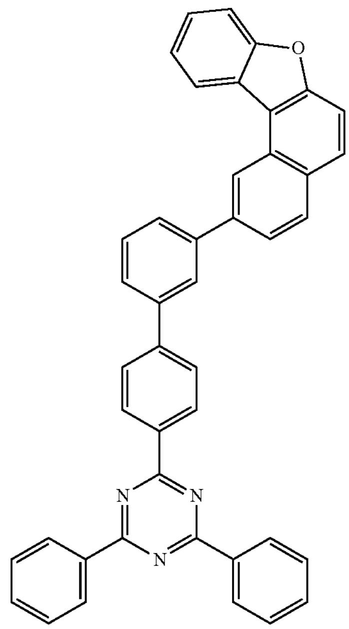
H2-840
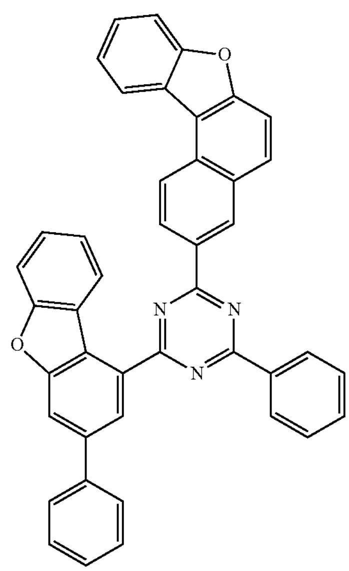
H2-841
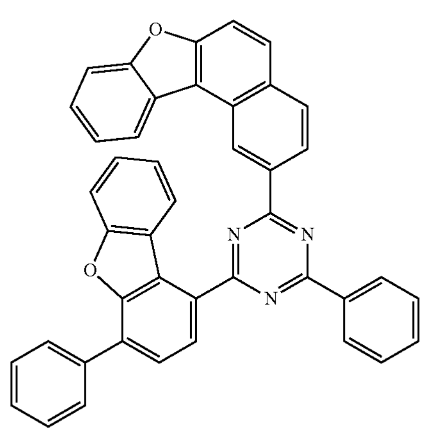
-continued
H2-842
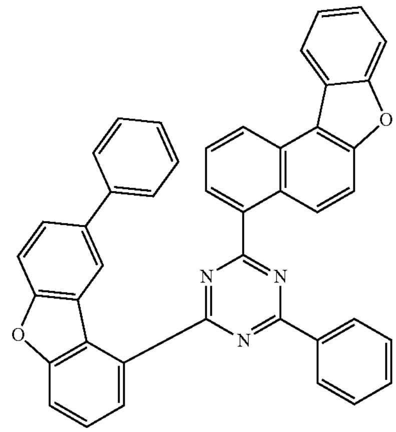
H2-843
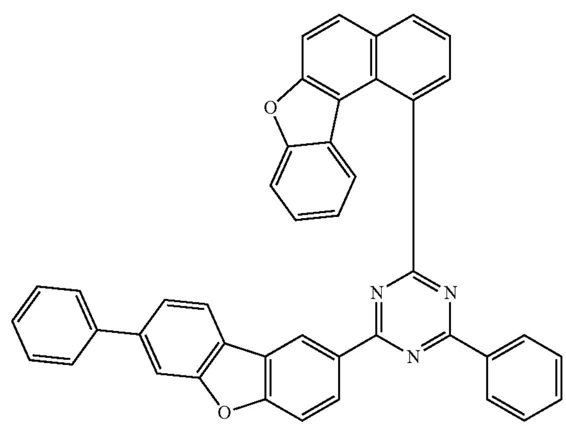
H2-844
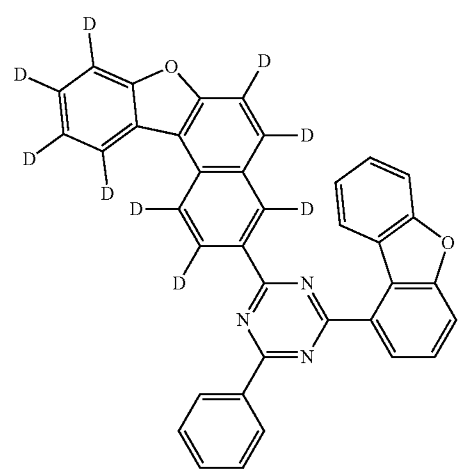

-continued
H2-845
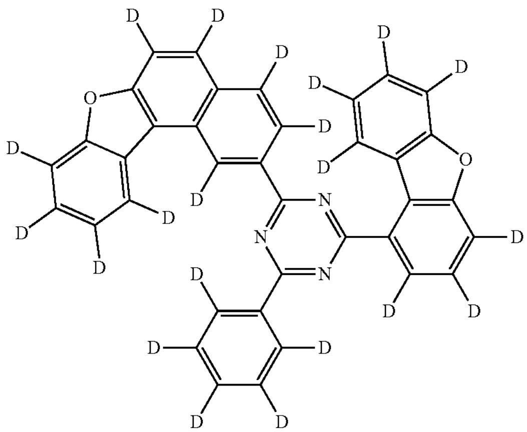
H2-846
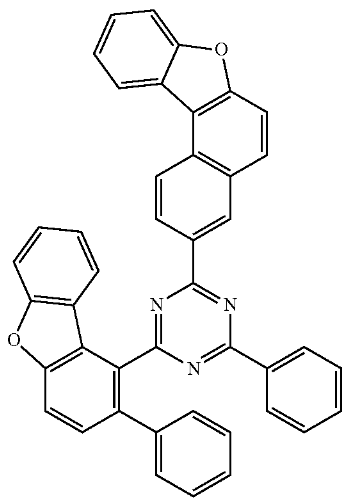
H2-847
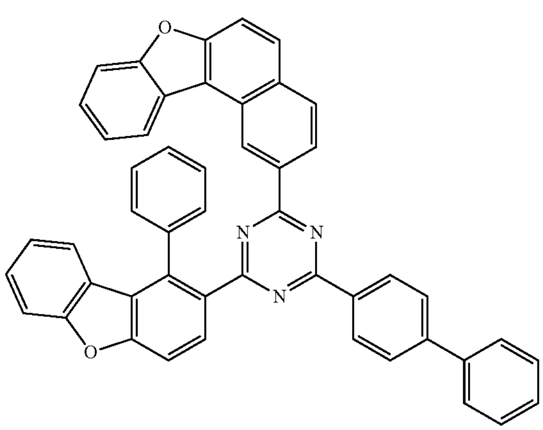
-continued
H2-848
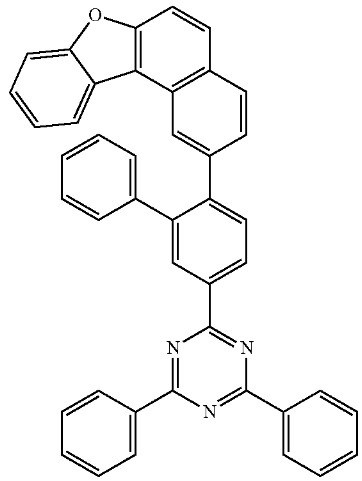
H2-849
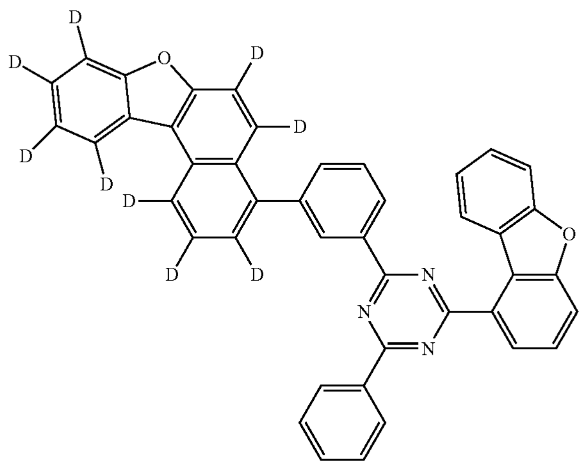
H2-850
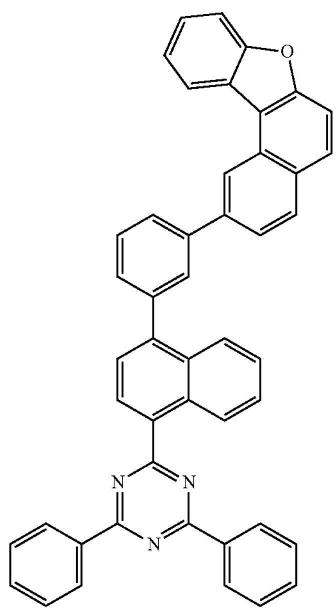

-continued
H2-851
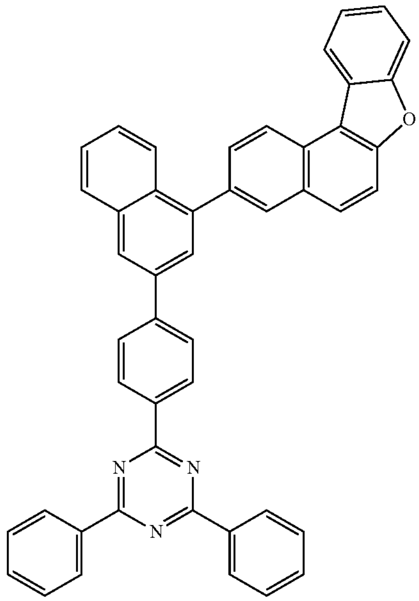
H2-852
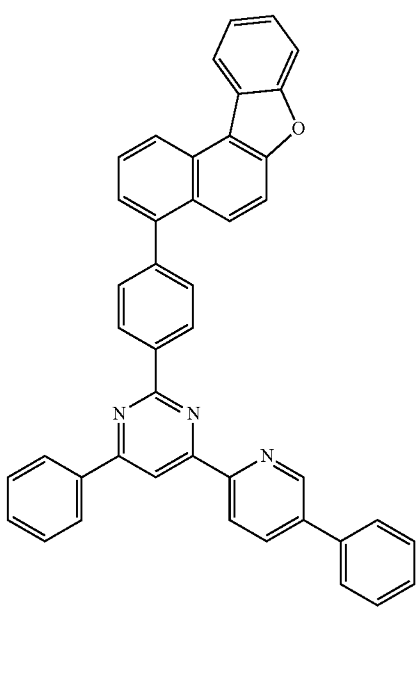
-continued
H2-853
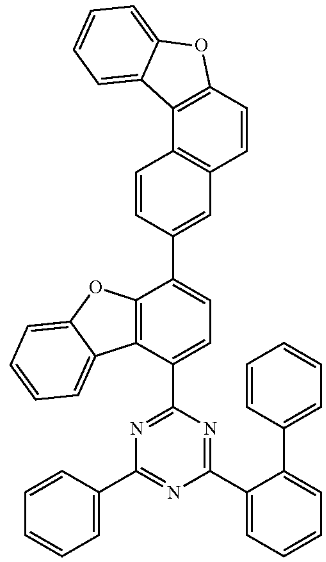
H2-854
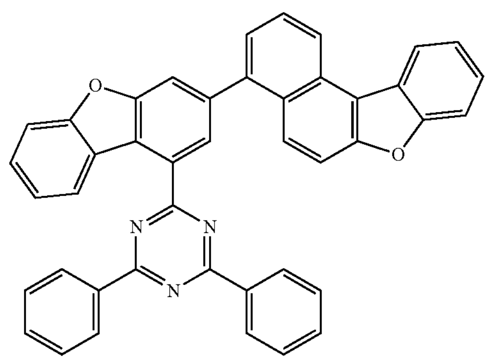
H2-855
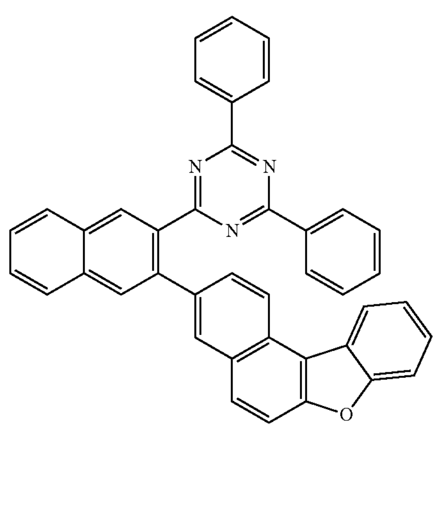

-continued
H2-856
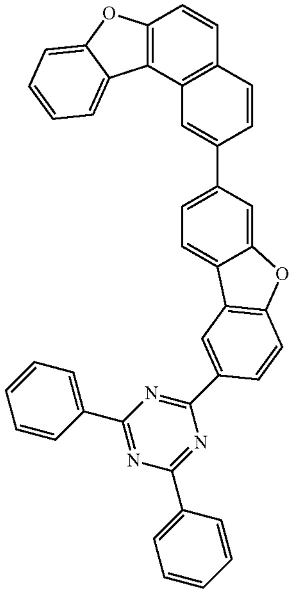
H2-857
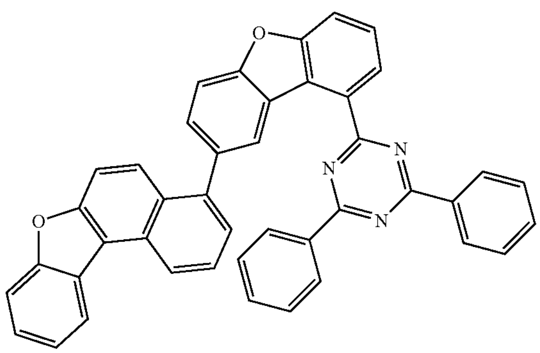
H2-858
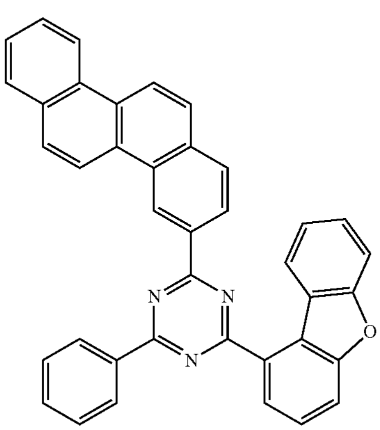
-continued
H2-859
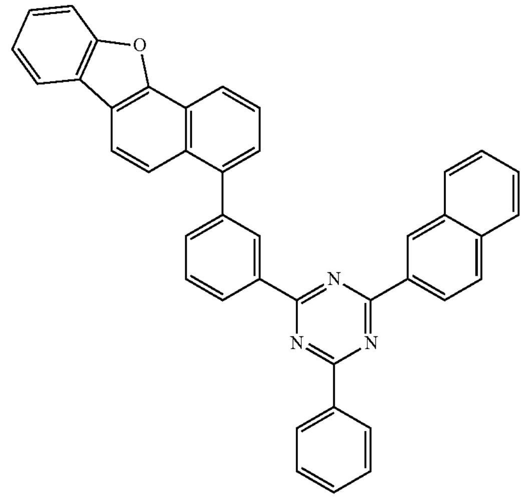
H2-860
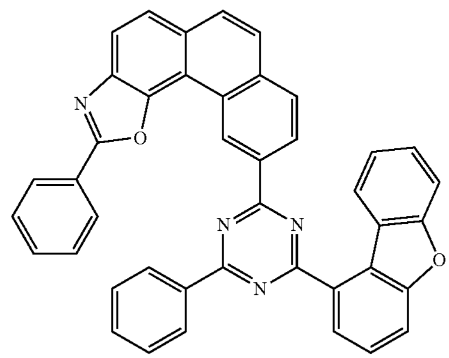
H2-861
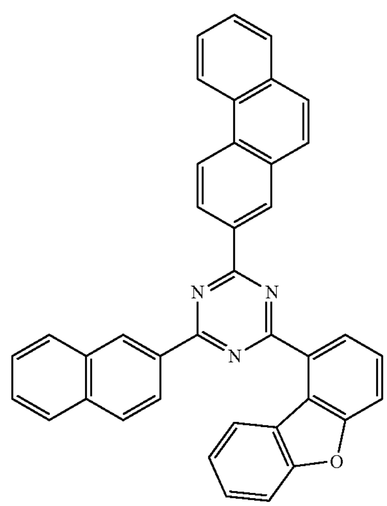

-continued
H2-862
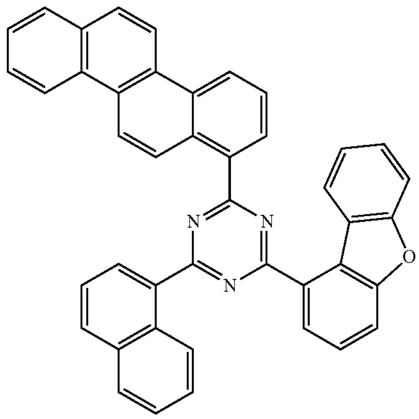
H2-863
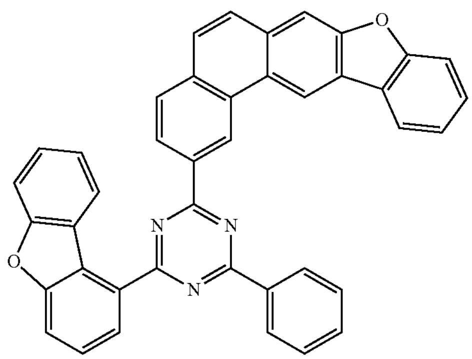
and
-continued
H2-864
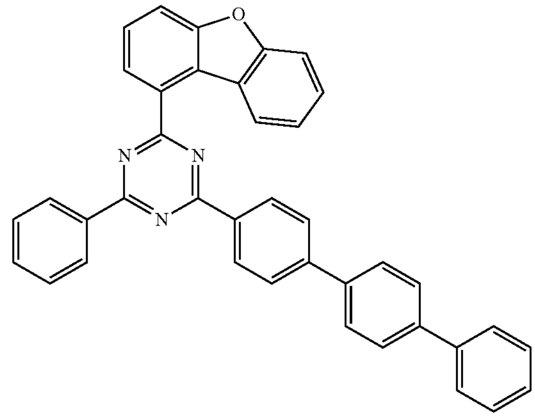
.
11. An organic electroluminescent device comprising an anode, a cathode, and at least one light-emitting layer between the anode and the cathode, wherein at least one of the light-emitting layers comprises the plurality of host materials according to claim 1.
* * * * *